US009085576B2

(12) United States Patent
Minatti et al.

(10) Patent No.: US 9,085,576 B2
(45) Date of Patent: Jul. 21, 2015

(54) PERFLUORINATED CYCLOPROPYL FUSED 1,3-OXAZIN-2-AMINE COMPOUNDS AS BETA-SECRETASE INHIBITORS AND METHODS OF USE

(71) Applicant: AMGEN INC., Thousand Oaks, CA (US)

(72) Inventors: Ana Elena Minatti, Santa Monica, CA (US); Jonathan D. Low, Tarzana, CA (US); Jennifer R. Allen, Newbury Park, CA (US); Albert Amegadzie, Moorpark, CA (US); James Brown, Moorpark, CA (US); Michael J. Frohn, Thousand Oaks, CA (US); Angel Guzman-Perez, Belmont, MA (US); Paul E. Harrington, Camarillo, CA (US); Patricia Lopez, Woodland Hills, CA (US); Vu Van Ma, Oak Park, CA (US); Nobuko Nishimura, West Hills, CA (US); Wenyuan Qian, Newbury Park, CA (US); Shannon Rumfelt, Camarillo, CA (US); Robert M. Rzasa, Ventura, CA (US); Kelvin Sham, Thousand Oaks, CA (US); Adrian L. Smith, Simi Valley, CA (US); Ryan White, Somerville, MA (US); Qiufen Xue, Newbury Park, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 14/199,844

(22) Filed: Mar. 6, 2014

(65) Prior Publication Data

US 2014/0275058 A1    Sep. 18, 2014

Related U.S. Application Data

(60) Provisional application No. 61/939,580, filed on Feb. 13, 2014, provisional application No. 61/775,380, filed on Mar. 8, 2013.

(51) Int. Cl.
| | |
|---|---|
| *C07D 471/04* | (2006.01) |
| *C07D 265/12* | (2006.01) |
| *C07D 417/12* | (2006.01) |

(Continued)

(52) U.S. Cl.
CPC ............ *C07D 471/04* (2013.01); *C07D 265/12* (2013.01); *C07D 413/10* (2013.01); *C07D 413/12* (2013.01); *C07D 413/14* (2013.01); *C07D 417/12* (2013.01); *C07D 417/14* (2013.01); *C07D 491/048* (2013.01)

(58) Field of Classification Search
CPC .. C07D 471/04; C07D 413/12; C07D 413/14; C07D 417/12; C07D 417/14; C07D 265/12

USPC ................................... 544/90, 96; 514/230.5
See application file for complete search history.

(56) References Cited

U.S. PATENT DOCUMENTS

| 5,441,870 A | 8/1995 | Seubert et al. |
|---|---|---|
| 5,712,130 A | 1/1998 | Hajko et al. |

(Continued)

FOREIGN PATENT DOCUMENTS

| EP | 01942105 B8 | 4/2014 |
|---|---|---|
| JP | 2012250933 A | 12/2012 |

(Continued)

OTHER PUBLICATIONS

Vassar & Yan, *Lancet Neurology*, 13:319-329 (2014).
Joachim et al., *Alz. Dis. Assoc. Dis.*, 6:7-34 (1992).
Selkoe, *Neuron*, 6:487 (1991).
Seubert et al., *Nature*, 359:325-327 (1992).
Citron, *Trends in Pharmacological Sciences*, 25(2):92-97 (2004).
Shankar, G.M., *Nature Medicine* (Jun. 22, 2008) online doi 10:1038 nm 1782.

(Continued)

*Primary Examiner* — Kahsay Habte
(74) *Attorney, Agent, or Firm* — Bernard P. Friedrichsen; G. Prabhakar Reddy

(57) ABSTRACT

The present invention provides a new class of compounds useful for the modulation of beta-secretase enzyme (BACE) activity. The compounds have a general Formula I:

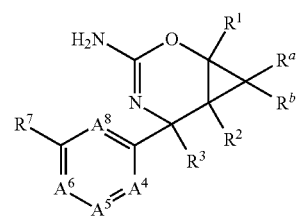

wherein variables $A^4$, $A^5$, $A^6$, $A^8$, each of $R^a$, $R^b$, $R^1$, $R^2$, $R^3$ and $R^7$ of Formula I, independently, are defined herein. The invention also provides pharmaceutical compositions comprising the compounds, and uses of the compounds and compositions for treatment of disorders and/or conditions related to A-beta plaque formation and deposition, resulting from the biological activity of BACE. Such BACE mediated disorders include, for example, Alzheimer's Disease, cognitive deficits, cognitive impairments, schizophrenia and other central nervous system conditions. The invention further provides compounds of Formulas II and III, and sub-formula embodiments thereof, intermediates and methods for preparing compounds of the invention.

60 Claims, No Drawings

(51) Int. Cl.

| | | |
|---|---|---|
| C07D 417/14 | (2006.01) | |
| C07D 413/12 | (2006.01) | |
| C07D 413/14 | (2006.01) | |
| A61K 31/537 | (2006.01) | |
| C07D 413/10 | (2006.01) | |
| C07D 491/048 | (2006.01) | |

(56) References Cited

U.S. PATENT DOCUMENTS

| | | |
|---|---|---|
| 5,942,400 A | 8/1999 | Anderson et al. |
| 2009/0082560 A1 | 3/2009 | Kobayashi et al. |
| 2010/0160290 A1 | 6/2010 | Kobayashi et al. |
| 2011/0294149 A1 | 12/2011 | Gurney et al. |
| 2012/0202803 A1 | 8/2012 | Hilpert et al. |
| 2012/0238557 A1 | 9/2012 | Masui et al. |
| 2012/0245154 A1 | 9/2012 | Anan et al. |
| 2012/0245157 A1 | 9/2012 | Masui et al. |
| 2012/0258962 A1 | 10/2012 | Hilpert et al. |
| 2013/0072478 A1 | 3/2013 | Hilpert et al. |
| 2014/0051691 A1 | 2/2014 | Masui et al. |

FOREIGN PATENT DOCUMENTS

| | | |
|---|---|---|
| WO | 2011/009898 A1 | 1/2011 |
| WO | 2011/020806 A1 | 2/2011 |
| WO | 2011/058763 A1 | 5/2011 |
| WO | 2011/069934 A1 | 6/2011 |
| WO | 2011/070029 A1 | 6/2011 |
| WO | 2011/070781 A1 | 6/2011 |
| WO | 2011/071109 A1 | 6/2011 |
| WO | 2012/139993 A1 | 10/2012 |
| WO | 2012147763 A1 | 11/2012 |
| WO | 2012/156284 A1 | 12/2012 |
| WO | 2012/168164 A1 | 12/2012 |
| WO | 2012/168175 A1 | 12/2012 |
| WO | 2013027188 A1 | 2/2013 |
| WO | 2013110622 A1 | 8/2013 |
| WO | 2013/142613 A1 | 9/2013 |
| WO | 2014/001228 A1 | 5/2014 |
| WO | 2014065434 A1 | 5/2014 |
| WO | 2014114532 A1 | 7/2014 |

OTHER PUBLICATIONS

Sinha et al., *Nature*, 402:537-554 (1999) (p. 510).
Sabbagh, M. et al., *Alz. Dis. Rev.* 3:1-19 (1997).
Cole, S.L., Vasser, R., *Molecular Degeneration* 2:22, 2007.
Luo et al., *Nature Neuroscience*, 4:231-232 (2001).
Henley et al., *Expert Opin. Pharmacother*. (2009), 10 (10).
Siemers et al., *Clin. Neuropharmacol*. 2007; 30 (pp. 317-325).
Siemers et al., *Neurology*, 2006, 66 (pp. 602-624).
Shacka et al., *Autophagy*, 2007, Sep.-Oct.;3(5):474-476.
Follo et al., *PLoS One*, 2011; 6(7):e21908, published Jul. 1, 2011.
Karran, Nature Reviews, 2011, 10 (pp. 698-712).

PERFLUORINATED CYCLOPROPYL FUSED 1,3-OXAZIN-2-AMINE COMPOUNDS AS BETA-SECRETASE INHIBITORS AND METHODS OF USE

RELATED APPLICATIONS

This application claims the benefit of U.S. Provisional Patent Application Nos. 61/775,380, filed on Mar. 8, 2013 and 61/939,580, filed on Feb. 13, 2014, which specifications are hereby incorporated herein by reference in their entireties.

FIELD OF THE INVENTION

The invention relates generally to pharmaceutically active compounds, pharmaceutical compositions and methods of use thereof, to treat beta-secretase mediated diseases and conditions, including, without limitation, Alzheimer's disease, plaque formation and associated central nervous system (CNS) disorders.

BACKGROUND OF THE INVENTION

Alzheimer's disease (AD) affects greater than 12 million aging people worldwide, and importantly, the number affected continues to grow. AD accounts for the majority of dementias clinically diagnosed after the age of 60. AD is generally characterized by the progressive decline of memory, reasoning, judgement and orientation. As the disease progresses, motor, sensory, and vocal abilities are affected until there is global impairment of multiple cognitive functions. The loss of cognitive function occurs gradually, typically leading to a diminished cognition of self, family and friends. Patients with severe cognitive impairment and/or diagnosed as end-stage AD are generally bedridden, incontinent, and dependent on custodial care. The AD patient eventually dies in about nine to ten years, on average, after initial diagnosis. Due to the incapacitating, generally humiliating and ultimately fatal effects of AD, there is a need to treat AD effectively upon diagnosis.

AD is characterized by two major physiological changes in the brain. The first change, beta amyloid plaque formation, supports the "amyloid cascade hypothesis" which conveys the thought that AD is caused by the formation of characteristic beta amyloid peptide (A-beta), or A-beta fragments thereof, deposits in the brain (commonly referred to as beta amyloid "plaques" or "plaque deposits") and in cerebral blood vessels (beta amyloid angiopathy). A wealth of evidence suggests that beta-amyloid and accompanying amyloid plaque formation is central to the pathophysiology of AD and is likely to play an early role in this intractable neurodegenerative disorder. Vassar & Yan, *Lancet Neurology*, 13:319-329 (2014). The second change in AD is the formation of intraneuronal tangles, consisting of an aggregate form of the protein tau. Besides being found in patients with AD, intraneuronal tangles are also found in other dementia-inducing disorders. Joachim et al., *Alz. Dis. Assoc. Dis.*, 6:7-34 (1992).

Several lines of evidence indicate that progressive cerebral deposition of A-beta plays a seminal role in the pathogenisis of AD and can precede cognitive symptoms by years or even decades. Selkoe, *Neuron*, 6:487 (1991). Release of A-beta from neuronal cells grown in culture and the presence of A-beta in cerebrospinal fluid (CSF) of both normal individuals and AD patients has been demonstrated. Seubert et al., *Nature*, 359:325-327 (1992). Autopsies of AD patients have revealed large numbers of lesions comprising these 2 factors in areas of the human brain believed to be important for memory and cognition.

Smaller numbers of these lesions in a more restricted anatomical distribution are found in the brains of most aged humans who do not have clinical AD. Amyloid containing plaques and vascular amyloid angiopathy were also found in the brains of individuals with Down's Syndrome, Hereditary Cerebral Hemorrhage with Amyloidosis of the Dutch-type (HCHWA-D), and other neurodegenerative disorders.

It has been hypothesized that A-beta formation is a causative precursor or factor in the development of AD. More specifically, deposition of A-beta in areas of the brain responsible for cognitive factors is believed to be a major factor in the development of AD. Beta amyloid plaques are primarily composed of amyloid beta peptide (A-beta peptide). A-beta peptide is derived from the proteolytic cleavage of a large transmembrane amyloid precursor protein (APP), and is a peptide comprised of about 39-42 amino acid residues. A-beta 42 (42 amino acids long) is thought to be the major component of these plaque deposits in the brains of Alzheimer's Disease patients. Citron, *Trends in Pharmacological Sciences*, 25(2):92-97 (2004).

Similar plaques appear in some variants of Lewy body dementia and in inclusion body myositis, a muscle disease. Aβ also forms aggregates coating cerebral blood vessels in cerebral amyloid angiopathy. These plaques are composed of a tangle of regularly ordered fibrillar aggregates called amyloid fibers, a protein fold shared by other peptides such as prions associated with protein misfolding diseases. Research on laboratory rats suggest that the dimeric, soluble form of the peptide is a causative agent in the development of Alzheimer's and is the smallest synaptotoxic species of soluble amyloid beta oligomer. Shankar, G. M., *Nature Medicine* (Jun. 22, 2008) online doi 10:1038 nm 1782.

Several aspartyl proteases, including beta-secretase and gamma-secretase, are thought to be involved in the processing or cleavage of APP, resulting in the formation of A-beta peptide. Beta secretase (BACE, also commonly referred to as memapsin) is thought to first cleave APP to generate two fragments: (1) a first N-terminus fragment (beta APP) and (2) a second C-99 fragment, which is subsequently cleaved by gamma secretase to generate the A-beta peptide. APP has also found to be cleaved by alpha-secretase to produce alpha-sAPP, a secreted form of APP that does not result in beta-amyloid plaque formation. This alternate pathway precludes the formation of A-beta peptide. A description of the proteolytic processing fragments of APP is found, for example, in U.S. Pat. Nos. 5,441,870, 5,712,130 and 5,942,400.

BACE is an aspartyl protease enzyme comprising 501 amino acids and responsible for processing APP at the beta-secretase specific cleavage site. BACE is present in two forms, BACE 1 and BACE 2, designated as such depending upon the specific cleavage site of APP. Beta secretase is described in Sinha et al., *Nature*, 402:537-554 (1999) (p510) and PCT application WO 2000/17369. It has been proposed that A-beta peptide accumulates as a result of APP processing by BACE. Moreover, in vivo processing of APP at the beta secretase cleavage site is thought to be a rate-limiting step in A-beta production. Sabbagh, M. et al., *Alz. Dis. Rev.* 3:1-19 (1997). Thus, inhibition of the BACE enzyme activity is desirable for the treatment of AD.

Studies have shown that the inhibition of BACE may be linked to the treatment of AD. The BACE enzyme is essential for the generation of beta-amyloid or A-beta. BACE knockout mice do not produce beta-amyloid and are free from Alzheimer's associated pathologies including neuronal loss and certain memory deficits. Cole, S. L., Vasser, R., *Molecular Degeneration* 2:22, 2007. When crossed with transgenic mice that over express APP, the progeny of BACE deficient mice show reduced amounts of A-beta in brain extracts as compares with control animals (Luo et al., *Nature Neuroscience*, 4:231-232 (2001)). The fact that BACE initiates the formation of beta-amyloid, and the observation that BACE levels are elevated in this disease provide direct and compelling reasons to develop therapies directed at BACE inhibition thus reducing beta-amyloid and its associated toxicities. To this end, inhibition of beta secretase activity and a corresponding reduction of A-beta in the brain should provide a therapeutic method for treating AD and other beta amyloid or plaque related disorders.

Consequently, the approach of regulating or reducing the formation of A-beta peptide formation and deposition as a potential treatment for AD has received tremendous attention, support and commitment from both researchers and investors alike. A small molecule gamma-secretase inhibitor, LY450139 ("Semagacestat"), an A-beta lowering agent, advanced to phase III clinical trials for the treatment of Alzheimer's Disease. The pharmacokinetics of semagacestat in plasma, as well as the plasma and cerebral spinal fluid (CSF) A-Beta peptide levels as pharmacodynamic responses to semagacestat administration were evaluated in healthy human subjects in single and multiple doses, and pharmacokinetic and pharmacodynamic changes were also assessed in mild to moderate AD patients in two (2) clinical trials (*Expert Opin. Pharmacother.* (2009), 10(10); *Clin. Neuropharmacol.* 2007; 30 (pgs 317-325); and *Neurology*, 2006, 66 (pgs 602-624)).

Additional approaches have been taken in attempts to treat AD and plaque-related disorders. One such approach to reduce the formation of plaque deposits in the brain involves the inhibition of and, therefore, the reduction of BACE activity. Vassar & Yan, *Lancet Neurology*, 13:319-329 (2014). For example, each of the following PCT publications: WO07/049532, WO12/147763, WO12/107371, WO12/168164, WO12/168175, WO12/156284, WO11/070781, WO11/020806, WO 11/070029, WO11/058763, WO11/071109, WO11/071135, WO11/069934, WO12/139993, WO11/009898, WO2008133273, WO13/142613, WO14/001228, US2009082560 (US equivalent of WO07/049532), US20100160290 (US equivalent of WO08/133273), US20120238557, US20120245154, US20120245157, US20120202803 (US equivalent of WO12/107371), US20120258962, US20130072478 and EP01942105 describe inhibitors of BACE, useful for treating AD and other beta-secretase mediated disorders. For Example, US20120245157 describes "Oxazine Derivatives" as BACE inhibitors for the treatment of neurological disorders of the general formula:

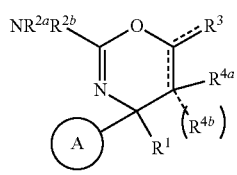

while WO2012168164 describes "Halogen-Alkyl-1,3-Oxazines as BACE1 and/or BACE2 Inhibitors" and discloses compounds of the general formula:

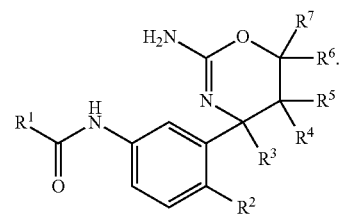

The lysosomal aspartic protease Cathepsin D (CatD) is ubiquitously expressed in eukaryotic organisms. CatD activity is essential to accomplish the acid-dependent extensive or partial proteolysis of protein substrates within endosomal and lysosomal compartments therein delivered via endocytosis, phagocytosis or autophagocytosis. CatD may also act at physiological pH on small-size substrates in the cytosol and in the extracellular milieu. Mouse and fruit fly CatD knock-out models have highlighted the multi-pathophysiological roles of CatD in tissue homeostasis and organ development.

Inhibition of protein Cathepsin D has been implicated in undesirable side effects. For instance, the inhibition of Cathepsin D is believed to be linked to adverse retinal development and retinal atrophy. Particularly, in mice it was found that cathepsin D is essential for the metabolic maintenance of retinal photoreceptor cells and that its deficiency induces apoptosis of the cells, while the loss of INL neurons is mediated by nitre oxide release from microglial cells. However, in the very same mice, it was also found that no atrophic change was detected in the retina of mice deficient in cathepsin B or L. *Mol. Cell. Neurosci*, 2003, Feb. 22(2):146-161. Further, Animal models of cathepsin D (CatD) deficiency are characterized by a progressive and relentless neurodegenerative phenotype similar to that observed in Neuronal Ceroid Lipofuscinoses (NCL), a group of pediatric neurodegenerative diseases known collectively as Batten Disease. It has been shown that the targeted deletion of the pro-apoptotic molecule Bax prevents apoptotic markers but not neuronal cell death and neurodegeneration induced by CatD deficiency, which suggests that alterations in the macroautophagy-lysosomal degradation pathway can mediate neuronal cell death in NCL/Batten Disease in the absence of apoptosis. *Autophagy*, 2007, September-October; 3(5):474-476. Finally, an adverse effect of the inhibition of Cat D is evident from the data presented in *PLoS One*, 2011; 6(7):e21908, published Jul. 1, 2011. The authors of the PLoS One paper found that knock-down of cathepsin D affects the retinal pigment epithelium, impairs swim-bladder ontogenesis and causes premature death in zebrafish. The main phenotypic alterations produced by CatD knock-down in zebrafish were: 1. abnormal development of the eye and of retinal pigment epithelium; 2. absence of the swim-bladder; 3. skin hyper-pigmentation; 4. reduced growth and premature death. Rescue experiments confirmed the involvement of CatD in the developmental processes leading to these phenotypic alterations.

Moreover, such toxicity findings which, in view of the literature, may have played a role in the termination of a human Bace-mediated Alzheimer's Disease clinical trial. Eli Lilly terminated a phase I clinical trial of LY 2811376 after rat toxicology studies showed that a higher compound dose given for three months damaged the pigment epithelium of the rat's eye. The retinal layer had inclusions and extensive damage. The Ph I dosing trial was terminated and people brought in for eye assessments did not show any abnormalities (Alzheimer's Research Forum News, Mar. 31, 2011 reporting on Martin Citron's presentation at the AD/PD Conference 3-2011 in Barcelona, Spain)

Hence, it is desirable to provide compounds which modulate the activity of and are reasonably selective for BACE, while not suffering from undesirable side effects possibly due to intervention with or the reduction and/or direct or indirect inhibition of the expression and/or function of other proteins or biological pathways.

BRIEF DESCRIPTION OF THE INVENTION

The present invention provides a new class of compounds useful for the modulation of beta secretase activity, and as treatment of AD. Particularly, the compounds of the invention are useful for the regulation or reduction of the formation of A-beta peptide and, consequently, the regulation and/or reduction of formation of beta amyloid plaque both on the brain, as well as in the CNS. To this end, the compounds are useful for the treatment of AD and other beta secretase and/or plaque-related and/or mediated disorders. For example, the compounds are useful for the prophylaxis and/or treatment, acute and/or chronic, of AD and other diseases or conditions involving the deposition or accumulation of beta amyloid peptide, and formation of plaque, on the brain.

The compounds provided by the invention, including stereoisomers, tautomers, hydrates, solvates and pharmaceutically acceptable salts thereof, are generally defined by Formula I

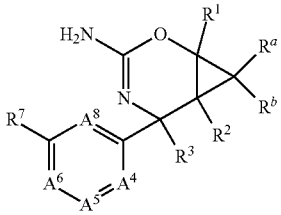

wherein each of $A^4$, $A^5$, $A^6$, $A^8$, $R^a$, $R^b$, $R^1$, $R^2$, $R^3$ and $R^7$ of Formula I are defined below. The invention also provides procedures for making compounds of Formula I, and sub-Formulas thereof, as well as intermediates useful in such procedures.

The invention further provides pharmaceutical compositions comprising compounds of the invention, and uses of these compositions in the treatment of beta secretase mediated diseases. For example, and in one embodiment, the invention provides a pharmaceutical composition comprising an effective dosage amount of a compound of Formula I in association with at least one pharmaceutically acceptable excipient.

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In embodiment 1 of the invention, there are provided compounds, including stereoisomers, tautomers, hydrates, solvates and pharmaceutically acceptable salts thereof, which are generally defined by Formula I:

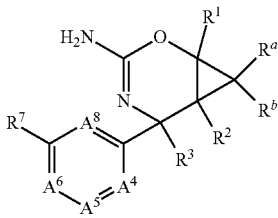

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than two of $A^4$, $A^5$, $A^6$ and $A^8$ is N;

each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxy, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl, provided the compound is not
N-(3-((1R,5R,6R)-3-amino-5-methyl-2-oxa-4-azabicyclo[4.1.0]hept-3-en-5-yl)-4-fluorophenyl)-3-methoxy-1,7-naphthyridin-8-amine or
N-(3-((1R,5R,6R)-3-amino-5-methyl-2-oxa-4-azabicyclo[4.1.0]hept-3-en-5-yl)-4-fluorophenyl)-5-methoxy-2-pyrazinecarboxamide.

In embodiment 2, the invention provides compounds according to embodiment 1, or a stereoisomer or pharmaceutically acceptable salt thereof, wherein each of $R^1$ and $R^2$, independently, is H, F, $CH_3$, $CH_2F$, $CHF_2$ or $CF_3$.

In embodiment 3, the invention provides compounds according to any one of embodiments 1 and 2, or a stereoisomer or pharmaceutically acceptable salt thereof, wherein each of $R^a$ and $R^b$, independently, is H, F, $CH_3$, $CH_2F$, $CHF_2$ or $CF_3$.

In embodiment 4, the invention provides compounds according to any one of embodiments 1, 2 and 3, or a stereoisomer or pharmaceutically acceptable salt thereof, wherein each of $R^1$ and $R^2$, independently, is H, F or $CF_3$.

In embodiment 5, the invention provides compounds according to any one of embodiments 1-4, or a stereoisomer or pharmaceutically acceptable salt thereof, wherein each of $R^a$ and $R^b$, independently, is H or F.

In embodiment 6, the invention provides compounds according to any one of embodiments 1-5, or a stereoisomer or pharmaceutically acceptable salt thereof, wherein each of $R^1$ and $R^2$, independently, is H, F or $CF_3$; and each of $R^a$ and $R^b$, independently, is H or F.

In embodiment 7, the invention provides compounds according to any one of embodiments 1-6, or a stereoisomer or pharmaceutically acceptable salt thereof, wherein each of $R^1$, $R^2$, $R^a$ and $R^b$, independently, is H.

In embodiment 8, the invention provides compounds according to any one of embodiments 1-7, or a stereoisomer or pharmaceutically acceptable salt thereof, wherein $R^3$ is $CH_3$, $CF_3$, $CH_2F$ or $CHF_2$.

In embodiment 9, the invention provides compounds according to any one of embodiments 1-8, or a stereoisomer or pharmaceutically acceptable salt thereof, wherein $R^7$ is —NH—$CH_2$—$R^9$ or —NH—C(=O)—$R^9$;
or $R^7$ is

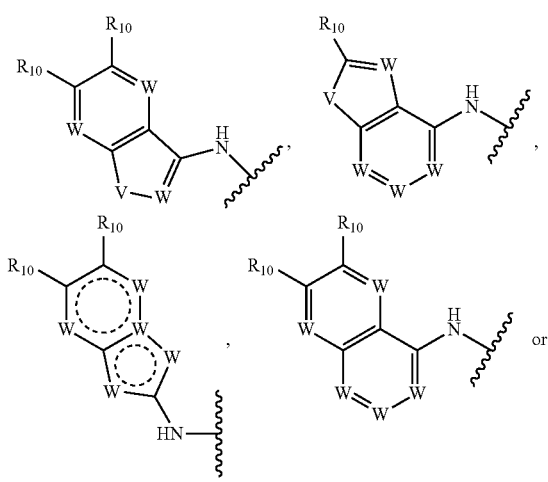

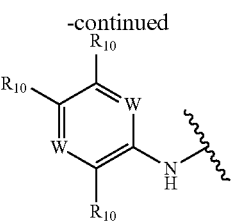

wherein V is $NR^{10}$, O or S; and each W, independently, is CH, CF, CCl, $CCH_3$ or N.

In embodiment 10, the invention provides compounds according to any one of embodiments 1 and 9, or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^a$ and $R^b$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
each of $R^1$ and $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$.

In embodiment 11, the invention provides compounds according to any one of embodiments 1-9, or a stereoisomer or pharmaceutically acceptable salt thereof, wherein
each of $R^1$ and $R^2$, independently, is H, F or $CF_3$;
each of $R^a$ and $R^b$, independently, is H or F;
$R^3$ is $CH_3$, $CF_3$, $CH_2F$ or $CHF_2$; and
$R^7$ is —NH—$R^9$, —NH—C(=O)—$R^9$ or

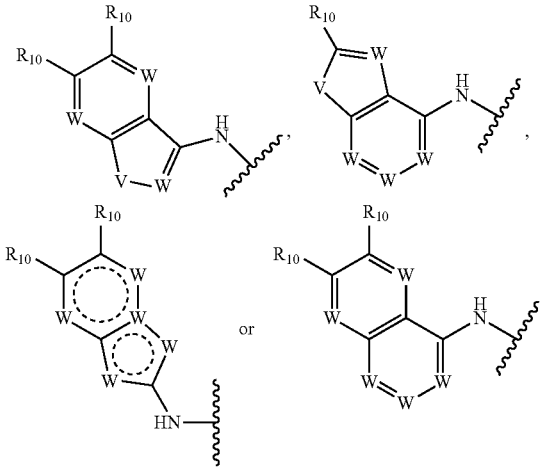

wherein V is $NR^{10}$, O or S; and
each W, independently, is CH, CF, CCl, $CCH_3$ or N.

In embodiment 12, the invention provides compounds according to any one of embodiments 1-11, or a stereoisomer or pharmaceutically acceptable salt thereof, wherein $R^7$ is —NH—C(=O)—$R^9$.

In embodiment 13, the invention provides compounds according to any one of embodiments 1-11, or a stereoisomer or pharmaceutically acceptable salt thereof, wherein

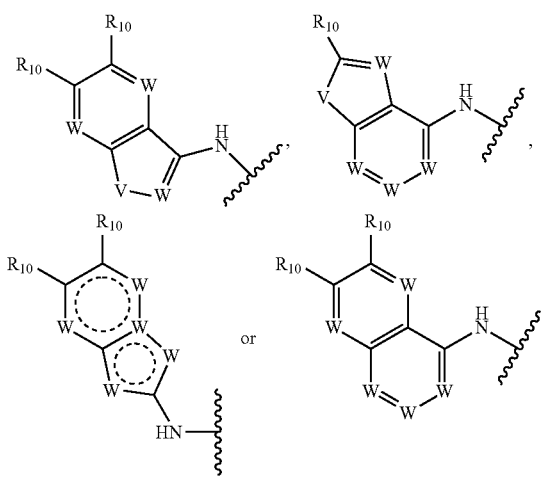

$R^7$ is
wherein V is $NR^{10}$, O or S; and
each W, independently, is CH, CF, CCl, $CCH_3$ or N.

In embodiment 14, the invention provides compounds according to any one of embodiments 1-13, or a stereoisomer or pharmaceutically acceptable salt thereof, wherein
$A^4$ is $CR^4$;
$A^5$ is $CR^5$ or N;
$A^6$ is $CR^6$; and
$A^8$ is $CR^8$ or N, provided only one of $A^5$ and $A^8$ is N, and wherein each of $R^4$, $R^5$, $R^6$ and $R^8$, independently, is H, F, Cl, $CF_3$, $CF_2H$, $CH_2F$ or $CH_3$.

In embodiment 15, the invention provides compounds, including stereoisomers, tautomers, hydrates, solvates and pharmaceutically acceptable salts thereof, which are generally defined by Formula I:

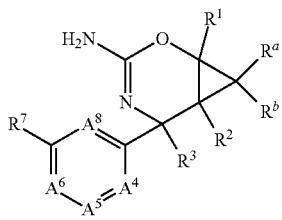

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^1$ and $R^2$, independently, is H, F, $CH_3$, $CH_2F$, $CHF_2$ or $CF_3$;
each of $R^a$ and $R^b$, independently, is H, F, $CH_3$, $CH_2F$, $CHF_2$ or $CF_3$;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is $-NH-R^9$ or $-NH-C(=O)-R^9$;
or $R^7$ is

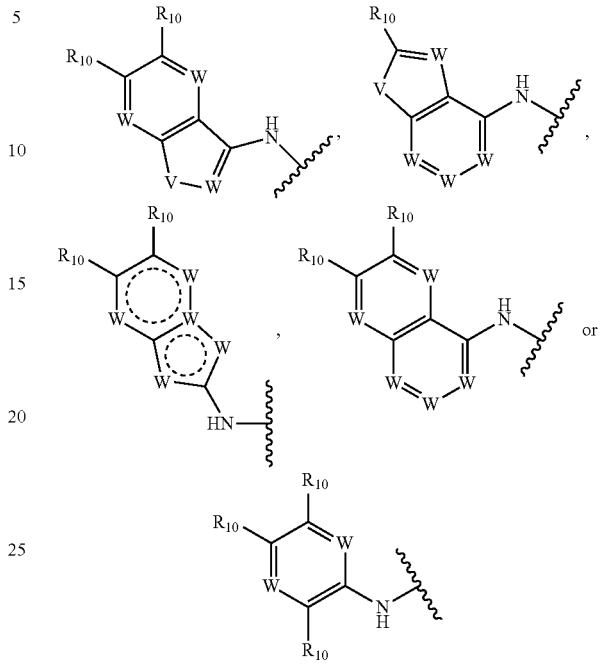

wherein V is $NR^{10}$, O or S; and
each W, independently, is CH, CF, CCl, $CCH_3$ or N;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, $-C(O)NHCH_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl, provided the compound is not
N-(3-((1R,5R,6R)-3-amino-5-methyl-2-oxa-4-azabicyclo[4.1.0]hept-3-en-5-yl)-4-fluorophenyl)-3-methoxy-1,7-naphthyridin-8-amine or
N-(3-((1R,5R,6R)-3-amino-5-methyl-2-oxa-4-azabicyclo[4.1.0]hept-3-en-5-yl)-4-fluorophenyl)-5-methoxy-2-pyrazinecarboxamide.

In embodiment 16, the invention provides compounds, including stereoisomers, tautomers, hydrates, solvates and pharmaceutically acceptable salts thereof, which are generally defined by Formula II:

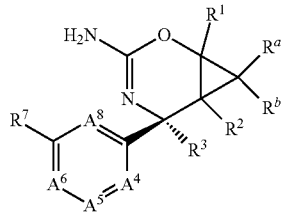

wherein $A^4$ is $CR^4$ or N;

$A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$;

or $R^7$ is

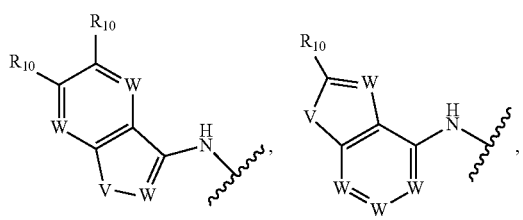

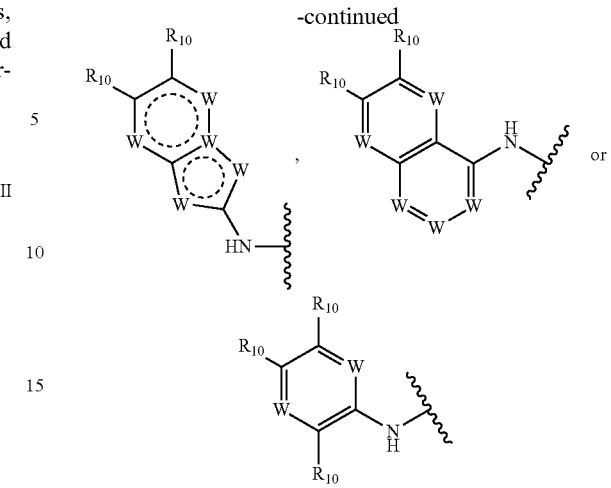

wherein V is $NR^{10}$, O or S; and each W, independently, is CH, CF, CCl, $CCH_3$ or N;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 17, the invention provides compounds according any one of embodiments 1 and 16, or a stereoisomer, tautomer or pharmaceutically acceptable salt thereof, wherein $A^4$ is $CR^4$ or N;

$A^5$ is $CR^5$ or N;

$A^6$ is $CR^6$ or N;

$A^8$ is $CR^8$ or N, provided no more than one of $A^4$, $A^5$, $A^6$ and $A^8$ is N;

each of $R^a$ and $R^b$, independently, is H, F, $CH_3$, $CH_2F$, $CHF_2$ or $CF_3$;

each of $R^1$ and $R^2$, independently, is H, F, $CH_3$, $CH_2F$, $CHF_2$ or $CF_3$;

$R^3$ is $C_{1-4}$alkyl, $C_{1-4}$haloalkyl, $CH_2OH$, $CH_2OCHF_2$ or cyclopropyl; and each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$.

In embodiment 18, the invention provides compounds according to any one of embodiments 1-6, 7 and 16-17, or a stereoisomer or pharmaceutically acceptable salt thereof, wherein $A^4$ is $CR^4$;
$A^5$ is $CR^5$; and
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$;
$R^3$ is $CH_3$, $CF_3$, $CH_2F$ or $CHF_2$; and
$R^7$ is —NH—C(=O)—$R^9$ or

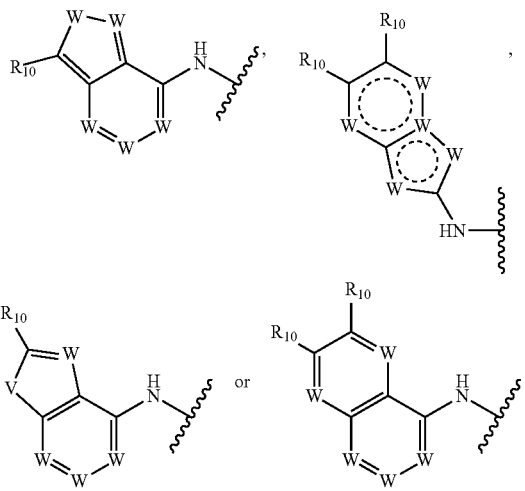

wherein V is $NR^{10}$, O or S; and
each W, independently, is CH, CF, CCl or N.

In embodiment 19, the invention provides compounds according to any one of embodiments 16-17, or a stereoisomer or pharmaceutically acceptable salt thereof, wherein $R^7$ is —NH—C(=O)—$R^9$.

In embodiment 20, the invention provides compounds according to any one of embodiments 16-18, or a stereoisomer or pharmaceutically acceptable salt thereof, wherein $R^7$ is

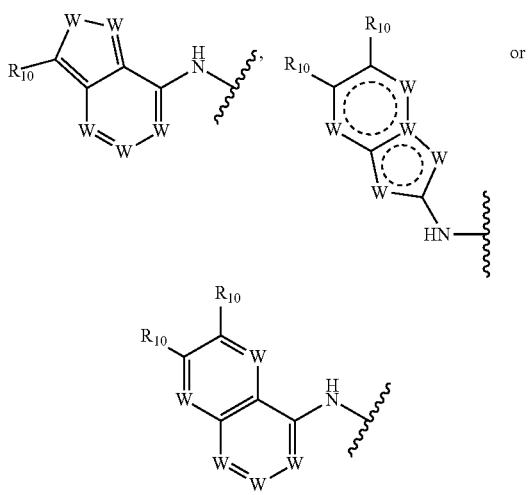

wherein V is $NR^{10}$, O or S; and
each W, independently, is CH, CF, CCl, $CCH_3$ or N.

In embodiment 21, the invention provides compounds according to any one of embodiments 16-20, or a stereoisomer or pharmaceutically acceptable salt thereof, wherein each of $R^1$ and $R^2$, independently, is H, F or $CF_3$; and each of $R^a$ and $R^b$, independently, is H or F.

In embodiment 22, the invention provides compounds according to any one of embodiments 1-12, or a stereoisomer or pharmaceutically acceptable salt thereof, having a Formula I-A

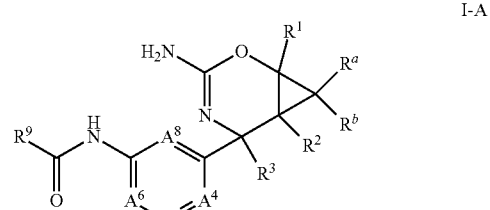

I-A wherein
$A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH;
$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;
each of $R^4$, $R^5$, $R^6$ and $R^8$, independently, is H, F, Cl or $CH_3$;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 23, the invention provides compounds according to any one of embodiments 1-3, 8-20 and 22, or a stereoisomer, tautomer or pharmaceutically acceptable salt thereof, wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$;
$R^3$ is $CH_3$, $C_2H_5$, $CF_2H$ or $CH_2F$;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 24, the invention provides compounds according to any one of embodiments 1-19 and 22-23, or a stereoisomer or pharmaceutically acceptable salt thereof, wherein $A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H, F, Cl or $CH_3$, provided no more than one of $A^4$, $A^5$, $A^6$ and $A^8$ is N;
each of $R^1$, $R^2$, $R^a$ and $R^b$, independently, is H; and
$R^3$ is $CF_3$, $CH_3$, $CF_2H$ or $CH_2F$.

In embodiment 25, the invention provides compounds according to any one of embodiments 1-12, 16-19 and 22-24, or a stereoisomer or pharmaceutically acceptable salt thereof, having a Formula II-A

II-A wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F, provided that no more than one of $A^5$ and
$A^8$ is N;
each of $R^a$ and $R^b$, independently, is H or F;
each of $R^1$ and $R^2$, independently, is H or F;
$R^3$ is $CH_3$, $CF_3$, $CH_2F$ or $CHF_2$;
$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 26, the invention provides compounds according to embodiment 25, or a stereoisomer or pharmaceutically acceptable salt thereof, wherein each of $R^a$, $R^b$, $R^1$ and $R^2$, independently, is H.

In embodiment 27, the invention provides compounds according ng any one of embodiments 25 and 26, or a stereoisomer or pharmaceutically acceptable salt thereof, wherein $R^3$ is $CH_3$, $CH_2F$ or $CHF_2$.

In embodiment 28, the invention provides compounds according to any one of embodiments 25-27, or a stereoisomer or pharmaceutically acceptable salt thereof, wherein $R^3$ is $CH_2F$ or $CHF_2$.

In embodiment 29, the invention provides compounds according to any one of embodiments 25-28, or a stereoisomer or pharmaceutically acceptable salt thereof, wherein $R^3$ is $CH_2F$.

In embodiment 30, the invention provides compounds according to any one of embodiments 25-28, or a stereoisomer or pharmaceutically acceptable salt thereof, wherein $R^3$ is $CHF_2$.

In embodiment 31, the invention provides compounds according to any one of embodiments 25-30, or a stereoisomer or pharmaceutically acceptable salt thereof, wherein $A^4$ is CF or CCl;

$A^5$ is CH, CF, $CH_3$ or N;

$A^6$ is CH; and $A^8$ is CH.

In embodiment 32, the invention provides compounds according to any one of embodiments 25-31, or a stereoisomer or pharmaceutically acceptable salt thereof, wherein $A^4$ is CF;

$A^5$ is CH, CF or N;

$A^6$ is CH; and $A^8$ is CH.

In embodiment 33, the invention provides compounds according to any one of embodiments 25-31, or a stereoisomer or pharmaceutically acceptable salt thereof, wherein $A^4$ is CCl;

$A^5$ is CH or CF;

$A^6$ is CH; and $A^8$ is CH.

In embodiment 34, the invention provides compounds according to any one of embodiments 25-33, or a stereoisomer or pharmaceutically acceptable salt thereof, wherein $R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, $—C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 35, the invention provides compounds according to any one of embodiments 25-33, or a stereoisomer or pharmaceutically acceptable salt thereof, wherein $R^9$ is a ring selected from pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$.

In embodiment 36, the invention provides compounds according to any one of embodiments 25-35 or a stereoisomer or pharmaceutically acceptable salt thereof, wherein $R^9$ is

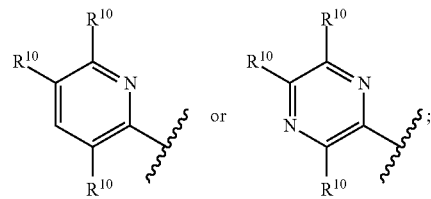

and each $R^{10}$, independently, is H, F, Cl, Br, $CF_3$, $CHF_2$, $CH_2F$, CN, OH, $—C(O)NHCH_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl and $C_{1-6}$thioalkoxyl is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxazolyl or thiazolyl.

In embodiment 37, the invention provides compounds according to any one of embodiments 25-36, or a stereoisomer or pharmaceutically acceptable salt thereof, wherein $R^3$ is $CHF_2$; and $R^9$ is

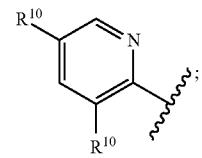

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 38, the invention provides compounds according to any one of embodiments 25-36, or a stereoisomer or pharmaceutically acceptable salt thereof, wherein $R^3$ is $CH_2F$; and $R^9$ is

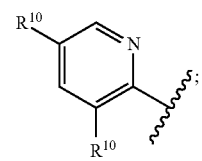

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 39, the invention provides compounds according to any one of embodiments 25-36, or a stereoisomer or pharmaceutically acceptable salt thereof, wherein $R^3$ is $CHF_2$; and $R^9$ is

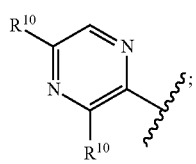

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 40, the invention provides compounds according to any one of embodiments 25-36, or a stereoisomer or pharmaceutically acceptable salt thereof, wherein $R^3$ is $CH_2F$; and $R^9$ is

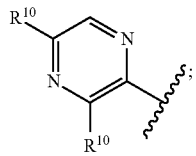

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 41, the invention provides compounds according to any one of embodiments 1-11, 13-18 and 20-21, or a stereoisomer, tautomer, hydrate, solvate or pharmaceutically acceptable salt thereof, having a Formula II-B:

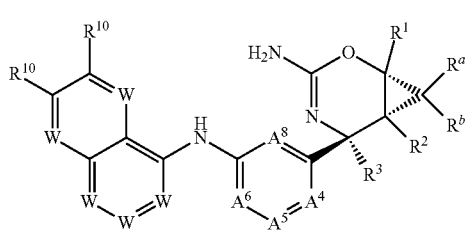

II-B wherein $A^4$ is $CR^4$, wherein $R^4$ is H, F or Cl;

$A^5$ is $CR^5$ or N, wherein $R^5$ is H, F, Cl or $CH_3$;

$A^6$ is CH;

$A^8$ is $CR^8$ or N, wherein $R^8$ is H or F, provided that no more than one of $A^5$ and $A^8$ is N;

each of $R^a$ and $R^b$, independently, is H or F;

each of $R^1$ and $R^2$, independently, is H or F;

$R^3$ is $CH_3$, $CF_3$, $CH_2F$ or $CHF_2$;

$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and each $R^{10}$, independently, is H, halo, haloalkyl, CN, OH, $NO_2$, $NH_2$, $SF_5$, acetyl, $-C(O)NHCH_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl; and each W, independently, is CH, CF, CCl, $CCH_3$ or N.

In embodiment 42, the invention provides compounds according to embodiment 40, or a stereoisomer or pharmaceutically acceptable salt thereof, wherein each of $R^a$, $R^b$, $R^1$ and $R^2$, independently, is H.

In embodiment 43, the invention provides compounds according to any one of embodiments 41 and 42, or a stereoisomer or pharmaceutically acceptable salt thereof, wherein $R^3$ is $CH_3$, $CH_2F$ or $CHF_2$.

In embodiment 44, the invention provides compounds according to any one of embodiments 41-43, or a stereoisomer or pharmaceutically acceptable salt thereof, wherein $R^3$ is $CH_2F$ or $CHF_2$.

In embodiment 45, the invention provides compounds according to any one of embodiments 41-44, or a stereoisomer or pharmaceutically acceptable salt thereof, wherein $R^3$ is $CH_2F$.

In embodiment 46, the invention provides compounds according to any one of embodiments 41-44, or a stereoisomer or pharmaceutically acceptable salt thereof, wherein $R^3$ is $CHF_2$.

In embodiment 47, the invention provides compounds according to any one of embodiments 41-46, or a stereoisomer or pharmaceutically acceptable salt thereof, wherein $A^4$ is CF or CCl;

$A^5$ is CH, CF, $CH_3$ or N;

$A^6$ is CH; and $A^8$ is CH.

In embodiment 48, the invention provides compounds according to any one of embodiments 41-47, or a stereoisomer or pharmaceutically acceptable salt thereof, wherein $A^4$ is CF;

$A^5$ is CH, CF or N;

$A^6$ is CH; and $A^8$ is CH.

In embodiment 49, the invention provides compounds according to any one of embodiments 41-47, or a stereoisomer or pharmaceutically acceptable salt thereof, wherein $A^4$ is CCl;

$A^5$ is CH or CF;

$A^6$ is CH; and $A^8$ is CH.

In embodiment 50, the invention provides compounds according to any one of embodiments 41-49 or a stereoisomer or pharmaceutically acceptable salt thereof, wherein

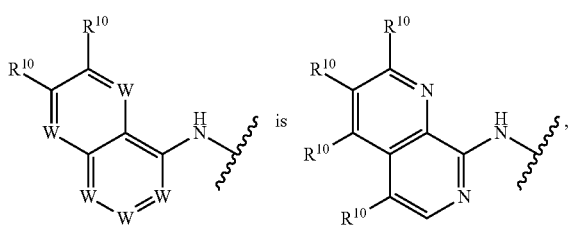 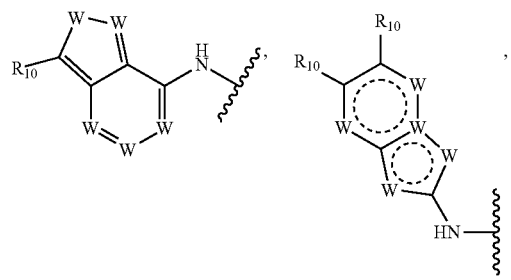

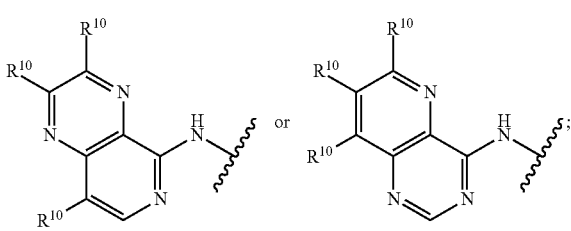 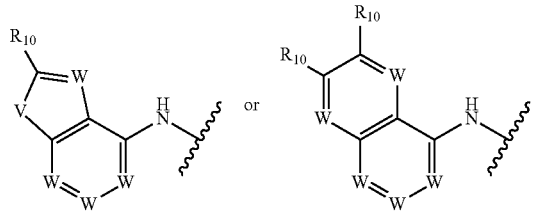

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 51, the invention provides compounds, including stereoisomers, tautomers, hydrates, solvates and pharmaceutically acceptable salts thereof, which are generally defined by Formula III:

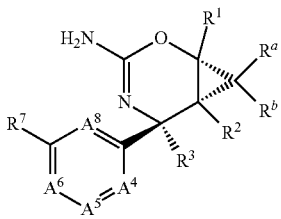

III wherein $A^4$ is $CR^4$ or N;

$A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each of $R^a$ and $R^b$, independently, is H, F, $CH_3$, $CH_2F$, $CHF_2$ or $CF_3$;

each of $R^1$ and $R^2$, independently, is H, F, $CH_3$, $CH_2F$, $CHF_2$ or $CF_3$;

$R^3$ is $CH_3$, $CF_3$, $CH_2F$ or $CHF_2$;

each of $R^4$, $R^5$, $R^6$ and $R^8$, independently, is H, F, Cl or $CH_3$;

$R^7$ is —NH—C(=O)—$R^9$, or $R^7$ is wherein V is $NR^{10}$, O or S; and each W, independently, is CH, CF, CCl, $CCH_3$ or N;

$R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 52, the invention provides compounds including stereoisomers, tautomers, hydrates, solvates and pharmaceutically acceptable salts thereof, according to embodiment 51, which are generally defined by Formula III-A:

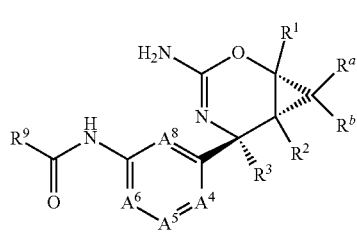

III-A wherein

A⁴ is CR⁴, wherein R⁴ is H, F or Cl;

A⁵ is CR⁵ or N, wherein R⁵ is H, F, Cl or CH₃;

A⁶ is CH;

A⁸ is CR⁸ or N, wherein R⁸ is H or F, provided that no more than one of A⁵ and A⁸ is N;

each of $R^a$ and $R^b$, independently, is H or F;

each of $R^1$ and $R^2$, independently, is H or F;

$R^3$ is CH₃, CH₂F or CHF₂;

$R^9$ is a ring selected from phenyl, pyridyl, pyrimidyl, pyrazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and each $R^{10}$, independently, is H, halo, haloalkyl, CN, OH, NO₂, NH₂, SF₅, acetyl, —C(O)NHCH₃, oxo, cyclopropylmethoxy, 2-butynyloxy, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, C₁₋₆alkyl, C₂₋₆alkenyl, C₂₋₆alkynyl, C₃₋₆cycloalkyl, C₁₋₆alkylamino-, C₁₋₆dialkylamino-, C₁₋₆alkoxyl, C₁₋₆thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, NO₂, NH₂, OH, oxo, CF₃, CHF₂, CH₂F, methyl, methoxy, ethyl, ethoxy, CH₂CF₃, CH₂CHF₂, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, C₁₋₃alkylamino-, C₁₋₃dialkylamino, C₁₋₃thioalkoxyl tetrahydropyranyl, tetrahydropyrrolyl or oxetan-3yl.

In embodiment 53, the invention provides compounds according to any one of embodiments 51-52 or a stereoisomer or pharmaceutically acceptable salt thereof, wherein $R^9$ is

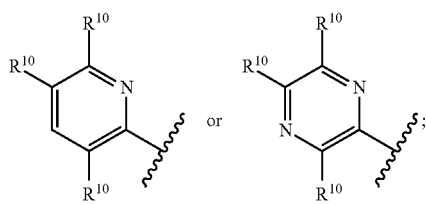

and each $R^{10}$, independently, is H, F, Cl, Br, CF₃, CHF₂, CH₂F, CN, OH, —C(O)NHCH₃, cyclopropylmethoxy, 2-propynyloxy, 2-butynyloxy, C₁₋₆alkyl, C₂₋₆alkenyl, C₂₋₆alkynyl, C₃₋₆cycloalkyl, C₁₋₆alkoxyl or C₁₋₆thioalkoxyl, wherein each of the cyclopropylmethoxy, 2-propynyloxy, 2-butynyloxy, C₁₋₆alkyl, C₂₋₆alkenyl, C₂₋₆alkynyl, C₃₋₆cycloalkyl, C₁₋₆alkoxyl and C₁₋₆thioalkoxyl is optionally substituted independently with 1-5 substituents of F, Cl, CN, NO₂, NH₂, OH, oxo, CF₃, CHF₂, CH₂F, methyl, methoxy, ethyl, ethoxy, CH₂CF₃, CH₂CHF₂, propyl, propoxy, isopropyl, isopropoxy, cyclopropyl, butyl, butoxyl, cyclobutyl, isobutoxy, tert-butoxy, isobutyl, sec-butyl, tert-butyl, C₁₋₃alkylamino-, C₁₋₃dialkylamino, C₁₋₃thioalkoxyl, oxazolyl or thiazolyl.

In embodiment 54, the invention provides compounds according to any one of embodiments 51-53, or a stereoisomer or pharmaceutically acceptable salt thereof, wherein $R^3$ is CHF₂; and $R^9$ is

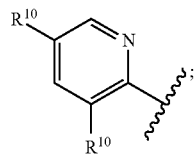

and each $R^{10}$, independently, is H, F, Cl, Br, CH₃, CHF₂, CH₂F, CN, 2-propynyloxy, 2-butynyloxy or C₁₋₂alkoxyl, wherein the C₁₋₂alkoxyl is optionally substituted independently with 1-5 substituents of F, Cl, methyl, methoxy, ethyl, ethoxy, oxazolyl or thiazolyl.

In embodiment 55, the invention provides compounds according to any one of embodiments 51-53, or a stereoisomer or pharmaceutically acceptable salt thereof, wherein $R^3$ is CH₂F; and $R^9$ is

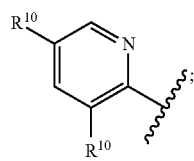

and each $R^{10}$, independently, is H, F, Cl, Br, CH₃, CHF₂, CH₂F, CN, 2-propynyloxy, 2-butynyloxy or C₁₋₂alkoxyl, wherein the C₁₋₂alkoxyl is optionally substituted independently with 1-5 substituents of F, Cl, methyl, methoxy, ethyl, ethoxy, oxazolyl or thiazolyl.

In embodiment 56, the invention provides compounds according to any one of embodiments 51-53 or a stereoisomer or pharmaceutically acceptable salt thereof, wherein $R^3$ is CHF₂; and $R^9$ is

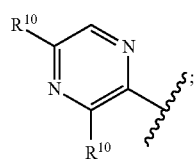

and each $R^{10}$, independently, is H, F, Cl, Br, CH₃, CHF₂, CH₂F, CN, 2-propynyloxy, 2-butynyloxy or C₁₋₂alkoxyl, wherein the C₁₋₂alkoxyl is optionally substituted independently with 1-5 substituents of F, Cl, methyl, methoxy, ethyl, ethoxy, oxazolyl or thiazolyl.

In embodiment 57, the invention provides compounds according to any one of embodiments 51-53, or a stereoisomer or pharmaceutically acceptable salt thereof, wherein $R^3$ is CH₂F; and $R^9$ is

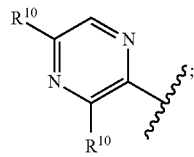

and each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 58, the invention provides compounds, including stereoisomers, tautomers, hydrates, solvates and pharmaceutically acceptable salts thereof, which are generally defined by Formula III-B:

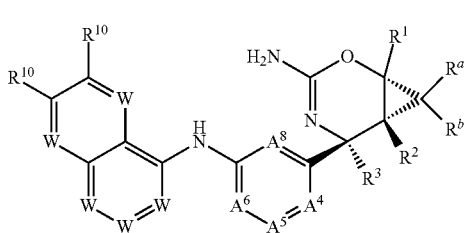

III-B wherein $A^4$ is $CR^4$, wherein $R^4$ is H, F or Cl;

$A^5$ is $CR^5$ or N, wherein $R^5$ is H, F, Cl or $CH_3$;

$A^6$ is CH;

$A^8$ is $CR^8$ or N, wherein $R^8$ is H or F, provided that no more than one of $A^5$ and $A^8$ is N;

each of $R^a$ and $R^b$, independently, is H or F;

each of $R^1$ and $R^2$, independently, is H or F;

$R^3$ is $CH_3$, $CH_2F$ or $CHF_2$;

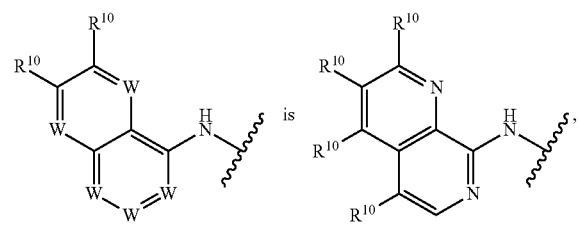 is

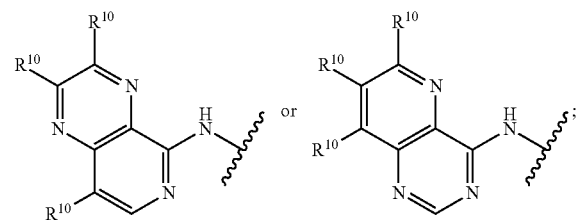 or and each $R^{10}$, independently, is H, F, Cl, Br, $CH_3$, $CHF_2$, $CH_2F$, CN, 2-propynyloxy; 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 59, the invention provides compounds of formula III-A-1, or a pharmaceutically acceptable salt or tautomer thereof,

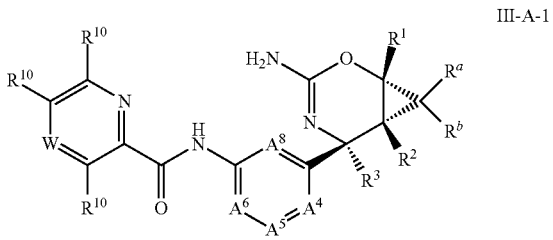

III-A-1 wherein, $A^4$ is CF;

$A^5$ is CH, CF, CCl, $CCH_3$ or N;

$A^6$ is CH;

$A^8$ is CH or N, provided that no more than one of $A^5$ and $A^8$ is N;

each of $R^a$ and $R^b$, independently, is H;

each of $R^1$ and $R^2$, independently, is H or F;

$R^3$ is $CH_3$, $CH_2F$ or $CHF_2$;

W is $CR^{10}$ or N; and each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In embodiment 60, the invention provides compounds of formula III-A-2, or a pharmaceutically acceptable salt or tautomer thereof,

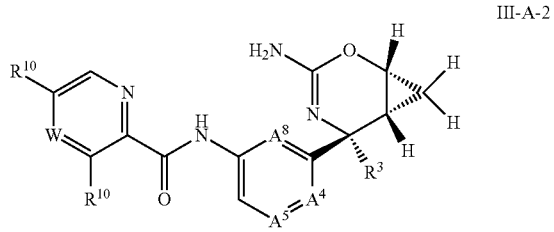

III-A-2 wherein $A^4$ is CF or CCl;

$A^5$ is CH, CF, CCl, $CCH_3$ or N;

$A^8$ is CH or N, provided no more than one of $A^5$ and $A^8$ is N;

$R^3$ is $CH_3$, $CH_2F$ or $CHF_2$;

W is CH or N; and each $R^{10}$, independently, is H, F, Cl, Br, $CH_3$, $CHF_2$, $CH_2F$, CN, 2-propynyloxy; 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 61, the invention provides compounds according to any one of embodiments 59-60, or a stereoisomer or pharmaceutically acceptable salt thereof, wherein $R^3$ is $CHF_2$.

In embodiment 62, the invention provides compounds according to any one of embodiments 59-60, or a stereoisomer or pharmaceutically acceptable salt thereof, wherein $R^3$ is $CH_2F$.

In embodiment 63, the invention provides compounds according to any one of embodiments 59-62, or a stereoisomer or pharmaceutically acceptable salt thereof, wherein W is CH.

In embodiment 64, the invention provides compounds according to any one of embodiments 59-62, or a stereoisomer or pharmaceutically acceptable salt thereof, wherein W is N.

In embodiment 65, the invention provides compounds according to any one of embodiments 59-64, or a stereoisomer or pharmaceutically acceptable salt thereof, wherein each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, oxazolyl or thiazolyl.

In embodiment 66, the invention provides compounds according to any one of embodiments 59-65, or a stereoisomer or pharmaceutically acceptable salt thereof, wherein each $R^{10}$, independently, is H, F, Cl, Br, $CH_3$, $CHF_2$, $CH_2F$, CN, 2-propynyloxy, 2-butynyloxy, —$OCHF_2$ or —$OCH_3$.

In embodiment 67, the invention provides compounds according to any one of embodiments 59-66, or a stereoisomer or pharmaceutically acceptable salt thereof, wherein $A^8$ is CH.

In embodiment 68, the invention provides compounds according to any one of embodiments 59-67, or a stereoisomer or pharmaceutically acceptable salt thereof, wherein $A^5$ is CH, CF, CCl, $CCH_3$ or N.

In embodiment 68, the invention provides compounds according to any one of embodiments 59-67, or a stereoisomer or pharmaceutically acceptable salt thereof, wherein $A^5$ is CH, CF, $CCH_3$ or N.

In embodiment 68, the invention provides compounds according to any one of embodiments 59-67, or a stereoisomer or pharmaceutically acceptable salt thereof, wherein $A^5$ is CH or N.

In embodiment 69, the invention provides compounds of formula III-A-3, or a pharmaceutically acceptable salt or tautomer thereof,

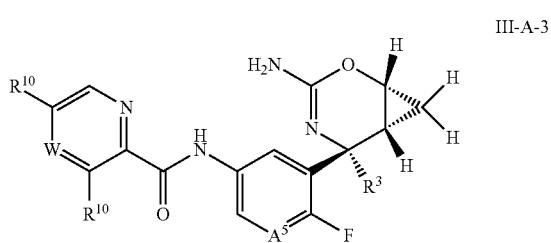

III-A-3 wherein
$A^5$ is CH, CF, CCl, $CCH_3$ or N;
$R^3$ is $CH_3$, $CH_2F$ or $CHF_2$;
W is CH or N; and
each $R^{10}$, independently, is H, F, Cl, Br, $CH_3$, $CHF_2$, $CH_2F$, CN, 2-propynyloxy; 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

In embodiment 70, the invention provides compounds according to any one of embodiment 69, or a stereoisomer or pharmaceutically acceptable salt thereof, wherein $R^3$ is $CHF_2$.

In embodiment 71, the invention provides compounds according to any one of embodiment 69, or a stereoisomer or pharmaceutically acceptable salt thereof, wherein $R^3$ is $CH_2F$.

In embodiment 72, the invention provides compounds according to any one of embodiments 69-71, or a stereoisomer or pharmaceutically acceptable salt thereof, wherein W is CH.

In embodiment 73, the invention provides compounds according to any one of embodiments 69-71, or a stereoisomer or pharmaceutically acceptable salt thereof, wherein W is N.

In embodiment 74, the invention provides compounds according to any one of embodiments 69-74, or a stereoisomer or pharmaceutically acceptable salt thereof, wherein each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, oxazolyl or thiazolyl.

In embodiment 75, the invention provides compounds according to any one of embodiments 69-75, or a stereoisomer or pharmaceutically acceptable salt thereof, wherein each $R^{10}$, independently, is H, F, Cl, Br, $CH_3$, $CHF_2$, $CH_2F$, CN, 2-propynyloxy, 2-butynyloxy, —$OCHF_2$ or —$OCH_3$.

In embodiment 77, the invention provides compounds according to any one of embodiments 69-76, or a stereoisomer or pharmaceutically acceptable salt thereof, wherein $A^5$ is CH, CF, $CCH_3$ or N.

In embodiment 78, the invention provides compounds according to any one of embodiments 69-77, or a stereoisomer or pharmaceutically acceptable salt thereof, wherein $A^5$ is CH, CF or N.

In embodiment 79, the invention provides compounds according to any one of embodiments 69-78, or a stereoisomer or pharmaceutically acceptable salt thereof, wherein $A^5$ is CH or N.

In embodiment 80, the invention provides compounds according to any one of embodiments 69-79, or a stereoisomer or pharmaceutically acceptable salt thereof, wherein $A^5$ is CH.

In embodiment 81, the invention provides compounds according to any one of embodiments 69-79, or a stereoisomer or pharmaceutically acceptable salt thereof, wherein $A^5$ is N.

Similarly, the invention provides compounds of sub-formulas III-C, III-E and III-F, respectively, as described below.

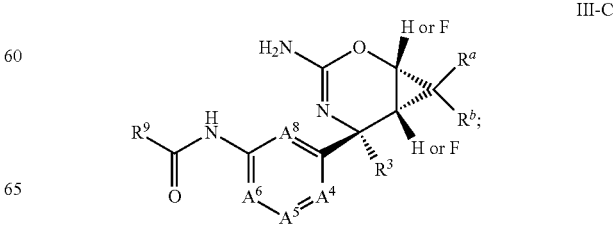

III-C

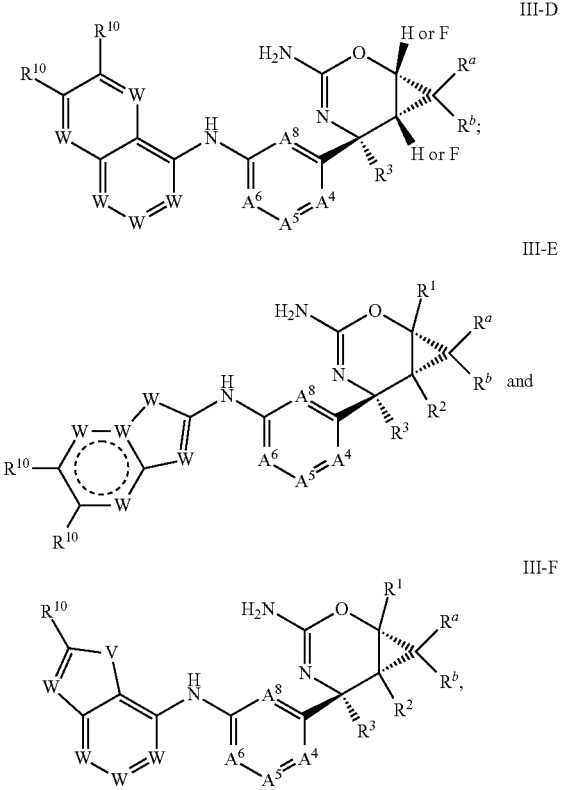

in conjunction with any of the above or below embodiments, including those described in embodiments A, A-1 to A-4, B, B-1 to B-10, C, C-1 to C-10, D, D-1 to D-4, E, E-1 to E-4, F, F-1 to F-4, G, G-1 to G-4, H, H-1 to H-4, I, I-1 to I-9, J, J-1 to J-8, K, K-1 to K-2, L, M, N-1 to N-2, O-1 to O-2, P-1 to P-2, Q and Q-1 to Q-2 described herein.

The present invention contemplates that the various different embodiments of Formulas I, II and III, and sub-Formulas I-A, I-B, I-C and III-A through III-F thereof, described herein, may comprise the following embodiments with respect to individual variables of $A^4$, $A^5$, $A^6$, $A^8$, $R^1$, $R^2$, $R^3$, $R^7$, V and W, where applicable, as described below. Hence, these embodiments with respect to individual variables $A^4$, $A^5$, $A^6$, $A^8$, $R^1$, $R^2$, $R^3$, $R^7$, V and W where applicable, may be applied "in conjunction with any of the other {above and below} embodiments" to create various embodiments of general Formulas I, II and III, and each sub-formula thereof, which are not literally or identically described herein. More specifically, the term "in conjunction with any of the above or below embodiments" includes embodiments A, A-1 to A-4, B, B-1 to B10, C, C-1 to C-10, D, D-1 to D-4, E, E-1 to E-4, F, F-1 to F-4, G, G-1 to G-4, H, H-1 to H-4, I, I-1 to I-9, J, J-1 to J-9, K, K-1 to K-2, L, M, N-1 to N-2, O-1 to O-2, P-1 to P-2, Q and Q-1 to Q-2 described herein, as it applies to general Formulas I, II and III, and sub-formulas I-A, I-B and I-C and III-A through III-F, also described herein.

In another embodiment A, the invention includes compounds wherein each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment A-1, the invention includes compounds wherein each of $R^a$ and $R^b$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment A-2, the invention includes compounds wherein each of $R^a$ and $R^b$, independently, is H, F, $CF_3$, $CH_3$, $CF_2H$ or $CH_2F$, in conjunction with any of the above or below embodiments.

In another embodiment A-3, the invention includes compounds wherein $R^1$ is H or F, in conjunction with any of the above or below embodiments.

In another embodiment A-4, the invention includes compounds wherein $R^1$ is H, in conjunction with any of the above or below embodiments.

In another embodiment B, the invention includes compounds wherein $R^1$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)_oC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment B-1, the invention includes compounds wherein $R^1$ is H, F, Cl, $C_{2-4}$alkenyl, $C_{2-4}$alkynyl, CN, —$CH_2OC_{1-3}$-alkyl, —$OC_{1-3}$-alkyl, wherein each of the $C_{2-4}$alkenyl, $C_{2-4}$alkynyl and $C_{1-3}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment B-2, the invention includes compounds wherein $R^1$ is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment B-3, the invention includes compounds wherein $R^1$ is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment B-4, the invention includes compounds wherein $R^1$ is H, F, Cl, $CF_3$, $CH_3$, $CF_2H$ or $CH_2F$, in conjunction with any of the above or below embodiments.

In another embodiment B-5, the invention includes compounds wherein $R^1$ is H, F, $CF_3$, $CH_3$, $CF_2H$ or $CH_2F$, in conjunction with any of the above or below embodiments.

In another embodiment B-6, the invention includes compounds wherein $R^1$ is H, F or $CF_3$, in conjunction with any of the above or below embodiments.

In another embodiment B-7, the invention includes compounds wherein $R^1$ is H or F, in conjunction with any of the above or below embodiments.

In another embodiment B-8, the invention includes compounds wherein $R^1$ is H, in conjunction with any of the above or below embodiments.

In another embodiment B-9, the invention includes compounds wherein $R^1$ is F, in conjunction with any of the above or below embodiments.

In another embodiment B-10, the invention includes compounds wherein $R^1$ is $CF_3$, in conjunction with any of the above or below embodiments.

In another embodiment C, the invention includes compounds wherein $R^2$ is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)_oC_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$NHC_{1-6}$-alkyl and —$C(O)C_{1-6}$-alkyl are optionally substituted with 1-4 substituents of F, oxo or OH, in conjunction with any of the above or below embodiments.

In another embodiment C-1, the invention includes compounds wherein $R^2$ is H, F, Cl, $C_{2-4}$alkenyl, $C_{2-4}$alkynyl, CN, —$CH_2OC_{1-3}$-alkyl, —$OC_{1-3}$-alkyl, wherein each of the $C_{2-4}$alkenyl, $C_{2-4}$alkynyl and $C_{1-3}$-alkyl portion of —$CH_2OC_{1-3}$-alkyl and —$OC_{1-3}$-alkyl are optionally substituted with 1-4 substituents of F, in conjunction with any of the above or below embodiments.

In another embodiment C-2, the invention includes compounds wherein $R^2$ is H, F, Cl, $CF_3$, $OCF_3$, methyl, ethyl, CN, OH, $OCH_3$, $SCH_3$, $NHCH_3$, $C(O)CH_3$ or $CH_2OCHF_2$, in conjunction with any of the above or below embodiments.

In another embodiment C-3, the invention includes compounds wherein $R^2$ is H, F, $CH_3$, $C_2H_5$, $CF_2H$, $CH_2F$, $CH_2OCH_2F$, $CH_2OCF_2H$ or $CH_2OCF_3$, in conjunction with any of the above or below embodiments.

In another embodiment C-4, the invention includes compounds wherein $R^2$ is H, F, Cl, $CF_3$, $CH_3$, $CF_2H$ or $CH_2F$, in conjunction with any of the above or below embodiments.

In another embodiment C-5, the invention includes compounds wherein $R^1$ is H, F, $CF_3$, $CH_3$, $CF_2H$ or $CH_2F$, in conjunction with any of the above or below embodiments.

In another embodiment C-6, the invention includes compounds wherein $R^1$ is H, F or $CF_3$, in conjunction with any of the above or below embodiments.

In another embodiment C-7, the invention includes compounds wherein $R^2$ is H or F, in conjunction with any of the above or below embodiments.

In another embodiment C-8, the invention includes compounds wherein $R^2$ is H, in conjunction with any of the above or below embodiments.

In another embodiment C-9, the invention includes compounds wherein $R^2$ is F, in conjunction with any of the above or below embodiments.

In another embodiment C-10, the invention includes compounds wherein $R^2$ is $CF_3$, in conjunction with any of the above or below embodiments.

In another embodiment D, the invention includes compounds wherein $R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms, in conjunction with any of the above or below embodiments.

In another embodiment D-1, the invention includes compounds wherein $R^3$ is $C_{1-4}$alkyl, $C_{1-4}$haloalkyl, $CH_2OH$, $CH_2OCHF_2$ or cyclopropyl, wherein each of the $C_{1-4}$alkyl, $C_{1-4}$haloalkyl and cyclopropyl is optionally substituted with 1-4 F atoms, in conjunction with any of the above or below embodiments.

In another embodiment D-2, the invention includes compounds wherein $R^3$ is $C_{1-4}$alkyl, $CH_2OH$, $CH_2OCH_2F$, $CH_2OCF_2H$, or cyclopropyl, wherein each of the $C_{1-4}$alkyl and cyclopropyl is optionally substituted with 1-2 F atoms, in conjunction with any of the above or below embodiments.

In another embodiment D-3, the invention includes compounds wherein $R^3$ is
$CH_3$, $CF_3$, $C_2H_5$, $CF_2H$ or $CH_2F$, in conjunction with any of the above or below embodiments.

In another embodiment D-4, the invention includes compounds wherein $R^3$ is $CF_3$, $CH_3$, $CF_2H$ or $CH_2F$, in conjunction with any of the above or below embodiments.

In another embodiment E, the invention includes compounds wherein $A^4$ is $CR^4$ wherein $R^4$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment E-1, the invention includes compounds wherein $A^4$ is $CR^4$ wherein $R^4$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment E-2, the invention includes compounds wherein $A^4$ is $CR^4$ wherein $R^4$ is H, F, $CF_3$, $CF_2H$, $CH_2F$ or $CH_3$, in conjunction with any of the above or below embodiments.

In another embodiment E-3, the invention includes compounds wherein $A^4$ is $CR^4$ wherein $R^4$ is H or F, in conjunction with any of the above or below embodiments.

In another embodiment E-4, the invention includes compounds wherein $A^4$ is N, in conjunction with any of the above or below embodiments.

In another embodiment F, the invention includes compounds wherein $A^5$ is $CR^5$ wherein $R^5$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment F-1, the invention includes compounds wherein $A^5$ is $CR^5$ wherein $R^5$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment F-2, the invention includes compounds wherein $A^5$ is $CR^5$ wherein $R^5$ is H, F, $CF_3$, $CF_2H$, $CH_2F$ or $CH_3$, in conjunction with any of the above or below embodiments.

In another embodiment F-3, the invention includes compounds wherein $A^5$ is $CR^5$ wherein $R^5$ is H or F, in conjunction with any of the above or below embodiments.

In another embodiment F-4, the invention includes compounds wherein $A^5$ is N, in conjunction with any of the above or below embodiments.

In another embodiment G, the invention includes compounds wherein $A^6$ is $CR^6$ wherein $R^6$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment G-1, the invention includes compounds wherein $A^6$ is $CR^6$ wherein $R^6$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment G-2, the invention includes compounds wherein $A^6$ is $CR^6$ wherein $R^6$ is H, F, $CF_3$, $CF_2H$, $CH_2F$ or $CH_3$, in conjunction with any of the above or below embodiments.

In another embodiment G-3, the invention includes compounds wherein $A^6$ is $CR^6$ wherein $R^6$ is H or F, in conjunction with any of the above or below embodiments.

In another embodiment G-4, the invention includes compounds wherein $A^6$ is N, in conjunction with any of the above or below embodiments.

In another embodiment H, the invention includes compounds wherein $A^8$ is $CR^8$ wherein $R^8$ is H, halo, haloalkyl, haloalkoxyl, $C_{1-4}$-alkyl, CN, OH, $OC_{1-4}$-alkyl, $S(O)_oC_{1-4}$-alkyl, $NHC_{1-4}$-alkyl or $C(O)C_{1-4}$-alkyl, in conjunction with any of the above or below embodiments.

In another embodiment H-1, the invention includes compounds wherein $A^8$ is $CR^8$ wherein $R^8$ is H, F, Cl, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment H-2, the invention includes compounds wherein $A^8$ is $CR^8$ wherein $R^8$ is H, F, $CF_3$, $CF_2H$, $CH_2F$ or $CH_3$, in conjunction with any of the above or below embodiments.

In another embodiment H-3, the invention includes compounds wherein $A^8$ is $CR^8$ wherein $R^8$ is H or F, in conjunction with any of the above or below embodiments.

In another embodiment H-4, the invention includes compounds wherein $A^8$ is N, in conjunction with any of the above or below embodiments.

In another embodiment I, the invention includes compounds wherein no more than two of $A^4$, $A^5$, $A^6$ and $A^8$ is N, in conjunction with any of the above or below embodiments.

In another embodiment I-1, the invention includes compounds wherein no more than one of $A^4$, $A^5$, $A^6$ and $A^8$ is N, in conjunction with any of the above or below embodiments.

In another embodiment I-2, the invention includes compounds wherein $A^4$ is $CR^4$, $A^5$ is $CR^5$ or N, $A^6$ is $CR^6$ and $A^8$ is $CR^8$, in conjunction with any of the above or below embodiments.

In another embodiment, the invention includes compounds wherein $A^4$ is $CR^4$ or N, $A^5$ is $CR^5$, $A^6$ is $CR^6$ and $A^8$ is $CR^8$, in conjunction with any of the above or below embodiments.

In another embodiment I-3, the invention includes compounds wherein $A^4$ is N, $A^5$ is $CR^5$, $A^6$ is $CR^6$ and $A^8$ is $CR^8$, in conjunction with any of the above or below embodiments.

In another embodiment I-4, the invention includes compounds wherein $A^4$ is $CR^4$, $A^5$ is N, $A^6$ is $CR^6$, and $A^8$ is $CR^8$, in conjunction with any of the above or below embodiments.

In another embodiment I-5, the invention includes compounds wherein $A^4$ is $CR^4$, $A^5$ is $CR^5$, $A^6$ is N, and $A^8$ is $CR^8$, in conjunction with any of the above or below embodiments.

In another embodiment I-6, the invention includes compounds wherein $A^4$ is $CR^5$, $A^5$ is $CR^5$, $A^6$ is $CR^6$, and $A^8$ is N, in conjunction with any of the above or below embodiments.

In another embodiment I-7, the invention includes compounds of Formulas I, II or III, wherein $A^4$ is $CR^4$ or N;
$A^5$ is $CR^5$ or N;
$A^6$ is $CR^6$ or N;
$A^8$ is $CR^8$ or N, provided that no more than one of $A^4$, $A^5$, $A^6$ and $A^8$ is N;
each of $R^a$ and $R^b$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
each of $R^1$ and $R^2$, independently, is H, F, Cl, $CF_3$, $OCF_3$, methyl, ethyl, CN, OH, $OCH_3$, $SCH_3$, $NHCH_3$, $C(O)CH_3$ or $CH_2OCHF_2$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment I-8, the invention includes compounds of Formulas I, II or III, wherein $A^4$ is $CR^4$;
$A^5$ is $CR^5$;
$A^6$ is $CR^6$; and
$A^8$ is $CR^8$; wherein each of $R^4$, $R^5$, $R^6$ and $R^8$, independently, is H, F, $CF_3$, $CF_2H$, $CH_2F$ or $CH_3$, in conjunction with any of the above or below embodiments.

In another embodiment I-9, the invention includes compounds of Formulas I, II or III, wherein $A^4$ is CH, CF or N, $A^5$ is CH, CF or N, $A^6$ is CH, CF or N, $A^8$ is CH, CF or N, one of $A^4$, $A^5$, $A^6$ and $A^8$ is N, in conjunction with any of the above or below embodiments.

In another embodiment J, the invention includes compounds of Formulas I, II or III, wherein $R^7$ is —NH—$R^9$, —NH—C(=O)—$R^9$, —C(=O)NH—$R^9$, —O—$R^9$, —S—$R^9$; or $R^7$ is

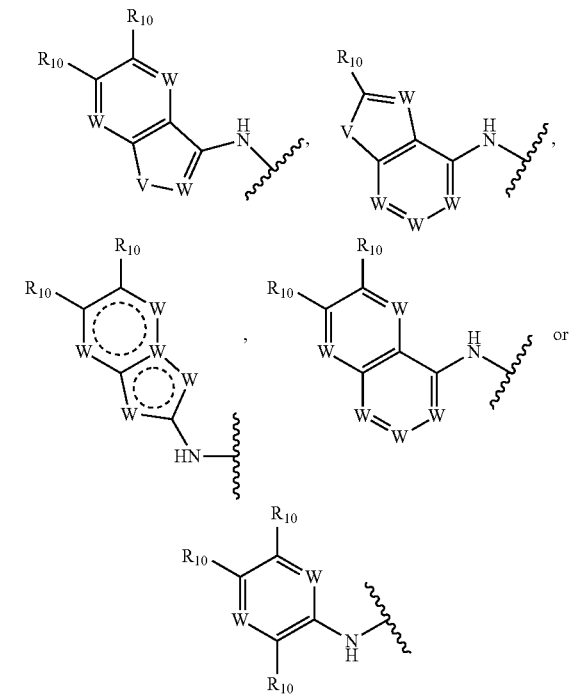

wherein V is $NR^{10}$, O or S; and
each W, independently, is CH, CF, CCl, $CCH_3$ or N, in conjunction with any of the above or below embodiments.

In another embodiment J-1, the invention includes compounds of Formulas I, II or III, wherein $R^7$ is —NH—$R^9$, —NH—C(=O)—$R^9$ or

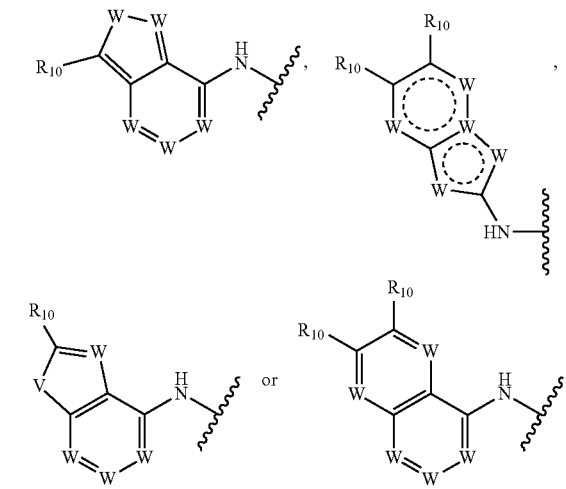

wherein V is $NR^{10}$, O or S; and
each W, independently, is CH, CF, CCl, $CCH_3$ or N, in conjunction with any of the above or below embodiments.

In another embodiment J-2, the invention includes compounds of Formulas I, II or III, wherein $R^7$ is —NH—C(=O)—$R^9$ or

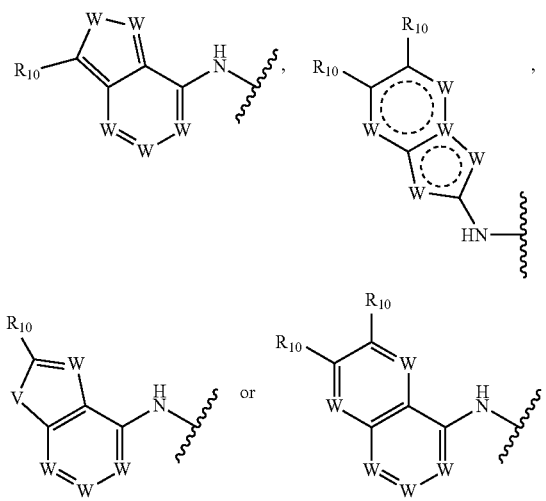

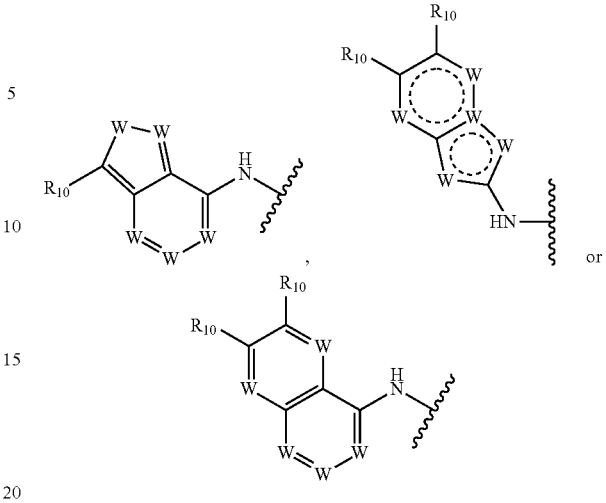

wherein V is NR$^{10}$, O or S; and each W, independently, is CH, CF, CCl or N, in conjunction with any of the above or below embodiments.

In another embodiment J-3, the invention includes compounds of Formulas I, II or III, wherein R$^7$ is —NH—C(=O)—R$^9$, in conjunction with any of the above or below embodiments.

In another embodiment J-4, the invention includes compounds of Formulas I, II or III, wherein R$^7$ is —NH—R$^9$, in conjunction with any of the above or below embodiments.

In another embodiment J-5, the invention includes compounds wherein R$^7$ is

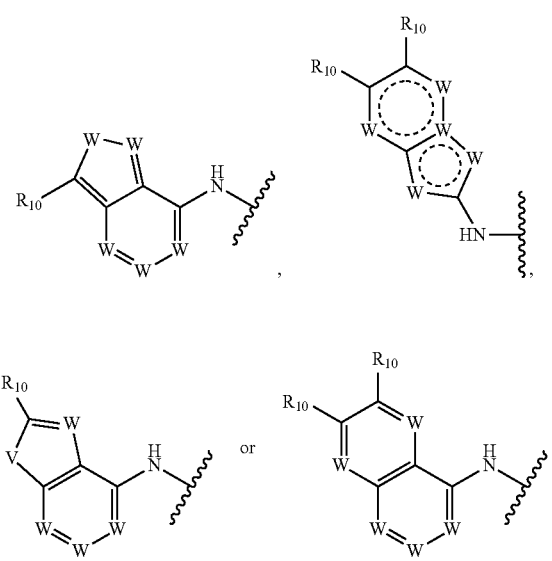

wherein V is NR$^{10}$, O or S; and each W, independently, is CH, CF, CCl, CCH$_3$ or N, in conjunction with any of the above or below embodiments.

In another embodiment J-6, the invention includes compounds wherein R$^7$ is wherein V is NR$^{10}$, O or S; and each W, independently, is CH, CF, CCl, CCH$_3$ or N, in conjunction with any of the above or below embodiments.

In another embodiment J-7, the invention includes compounds wherein R$^7$ is —NH—R$^9$, —O—R$^9$ or —S—R$^9$ i, in conjunction with any of the above or below embodiments.

In another embodiment J-8, the invention includes compounds wherein R$^7$ is —O—R$^9$ or —S—R$^9$, in conjunction with any of the above or below embodiments.

In another embodiment J-9, the invention includes compounds wherein R$^7$ is —NH—R$^9$, —NH—C(=O)—R$^9$, —C(=O)NH—R$^9$, —O—R$^9$ or —S—R$^9$, wherein R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$, in conjunction with any of the above or below embodiments.

In another embodiment K, the invention includes compounds wherein R$^9$ is acetyl, C$_{1-6}$-alkyl, C$_{2-4}$alkenyl, C$_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the C$_{1-6}$-alkyl, C$_{2-4}$alkenyl, C$_{2-4}$alkynyl and ring are optionally substituted, independently, with 1-5 substituents of R$^{10}$, in conjunction with any of the above or below embodiments.

In another embodiment K-1, the invention includes compounds wherein each R$^9$, independently, is acetyl, C$_{1-6}$-alkyl, C$_{2-4}$alkenyl, C$_{2-4}$alkynyl or a ring selected from phenyl, pyridyl, pyrimidyl, pyrazinyl, pyridazinyl, pyrazolyl, isoxazolyl, thiazolyl, naphthyl, quinolinyl, isoquinolinyl, quinazolinyl, naphthyridinyl, phthalazinyl, pyranyl, dihydropyranyl, tetrahydropyranyl, furanyl, dihydrofuranyl, tetrahydrofuranyl, thienyl, pyrrolyl, pyrrolidinyl, tetrahydropyrrolyl, piperidinyl, piperazinyl, morpholinyl, azetidinyl, 8-oxo-3-aza-bicyclo[3.2.1]oct-3-yl, aza-bicyclo[2.2.1]hept-5-yl, 2-oxo-7-aza-[3,5]-spironon-7-yl, cyclopropyl, cyclobutyl, cyclopentyl and cyclohexyl, wherein the C$_{1-6}$-alkyl, C$_{2-4}$alkenyl, C$_{2-4}$alkynyl and ring are optionally substituted, independently, with 1-5 substituents of R$^{10}$, in conjunction with any of the above or below embodiments.

In another embodiment K-2, the invention includes compounds wherein each $R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$, in conjunction with any of the above or below embodiments.

In another embodiment K-2, the invention includes compounds of Formulas I, II, and III, and any sub-formula thereof as described herein, wherein $R^9$ is a ring selected from the group consisting of phenyl, pyridyl, pyrimidyl, pyrazinyl, pyridazinyl, pyrazolyl, isoxazolyl, thiazolyl, thienyl, furanyl and pyrrolyl, wherein the ring is optionally substituted, independently, with 1-3 substituents of $R^{10}$, wherein each $R^{10}$, independently, is F, Cl, CN, $NO_2$, $NH_2$, OH, $CF_3$, $CHF_2$, $CH_2F$, $CH_3$, —$OCH_3$, $C_2H_5$, —$OC_2H_5$, —$CH_2CF_3$, —$CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopropylmethoxy, 2-butynyloxy or oxetan-3yl, in conjunction with any of the above or below embodiments.

In another embodiment L, the present invention provides compounds, and solvates, tautomers, hydrates, stereoisomers and pharmaceutically acceptable salts thereof, as defined by Formulas I, I-A, I-B, I-C or II, wherein
$A^4$ is $CR^4$ or N;
$A^5$ is $CR^5$ or N;
$A^6$ is $CR^6$ or N;
$A^8$ is $CR^8$ or N, provided no more than one of $A^4$, $A^5$, $A^6$ and $A^8$ is N;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$;
$R^3$ is $C_{1-4}$alkyl, $C_{1-4}$haloalkyl, $CH_2OH$, $CH_2OCHF_2$ or cyclopropyl; and
each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$, in conjunction with any of the above or below embodiments.

In another embodiment M, the present invention provides compounds, and solvates, tautomers, hydrates, stereoisomers and pharmaceutically acceptable salts thereof, as defined by Formulas I and II, wherein
$R^7$ is —NH—$R^9$, —NH—C(=O)—$R^9$ or

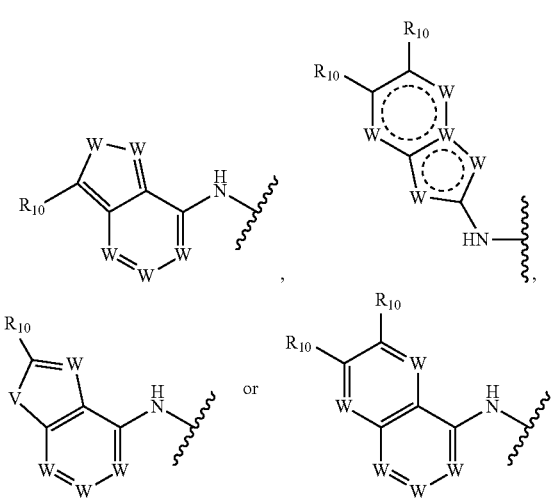

wherein V is $NR^{10}$, O or S; and
each W, independently, is CH, CF, CCl, $CCH_3$ or N, in conjunction with any of the above or below embodiments.

In another embodiment N-1, the invention includes compounds of Formula I-A wherein $A^4$ is $CR^4$;
$A^5$ is $CR^5$ or N;
$A^6$ is $CR^6$;
$A^8$ is $CR^8$; wherein each of $R^4$, $R^5$, $R^6$ and $R^8$, independently, is H, F, Cl, $CF_3$,
$OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$;
$R^3$ is $CH_3$, $C_2H_5$, $CF_2H$ or $CH_2F$;
$R^9$ is acetyl, $C_{1-6}$-alkyl, $C_2$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In another embodiment N-2, the invention includes compounds of Formula I-A wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, $CF_3$, $OCF_3$, methyl, ethyl, CN or $OCH_3$;
each of $R^a$ and $R^b$, independently, is H or F;
each of $R^1$ and $R^2$, independently, is H, F or $CF_3$;
$R^3$ is $CF_3$, $CH_3$, $CF_2H$ or $CH_2F$;
$R^9$ is a ring selected from phenyl, pyridyl, pyrimidyl, pyrazinyl, pyridazinyl, pyrazolyl, isoxazolyl, thiazolyl, furanyl, thienyl and pyrrolyl, wherein the ring is optionally substituted, independently, with 1-3 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

In another embodiment 0-1, the invention includes compounds of Formula I-B wherein $A^4$ is $CR^4$;

$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$; and
$R^3$ is $CH_3$, $C_2H_5$, $CF_2H$ or $CH_2F$, in conjunction with any of the above or below embodiments with respect to Formula I-B.

In another embodiment 0-2, the invention includes compounds of Formula I-B wherein $A^4$ is $CR^4$ or N;

$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F or $CF_3$;
each of $R^a$ and $R^b$, independently, is H or F; and
$R^3$ is $CF_3$, $CH_3$, $CF_2H$ or $CH_2F$, in conjunction with any of the above or below embodiments with respect to Formula I-B.

In another embodiment P-1, the invention includes compounds of Formula I-C wherein $A^4$ is $CR^4$;

$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_3$, $OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$; and
$R^3$ is $CH_3$, $C_2H_5$, $CF_2H$ or $CH_2F$, in conjunction with any of the above or below embodiments with respect to Formula I-C.

In another embodiment P-2, the invention includes compounds of Formula I-C wherein $A^4$ is $CR^4$ or N;

$A^5$ is $CR^5$ or N;
$A^6$ is $CR^6$ or N;
$A^8$ is $CR^8$ or N, wherein each of $R^4$, $R^5$, $R^6$ and $R^8$, independently, is H or F and provided no more than one of $A^4$, $A^5$, $A^6$ and $A^8$ is N;
each of $R^1$ and $R^2$, independently, is H, F or $CF_3$;
each of $R^a$ and $R^b$, independently, is H or F; and
$R^3$ is $CF_3$, $CH_3$, $CF_2H$ or $CH_2F$, in conjunction with any of the above or below embodiments with respect to Formula I-C.

In another embodiment, the invention provides one or more of the compounds, or a pharmaceutically acceptable salt thereof, of Formulas I, II and III, and sub-formulas thereof, as taught and described herein.

In another embodiment, the invention provides the compound of Formula I, II or III, or a stereoisomer or pharmaceutically acceptable salt thereof, selected from N-(3-((1R,5S,6R)-3-amino-5-methyl-2-oxa-4-azabicyclo[4.1.0]hept-3-en-5-yl)-4-fluorophenyl)-5-methoxy-2-pyrazinecarboxamide;

Racemic mixture of N-(3-((1R,5R,6R)-3-amino-5-methyl-2-oxa-4-azabicyclo[4.1.0]hept-3-en-5-yl)-4-fluorophenyl)-5-methoxy-2-pyrazinecarboxamide and N-(3-((1S,5S,6  S)-3-amino-5-methyl-2-oxa-4-azabicyclo[4.1.0]hept-3-en-5-yl)-4-fluorophenyl)-5-methoxy-2-pyrazinecarboxamide;

N-(3-((1S,5S,6S)-3-amino-5-methyl-2-oxa-4-azabicyclo[4.1.0]hept-3-en-5-yl)-4-fluorophenyl)-5-methoxy-2-pyrazinecarboxamide;

N-(3-((1R,5S,6R)-3-amino-5-methyl-2-oxa-4-azabicyclo[4.1.0]hept-3-en-5-yl)-4-fluorophenyl)-3-methoxy-1,7-naphthyridin-8-amine; and N-(3-((1S,5S,6S)-3-amino-5-methyl-2-oxa-4-azabicyclo[4.1.0]hept-3-en-5-yl)-4-fluorophenyl)-3-methoxy-1,7-naphthyridin-8-amine Additional generic and specific compounds representative of the invention include:

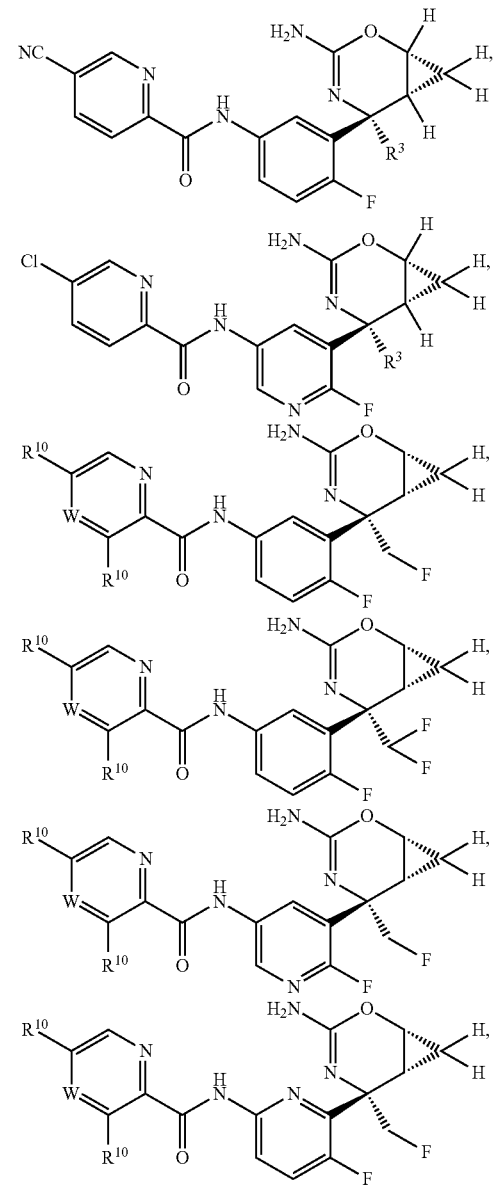

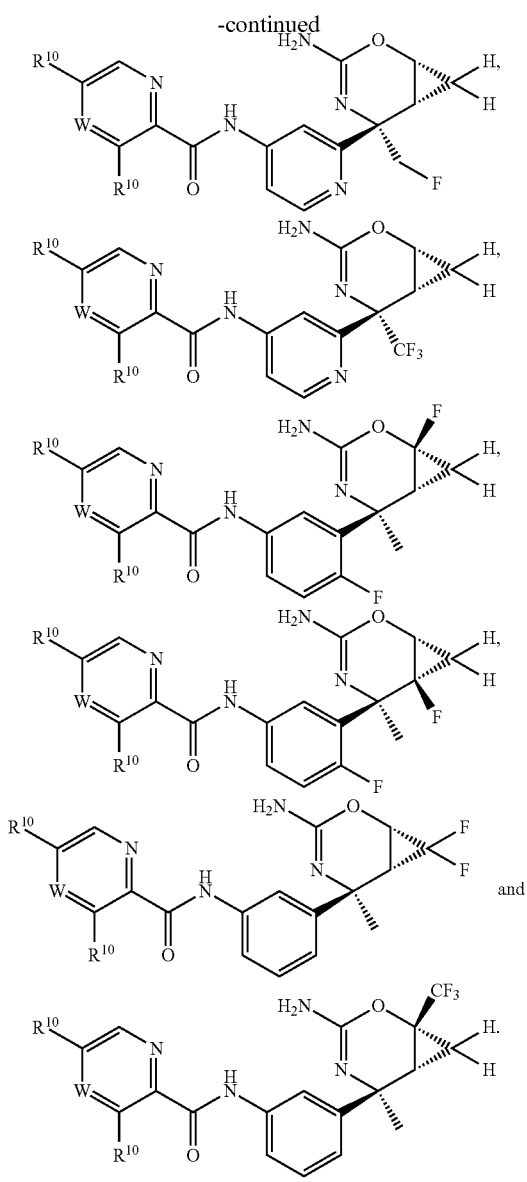

In embodiment 82, the invention provides a compound, or a pharmaceutically acceptable salt or tautomer thereof, selected from:

N-(3-([[(1R,S),(5S,R),(6R,S)]-3-amino-5-(difluoromethyl)-2-oxa-4-azabicyclo[4.1.0]hept-3-en-5-yl)-4-fluoro-5-methylphenyl)-5-chloropicolinamide;

N-(3-((1R,5S,6R)-3-amino-5-(fluoromethyl)-2-oxa-4-azabicyclo[4.1.0]hept-3-en-5-yl)-4,5-difluorophenyl)-5-(prop-2-yn-1-yloxy)pyrazine-2-carboxamide;

N-(3-((1R,5S,6R)-3-amino-5-(fluoromethyl)-2-oxa-4-azabicyclo[4.1.0]hept-3-en-5-yl)-4,5-difluorophenyl)-5-(but-2-yn-1-yloxy)pyrazine-2-carboxamide;

N-(3-((1R,5S,6R)-3-amino-5-(fluoromethyl)-2-oxa-4-azabicyclo[4.1.0]hept-3-en-5-yl)-4,5-difluorophenyl)-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-5-chloro-3-(methoxymethyl)picolinamide;

N-(3-((1R,5S,6R)-3-amino-5-(difluoromethyl)-2-oxa-4-azabicyclo[4.1.0]hept-3-en-5-yl)-4-fluorophenyl)-5-chloro-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-5-cyano-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-5-cyano-3-methoxypicolinamide;

N-(3-([1(R,S),5(S,R),6(R,S)]-3-amino-5-(difluoromethyl)-2-oxa-4-azabicyclo[4.1.0]hept-3-en-5-yl)-4-fluorophenyl)-5-chloropicolinamide;

N-(3-([1(R,S),5(S,R),6(R,S)]-3-amino-5-(difluoromethyl)-2-oxa-4-azabicyclo[4.1.0]hept-3-en-5-yl)-4-fluorophenyl)-5-cyanopicolinamide compound;

N-(3-((1R,5S,6R)-3-amino-5-(difluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-3-chloro-5-methoxypicolinamide;

N-(3-((1R,5S,6R)-3-amino-5-(difluoromethyl)-2-oxa-4-azabicyclo[4.1.0]hept-3-en-5-yl)-4-fluorophenyl)-3,5-dichloropicolinamide;

N-(3-((1R,5S,6R)-3-amino-5-(difluoromethyl)-2-oxa-4-azabicyclo[4.1.0]hept-3-en-5-yl)-4-fluorophenyl)-5-bromopicolinamide;

N-(3-((1R,5S,6R)-3-amino-5-(difluoromethyl)-2-oxa-4-azabicyclo[4.1.0]hept-3-en-5-yl)-4-fluorophenyl)-5-chloropicolinamide;

N-(3-((1R,5S,6R)-3-amino-5-(difluoromethyl)-2-oxa-4-azabicyclo[4.1.0]hept-3-en-5-yl)-4-fluorophenyl)-5-cyanopicolinamide;

N-(3-((1S,5R,6S)-3-amino-5-(fluoromethyl)-2-oxa-4-azabicyclo[4.1.0]hept-3-en-5-yl)-2,4-difluorophenyl)-5-methoxypicolinamide;

N-(3-((1R,5S,6R)-3-amino-5-(fluoromethyl)-2-oxa-4-azabicyclo[4.1.0]hept-3-en-5-yl)-5-chloro-4-fluorophenyl)-5-cyano-3-methoxypicolinamide;

N-(3-((1R,5S,6R)-3-amino-5-(difluoromethyl)-2-oxa-4-azabicyclo[4.1.0]hept-3-en-5-yl)-4-chlorophenyl)-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-5-(prop-2-yn-1-yloxy)pyrazine-2-carboxamide trifluoroacetate;

N-(3-((1R,5S,6R)-3-amino-5-(difluoromethyl)-2-oxa-4-azabicyclo[4.1.0]hept-3-en-5-yl)-4-fluorophenyl)-5-(but-2-yn-1-yloxy)pyrazine-2-carboxamide trifluoroacetate;

N-(3-((1R,5S,6R)-3-amino-5-(difluoromethyl)-2-oxa-4-azabicyclo[4.1.0]hept-3-en-5-yl)-4-chlorophenyl)-5-chloropicolinamide;

N-(3-((1R,5S,6R)-3-amino-5-(difluoromethyl)-2-oxa-4-azabicyclo[4.1.0]hept-3-en-5-yl)-4-chlorophenyl)-5-(oxazol-4-ylmethoxy)pyrazine-2-carboxamide;

N-(3-((1R,5S,6R)-3-amino-5-(difluoromethyl)-2-oxa-4-azabicyclo[4.1.0]hept-3-en-5-yl)-4,5-difluorophenyl)-5-cyanopicolinamide;

N-(3-((1R,5S,6R)-3-amino-5-(difluoromethyl)-2-oxa-4-azabicyclo[4.1.0]hept-3-en-5-yl)-4,5-difluorophenyl)-4-chloro-1-(difluoromethyl)-1H-pyrazole-3-carboxamide;

N-(3-((1R,5S,6R)-3-amino-5-(fluoromethyl)-2-oxa-4-azabicyclo[4.1.0]hept-3-en-5-yl)-4-fluorophenyl)-5-chloropicolinamide;

N-(3-((1R,5S,6R)-3-amino-5-(fluoromethyl)-2-oxa-4-azabicyclo[4.1.0]hept-3-en-5-yl)-4-chlorophenyl)-3-methyl-5-(trifluoromethyl)picolinamide;

N-(3-((1R,5S,6R)-3-amino-5-(fluoromethyl)-2-oxa-4-azabicyclo[4.1.0]hept-3-en-5-yl)-4-chlorophenyl)-3-chloro-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-5-chloro-3-fluoropicolinamide;

N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methylpicolinamide;

N-(3-((1R,5S,6R)-3-amino-5-(difluoromethyl)-2-oxa-4-azabicyclo[4.1.0]hept-3-en-5-yl)-4-fluoro-5-methylphenyl)-3-chloro-5-cyanopicolinamide;

N-(3-((1R,5S,6R)-3-amino-5-(difluoromethyl)-2-oxa-4-azabicyclo[4.1.0]hept-3-en-5-yl)-4-fluoro-5-methylphenyl)-3,5-dichloropicolinamide;

N-(3-((1R,5S,6R)-3-amino-5-(fluoromethyl)-2-oxa-4-azabicyclo[4.1.0]hept-3-en-5-yl)-4-chloro-5-fluorophenyl)-5-cyano-3-methylpicolinamide;

N-(3-((1R,5S,6R)-3-amino-5-(fluoromethyl)-2-oxa-4-azabicyclo[4.1.0]hept-3-en-5-yl)-4-fluorophenyl)-4-chloro-1-(difluoromethyl)-1H-pyrazole-3-carboxamide;

N-(3-((1R,5S,6R)-3-amino-5-(difluoromethyl)-2-oxa-4-azabicyclo[4.1.0]hept-3-en-5-yl)-4-fluorophenyl)-5-(oxazol-2-ylmethoxy)pyrazine-2-carboxamide;

N-(3-((1R,5S,6R)-3-amino-5-(difluoromethyl)-2-oxa-4-azabicyclo[4.1.0]hept-3-en-5-yl)-4-fluorophenyl)-5-(oxazol-4-ylmethoxy)pyrazine-2-carboxamide;

N-(3-((1R,5S,6R)-3-amino-5-(difluoromethyl)-2-oxa-4-azabicyclo[4.1.0]hept-3-en-5-yl)-4-fluorophenyl)-5-(difluoromethyl)-3-methylpicolinamide;

N-(3-((1R,5S,6R)-3-amino-5-(fluoromethyl)-2-oxa-4-azabicyclo[4.1.0]hept-3-en-5-yl)-4-fluorophenyl)-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-3,5-dichloropicolinamide;

N-(3-((1R,5S,6R)-3-amino-5-(fluoromethyl)-2-oxa-4-azabicyclo[4.1.0]hept-3-en-5-yl)-4-fluorophenyl)-5-(prop-2-yn-1-yloxy)pyrazine-2-carboxamide;

N-(3-((1R,5S,6R)-3-amino-5-(fluoromethyl)-2-oxa-4-azabicyclo[4.1.0]hept-3-en-5-yl)-4-fluorophenyl)-5-(but-2-yn-1-yloxy)pyrazine-2-carboxamide;

N-(3-((1R,5S,6R)-3-amino-5-(fluoromethyl)-2-oxa-4-azabicyclo[4.1.0]hept-3-en-5-yl)-4-fluorophenyl)-5-(prop-2-yn-1-yloxy)picolinamide;

N-(3-([1(R,S),5(S,R),6(R,S)]-3-amino-5-(difluoromethyl)-2-oxa-4-azabicyclo[4.1.0]hept-3-en-5-yl)-4-chlorophenyl)-5-(but-2-yn-1-yloxy)pyrazine-2-carboxamide;

N-(3-((1R,5S,6R)-3-amino-5-(difluoromethyl)-2-oxa-4-azabicyclo[4.1.0]hept-3-en-5-yl)-4-chlorophenyl)-5-(but-2-yn-1-yloxy)pyrazine-2-carboxamide;

N-(3-((1(R,S),5(S,R),6(R,S))-3-amino-5-(fluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-3-chloro-5-methoxypicolinamide;

N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)pyrazine-2-carboxamide;

N-(3-((1R,5S,6R)-3-amino-5-(difluoromethyl)-2-oxa-4-azabicyclo[4.1.0]hept-3-en-5-yl)-4-fluorophenyl)-5-bromopyrimidine-2-carboxamide;

N-(3-((1R,5S,6R)-3-amino-5-(fluoromethyl)-2-oxa-4-azabicyclo[4.1.0]hept-3-en-5-yl)-4-chlorophenyl)-3,5-dichloropicolinamide;

N-(3-((1R,5S,6R)-3-amino-5-(fluoromethyl)-2-oxa-4-azabicyclo[4.1.0]hept-3-en-5-yl)-4-chlorophenyl)-5-cyano-3-methylpicolinamide;

N-(3-((1R,5S,6R)-3-amino-5-(fluoromethyl)-2-oxa-4-azabicyclo[4.1.0]hept-3-en-5-yl)-4-chlorophenyl)-5-(but-2-yn-1-yloxy)pyrazine-2-carboxamide;

N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide;

N-(5-((1(R,S),5(S,R),6(R,S)-3-amino-5-methyl-2-oxa-4-azabicyclo[4.1.0]hept-3-en-5-yl)-6-fluoropyridin-3-yl)-5-chloropicolinamide;

N-(3-((1R,5S,6R)-3-amino-5-(fluoromethyl)-2-oxa-4-azabicyclo[4.1.0]hept-3-en-5-yl)-4-chlorophenyl)-5-cyano-3-(methoxymethyl)picolinamide; and N-(3-((1R,5S,6R)-3-amino-5-(difluoromethyl)-2-oxa-4-azabicyclo[4.1.0]hept-3-en-5-yl)-4-fluorophenyl)-5-cyano-3-fluoropicolinamide; and N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methoxypicolinamide.

In embodiment 83, the invention provides a compound, or a pharmaceutically acceptable salt or tautomer thereof, selected from:

N-(3-((1R,5S,6R)-3-amino-5-(difluoromethyl)-2-oxa-4-azabicyclo[4.1.0]hept-3-en-5-yl)-4-fluorophenyl)-5-chloro-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-5-cyano-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-3-chloro-5-methoxypicolinamide;

N-(3-((1R,5S,6R)-3-amino-5-(difluoromethyl)-2-oxa-4-azabicyclo[4.1.0]hept-3-en-5-yl)-4-fluorophenyl)-3,5-dichloropicolinamide;

N-(3-((1R,5S,6R)-3-amino-5-(difluoromethyl)-2-oxa-4-azabicyclo[4.1.0]hept-3-en-5-yl)-4-fluorophenyl)-5-bromopicolinamide;

N-(3-((1R,5S,6R)-3-amino-5-(difluoromethyl)-2-oxa-4-azabicyclo[4.1.0]hept-3-en-5-yl)-4-fluorophenyl)-5-chloropicolinamide;

N-(3-((1R,5S,6R)-3-amino-5-(difluoromethyl)-2-oxa-4-azabicyclo[4.1.0]hept-3-en-5-yl)-4-fluorophenyl)-5-cyanopicolinamide;

N-(3-((1S,5R,6S)-3-amino-5-(fluoromethyl)-2-oxa-4-azabicyclo[4.1.0]hept-3-en-5-yl)-2,4-difluorophenyl)-5-methoxypicolinamide;

N-(3-((1R,5S,6R)-3-amino-5-(difluoromethyl)-2-oxa-4-azabicyclo[4.1.0]hept-3-en-5-yl)-4-chlorophenyl)-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-5-(prop-2-yn-1-yloxy)pyrazine-2-carboxamide trifluoroacetate;

N-(3-((1R,5S,6R)-3-amino-5-(difluoromethyl)-2-oxa-4-azabicyclo[4.1.0]hept-3-en-5-yl)-4-chlorophenyl)-5-chloropicolinamide;

N-(3-((1R,5S,6R)-3-amino-5-(difluoromethyl)-2-oxa-4-azabicyclo[4.1.0]hept-3-en-5-yl)-4-chlorophenyl)-5-(oxazol-4-ylmethoxy)pyrazine-2-carboxamide;

N-(3-((1R,5S,6R)-3-amino-5-(fluoromethyl)-2-oxa-4-azabicyclo[4.1.0]hept-3-en-5-yl)-4-fluorophenyl)-5-chloropicolinamide;
N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methylpicolinamide;
N-(3-((1R,5S,6R)-3-amino-5-(difluoromethyl)-2-oxa-4-azabicyclo[4.1.0]hept-3-en-5-yl)-4-fluoro-5-methylphenyl)-3-chloro-5-cyanopicolinamide;
N-(3-((1R,5S,6R)-3-amino-5-(fluoromethyl)-2-oxa-4-azabicyclo[4.1.0]hept-3-en-5-yl)-4-fluorophenyl)-5-cyanopicolinamide;
N-(3-((1R,5S,6R)-3-amino-5-(fluoromethyl)-2-oxa-4-azabicyclo[4.1.0]hept-3-en-5-yl)-4-fluorophenyl)-3,5-dichloropicolinamide;
N-(3-((1R,5S,6R)-3-amino-5-(fluoromethyl)-2-oxa-4-azabicyclo[4.1.0]hept-3-en-5-yl)-4-fluorophenyl)-5-(but-2-yn-1-yloxy)pyrazine-2-carboxamide;
N-(3-((1R,5S,6R)-3-amino-5-(fluoromethyl)-2-oxa-4-azabicyclo[4.1.0]hept-3-en-5-yl)-4-fluorophenyl)-3-chloro-5-cyanopicolinamide;
N-(3-((1R,5S,6R)-3-amino-5-(fluoromethyl)-2-oxa-4-azabicyclo[4.1.0]hept-3-en-5-yl)-4-fluorophenyl)-3-chloro-5-methoxypicolinamide;
N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)-3-methylpicolinamide;
N-(3-((1R,5S,6R)-3-amino-5-(fluoromethyl)-2-oxa-4-azabicyclo[4.1.0]hept-3-en-5-yl)-4-chlorophenyl)-5-cyano-3-methylpicolinamide;
N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide;
N-(3-((1R,5S,6R)-3-amino-5-(fluoromethyl)-2-oxa-4-azabicyclo[4.1.0]hept-3-en-5-yl)-4-chlorophenyl)-5-cyano-3-(methoxymethyl)picolinamide; and
N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methoxypicolinamide.

In embodiment 84, the invention provides a compound, or a pharmaceutically acceptable salt or tautomer thereof, selected from:

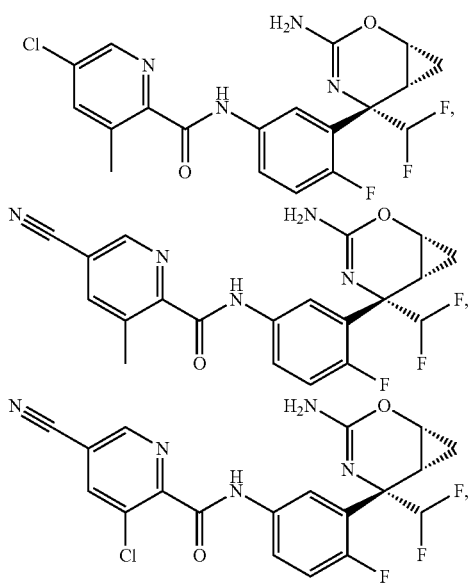
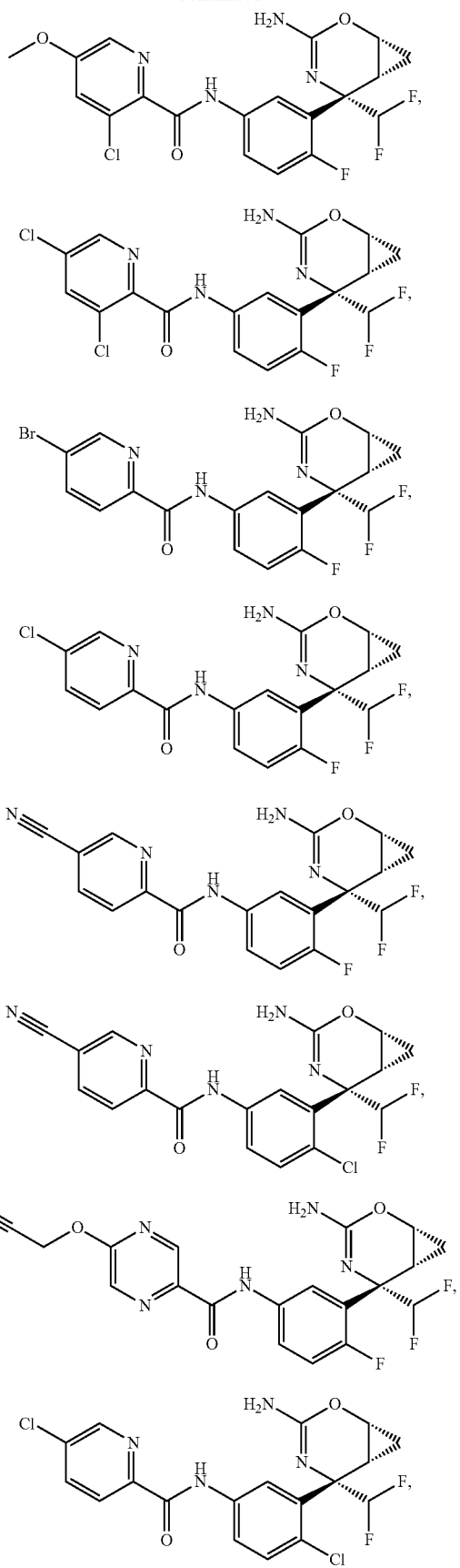

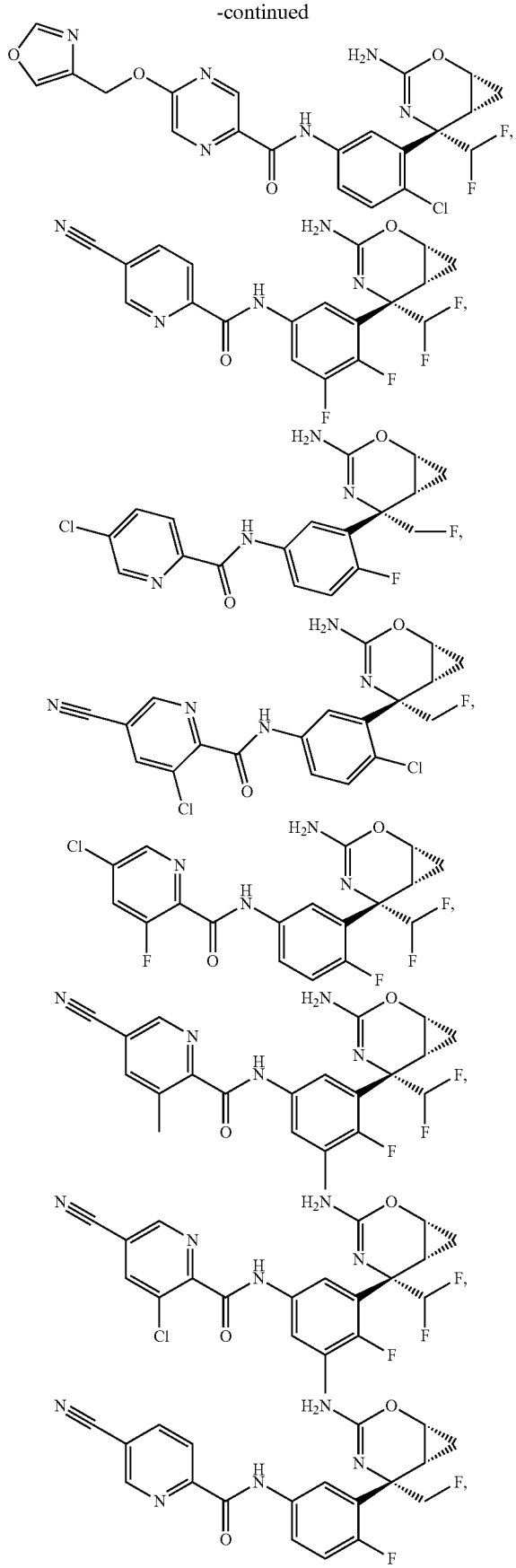
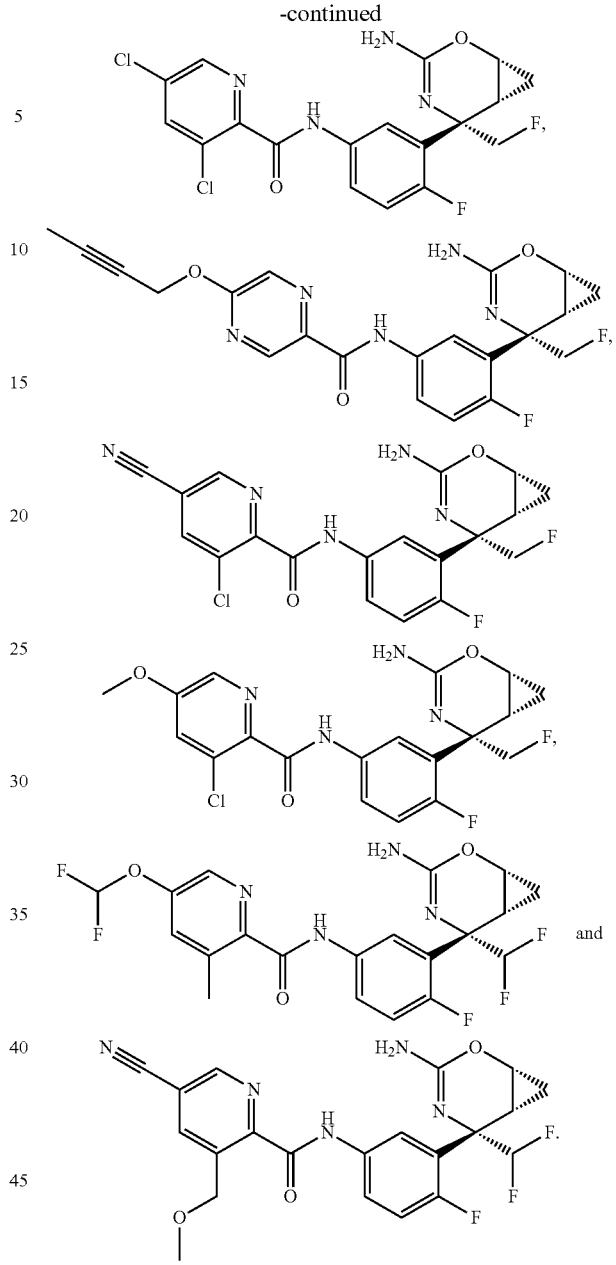
In embodiment 85, the invention provides each individual compound according to embodiments 82-84, or a pharmaceutically acceptable salt or tautomer thereof.
For instance, in embodiment 86, the invention provides the compound
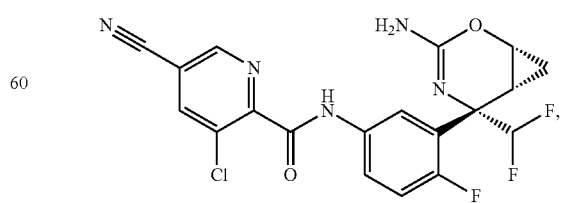
or a pharmaceutically acceptable salt or tautomer thereof In embodiment 87, the invention provides the compound

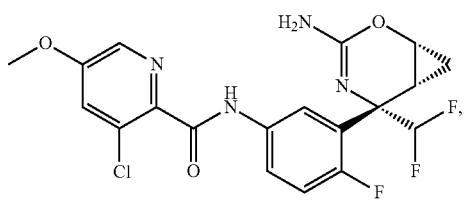 [SMILES: COc1cnc(C(=O)Nc2ccc(F)c([C@@]3(C(F)F)N=C(N)O[C@@H]4C[C@@H]43)c2)c(Cl)c1]

or a pharmaceutically acceptable salt or tautomer thereof

In embodiment 88, the invention provides the compound

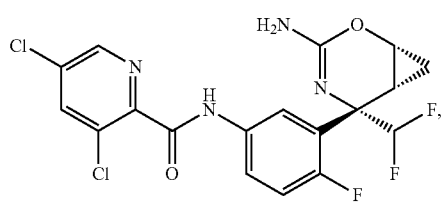 [SMILES: NC1=N[C@@](c2cc(NC(=O)c3ncc(Cl)cc3Cl)ccc2F)(C(F)F)[C@H]2C[C@H]2O1]

or a pharmaceutically acceptable salt or tautomer thereof

In embodiment 89, the invention provides the compound

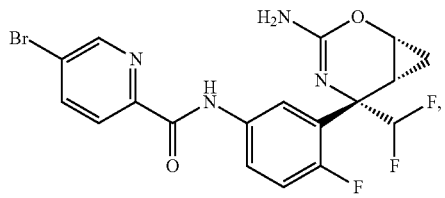 [SMILES: NC1=N[C@@](c2cc(NC(=O)c3ccc(Cl)cn3)ccc2F)(C(F)F)[C@H]2C[C@H]2O1]

or a pharmaceutically acceptable salt or tautomer thereof

In embodiment 90, the invention provides the compound

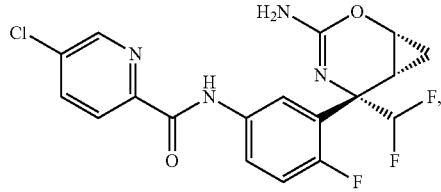

or a pharmaceutically acceptable salt or tautomer thereof

In embodiment 91, the invention provides the compound

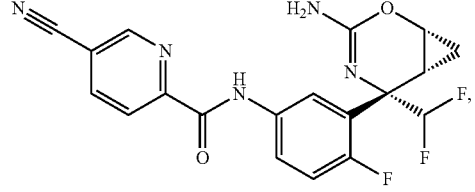 [SMILES: N#Cc1ccc(C(=O)Nc2ccc(F)c([C@@]3(C(F)F)N=C(N)O[C@@H]4C[C@@H]43)c2)nc1]

or a pharmaceutically acceptable salt or tautomer thereof

In embodiment 92, the invention provides the compound

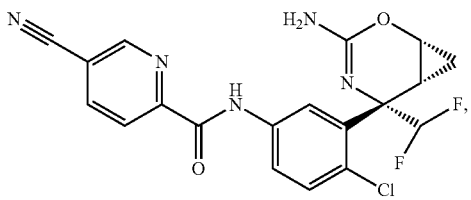 [SMILES: N#Cc1ccc(C(=O)Nc2ccc(Cl)c([C@@]3(C(F)F)N=C(N)O[C@@H]4C[C@@H]43)c2)nc1]

or a pharmaceutically acceptable salt or tautomer thereof

In embodiment 93, the invention provides the compound

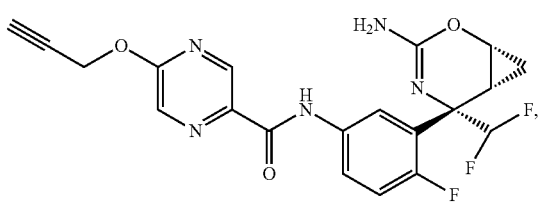 [SMILES: C#CCOc1cnc(C(=O)Nc2ccc(F)c([C@@]3(C(F)F)N=C(N)O[C@@H]4C[C@@H]43)c2)cn1]

or a pharmaceutically acceptable salt or tautomer thereof

In embodiment 94, the invention provides the compound

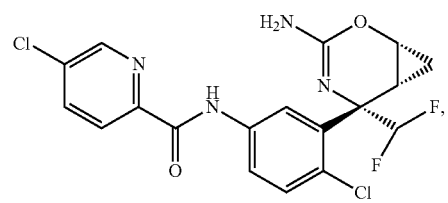 [SMILES: NC1=N[C@@](c2cc(NC(=O)c3ccc(Cl)cn3)ccc2Cl)(C(F)F)[C@H]2C[C@H]2O1]

or a pharmaceutically acceptable salt or tautomer thereof

In embodiment 95, the invention provides the compound

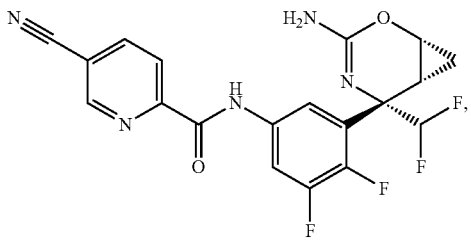 [SMILES: N#Cc1ccc(C(=O)Nc2cc(F)c(F)c([C@@]3(C(F)F)N=C(N)O[C@@H]4C[C@@H]43)c2)nc1]

or a pharmaceutically acceptable salt or tautomer thereof

In embodiment 96, the invention provides the compound

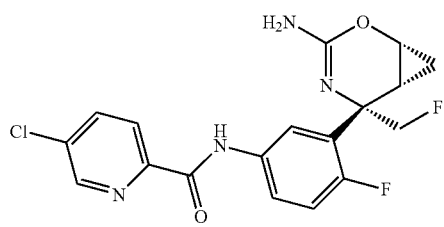

or a pharmaceutically acceptable salt or tautomer thereof

In embodiment 97, the invention provides the compound

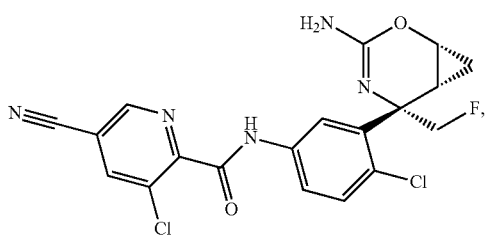 [SMILES: N#Cc1cnc(C(=O)Nc2ccc(Cl)c([C@@]3(CF)N=C(N)O[C@@H]4C[C@@H]43)c2)c(Cl)c1]

or a pharmaceutically acceptable salt or tautomer thereof

In embodiment 98, the invention provides the compound

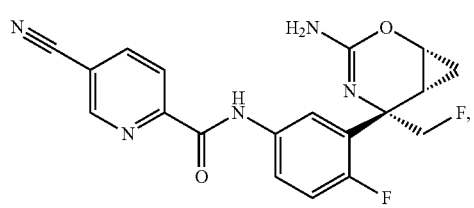 [SMILES: N#Cc1ccc(C(=O)Nc2ccc(F)c([C@@]3(CF)N=C(N)O[C@@H]4C[C@@H]43)c2)nc1]

or a pharmaceutically acceptable salt or tautomer thereof

In embodiment 99, the invention provides the compound

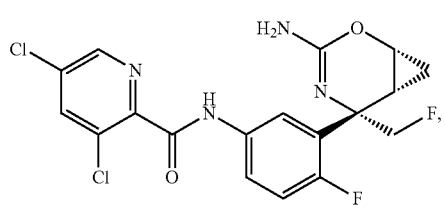 [SMILES: NC1=N[C@](CF)(c2cc(NC(=O)c3ncc(Cl)cc3Cl)ccc2F)[C@H]2C[C@H]2O1]

or a pharmaceutically acceptable salt or tautomer thereof

In embodiment 100, the invention provides the compound

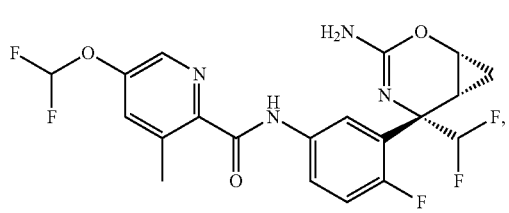 [SMILES: Cc1cc(OC(F)F)cnc1C(=O)Nc1ccc(F)c([C@@]2(C(F)F)N=C(N)O[C@@H]3C[C@@H]32)c1]

or a pharmaceutically acceptable salt or tautomer thereof

In embodiment 101, the invention provides the compound

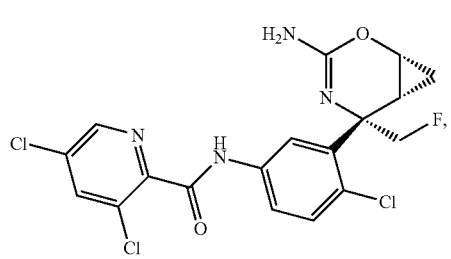 [SMILES: NC1=N[C@](CF)(c2cc(NC(=O)c3ncc(Cl)cc3Cl)ccc2Cl)[C@H]2C[C@H]2O1]

or a pharmaceutically acceptable salt or tautomer thereof

In embodiment 102, the invention provides the compound

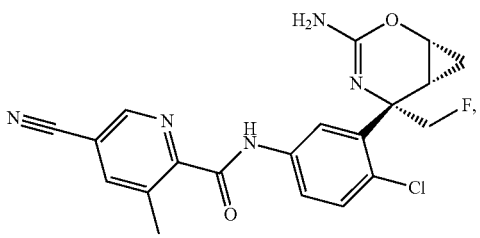 [SMILES: Cc1cc(C#N)cnc1C(=O)Nc1ccc(Cl)c([C@@]2(CF)N=C(N)O[C@@H]3C[C@@H]32)c1]

or a pharmaceutically acceptable salt or tautomer thereof

In embodiment 103, the invention provides the compound

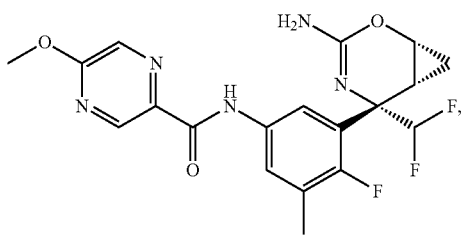 [SMILES: COc1cnc(C(=O)Nc2cc(C)c(F)c([C@@]3(C(F)F)N=C(N)O[C@@H]4C[C@@H]43)c2)cn1]

or a pharmaceutically acceptable salt or tautomer thereof

In embodiment 104, the invention provides the compound

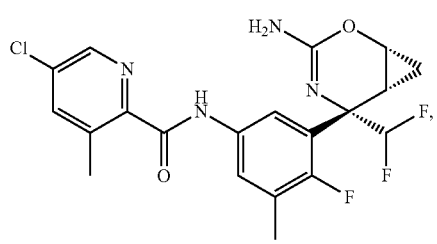 [SMILES: Cc1cc(Cl)cnc1C(=O)Nc1cc(C)c(F)c([C@@]2(C(F)F)N=C(N)O[C@@H]3C[C@@H]32)c1]

or a pharmaceutically acceptable salt or tautomer thereof

In embodiment 105 the invention provides the compound

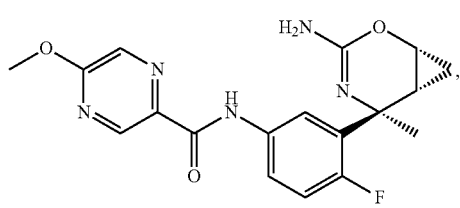 [SMILES: COc1cnc(C(=O)Nc2ccc(F)c([C@@]3(C)N=C(N)O[C@@H]4C[C@@H]43)c2)cn1]

or a pharmaceutically acceptable salt or tautomer thereof

In embodiment 106, the invention provides the compound

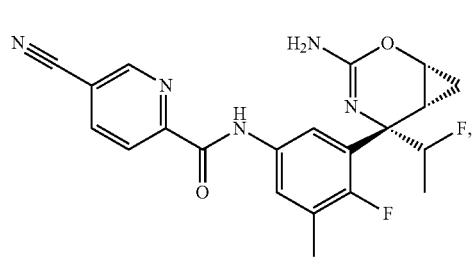 [SMILES: Cc1cc(NC(=O)c2ccc(C#N)cn2)cc([C@@]2(C(C)F)N=C(N)O[C@@H]3C[C@@H]32)c1F]

or a pharmaceutically acceptable salt or tautomer thereof

In embodiment 107, the invention provides the compound

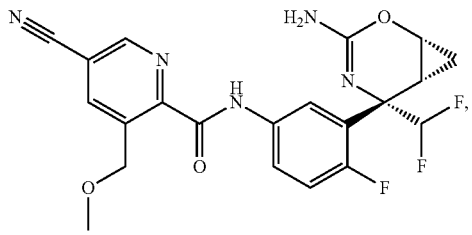 [SMILES: COCc1cc(C#N)cnc1C(=O)Nc1ccc(F)c([C@@]2(C(F)F)N=C(N)O[C@@H]3C[C@@H]32)c1]

or a pharmaceutically acceptable salt or tautomer thereof

In the structures depicted hereinabove, an "—N" in the 1,3-oxazine head group is intended to be an —NH₂ (an amine groups); and lines ending without an atom are understood by persons of ordinary skill in the art to be a —CH₃ group.

In another embodiment, the invention provides the compound of Formula I-A, I-B and I-C, II, II-A, or a stereoisomer or pharmaceutically acceptable salt thereof, as exemplified herein, provided the compound is not
N-(3-((1R,5R,6R)-3-amino-5-methyl-2-oxa-4-azabicyclo [4.1.0]hept-3-en-5-yl)-4-fluorophenyl)-3-methoxy-1,7-naphthyridin-8-amine or
N-(3-((1R,5R,6R)-3-amino-5-methyl-2-oxa-4-azabicyclo [4.1.0]hept-3-en-5-yl)-4-fluorophenyl)-5-methoxy-2-pyrazinecarboxamide.

All of the possible embodiments described herein for various of the R groups of the compounds of Formula I may be applied, as appropriate, to compounds of Formulas II and III, and any sub-formulas thereof In another embodiment, the invention provides each of the Exemplary compounds, and stereoisomers, tautomers, solvates, pharmaceutically acceptable salts, derivatives or prodrugs thereof, and related intermediates, described herein.

In another embodiment, the invention provides the exemplified compounds described herein, and pharmaceutically acceptable salt forms of each thereof.

The invention does not include the following compounds:
N-(3-((1R,5R,6R)-3-amino-5-methyl-2-oxa-4-azabicyclo [4.1.0]hept-3-en-5-yl)-4-fluorophenyl)-3-methoxy-1,7-naphthyridin-8-amine; and
N-(3-((1R,5R,6R)-3-amino-5-methyl-2-oxa-4-azabicyclo [4.1.0]hept-3-en-5-yl)-4-fluorophenyl)-5-methoxy-2-pyrazinecarboxamide.

DEFINITIONS

The following definitions should assist in understanding the metes and bounds of the invention.

The term "comprising" is meant to be open ended, i.e., all encompassing and non-limiting. It may be used herein synonymously with "having." Comprising is intended to include each and every indicated or recited component or element(s) while not excluding any other components or elements.

The term "$C_{\alpha-\beta}$alkyl", when used either alone or within other terms such as "haloalkyl" and "alkylamino", embraces linear or branched radicals having α to β number of carbon atoms (such as $C_1$-$C_{10}$; $C_1$-$C_6$; or $C_1$-$C_4$). Unless otherwise specified, one or more carbon atoms of the "alkyl" radical may be substituted, such as with a cycloalkyl moiety. Examples of "alkyl" radicals include methyl, cyclopropylmethyl, cyclobutylmethyl, cyclopentylmethyl, ethyl, cyclopropylethyl, cyclobutylethyl, cyclopentylethyl, n-propyl, isopropyl, n-butyl, cyclopropylbutyl, isobutyl, sec-butyl, tert-butyl, pentyl, isoamyl, hexyl and the like.

The term "$C_{\alpha-\beta}$alkenyl", when used alone or in combination, embraces linear or branched radicals having at least one carbon-carbon double bond in a moiety having a number of carbon atoms in the range from α and β. Included within alkenyl radicals are "lower alkenyl" radicals having two to about six carbon atoms and, for example, those radicals having two to about four carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "$C_{\alpha-\beta}$alkynyl", when used alone or in combination, denotes linear or branched radicals having at least one carbon-carbon triple bond in a moiety having a number of carbon atoms in the range from α and β. Examples of alkynyl radicals include "lower alkynyl" radicals having two to about six carbon atoms and, for example, lower alkynyl radicals having two to about four carbon atoms. Examples of such radicals include, without limitation, ethynyl, propynyl (propargyl), butynyl, and the like.

The term "$C_{\alpha-\beta}$-alkyl", "$C_{\alpha-\beta}$-alkenyl" and "$C_{\alpha-\beta}$-alkynyl", when used with other terms such as "wherein 1, 2 or 3 carbon atoms of said $C_{\alpha-\beta}$-alkyl, $C_{\alpha-\beta}$-alkenyl or $C_{2\alpha-\beta}$-alkynyl is optionally replaced with a heteroatom selected from O, S, S(O), S(O)₂ and N" embraces linear or branched radicals wherein one or more of the carbon atoms may be replaced with a heteroatom. Examples of such "alkyl" radicals include —O-methyl, —O— ethyl, —CH₂—O—CH₃, —CH₂CH₂—O—CH₃, —NH—CH₂, —CH₂CH₂—N(CH₃)—CH₃, —S—(CH₂)₃CH₂, —CH₂CH₂—S—CH₃ and the like. Accordingly, such radicals also include radicals encompassed by —OR⁷ where R⁷ may be defined as a $C_{\alpha-\beta}$-alkyl. Examples of such "alkenyl" radicals include —NH—CH₂CH=CH₂, —S—CH₂CH₂CH=CHCH₃ and the like. Similar examples exist for such "alkynyl" radicals, as appreciated by those skilled in the art.

The term "$C_{\alpha-\beta}$alkoxyl" or "—OC$_{\alpha-\beta}$alkyl" when used alone or in combination, embraces linear or branched oxygen-containing alkyl radicals each having α to β number of carbon atoms (such as $C_1$-$C_{10}$). The terms "alkoxy" and "alkoxyl", when used alone or in combination, embraces linear or branched oxygen-containing radicals each having alkyl and substituted alkyl portions of one or more carbon atoms. Examples of such radicals include methoxy, ethoxy, propoxy, butoxy, tert-butoxy and neopentoxy. Alkoxy radicals may be further substituted with one or more halo atoms, such as fluoro, chloro or bromo, to provide "haloalkoxy" radicals or with other substitution. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" multi-ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. The "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH₂—O— or —O—CH₂—CH₂—O— forms an aryl benzodioxolyl substituent.

The term "$C_{\alpha-\beta}$-cycloalkyl", also referred to herein as "carbocyclic", when used alone or in combination, denotes a partially or fully saturated ring radical having a number of carbon atoms in the range from $\alpha$ and $\beta$. The "cycloalkyl" may contain one ("monocyclic"), two ("bicyclic") or even three ("tricyclic") rings wherein such rings may be attached together in a fused manner and each formed from carbon atoms. Examples of saturated carbocyclic radicals include saturated 3 to 6-membered monocyclic groups such as cyclopropane, cyclobutane, cyclopentane and cyclohexane. Cycloalkyls may be substituted as described herein.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents. This includes carbocyclics, heterocyclics, aryl and heteroaryl rings.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of unsaturated heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, azaquinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The terms "heterocycle" or "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of saturated heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

The term "heterocycle" also embraces radicals where heterocyclic radicals are fused/condensed with aryl radicals: unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

Examples of partially saturated and fully saturated heterocyclyls include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted" refers to a single ring of 3-, 4-, 5-, 6-, 7- or 8-atom membered or a 6-, 7-, 8-, 9-, 10-, 11 or 12-atom membered bicyclic ring system comprising the delineated number of atoms, the atoms being carbon or, where indicated, a heteroatom such as nitrogen (N), oxygen (O) or sulfur (S). Where the number of atoms is not delineated, such as a "monocyclic ring system" or a "bicyclic ring system", the numbers of atoms are 3-8 for a monocyclic and 6-12 for a bicyclic ring. The ring or ring system may contain substitutents thereon, attached at any atom that allows a stable compound to be formed. A bicyclic ring is intended to include fused ring systems as well as spiro-fused rings. This phrase encompasses carbocyclics, heterocyclics, aryl and heteroaryl rings.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N, N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The term "carbonyl", whether used alone or with other terms, such as "aminocarbonyl", denotes —(C=O)—. "Carbonyl" is also used herein synonymously with the term "oxo".

The term "alkylthio" or "thioalkoxy" embraces radicals containing a linear or branched alkyl radical, of one to ten carbon atoms, attached to a divalent sulfur atom. An example of "alkylthio" or "thioalkoxy" is methylthio, ($CH_3S$—).

The term "Formula I" includes any sub formulas, such as Formulas II and III. Similar with Formulas II and III, in that they include sub-formulas where described.

The present invention also includes tautomeric forms of compounds of the invention. For example, the invention comprises compounds of formula I as well as their tautomers, as shown:

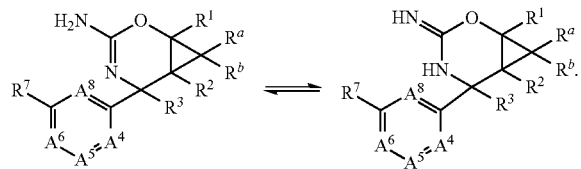

Similarly, tauatomers of compounds of Formulas II and III, and of compounds of sub-formulas of compounds of Formulas I, II and III, are also included in the invention.

The term "pharmaceutically-acceptable" when used with reference to a compound of Formulas I-III is intended to refer to a form of the compound that is safe for administration. For example, a salt form, a solvate, a hydrate, a prodrug or derivative form of a compound of Formulas I-III, which has been approved for mammalian use, via oral ingestion or other routes of administration, by a governing body or regulatory agency, such as the Food and Drug Administration (FDA) of the United States, is pharmaceutically acceptable.

Included in the compounds of Formulas I-III are the pharmaceutically acceptable salt forms of the free-base compounds. The term "pharmaceutically-acceptable salts" embraces salts commonly used to form alkali metal salts and to form addition salts of free acids or free bases. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I-III may be prepared from an inorganic acid or from an organic acid. Examples of such inorganic acids are hydrochloric, hydrobromic, hydroiodic, hydrofluoric, nitric, carbonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I-III include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I-III.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66:1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "pharmaceutically-acceptable derivative" as used herein, denotes a derivative which is pharmaceutically acceptable.

The compound(s) of Formulas I-III may be used to treat a subject by administering the compound(s) as a pharmaceutical composition. To this end, the compound(s) can be combined with one or more excipients, including without limitation, carriers, diluents or adjuvants to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective dosage amount" is intended to quantify the amount of each agent, which will achieve the goal of improvement in disorder severity and the frequency of incidence over treatment of each agent by itself, while avoiding adverse side effects typically associated with alternative therapies. Accordingly, this term is not limited to a single dose, but may comprise multiple dosages required to bring about a therapeutic or prophylactic response in the subject. For example, "effective dosage amount" is not limited to a single capsule or tablet, but may include more than one capsule or tablet, which is the dose prescribed by a qualified physician or medical care giver to the subject.

The term "leaving group" (also denoted as "LG") generally refers to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., SCH$_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

GENERAL SYNTHETIC PROCEDURES

The present invention further comprises procedures for the preparation of compounds of Formulas I-III. The compounds of Formulas I-III can be synthesized according to the procedures described in the following Schemes 1, 2, 3a, 3b, 4 and 5, wherein the substituents are as defined for Formulas I-III above, except where further noted. The synthetic methods described below are merely exemplary, and the compounds of the invention may also be synthesized by alternate routes utilizing alternative synthetic strategies, as appreciated by persons of ordinary skill in the art.

The following list of abbreviations used throughout the specification represent the following and should assist in understanding the invention:

ACN, MeCN—acetonitrile
Aq., aq.—aqueous
Ar—argon (gas)
BOC—tert-butoxycarbonyl
BOP—benzotriazol-1-yl-oxy Hexafluorophosphate
BuLi—Butyllithium
Cs$_2$CO$_3$—cesium carbonate
CHCl$_3$—chloroform
CH$_2$Cl$_2$, DCM—dichloromethane, methylene chloride
Cu(1)I—copper(1) iodide
DCC—dicyclohexylcarbodiimide
DEA—diethylamine
DIC—1,3-diisopropylcarbodiimide
DIEA, DIPEA—diisopropylethylamine
DME—dimethoxyethane
DMF—dimethylformamide
DMAP—4-dimethylaminopyridine
DMSO—dimethylsulfoxide
EDC, EDCI—1-(3-dimethylaminopropyl)-3-ethylcarbodiimide
Et$_2$O—diethyl ether
EtOAc—ethyl acetate
g, gm—gram
h, hr—hour
H$_2$—hydrogen (gas)
H$_2$O—water
HATU—O-(7-azabenzotriazol-1-yl)-N,N,N',N'-tetramethyluroniumhexafluorophosphate
HBr—hydrobromic acid
HCl—hydrochloric acid
HOBt—1-hydroxybenzotriazole hydrate
HOAc—acetic acid
HPLC—high pressure liquid chromatography
IPA, IpOH—isopropyl alcohol
K$_2$CO$_3$—potassium carbonate
KI—potassium iodide
LG—leaving group
LDA—Lithium diisopropylamide
LiOH—lithium hydroxide
MgSO$_4$—magnesium sulfate
MS—mass spectrum
MeOH—methanol
N$_2$—nitrogen (gas)
NaCNBH$_3$—sodium cyanoborohydride
Na$_2$CO$_3$—sodium carbonate
NaHCO$_3$—sodium bicarbonate
NaH—sodium hydride
NaI—sodium iodide
NaBH$_4$—sodium borohydride
NaOH—sodium hydroxide
Na$_2$SO$_4$—sodium sulfate
NH$_4$Cl—ammonium chloride
NH$_4$OH—ammonium hydroxide
P(t-bu)$_3$—tri(tert-butyl)phosphine
Ph$_3$P—triphenylphosphine
Pd/C—palladium on carbon
Pd(PPh$_3$)$_4$—palladium(0)triphenylphosphine tetrakis
Pd(dppf)Cl$_2$—palladium(1,1-bisdiphenylphosphinoferrocene) II chloride
Pd(PhCN)$_2$Cl$_2$—palladium di-cyanophenyl dichloride
Pd(OAc)$_2$—palladium acetate
Pd$_2$(dba)$_3$—tris(dibenzylideneacetone) dipalladium
PyBop—benzotriazol-1-yl-oxy-tripyrrolidino-phosphonium hexafluorophosphate
RT, rt—room temperature
RBF, rbf—round bottom flask
TLC, tlc—thin layer chromatography TBAF—Tetrabutylammonium flouride
TBTU—O-benzotriazol-1-yl-N,N,N,N'-tetramethyluronium tetrafluoroborate
TEA, Et₃N—triethylamine
TFA—trifluoroacetic acid
THF—tetrahydrofuran
UV—ultraviolet light Scheme 1-A

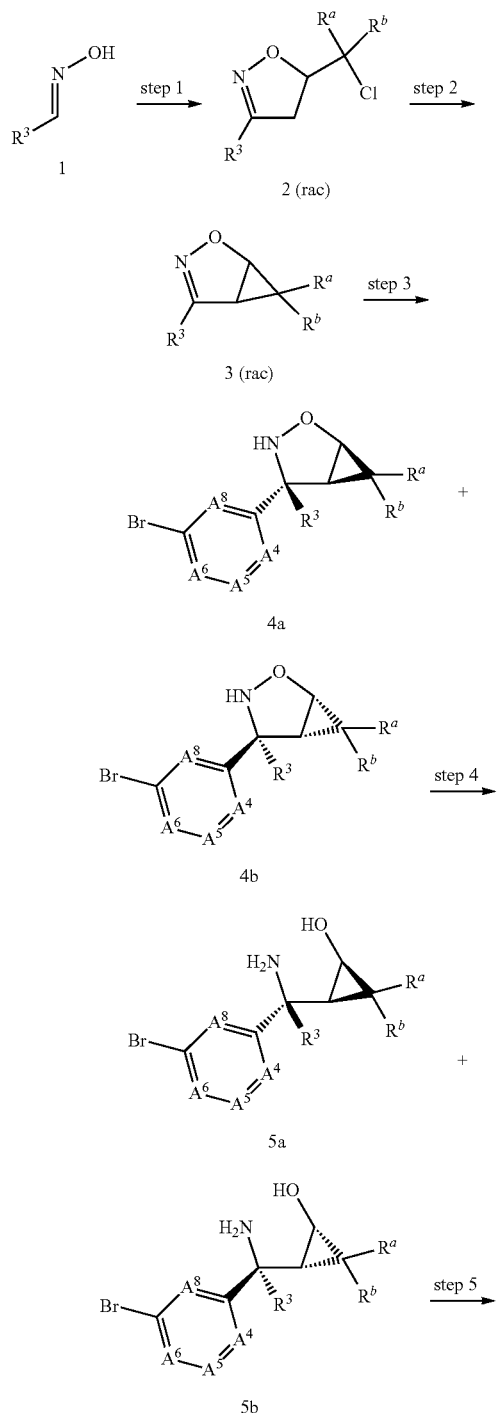

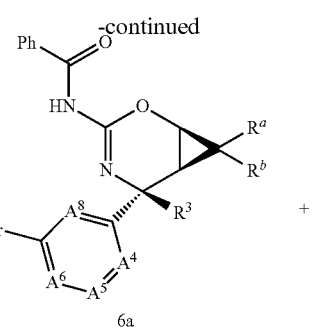

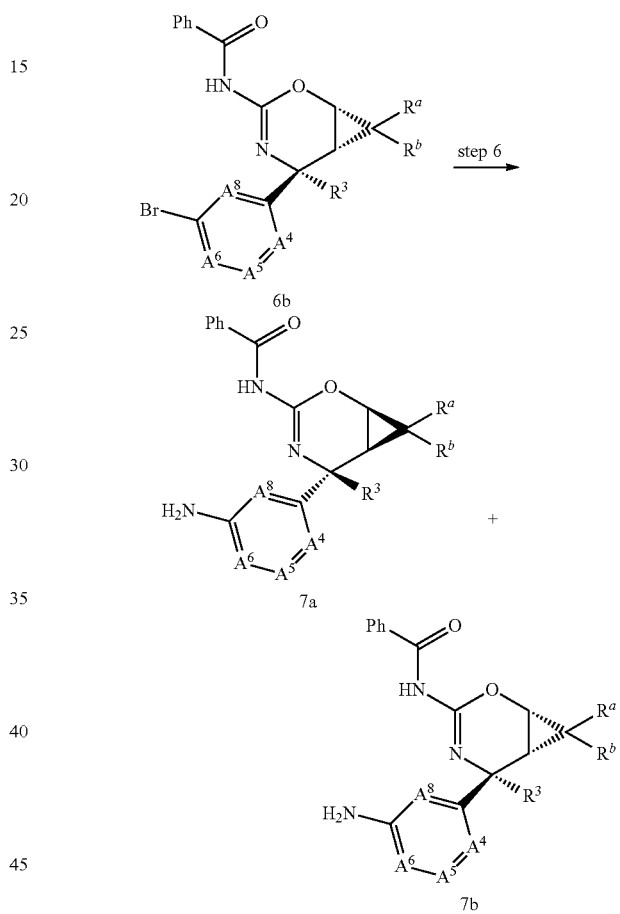

Scheme 1 describes an exemplary method for preparing compounds 7a and 7b of Formulas I, II and III, wherein each of $A^4$, $A^5$, $A^6$ and $A^8$ is, independently, as defined hereunder, each of $R^1$ and $R^2$, independently, is H, and $R^3$ is $CH_3$. Beginning with compound 1, aldehyde oxime may be converted to the corresponding chloride using N-chlorosuccinimide under suitable conditions. The chloride of compound 1 may be converted to intermediate 2 by treatment with allyl chloride under suitable conditions and in suitable solvents, to afford racemate 2. Ring closure of intermediate 2 can be effected by treating 2 with a sufficiently strong base, such as potassium t-butoxide, to provide racemic intermediate 3. The (hetero) aryl group can be installed in compounds of Formulas I, II and III, using a lewis acid, such as a boron agent, with methyllithium lithium bromide under suitable conditions to afford intermediates 4a and 4b as a racemic mixture. The oxazole ring of racemic intermediate 4 can be opened using zinc in acetic acid under suitable conditions to afford intermediates 5a and 5b as a racemic mixture. Racemic mixture 5a and 5b can be re-closed to the corresponding 6-membered ring by treatment of mixture 5a and 5b with benzoylisothiocyante under suitable conditions and solvent, to provide intermediates 6a and 6b as a racemic mixture. The bromide of intermediates 6a and 6b can be converted to the corresponding amine by first converting the bromide of 6a and 6b to the corresponding azide by conventional methods, such as those described in Example 1 herein. The azide is then reduced with a suitable reducing agent, such as sodium borohydride, under conventional conditions to provide the intermediates 7a and 7b, as a racemic mixture. Intermediates 7a and 7b, either as a racemic mixture or separately, may then used as described herein to prepare compounds of Formulas I, II and III wherein each of $R^1$ and $R^2$ are H, respectively, $R^3$ is $CH_3$ and having the desired $R^7$ group. Such compounds may be prepared using the schemed shown and described hereinbelow and/or using the methods described in the Examples provided herein.

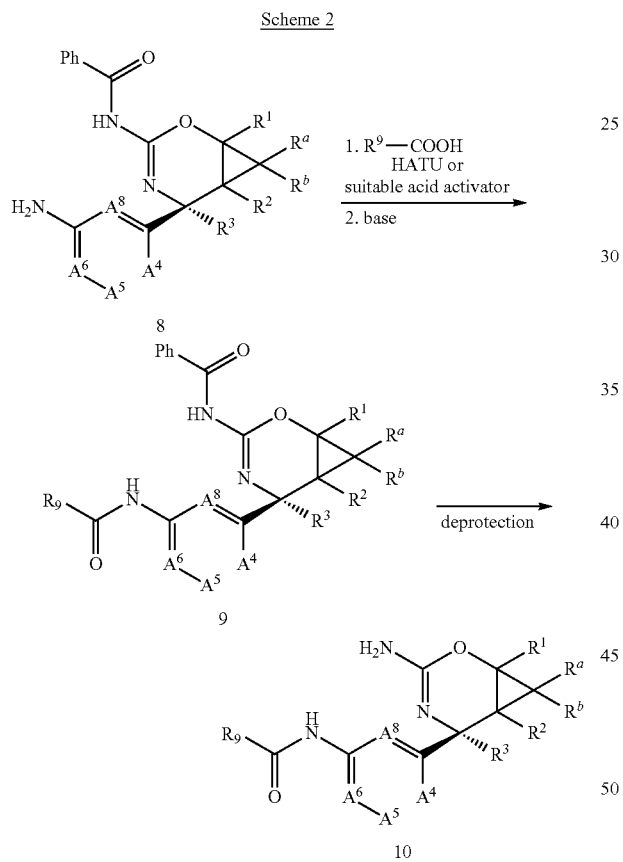

As shown, desired $R^9$-amide-linked compounds 10 can be prepared as desired, such as by treatment of aniline 8 with a desired $R^9$-carboxylic acid in conjunction with a known acid activating reagent, such as HATU, TBTU or DMTMM (see Method A and B for Example 2) to afford the desired protected amide-linked adduct 9. Compound 9 can be deprotected using known conditions, such as with a base, such as ammonia or DBU in a suitable solvent, to afford final compounds 10 of Formula I and I-A.

Acid activating groups convert the OH of the acid into a strong leaving group "LG." A "leaving group" which may be a halide such as an iodide, bromide, chloride or fluoride. LG may also be a non-halide moiety such as an alkylsulfonate or other known groups which generally form an electrophilic species (E+) Coupling reactions generally occur more readily in one or a combination of solvents and a base. Suitable solvents include, without limitation, generally non-nucleophilic, anhydrous solvents such as toluene, $CH_2Cl_2$, THF, DMF, N,N-dimethylacetamide and the like. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH and the like, alkoxides such as $NaOCH_3$, and the like. The base itself may also serve as a solvent. These coupling reactions are generally fast and conversion occurs typically in ambient conditions. However, depending upon the particular substrate, such reactions may require heat, as appreciated by those skilled in the art.

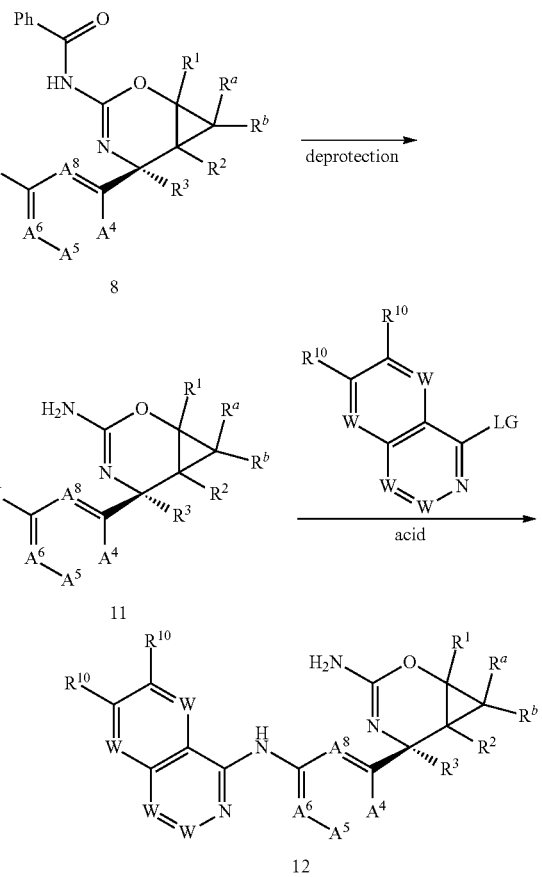

As shown, desired compounds 12 of Formulas I, I-B, II and III can be prepared as shown in scheme 3. First, compound 8 is deprotected using conventional techniques, and the aniline adduct 11 can be functionalized to the desired compound. A desired bicyclic $R^7$ group having a suitable leaving group, such as a chloride (Cl) or other aromatic leaving group, can be reacted with compound 11 in the presence of a suitable acid, such as of sulfuric acid. This allows coupling of the bicyclic heteroaromatic $R^7$ group to the amine to form compounds 12 of Formulas I, I-B, II and III.

EXAMPLES

The Examples, described herein below, represent various exemplary starting materials, intermediates and compounds of Formulas I-III, which should assist in a better understanding and appreciation of the scope of the present invention and of the various methods which may be used to synthesize compounds of Formulas I-III. It should be appreciated that the general methods above and specific examples below are illustrative only, for the purpose of assistance and of understanding the present invention, and should not be construed as limiting the scope of the present invention in any manner.

Chromatography:

Unless otherwise indicated, crude product-containing residues were purified by passing the crude material or concentrate through either a Biotage or Isco brand silica gel column (pre-packed or individually packed with SiO$_2$) and eluting the product off the column with a solvent gradient as indicated. For example a description of (330 g SiO$_2$, 0-40% EtOAc/Hexane) means the product was obtained by elution from the column packed with 330 gms of silica, with a solvent gradient of 0% to 40% EtOAc in Hexanes.

Preparative HPLC Method:

Where so indicated, the compounds described herein were purified via reverse phase HPLC using one of the following instruments: Shimadzu, Varian, Gilson; utilizing one of the following two HPLC columns: (a) a Phenomenex Luna or (b) a Gemini column (5 micron or 10 micron, C18, 150×50 mm)

A typical run through the instrument included: eluting at 45 ml/min with a linear gradient of 10% (v/v) to 100% MeCN (0.1% v/v TFA) in water (0.1% TFA) over 10 minutes; conditions can be varied to achieve optimal separations.

Proton NMR Spectra:

Unless otherwise indicated, all $^1$H NMR spectra were run on a Bruker series 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method (commonly referred to as an ESI MS) utilizing a PE SCIEX API 150EX MS instrument or an Agilent 1100 series LC/MSD system. Compounds having an isotopic atom, such as bromine and the like, are generally reported according to the detected isotopic pattern, as appreciated by those skilled in the art.

The compounds disclosed and described herein have been named using either (1) the naming convention provided with Chem-Draw Ultra 11.0 software, available in Chem Office, or (2) by the ISIS database software (Advanced Chemistry Design Labs or ACD software).

Example 1

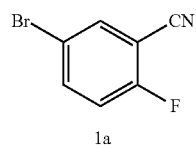

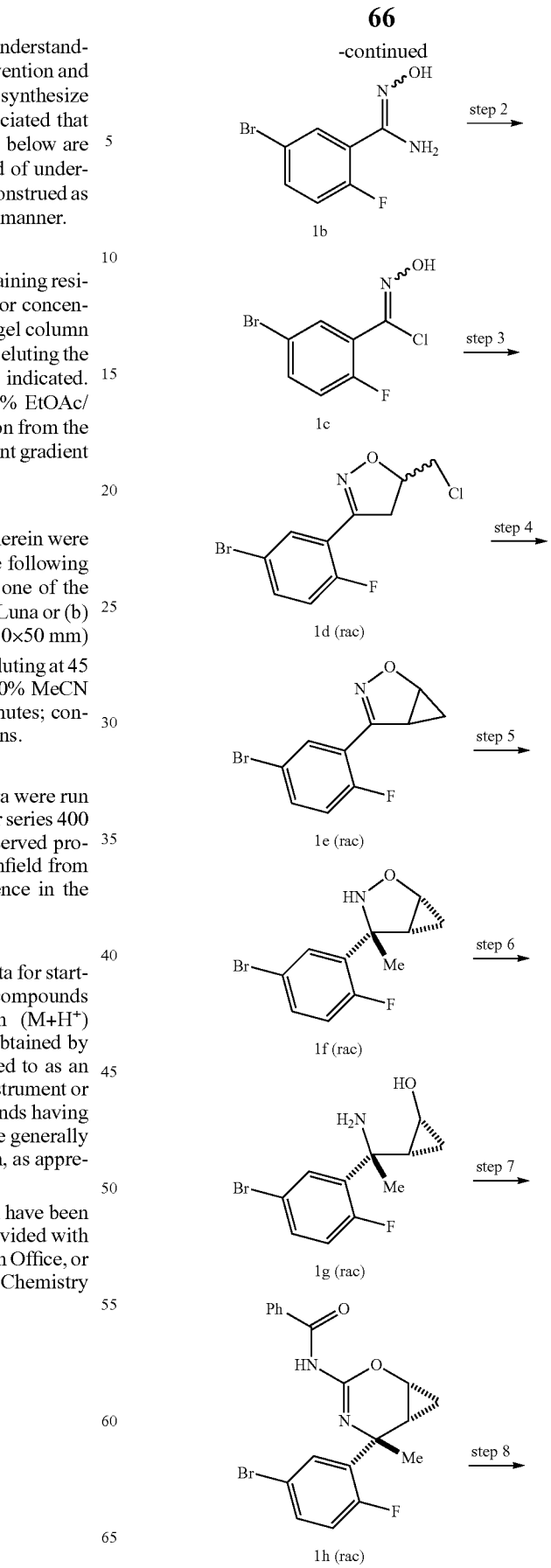

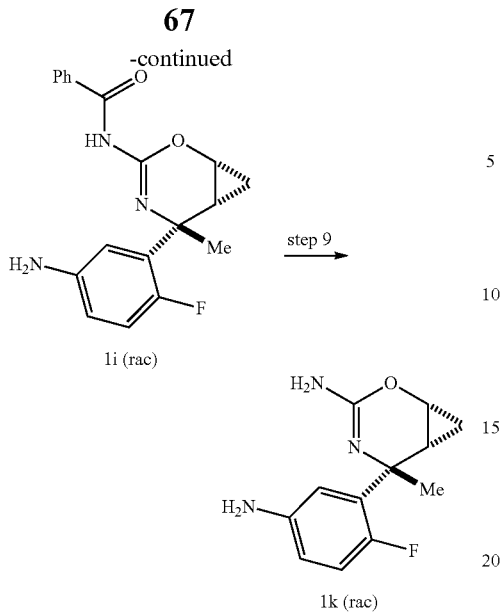

1i (rac)

1k (rac)

Synthesis of Intermediate 1i

Step 1: (E,Z)-5-bromo-2-fluoro-N'-hydroxybenzimidamide (1b)

5-Bromo-2-fluorobenzonitrile (65 g, 325 mmol, Matrix) was suspended in water (325 mL) and hydroxyl ammonium chloride (49.7 g, 715 mmol) was added. The pH was adjusted to pH=10 by adding 1 M NaOH solution (500 mL), followed by 10 M NaOH (5 mL). The suspension was stirred for 1 h at RT and subsequently heated to 100° C. for 3 hs. The reaction mixture was cooled to 0° C., upon which a white solid precipitated, which was filtered off. The solid was dissolved in EtOAc and dried over MgSO$_4$. The solvent was removed under reduced pressure to obtain the title compound as a beige solid (70 g, 300 mmol, 92% yield) which was taken onto the next step without further purification.

MS m/z=232.9 M$^+$. Calculated for $C_7H_6BrFN_2O$: 233.04

Step 2: (E,Z)-5-bromo-2-fluoro-N-hydroxybenzimidoyl chloride (1c)

(E,Z)-5-Bromo-2-fluoro-N'-hydroxybenzimidamide (1b, 19.9 g, 85 mmol) was suspended in water (100 mL). The suspension was cooled to 5° C. and hydrochloric acid (37%, 42.1 ml, 512 mmol) was added, followed by drop wise addition of a solution of sodium nitrite (5.89 g, 85 mmol, Aldrich) in 30 mL water. The internal reaction temperature was maintained below 5° C. for 4 h and then raised to 30° C. for 1 h. The reaction mixture was cooled to RT. The solid was filtered off and dissolved in $CH_2Cl_2$. The solution was washed with water and dried over MgSO$_4$. The solvent was removed under reduced pressure. The residue was dissolved in Et$_2$O and hexanes. Upon removing the solvent under reduced pressure a fine yellow solid formed which was filtered off and dried. The solid was identified as title compound (6 g) and taken onto the next step without further purification. MS m/z=253.9 [M+H]$^+$. Calculated for $C_7H_4BrClFNO$: 252.47.

Step 3: 3-(5-bromo-2-fluorophenyl)-5-(chloromethyl)-4,5-dihydroisoxazole (1d-rac)

TEA (0.551 ml, 3.96 mmol, Aldrich) was added drop wise to a stirred solution of (Z)-5-bromo-2-fluoro-N-hydroxybenzimidoyl chloride (1c, 1 g, 3.96 mmol) at 0° C., followed by a solution of allyl chloride (0.968 ml, 11.88 mmol, Aldrich) in Et$_2$O (20 mL). The reaction mixture was allowed to stir at RT for 4 hs. 2 M HCl (10 mL) was added, followed by water and EtOAc. The organic phase was separated and dried over MgSO$_4$. The solvent was removed under reduced pressure. The crude material was absorbed onto a plug of silica gel and purified by chromatography eluting with a gradient of 3% to 35% EtOAc in hexane, to provide the title compound as colorless oil (0.604 g, 2.065 mmol, 52.1% yield). MS m/z=293.9 [M+H]$^+$. Calculated for $C_{10}H_8BrClFNO$ 292.53.

Step 4: 4-(5-bromo-2-fluorophenyl)-2-oxa-3-azabicyclo[3.1.0]hex-3-ene (1e-rac)

Potassium t-butoxide (176 mg, 1.572 mmol, Aldrich) was added in small portions over a time period of 20 min to a solution of 3-(5-bromo-2-fluorophenyl)-5-(chloromethyl)-4,5-dihydroisoxazole (200 mg, 0.684 mmol, 1d rac) in DMSO (4 mL) cooled with a water bath. After completed, the reaction was quenched by the addition of ice. EtOAc was added and the organic phase was separated. The organic phase was dried over MgSO$_4$ and the solvent was removed under reduced pressure. The crude material was absorbed onto a plug of silica gel and purified by chromatography, eluting with 3% to 5% EtOAc in hexane, to provide the title compound as a colorless oil (154 mg, 0.601 mmol, 88% yield). MS m/z=257.9 [M+H]$^+$. Calculated for $C_{10}H_7BrFNO$: 256.07.

Step 5: [1(S,R),4(S,R),5(S,R)]-4-(5-bromo-2-fluorophenyl)-4-methyl-2-oxa-3-azabicyclo[3.1.0]hexane (1f-rac)

A solution of 4-(5-bromo-2-fluorophenyl)-2-oxa-3-azabicyclo[3.1.0]hex-3-ene (1e rac; 10 g, 39.1 mmol) in DCM (400 mL) was cooled to −78° C. Boron fluoride diethyl etherate (8.19 ml, 66.4 mmol, Aldrich) was added and the reaction mixture was stirred for 5 min. A solution of methyllithium lithium bromide (1.5 M solution in Et$_2$O; 31.2 ml, 46.9 mmol) was added drop wise. The temperature was maintained at −78° C. After 2 hs, additional methyllithium lithium bromide solution (31.2 ml, 46.9 mmol) was added drop wise. After 4 hs reaction time, additional boron fluoride diethyl etherate (8.19 ml, 66.4 mmol) and an additional portion of MeLi lithium bromide solution (1.5 M solution in Et$_2$O; 31.2 ml, 46.9 mmol) were added. The reaction mixture was stirred for one more hour at −78° C. The reaction was quenched by the addition of aqueous, saturated ammonium chloride solution. EtOAc was added to the mixture and the organic phase was separated and dried over MgSO$_4$. The solvent was removed under reduced pressure. The crude material was loaded onto a plug of silica gel and purified by chromatography, eluting with a gradient of 5% to 25% EtOAc in hexane, to provide the title compound as a light-yellow oil (2.48 g, 9.11 mmol, 23.34% yield). MS m/z=272.0/274.0 M$^+$/[M+2]$^+$. Calculated for $C_{11}H_{11}BrFNO$: 272.11

Step 6: [1(S,R),2(S,R)]-2-[(S,R)-1-amino-1-(5-bromo-2-fluorophenyl)ethyl]-cyclopropanol (1g-rac)

[1(S,R),4(S,R),5(S,R)]-4-(5-bromo-2-fluorophenyl)-4-methyl-2-oxa-3-azabicyclo[3.1.0]hexane (1f rac; 5.197 g, 19.10 mmol) was dissolved in glacial acetic acid (49.6 ml, 859 mmol, EMD). Zinc dust (12.49 g, 191 mmol, Aldrich) was added portion wise at RT. The resulting thick suspension was stirred for 1 hour. The reaction mixture was filtered. The filter cake was washed with acetic acid and water. The filtrate was concentrated under reduced pressure. Water was added to the residue and the pH was adjusted to pH 10 with aqueous, saturated potassium carbonate solution. A suspension formed. The solid was filtered off and the filtrate was extracted with $CHCl_3$, followed by extraction with a solution of 10% MeOH/DCM. The combined organic phases were concentrated under reduced pressure. The residue was dissolved in DCM and dried over $MgSO_4$. The solvent was removed under reduced pressure to obtain the title compound as a yellow oil (5.044 g, 18.40 mmol, 96% yield), which was used in the next step without further purification. MS m/z=275.9 $[M+H]^+$. Calculated for $C_{11}H_{13}BrFNO$: 274.13.

Step 7: N-[[1(S,R),5(S,R),6(S,R)]-5-(5-bromo-2-fluorophenyl)-5-methyl-2-oxa-4-azabicyclo[4.1.0]hept-3-en-3-yl]benzamide (1h-rac)

[1(S,R),2(S,R)]-2-[(S,R)-1-amino-1-(5-bromo-2-fluorophenyl)ethyl]cyclopropanol (1g rac; 5.044 g, 18.40 mmol) was dissolved in THF (100 mL) and benzoyl isothiocyanate (2.72 mL, 20.24 mmol, Aldrich) was added. The reaction mixture was allowed to stir at RT. After 10 min reaction time, the solvent was removed under reduced pressure to obtain a yellow foam, which was taken up in acetonitrile (100 mL). A solution of 1,3-dicyclohexylcarbodiimide (1 M in DCM, 18.40 mL, 18.40 mmol, Aldrich) was added, followed by triethylamine (0.512 mL, 3.68 mmol, Aldrich). The reaction mixture was heated to 80° C. for 3 hs. The reaction mixture was cooled to room temperature upon which a solid precipitated. The reaction mixture was filtered and the filtrate was loaded onto a plug of silica gel and purified by chromatography, eluting with a gradient of 5% to 35% EtOAc in hexane, to provide the title compound as a yellow oil (6.438 g, 15.97 mmol, 87% yield; 90% purity). MS m/z=403.0 $M^+$. Calculated for $C_{19}H_{16}BrFN_2O_2$: 403.25

Step 8: N-[[1(S,R),5(S,R),6(S,R)]-5-(5-amino-2-fluorophenyl)-5-methyl-2-oxa-4-azabicyclo[4.1.0]hept-3-en-3-yl]benzamide (1i-rac)

A sealable flask was charged with sodium azide (2.322 g, 35.7 mmol, Aldrich), copper(I) iodide (0.453 g, 2.381 mmol, Aldrich) and (+)-sodium L-ascorbate (0.236 g, 1.190 mmol, Acros). The flask was evacuated and backfilled with nitrogen gas. A solution of N-[[1(S,R),5(S,R),6(S,R)]-5-(5-bromo-2-fluorophenyl)-5-methyl-2-oxa-4-azabicyclo[4.1.0]hept-3-en-3-yl]benzamide (1h rac, 4.8 g, 11.90 mmol) in ethanol (40.5 ml) was added, followed by water (16.20 ml). The reaction mixture was purged with nitrogen gas for 2 min. Trans-N,N'-dimethyl-1,2-cyclohexanediamine (0.563 ml, 3.57 mmol, Aldrich) was added and the reaction mixture was heated to 80° C. for 2.5 hs. The reaction was poured into a mixture of aqueous $NH_4Cl/NH_4OH$ (200 mL, 9:1) and subsequently extracted with EtOAc. The organic layer was washed with brine, dried over $Na_2SO_4$, and concentrated under reduced pressure. The residue was dissolved in MeOH (150 mL) and sodium borohydride (0.901 g, 23.81 mmol, Aldrich) was added portion wise at RT. Additional portions of sodium borohydride (0.901 g, 23.81 mmol, Aldrich) were added after 1 hs and 2 hs reaction time. Copper(I) iodide (2.2 g, 11.9 mmol, Aldrich) was added, followed by an additional portion sodium borohydride (0.901 g, 23.81 mmol, Aldrich). After 20 min, water was added and the reaction mixture was concentrated under reduced pressure. The remaining aqueous solution was extracted with EtOAc. The organic phase was washed with brine and dried over $Na_2SO_4$. The filtrate was concentrated and purified by silica gel column (10-100% EtOAc/hexanes) to afford the title compound (2.55 g, 7.51 mmol, 63.1% yield) as a beige solid.

MS m/z=340.1 $[M+H]^+$. Calculated for $C_{19}H_{18}FN_3O_2$: 339.36.

Step 9: [1(S,R),5(S,R),6(S,R)]-5-(5-amino-2-fluorophenyl)-5-methyl-2-oxa-4-azabicyclo[4.1.0]hept-3-en-3-amine (1k-rac)

A solution of N-[[1(S,R),5(S,R),6(S,R)]-5-(5-azido-2-fluorophenyl)-5-methyl-2-oxa-4-azabicyclo[4.1.0]hept-3-en-3-yl]benzamide (1i-rac, 0.7 g, 2.063 mmol) in ammonia (2M solution in methanol; 30.9 ml, 61.9 mmol, Aldrich) was heated to 80° C. After 12 hs, additional ammonia (2M solution in methanol; 30.9 ml, 61.9 mmol, Aldrich) was added and the reaction mixture was heated for 24 hs. The solvent was removed under reduced pressure and water (50 mL) and 1 N HCl (50 mL) were added to the residue. The solution was extracted with EtOAc. The aqueous acidic phase was neutralized (pH=7) by the addition of aqueous saturated bicarbonate solution. The aqueous phase was extracted 4 times with EtOAc. The combined organic phases were dried over $MgSO_4$ and the solvent was removed under reduced pressure to obtain the title compound (350 mg), which was taken onto the next step without further purification. MS m/z=236.1 $[M+H]^+$. Calculated for $C_{12}H_{14}FN_3O$: 235.26

Example 2

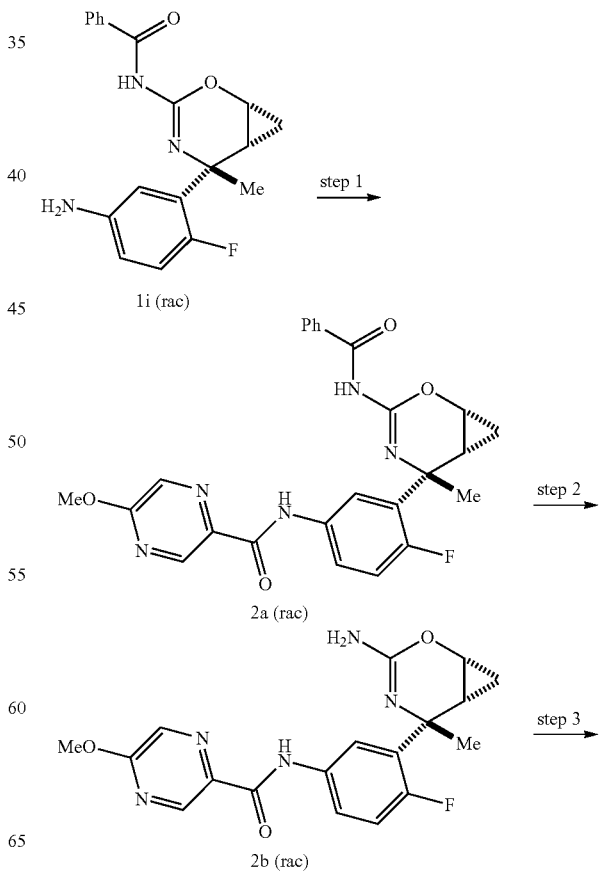

-continued

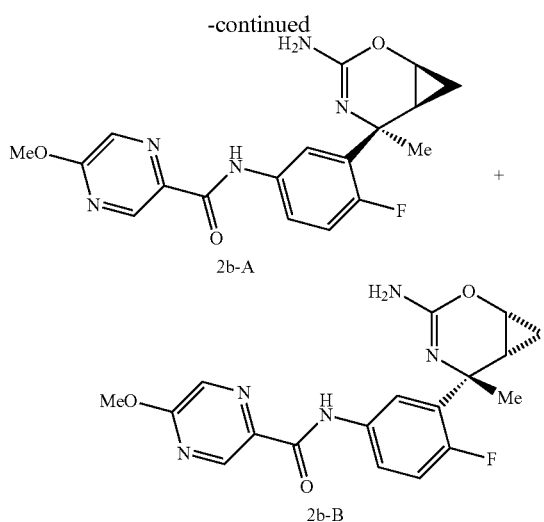

Step 1: N[3-[[1(S,R),5(S,R),6(S,R)]-3-benzamido-5-methyl-2-oxa-4-azabicyclo[4.1.0]hept-3-en-5-yl]-4-fluorophenyl]-5-methoxypyrazine-2-carboxamide (2a-rac)

To a solution of N-[[1(S,R),5(S,R),6(S,R)]-5-(5-amino-2-fluorophenyl)-5-methyl-2-oxa-4-azabicyclo[4.1.0]hept-3-en-3-yl]benzamide (1i-rac; 0.620 g, 1.827 mmol) in DMF (8.0 mL) were added 5-methoxypyrazine-2-carboxylic acid (0.282 g, 1.827 mmol, Ark Pharm), 1[bis(dimethylamino)methylene]-1H-1,2,3-triazolo[4,5-b]pyridinium 3-oxid hexafluorophosphate (1.042 g, 2.74 mmol, Aldrich) and diisopropylethylamine (0.636 mL, 3.65 mmol, Aldrich). The reaction was stirred at ambient temperature for 25 min. Water (50 mL) was added and the resulting suspension was stirred for 15 min, and then filtered. The solid was dried to afford the title compound as a yellow solid (0.75 g, 1.577 mmol, 86% yield). MS m/z=476.0 [M+H]$^+$. Calculated for $C_{25}H_{22}FN_5O_4$: 475.47

Step 2: N-[3-[(1(S,R),5(S,R),6(S,R))-3-amino-5-methyl-2-oxa-4-azabicyclo[4.1.0]hept-3-en-5-yl]-4-fluorophenyl]-5-methoxypyrazine-2-carboxamide (Example 2b-rac)

A sealable vial was charged with N-[3-[[1(S,R),5(S,R),6(S,R)]-3-benzamido-5-methyl-2-oxa-4-azabicyclo[4.1.0]hept-3-en-5-yl]-4-fluorophenyl]-5-methoxypyrazine-2-carboxamide (2a rac; 1.28 g, 2.69 mmol) and ammonia (2.0M solution in methanol; 30 ml, 60.0 mmol, Aldrich). The reaction mixture was heated to 80° C. for 34 hs. The reaction mixture was filtered. The filter cake was rinsed with MeOH and dried to afford the title compound as a tan solid (230 mg, 0.62 mmol, 46% yield).

MS m/z=372.0 [M+H]$^+$. Calculated for $C_{18}H_{18}FN_5O_3$: 371.37

$^1$H NMR (400 MHz, DMSO-d$_6$) δ ppm 0.36 (td, J=6.36, 2.74 Hz, 1H) 0.59 (dt, J=9.44, 6.24 Hz, 1H) 1.57 (s, 3H) 1.69 (dd, J=6.75, 3.23 Hz, 1H) 3.96-4.07 (m, 4H) 5.36 (s, 2H) 7.11 (dd, J=11.74, 8.80 Hz, 1H) 7.70 (dt, J=8.22, 3.72 Hz, 1H) 8.02 (dd, J=7.24, 2.74 Hz, 1H) 8.40 (d, J=1.37 Hz, 1H) 8.88 (d, J=1.17 Hz, 1H) 10.33 (s, 1H)

Step 3: N-(3-((1S,5S,6S)-3-amino-5-methyl-2-oxa-4-azabicyclo[4.1.0]hept-3-en-5-yl)-4-fluorophenyl)-5-methoxypyrazine-2-carboxamide (Example 2b-A) and N-(3-((1R,5R,6R)-3-amino-5-methyl-2-oxa-4-azabicyclo[4.1.0]hept-3-en-5-yl)-4-fluorophenyl)-5-methoxypyrazine-2-carboxamide (Example 2b-B)

N-[3-[(1(S,R),5(S,R),6(S,R))-3-amino-5-methyl-2-oxa-4-azabicyclo[4.1.0]hept-3-en-5-yl]-4-fluorophenyl]-5-methoxypyrazine-2-carboxamide (2b rac, 230 mg) was subjected to chromatography using supercritical $CO_2$ (additives 40% methanol with 20 mM $NH_3$) on a OD-H column (21×250 mm, 5 μm) eluting at a flow rate 70 ml/min (100 bar pressure, 40° C. column temperature). The first peak (retention time=1.19 min) provided (1S,5S,6S)-5-(2-fluoro-5-((3-methoxy-1,7-naphthyridin-8-yl)amino)phenyl)-5-methyl-2-oxa-4-azabicyclo[4.1.0]hept-3-en-3-amine (Example 2b-A, 108 mg, 0.28 mmol, 47% yield; 99% de; 99% ee) as a tan powder. The second peak (retention time=2.28 min) provided (1R,5R,6R)-5-(2-fluoro-5-((3-methoxy-1,7-naphthyridin-8-yl)amino)phenyl)-5-methyl-2-oxa-4-azabicyclo[4.1.0]hept-3-en-3-amine (Example 2b-B; 106 mg, 0.28 mmol, 46% yield; 99% de; 99% ee) as a tan powder.

MS m/z=372.1 [M+H]$^+$. Calculated for $C_{18}H_{18}FN_5O_3$: 371.37 (for both enantiomers) $^1$H NMR (Example 2-A; 400 MHz, CHLOROFORM-d) δ ppm 0.51 (td, J=6.94, 2.93 Hz, 1H) 0.69 (dt, J=9.68, 6.60 Hz, 1H) 0.79-0.95 (m, 1H) 1.72 (s, 4H) 1.79-1.91 (m, 1H) 3.95-4.14 (m, 4H) 7.06 (dd, J=11.44, 8.71 Hz, 1H) 7.65 (dd, J=6.85, 2.74 Hz, 1H) 7.97-8.05 (m, 1H) 8.14 (d, J=1.17 Hz, 1H) 9.02 (d, J=1.17 Hz, 1H) 9.51 (br. s., 1H) $^1$H NMR (Example 2-B; 400 MHz, CHLOROFORM-d) δ ppm 0.51 (td, J=6.94, 2.93 Hz, 1H) 0.69 (dt, J=9.83, 6.63 Hz, 1H) 1.72 (s, 4H) 1.84 (dtd, J=10.32, 6.97, 6.97, 3.91 Hz, 1H) 3.95-4.13 (m, 4H) 7.06 (dd, J=11.35, 8.80 Hz, 1H) 7.65 (dd, J=6.94, 2.84 Hz, 1H) 7.95-8.05 (m, 1H) 8.14 (d, J=1.17 Hz, 1H) 9.02 (d, J=1.17 Hz, 1H) 9.51 (br. s., 1H)

Example 3

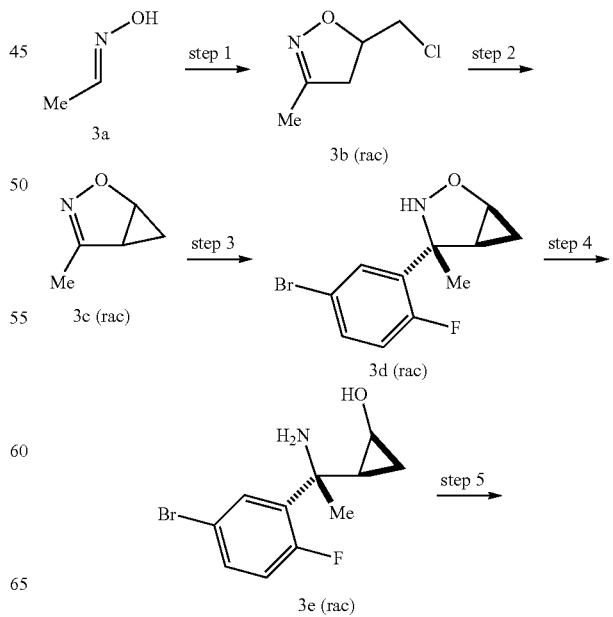

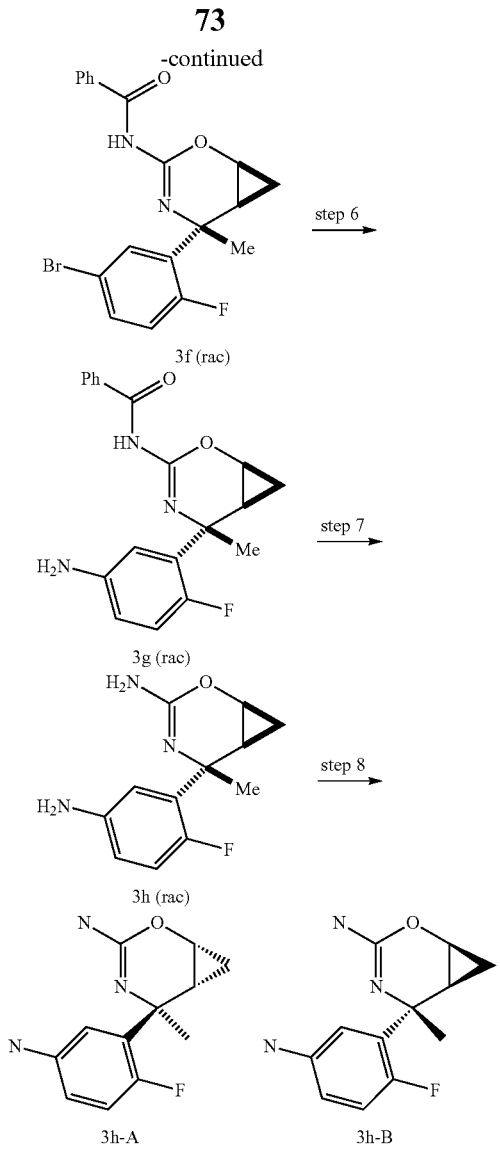

organic phase was separated and dried over MgSO$_4$. The solvent was removed under reduced pressure. The crude material was loaded onto a plug of silica gel and purified by chromatography eluting with a gradient of 5% to 35% EtOAc in hexane, to provide a yellow oil, which was dissolved in EtOAc and washed with aqueous CuSO$_4$ solution. The organic phase was separated and dried over MgSO$_4$. The solvent was removed under reduced pressure to obtain the title compound as a yellow oil (1.9 g, 14.22 mmol, 42.0% yield). MS m/z=134.0 [M+H]$^+$. Calculated for C$_5$H$_8$ClNO: 133.58

Step 2: [1(S,R),5(S,R)]-4-methyl-2-oxa-3-azabicyclo[3.1.0]hex-3-ene (3c-rac)

Potassium 2-methylpropan-2-olate (63.8 g, 568 mmol, Aldrich) was added portion wise to a solution of 5-(chloromethyl)-3-methyl-4,5-dihydroisoxazole (3b rac; 33 g, 247 mmol) in DMSO (618 mL) cooled with a water bath. The reaction was quenched after 30 min by the addition of ice. Et$_2$O was added and the organic phase was separated. The organic phase was washed with aqueous saturated LiCl solution and dried over MgSO$_4$. The Et$_2$O was removed by distillation under ambient pressure. The remaining liquid was distilled under reduced pressure and the title compound was obtained as a colorless oil (13 g, 134 mmol, 54.2% yield; boiling point 85° C. at 35 Torr). GCMS m/z=97 M$^+$. Calculated for C$_5$H$_7$NO: 97.12

Step 3: [1(S,R),4(R,S),5(S,R))-4-(5-bromo-2-fluorophenyl)-4-methyl-2-oxa-3-azabicyclo[3.1.0]hexane (3d-rac)

A solution of 4-bromo-1-fluoro-2-iodobenzene (8.52 g ml, 28.3 mmol, Matrix Scientific) in ether (20 ml) was cooled to −78° C. before adding a solution of n-butyllithium (2.5M in hexanes; 11.33 ml, 28.3 mmol, Aldrich) drop wise. The reaction mixture was stirred at −78° C. for 30 minutes. In a separate flask, a solution of [1(S,R),5(S,R)]-4-methyl-2-oxa-3-azabicyclo[3.1.0]hex-3-ene (1.1 g, 11.33 mmol, 3c rac) in toluene (110 ml) was cooled to −78° C. before adding boron fluoride diethyl etherate (1.677 ml, 13.59 mmol, Aldrich) drop wise. The solution was stirred at −78° C. for 15 minutes. The aryl-lithium solution was added to the isoxazoline solution drop wise via cannula. Upon complete addition the reaction was warmed to RT and stirred for 16 hours. The reaction was quenched with aqueous saturated ammonium chloride solution and diluted with water and EtOAc. The aqueous layer was washed with additional EtOAc and the organic layers were combined, washed with brine, dried over magnesium sulfate, and concentrated under reduced pressure. The crude residue was purified by silica gel flash chromatography using a gradient of 5-30% EtOAc in Hexanes to afford the title compound (1.969 g, 7.24 mmol, 63.9% yield). MS m/z=272.0 [M+H]$^+$. Calculated for C$_{11}$H$_{11}$BrFNO: 272.11

Step 4: [1(S,R),2(S,R)]-2-[(R,S)-1-amino-1-(5-bromo-2-fluorophenyl)ethyl]-cyclopropanol (3e-rac)

[1(S,R),4(R,S),5(S,R))-4-(5-bromo-2-fluorophenyl)-4-methyl-2-oxa-3-azabicyclo[3.1.0]hexane (2.5 g, 9.11 mmol, 3d rac) was dissolved in glacial acetic acid. (44.7 ml, 775 mmol, Aldrich). Zinc dust (5.96 g, 91 mmol, Aldrich) was added portion wise. The reaction was heated to 40° C. for 3.5 hours. The reaction was cooled to RT, filtered and the filter cake was washed with additional HOAc. The filtrate was concentrated under reduced pressure. The crude residue was Step 1:
5-(Chloromethyl)-3-methyl-4,5-dihydroisoxazole (3b-rac)

To a solution of acetaldehyde oxime (2.070 mL, 33.9 mmol, Alrich) in THF (30 mL)/Chloroform (15 mL) was added N-chlorosuccinimide (4.75 g, 35.6 mmol, Aldrich) in one portion, followed by drop wise addition of pyridine (1.369 mL, 16.93 mmol, Aldrich) at rt. After completed addition the reaction mixture was allowed to stir at RT for 4 hs. The solid was filtered off and the filtrate was cooled to 0° C. Additional solid precipitated out. The solution was decanted off and concentrated under reduced pressure to give a light-yellow oil, which was taken onto the next step assuming 100% theoretical yield (according to WO2008062739). The oil was dissolved in Et$_2$O (100 mL) and THF (5 mL). Allyl chloride (8.28 mL, 102 mmol, Aldrich) was added, followed by triethylamine (4.71 mL, 33.9 mmol, Aldrich). The reaction mixture was cooled to 0° C. The reaction mixture was allowed to warm up to RT and stirred for 3 days. The reaction mixture was filtered and the filtrate was washed with aqueous saturated ammonium chloride solution, followed by water. The dissolved in water and the solution was basified to pH=10 by the addition of saturated sodium bicarbonate aqueous solution and a few drops of 2M NaOH solution. The basic solution was extracted with chloroform three times. The combined organic layers were washed with brine, dried over magnesium sulfate and concentrated under reduced pressure to afford the title compound as a yellow solid. (2.4209 g, 8.83 mmol, 97% yield). MS m/z=274 [M+H]⁺.

Calculated for $C_{11}H_{13}BrFNO$: 274.129

Step 5: N-[[1(S,R),5(R,S),6(S,R)]-5-(5-bromo-2-fluorophenyl)-5-methyl-2-oxa-4-azabicyclo[4.1.0]hept-3-en-3-yl]benzamide (3f-rac)

The title compound was prepared using a procedure similar to that described in step 7 for the synthesis of 1h-rac, but using [1(S,R),2(S,R)]-2-[(R,S)-1-amino-1-(5-bromo-2-fluorophenyl)ethyl]-cyclopropanol (3e-rac). MS m/z=403.0 [M+H]⁺.

Calculated for $C_{19}H_{16}BrFN_2O_2$: 403.245

Step 6: N-[[1(S,R),5(R,S),6(S,R)]-5-(5-amino-2-fluorophenyl)-5-methyl-2-oxa-4-azabicyclo[4.1.0]hept-3-en-3-yl]benzamide (3g-rac)

The title compound was prepared using a procedure similar to that described in step 8 for the synthesis of 1i-rac, but using N-[[1(S,R),5(R,S),6(S,R)]-5-(5-bromo-2-fluorophenyl)-5-methyl-2-oxa-4-azabicyclo[4.1.0]hept-3-en-3-yl]benzamide (3f-rac). MS m/z=340.1 [M+H]⁺. Calculated for $C_{19}H_{18}FN_3O_2$: 339.364

Step 7: N-[[1(S,R),5(R,S),6(S,R)]-5-(5-amino-2-fluorophenyl)-5-methyl-2-oxa-4-azabicyclo[4.1.0]hept-3-en-3-amine (3h-rac)

The title compound was prepared using a procedure similar to that described in step 9 for the synthesis of 1k-rac, but using N-[[1(S,R),5(R,S),6(S,R)]-5-(5-amino-2-fluorophenyl)-5-methyl-2-oxa-4-azabicyclo[4.1.0]hept-3-en-3-yl]benzamide (3g-rac).

MS m/z=236.0 [M+H]⁺. Calculated for $C_{12}H_{14}FN_3O$: 235.25

Step 8: (1R,5S,6R)-5-(5-amino-2-fluorophenyl)-5-methyl-2-oxa-4-azabicyclo[4.1.0]hept-3-en-3-amine (3h-A) and (1S,5R,6S)-5-(5-amino-2-fluorophenyl)-5-methyl-2-oxa-4-azabicyclo[4.1.0]hept-3-en-3-amine (3h-B)

N-[[1(S,R),5(R,S),6(S,R)]-5-(5-amino-2-fluorophenyl)-5-methyl-2-oxa-4-azabicyclo[4.1.0]hept-3-en-3-amine (3h-rac) was subjected to chromatography using supercritical CO₂ (additives 22% EtOH with 20 mM NH₃) on a CHIRALPAK AD-H SFC column (21×250 mm, 5 μm) eluting at a flow rate 70 ml/min (100 bar pressure, 40° C. column temperature). The first peak (retention time=1.57 min) provided (Example 3h-A, 454 mg, 1.930 mmol, 41% yield; 99% de; 99% ee) as a white powder. The second peak (retention time=2.31 min) provided (Example 3h-B, 464 mg, 1.972 mmol, 42% yield; 99% de; 99% ee) as a white powder. MS m/z=236.2 [M+H]⁺. Calculated for $C_{12}H_{14}FN_3O$=235.112 (for both enantiomers)

¹H NMR (400 MHz, CHLOROFORM-d) δ ppm 0.76-0.84 (m, 1H) 0.94 (td, J=6.80, 2.64 Hz, 1H) 1.58 (d, J=1.37 Hz, 3H) 1.71-1.80 (m, 1H) 3.54 (br. s, 4H) 3.88 (ddd, J=7.48, 6.02, 2.74 Hz, 1H) 6.51 (dt, J=8.22, 3.42 Hz, 1H) 6.73 (dd, J=6.85, 2.93 Hz, 1H) 6.83 (dd, J=11.84, 8.51 Hz, 1H)

Example 4

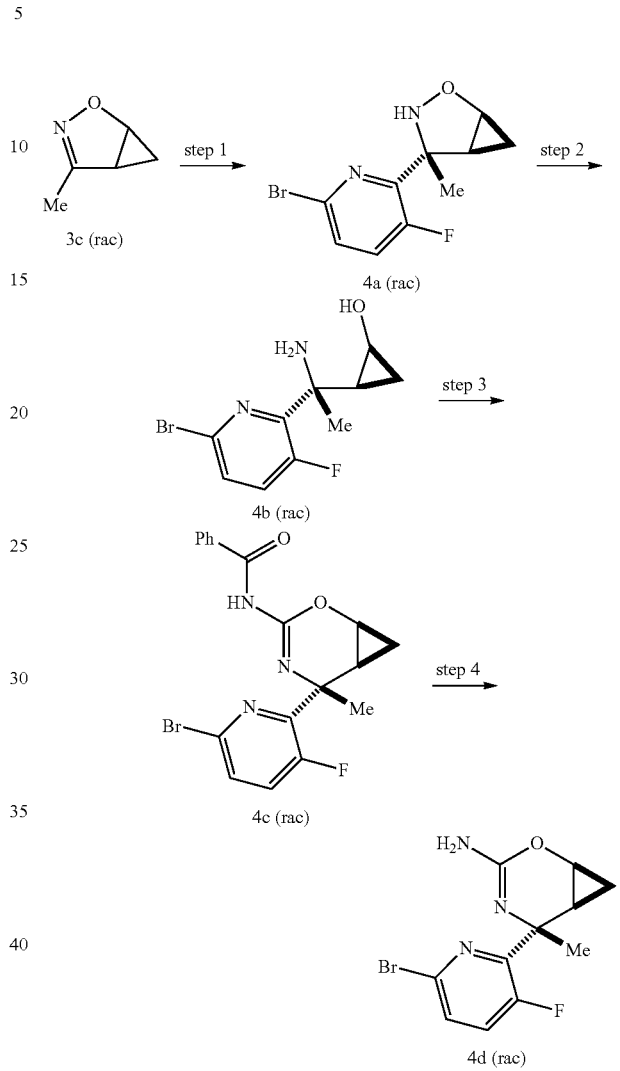

Step 1: [1(R,S),4(S,R),5(R,S)]-4-(6-bromo-3-fluoropyridin-2-yl)-4-methyl-2-oxa-3-azabicyclo[3.1.0]hexane (4a rac)

A solution of n-butyllithium solution, (1.6M in hexane; 3.22 ml, 5.15 mmol) was added dropwise to solution of 2-bromo-5-fluoropyridine (0.906 g, 5.15 mmol) in Et₂O (20 mL; anhydrous) at −78 C. The reaction mixture was allowed to stir for 25 min at −78° C. An additional flask was charged with 4-methyl-2-oxa-3-azabicyclo[3.1.0]hex-3-ene (0.25 g, 2.57 mmol, 3c-rac) and toluene (20 mL). The solution was cooled to −78 C and boron fluoride diethyl etherate (0.477 ml, 3.86 mmol) was added. The solution was stirred for 15 minutes and then transferred via cannula to the heteroaryl lithium solution. Upon complete addition the reaction mixture was stirred at −78 C for 20 min and then allowed to warm gradually to 10° C. After 1 h, the reaction mixture was quenched by the addition of aq. sat ammonium chloride solution. EtOAc was added and the organic extract was washed with brine and dried over MgSO4. The solution was filtered and concentrated in vacuo to give the crude material. The crude material was absorbed onto a plug of silica gel and purified by silica gel chromatography, eluting with a gradient of 5% to 45% EtOAc in hexane, to provide the title compound as a single diastereoisomer (0.226 g, 0.828 mmol, 32.1% yield, >95% de). MS m/z=274.9 [M+H]$^+$.

Steps 2: [(1R,S),(2R,S)]-2-((S,R)-1-amino-1-(6-bromo-3-fluoropyridin-2-yl)ethyl)cyclopropanol (4b rac)

A flask was charged with [1(R,S),4(S,R),5(R,S)]-4-(6-bromo-3-fluoropyridin-2-yl)-4-methyl-2-oxa-3-azabicyclo[3.1.0]hexane (14.14 g, 51.8 mmol, 4a rac) and TFA (105 ml, 1363 mmol). After 5 min, the solution was cooled to 0 C and zinc dust (33.9 g, 518 mmol) was added portion wise. The reaction mixture was filtered after 10 min through celite and the filter cake was washed with TFA. The filtrate was poured into ice water and the pH was adjusted to pH=12 with 5N NaOH solution. The aqueous mixture was extracted twice with EtOAc. The combined organic layers were washed with brine and dried over MgSO$_4$. The filtrate was concentrated under reduced pressure to afford the title compound (13.76 g, 50.0 mmol, 97% yield) as a yellow solid. MS m/z=275.0 [M+H]$^+$.

Step-3: N-[(1R,S),(5S,R),(6R,S)]-5-(6-bromo-3-fluoropyridin-2-yl)-5-methyl-2-oxa-4-azabicyclo[4.1.0]hept-3-en-3-yl)benzamide (4c rac)

The title compound was prepared using a procedure similar to that described in step 7 for the synthesis of 1h-rac, but using [(1R,S),(2R,S)]-2-4S,R)-1-amino-1-(6-bromo-3-fluoropyridin-2-yl)ethyl)cyclopropanol (4b rac). MS m/z=403.9 [M+H]$^+$.

Step 4: [(1R,S),(5S,R),(6R,S)]-5-(6-bromo-3-fluoropyridin-2-yl)-5-methyl-2-oxa-4-azabicyclo[4.1.0]hept-3-en-3-amine (4d rac)

To a solution of N-[(1R,S),(5S,R),(6R,S)]-5-(6-bromo-3-fluoropyridin-2-yl)-5-methyl-2-oxa-4-azabicyclo[4.1.0]hept-3-en-3-yl)benzamide (3 g, 7.42 mmol, 4c-rac) in MeOH (49.5 ml) was added DBU (3.36 mL, 22.3 mmol). The reaction mixture was heated to 70° C. over night. Upon cooling, a white solid precipitated out, which was filtered off. The solid was taken up in EtOAc (70 mL), washed with saturated ammonium chloride solution (70 mL) and brine. The organic layer was dried over magnesium sulfate and concentrated under reduced pressure to afford the title compound (1.67 g, 5.56 mmol, 75.0% yield) as a fine white solid.
MS m/z=301.9 [M+H]$^+$.

Example 5

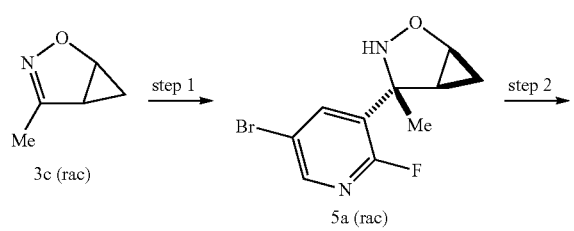

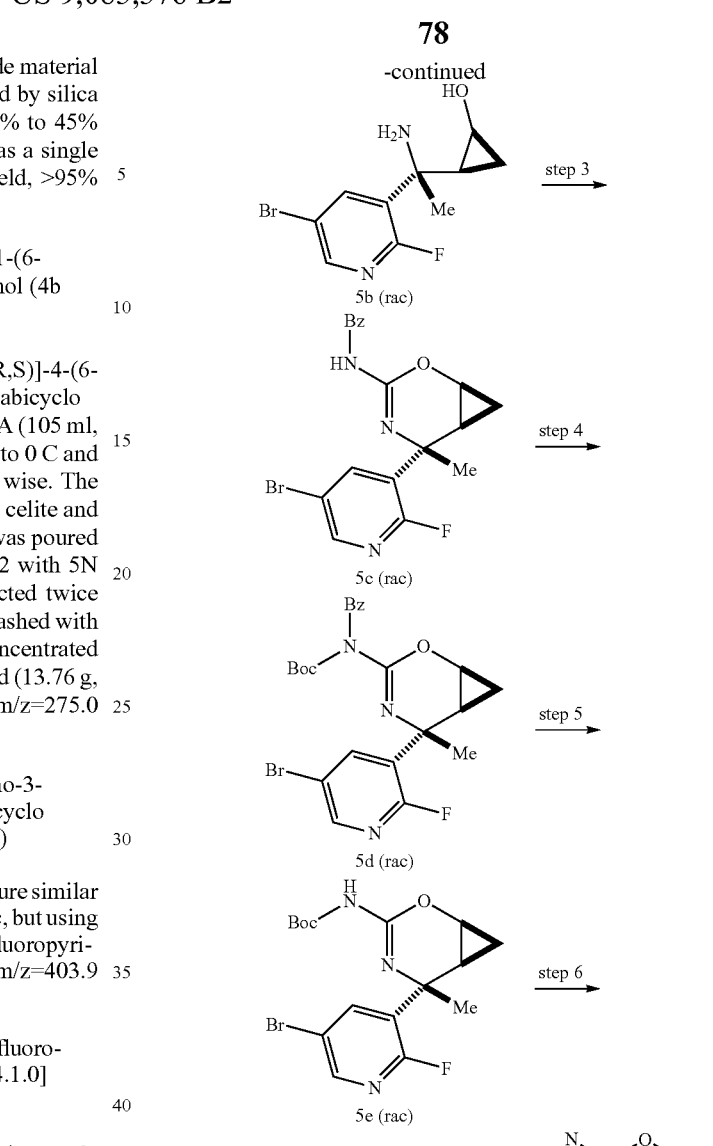

Step 1: [1(S,R),4(R,S),5(S,R)]-4-(5-Bromo-2-fluoropyridin-3-yl)-4-methyl-2-oxa-3-azabicyclo[3.1.0]hexane (5a rac)

A solution of 3,5-dibromo-2-fluoropyridine (4.88 g, 19.14 mmol) and toluene (55 mL) under argon atmosphere was cooled to 0° C. A solution of isopropylmagnesium chloride lithium chloride (1.3 M solution in THF, 14.8 ml, 19.24 mmol) was added dropwise. The resulting mixture was stirred at 0° C. for 30 min and then cooled to −78° C. In a separate flask, a solution of 4-methyl-2-oxa-3-azabicyclo[3.1.0]hex-3-ene (3c rac, 0.93 g, 9.57 mmol) and toluene (53 mL) under argon atmosphere was cooled to −78° C. and boron trifluoride diethyl etherate (3.54 ml, 28.7 mmol) was added dropwise. The reaction mixture was stirred at −78° C. for 15 min and added via syringe to the 3,5-dibromo-2-fluoropyridine-Grignard mixture. The resulting mixture was allowed to warm to RT and stirred for additional 2 h. The reaction was quenched with aqueous saturated NH₄Cl solution and partitioned between EtOAc and water. The organic layer was dried over MgSO₄). The filtrate was concentrated in vacuo and the residue was purified by silica gel chromatography (0% to 25% EtOAc/Hexanes) to afford the title compound as a a tan solid. MS m/z=272.9, 275.0 [M+H]⁺.

Step 2 and 3: N-[(1(S,R),5(R,S),6(S,R)]-5-(5-Bromo-2-fluoropyridin-3-yl)-5-methyl-2-oxa-4-azabicyclo[4.1.0]hept-3-en-3-yl)benzamide (5c rac)

The title compound was prepared using procedures similar to that described in steps 6 and 7 for the synthesis of 1h-rac, but using [1(S,R),4(R,S),5(S,R)]-4-(5-Bromo-2-fluoropyridin-3-yl)-4-methyl-2-oxa-3-azabicyclo[3.1.0]hexane (5a rac). MS m/z=404.0, 406.0 [M+H]⁺.

Step 4: tert-Butyl benzoyl[(1(S,R),5(R,S),6(S,R)]-5-(5-bromo-2-fluoropyridin-3-yl)-5-methyl-2-oxa-4-azabicyclo[4.1.0]hept-3-en-3-yl)carbamate (5d rac)

To a solution of N-((1(S,R),5(R,S),6(S,R))-5-(5-bromo-2-fluoropyridin-3-yl)-5-methyl-2-oxa-4-azabicyclo[4.1.0]hept-3-en-3-yl)benzamide (5c rac, 0.718 g, 1.77 mmol) in DCM (8.9 ml, 1.77 mmol) under argon atmosphere was added di-tert-butyl dicarbonate (0.46 g, 2.13 mmol), followed by 4-(dimethylamino)-pyridine (0.11 g, 0.88 mmol). The reaction mixture was stirred at room temperature for 1 h. CH₂Cl₂ was added. The phases were separated and the aqueous layer was back-extracted with CH₂Cl₂. The combined organic extracts were washed with water, dried over MgSO₄ and the filtrate was concentrated in vacuo. The residue was purified by silica gel chromatography (0% to 15% EtOAc/Hexanes) afforded the title compound as a colorless foam. MS m/z=503.9, 506.0 [M+H]⁺.

Step 5: tert-butyl[(1(S,R),5(R,S),6(S,R)-5-(5-bromo-2-fluoropyridin-3-yl)-5-methyl-2-oxa-4-azabicyclo[4.1.0]hept-3-en-3-yl]carbamate (5e rac)

To a solution of tert-butyl benzoyl[(1(S,R),5(R,S),6(S,R))-5-(5-bromo-2-fluoropyridin-3-yl)-5-methyl-2-oxa-4-azabicyclo[4.1.0]hept-3-en-3-yl]carbamate (5d rac; 486 mg, 0.964 mmol) in MeOH (6 mL) was added potassium carbonate (0.029 mL, 0.482 mmol) and the resulting reaction mixture was stirred at RT for 30 min. The reaction mixture was cooled to −78° C. and quenched with aqueous saturated ammonium chloride solution, followed by extraction with EtOAc (2×20 mL). The combined organic extracts were dried over MgSO₄ and concentrated in vacuo. The residue was purified by silica gel flash column chromatography (0%-100% EtOAc/hexane) to give 368 mg of the title compound as a white solid. MS (ESI, positive ion) m/z: 400.1, 401.9 (M+H).

Step 6: (1(S,R),5(R,S),6(S,R))-5-(5-bromo-2-fluoropyridin-3-yl)-5-methyl-2-oxa-4-azabicyclo[4.1.0]hept-3-en-3-amine (5f rac)

To a solution of tert-butyl((1(S,R),5(R,S),6(S,R)-5-(5-bromo-2-fluoropyridin-3-yl)-5-methyl-2-oxa-4-azabicyclo[4.1.0]hept-3-en-3-yl)carbamate (5e rac, 368 mg, 0.919 mmol) in DCM (2.5 mL) was added trifluoroacetic acid (0.956 mL, 12.87 mmol). The resulting mixture was stirred at room temperature for 45 min. Additional trifluoroacetic acid (0.5 mL) was added and the mixture reaction was stirred at RT for 1 h. The reaction mixture was concentrated under reduced pressure and the residue was dissolved in DCM (10 mL). The solution was cooled to −50° C. and aqueous saturated NaHCO₃ solution (4 mL) was added dropwise. The reaction mixture was stirred at RT for 10 min, followed by extraction with DCM (2×15 mL). The combined organic extracts were dried over MgSO₄ and concentrated in vacuo. The residue was absorbed onto silica gel. Purification by silica gel flash column chromatography (0%-20% ammonia in MeOH 2M/DCM) gave 267 mg of the title compound as a light yellow solid. MS (ESI, positive ion) m/z: 300.0, 302.0 (M+H).

Example 6

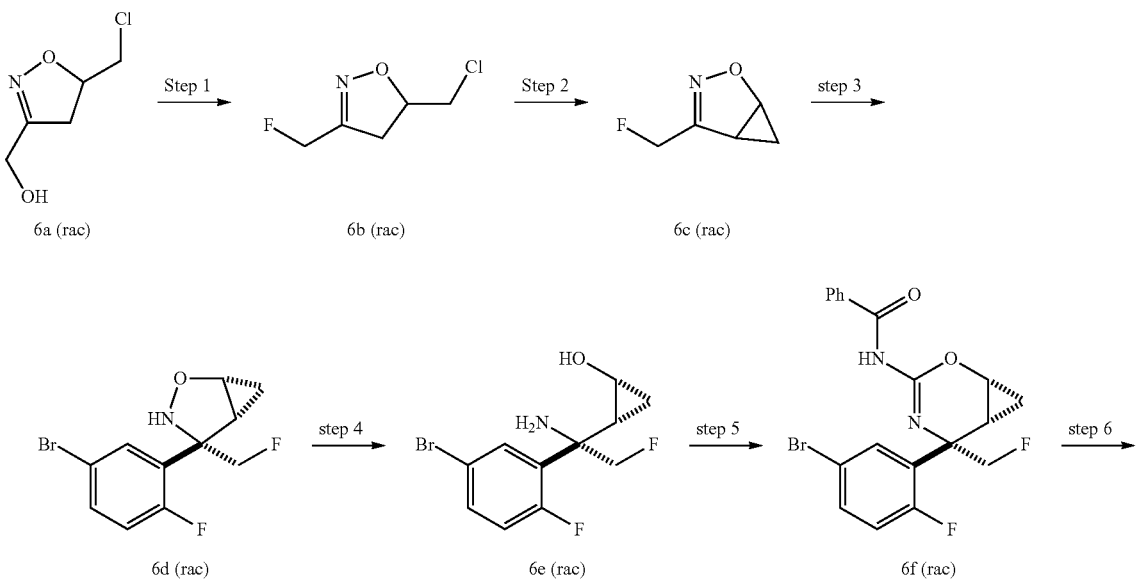

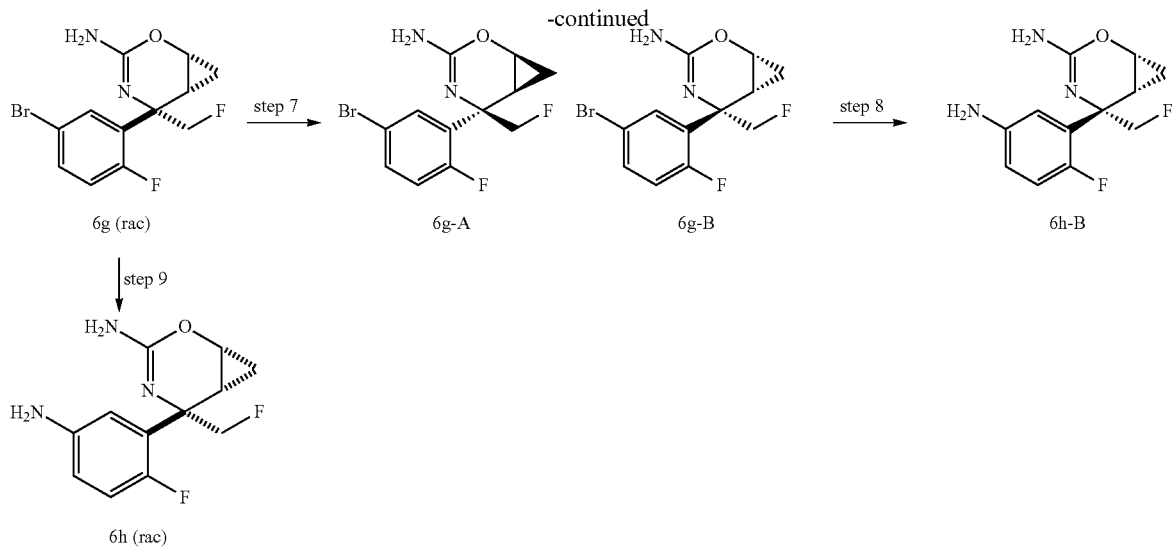

6g (rac)    6g-A    6g-B    6h-B 6h (rac)

Step 1: 5-(Chloromethyl)-3-(fluoromethyl)-4,5-dihydroisoxazole (6b rac)

To a solution of (5-(chloromethyl)-4,5-dihydroisoxazol-3-yl)methanol (1.58 g, 10.56 mmol, 6a rac, Tetrahedron 1986, 42, 5267) in DCM (30 mL) at −78° C. was added (diethylamino)sulfur trifluoride (1.60 ml, 12.11 mmol). The reaction mixture was stirred at −78° C. for 10 min, warmed from −78° C. to room temperature over 15 min, stirred at room temperature for 1 h and quenched with saturated aq. saturated NaHCO$_3$ solution. The reaction mixture was diluted with diethyl ether and water. The aqueous phase was extracted with diethyl ether (4×) and the combined organic extracts were washed with brine (1×), dried over MgSO$_4$, filtered, and concentrated in vacuo to give a dark red oil. Purification by flash column chromatography on silica gel (20% diethyl ether in pentane) gave the title compound (0.79 g, 49% yield).

Step 2: 4-(fluoromethyl)-2-oxa-3-azabicyclo[3.1.0]hex-3-ene (6c rac)

To a solution of 5-(chloromethyl)-3-(fluoromethyl)-4,5-dihydroisoxazole (0.78 g, 5.13 mmol, 6b rac) in THF (25 mL) at 0° C. was added potassium tert-butoxide, (1.0M solution in THF; 5.50 ml, 5.50 mmol). The reaction mixture was stirred at 0° C. for 20 min and additional potassium tert-butoxide solution (0.50 mL) was added. Stirring was continued at 0° C. for additional 20 min. The reaction mixture was warmed to RT, stirred for 20 min and quenched with saturated NH$_4$Cl solution. The reaction mixture was diluted with diethyl ether and water. The aqueous phase was extracted with diethyl ether (3×). The combined organic extracts were washed with brine and dried over MgSO4. The filtrate was concentrated under reduced pressure to give a dark red oil. Purification by flash column chromatography on silica gel (20% diethyl ether in pentane) gave the title compound (0.57 g, 96% yield).

Step 3: [1 (R,S),4(S,R),5(R,S)]-4-(5-bromo-2-fluorophenyl)-4-(fluoromethyl)-2-oxa-3-azabicyclo[3.1.0]hexane (6d rac)

To a solution of 4-bromo-1-fluoro-2-iodobenzene (22.1 g, 73.6 mmol) in Et$_2$O (150 mL) at −78° C. was added n-butyllithium (1.6 M in hexane, 46.0 mL, 73.6 mmol). The solution was stirred at −78° C. for 15 min. An additional flask was charged with a solution of [1(S,R),5(S,R)]-4-(fluoromethyl)-2-oxa-3-azabicyclo[3.1.0]hex-3-ene (6c rac, 4.21 g, 36.6 mmol) and boron trifluoride diethyl etherate (4.65 mL, 36.7 mmol) in PhMe (170 mL) at −78° C. The second solution was added dropwise via cannula over 10 min to the aryl lithium solution. The reaction mixture was stirred at −78° C. for 30 min and quenched with aqueous saturated NH$_4$Cl solution. The reaction mixture was warmed to RT and diluted with EtOAc and water. The aqueous phase was extracted with EtOAc (2×) and the combined organic extracts were washed with brine and dried over MgSO$_4$. The filtrate was concentrated under reduced pressure and the residue was purified by silica gel flash column chromatography (5% to 20% EtOAc in hexanes) to give the title compound (9.58 g, 33.0 mmol, 90% yield) as a yellow oil. LC/MS (ESI$^+$) m/z=289.9.0 (M+H). Calculated for $C_{11}H_{10}BrF_2NO$ 289.0.

Steps 4-5: N-(((1R,S),(5S,R),(6R,S))-5-(5-bromo-2-fluorophenyl)-5-(fluoromethyl)-2-oxa-4-azabicyclo[4.1.0]hept-3-en-3-yl)benzamide (6f-rac)

The title compound was prepared following procedures similar to those described in steps 2 and 3 for the synthesis of 4c rac, but using [1(R,S),4(S,R),5(R,S)]-4-(5-bromo-2-fluorophenyl)-4-(fluoromethyl)-2-oxa-3-azabicyclo[3.1.0]hexane (6d rac). MS m/z=422.9 [M+H]$^+$.

Step 6: [1(S,R),5(R,S),6(S,R)]-5-(5-Bromo-2-fluorophenyl)-5-(fluoromethyl)-2-oxa-4-azabicyclo[4.1.0]hept-3-en-3-amine (6g-rac)

The title compound was prepared following a procedure similar to that described in step 4 for the synthesis of 4d rac, but using N-(((1R,S),(5S,R),(6R,S))-5-(5-bromo-2-fluorophenyl)-5-(fluoromethyl)-2-oxa-4-azabicyclo[4.1.0]hept-3-en-3-yl)benzamide (6f-rac) MS m/z=316.9 [M+H]$^+$. Calculated for $C_{12}H_{11}BrF_2N_2O$ 316.0.

Step 7: (1S,5R,6S)-5-(5-bromo-2-fluorophenyl)-5-(fluoromethyl)-2-oxa-4-azabicyclo[4.1.0]hept-3-en-3-amine (6g-A) and (1R,5S,6R)-5-(5-bromo-2-fluorophenyl)-5-(fluoromethyl)-2-oxa-4-azabicyclo[4.1.0]hept-3-en-3-amine (6g-B)

[1(S,R),5(R,S),6(S,R)]-5-(5-Bromo-2-fluorophenyl)-5-(fluoromethyl)-2-oxa-4-azabicyclo[4.1.0]hept-3-en-3-amine (6g-rac, 493 mg, 1.39 mmol) was subjected to chromatography using supercritical CO$_2$ (additives 35% MeOH with 20 mM NH$_3$) on a Chiralpak ICH (20×250 mm, 5 μm) eluting at a flow rate 75 mL/min (100 bar pressure, ambient column temperature).

The first peak (retention time=1.97 min) provided (Example 6g-A; 220 mg, 0.69 mmol, 45% yield; >99% de; >99% ee) as a light yellow solid. LC/MS (ESI$^+$) m/z=317.0 (M+H). Calculated for C$_{12}$H$_{11}$BrF$_2$N$_2$O 316.0.

$^1$H NMR (CD$_3$OD) δ: 7.59 (dd, J=7.0, 2.5 Hz, 1H), 7.51 (ddd, J=8.6, 4.2, 2.6 Hz, 1H), 7.11 (dd, J=11.7, 8.6 Hz, 1H), 4.67-4.80 (m, 1H), 4.51-4.65 (m, 1H), 3.96-4.12 (m, 1H), 1.63-1.80 (m, 1H), 1.17 (td, J=6.8, 2.6 Hz, 1H), 0.92 (dt, J=9.4, 6.7 Hz, 1H). The second peak (retention time=3.00 min) provided (Example 6g-B; 210 mg, 0.66 mmol, 43% yield; >99% de; >99% ee) as a light yellow solid. MS m/z=316.9 [M+H]$^+$. Calculated for C$_{12}$H$_{11}$BrF$_2$N$_2$O 316.0. $^1$H NMR (CD$_3$OD) δ: 7.59 (dd, J=7.0, 2.3 Hz, 1H), 7.45-7.55 (m, 1H), 7.10 (dd, J=11.7, 8.8 Hz, 1H), 4.67-4.79 (m, 1H), 4.51-4.65 (m, 1H), 3.95-4.16 (m, 1H), 1.60-1.86 (m, 1H), 1.17 (td, J=6.7, 2.4 Hz, 1H), 0.84-1.00 (m, 1H).

Step 8: (1R,5S,6R)-5-(5-amino-2-fluorophenyl)-5-(fluoromethyl)-2-oxa-4-azabicyclo[4.1.0]hept-3-en-3-amine (6h-B)

To a mixture of (1R,5S,6R)-5-(5-bromo-2-fluorophenyl)-5-(fluoromethyl)-2-oxa-4-azabicyclo[4.1.0]hept-3-en-3-amine (6g-B, 0.61 g, 1.9 mmol), sodium azide (0.388 g, 5.96 mmol), (+)-sodium 1-ascorbate (0.080 g, 0.41 mmol), copper (I) iodide (0.086 g, 0.45 mmol) and (1R,2R)-(−)-N,N"-dimethylcyclohexane-1,2-diamine (0.075 mL, 0.47 mmol) under argon atmosphere were added EtOH (2.40 mL) and water (1.2 mL). The reaction mixture was heated at 70° C. for 1.5 h. The cooled reaction mixture was poured into a mixture of 10:1 NH$_4$Cl/ammonium hydroxide and diluted with CH$_2$Cl$_2$. The aqueous layer was extracted with CH$_2$Cl$_2$ (3×) and the combined organic extracts were washed with aqueous saturated NH$_4$Cl solution. The solution was dried over MgSO$_4$ and the filtrate was concentrated in vacuo to give a yellow solid, which was dissolved in THF (8.4 mL) and water (2.8 mL). Trimethylphosphine (1.0 M solution in THF, 1.924 mL, 1.924 mmol) was added and the reaction mixture was stirred at RT for 20 min. The reaction was diluted with CH$_2$Cl$_2$ and water. The phases were separated and the aqueous layer was extracted with CH$_2$Cl$_2$. The combined organic extracts were dried over MgSO$_4$ and the filtrate was purified by silica gel flash column chromatography (0% to 5% 2 M NH$_3$ in MeOH/CH$_2$Cl$_2$) to afford the title compound (0.4473 g, 1.766 mmol, 92% yield) as a maize color solid. MS m/z=254.0 [M+H]$^+$. Calculated for C$_{12}$H$_{13}$F$_2$N$_3$O 253.1.

Step 9: [(1R,S),(5S,R),(6R,S)]-5-(5-amino-2-fluorophenyl)-5-(fluoromethyl)-2-oxa-4-azabicyclo[4.1.0]hept-3-en-3-amine (6h-rac)

The title compound was prepared following a procedure similar to that described in step 8 for the synthesis of (1R,5S,6R)-5-(5-amino-2-fluorophenyl)-5-(fluoromethyl)-2-oxa-4-azabicyclo[4.1.0]hept-3-en-3-amine (6h-B), but using [1(S,R),5(R,S),6(S,R)]-5-(5-Bromo-2-fluorophenyl)-5-(fluoromethyl)-2-oxa-4-azabicyclo[4.1.0]hept-3-en-3-amine (6g-rac) MS m/z=254.0 [M+H]$^+$.

Example 7

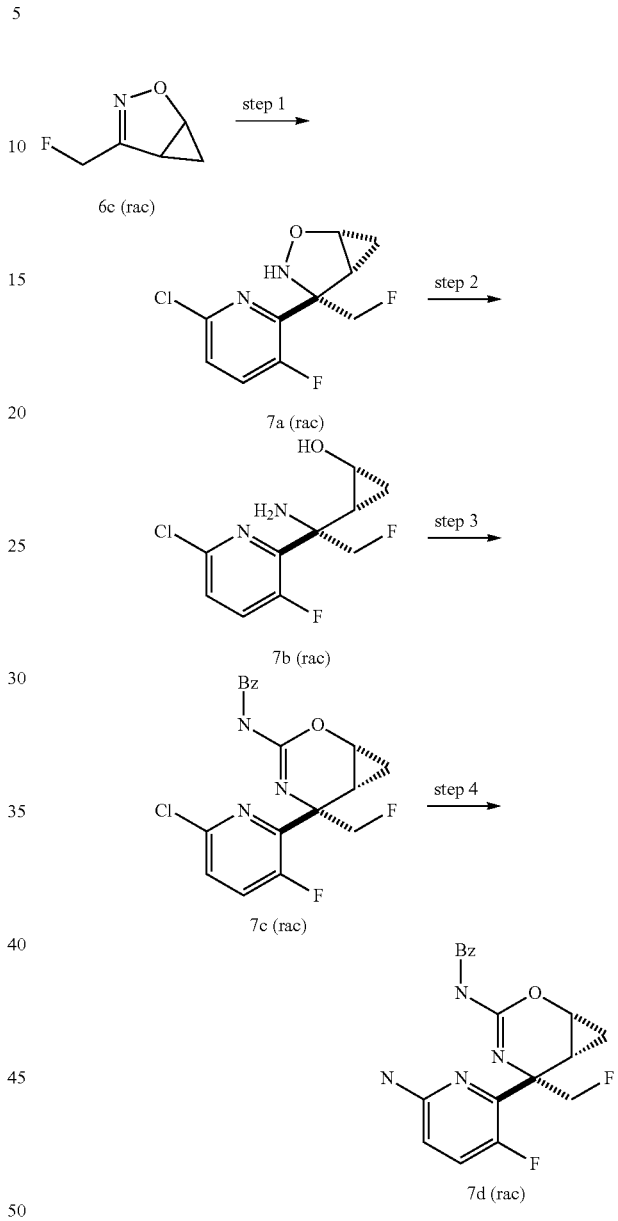

Step 1: [(1R,S),(4S,R),(5R,S)]-4-(6-Chloro-3-fluoropyridin-2-yl)-4-(fluoromethyl)-2-oxa-3-azabicyclo[3.1.0]hexane (7a rac)

A solution of 2-chloro-5-fluoropyridine (1.8 ml, 17.75 mmol) in diethyl ether (50 mL) under nitrogen atmosphere was cooled to −78 C. A solution of n-butyllithium (2.5 M in hexanes, 6.8 ml, 17.00 mmol) was added dropwise and the solution was stirred for 20 minutes. In a separate flask, 4-(fluoromethyl)-2-oxa-3-azabicyclo[3.1.0]hex-3-ene (1.0 g, 8.69 mmol, 6c rac) was dissolved in dry toluene (10 mL) and cooled to −78 C under nitrogen atmosphere. Boron fluoride diethyl etherate (1.2 ml, 9.72 mmol) was added dropwise and the reaction mixture was stirred for 5 minutes. The solution of the pyridyl anion was transferred to the isoxazole/boron trifluoride mixture via cannula. The reaction mixture was stirred for additional 25 minutes and then quenched by addition of saturated ammonium chloride solution (10 mL). The reaction mixture was allowed to warm to rt and diethyl ether (200 mL) was added. The organic layer was separated, washed with brine (70 mL) and dried over magnesium sulfate. The filtrate was concentrated under reduced pressure and the crude residue was purified using silica chromatography (0-100% ethyl acetate/hexanes) to give the title compound (1.30 g, 5.27 mmol, 60.7% yield. >95% de). MS m/z=246.9 [M+H]$^+$.

Step 2: [(1R,S),(2R,S)]-2-((S,R)-1-amino-1-(6-chloro-3-fluoropyridin-2-yl)-2-fluoroethyl)cyclopropanol (7b rac)

The title compound was prepared using a procedure similar to that described in step 2 for the synthesis of 4b-rac, but using [(1R,S),(4S,R),(5R,S)]-4-(6-Chloro-3-fluoropyridin-2-yl)-4-(fluoromethyl)-2-oxa-3-azabicyclo[3.1.0]hexane (7a rac). MS m/z=249.1 [M+H]$^+$.

Step 3: N-[(1R,S),(5S,R),(6R,S)]-5-(6-Chloro-3-fluoropyridin-2-yl)-5-(fluoromethyl)-2-oxa-4-azabicyclo[4.1.0]hept-3-en-3-yl)benzamide (7c rac)

The title compound was prepared using a procedure similar to that described in step 7 for the synthesis of 1h-rac, but using [(1R,S),(2R,S)]-2-4S,R)-1-amino-1-(6-chloro-3-fluoropyridin-2-yl)-2-fluoroethyl)cyclopropanol (7b rac). MS m/z=377.9 [M+H]$^+$.

Step 4: N-[(1R,S),(5S,R),(6R,S)]-5-(6-amino-3-fluoropyridin-2-yl)-5-(fluoromethyl)-2-oxa-4-azabicyclo[4.1.0]hept-3-en-3-yl)benzamide (7d rac)

The title compound was prepared using a procedure similar to that described in step 8 for the synthesis of 1i-rac, but using -[(1R,S),(5S,R),(6R,S)]-5-(6-Chloro-3-fluoropyridin-2-yl)-5-(fluoromethyl)-2-oxa-4-azabicyclo[4.1.0]hept-3-en-3-yl)benzamide (7c rac). MS m/z=359.0 [M+H]$^+$.

Example 8

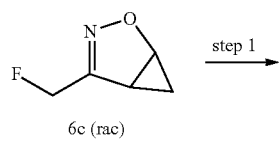

6c (rac)

step 1

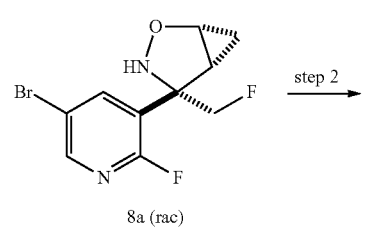

8a (rac)

step 2

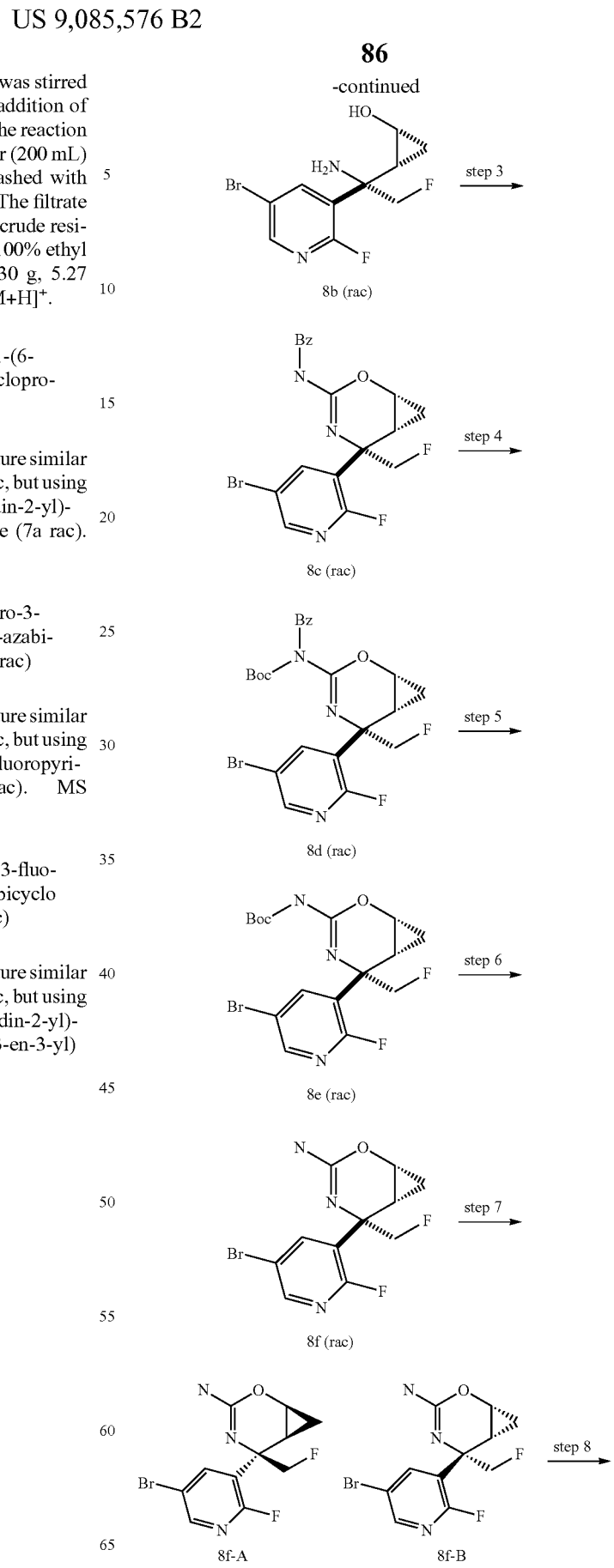

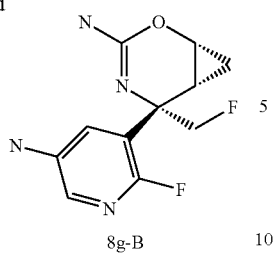

8g-B

Step 1: [1(S,R),4(R,S),5(S,R)]-4-(5-bromo-2-fluoro-pyridin-3-yl)-4-(fluoromethyl)-2-oxa-3-azabicyclo [3.1.0]hexane (8a rac)

To a solution of diisopropylamine (3.65 mL, 26.1 mmol) in THF (25 mL) under nitrogen atmosphere, cooled to 0° C., was added a solution of butyllithium (1.6M in hexane, 16.29 mL, 26.1 mmol) dropwise. After completed addition, the reaction mixture was stirred at 0° C. for 10 min. Then, the mixture was cooled to −78° C. and 5-bromo-2-fluoropyridine (3.00 mL, 26.1 mmol) was added dropwise. The reaction mixture was stirred at −78° C. for 30 min, followed by the addition of N,N,N',N'-tetra-methyl-ethylenediamine (3.90 mL, 26.1 mmol). The resulting mixture was stirred at −78° C. for 5 min. In an additional flask, a solution of [1(R,S),5(R,S)]-4-(fluoromethyl)-2-oxa-3-azabicyclo[3.1.0]hex-3-ene (6c rac, 1.5 g, 13.03 mmol) in toluene (37.5 mL) was treated with boron trifluoride diethyl etherate (1.608 mL, 13.03 mmol) at −78° C. under nitrogen atmosphere. After 10 min, this solution was added dropwise via cannula to the aryl lithium solution. The resulting reaction mixture was then stirred at −78° C. for 1 h. The reaction was quenched with aqueous saturated NH$_4$Cl solution and diluted with EtOAc. The organic extract was dried over MgSO$_4$ and the filtrate was concentrated in vacuo. The residue was absorbed onto silica gel and purified by silica gel flash column chromatography (0%-35% EtOAc/heptane) to give 1259 mg of the title compound as a light yellow solid. MS (ESI, positive ion) m/z: 290.9, 292.9 (M+H).

Step 2-6: [1 (S,R),5(R,S),6(S,R)]-5-(5-bromo-2-fluoropyridin-3-yl)-5-(fluoromethyl)-2-oxa-4-azabicyclo [4.1.0]hept-3-en-3-amine (8f rac)

The title compound was prepared following procedures similar to those described in steps 2 to 6 for the synthesis of 6f rac, but using [1(S,R),4(R,S),5(S,R)]-4-(5-bromo-2-fluoro-pyridin-3-yl)-4-(fluoromethyl)-2-oxa-3-azabicyclo[3.1.0] hexane (8a rac) MS (ESI, positive ion) m/z: 317.9, 320.9 (M+H).

Step 7: (1S,5R,6S)-5-(5-bromo-2-fluoropyridin-3-yl)-5-(fluoromethyl)-2-oxa-4-azabicyclo[4.1.0]hept-3-en-3-amine (8f-A) and (1R,5S,6R)-5-(5-bromo-2-fluoropyridin-3-yl)-5-(fluoromethyl)-2-oxa-4-azabicyclo[4.1.0]hept-3-en-3-amine (8f-B)

[1(S,R),5(R,S),6(S,R)]-5-(5-bromo-2-fluoropyridin-3-yl)-5-(fluoromethyl)-2-oxa-4-azabicyclo[4.1.0]hept-3-en-3-amine (8f rac, 345 mg) was subjected to chromatography using supercritical CO$_2$ (25% MeOH) on a IC-H column (21.2×250 nm, 5 µm) eluting at a flow rate 80 mL/min (209 bar, 40° C. column temperature). The first peak (retention time=3.7 min) provided (1S,5R,6S)-5-(5-bromo-2-fluoropyridin-3-yl)-5-(fluoromethyl)-2-oxa-4-azabicyclo[4.1.0]hept-3-en-3-amine (8f-A, 108 mg, 0.40 mmol, 63% yield, 99% de; 99% ee) as a white solid. MS (ESI, positive ion) m/z: 317.9, 320.9 (M+H).

$^1$H NMR (MeOH) δ: 8.22-8.24 (m, 1H), 8.06 (dd, J=8.6, 2.5 Hz, 1H), 4.52-4.76 (m, 2H), 4.04-4.09 (m, 1H), 1.64-1.71 (m, 1H), 1.13 (td, J=6.8, 2.6 Hz, 1H), 0.93 (dt, J=9.6, 6.7 Hz, 1H). The second peak (retention time=4.5 min) provided (1R,5S,6R)-5-(5-bromo-2-fluoropyridin-3-yl)-5-(fluoromethyl)-2-oxa-4-azabicyclo[4.1.0]hept-3-en-3-amine (8f-B, 112 mg, 0.352 mmol, 65% yield, 99% de; 99% ee) as a light yellow solid. MS (ESI, positive ion) m/z: 317.9, 320.9 (M+H).

$^1$H NMR (MeOH) δ: 8.24-8.27 (m, 1H), 8.08 (dd, J=8.6, 2.5 Hz, 1H), 4.54-4.80 (m, 2H), 4.12 (br. s., 1H), 1.67-1.74 (m, 1H), 1.13-1.20 (m, 1H), 0.97 (dt, J=9.5, 6.7 Hz, 1H)

Step 8: (1R,5S,6R)-5-(5-amino-2-fluoropyridin-3-yl)-5-(fluoromethyl)-2-oxa-4-azabicyclo[4.1.0]hept-3-en-3-amine (8g-B)

A sealable vial was charged with (1R,5S,6R)-5-(5-bromo-2-fluoropyridin-3-yl)-5-(fluoromethyl)-2-oxa-4-azabicyclo [4.1.0]hept-3-en-3-amine (8f-B, 0.1016 g, 0.319 mmol), trifluoroacetamide (0.072 g, 0.639 mmol), copper(I) iodide (0.018 g, 0.096 mmol) and potassium carbonate (0.177 g, 1.278 mmol), followed by dioxane (1.8 mL) and trans-N,N'-dimethylcyclohexane-1,2-diamine (0.015 mL, 0.096 mmol). The reaction mixture was purged with nitrogen for 5 min and then heated at 120° C. for 20 h. The cooled reaction mixture was diluted with CH$_2$Cl$_2$ and washed with aqueous saturated NaHCO$_3$ solution. The layers were separated and the aqueous layer was extracted with 15% MeOH/CH$_2$Cl$_2$. The combined organic extracts were dried over MgSO$_4$ and the filtrate was concentrated in vacuo. The residue was purified by silica gel flash chromatography (1% to 10% MeOH/CH$_2$Cl$_2$) afforded the title compound (0.061 g, 0.240 mmol, 75% yield) as a tan amorphous solid. MS (ESI, positive ion) m/z: 255.1 (M+H)

Example 9

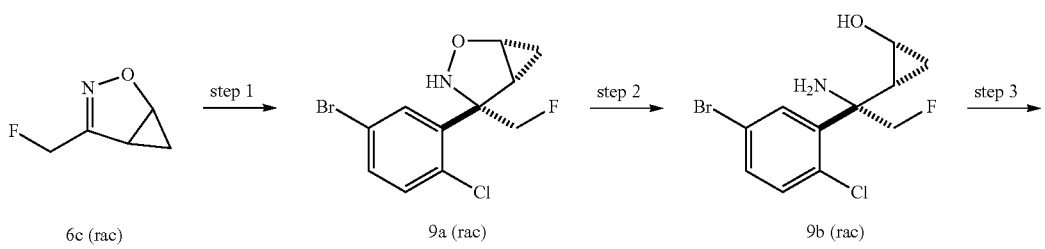

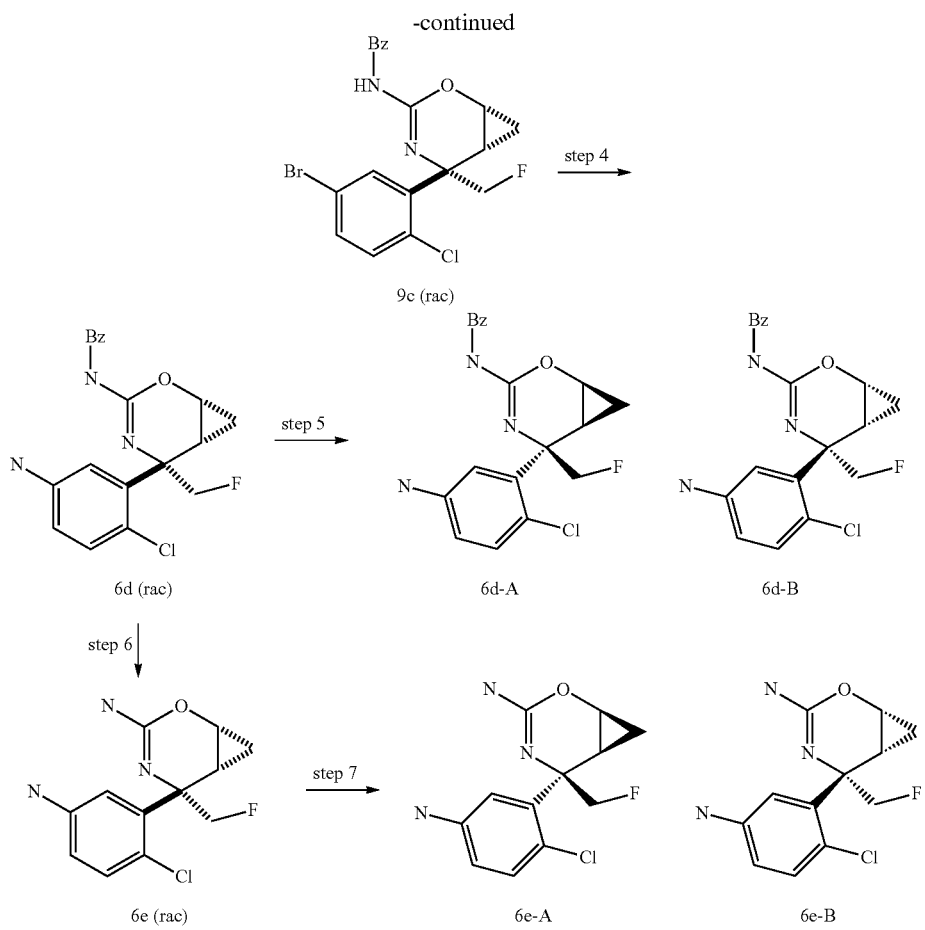

Step 1: [(1R,S),(4S,R),(5R,S)]-4-(5-bromo-2-chlorophenyl)-4-(fluoromethyl)-2-oxa-3-azabicyclo[3.1.0]hexane (9a rac)

A flame dried round bottom flask was charged with 4-bromo-1-chloro-2-iodobenzene (33.1 g, 104 mmol) and Et$_2$O (206 mL). The solution was cooled to −78° C. and a solution of n-butyllithium solution (2.5 M in hexanes, 41.7 mL, 104 mmol) was added dropwise. The reaction mixture was stirred at −78° C. for 15 minutes. A second, flame dried round bottom flask was charged with a solution of 4-(fluoromethyl)-2-oxa-3-azabicyclo[3.1.0]hex-3-ene (6c rac; 6 g, 52.1 mmol) in toluene (229 mL) and cooled to −78° C. Boron trifluoride diethyl etherate (6.61 mL, 52.1 mmol) was added, the reaction mixture was stirred for 5 minutes at −78 C and added via cannula to the aryllithium species. The reaction mixture was stirred at −78° C. for 10 minutes. The reaction was quenched with saturated ammonium chloride solution and warmed to RT. The reaction mixture was diluted with water and EtOAc. The organic layer was separated and the aqueous layer was washed with additional EtOAc. The combined organic layers were washed with brine and dried over magnesium sulfate. The filtrate was concentrated under reduced pressure and the crude material was purified via silica gel chromatography, eluting with 5-45% EtOAc:Hexanes to afford the title compound (10.19 g, 33.2 mmol, 63.8% yield). MS m/z=305.9 [M+H]$^+$. Calculated for C$_{11}$H$_{10}$BrClFNO: 306.6

Step 2: [(1R,S),(2R,S)]-2-((S,R)-1-amino-1-(5-bromo-2-chlorophenyl)-2-fluoroethyl)cyclopropanol (6b rac)

To a solution of [(1R,S),(4S,R),(5R,S)]-4-(5-bromo-2-chlorophenyl)-4-(fluoromethyl)-2-oxa-3-azabicyclo[3.1.0]hexane (6a rac, 14.06 g, 45.9 mmol) in acetic acid (180 mL, 3119 mmol) was added zinc dust (17.99 g, 275 mmol) in portions at RT. TFA (81 mL, 1055 mmol) was added and the reaction was stirred at RT for one hour. The reaction was filtered through celite and the filter cake was washed with additional acetic acid. The filtrate was poured over ice and the solution was basified to pH=14 by the addition of 5 M NaOH solution. The basic aqueous solution was back extracted with EtOAc (2×). The combined organic layers were washed with brine, dried over magnesium sulfate and concentrated under reduced pressure to afford the title compound (13.88 g, 45.0 mmol, 98% yield). MS m/z=307.9 [M+H]$^+$. Calculated for C$_{11}$H$_{12}$BrClFNO: 308.6

Step 3-4: N-(((1R,S),(5S,R),(6R,S))-5-(5-amino-2-chlorophenyl)-5-(fluoromethyl)-2-oxa-4-azabicyclo[4.1.0]hept-3-en-3-yl)benzamide (9d rac)

The title compound was prepared following procedures similar to those described in steps 7 and 8 for the synthesis of 1i rac, but using [(1R,S),(2R,S)]-2((S,R)-1-amino-1-(5-bromo-2-chlorophenyl)-2-fluoroethyl)cyclopropanol (6b rac) MS m/z=374.0 [M+H]$^+$. Calculated for C$_{19}$H$_{17}$ClFN$_3$O$_2$: 373.8

Step 5: N-((1S,5R,6S)-5-(5-amino-2-chlorophenyl)-5-(fluoromethyl)-2-oxa-4-azabicyclo[4.1.0]hept-3-en-3-yl)benzamide (6x-A) & N-((1R,5S,6R)-5-(5-amino-2-chlorophenyl)-5-(fluoromethyl)-2-oxa-4-azabicyclo[4.1.0]hept-3-en-3-yl)benzamide (9d-B)

N-(((1R,S),(5S,R),(6R,S))-5-(5-amino-2-chlorophenyl)-5-(fluoromethyl)-2-oxa-4-azabicyclo[4.1.0]hept-3-en-3-yl)benzamide (9d rac, 2.1g) was subjected to chromatography using supercritical $CO_2$ (additives 35% (MeOH with 20 mM $NH_3$) on a Chiralpak OD column (21×250 mm, 10 μm) eluting at a flow rate 70 ml/min (130 bar pressure, 40° C. column temperature). The first peak (retention time=1.45 min) provided N-((1S,5R,6S)-5-(5-amino-2-chlorophenyl)-5-(fluoromethyl)-2-oxa-4-azabicyclo[4.1.0]hept-3-en-3-yl)benzamide (9d-A, 876 mg, 2.34 mmol, 41.7% yield; 99% de; 99% ee) as a light yellow powder. The second peak (retention time=2.14 min) provided N-((1R,5S,6R)-5-(5-amino-2-chlorophenyl)-5-(fluoromethyl)-2-oxa-4-azabicyclo[4.1.0]hept-3-en-3-yl)benzamide (9d-B, 932 mg, 2.49 mmol, 44.4 yield; 99% de; 99% ee) as a light yellow powder. MS m/z=374.0 [M+H]$^+$. Calculated for $C_{19}H_{17}ClFN_3O_2$: 373.8 for both enantiomers.

Step 6: [(1R,S),(5S,R),(6R,S)]-5-(5-amino-2-chlorophenyl)-5-(fluoromethyl)-2-oxa-4-azabicyclo[4.1.0]hept-3-en-3-amine (9e rac)

The title compound was prepared following a procedure similar to that described in steps 4 for the synthesis of 4d rac, but using N-(((1R,S),(5S,R),(6R,S))-5-(5-amino-2-chlorophenyl)-5-(fluoromethyl)-2-oxa-4-azabicyclo[4.1.0]hept-3-en-3-yl)benzamide (9d rac) MS m/z=269.9 [M+H]$^+$. Calculated for $C_{12}H_{13}ClFN_3O$: 269.7

Step 7: (1S,5R,6S)-5-(5-amino-2-chlorophenyl)-5-(fluoromethyl)-2-oxa-4-azabicyclo[4.1.0]hept-3-en-3-amine (9e-A) and (1R,5S,6R)-5-(5-amino-2-chlorophenyl)-5-(fluoromethyl)-2-oxa-4-azabicyclo[4.1.0]hept-3-en-3-amine (9e-B)

[(1R,S),(5S,R),(6R,S)]-5-(5-amino-2-chlorophenyl)-5-(fluoromethyl)-2-oxa-4-azabicyclo[4.1.0]hept-3-en-3-amine (9e rac, 130 mg) was subjected to chromatography using supercritical $CO_2$ (additives 35% (MeOH with 20 mM $NH_3$) on a Chiralpak ODH column (20×250 mm, 10 μm) eluting at a flow rate 70 ml/min (172 bar pressure, 40° C. column temperature). The first peak (retention time=1.71 min) provided (1S,5R,6S)-5-(5-amino-2-chlorophenyl)-5-(fluoromethyl)-2-oxa-4-azabicyclo[4.1.0]hept-3-en-3-amine (9e-A, 33 mg, 0.12 mmol, 25% yield; 99% de; 99% ee) as a light yellow powder. The second peak (retention time=2.42 min) provided (1R,5S,6R)-5-(5-amino-2-chlorophenyl)-5-(fluoromethyl)-2-oxa-4-azabicyclo[4.1.0]hept-3-en-3-amine (9e-B, 33 mg, 0.12 mmol, 25% yield; 99% de; 99% ee) as a light yellow powder.

MS m/z=270.0 [M+H]$^+$ (for both enantiomers)

Peak 1: $^1$H NMR (300 MHz, DMSO-$d_6$) δ ppm 0.68-0.85 (m, 1H) 0.92 (td, J=6.58, 2.63 Hz, 1H) 1.70 (dt, J=9.90, 6.96 Hz, 1H) 3.80-3.94 (m, 2H) 4.48-4.65 (m, 1H) 4.68-4.83 (m, 1H) 5.16 (s, 2H) 5.55 (s, 13H) 6.45 (dd, J=8.40, 2.85 Hz, 7H) 6.87 (d, J=2.78 Hz, 1H) 7.01 (d, J=8.48 Hz, 1H)

Peak 2: $^1$H NMR (300 MHz, DMSO-$d_6$) δ ppm 0.79 (dt, J=9.68, 6.27 Hz, 1H) 0.92 (td, J=6.58, 2.78 Hz, 1H) 1.70 (dt, J=9.79, 7.09 Hz, 1H) 3.73-3.96 (m, 1H) 4.39-4.65 (m, 1H) 4.68-4.84 (m, 1H) 5.16 (s, 2H) 5.54 (s, 2H) 6.45 (dd, J=8.48, 2.78 Hz, 1H) 6.87 (d, J=2.92 Hz, 1H) 7.01 (d, J=8.33 Hz, 7H)

Example 10

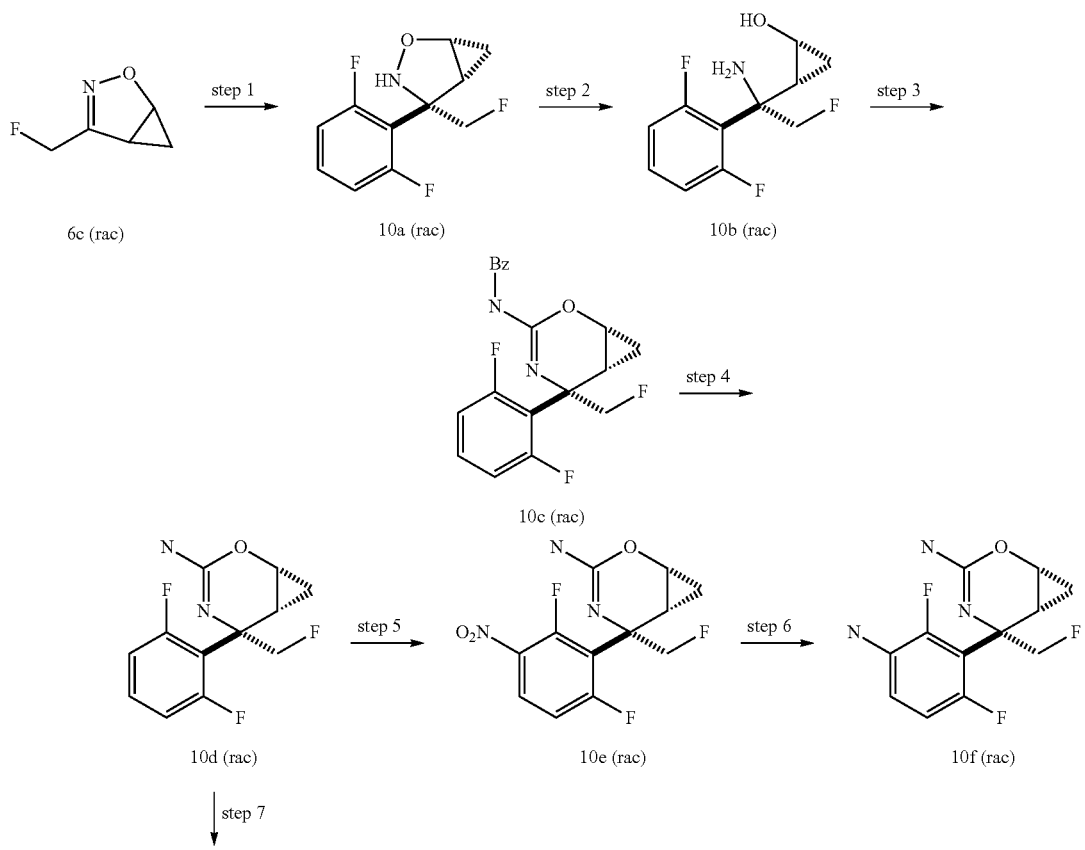

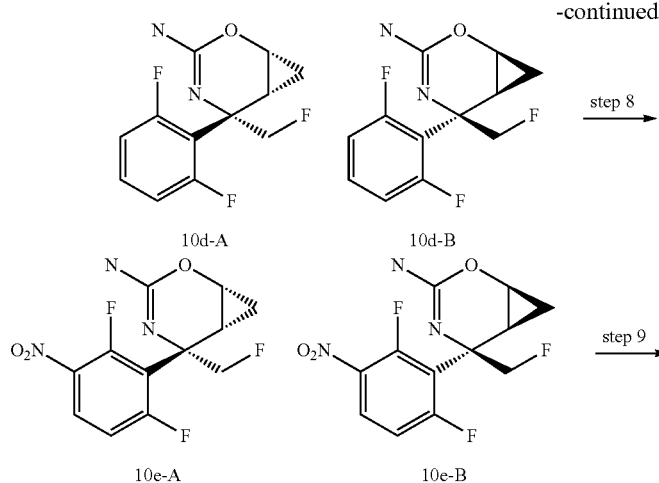
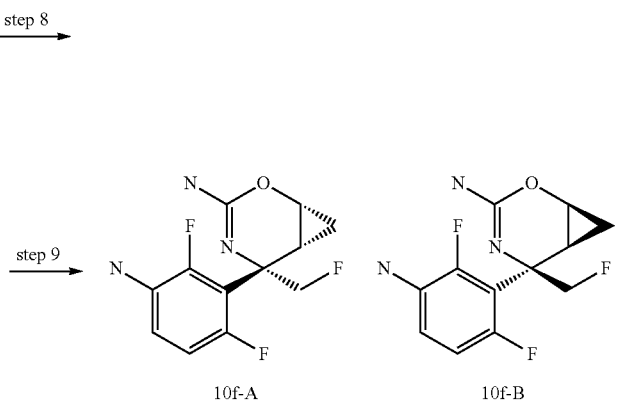

Step 1: [(1R,S),(4S,R),(5R,S)]-4-(2,6-difluorophenyl)-4-(fluoromethyl)-2-oxa-3-azabicyclo[3.1.0]hexane (10a rac)

A solution of 1-bromo-2,6-difluorobenzene (2.51 ml, 16.94 mmol) in $Et_2O$ (25 mL) was cooled to −78° C. and a solution of n-butyllithium (2.5M in hexanes, 6.78 ml, 16.94 mmol) was added dropwise. The resulting mixture was stirred at −78° C. for 20 min. A second flask was charged with a solution of 4-(fluoromethyl)-2-oxa-3-azabicyclo[3.1.0]hex-3-ene (6c rac, 1.3 g, 11.29 mmol) in toluene (5 mL) The reaction mixture was cooled to −78° C. and boron trifluoride diethyl etherate (1.464 ml, 11.86 mmol) was added. The reaction mixture was stirred for 5 min at −78 C and transferred via cannula to the aryllithium solution. The resulting reaction mixture was stirred at −78° C. for 30 min. The reaction was quenched with saturated $NH_4Cl$ solution. The reaction mixture was allowed to warm to room temperature and diluted with EtOAc and water. The organic layer was separated and the aqueous phase was extracted with EtOAc (2×). The combined organic layers were dried over $Na_2SO_4$ and the filtrate was concentrated under reduced pressure. The residue was purified by silica gel chromatography, eluting with 0-15% EtOAc/hexanes, to afford the title compound (2.02 g, 8.81 mmol, 78% yield). MS m/z=230 [M+H]$^+$. Calculated for $C_{11}H_{10}F_3NO$: 229.07

Step 2-4: [(1R,S),(5S,R),(6R,S)]-5-(2,6-difluorophenyl)-5-(fluoromethyl)-2-oxa-4-azabicyclo[4.1.0]hept-3-en-amine (10d rac)

The title compound was prepared following procedures similar to those described in steps 2 to 4 for the synthesis of 4d rac, but using [(1R,S),(4S,R),(5R,S)]-4-(2,6-difluorophenyl)-4-(fluoromethyl)-2-oxa-3-azabicyclo[3.1.0]hexane (10a rac)

MS m/z=256.9 [M+H]$^+$. Calculated for $C_{12}H_{11}F_3N_2O$: 256.08

Step 5: [(1R,S),(5S,R),(6R,S)]-5-(2,6-difluoro-3-nitrophenyl)-5-(fluoromethyl)-2-oxa-4-azabicyclo[4.1.0]hept-3-en-3-amine (10e rac)

[(1R,S),(5S,R),(6R,S)]-5-(2,6-difluorophenyl)-5-(fluoromethyl)-2-oxa-4-azabicyclo[4.1.0]hept-3-en-3-amine (10d rac, 0.107 g, 0.418 mmol) was dissolved in conc. $H_2SO_4$ (5 mL) and the flask containing the solution was placed in an ice-bath. Potassium nitrate (0.063 g, 0.626 mmol) was added in one portion and the reaction mixture was stirred for 5 min. The ice-bath was removed and the reaction was quenched after 10 min by the addition of ice. DCM, water and potassium phosphate tribasic (7 g, 33.0 mmol) were added and the reaction mixture was stirred for 5 min, followed by slow addition of aqueous saturated $NaHCO_3$ solution. The reaction mixture was neutralized with 5 N NaOH solution and extracted with DCM. The combined organic layers were dried over $Na_2SO_4$. The filtrate was concentrated under reduced pressure to afford the title compound (0.116 g, 0.385 mmol, 92% yield). MS m/z=301.9 [M+H]$^+$. Calculated for $C_{12}H_{10}F_3N_3O_3$: 301.07

Step 6: [(1R,S),(5S,R),(6R,S)]-5-(3-amino-2,6-difluorophenyl)-5-(fluoromethyl)-2-oxa-4-azabicyclo[4.1.0]hept-3-en-3-amine (10f rac)

A solution of [(1R,S),(5S,R),(6R,S)]-5-(2,6-difluoro-3-nitrophenyl)-5-(fluoromethyl)-2-oxa-4-azabicyclo[4.1.0]hept-3-en-3-amine (10e rac, 0.111 g, 0.368 mmol) in EtOH (5 mL) was purged with Nitrogen followed by the addition of palladium (10% wt. on activated carbon, 0.196 g, 0.184 mmol) and acetic acid (0.128 ml, 2.211 mmol). The reaction mixture was purged with Hydrogen for 35 min. The reaction mixture was filtered through celite and the filtrate was concentrated under reduced pressure. The residue was dissolved in DCM and washed with 10% aqueous $Na_2CO_3$ solution. The organic layer was dried over $Na_2SO_4$ and the filtrate was concentrated to afford the title compound (0.082 g, 0.302 mmol, 82% yield).

Step 7: (1R,5S,6R)-5-(2,6-difluorophenyl)-5-(fluoromethyl)-2-oxa-4-azabicyclo[4.1.0]hept-3-en-3-amine (Example 10d-A) and (1S,5R,6S)-5-(2,6-difluorophenyl)-5-(fluoromethyl)-2-oxa-4-azabicyclo[4.1.0]hept-3-en-3-amine (Example 10d-B)

[(1R,S),(5S,R),(6R,S)]-5-(2,6-difluorophenyl)-5-(fluoromethyl)-2-oxa-4-azabicyclo[4.1.0]hept-3-en-3-amine (10d rac) was subjected to chromatography using supercritical $CO_2$ (additive 35% MeOH with 20 mM $NH_3$) on a IC column (21×250 mm, 5 μm) eluting at a flow rate 50 ml/min (100 bar pressure, 40° C. column temperature). The first peak (retention time=1.13 min) provided (1R,5S,6R)-5-(2,6-difluorophenyl)-5-(fluoromethyl)-2-oxa-4-azabicyclo[4.1.0]hept-3-en-3-amine (Example 10d-A; 571 mg, mmol, 48% yield; 99% de; 99% ee) as a light-yellow powder, MS m/z=256.9 [M+H]$^+$ and (1S,5R,6S)-5-(2,6-difluorophenyl)-5-(fluoromethyl)-2-oxa-4-azabicyclo[4.1.0]hept-3-en-3-amine (Example 10d-B; 560 mg, mmol, 47% yield; 99% de; 99% ee) as a light-yellow powder. MS m/z=256.9 [M+H]$^+$.

Step 8-9: (1R,5S,6R)-5-(3-amino-2,6-difluorophenyl)-5-(fluoromethyl)-2-oxa-4-azabicyclo[4.1.0]hept-3-en-3-amine (10f-A)

The title compound was prepared following procedures similar to those described in steps 5 and 6 for the synthesis of 10f rac, but using (1S,5R,6S)-5-(2,6-difluorophenyl)-5-(fluoromethyl)-2-oxa-4-azabicyclo[4.1.0]hept-3-en-3-amine (Example 10d-A). MS m/z=272.0 [M+H]$^+$.

Step 8-9: (1S,5R,6S)-5-(3-amino-2,6-difluorophenyl)-5-(fluoromethyl)-2-oxa-4-azabicyclo[4.1.0]hept-3-en-3-amine (10f-B)

The title compound was prepared following procedures similar to those described in steps 5 and 6 for the synthesis of 10f rac, but using (1S,5R,6S)-5-(2,6-difluorophenyl)-5-(fluoromethyl)-2-oxa-4-azabicyclo[4.1.0]hept-3-en-3-amine (Example 10d-B). MS m/z=271.9 [M+H]$^+$.

Example 11

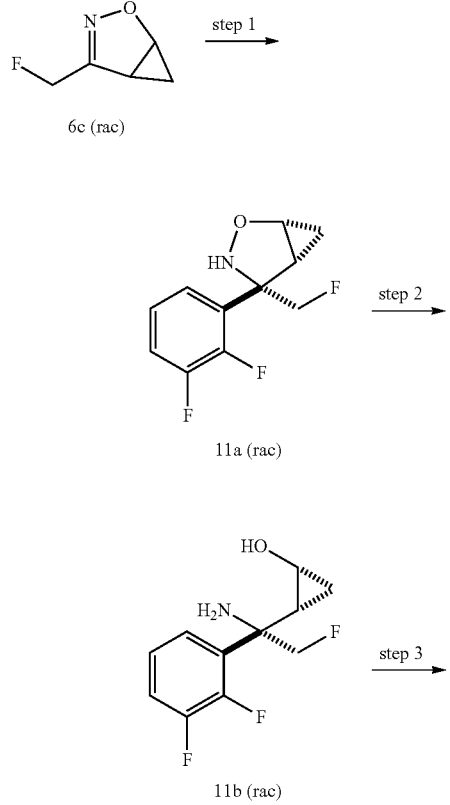

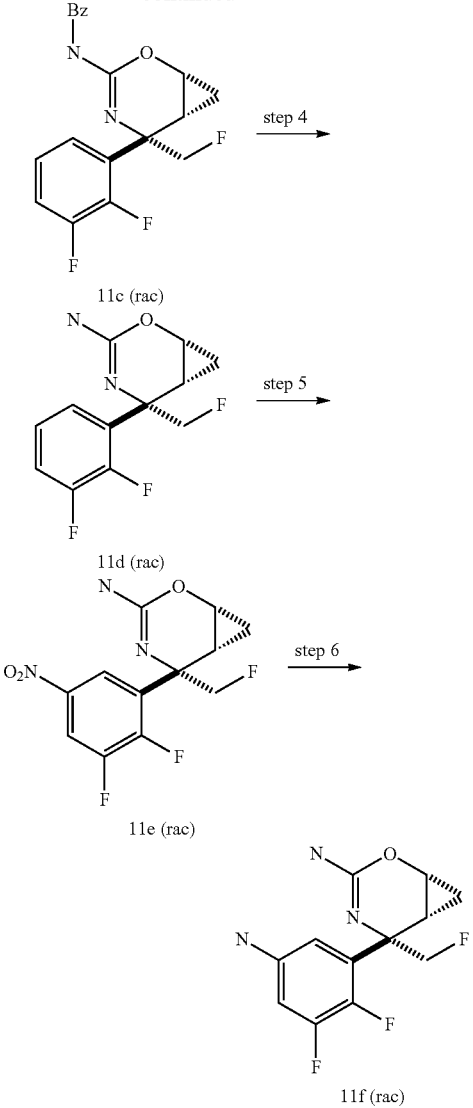

Step 1: [(1R,S),(4S,R),(5R,S)]-4-(2,3-difluorophenyl)-4-(fluoromethyl)-2-oxa-3-azabicyclo[3.1.0]hexane (11a rac)

A solution of n-butyllithium (2.5 M in hexanes, 35.4 mL, 89 mmol) was added to a solution of 1-bromo-2,3-difluorobenzene (16.10 g, 83 mmol) in diethyl ether (60 mL) under nitrogen atmosphere at −78 C. The resulting reaction mixture was stirred for 15 minutes. An additional flask was charged with 4-(fluoromethyl)-2-oxa-3-azabicyclo[3.1.0]hex-3-ene (6c rac, 6 g, 52.1 mmol) and toluene (30 mL). The reaction mixture was placed under nitrogen atmosphere and cooled to −78° C. Boron fluoride diethyl etherate (7.08 mL, 57.3 mmol) was added and the solution was stirred for 5 minutes. This solution was transferred via cannula to the aryl lithium solution. The resulting reaction mixture was stirred for 25 minutes. The reaction was quenched by addition of saturated NH$_4$Cl solution and subsequently partitioned between water and ethyl acetate. The organic phase was dried over sodium sulfate and the filtrate evaporated under reduced pressure. The residue was purified by flash chromatography (hexane to DCM=4:1 to 3:1 to 1:1) to give the title compound (6.5 g, 28.4 mmol, 54.4% yield). MS m/z=230 [M+H]⁺.

Step 2: [(1R,S),(2R,S)]-2-((S,R)-1-amino-1-(2,3-difluorophenyl)-2-fluoroethyl)cyclopropanol (11b rac)

The title compound was prepared following a procedure similar to that described in step 2 for the synthesis of 4b rac, but using [(1R,S),(4S,R),(5R,S)]-4-(2,3-difluorophenyl)-4-(fluoromethyl)-2-oxa-3-azabicyclo[3.1.0]hexane (11a rac). MS m/z=232 [M+H]⁺.

Step 3: N-(((1R,S),(5S,R),(6R,S))-5-(2,3-difluorophenyl)-5-(fluoromethyl)-2-oxa-4-azabicyclo[4.1.0]hept-3-en-3-yl)benzamide (11c rac)

To a solution of [(1R,S),(2R,S)]-2-(S,R)-1-amino-1-(2,3-difluorophenyl)-2-fluoroethyl)cyclopropanol (11b rac, 6.46 g, 27.9 mmol) in dry tetrahydrofuran (30 mL) under nitrogen was added benzoyl isothiocyanate (3.76 mL, 27.9 mmol) dropwise. After 10 minutes, N,N-diisopropylethylamine (1 mL) was added and the reaction mixture was stirred for an additional 10 minutes. Additional N,N-diisopropylethylamine (9.72 mL, 55.9 mmol) was added followed by 1-(3-dimethylaminopropyl)-3-ethylcarbodiimide HCl (5.89 g, 30.7 mmol. The reaction mixture was stirred at room temperature overnight. The reaction mixture was diluted with DCM (100 mL) and water (100 mL), the phases were separated and the organic phase was dried over magnesium sulfate. The filtrate was concentrated under reduced pressure. The residue was purified by flash chromatography to give the title compound (8.2 g, 22.76 mmol, 81% yield) as a sticky, light yellow tar. MS m/z=361 [M+H]⁺.

Step 4: [(1R,S),(5S,R),(6R,S)]-5-(2,3-difluoromethyl)-5-fluoromethyl)-2-oxa-4-azabicyclo[4.1.0]hept-3-en-3-amine (11d rac)

The title compound was prepared following a procedure similar to that described in step 4 for the synthesis of 4d rac, but using N-(((1R,S),(5S,R),(6R,S))-5-(2,3-difluorophenyl)-5-(fluoromethyl)-2-oxa-4-azabicyclo[4.1.0]hept-3-en-3-yl)benzamide (11e rac) MS m/z=257 [M+H]⁺.

Step 5: [(1R,S),(5S,R),(6R,S)]-5-(2,3-difluoro-5-nitrophenyl)-5-(fluoromethyl)-2-oxa-4-azabicyclo[4.1.0]hept-3-en-3-amine (11e rac)

[(1R,S),(5S,R),(6R,S)]-5-(2,3-difluorophenyl)-5-(fluoromethyl)-2-oxa-4-azabicyclo[4.1.0]hept-3-en-3-amine (11d rac, 5.4 g, 21.08 mmol) was dissolved in concentrated sulfuric acid (25 mL) and the solution was cooled to 0° C. Sodium nitrate (2.69 g, 31.6 mmol) was added in one portion and the reaction mixture was stirred for 5 minutes at 0° C. The cold bath was removed and the reaction mixture was allowed warm to room temperature. After 10 minutes, ice (~100 mL) was added, and the reaction mixture was poured into a mixture of dichloromethane (200 mL), water (200 mL), ice (~100 mL), and tribasic potassium phosphate (65 g). The resulting mixture was stirred for 5 minutes, followed by the addition of saturated sodium bicarbonate solution (50 mL). The organic phase was separated and the aqueous phase was extracted with ethyl acetate (2×150 mL). The combined organic extracts were dried over magnesium sulfate and the filtrate was concentrated under reduced pressure and taken into the next step without further purification.

Step 6: [(1R,S),(5S,R),(6R,S)]-5-(5-amino-2,3-difluorophenyl)-5-(fluoromethyl)-2-oxa-4-azabicyclo[4.1.0]hept-3-en-3-amine (11f rac)

The residue obtained in step 5 was dissolved in acetic acid (40 mL) and treated with zinc dust (13.78 g, 211 mmol). The reaction mixture was stirred for 30 minutes and the slurry was filtered. The filter cake was washed with ethyl acetate (200 mL). The combined filtrate was concentrated under reduced pressure and the residue was purified by flash chromatography (100% DCM to DCM/EtOAc=4:1 to DCM/EtOAc 2:1 to DCM/EtOAc 1:1 to 100% EA) to give the title compound (5.2 g, 19.17 mmol, 91% yield). MS m/z=272.1 [M+H]⁺.

Example 12

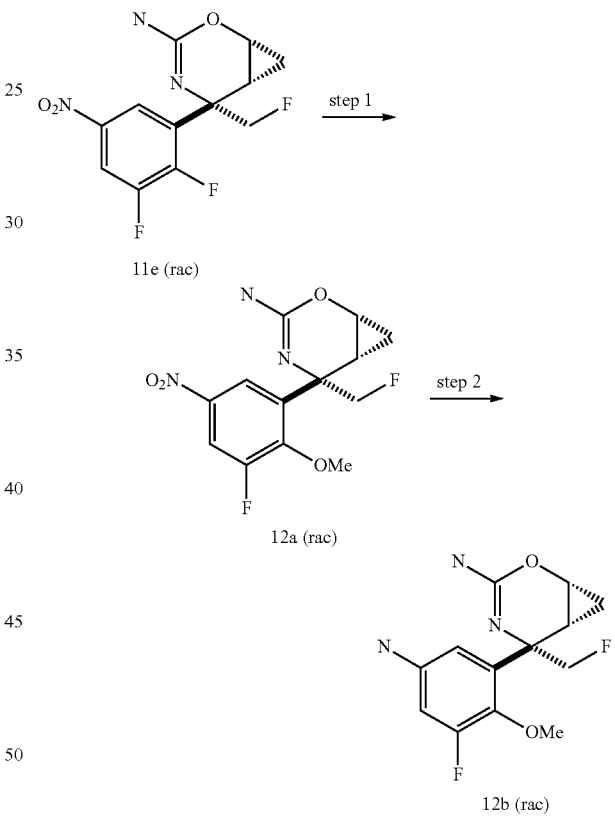

Step 1: [(1R,S),(5S,R),(6R,S)]-5-(3-fluoro-2-methoxy-5-nitrophenyl)-5-(fluoromethyl)-2-oxa-4-azabicyclo[4.1.0]hept-3-en-3-amine (12a rac)

To a solution of [(1R,S),(5S,R),(6R,S)]-5-(2,3-difluoro-5-nitrophenyl)-5-(fluoromethyl)-2-oxa-4-azabicyclo[4.1.0]hept-3-en-3-amine (11e rac, 500 mg, 1.660 mmol) in MeOH (10 mL) was added potassium carbonate (459 mg, 3.32 mmol). The reaction mixture was heated to 60° C. for 1 h. The reaction mixture was cooled to rt and the solvent was evaporated under reduced pressure. The residue was purified by flash chromatography (100% DCM to DCM/EtOAc=4:1 to DCM/EtOAc 1:1) to give the title compound (420 mg, 1.341 mmol, 81% yield). MS m/z=313.9 [M+1][1]. Calculated for $C_{13}H_{13}F_2N_3O_4$: 313.3.

Step 2: [(1R,S),(5S,R),(6R,S)]-5-(5-amino-3-fluoro-2-methoxyphenyl)-5-(fluoromethyl)-2-oxa-4-azabicyclo[4.1.0]hept-3-en-3-amine (12b rac)

A suspension of [(1R,S),(5S,R),(6R,S)]-5-(3-fluoro-2-methoxy-5-nitrophenyl)-5-(fluoromethyl)-2-oxa-4-azabicyclo[4.1.0]hept-3-en-3-amine (12a rac, 160 mg, 0.511 mmol) and palladium (10% on activated carbon, 109 mg, 0.102 mmol) in EtOH (20 mL) was purged with Nitrogen, followed by Hydrogen. The flask was fitted with a balloon filled with Hydrogen and the reaction mixture was stirred overnight. The reaction mixture was filtered through a pad of celite and the filter cake was rinsed with EtOAc. The filtrate was absorbed onto silica gel and purified by flash chromatography (100% EtOAc to EtOAc/MeOH=10:1) to give the title compound (140 mg, 0.494 mmol, 97% yield). MS m/z=284.0 [M+1]$^+$. Calculated for $C_{13}H_{15}F_2N_3O_2$: 283.2.

$^1$H NMR (400 MHz, CHLOROFORM-d) δ=6.54-6.46 (m, 1H), 6.41 (dd, J=2.7, 12.9 Hz, 1H), 4.74 (s, 1H), 4.63 (s, 1H), 3.88 (d, J=1.8 Hz, 3H), 3.77-3.62 (m, 1H), 1.76 (td, J=7.2, 9.7 Hz, 1H), 1.13 (dt, J=2.8, 6.8 Hz, 1H), 0.90-0.79 (m, 1H).

Example 13

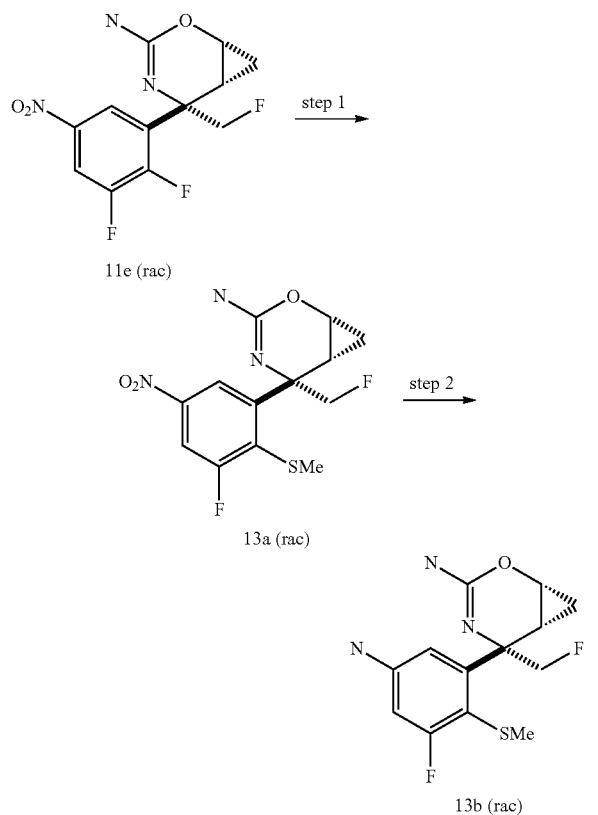

Step 1: [(1R,S),(5S,R),(6R,S)]-5-(3-fluoro-2-(methylthio)-5-nitrophenyl)-5-(fluoromethyl)-2-oxa-4-azabicyclo[4.1.0]hept-3-en-3-amine (13a rac)

[(1R,S),(5S,R),(6R,S)]-5-(2,3-difluoro-5-nitrophenyl)-5-(fluoromethyl)-2-oxa-4-azabicyclo[4.1.0]hept-3-en-3-amine (11e rac, 0.100 g, 0.332 mmol) was dissolved in MeOH (0.75 mL) and S-methyl benzothioate (0.056 g, 0.365 mmol) was added to the solution, followed by a solution of sodium methoxide (0.5M solution in methanol, 0.730 ml, 0.365 mmol). The reaction mixture was stirred at room temperature for 30 min and subsequently partitioned between EtOAc and water. The aqueous layer was separated and extracted with EtOAc. The combined organic layers were washed with brine, dried over sodium sulfate, and the filtrate was concentrated under reduced pressure. The crude material was purified by column chromatraphy, eluting with a gradient of 10-100% EtOAc/Hexanes to give the title compound (81 mg, 74% yield).

Step 2: [(1R,S),(5S,R),(6R,S)]-5-(5-amino-3-fluoro-2-(methylthio)phenyl)-5-(fluoromethyl)-2-oxa-4-azabicyclo[4.1.0]hept-3-en-3-amine (13b rac)

A flask was charged with [(1R,S),(5S,R),(6R,S)]-5-(3-fluoro-2-(methylthio)-5-nitrophenyl)-5-(fluoromethyl)-2-oxa-4-azabicyclo[4.1.0]hept-3-en-3-amine (13a rac, 0.073 g, 0.222 mmol), palladium (10% wt. on activated carbon, 1.963 µl, 0.022 mmol), EtOAc (600 µL) and MeOH (600 µL). The reaction mixture was purged with Nitrogen, followed by Hydrogen. The flask was fitted with a balloon filled with hydrogen and the reaction mixture was stirred at rt overnight. The reaction mixture was filtered through a pad of celite and the filter cake was washed with EtOAc. The filtrate was concentrated under reduced pressure to obtain the title compound. MS m/z=299.9 [M+H]$^+$. Calculated for $C_{13}H_{15}F_2N_3OS$: 299.3

Example 14

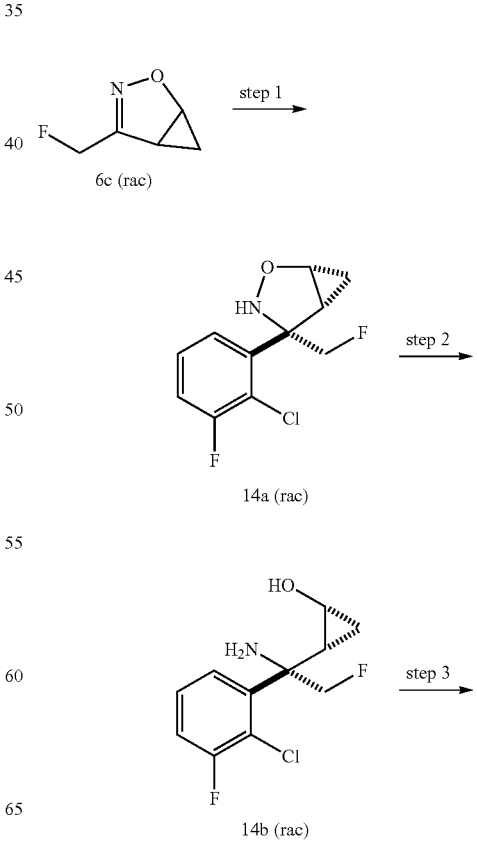

101

-continued

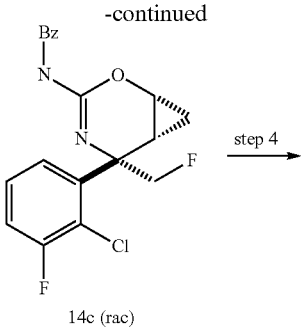

14c (rac)

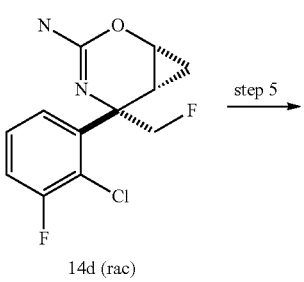

14d (rac)

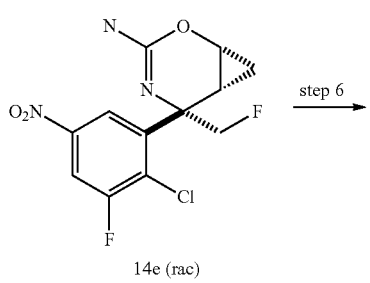

14e (rac)

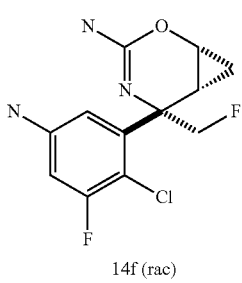

14f (rac)

102

Step 1: [1(S,R,4(R,S),5(S,R)]-4-(2-chloro-3-fluorophenyl)-4-(fluoromethyl)-2-oxa-3-azabicyclo[3.1.0]hexane (14a rac)

To a cooled (−78° C., internal) solution of 1-bromo-2-chloro-3-fluorobenzene (18.02 g, 86 mmol) in Et$_2$O (90 mL) was added a solution of n-butyllithium (2.5M in toluene, 34.0 ml, 85 mmol) over a period of 20 min. After completed addition, the reaction mixture was stirred for additional 30 min at that temperature. In a separate flask, a cooled (−78° C.) solution of 6c (4.0 g, 34.8 mmol) in toluene (24 ml) was treated with boron trifluoride diethyl etherate (4.3 ml, 34.8 mmol). The reaction mixture was stirred at that temperature for 20 min. This solution was added via cannula to the organilithium mixture. After 30 min, the reaction was quenched with 5% aq KHSO$_4$ solution (75 mL) and the reaction mixture was allowed to warm to rt. The layers were separated and the aqueous layer was extracted with EtOAc (3×). The combined organic layers were washed with brine and dried over Na$_2$SO$_4$. The filtrate was absorbed onto silica gel and purified by flash chromatography, eluting with a gradient 0:1→1:4 EtOAc:hexane, to give the title compound as a light-yellow crystalline solid (4.87 g, 57%). MS m/z=245.9, 248.0 [M+H]$^+$. Calculated for C$_{11}$H$_{10}$ClF$_2$NO: 245.6

Steps 2-6: [1(S,R),5(R,S),6(S,R)]-5-(5-amino-2-chloro-3-fluorophenyl)-5-(fluoromethyl)-2-oxa-4-azabicyclo[4.1.0]hept-3-en-3-amine (14f rac)

The title compound was prepared following procedures similar to those described in steps 2-6 for the synthesis of 11f rac, but using [1(S,R,4(R,S),5(S,R)]-4-(2-chloro-3-fluorophenyl)-4-(fluoromethyl)-2-oxa-3-azabicyclo[3.1.0]hexane (14a rac) MS m/z=287.9, 290.0 [M+H]$^+$. Calculated for C$_{12}$H$_{12}$ClF$_2$N$_3$O: 287.7

Example 15

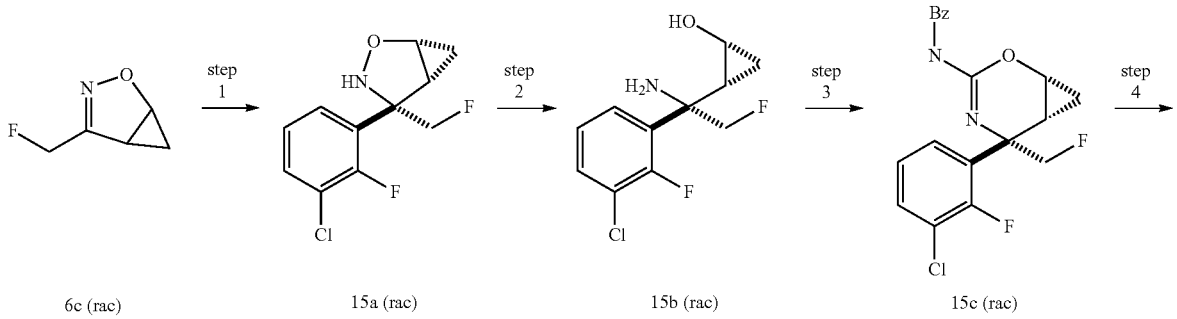

6c (rac)     15a (rac)     15b (rac)     15c (rac)

-continued

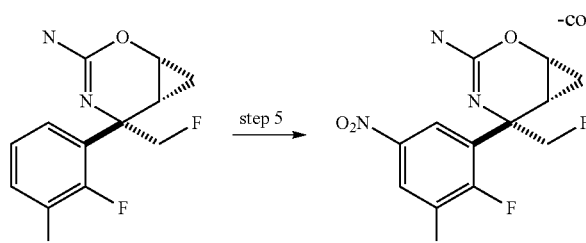

15d (rac) → step 5 → 15e (rac) → step 6 → 15f (rac)

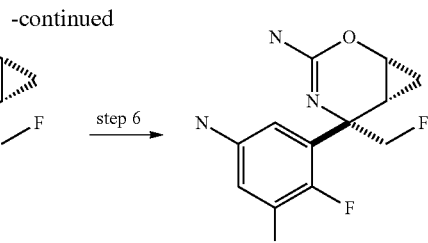

↓ step 7

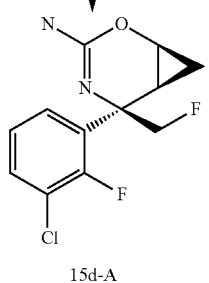 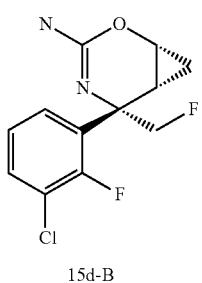

15d-A    15d-B

→ step 8 →

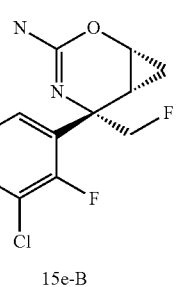

15e-B

→ step 9 →

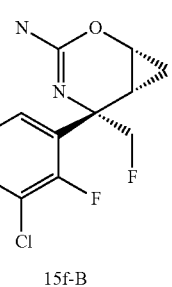

15f-B

Step 1: [(1R,S),(4S,R),(5R,S)]-4-(3-chloro-2-fluorophenyl)-4-(fluoromethyl)-2-oxa-3-azabicyclo[3.1.0]hexane (15a rac)

A solution of n-butyllithium (2.5M in hexanes, 5.21 ml, 13.03 mmol) was added dropwise to a cooled (−78 C) solution of 1-bromo-3-chloro-2-fluorobenzene (2.73 g, 13.03 mmol) in $Et_2O$ (40 mL). The resulting reaction mixture was stirred at −78° C. for 20 min. In a separate flask, a solution of 4-(fluoromethyl)-2-oxa-3-azabicyclo[3.1.0]hex-3-ene (6c rac, 1.0 g, 8.69 mmol) in toluene (10 mL) was cooled to −78° C. Boron trifluoride diethyl etherate (1.126 ml, 9.12 mmol) was added and the reaction mixture was stirred for 5 min. This solution was subsequently transferred via cannula to the aryl lithium solution. The resulting reaction mixture was stirred at −78° C. for 30 min. The reaction was quenched with aqueous saturated $NH_4Cl$ solution and allowed to warm to room temperature. EtOAc and water were added. The aqueous phase was separated and extracted with EtOAc. The combined organic layers were dried over $Na_2SO_4$ and the filtrate was concentrated under reduced pressure. The residue was purified by silica gel chromatography (0-10% EtOAc/hexanes) to afford the title compound (1.81 g, 7.37 mmol, 85% yield). MS m/z=245.9 $[M+H]^+$. Calculated for $C_{11}H_{10}ClF_2NO$: 245.04.

Steps 2-4: [(1R,S),(5S,R),(6R,S)]-5-(3-chloro-2-fluorophenyl)-5-(fluoromethyl)-2-oxa-4-azabicyclo[4.1.0]hept-3-en-3-amine (15d rac)

The title compound was prepared following procedures similar to those described in steps 2-4 for the synthesis of 11d rac, but using [(1R,S),(4S,R),(5R,S)]-4-(3-chloro-2-fluorophenyl)-4-(fluoromethyl)-2-oxa-3-azabicyclo[3.1.0]hexane (15a rac). MS m/z=272.9 $[M+H]^+$. Calculated for $C_{12}H_{11}ClF_2N_2O$: 272.05.

Step 5-6: [(1R,S),(5S,R),(6R,S)]-5-(5-amino-3-chloro-2-fluorophenyl)-5-(fluoromethyl)-2-oxa-4-azabicyclo[4.1.0]hept-3-en-3-amine (15f rac)

The title compound was prepared following procedures similar to those described in steps 5-6 for the synthesis of 11f rac, but using [(1R,S),(5S,R),(6R,S)]-5-(3-chloro-2-fluorophenyl)-5-(fluoromethyl)-2-oxa-4-azabicyclo[4.1.0]hept-3-en-3-amine (15d rac). MS m/z=287.9 $[M+H]^+$. Calculated for $C_{12}H_{12}ClF_2N_3O$: 287.06.

Step 7: (1S,5R,6S)-5-(3-chloro-2-fluorophenyl)-5-(fluoromethyl)-2-oxa-4-azabicyclo[4.1.0]hept-3-en-3-amine (15d-A) and (1R,5S,6R)-5-(3-chloro-2-fluorophenyl)-5-(fluoromethyl)-2-oxa-4-azabicyclo[4.1.0]hept-3-en-3-amine (15d-B)

[(1R,S),(5S,R),(6R,S)]-5-(3-chloro-2-fluorophenyl)-5-(fluoromethyl)-2-oxa-4-azabicyclo[4.1.0]hept-3-en-3-amine (15d rac) was subjected to chromatography using supercritical $CO_2$ (additives 30% MeOH with 20 mM $NH_3$) on a IC column (30×250 mm, 5 μm) eluting at a flow rate 120 ml/min (158 bar pressure, 40° C. column temperature). The first peak (retention time=1.28 min) provided (1S,5R,6S)-5-(3-chloro-2-fluorophenyl)-5-(fluoromethyl)-2-oxa-4-azabicyclo[4.1.0]hept-3-en-3-amine (Example 15d-A, 863 mg, 3.17 mmol, 39% yield; 99% de; 99% ee) as a light-yellow powder. MS m/z=272.9 $[M+H]^+$. The second peak (retention time=1.93 min) provided (1R,5S,6R)-5-(3-chloro-2-fluorophenyl)-5-(fluoromethyl)-2-oxa-4-azabicyclo[4.1.0]hept-3-en-3-amine (Example 15d-B; 878 mg, 3.22 mmol, 40% yield; 99% de; 99% ee) as a light-yellow powder. MS m/z=272.9 $[M+H]^+$.

Steps 8-9: (1R,5S,6R)-5-(5-amino-3-chloro-2-fluorophenyl)-5-(fluoromethyl)-2-oxa-4-azabicyclo[4.1.0]hept-3-en-3-amine (15f-B)

The title compound was prepared following procedures similar to those described in steps 5-6 for the synthesis of 15f rac, but using (1R,5S,6R)-5-(3-chloro-2-fluorophenyl)-5-(fluoromethyl)-2-oxa-4-azabicyclo[4.1.0]hept-3-en-3-amine (Example 15d-B). MS m/z=287.9 $[M+H]^+$. Calculated for $C_{12}H_{12}ClF_2N_3O$: 287.06.

Example 16

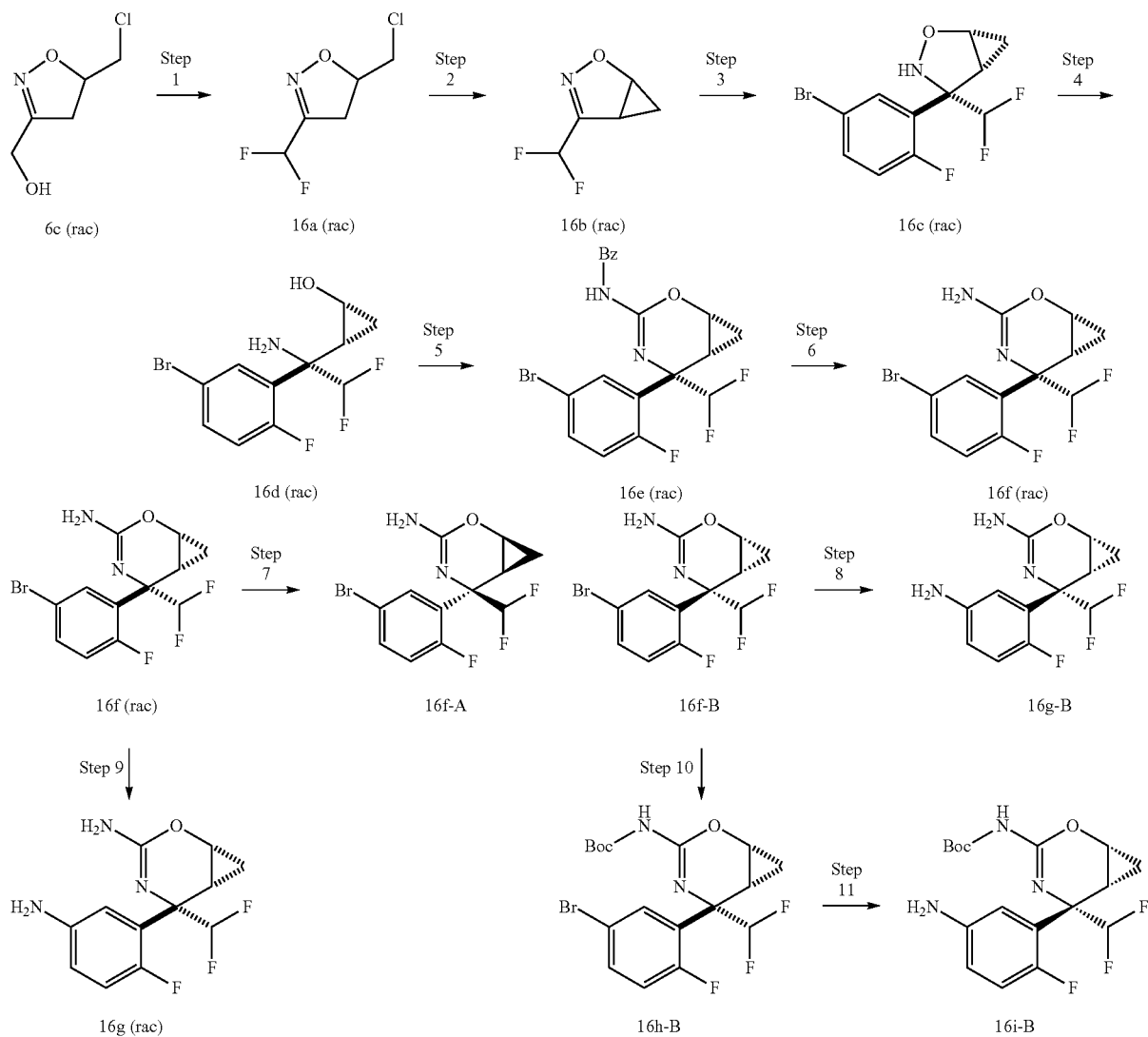

Step 1: 5-(Chloromethyl)-3-(difluoromethyl)-4,5-dihydroisoxazole (16a rac)

A solution of dimethyl sulfoxide (35.6 ml, 501 mmol) in DCM (50 mL) was added dropwise to a solution of oxalyl chloride (20.47 ml, 231 mmol) in DCM (400 mL) at −78° C. This solution was stirred for 10 min before a solution of (5-(chloromethyl)-4,5-dihydroisoxazol-3-yl)methanol (15.0 g, 100 mmol, synthesized according to Tetrahedron 1986, 42, 5267) in DCM (50 mL) was added dropwise. This mixture was stirred for 15 minutes at −78° C. before triethylamine (13.98 ml, 100 mmol) was added dropwise. The dry ice bath was removed and replaced with an ice bath. After 30 min, water and Et$_2$O were added and the layers were separated. The organic layer was washed with water, dried over MgSO$_4$ and the filtrate was concentrated in vacuo. The residue was dissolved in DCM (300 mL), the solution was cooled to −78° C. solution and (diethylamino)sulfur trifluoride (39.7 ml, 301 mmol) was added. The dry ice bath was replaced with an ice bath and the reaction mixture was stirred for 30 min. The reaction was quenched by addition of aqueous saturated NaHCO$_3$ solution, and the resulting biphasic mixture was separated. The aqueous layer was extracted with DCM. The combined organic extracts were dried over MgSO$_4$ and the filtrate was concentrated in vacuo to give an oil. The oil was purified by silica gel chromatography (0 to 60% Et$_2$O/hexane gradient) to give the title compound (11.0 g, 65% yield for the two steps).

Step 2: 4-(Difluoromethyl)-2-oxa-3-azabicyclo[3.1.0]hex-3-ene (16b rac)

A solution of potassium tert-butoxide (1.0 M in THF, 66.3 mL, 66.3 mmol) was added dropwise to a solution of 5-(chloromethyl)-3-(difluoromethyl)-4,5-dihydroisoxazole (16a rac, 9.0 g, 53.1 mmol) in THF (70 mL) at 0° C. The reaction mixture was stirred for 30 min, then aqueous saturated NH$_4$Cl solution was added slowly. The mixture was extracted with Et$_2$O (2×), and the combined organic extracts were dried over MgSO$_4$. The filtrate was concentrated under reduced pressure. The residue was purified by silica gel chromatography (0-60% Et$_2$O/pentane gradient) to give the title compound as an oil (5.29 g, 75% yield)

$^1$H NMR (300 MHz, CHLOROFORM-d) δ ppm 6.43-6.45 (s, 1H) 5.08 (td, J=5.41, 2.34 Hz, 1H) 2.75-2.83 (m, 1H) 1.04-1.14 (m, 1H) 0.38 (dd, J=1.90, 1.61 Hz, 1H)

Step 3: [(1(R,S), 4(S,R), 5(R,S)]-4-(5-bromo-2-fluorophenyl)-4-(difluoromethyl)-2-oxa-3-azabicyclo[3.1.0]hexane (16c rac)

A solution of n-butyllithium (2.5 M in hexanes, 49.6 mL, 124 mmol) was added slowly over 20 min to a stirred solution of 4-bromo-1-fluoro-2-iodobenzene (37.7 g, 125 mmol) in diethyl ether (240 mL) at −78° C. under a nitrogen atmosphere. The reaction mixture was stirred at −78° C. for 15 min. A separate flask was charged with a solution of 4-(difluoromethyl)-2-oxa-3-azabicyclo[3.1.0]hex-3-ene (8.25 g, 62.0 mmol) in toluene (280 mL) and cooled to −78° C. Boron trifluoride diethyl etherate (7.80 mL, 63.2 mmol) was added and after stirring the reaction mixture for 5 min at −78° C., it was transferred via cannula to the aryl lithium solution. The reaction mixture was stirred at −78° C. for 1 h and subsequently quenched with saturated aqueous NH$_4$Cl solution. The mixture was warmed to RT and diluted with EtOAc and water. The organic layer was separated. The aqueous layer was extracted once more with EtOAc. The combined organic layers were washed with brine, dried over MgSO$_4$. The filtrate was concentrated in vacuo and the resulting crude product was purified via silica gel flash column chromatography eluting with 0 to 20% EtOAc in heptane to give the title compound as a light orange solid (15.14 g, 79% yield).

Steps 4-6: [(1R,S),(5S,R),(6R,S)]-5-(5-bromo-2-fluorophenyl)-5-(difluoromethyl)-2-oxa-4-azabicyclo[4.1.0]hept-3-en-3-amine (16f rac)

The title compound was prepared following procedures similar to those described in steps 2-4 for the synthesis of 4d rac, but using [(1(R,S), 4(S,R), 5(R,S)]-4-(5-bromo-2-fluorophenyl)-4-(difluoromethyl)-2-oxa-3-azabicyclo[3.1.0]hexane (16c rac). LC/MS (ESI$^+$) m/z=334.9 (M+H).

Step 7: (1S,5R,6S)-5-(5-bromo-2-fluorophenyl)-5-(difluoromethyl)-2-oxa-4-azabicyclo[4.1.0]hept-3-en-3-amine (16f-A) and (1R,5S,6R)-5-(5-bromo-2-fluorophenyl)-5-(difluoromethyl)-2-oxa-4-azabicyclo[4.1.0]hept-3-en-3-amine (16f-B)

[1(S,R),5(R,S),6(S,R)]-5-(5-bromo-2-fluorophenyl)-5-(difluoromethyl)-2-oxa-4-azabicyclo[4.1.0]hept-3-en-3-amine (16f-rac) (9.39 g, 28 mmol) was subjected to chromatography using supercritical CO$_2$ (additives 10% MeOH with 20 mM NH$_3$) on a Chiralpak ADH (30×250 mm, 5 μm) eluting at a flow rate 100 mL/min (120 bar pressure, ambient column temperature). The first peak (retention time=4.94 min) provided (Example 16f-A; 3.54 g, 10.6 mmol, 38% yield; >99% de; >99% ee) as a white solid. LC/MS (ESI$^+$) m/z=334.9 (M+H). Calculated for C$_{12}$H$_{10}$BrF$_3$N$_2$O 334.0. $^1$H NMR (400 MHz, CDCl$_3$) δ 0.95 (dt, J=9.34, 6.97 Hz, 1H), 1.28-1.42 (m, 1H), 1.78 (dt, J=9.49, 7.09 Hz, 1H), 3.89-3.94 (m, 1H), 4.42 (br s, 2H), 6.13 (t, J=56.70 Hz, 1H), 6.97 (dd, J=11.54, 8.61 Hz, 1H), 7.42 (ddd, J=8.61, 4.30, 2.54 Hz, 1H), 7.65 (dd, J=6.85, 2.54 Hz, 1H). The second peak (retention time=6.26 min) provided (Example 16f-B; 3.52 g, 10.5 mmol, 38% yield; >99% de; >98.4% ee) as a white solid. LC/MS m/z=334.9 [M+H]$^+$. Calculated for C$_{12}$H$_{10}$BrF$_3$N$_2$O 334.0. $^1$H NMR (400 MHz, CDCl$_3$) δ 0.95 (dt, J=9.44, 6.92 Hz, 1H), 1.37 (t, J=7.04 Hz, 1H), 1.78 (dt, J=9.54, 7.16 Hz, 1H), 3.89-3.94 (m, 1H), 4.45 (br s, 2H), 6.15 (t, J=56.10 Hz, 1H), 6.97 (dd, J=11.54, 8.80 Hz, 1H), 7.42 (ddd, J=8.61, 4.21, 2.64 Hz, 1H), 7.65 (dd, J=7.04, 2.54 Hz, 1H).

Step 8: (1S,5R,6S)-5-(5-amino-2-fluorophenyl)-5-(difluoromethyl)-2-oxa-4-azabicyclo[4.1.0]hept-3-en-3-amine (16g-B)

The title compound was prepared following a procedure similar to that described in step 8 for the synthesis of 6h-B, but using (1R,5S,6R)-5-(5-bromo-2-fluorophenyl)-5-(difluoromethyl)-2-oxa-4-azabicyclo[4.1.0]hept-3-en-3-amine (16f-B) MS m/z=272.0 [M+H]+.

Step 9: [(1R,S),(5S,R),(6R,S)]-5-(5-amino-2-fluorophenyl)-5-(difluoromethyl)-2-oxa-4-azabicyclo[4.1.0]hept-3-en-3-amine (16g rac)

The title compound was prepared following a procedure similar to that described in step 9 for the synthesis of 6h rac, but using [(1R,S),(5S,R),(6R,S)]-5-(5-bromo-2-fluorophenyl)-5-(difluoromethyl)-2-oxa-4-azabicyclo[4.1.0]hept-3-en-3-amine (16f rac). MS m/z=272.0 [M+H]+.

Step 10: tert-butyl((1R,5S,6R)-5-(5-bromo-2-fluorophenyl)-5-(difluoromethyl)-2-oxa-4-azabicyclo[4.1.0]hept-3-en-3-yl)carbamate (16h-B)

To a solution of (1R,5S,6R)-5-(5-bromo-2-fluorophenyl)-5-(difluoromethyl)-2-oxa-4-azabicyclo[4.1.0]hept-3-en-3-amine (16f-B, 1.22 g, 3.64 mmol) in dioxane (10 mL) at room temperature was added saturated aqueous NaHCO$_3$ (15 mL) and di-tert-butyl dicarbonate (0.975 g, 4.47 mmol). The reaction mixture was heated to 40° C. for 21 h. Additional di-tert-butyl dicarbonate (1.02 g, 4.68 mmol) was added. Stirring at 40° C. was continued for 1 d. The reaction mixture was cooled to RT and diluted with EtOAc. The organic phase was washed with brine and dried over MgSO$_4$. The filtrate was concentrated under reduced pressure and the residue was purified by flash column chromatography on silica gel (40 g, 5% to 50% EtOAc in hexanes) to give the title compound (1.47 g, 3.38 mmol, 93% yield) as a white solid. MS m/z=434.9 [M+H]+. Calculated for C$_{17}$H$_{18}$BrF$_3$N$_2$O$_3$ 434.0.

Step 11: tert-butyl((1R,5S,6R)-5-(5-amino-2-fluorophenyl)-5-(difluoromethyl)-2-oxa-4-azabicyclo[4.1.0]hept-3-en-3-yl)carbamate (16i-B)

To a mixture of tert-butyl((1R,5S,6R)-5-(5-bromo-2-fluorophenyl)-5-(difluoromethyl)-2-oxa-4-azabicyclo[4.1.0]hept-3-en-3-yl)carbamate (16h-B, 1.47 g, 3.38 mmol), copper(I) iodide (0.139 g, 0.730 mmol), (+)-sodium 1-ascorbate (0.131 g, 0.661 mmol), and sodium azide (0.688 g, 10.6 mmol) were added EtOH (4.6 mL) and water (2.3 mL). The reaction mixture was purged with Nitrogen for 10 min, followed by the addition of (1R,2R)-(−)-N,N'''-dimethylcyclohexane-1,2-diamine (0.110 mL, 0.698 mmol). The reaction mixture was heated to 70° C. for 1.5 h and cooled to RT. The reaction mixture was poured into 10:1 saturated NH$_4$Cl/ammonium hydroxide, and diluted with EtOAc. The aqueous phase was extracted with EtOAc (2×) and the combined organic extracts were washed with brine and dried over MgSO$_4$. The filtrate was concentrated under reduced pressure to give a solid, which was dissolved in THF (12 mL) and water (4 mL). A solution of trimethyl phosphine (1.0 M in THF, 3.40 mL, 3.40 mmol) was added and the reaction mixture was stirred at RT for 15 min. The reaction mixture was diluted with EtOAc and water, the aqueous phase was separated and extracted with EtOAc. The combined organic extracts were washed with brine and dried over MgSO$_4$. The filtrate was concentrated under reduced pressure and the residue was purified by flash column chromatography on silica gel (20% to 70% EtOAc in heptane) to give the title compound (1.03 g, 2.77 mmol, 82% yield) as a white solid. MS m/z=372.0 [M+H]+. Calculated for C$_{17}$H$_{20}$F$_3$N$_3$O$_3$ 371.1.

Example 17

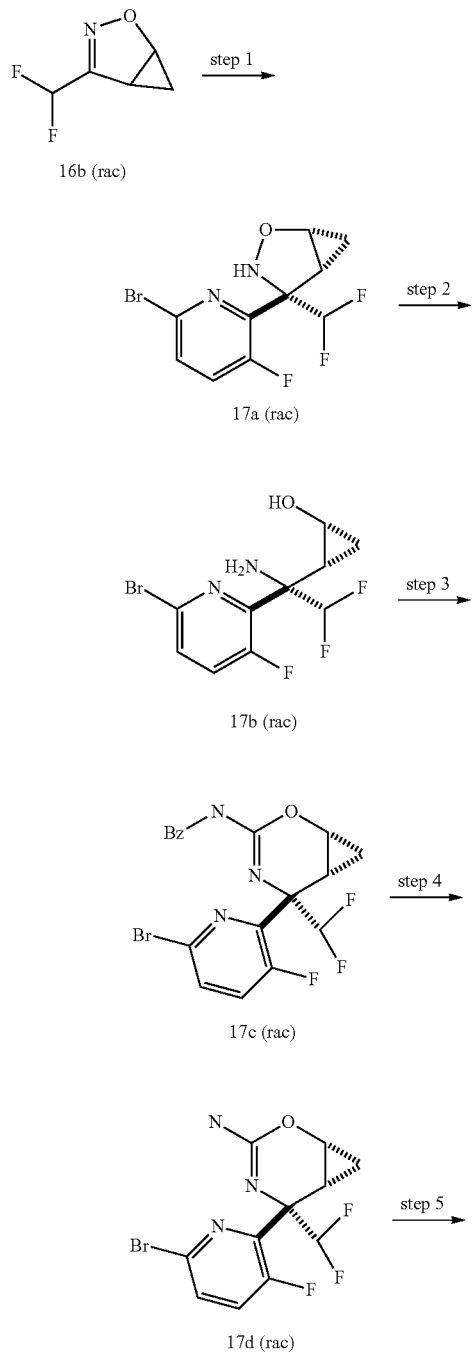

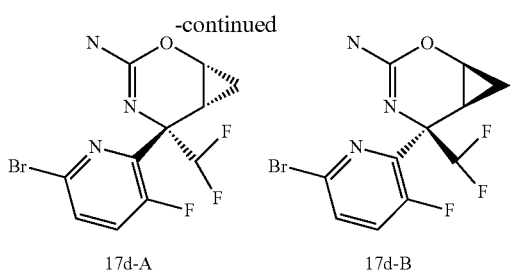

17d-A 17d-B

Step 1: [(1R,S),(4S,R),(5R,S)]-4-(6-bromo-3-fluoropyridin-2-yl)-4-(difluoromethyl)-2-oxa-3-azabicyclo [3.1.0]hexane (17a rac)

A flame dried RBF was charged with 2-bromo-5-fluoropyridine (10.23 g, 58.2 mmol) and diethyl ether (240 mL). The solution was cooled to −78° C. before adding a solution of n-butyllithium (2.5M in hexane, 23.26 ml, 58.2 mmol) dropwise. The reaction mixture was stirred at −78° C. for 30 min. A second flask was charged with a solution of 4-(difluoromethyl)-2-oxa-3-azabicyclo[3.1.0]hex-3-ene (16b rac, 3.87 g, 29.1 mmol) in DCM (100 mL) and cooled to −78° C. solution. Boron fluoride diethyl etherate (3.59 ml, 29.1 mmol) was added and after 15 min, this reaction mixture was transferees via cannula to the aryl lithium solution. Upon complete addition the reaction mixture was stirred at −78° C. for 30 minutes and then gradually warmed to RT for 2 hours. The reaction was diluted with water and DCM. The organic layer was separated, washed with brine and dried over magnesium sulfate. The filtrate was concentrated under reduced pressure and the crude material was purified via silica gel flash chromatography using a gradient of 5-40% EtOAc in hexanes to afford the title compound (3.74 g, 12.10 mmol, 41.6% yield) as a brown solid. MS m/z=308.9 M+. Calculated for C$_{10}$H$_8$BrF$_3$N$_2$O: 309.1

Steps 2-4: [(1R,S),(5S,R),(6R,S)]-5-(6-bromo-3-fluoropyridin-2-yl)-5-(difluoromethyl)-2-oxa-4-azabicyclo[4.1.0]hept-3-en-3-amine (17d rac)

The title compound was prepared following procedures similar to those described in steps 2-4 for the synthesis of 4d rac, but using [(1R,S),(4S,R),(5R,S)]-4-(6-bromo-3-fluoropyridin-2-yl)-4-(difluoromethyl)-2-oxa-3-azabicyclo[3.1.0] hexane (17a rac) MS m/z=335.9 M+. Calculated for C$_{11}$H$_9$BrF$_3$N$_3$O: 336.1

Step 5: (1R,5S,6R)-5-(6-bromo-3-fluoropyridin-2-yl)-5-(difluoromethyl)-2-oxa-4-azabicyclo[4.1.0] hept-3-en-3-amine (17d-A) and (1S,5R,6S)-5-(6-bromo-3-fluoropyridin-2-yl)-5-(difluoromethyl)-2-oxa-4-azabicyclo[4.1.0]hept-3-en-3-amine (17d-B)

[(1R,S),(5S,R),(6R,S)]-5-(6-bromo-3-fluoropyridin-2-yl)-5-(difluoromethyl)-2-oxa-4-azabicyclo[4.1.0]hept-3-en-3-amine (17d rac) was subjected to chromatography using supercritical CO$_2$ (additives 12% MeOH with 20 mM NH$_3$) on an ODH column (20×250 mm, 5 μm) eluting at a flow rate 75 ml/min (100 bar pressure, 40° C. column temperature). The first peak (retention time=1.02 min) provided (Example 17d-A; 510 mg, 1.518 mmol, 43% yield; 99% de; 99% ee) as a white powder. The second peak (retention time=1.29 min) provided (Example 17d-B; 490 mg, 1.458 mmol, 41% yield;

99% de; 99% ee) as a white powder. MS m/z=335.9 M+. Calculated for $C_{11}H_9BrF_3N_3O$: 336.1 for both enantiomers.

Example 18

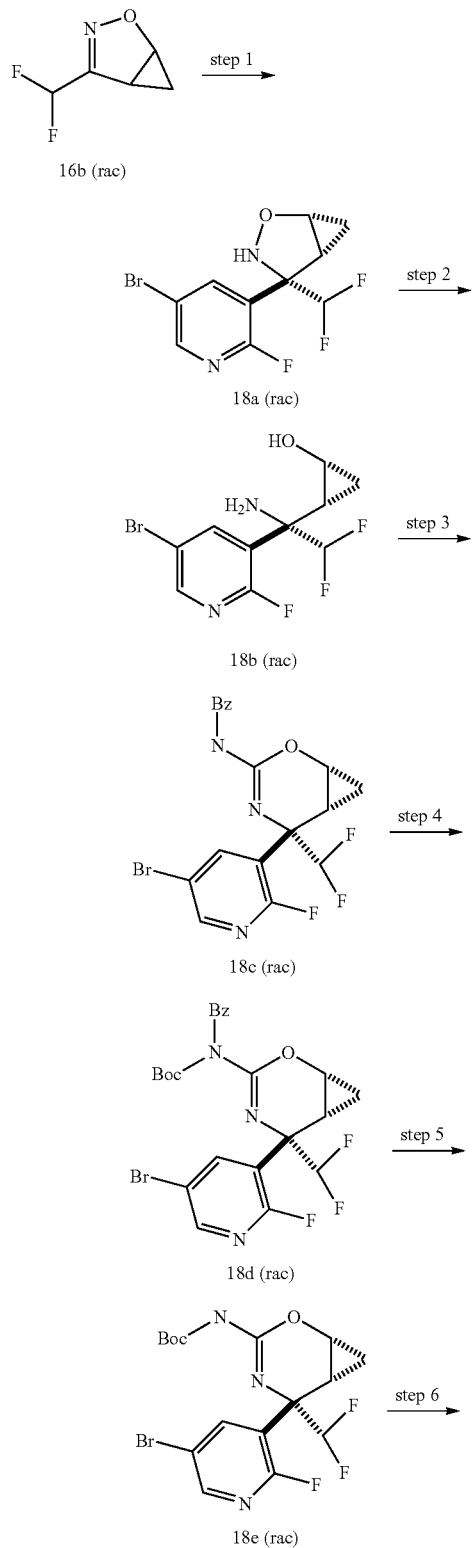

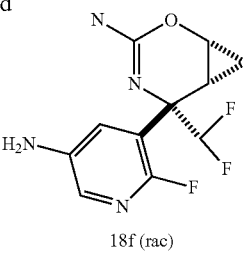

Step 1: [(1R,S),(4S,R),(5R,S)]-4-(5-bromo-2-fluoro-pyridin-3-yl)-4-(difluoromethyl)-2-oxa-3-azabicyclo[3.1.0]hexane (18a rac)

A solution of n-butyllithium (9.39 mL, 15.03 mmol, 1.60 M in hexanes) was added to a solution of diisopropylamine (2.106 mL, 15.03 mmol) in THF (30 mL) at 0° C. under a nitrogen atmosphere. The reaction mixture was stirred at 0° C. for 10 min and then cooled to −78° C. 5-Bromo-2-fluoro-pyridine (1.729 mL, 15.03 mmol) was added dropwise, the reaction mixture was stirred at −78° C. for 30 min, followed by the addition of N,N,N',N'-tetramethylethanediamine (2.249 mL, 15.03 mmol). A separate flask was charged with a solution of 4-(difluoromethyl)-2-oxa-3-azabicyclo[3.1.0]hex-3-ene (16b rac, 1.00 g, 7.51 mmol) in toluene (20 mL) and cooled to −78° C. solution. Boron fluoride diethyl etherate (0.927 mL, 7.51 mmol) and after 3 min, this reaction mixture was transferred via cannula to the aryl lithium solution. Upon complete addition the reaction mixture was stirred at −78° C. for 1 h, then allowed to warm to 0° C. and quenched with saturated aqueous ammonium chloride solution. The biphasic mixture was extracted with EtOAc. The organic layer was separated, washed with brine and dried over magnesium sulfate. The filtrate was concentrated in vacuo and the resulting crude residue was purified via silica gel flash column chromatography (eluent: 0% to 30% EtOAc in hexanes) to yield a 2:1 mixture of the regioisomers [(1R,S),(4S,R),(5R,S)]-4-(5-bromo-2-fluoropyridin-3-yl)-4-(difluoromethyl)-2-oxa-3-azabicyclo[3.1.0]hexane (18a rac) and [(1R,S),(4S,R),(5R,S)]-4-(5-bromo-2-fluoropyridin-4-yl)-4-(difluoromethyl)-2-oxa-3-azabicyclo[3.1.0]hexane as a yellow solid (1.164 g). The mixture was taken onto the next step. MS m/z=308.9 [M+H]+. (for both regioisomers) Calculated for $C_{10}H_8BrF_3N_2O$: 307.977.

Steps 2: [(1R,S),(2R,S)]-2-((S,R)-1-amino-1-(5-bromo-2-fluoropyridin-3-yl)-2,2-difluoroethyl)cyclopropanol (18b rac)

To a stirred solution of a 2:1 mixture of [(1R,S),(4S,R),(5R,S)]-4-(5-bromo-2-fluoropyridin-3-yl)-4-(difluoromethyl)-2-oxa-3-azabicyclo[3.1.0]hexane (18a rac) and [(1R,S),(4S,R),(5R,S)]-4-(5-bromo-2-fluoropyridin-4-yl)-4-(difluoromethyl)-2-oxa-3-azabicyclo[3.1.0]hexane (0.879 g, 2.84 mmol) in trifluoroacetic acid (10.6 mL, 142 mmol) was added zinc dust (1.86 g, 28.4 mmol). The reaction mixture was stirred at room temperature for 1.5 h before being diluted with DCM and filtered. The filtrate was diluted with saturated aqueous sodium bicarbonate and brought to pH 9 with 1 M aqueous NaOH. The organic layer was separated, and the aqueous layer was extracted once more with DCM. The combined organic layers were dried over magnesium sulfate and the filtrate was concentrated under reduced pressure. The resulting crude residue was purified via silica gel flash column chromatography (eluent: 0 to 50% EtOAc in hexanes) to give [(1R,S),(2R,S)]-2-((S,R)-1-amino-1-(5-bromo-2-fluoropyridin-3-yl)-2,2-difluoroethyl)cyclopropanol (0.322 g, 1.04 mmol, 36.4% yield) as a light yellow oil that partially solidified upon standing. MS m/z=312.8 [M+H]+.

Steps 3-6: [1(R,S),5(S,R),6(R,S)]-5-(5-amino-2-fluoropyridin-3-yl)-5-(difluoromethyl)-2-oxa-4-azabicyclo[4.1.0]hept-3-en-3-amine (18f rac)

The title compound was prepared following procedures similar to those described in steps 3-5 for the synthesis of 5e rac, and step 8 for the synthesis of 8g-B but using [(1R,S),(2R,S)]-2-((S,R)-1-amino-1-(5-bromo-2-fluoropyridin-3-yl)-2,2-difluoroethyl)cyclopropanol (18b rac). MS m/z=273.0 [M+H]+. Calculated for $C_{11}H_{1}F_{3}N_{4}O$: 272.088

Example 19

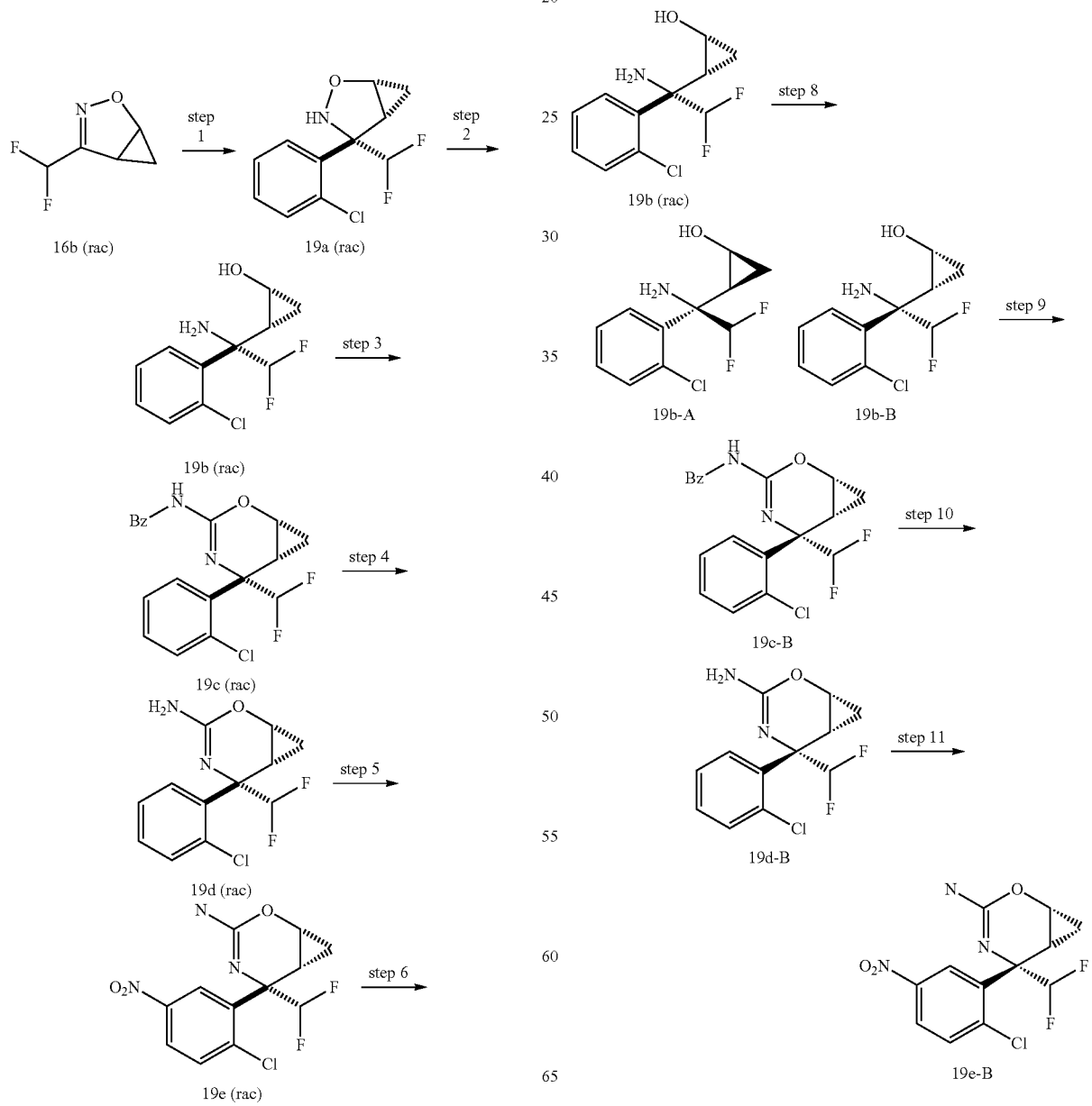

Step 1: [(1R,S),(4S,R),(5R,S)]-4-(2-chlorophenyl)-4-(difluoromethyl)-2-oxa-3-azabicyclo[3.1.0]hexane (19a rac)

A solution of n-butyllithium (2.5M in hexanes, 9.80 mL, 24.50 mmol) was added dropwise to a stirred solution of 1-chloro-2-iodobenzene (3.00 mL, 24.62 mmol) in toluene (24 mL) and THF (8 mL) at −70° C. After completed addition, the reaction mixture was stirred at −70° C. for 5 min. Subsequently, a solution of 4-(difluoromethyl)-2-oxa-3-azabicyclo[3.1.0]hex-3-ene (16b rac, 1.4582 g, 9.97 mmol) in toluene (6 mL) was added over a period of 9 min. After 5 min stirring at that temperature boron fluoride diethyl etherate (1.30 mL, 10.26 mmol) was added and the resulting reaction mixture was stirred at −70° C. for additional 30 min. A solution of saturated aqueous NH$_4$Cl (20 mL) was added and the cold bath was removed, allowing the reaction mixture to warm up to rt. The mixture was partitioned between water (20 mL) and EtOAc (10 mL). The aqueous phase was extracted with EtOAc (2×30 mL). The combined organic phases were washed with saturated aqueous sodium bicarbonate (50 mL), water (50 mL) brine (50 mL). The organic phase was dried over sodium sulfate and the filtrate was concentrated in vacuo. The crude product was purified by silica gel flash chromatography (EtOAc in hexanes 0%-20%) to afford 1.3566 g of the title compound as a yellow oil. MS m/z=245.9 [M+H]$^+$ $^1$H NMR (400 MHz, CHLOROFORM-d) δ=8.10-8.02 (m, 1H), 7.45-7.27 (m, 3H), 7.12-6.80 (m, 1H), 6.27 (d, J=5.5 Hz, 1H), 4.08-4.00 (m, 1H), 2.73-2.64 (m, 1H), 1.37 (dd, J=2.6, 5.0 Hz, 1H), 0.71 (dt, J=5.5, 8.5 Hz, 1H).

Steps 2-6: [(1R,S),(5S,R),(6R,S)]-5-(5-amino-2-chlorophenyl)-5-(difluoromethyl)-2-oxa-4-azabicyclo[4.1.0]hept-3-en-3-amine (19f-rac)

The title compound was prepared following procedures similar to those described in steps 2-6 for the synthesis of 10f rac, but using [(1R,S),(4S,R),(5R,S)]-4-(2-chlorophenyl)-4-(difluoromethyl)-2-oxa-3-azabicyclo[3.1.0]hexane (19a rac) MS m/z=287.9 [M+H]$^+$ $^1$H NMR (400 MHz, CDCl$_3$): δ 7.15 (d, J=8.4 Hz, 1H), 7.02 (d, J=2.7 Hz, 1H), 6.81 (t, J=57.7 Hz, 1H), 6.55 (dd, J=8.4, 2.7 Hz, 1H), 4.66 (br s, 2H), 3.82 (t, J=5.7 Hz, 2H), 3.69 (br s., 2H), 2.00-2.11 (m, 1H), 1.32 (t, J=6.8 Hz, 1H), 0.93 (dt, J=9.7, 6.8 Hz, 1H)

Step 7: (1S,5R,6S)-5-(5-amino-2-chlorophenyl)-5-(difluoromethyl)-2-oxa-4-azabicyclo[4.1.0]hept-3-en-3-amine (19f-A) and (1R,5S,6R)-5-(5-amino-2-chlorophenyl)-5-(difluoromethyl)-2-oxa-4-azabicyclo[4.1.0]hept-3-en-3-amine (19f-B)

[(1R,S),(5S,R),(6R,S)]-5-(5-amino-2-chlorophenyl)-5-(difluoromethyl)-2-oxa-4-azabicyclo[4.1.0]hept-3-en-3-amine (16f rac; 0.96 g) was subjected to chromatography using supercritical CO$_2$ (additives 25% (MeOH with 20 mM NH$_3$) on a Chiralpak OJ-H column (20×250 mm, 5 μm) eluting at a flow rate 50 ml/min (165 bar pressure, 40° C. column temperature). The first peak (retention time=0.87 min) provided (1S,5R,6S)-5-(5-amino-2-chlorophenyl)-5-(difluoromethyl)-2-oxa-4-azabicyclo[4.1.0]hept-3-en-3-amine (19f-A, 380 mg, 1.32 mmol, 40 yield; 99% de; 99% ee) as a light-yellow powder.

$^1$H NMR (300 MHz, DMSO-d$_6$)=7.04 (d, J=8.3 Hz, 1H), 6.91-6.43 (m, 3H), 5.80 (s, 2H), 5.23 (s, 2H), 3.88 (br. s., 1H), 1.86 (q, J=8.1 Hz, 1H), 1.02 (br. s., 1H), 0.93-0.81 (m, 1H). Residual MeOH. MS m/z=287.9 [M]+

The second peak (retention time=1.22 min) provided (1R,5S,6R)-5-(5-amino-2-chlorophenyl)-5-(difluoromethyl)-2-oxa-4-azabicyclo[4.1.0]hept-3-en-3-amine (19f-B, 380 mg, 1.32 mmol, 40% yield; 99% de; 99% ee) as a light-yellow powder. $^1$H NMR (300 MHz, DMSO-d$_6$)=7.05 (d, J=8.5 Hz, 1H), 6.92-6.44 (m, 3H), 5.80 (s, 2H), 5.23 (s, 2H), 3.94-3.83 (m, 1H), 1.93-1.80 (m, 1H), 1.02 (t, J=6.7 Hz, 1H), 0.87 (td, J=6.3, 9.4 Hz, 1H). Residual MeOH.

MS m/z=287.9 [M+H]$^+$

Step 8: (1S,2S)-2-((R)-1-amino-1-(2-chlorophenyl)-2,2-difluoroethyl)cyclopropanol (19b-A) and (1R,2R)-2-((S)-1-amino-1-(2-chlorophenyl)-2,2-difluoroethyl)cyclopropanol (19b-B)

[(1R,S),(2R,S)]-2-((S,R)-1-amino-1-(2-chlorophenyl)-2,2-difluoroethyl)cyclopropanol (19-b rac; 17.4 g) was subjected to chromatography using supercritical CO$_2$ (additives 25% (MeOH with 20 mM NH$_3$) on a Chiralpak AD-H column (30×250 mm, 5 μm) eluting at a flow rate 120 ml/min (165 bar pressure, 40° C. column temperature). The first peak (retention time=1.03 min) provided (1S,2S)-2-((R)-1-amino-1-(2-chlorophenyl)-2,2-difluoroethyl)cyclopropanol (19b-A, 6.39 g, 25.7 mmol, 40% yield; 99% de, 99% ee). MS m/z=248.0 [M]+. The second peak (retention time=1.51 min) provided (1R,2R)-2-((S)-1-amino-1-(2-chlorophenyl)-2,2-difluoroethyl)cyclopropanol (19b-B, 6.39 g, 25.7 mmol, 40% yield; 99% de, 99% ee). MS m/z=248.0 [M+H]$^+$

Steps 9-11: (1R,5S,6R)-5-(2-chloro-5-nitrophenyl)-5-(difluoromethyl)-2-oxa-4-azabicyclo[4.1.0]hept-3-en-3-amine (19e-B)

The title compound was prepared following procedures similar to those described in steps 3-5 for the synthesis of 19e rac, but using (1R,2R)-2-(S)-1-amino-1-(2-chlorophenyl)-2,2-difluoroethyl)cyclopropanol (19b-B). $^1$H NMR (400 MHz, CHLOROFORM-d) δ ppm 8.68-8.70 (m, 1H) 8.11-8.16 (m, 1H) 7.60 (dd, J=8.90, 1.66 Hz, 1H) 6.85 (s, 1H) 6.71 (s, 1H) 6.56-6.58 (m, 1H) 3.91-3.97 (m, 1H) 1.94-2.02 (m, 1H) 1.37-1.43 (m, 1H) 1.02-1.10 (m, 1H) MS m/z=317.9 [M]+

Example 20

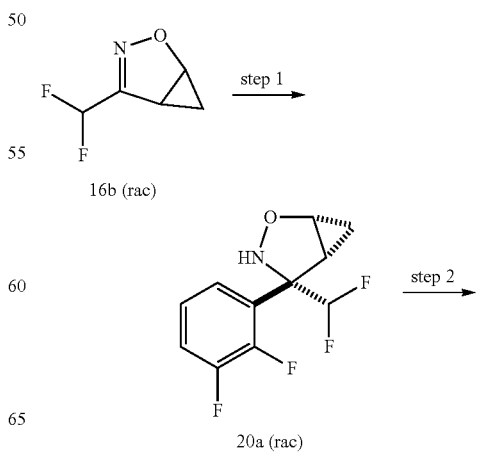

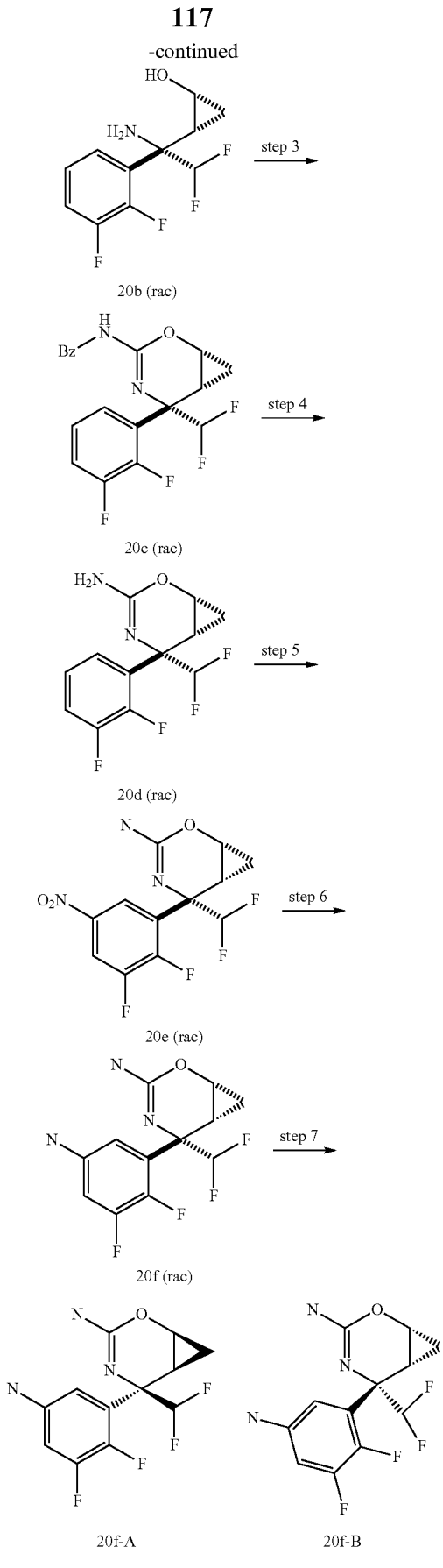

Step 1: [(1R,S),(4S,R),(5R,S)]-4-(difluoromethyl)-4-(2,3-difluorophenyl)-2-oxa-3-azabicyclo[3.1.0]hexane (20a rac)

A solution of 1-bromo-2,3-difluorobenzene (1.1 ml, 9.83 mmol) in diethyl ether (60 mL) under nitrogen atmosphere was cooled to −78 C. A solution of n-butyllithium (2.5 M in hexanes, 4 ml, 10.00 mmol) was added dropwise and the reaction stirred for 20 minutes at −78 C. A second flask was charged with a solution of 4-(difluoromethyl)-2-oxa-3-azabicyclo[3.1.0]hex-3-ene (1.0 g, 7.51 mmol, 16b rac) in toluene (20 mL) under nitrogen atmosphere and cooled to −78 C. Boron fluoride diethyl etherate (1.0 ml, 8.10 mmol) was added and the reaction mixture stirred for 5 minutes. This solution was added to the aryl lithium solution via cannula. Upon complete addition, the reaction was stirred for 10 minutes and then quenched by addition of aqueous citric acid solution (10%; 5 mL). Water (50 mL) and ethyl acetate (100 mL) were added and the organic layer was separated and dried over magnesium sulfate. The solvent was evaporated under reduced pressure and the crude residue was purified using silica chromatography (0-100% ethyl acetate/hexanes) to give the title compound (1.33 g, 5.38 mmol, 71.6% yield).
MS m/z=248.0 [M+H]

Steps 2-6: [(1R,S),(5S,R),(6R,S)]-5-(5-amino-2,3-difluorophenyl)-5-(difluoromethyl)-2-oxa-4-azabicyclo[4.1.0]hept-3-en-3-amine (20f rac)

The title compound was prepared following procedures similar to those described in steps 2-6 for the synthesis of 10f rac, but using [(1R,S),(4S,R),(5R,S)]-4-(difluoromethyl)-4-(2,3-difluorophenyl)-2-oxa-3-azabicyclo[3.1.0]hexane (20a rac).
MS m/z=290.0 [M+H]

Step 7: (1S,5R,6S)-5-(5-amino-2,3-difluorophenyl)-5-(difluoromethyl)-2-oxa-4-azabicyclo[4.1.0]hept-3-en-3-amine (20f-A) and (1R,5S,6R)-5-(5-amino-2,3-difluorophenyl)-5-(difluoromethyl)-2-oxa-4-azabicyclo[4.1.0]hept-3-en-3-amine (20f-B)

[(1R,S),(5S,R),(6R,S)]-5-(5-amino-2,3-difluorophenyl)-5-(difluoromethyl)-2-oxa-4-azabicyclo[4.1.0]hept-3-en-3-amine (20f rac; 2.0 g) was subjected to chromatography using supercritical $CO_2$ (additives 15% (EtOH with 20 mM $NH_3$) on a Chiralpak OJ-H column (21×250 mm, 5 μm) eluting at a flow rate 50 ml/min (100 bar pressure, 40° C. column temperature). The first peak (retention time=2.7 min) provided ((1S,5R,6S)-5-(5-amino-2,3-difluorophenyl)-5-(difluoromethyl)-2-oxa-4-azabicyclo[4.1.0]hept-3-en-3-amine (20f-A, 830 mg, 2.87 mmol, 41.5 yield; 99% de; 99% ee) as a light-yellow powder.
1H NMR (CHLOROFORM-d) δ: 6.54 (ddd, J=5.2, 3.0, 1.8 Hz, 1H), 6.44 (ddd, J=11.2, 6.2, 2.9 Hz, 1H), 6.14 (td, J=56.1, 1.0 Hz, 1H), 4.91 (br. s., 2H), 3.81-3.94 (m, 1H), 3.66 (br. s, 2H), 1.72-1.84 (m, 1H), 1.33-1.43 (m, 1H), 0.85-0.97 (m, 1H)
$^{19}$F NMR (CHLOROFORM-d) δ: −127.37 (dd, J=275.9, 10.9 Hz, 1F), −129.71 (dd, J=275.9, 7.5 Hz, 1F), −137.53 (d, J=21.8 Hz, 1F), −150.81 (ddd, J=21.9, 10.6, 7.5 Hz, 1F) MS m/z=290.0 [M+H]

The second peak (retention time=3.4 min) provided (1R,5S,6R)-5-(5-amino-2,3-difluorophenyl)-5-(difluoromethyl)-2-oxa-4-azabicyclo[4.1.0]hept-3-en-3-amine (20f-B, 840 mg, 2.90 mmol, 42% yield; 99% de; 99% ee) as a light-yellow powder.

<sup>1</sup>H NMR (CHLOROFORM-d) δ: 6.54 (ddd, J=5.2, 3.0, 1.8 Hz, 1H), 6.44 (ddd, J=11.3, 6.3, 2.9 Hz, 1H), 6.14 (td, J=55.9, 1.0 Hz, 1H), 4.84 (br. s., 2H), 3.84-3.93 (m, 1H), 3.64 (br. s., 2H), 1.73-1.84 (m, 1H), 1.33-1.42 (m, 1H), 0.86-0.97 (m, 1H)

<sup>19</sup>F NMR (CHLOROFORM-d) δ: −127.40 (dd, J=275.9, 10.9 Hz, 1F), −129.72 (dd, J=275.9, 7.5 Hz, 1F), −137.53 (d, J=21.8 Hz, 1F), −150.80 (ddd, J=21.8, 10.9, 7.5 Hz, 1F) MS m/z=290.0 [M+H]$^+$.

Example 21

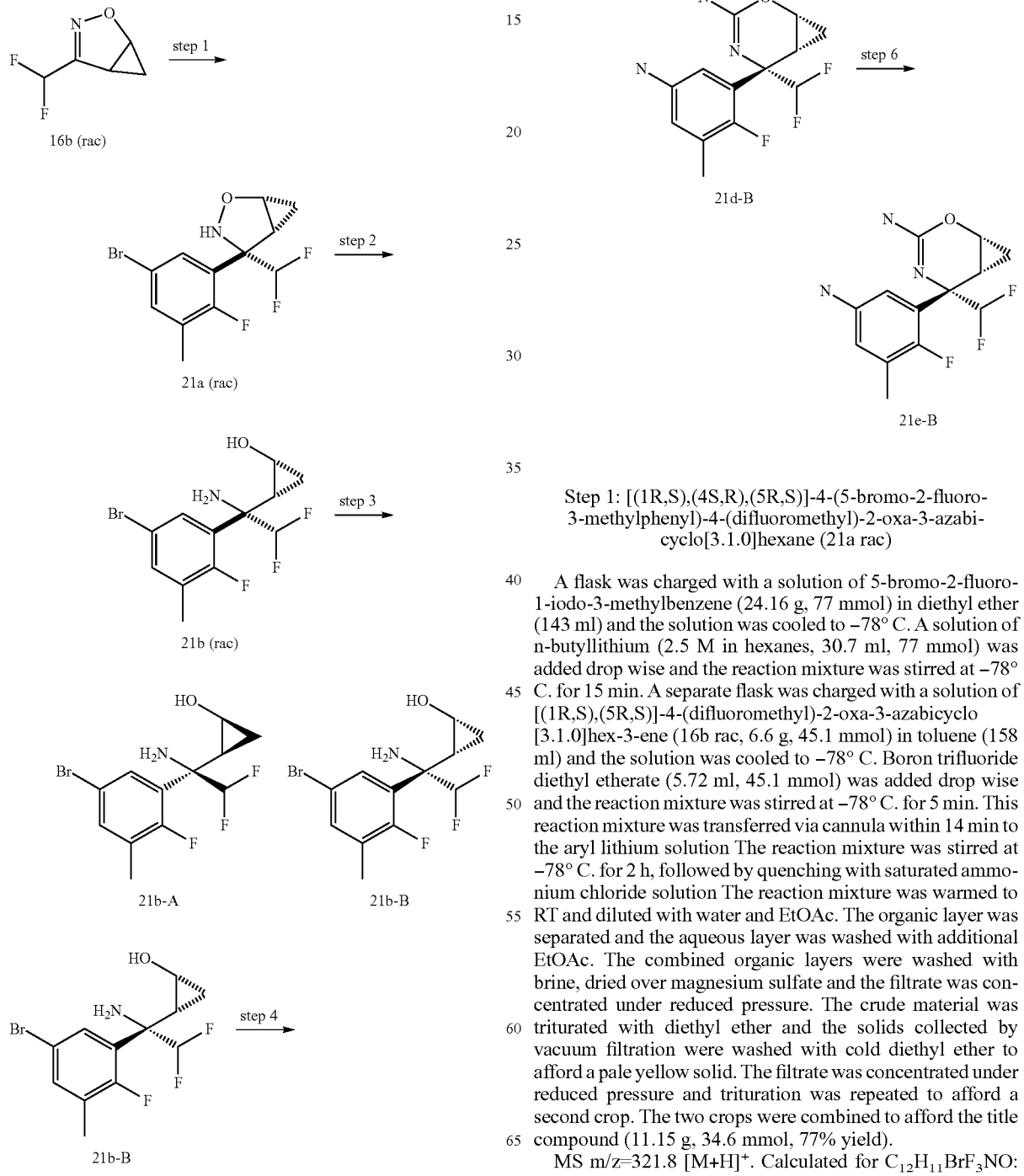

Step 1: [(1R,S),(4S,R),(5R,S)]-4-(5-bromo-2-fluoro-3-methylphenyl)-4-(difluoromethyl)-2-oxa-3-azabi-cyclo[3.1.0]hexane (21a rac)

A flask was charged with a solution of 5-bromo-2-fluoro-1-iodo-3-methylbenzene (24.16 g, 77 mmol) in diethyl ether (143 ml) and the solution was cooled to −78° C. A solution of n-butyllithium (2.5 M in hexanes, 30.7 ml, 77 mmol) was added drop wise and the reaction mixture was stirred at −78° C. for 15 min. A separate flask was charged with a solution of [(1R,S),(5R,S)]-4-(difluoromethyl)-2-oxa-3-azabicyclo [3.1.0]hex-3-ene (16b rac, 6.6 g, 45.1 mmol) in toluene (158 ml) and the solution was cooled to −78° C. Boron trifluoride diethyl etherate (5.72 ml, 45.1 mmol) was added drop wise and the reaction mixture was stirred at −78° C. for 5 min. This reaction mixture was transferred via cannula within 14 min to the aryl lithium solution The reaction mixture was stirred at −78° C. for 2 h, followed by quenching with saturated ammonium chloride solution The reaction mixture was warmed to RT and diluted with water and EtOAc. The organic layer was separated and the aqueous layer was washed with additional EtOAc. The combined organic layers were washed with brine, dried over magnesium sulfate and the filtrate was concentrated under reduced pressure. The crude material was triturated with diethyl ether and the solids collected by vacuum filtration were washed with cold diethyl ether to afford a pale yellow solid. The filtrate was concentrated under reduced pressure and trituration was repeated to afford a second crop. The two crops were combined to afford the title compound (11.15 g, 34.6 mmol, 77% yield).

MS m/z=321.8 [M+H]$^+$. Calculated for $C_{12}H_{11}BrF_3NO$: 322.1

Step 2: [(1R,S),(2R,S)]-2-[(S,R)-1-amino-1-(5-bromo-2-fluoro-3-methylphenyl)-2,2-difluoroethyl]cyclopropanol (21b rac)

The title compound was prepared following a procedure similar to that described in step 2 for the synthesis of 4b rac, but using [(1R,S),(4S,R),(5R,S)]-4-(5-bromo-2-fluoro-3-methylphenyl)-4-(difluoromethyl)-2-oxa-3-azabicyclo[3.1.0]hexane (21a rac). MS m/z=323.9 [M+H]$^+$. Calculated $C_{12}H_{13}BrF_3NO$: 324.1

Step 3: (1S,2S)-2-((R)-1-amino-1-(5-bromo-2-fluoro-3-methylphenyl)-2,2-difluoroethyl)cyclopropanol (21b-A) and (1R,2R)-2-((S)-1-amino-1-(5-bromo-2-fluoro-3-methylphenyl)-2,2-difluoroethyl)cyclopropanol (21b-B)

[(1R,S),(2R,S)]-2-[(S,R)-1-amino-1-(5-bromo-2-fluoro-3-methylphenyl)-2,2-difluoroethyl]cyclopropanol (21b rac, 13 g) was subjected to chromatography using supercritical $CO_2$ (additives 25% (EtOH with 20 mM $NH_3$) on a Chiralpak ADH column (30×250 mm, 5 μm) eluting at a flow rate 120 ml/min (100 bar pressure, 40° C. column temperature). The first peak (retention time=0.8 min) provided (1S,2S)-2-((R)-1-amino-1-(5-bromo-2-fluoro-3-methylphenyl)-2,2-difluoroethyl)cyclopropanol (21b-A, 5.3 g, 20.3 mmol, 40.5% yield; 99% de; 99% ee) as a light yellow powder. The second peak (retention time=1.52 min) provided (1R,2R)-2-((S)-1-amino-1-(5-bromo-2-fluoro-3-methylphenyl)-2,2-difluoroethyl)cyclopropanol (21b-B, 5.2 g, 20.0 mmol, 40.0% yield; 99% de; 99% ee) as a light yellow powder. MS m/z=323.9 [M+H]$^+$. Calculated $C_{12}H_{13}BrF_3NO$: 324.1 for both enantiomers.

Steps 4 and 5: N-((1R,5S,6R)-5-(5-amino-2-fluoro-3-methylphenyl)-5-(difluoromethyl)-2-oxa-4-azabicyclo[4.1.0]hept-3-en-3-yl)benzamide (21d-B)

The title compound was prepared following procedures similar to those described in steps 3 and 4 for the synthesis of 1i rac, but using (1R,2R)-2-(S)-1-amino-1-(5-bromo-2-fluoro-3-methylphenyl)-2,2-difluoroethyl)cyclopropanol (21b-B) MS m/z=390.0 [M+H]$^+$. Calculated $C_{20}H_{18}F_3N_3O_2$: 389.4

Step 6: (1R,5S,6R)-5-(5-amino-2-fluoro-3-methylphenyl)-5-(difluoromethyl)-2-oxa-4-azabicyclo[4.1.0]hept-3-en-3-amine (21e-B)

The title compound was prepared following a procedure similar to that described in step 4 for the synthesis of 4d rac, but using N-((1R,5S,6R)-5-(5-amino-2-fluoro-3-methylphenyl)-5-(difluoromethyl)-2-oxa-4-azabicyclo[4.1.0]hept-3-en-3-yl)benzamide (21d-B). MS m/z=286.0 [M+H]$^+$ Example 23

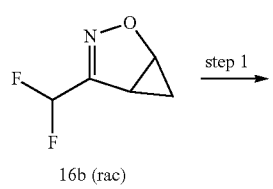

16b (rac)

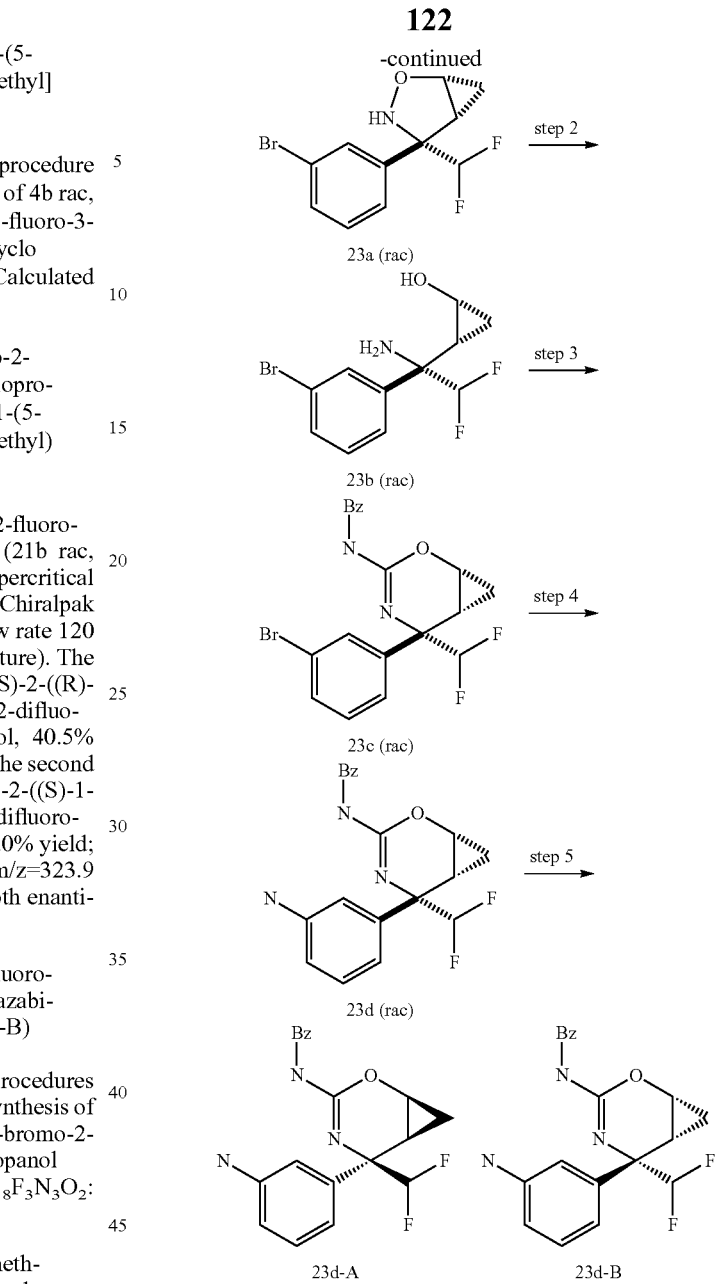

Step 1: [(1R,S),(4S,R),(5R,S)]-4-(3-bromophenyl)-4-(difluoromethyl)-2-oxa-3-azabicyclo[3.1.0]hexane (23a rac)

A flask was charged with a solution of 1,3-dibromobenzene (2.72 ml, 22.54 mmol) in diethyl ether (40 ml) and cooled to −78° C. A solution of n-butyllithium (2.5M in hexanes, 2.034 ml, 22.54 mmol) was added dropwise and the reaction mixture was allowed to stir at −78° C. for 1 hour. A separate flask was charged with a solution of 4-(difluoromethyl)-2-oxa-3-azabicyclo[3.1.0]hex-3-ene (16b rac, 1.000 g, 7.51 mmol) in toluene (37.6 ml) and cooled to −78° C. Boron trifluoride etherate (1.020 ml, 8.26 mmol) was added and the reaction mixture was allowed to stir for additional 5 minutes. The aryl lithium solution was transferred via cannula to this reaction mixture and the resulting reaction mixture was allowed to stir at −78° C. for 30 minutes. The reaction mixture was quenched with aqueous saturated NH₄Cl solution and then allowed to warm to room temperature. Ethyl acetate (200 ml) was added, the layers was separated and the aqueous layer was extracted with ethyl acetate. The combined organic extracts were dried over sodium sulfate and the filtrate was concentrated in vacuo. The crude material was absorbed on silica gel and purified by silica gel chromatography, eluting with a gradient of 0-20% ethyl acetate/hexanes, to provide the title compound (1.392 g, 4.80 mmol, 63.9% yield) as a tan oil. MS m/z=290.9 [M+H]$^+$. Calculated for $C_{11}H_{10}BrF_2NO$: 288.9.

$^1$H NMR (300 MHz, CHLOROFORM-d) δ ppm 7.84 (t, J=1.97 Hz, 1H) 7.46-7.64 (m, 2H) 7.24-7.32 (m, 1H) 5.92 (s, 1H) 4.08-4.17 (m, 1H) 2.21 (dd, J=4.75, 4.17 Hz, 1H) 1.36-1.43 (m, 1H) 0.73-0.82 (m, 1H)

Step 2-4: N-[(1R,S),(5S,R),(6R,S)-5-(3-aminophenyl)-5-(difluoromethyl)-2-oxa-4-azabicyclo[4.1.0]hept-3-en-3-yl]benzamide (23d rac)

The title compound was prepared following procedures similar to those described in steps 2 to 4 for the synthesis of 1i rac, but using [(1R,S),(4S,R),(5R,S)]-4-(3-bromophenyl)-4-(difluoromethyl)-2-oxa-3-azabicyclo[3.1.0]hexane (23a rac) MS m/z=358 [M+H]$^+$. Calculated for $C_{19}H_{17}F_2N_3O_2$: 357.

Step 5: N-((1S,5R,6S)-5-(3-aminophenyl)-5-(difluoromethyl)-2-oxa-4-azabicyclo[4.1.0]hept-3-en-3-yl)benzamide (23d-A) and N-((1R,5S,6R)-5-(3-aminophenyl)-5-(difluoromethyl)-2-oxa-4-azabicyclo[4.1.0]hept-3-en-3-yl)benzamide (23d-B)

N-[(1R,S),(5S,R),(6R,S)-5-(3-aminophenyl)-5-(difluoromethyl)-2-oxa-4-azabicyclo[4.1.0]hept-3-en-3-yl]benzamide (23d rac, 0.787 g, 2.202 mmol) was subjected to chromatography using supercritical $CO_2$ (20% methanol with 20 mM ammonia) on a chiralcel OD-H column (21×250 mm, 5 um) eluting at a flow rate 70 ml/min (165 bar pressure, 40° C. column temperature). The first peak (retention time=1.49 min) provided N-((1S,5R,6S)-5-(3-aminophenyl)-5-(difluoromethyl)-2-oxa-4-azabicyclo[4.1.0]hept-3-en-3-yl)benzamide (23d-A, 0.350 g, 0.979 mmol, 44.5% yield; >98% de) as off-white solid. MS m/z=358 [M+H]$^+$. Calculated for $C_{19}H_{17}F_2N_3O_2$: 357.

$^1$H NMR (400 MHz, CHLOROFORM-d) d ppm 8.22-8.27 (m, 2H) 7.49-7.55 (m, 1H) 7.41-7.47 (m, 2H) 7.18-7.27 (m, 1H) 6.83 (d, J=8.61 Hz, 1H) 6.74 (br. s., 1H) 6.68 (d, J=8.41 Hz, 1H) 6.00-6.02 (m, 1H) 4.26 (m, 1H) 1.99 (m, 1H) 1.69 (m, 1H) 1.21-1.27 (m, 1H).

The second peak (retention time=1.76) provided N-((1R,5S,6R)-5-(3-aminophenyl)-5-(difluoromethyl)-2-oxa-4-azabicyclo[4.1.0]hept-3-en-3-yl)benzamide (23d-B, 0.325 g, 0.909 mmol, 41.3% yield; >97% de) as off-white solid. MS m/z=358 [M+H]$^+$.

Calculated for $C_{19}H_{17}F_2N_3O_2$: 357.

$^1$H NMR (400 MHz, CHLOROFORM-d) d ppm 8.24 (d, J=7.04 Hz, 2H) 7.53 (br. s., 1H) 7.48-7.52 (m, 1H) 7.39-7.46 (m, 2H) 7.17-7.23 (m, 1H) 6.81 (s, 1H) 6.66-6.74 (m, 2H) 6.00 (s, 1H) 4.20-4.27 (m, 1H) 1.91-1.99 (m, 1H) 1.61-1.68 (m, 1H) 1.17-1.25 (m, 1H).

Example 24

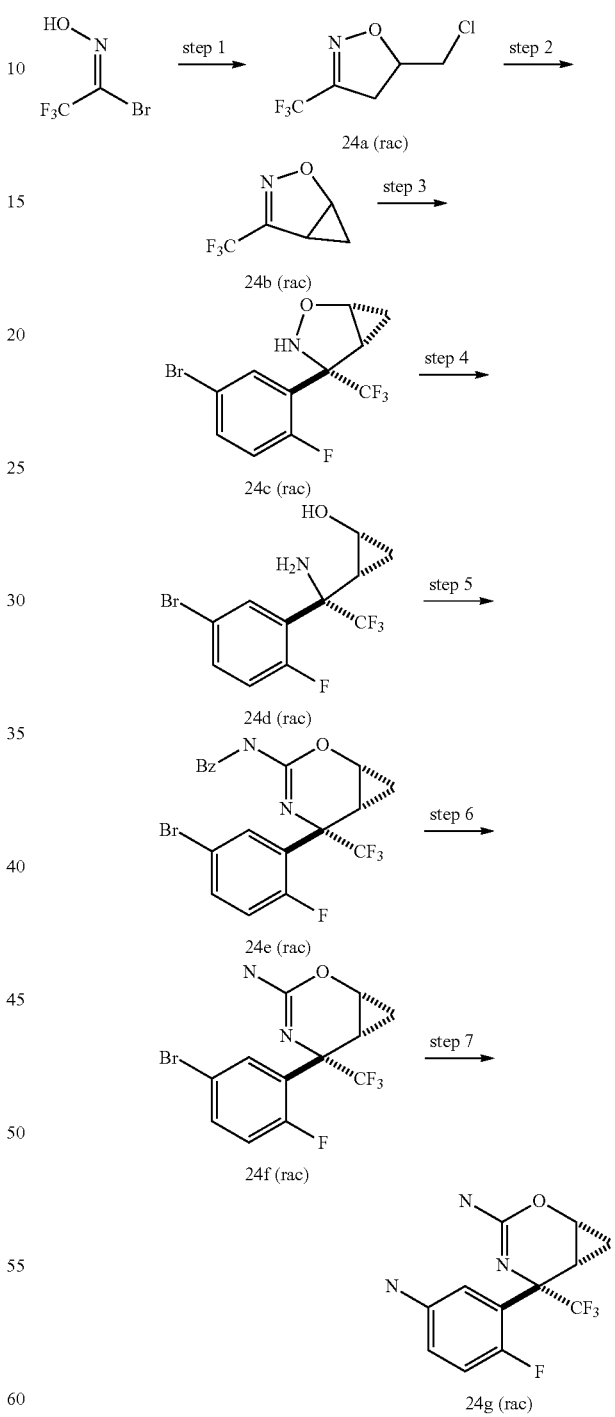

Step 1: (S,R)-5-(chloromethyl)-3-(trifluoromethyl)-4,5-dihydroisoxazole (24a rac)

A solution of 2,2,2-trifluoro-N-hydroxyacetimidoyl bromide (13.0 g, 40.6 mmol, WO2008135826) and 3-chloroprop-1-ene (10.0 mL, 123 mmol) in diethyl ether (50 mL) was cooled to 5° C. A solution of triethylamine (11.4 mL, 82 mmol) in diethyl ether (200 mL) was added over a period of 3 h, keeping the internal temperature below 10° C. The cold bath was removed and the reaction mixture was stirred at rt for 2 h. The precipitate was filtered off and the filtrate was washed with water (300 mL) and brine (300 mL). The organic phase was dried over sodium sulfate and the filtrate was concentrated in vacuo. The crude product was purified by silica gel column chromatography (ether in hexanes 0 to 40%) to afford the title compound (3.16 g, 16.8 mmol) as a clear oil. $^1$H NMR (300 MHz, CHLOROFORM-d) d=5.11 (dtd, J=4.2, 6.7, 10.9 Hz, 1H), 3.75-3.57 (m, 2H), 3.41-3.09 (m, 2H).

Step 2: [1 (R,S),5(R,S)]-4-(trifluoromethyl)-2-oxa-3-azabicyclo[3.1.0]hex-3-ene (24b rac)

A solution of potassium 2-methylpropan-2-olate (1M in THF, 20.2 mL, 20.2 mmol) was added over a period of 30 min to a stirred solution of (S,R)-5-(chloromethyl)-3-(trifluoromethyl)-4,5-dihydroisoxazole (24a rac, 3.16 g, 16.8 mmol) in tetrahydrofuran (50 mL) at 0° C. After 45 min, the reaction was quenched by addition of aqueous saturated ammonium chloride solution. The cold bath was removed and the reaction mixture was further diluted with aqueous saturated ammonium chloride solution and diethyl ether. The phases were separated and the aqueous phase was extracted with diethyl ether. The combined organic phases were washed with water, brine and dried over sodium sulfate. The filtrate was concentrated in vacuo and the crude product was purified by silica gel column chromatography (ether in pentanes 0 to 50%) to afford the title compound (1.50 g, 9.93 mmol) containing residual tetrahydrofuran and pentane. $^1$H NMR (300 MHz, CHLOROFORM-d) δ=5.18 (dt, J=2.2, 5.4 Hz, 1H), 2.85-2.69 (m, 1H), 1.19-1.08 (m, 1H), 0.46 (dt, J=1.9, 4.1 Hz, 1H).

Step 3: [1(R,S),4(S,R),5(R,S)]-4-(5-bromo-2-fluorophenyl)-4-(trifluoromethyl)-2-oxa-3-azabicyclo[3.1.0]hexane (24c rac)

A flask was charged with a solution of 4-bromo-1-fluoro-2-iodobenzene (5.00 ml, 16.6 mmol) in diethyl ether (25 mL) and the solution was cooled to −78° C. A solution of n-butyllithium (2.5 M in hexanes, 6.50 ml, 16.25 mmol) was added dropwise and the reaction mixture was stirred at this temperature for 15 min. A separate flask was charged with a solution of [1 (R,S),5(R,S)]-4-(trifluoromethyl)-2-oxa-3-azabicyclo[3.1.0]hex-3-ene (24b rac, 1.25 g, 8.27 mmol) in toluene (73 mL) and cooled to −78° C. Boron trifluoride diethyl etherate (1.05 ml, 8.51 mmol) was added and the reaction mixture was stirred for 5 min at −78° C. This solution was added via cannula to the aryl lithium solution. The resulting reaction mixture was stirred at that temperature for 40 min and then quenched by adding aqueous saturated ammonium chloride. The cold bath was removed and the reaction mixture was allowed to warm to rt. The reaction mixture was diluted with water and ethyl acetate. The layers were separated and the aqueous phase was extracted with ethyl acetate. The combined organic phases were washed with brine and dried over sodium sulfate. The filtrate was concentrated in vacuo and the crude product was purified by silica gel column chromatography (ethyl acetate in hexanes 0-30%) to afford the title compound (1.36 g, 4.16 mmol) as a pale orange solid. LC/MS (ESI$^+$) m/z=326 (M+H).

Steps 4-7: [1(R,S),5(S,R),6(R,S)]-5-(5-amino-2-fluorophenyl)-5-(trifluoromethyl)-2-oxa-4-azabicyclo[4.1.0]hept-3-en-3-amine (24 g rue)

The title compound was prepared following procedures similar to those described in steps 2 to 4 for the synthesis of 4d rac, and step 9 for the synthesis of 6h rac, but using [1(R,S),4(S,R),5(R,S)]-4-(5-bromo-2-fluorophenyl)-4-(trifluoromethyl)-2-oxa-3-azabicyclo[3.1.0]hexane (24c rac). LC/MS (ESI$^+$) m/z=290 (M+H).

Example 25

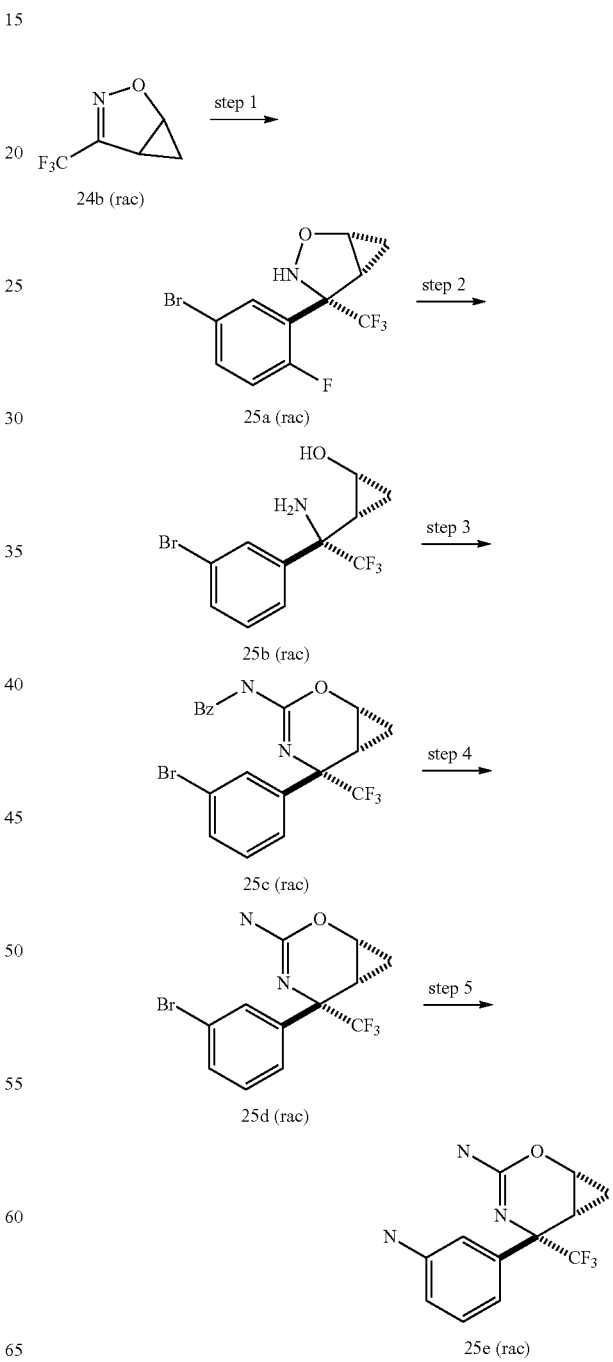

127

Step 1: [1(R,S),4(S,R),5(R,S)]-4-(3-bromophenyl)-4-(trifluoromethyl)-2-oxa-3-azabicyclo[3.1.0]hexane (25a rac)

A flask was charged with a solution of 1,3-dibromobenzene (1.90 mL, 15.72 mmol) in Et$_2$O (30 mL) and the solution was cooled to −78° C. A solution of n-butyllithium (2.5 M in hexanes, 6.20 mL, 15.50 mmol) was added dropwise and the reaction mixture was stirred at this temperature for 40 min. A separate flask was charged with a solution of [1(R,S),5(R,S)]-4-(trifluoromethyl)-2-oxa-3-azabicyclo[3.1.0]hex-3-ene (24b rac 1.90 g, 7.92 mmol) in toluene (70 mL) and cooled to −78° C. Boron trifluoride diethyl etherate (1.0 mL, 8.10 mmol) was added and the reaction mixture was stirred for 40 min at −78° C. This solution was added via cannula to the aryl lithium solution. The resulting reaction mixture was stirred at that temperature for 40 min and then quenched by adding aqueous saturated ammonium chloride. The cold bath was removed and the reaction mixture was allowed to warm to rt. The reaction mixture was diluted with water and ethyl acetate. The layers were separated and the aqueous phase was extracted with ethyl acetate. The combined organic phases were washed with brine and dried over sodium sulfate. The filtrate was concentrated in vacuo and the crude material was purified by silica gel chromatography, eluting with 10-30% EtOAc in hexanes, to provide the title compound (0.502 g, 1.63 mmol) as a brown oil. LC/MS (ESI$^+$) m/z=308.3 (M+H).

Steps 2-5: 1(S,R),5(R,S),6(S,R)-5-(3-aminophenyl)-5-(trifluoromethyl)-2-oxa-4-azabicyclo[4.1.0]hept-3-en-3-amine (25e rac)

The title compound was prepared following procedures similar to those described in steps 2 to 4 for the synthesis of 4d rac, and step 9 for the synthesis of 6h rac, but using [1(R,S),4(S,R),5(R,S)]-4-(3-bromophenyl)-4-(trifluoromethyl)-2-oxa-3-azabicyclo[3.1.0]hexane (25a rac). LC/MS (ESI$^+$) m/z=272.0 (M+H).

Example 26

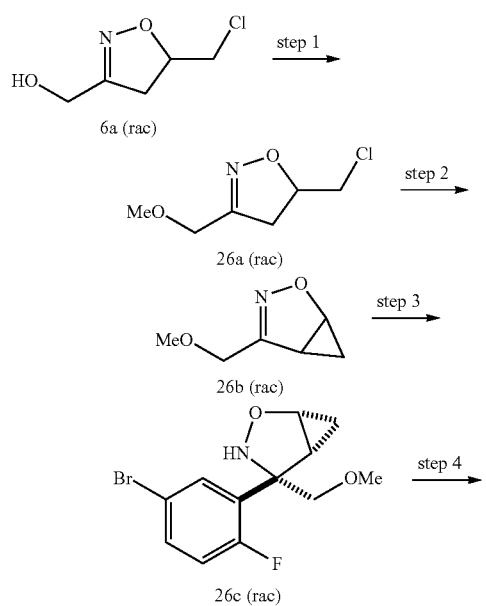

128

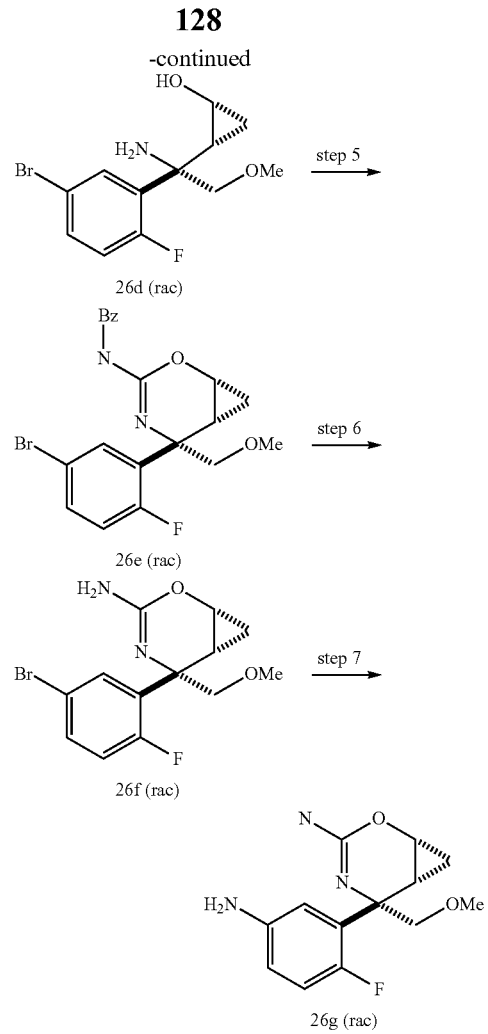

Step 1-2: 4-(Methoxymethyl)-2-oxa-3-azabicyclo[3.1.0]hex-3-ene (26b rac)

To a solution of (5-(chloromethyl)-4,5-dihydroisoxazol-3-yl)methanol (6c rac, 2.2 g, 14.71 mmol) in THF (40 mL) was added sodium hydride (60% dispersion in mineral oil, 0.372 ml, 17.65 mmol). The resulting mixture was stirred for 15 min followed by dropwise addition of methyl iodide (1.005 ml, 16.18 mmol). After 15 min, the reaction mixture was carefully quenched with aqueous saturated ammoniumchloride solution and diluted with water. The phases were separated and the aqueous phase was extracted with Et$_2$O. The combined organic layers were dried over Na$_2$SO$_4$ and the filtrate was concentrated under reduced pressure to afford the title compound as a pale yellow oil. The oil was dissolved in THF (20 mL) and the solution was cooled 0° C. A solution of potassium tert-butoxide (1M in THF, 17.65 ml, 17.65 mmol) was added dropwise and the reaction mixture was stirred for 30 min at 0° C. The mixture was quenched with aqueous saturated ammoniumchloride solution, the phases were separated and the aqueous phase was extracted with EtOAc. The combined organic layers were dried over Na$_2$SO$_4$ and the filtrate was concentrated under reduced pressure to afford the title compound as an orange oil as MS m/z=128.1[M+H]$^+$. Calculated for C$_6$H$_9$NO$_2$: 127.06.

Step 3: [(1R,S),(4S,R),(5R,S)]-4-(5-bromo-2-fluorophenyl)-4-(methoxymethyl)-2-oxa-3-azabicyclo[3.1.0]hexane (26c rac)

A flask was charged with a solution of 4-bromo-1-fluoro-2-iodobenzene (3.55 ml, 11.80 mmol) in Et₂O (40 mL) and the solution was cooled to −78° C. A solution of n-butyllithium (2.5M in hexanes, 4.72 ml, 11.80 mmol) was added dropwise and the reaction mixture was stirred at this temperature for 20 min. A separate flask was charged with a solution of 4-(methoxymethyl)-2-oxa-3-azabicyclo[3.1.0]hex-3-ene (26b rac, 1.0 g, 7.87 mmol) in toluene (10 mL) and cooled to −78° C. Boron trifluoride diethyl etherate (1.019 ml, 8.26 mmol) was added dropwise and the resulting reaction mixture was stirred at −78° C. for 5 min. This solution was added via cannula to the aryl lithium solution. The resulting reaction mixture was stirred at that temperature for 30 min and subsequently quenched with aqueous saturated ammoniumchloride solution. The reaction mixture was allowed to warm to room temperature and diluted with EtOAc and water. The aqueous phase was extracted with EtOAc (2×) and the combined organics were dried over Na₂SO₄. The filtrate was concentrated under reduced pressure and the residue was purified by silica gel chromatography (0-10% EtOAc/hexanes) to afford the title compound as a light yellow oil (0.500 g, 1.655 mmol, 21.04% yield). MS m/z=301.9 [M+H]⁺. Calculated for $C_{12}H_{13}BrFNO_2$: 301.01.

Steps 4-7: [(1R,S),(5S,R),(6R,S)]-5-(5-amino-2-fluorophenyl)-5-(methoxymethyl)-2-oxa-4-azabicyclo[4.1.0]hept-3-en-3-amine (26g rac)

The title compound was prepared following procedures similar to those described in steps 2 to 4 for the synthesis of 4d rac, and step 9 for the synthesis of 6h rac, but using [(1R,S),(4S,R),(5R,S)]-4-(5-bromo-2-fluorophenyl)-4-(methoxymethyl)-2-oxa-3-azabicyclo[3.1.0]hexane (26c rac). MS m/z=266 [M+H]⁺. Calculated for $C_{13}H_{16}FN_3O_2$: 265.12

Example 27

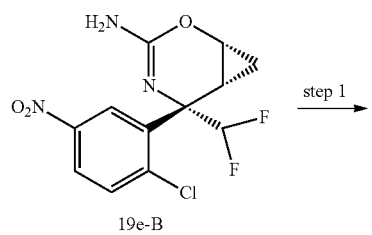

19e-B

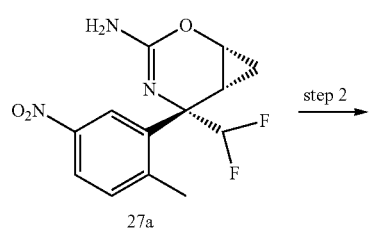

27a step 1 step 2

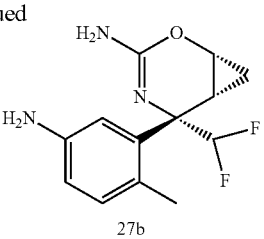

27b

Step 1: (1R,5S,6R)-5-(difluoromethyl)-5-(2-methyl-5-nitrophenyl)-2-oxa-4-azabicyclo[4.1.0]hept-3-en-3-amine (27a-B)

A flask was charged with (1R,5S,6R)-5-(2-chloro-5-nitrophenyl)-5-(difluoromethyl)-2-oxa-4-azabicyclo[4.1.0]hept-3-en-3-amine (19e-B 0.248 g, 0.781 mmol), cesium carbonate (0.763 g, 2.342 mmol) and a solvent mixture of THF (14.87 ml)/water (0.74 ml). The reaction mixture was purged with nitrogen gas for 5 min. Then 1,1'-bis(diphenylphosphino)ferrocene palladium(II)dichloride dichloromethane adduct (0.064 g, 0.078 mmol) and methylboronic acid (0.935 g, 15.61 mmol) were added. The flask was fitted with a reflux condensor, and the reaction mixture was heated under reflux overnight. Additional methylboronic acid (0.935 g, 15.61 mmol) and 1,1'-bis(diphenylphosphino)ferrocene palladium (II)dichloride dichloromethane adduct (0.064 g, 0.078 mmol) were added and stirring was continued at 88° C. overnight. The reaction mixture was cooled to ambient temperature and diluted with ethyl acetate (50 ml). The mixture was filtered through a pad of celite and the filter cake was rinsed with dichloromethane (2×). The combined organic extracts were concentrated in vacuo and. the crude material was purified by silica gel chromatography, eluting with a gradient of 0-55% ethyl acetate/hexanes, to provide a mixture of (1R,5S,6R)-5-(difluoromethyl)-5-(2-methyl-5-nitrophenyl)-2-oxa-4-azabicyclo[4.1.0]hept-3-en-3-amine (27a-B) and (1R,5S,6R)-5-(difluoromethyl)-5-(3-nitrophenyl)-2-oxa-4-azabicyclo[4.1.0]hept-3-en-3-amine (0.229 g, 77:23 ratio). MS m/z=298 [M+H]⁺. Calculated for 27a-B $C_{13}H_{13}F_2N_3O_3$: 297; MS m/z=284 [M+H]⁺ Calculated for $C_{12}H_{11}F_2N_3O_3$: 283

Step 2: (1R,5S,6R)-5-(5-amino-2-methylphenyl)-5-(difluoromethyl)-2-oxa-4-azabicyclo[4.1.0]hept-3-en-3-amine (27b-B)

A flask was charged with a 77:23 mixture of (1R,5S,6R)-5-(difluoromethyl)-5-(2-methyl-5-nitrophenyl)-2-oxa-4-azabicyclo[4.1.0]hept-3-en-3-amine (27a-B, 0.225 g, 0.757 mmol) and (1R,5S,6R)-5-(difluoromethyl)-5-(3-nitrophenyl)-2-oxa-4-azabicyclo[4.1.0]hept-3-en-3-amine Glacial acetic acid (0.262 ml, 4.54 mmol) and TFA (0.394 ml, 5.30 mmol) were added, followed by zinc (0.247 g, 3.78 mmol). The reaction mixture was allowed to stir for 30 min and was then diluted with methanol (5 ml). The suspension was filtered and the filtrate was concentrated in vacuo. The crude material was purified by chromatography, eluting with a gradient of 0-10% MeOH/DCM, to provide a 85:15 mixture of (1R,5S,6R)-5-(5-amino-2-methylphenyl)-5-(difluoromethyl)-2-oxa-4-azabicyclo[4.1.0]hept-3-en-3-amine (27b-B) and (1R,5S,6R)-5-(3-aminophenyl)-5-(difluoromethyl)-2-oxa-4-azabicyclo[4.1.0]hept-3-en-3-amine (0.113 g) as off-white solid. The mixture was used in the next step without further purification.

MS m/z=268 [M+H]⁺. Calculated for 27b-B C₁₃H₁₅F₂N₃O: 267.

MS m/z=254 [M+H]⁺. Calculated for C₁₂H₁₃F₂N₃O: 253.

Example 28

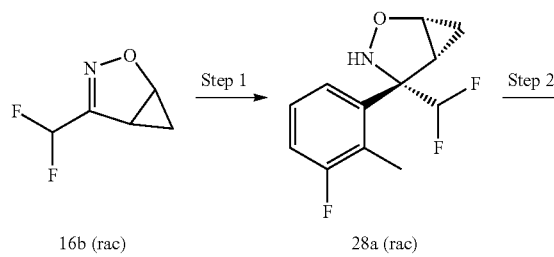

16b (rac)    28a (rac)

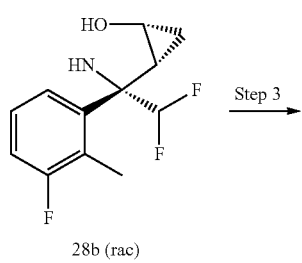

28b (rac)

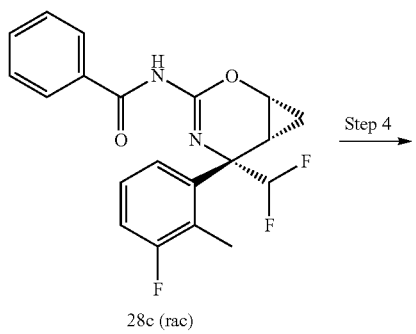

28c (rac)

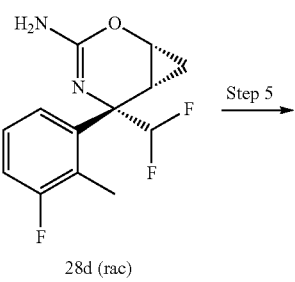

28d (rac)

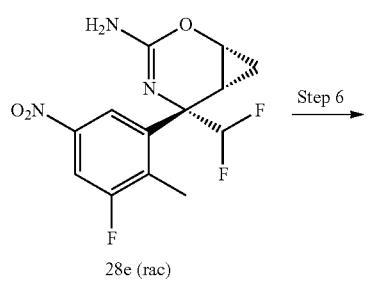

28e (rac)

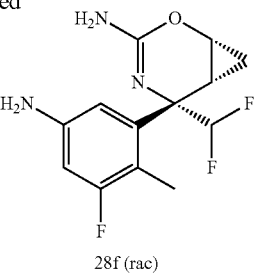

28f (rac)

Step 1: [(1R,S),(4S,R) (5R,S)],4-(difluoromethyl)-4-(3-fluoro-2-methylphenyl)-2-oxa-3-azabicyclo[3.1.0]hexane (28a rac)

To a flame dried RBF was added a solution of n-butyllithium (2.5M in hexanes; 3.01 ml, 7.51 mmol) and diethyl ether (15 ml). The solution was cooled to −78° C., and 2-fluoro-6-iodotoluene (0.981 ml, 7.51 mmol) was added dropwise and the reaction was stirred at −78° C. for 10 minutes. A −78° C. premixed solution of 4-(difluoromethyl)-2-oxa-3-azabicyclo[3.1.0]hex-3-ene (1.00 g, 7.51 mmol) and boron trifluoride diethyl etherate (0.927 ml, 7.51 mmol) in toluene (10 ml) was added to the reaction via syringe. The reaction was stirred at −78° C. for 10 minutes, quenched with saturated ammonium chloride and warmed to RT. The reaction was diluted with water and EtOAc. The organic layer was separated and concentrated under reduced pressure. The crude residue was purified via silica gel flash chromatography eluting with 0-20% ethyl acetate in hexanes to afford 4-(difluoromethyl)-4-(3-fluoro-2-methylphenyl)-2-oxa-3-azabicyclo[3.1.0]hexane (0.81 g, 3.33 mmol, 44.3% yield).

LC/MS (ESI⁺) m/z=244.1 (M+H).

Step 2: [(1R,S),(2R,S)]-2-((S,R)-1-amino-2,2-difluoro-1-(3-fluoro-2-methylphenyl)ethyl)cyclopropanol (28b rac)

To a solution of 4-(difluoromethyl)-4-(3-fluoro-2-methylphenyl)-2-oxa-3-azabicyclo[3.1.0]hexane (0.81 g, 3.33 mmol) in acetic acid, glacial (7.69 ml, 133 mmol) was added zinc (1.306 g, 19.98 mmol) portionwise at RT followed by trifluoroacetic acid (2.474 ml, 33.3 mmol). The reaction was stirred at RT for 1 hour. The reaction was filtered through a pad of celite and concentrated under vacuum. The residue was dissolved in iced water and the solution was basified by the addition of 5N NaOH to pH 12. The basic aqueous layer was back extracted with EtOAc. The organic layer was washed with brine, dried over sodium sulfate, and concentrated to dryness to afford the title compound 2-(1-amino-2,2-difluoro-1-(3-fluoro-2-methylphenyl)ethyl)cyclopropanol (0.61 g, 2.487 mmol, 74.7% yield). LC/MS (ESI⁺) m/z=246.1 (M+H).

Step 3: N-[(1R,S),(5S,R),(6R,S)]-(5-(difluoromethyl)-5-(3-fluoro-2-methylphenyl)-2-oxa-4-azabicyclo[4.1.0]hept-3-en-3-yl)benzamide (28c rac)

To a solution of 2-(1-amino-2,2-difluoro-1-(3-fluoro-2-methylphenyl)ethyl)cyclopropanol (0.61 g, 2.487 mmol) in dry THF (10 mL) under nitrogen was added benzoyl isothiocyanate (0.7 ml, 5.20 mmol) dropwise and the reaction was stirred for 30 min. Diisopropylethylamine (1.731 ml, 9.95 mmol) and 1-(3-dimethylaminopropyl)-3-ethylcarbodiimide hydrochloride (0.954 g, 4.97 mmol) were added and the reaction stirred at room temperature for 1 hour and then warmed to 60° C. for another 12 hr. The reaction mixture was diluted with dichloromethane and water. The phases were mixed, separated, and the organic was evaporated to dryness under reduced pressure. The crude residue was purified via silica gel flash chromatography eluting with 0-30% ethyl acetate in hexane afforded the title compound N-(5-(difluoromethyl)-5-(3-fluoro-2-methylphenyl)-2-oxa-4-azabicyclo[4.1.0]hept-3-en-3-yl)benzamide (0.8 g, 2.137 mmol, 86% yield). LC/MS (ESI+) m/z=375.0 (M+H).

Step 4: [(1R,S),(5S,R),(6R,S)]-5-(difluoromethyl)-5-(3-fluoro-2-methylphenyl)-2-oxa-4-azabicyclo[4.1.0]hept-3-en-3-amine (28d rac)

N-(5-(difluoromethyl)-5-(3-fluoro-2-methylphenyl)-2-oxa-4-azabicyclo[4.1.0]hept-3-en-3-yl)benzamide (1.0 g, 2.67 mmol) was dissolved in methanol (50 mL) under nitrogen and 1,8-diazabicyclo-[5.4.0]undec-7-ene (0.798 ml, 5.34 mmol) was added. The reaction was heated to 40° C. After 18 hours, the reaction mixture was concentrated to dryness under reduced pressure and the residue partitioned between water and ethyl acetate. The organic layer was isolated and concentrated under reduced pressure. The crude residue was purified via silica gel flash chromatography eluting with 0-60% ethyl acetate in hexanes afforded the title compound 5-(difluoromethyl)-5-(3-fluoro-2-methylphenyl)-2-oxa-4-azabicyclo[4.1.0]hept-3-en-3-amine (0.470 g, 1.739 mmol, 65.1% yield). LC/MS (ESI+) m/z=270.9 (M+H).

Step 5: [(1R,S),(5S,R),(6R,S)]-5-(difluoromethyl)-5-(3-fluoro-2-methyl-5-nitrophenyl)-2-oxa-4-azabicyclo[4.1.0]hept-3-en-3-amine (28e rac)

5-(Difluoromethyl)-5-(3-fluoro-2-methylphenyl)-2-oxa-4-azabicyclo[4.1.0]hept-3-en-3-amine (0.470 g, 1.739 mmol) was dissolved in sulfuric acid, 95% (5 mL) and cooled in an ice bath. Sodium nitrate (0.177 g, 2.087 mmol) was added in one portion and the reaction stirred for 5 minutes. The reaction was warmed to rt and stirred for 1 hr and poured into a mixture of dichloromethane (50 mL), iced water (90 mL), and potassium phosphate tribasic (20.02 g, 87 mmol). The mixture was stirred for 5 minutes then saturated sodium bicarbonate was added slowly until pH 8. The phases were separated and the aqueous extracted with ethyl acetate (2×50 mL). The combined organic layers were dried over magnesium sulfate and evaporated under reduced pressure. The crude residue was purified via silica gel flash chromatography eluting with 0-30% hexane to ethyl acetate to afford the title compound 5-(difluoromethyl)-5-(3-fluoro-2-methyl-5-nitrophenyl)-2-oxa-4-azabicyclo[4.1.0]hept-3-en-3-amine (0.22 g, 0.698 mmol, 40.1% yield). LC/MS (ESI+) m/z=316.1 (M+H).

Step 6: [(1R,S),(5S,R),(6R,S)]-5-(5-amino-3-fluoro-2-methylphenyl)-5-(difluoromethyl)-2-oxa-4-azabicyclo[4.1.0]hept-3-en-3-amine (28f rac)

5-(Difluoromethyl)-5-(3-fluoro-2-methyl-5-nitrophenyl)-2-oxa-4-azabicyclo[4.1.0]hept-3-en-3-amine (200 mg, 0.634 mmol) was dissolved in THF (20 ml). 10% palladium on carbon (135 mg, 0.127 mmol) was added and the reaction mixture was put under a balloon of $H_2$ and stirred at 18° C. for 4 h. The mixture was filtered through a pad of celite, washing well with ethyl acetate. The filtrate was concentrated under vacuum to yield crude 5-(5-amino-3-fluoro-2-methylphenyl)-5-(difluoromethyl)-2-oxa-4-azabicyclo[4.1.0]hept-3-en-3-amine (140 mg, 0.491 mmol, 77% yield) as a gray foam. LC/MS (ESI+) m/z=286.2 (M+H)

Intermediate 1

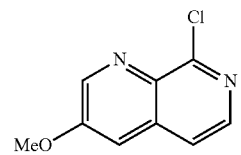 [SMILES: COc1cnc2c(Cl)nccc2c1]

Synthesis of 8-Chloro-3-methoxy-1,7-naphthyridine

Step 1: 3-chloro-5-methoxypicolinonitrile

To a solution of 3,5-dichloropicolinonitrile (22.5 g, 130 mmol) in DMF (500 mL) at 0° C. was added sodium methoxide (6.67 g, 124 mmol) slowly. The reaction was stirred for 5 minutes at 0° C., then it was allowed to warm to RT and stir for 30 minutes. The solution was partitioned between water and EtOAc. The organic layer was washed with water and concentrated. The crude product was purified via silica gel chromatography, eluting with 0-75% ethyl acetate in heptanes, to afford a 1:1 ratio of the desired isomer 3-chloro-5-methoxypicolinonitrile and 5-chloro-3-methoxypicolinonitrile (7.0 g, 41.5 mmol). The material was used without further purification. MS m/z=169 (M+H).

Step 2: 5-Methoxy-3-((triethylsilyl)ethynyl)picolinonitrile

A sealed vessel was charged with bis(acetonitrile)palladium (II) chloride (0.154 g, 0.593 mmol), dicyclohexyl(2',4',6'-triisopropyl-[1,1'-biphenyl]-2-yl)phosphine (0.848 g, 1.780 mmol), cesium carbonate (25.1 g, 77 mmol), the product of Intermediate 1, step 1 (5 g, 29.7 mmol), and ACN (60 mL). The vessel was flushed with argon, sealed, and stirred at RT for 25 minutes. To the reaction was added triethyl(ethynyl)silane (5.41 g, 38.6 mmol), and the vessel was resealed and stirred at 90° C. for 3 hours. The solution was concentrated, and the residue was purified via silica gel chromatography, eluting with 0-50% ethyl acetate in heptanes, to afford the title compound (3.8 g, 13.9 mmol). MS m/z=273 (M+H+.

Step 3: 3-(2,2-Dimethoxyethyl)-5-methoxypicolinonitrile

A pressure vessel was charged with 5-methoxy-3-((triethylsilyl)ethynyl) picolinonitrile (3.8 g, 13.95 mmol) and sodium methoxide (0.5 M in methanol, 69.7 mL, 34.9 mmol). The vessel was sealed and stirred at 55° C. for 2 hours. The reaction was concentrated to afford the title intermediate (3.1 g, 13.95 mmol).

Step 4: 3-(2,2-dimethoxyethyl)-5-methoxypicolinamide

To a 1 L round-bottomed flask was added 3-(2,2-dimethoxyethyl)-5-methoxypicolinonitrile (8.550 g, 38.5 mmol), water (480 ml), and acetone (120 ml). An aqueous solution of sodium carbonate (3M; 154 ml, 462 mmol) was added followed by hydrogen peroxide (35 wt. % solution in water; 138 ml, 1347 mmol). The tan mixture was stirred vigorously at rt for 2 h. The organic solvent was removed under reduced pressure and the aqueous residue was extracted with DCM (3×). The combined organic fractions were dried over sodium sulfate. The filtrate was concentrated under reduced pressure to afford 3-(2,2-dimethoxyethyl)-5-methoxypicolinamide (8.200 g, 34.1 mmol, 89% yield) as an off-white solid that was advanced without further purification. MS m/z=263.2 (M+Na)$^+$ Step 5: 3-Methoxy-1,7-naphthyridin-8(7H)-one To a mixture of 3-(2,2-dimethoxyethyl)-5-methoxypicolinamide (6.74 g, 28.1 mmol) in toluene (112 ml) was added 4-methylbenzene sulfonic acid (monohydrate; 0.534 g, 2.81 mmol). The reaction mixture was heated to reflux for 20 h. The reaction mixture was cooled to rt and concentrated in vacuo to a volume of ca. 15 mL. The residue was triturated with heptanes and filtered to afford 3-methoxy-1,7-naphthyridin-8(7H)-one (4.53 g, 25.7 mmol, 92% yield) as a crude, tan solid that was advanced without further purification. MS m/z=177.1 [M+H]$^+$ Step 6: 8-Chloro-3-methoxy-1,7-naphthyridine To a mixture of 3-methoxy-1,7-naphthyridin-8(7H)-one (4.50 g, 25.5 mmol) in acetonitrile (102 ml) was added phosphorus oxychloride (11.69 ml, 128 mmol). The reaction mixture was heated to 85° C. for 5 h. The solution was cooled to rt and concentrated in vacuo. The resulting brown residue was partitioned between CH2Cl2 and aqueous saturated NaHCO3 solution; the aqueous layer was back-extracted with DCM (3×). The combined organic extracts were dried over sodium sulfate, the filtrate was concentrated in vacuo, and the residue was purified by silica gel chromatography (5%-30% of 9:1 DCM:MeOH in DCM) to afford 8-chloro-3-methoxy-1,7-naphthyridine (3.00 g, 15.41 mmol, 60.3% yield) as an off-white solid. MS m/z=195 (M+H)$^+$.

Intermediate 2

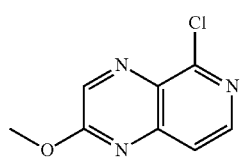

Synthesis of 3,8-Dichloro-1,7-naphthyridine

Step 1: 3-Bromo-5-chloropicolinonitrile

A microwave vial was charged with copper (I) cyanide (1.089 g, 12.16 mmol), 2,3-dibromo-5-chloropyridine (3 g, 11.06 mmol), and propionitrile (15 mL). The vial was capped and irradiated in a microwave reactor at 150° C. for 2.5 hours. The solution was concentrated, diluted with DCM (25 mL), and filtered. The filtrate was concentrated, and the residue was purified by silica gel chromatography, eluting with 0-30% EtOAc in heptanes, to afford the title compound (2 g, 9.20 mmol). MS m/z=219 (M+H)$^+$.

Step 2: 5-Chloro-3-((trimethylsilyl)ethynyl)picolinonitrile

A pressure vessel was charged with TEA (7.65 mL, 55.2 mmol), ethynyltrimethylsilane (2.32 mL, 16.6 mmol), copper (I) iodide (0.263 g, 1.380 mmol), palladium (0) tetrakis(triphenylphosphine) (0.558 g, 0.483 mmol), 3-bromo-5-chloropicolinonitrile (3.0 g, 13.8 mmol), and DMF (50 ml). The vessel was flushed with argon, sealed, stirred at ambient temperature for 15 minutes, and then heated at 50° C. for 4 hours. The solution was diluted with water and extracted with EtOAc. The combined organic layers were concentrated, and the residue was purified by silica-gel chromatography, eluting 0-50% ethyl acetate in hexane, to afford the title compound (1.3 g, 5.5 mmol). MS m/z=235 (M+H)$^+$.

Step 3: 5-Chloro-3-(2,2-dimethoxyethyl)picolinonitrile

A pressure vessel was charged with 5-chloro-3-((trimethylsilyl)ethynyl)picolinonitrile (2 g, 8.52 mmol) and sodium methoxide (0.5 M in methanol, 42.6 mL, 21.30 mmol), sealed, and stirred at 55° C. for one hour. The solution was concentrated, and the residue was purified via silica gel chromatography, eluting with 10% methanol in DCM to afford the title compound (1.7 g, 7.50 mmol). MS m/z=227 (M+H)$^+$.

Step 4: 3-Chloro-1,7-naphthyridin-8(7H)-one

To a solution of 5-chloro-3-(2,2-dimethoxyethyl)picolinonitrile (1.7 g, 7.50 mmol) in acetone (50 mL) and water (150 mL) was added aqueous saturated sodium carbonate (37.5 mL, 113 mmol) and 30% aqueous hydrogen peroxide (38.3 mL, 375 mmol). The reaction was stirred at RT for one hour, concentrated to remove most of the acetone, and extracted with DCM. The combined organic layers were concentrated.

To a solution of this intermediate (1.8 g, 7.36 mmol) in benzene (20 mL) was added p-toluenesulfonic acid (0.350 g, 1.839 mmol) and the reaction was sonicated for 10 minutes. The solution was stirred overnight at 80° C. and concentrated. The crude product was purified via silica gel, eluting with 0-100% (80/20/1 ethyl acetate/methanol/ammonium hydroxide) in EtOAc, to the title intermediate (1.1 g, 6.1 mmol). MS m/z=181 (M+H)$^+$.

Step 5: 3,8-Dichloro-1,7-naphthyridine

A suspension of -chloro-1,7-naphthyridin-8(7H)-one (250 mg, 1.384 mmol) in phosphorus oxychloride (1.94 mL, 20.8 mmol) was stirred at 95° C. for one hour. The solution was concentrated to afford the title compound (276 mg, 1.39 mmol). MS m/z=199 (M+H)$^+$.

Intermediate 3

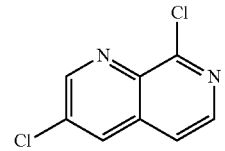 [SMILES: Clc1cnc2c(Cl)nccc2c1]

Synthesis of 5-Chloro-2-methoxypyrido[3,4-b]pyrazine

Step 1: 5-Chloropyrido[3,4-b]pyrazin-2(1H)-one

A suspension 2-chloropyridine-3,4-diamine (2.5 g, 17.41 mmol) and a 50% solution of ethyl glyoxalate in toluene (3.45 mL, 17.41 mmol) in ethanol (34.8 mL) was stirred at reflux for 24 hours. The solution was cooled to −20° C. for 16 hours, and the resulting precipitate was collected by vacuum filtration and rinsed with ethanol. The crude product was purified via reverse-phase HPLC, eluting with 5-50% acetonitrile/0.1% trifluoroacetic acid in water/0.1% TFA, to afford the title compound (570 mg, 3.14 mmol). MS m/z=182 (M+H)$^+$.

Step 2: 2,5-Dichloropyrido[3,4-b]pyrazine

A suspension of 5-chloropyrido[3,4-b]pyrazin-2(1H)-one (0.57 g, 3.14 mmol) in phosphorus oxychloride (10.24 mL, 110 mmol) was stirred at 110° C. for two hours, and then concentrated. The residue was dissolved in DCM, washed with saturated sodium bicarbonate, dried over anhydrous sodium sulfate, filtered, and concentrated to afford the title compound (580 mg, 2.90 mmol). MS m/z=200 (M+H)$^+$.

Step 3: 5-Chloro-2-methoxypyrido[3,4-b]pyrazine

To a solution of 2,5-dichloropyrido[3,4-b]pyrazine (580 mg, 2.90 mmol) in N,N-dimethylformamide (10 mL) was added a 0.5-M solution of sodium methoxide in methanol (6.09 mL, 3.04 mmol), and the reaction was stirred at RT for 5 minutes. The solution was diluted with water and extracted with ethyl acetate. The organic layer was dried with sodium sulfate, filtered and concentrated to afford the title compound (550 mg, 2.81 mmol). MS m/z=196 (M+H)$^+$.

Intermediate 4

Synthesis of 8-Chloro-1,7-naphthyridine-3-carbonitrile

A screw-cap vial was charged with 3-chloro-1,7-naphthyridin-8(7H)-one (100 mg, 0.554 mmol), zinc cyanide (52.7 μl, 0.831 mmol), 2-dicyclohexylphosphino-2',6'-dimethoxybiphenyl (45.5 mg, 0.111 mmol), tris(dibenzylideneacetone) dipalladium(0) (40.6 mg, 0.044 mmol), DMF (2.74 mL) and water (28 μL). The vial was purged with argon, sealed, and stirred at 110° C. for 1 hour. The mixture was filtered through a pad of Celite, which was rinsed with methanol and dimethylsulfoxide. The combined filtrates were concentrated, and a few drops of water were added. The resulting solids were collected by vacuum filtration, rinsed with water and dried. The solids were suspended in toluene (3.5 mL), and phosphorus oxychloride (98 μL, 1.052 mmol) and DIPEA (122 μL, 0.701 mmol) were added. The reaction was stirred at 120° C. for 1.5 hours, cooled to RT, diluted with EtOAc, and washed with 2 M aqueous sodium carbonate. The organic portion was dried over anhydrous sodium sulfate, filtered and concentrated. The crude material was purified by silica gel chromatography, eluting with 5-50% EtOAc in heptanes, to provide the title compound (50 mg, 0.264 mmol) as a white solid. LC/MS (ESI$^+$) m/z=190 (M+H)$^+$.

Intermediate 5

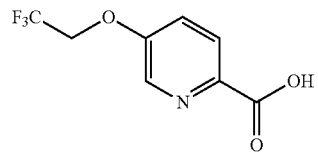 [SMILES: O=C(O)c1ccc(OCC(F)(F)F)cn1]

Step 1: methyl 5-(2,2,2-trifluoroethoxy)picolinate

To a solution of methyl 5-hydroxypicolinate (0.50 g, 3.27 mmol, Frontier Scientific) in DMF (5 mL) were added cesium carbonate (1.383 g, 4.24 mmol, Aldrich) and 2,2,2-trifluoroethyl ester (0.909 ml, 3.92 mmol) and the resulting suspension was stirred at RT for 1 hour. The reaction was diluted with water and EtOAc. The organic layer was washed with 1M LiCl (aq) solution and brine before drying over magnesium sulfate and concentrating under reduced pressure to afford the crude title compound as a yellow oil, which was used directly in the next step without further purification. M/S m/z=236.0 [M+H]$^+$. Calculated for $C_9H_8F_3NO_3$: 235.160

Step 2: 5-(2,2,2-trifluoroethoxy)picolinic acid

The crude material from the previous reaction was taken up in THF (5 mL) and lithium hydroxide, 2.0M, (aq) (4.90 ml, 9.80 mmol) was added. The reaction was stirred at RT for 16 hours. The reaction was diluted with water and acidified with 1.0N HCl (aq) solution was added until pH=1 (by pH paper). The solution was extracted with DCM and the organic layer was washed with brine, dried over magnesium sulfate and concentrated under reduced pressure to afford the title compound as a white solid. (0.194 g, 0.877 mmol, 26.9% yield). M/S m/z=221.9 [M+H]$^+$. Calculated for $C_8H_6F_3NO_3$: 221.133 $^1$H NMR (300 MHz, DMSO-$d_6$) δ ppm 5.00 (q, J=8.77 Hz, 2H) 7.66 (dd, J=8.77, 2.92 Hz, 1H) 8.07 (d, J=8.77 Hz, 1H) 8.50 (d, J=2.92 Hz, 1H) 13.00 (br. S., 1H)

Intermediate 6

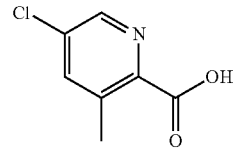

Step 1: Synthesis of 5-chloro-3-methylpicolinonitrile

A mixture of 2-bromo-5-chloro-3-methylpyridine (45 g, 218 mmol), zinc cyanide (8.30 mL, 131 mmol), tris(dibenzylideneacetone) dipalladium (0) (4.99 g, 5.45 mmol), and 1,1'-bis(diphenylphosphino)ferrocene (6.04 g, 10.90 mmol) in dimethylacetamide (40 mL) was heated to 110° C. for 4 hours. The reaction mixture was cooled to RT, diluted with water and extracted with ethyl acetate. The organic phase obtained was concentrated under reduced pressure and residue purified by chromatography on silica gel using ISCO eluting with 0-60% EtOAc/hex to afford the title compound 5-chloro-3-methylpicolinonitrile (25.4 g, 166 mmol, 76% yield). LC/MS (ESI+) m/z=153.1 (M+H).

Step 2: Synthesis of 5-chloro-3-methylpicolinic acid

To a solution of 5-chloro-3-methylpicolinonitrile (24.0 g, 157 mmol) in EtOH (100 mL) was added NaOH 5.0N (110 ml, 550 mmol). The resulting mixture was refluxed at 90° C. for 18 h. After cooling to RT, the reaction mixture was concentrated, diluted with water and the pH of the solution was adjusted to 4 by addition of 5N HCl. The solid that precipitated was filtered and set aside. The filtrate was extracted with EtOAc (2×). The aqueous layer was again acidified with 5N HCl to pH 4 and extracted with EtOAc (2×). The EtOAc extracts were combined, dried, and concentrated. The solid obtained from all the workup steps were combined and dried in a high vac oven at 40° C. for 12 h to give the title compound 5-chloro-3-methylpicolinic acid (24.1 g, 140 mmol, 89% yield). LC/MS (ESI+) m/z=172.0 (M+H)+; 1H NMR (400 MHz, CHLOROFORM-d) δ ppm 11.29 (br. s., 1H), 8.41 (d, J=1.76 Hz, 1H), 7.73 (d, J=1.76 Hz, 1H), 2.75 (s, 3H).

Intermediate 7

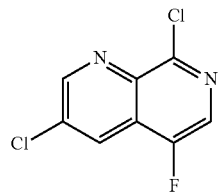

Synthesis of 3,8-Dichloro-5-fluoro-1,7-naphthyridine

Step 1: 3-chloro-5-fluoro-6-methoxy-6,7-dihydro-1,7-naphthyridin-8(5H)-one

A pressure bottle was charged with 3-chloro-1,7-naphthyridin-8(7H)-one (15 g, 83 mmol, Anichem), methanol (34.6 mL), ACN (173 mL) and 1-chloromethyl-4-fluoro-1,4-diazoniabicyclo[2.2.2]octane bis(tetrafluoroborate) (30.9 g, 87 mmol), and the mixture was heated at 45° C. for 15 hours. Water and ethyl acetate were added, and the layers were separated. The aqueous portion was extracted twice with ethyl acetate and once with DCM, and the combined organic layers were dried with anhydrous sodium sulfate, filtered and concentrated. The crude solid was triturated with a minimum amount of ethyl acetate and filtered. The title intermediate was isolated as an off-white solid (15.34 g, 80%) as a 3:1 mixture of diastereomers.

Step 2: 3,8-dichloro-5-fluoro-1,7-naphthyridine

A vial was charged with 3-chloro-5-fluoro-6-methoxy-6,7-dihydro-1,7-naphthyridin-8(5H)-one (7.5 g, 32.5 mmol), acetonitrile (130 mL) and phosphorus oxychloride (9.09 mL, 98 mmol), and the mixture was stirred at 75° C. for 15 hours. The mixture was concentrated, and the crude material was purified by silica gel chromatography, eluting with 0-50% ethyl acetate in heptanes, to provide the title compound (5.57 g, 25.7 mmol, 79% yield) as a white solid. LC/MS (ESI+) m/z=217(M+H)+.

Intermediate 8

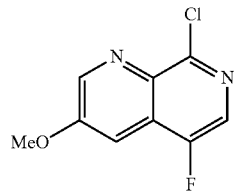 [SMILES: COc1cnc2c(Cl)ncc(F)c2c1]

Synthesis of 8-Chloro-5-fluoro-3-methoxy-1,7-naphthyridine

Using an analogous sequence of reactions to those described for Intermediate 7, 3-methoxy-1,7-naphthyridin-8 (7H)-one was converted to the title compound. LC/MS (ESI+) m/z=213 (M+H)+.

Intermediate 9

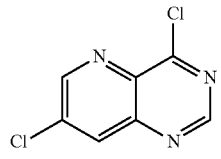 [SMILES: Clc1cnc2c(Cl)ncnc2c1]

Synthesis of 4,7-Dichloropyrido[3,2-d]pyrimidine

Step 1: 3-Amino-5-chloropicolinamide

To a suspension of 5-chloro-2-cyano-3-nitropyridine (1.274 mL, 10.9 mmol) in water (22 mL) was added 28% aqueous ammonium hydroxide (3.94 mL, 28.3 mmol), and the reaction was stirred at RT for 20 minutes. Sodium hydrosulfite (2.68 mL, 32.7 mmol) was added, and the reaction mixture was stirred at RT for 70 minutes. The yellow precipitate was collected by vacuum filtration to provide the title compound (1.097 g, 6.39 mmol) as yellow solid. 1H-NMR (400 MHz, DMSO-d6): δ 7.88 (br. s, 1H), δ7.73 (s, 1H), δ7.39 (br. s, 1H), δ7.23 (s, 1H), δ7.06 (br. s, 2H). LC/MS (ESI+) m/z=172 (M+H)+.

Step 2: 7-Chloropyrido[3,2-d]pyrimidin-4(1H)-one

A suspension of 3-amino-5-chloropicolinamide (1.1 g, 6.41 mmol) in triethyl orthoformate (15.99 mL, 96 mmol) was stirred at 155° C. for 22 hours. After cooling to RT, the yellow precipitate was collected by vacuum filtration and washed with hexanes to yield the title intermediate (1.03 g, 5.67 mmol) as a yellow solid. 1H NMR (400 MHz, DMSO-d6) δ ppm 8.20 (s, 1H) 8.27 (d, J=2.35 Hz, 1H) 8.80 (d, J=2.25 Hz, 1H) 12.68 (br. s., 1H). LC/MS (ESI+) m/z=182 (M+H)+.

Step 3: 4,7-Dichloropyrido[3,2-d]pyrimidine

To a mixture of 7-chloropyrido[3,2-d]pyrimidin-4(1H)-one (250 mg, 1.377 mmol) in toluene (12 mL) were added DIPEA (0.73 mL, 4.20 mmol) and phosphorus oxychloride (0.391 mL, 4.27 mmol), and the reaction was stirred at reflux for 1 hour. After cooling to RT, the reaction mixture was concentrated to provide the title compound. LC/MS (ESI⁺) m/z=200 (M+H)⁺.

Intermediate 10

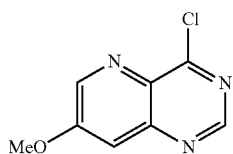 [SMILES: COc1cnc2c(Cl)ncnc2c1]

Synthesis of
4-Chloro-7-methoxypyrido[3,2-d]pyrimidine

Step 1: 7-Methoxypyrido[3,2-d]pyrimidin-4(1H)-one

A microwave vial was charged with 7-chloropyrido[3,2-d]pyrimidin-4(1H)-one (110 mg, 0.606 mmol), a 0.5 M solution of sodium methoxide in methanol (3.65 mL, 1.817 mmol) and sodium methoxide (327 mg, 6.06 mmol). The vial was capped and irradiated in a microwave reactor at 145° C. for 30 minutes. The reaction was neutralized with saturated aqueous ammonium chloride (3 mL), concentrated, and diluted with cold water. The resulting precipitate was collected by vacuum filtration and dried in vacuo to provide the title compound (107 mg, 0.604 mmol) as pink solid. ¹H NMR (400 MHz, DMSO-d₆) δ ppm 3.95 (s, 3H) 7.49 (d, J=2.74 Hz, 1H) 8.11 (s, 1H) 8.47 (d, J=2.74 Hz, 1H). LC/MS (ESI⁺) m/z=178 (M+H)⁺.

Step 2: 4-Chloro-7-methoxypyrido[3,2-d]pyrimidine

Using an analogous reaction to that described for Intermediate 9, step 3, 7-methoxypyrido[3,2-d]pyrimidin-4(1H)-one was converted to the title compound. LC/MS (ESI⁺) m/z=196 (M+H)⁺.

Intermediate 11

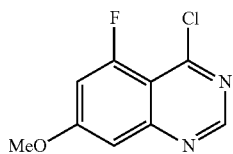 [SMILES: COc1cc(F)c2c(Cl)ncnc2c1]

Synthesis of
4-Chloro-5-fluoro-7-methoxyquinazoline

Step 1: 2-Amino-6-fluoro-4-methoxybenzonitrile

Ammonia gas was bubbled through a solution of 2,6-difluoro-4-methoxybenzonitrile (1.0 g, 5.91 mmol) in dimethylsulfoxide (11.83 mL) for 10 minutes. The reaction was then sealed and stirred at 90° C. for 24 hours. The reaction mixture was cooled to RT and concentrated in vacuo to afford a tan residue. The residue was triturated with water, collected be vacuum filtration, and dried in vacuo to afford the title intermediate (0.9 g, 5.42 mmol) as a white solid. LC/MS (ESI⁺) m/z=167 (M+H)⁺.

Step 2: 5-Fluoro-7-methoxyquinazolin-4-ol

To a mixture of formic acid (11.43 mL, 298 mmol) and sulfuric acid (0.866 mL, 16.25 mmol) was added 2-amino-6-fluoro-4-methoxybenzonitrile (0.9 g, 5.42 mmol) in portions. The reaction mixture was stirred at 100° C. for 1 hour, cooled to ambient temperature, and poured into 80 mL of an ice-water mixture. The resulting precipitate was collected by vacuum filtration and dried in vacuo to provide the title intermediate (0.8 g, 4.12 mmol) as an off-white solid. LC/MS (ESI⁺) m/z=195 (M+H)⁺.

Step 3: 4-Chloro-5-fluoro-7-methoxyquinazoline

To a suspension of 5-fluoro-7-methoxyquinazolin-4-ol (0.125 g, 0.644 mmol) in thionyl chloride (1.410 mL, 19.31 mmol) was added N,N-dimethylformamide (0.028 mL, 0.361 mmol). The reaction was stirred at 80° C. for 6 hours and concentrated in vacuo. The residue was suspended in saturated aqueous sodium bicarbonate and extracted with dichloromethane. The organic layer was concentrated in vacuo to generate the title compound (0.13 g, 0.611 mmol) as a yellow solid. LC/MS (ESI⁺) m/z=213 (M+H)⁺.

Intermediate 12

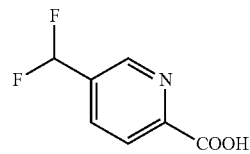 [SMILES: O=C(O)c1ccc(C(F)F)cn1]

Synthesis of 5-(Difluoromethyl)picolinic acid

Step 1: 5-Formylpicolinonitrile

A suspension of 2-bromo-5-formylpyridine (940 mg, 5.05 mmol) and copper (I) cyanide (233 μL, 7.58 mmol) in DMF (8.4 mL) was stirred at 120° C. for 1.5 hours, cooled to RT, and partitioned between water and EtOAc. The solids were removed from the aqueous layer by filtration, and the filtrate was extracted with ethyl acetate. The combined organic layers were washed with brine, dried over anhydrous magnesium sulfate, filtered and concentrated. The crude product was purified by silica-gel chromatography, eluting with a gradient of 40%-60% (40% ethyl acetate in heptane) in heptane, to provide the title compound (236 mg, 1.786 mmol) as white solid. LC/MS (ESI⁺) m/z=133 (M+H)⁺.

Step 2: 5-(Difluoromethyl)picolinonitrile

To a solution of 5-formylpicolinonitrile (74 mg, 0.560 mmol) in toluene (0.25 mL) was added bis(2-methoxyethyl)aminosulfur trifluoride (0.258 mL, 1.400 mmol), and the reaction was stirred at RT overnight. The reaction mixture was carefully quenched with saturated aqueous sodium bicarbonate, diluted with water, and extracted with DCM. The organic layer was washed with brine, dried over anhydrous magnesium sulfate, filtered, and concentrated. The crude material was purified by silica-gel chromatography, eluting with a gradient of 40% to 60% (40% ethyl acetate/heptane) in heptane, to provide the title compound (48 mg, 0.311 mmol) as white solid. LC/MS (ESI$^+$) m/z=155 (M+H)$^+$.

Step 3: 5-(difluoromethyl)picolinic acid

A suspension of 5-(difluoromethyl) picolinonitrile (48 mg, 0.311 mmol) in 12 N aqueous hydrochloric acid (4.3 mL, 140 mmol) was stirred at 110° C. for 1.5 hours. After cooling to ambient temperature, the reaction mixture was concentrated and treated with DIPEA (2 mL). The mixture was concentrated and dried in vacuo to provide the title compound in quantitative yield. LC/MS (ESI$^+$) m/z=174 (M+H)$^+$.

Intermediate 13

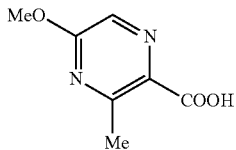

Synthesis of 5-methoxy-3-methylpyrazine-2-carboxylic acid

Step 1: Methyl 3-methylpyrazine-2-carboxylate

In a 2-L flask, 3-methylpyrazine-2-carboxylic acid (Matrix, 19.95 g, 144 mmol) was suspended in MeOH (500 mL). The suspension was cooled in an ice-water bath, and concentrated sulfuric acid (Fluka, 27.3 mL, 506 mmol) was added over a time period of 5 min. The reaction mixture was heated to 80° C. for 5 h. The reaction mixture was concentrated under reduced pressure and the residue was taken up in DCM (750 mL). The excess acid was neutralized carefully with of aqueous NaOH (5N or 5M, 200 mL). The aqueous layer was separated and extracted with DCM (250 mL). The combined organic layers were combined, dried over MgSO$_4$ and concentrated to afford 16.15 g of the title compound (106 mmol, 73%). MS m/z=153 [M+H]$^+$. Calculated for C$_7$H$_8$N$_2$O$_2$: 152.

Step 2: 3-(Methoxycarbonyl)-2-methylpyrazine 1-oxide

In a 1-L flask, the methyl 3-methylpyrazine-2-carboxylate (step 1, 16.08 g, 106 mmol) was suspended in CHCl$_3$ (300 mL). 3-chlorobenzoperoxoic acid (Aldrich, 24.62 g, 143 mmol) was added. The reaction mixture was heated to 70° C. for 16 h. The reaction mixture was quenched with saturated NaHCO$_3$ (200 mL). The layers were separated, and the aqueous layer was further extracted with DCM (2×100 mL). The combined organic layers were dried over MgSO$_4$, and the filtrate was concentrated to afford the title compound. MS m/z=169 [M+H]$^+$. Calculated for C$_7$H$_8$N$_2$O$_3$: 168.

Step 3: Methyl 5-chloro-3-methylpyrazine-2-carboxylate

In a 1-L flask, the crude 3-(methoxycarbonyl)-2-methylpyrazine 1-oxide (step 2, 17.77 g, 106 mmol) was dissolved in DMF (300 mL). Neat phosphoryl trichloride (29.6 mL, 317 mmol) was added. The reaction mixture was heated to 100° C. After 1 h, the reaction mixture was concentrated to remove most of the DMF. The flask was cooled in an ice water bath, and 1 M aqueous Na$_2$CO$_3$ (300 mL) was added slowly, followed by 80% EtOAc-hexane (400 mL). The mixture was filtered through Celite. The resulting filtrate was partitioned and the aqueous phase was extracted further with 80% EtOAc-hexane (2×250 mL). The combined organic layers were dried over MgSO$_4$ and concentrated. The material was purified through silica gel using 11% EtOAc-hexane to afford the title compound (4.29 g, 23 mmol, 22%). MS m/z=187 [M+H]$^+$. Calculated for C$_7$H$_7$ClN$_2$O$_2$: 186. $^1$H NMR in CDCl$_3$ δ: 8.51 (s, 1H), 4.01 (s, 3H), 2.86 (s, 3H).

Step 4: 5-Methoxy-3-methylpyrazine-2-carboxylic acid

A flask was charged with sodium (0.813 g, 35.4 mmol), purged with Argon. and placed in a room temperature water bath. Methanol (47.7 mL, 1179 mmol) was added slowly. After 40 min, methyl 5-chloro-3-methylpyrazine-2-carboxylate (step 3, 2.2 g, 11.79 mmol) was added. The vessel was sealed and heated to 45° C. for 1.5 hs. Sodium hydroxide (1M, 12.97 mL, 12.97 mmol) was added and heating was continued for 1.5 hs. The reaction mixture was concentrated uncle reduced pressure and the residue was dissolved in a minimum amount of water (50 mL). The aqueous phase was extracted with diethyl ether (15 mL), which was discarded. The aqueous phase was acidified with HCl (5M, 11 mL, 55 mmol). The mixture was extracted with DCM (3×60 mL). The combined organic extracts were dried over MgSO$_4$ and the filtrate was concentrated to afford the title compound (2.0 g, 100%). MS m/z=169 [M+H]$^+$. Calculated for C$_7$H$_8$N$_2$O$_3$: 168. $^1$H NMR in CDCl$_3$ δ: 10.70 (br, 1H), 7.98 (s, 1H), 4.00 (s, 3H), 2.91 (s, 3H).

Intermediate 14

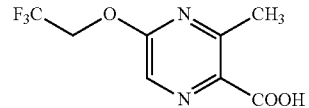

Synthesis of 3-methyl-5-(2,2,2-trifluoroethoxy)pyrazine-2-carboxylic acid

The title compound was synthesized according to Intermediate 13, using 2,2,2,-trifluoroethanol (Aldrich) in Step 4. MS m/z=237 (M+H)$^+$.

Intermediate 15

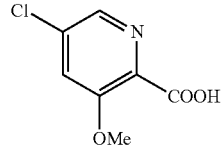 [SMILES: COc1cc(Cl)cnc1C(=O)O]

Synthesis of 5-chloro-3-methoxypicolinic acid

In a 1-L flask, 5-chloro-3-nitropicolinonitrile (Oakwood, 6.67 g, 36.3 mmol) was dissolved in MeOH (185 mL). The solution was cooled to 0° C., and sodium hydroxide (3M, 36.3 mL, 109 mmol) was added. The reaction mixture was warmed to room temperature and stirred overnight. The reaction was concentrated under reduced pressure and the residue was taken up in absolute ethanol (100 mL). NaOH (5M, 3 equiv, 109 mmol, 22 mL) was added, and the reaction mixture was heated to 100° C. for 1 h. The reaction mixture was concentrated under reduced pressure and the residue was taken up in water (100 mL). The aqueous layer was extracted with diethyl ether (30 mL), which was discarded. The aqueous phase was acidified with HCl (5M, 55 mL), saturated with NaCl, and extracted with EtOAc (5×75 mL). The combined organic extracts were dried over MgSO$_4$ and the filtrate was concentrated under reduced pressure. The resulting solid was triturated with diethyl ether to afford the title compound (5.63 g, 30 mmol, 83%). MS m/z=188 [M+H]$^+$. Calculated for C$_7$H$_6$ClNO$_3$: 187. $^1$H NMR in CDCl$_3$ δ: 8.18 (d, 1H, J=1.8), 7.49 (d, 1H, J=1.8), 4.03 (s, 3H).

Intermediate 16

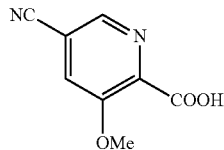 [SMILES: COc1cc(C#N)cnc1C(=O)O]

Synthesis of 5-cyano-3-methoxypicolinic acid

Step 1: Methyl 5-chloro-3-methoxypicolinate

In a 350-mL resealable vessel, 5-chloro-3-methoxypicolinic acid (intermediate 14, 7.51 g, 40.0 mmol) was dissolved in MeOH (120 mL). The solution was cooled to 0° C., and concentrated sulfuric acid (7.57 mL, 140 mmol) was added. The vessel was sealed and heated to 95° C. for 1.5 h. The reaction mixture was cooled to 0° C., and quenched with Na$_2$CO$_3$ (1M, 140 mL). The reaction mixture was concentrated under reduced pressure and the residue was extracted with EtOAc (3×100 mL). The combined organics extracts were dried over MgSO$_4$ and the filtrate was concentrated under reduced pressure. The residue was purified by silica gel chromatography (gradient 20%-33% EtOAc/hexane) to afford the title compound as a yellow solid (5.59 g, 27.7 mmol, 67%). MS m/z=202 [M+H]$^+$. Calculated for C$_8$H$_8$ClNO$_3$: 201. $^1$H NMR in CDCl$_3$ δ: 8.24 (d, 1H, J=1.9), 7.37 (d, 1H, J=1.9), 3.97 (s, 3H), 3.94 (s, 3H).

Step 2: Methyl 5-cyano-3-methoxypicolinate

In a 350-mL resealable vessel, Pd$_2$dba$_3$ (1.487 g, 1.623 mmol), dicyclohexyl(2',6'-dimethoxy-[1,1'-biphenyl]-2-yl)phosphine (1.444 g, 3.52 mmol), dicyanozinc (3.18 g, 27.1 mmol), and methyl 5-chloro-3-methoxypicolinate (step 1, 5.455 g, 27.1 mmol) were taken up in DMF (80 mL). The reaction mixture was purged with Argon and subsequently heated to 120° C. for 2 h. Upon cooling, the reaction mixture was concentrated under reduced pressure. The residue was filtered through Celite, and the filter cake was rinsed with 1% MeOH/DCM. The filtrate was concentrated under reduced pressure and the residue was purified by silica gel chromatography (33%-40% EtOAc/hexane) to afford the title compound as a white solid (4.51 g, 23.5 mmol, 87%). MS m/z=193 [M+H]$^+$. Calculated for C$_9$H$_8$N$_2$O$_3$: 192. $^1$H NMR in CDCl$_3$ δ: 8.51 (d, 1H, J=1.6), 7.55 (d, 1H, J=1.6), 4.00 (s, 3H), 3.97 (s, 3H).

Step 3: 5-Cyano-3-methoxypicolinic acid

In a 1-L flask, the methyl 5-cyano-3-methoxypicolinate (step 2, 4.51 g, 23.5 mmol) was taken up in THF (74 mL). The suspension was cooled to 0° C., and sodium hydroxide (1M, 24.64 mL, 24.64 mmol) was added. After 1 h, the reaction was concentrated under reduced pressure. The residue was taken up in 100 mL of water, and the aqueous phase was extracted with diethyl ether (50 mL), which was discarded. The aqueous phase was acidified with HCl (5M, 5.16 mL, 25.8 mmol). The aqueous phase was extracted with DCM (11×150 mL). The combined organic extracts were dried over MgSO$_4$ and the filtrate was concentrated under reduced pressure to afford the title compound as a white solid. MS m/z=179 [M+H]$^+$. Calculated for C$_8$H$_6$N$_2$O$_3$: 178. $^1$H NMR in CDCl$_3$ δ: 8.48 (d, 1H, J=1.6), 7.71 (d, 1H, J=1.6), 4.08 (s, 3H).

Intermediate 17

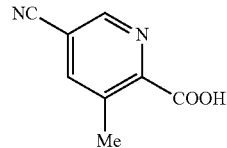

Synthesis of 5-cyano-3-methylpicolinic acid

To a solution of tert-butyl 5-cyano-3-methylpicolinate (synthesized according to procedure described in WO2012095521; 4.18 g, 19.15 mmol) in dichloromethane (96 ml) was added TFA (Aldrich, 148 ml, 1915 mmol). The reaction mixture was stirred at room temperature for 2 hrs. The reaction mixture was concentrated under reduced pressure and the residue was triturated with EtOAc. The yellow slurry was concentrated under reduced pressure. The residue was triturated with 30 mL of methyl tert-butyl ether (30 mL) and hexanes (50 mL) to yield 5-cyano-3-methylpicolinic acid (2.91 g, 17.95 mmol, 94% yield) as yellow solid. MS m/z=163.2 [M+H]$^+$. Calculated for C8H6N2O2: 162.0

Intermediate 18

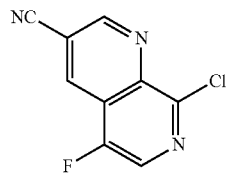 [SMILES: N#Cc1cnc2c(Cl)ncc(F)c2c1]

Step 1: 3-Chloro-5-fluoro-6-methoxy-6,7-dihydro-1,7-naphthyridin-8(5H)-one

A pressure bottle was charged with 3-chloro-1,7-naphthyridin-8(7H)-one (Anichem, 15 g, 83 mmol), MeOH (34 ml), acetonitrile (173 ml) and 1-(chloromethyl)-4-fluoro-1,4-diazabicyclo[2.2.2]octane-1,4-diium tetrafluoroborate (Aldrich, 30.9 g, 87 mmol). The mixture was heated to 45-50° C. After 6 hs additional 1-(chloromethyl)-4-fluoro-1,4-diazabicyclo[2.2.2]octane-1,4-diium tetrafluoroborate (2.5 g) was added and heating was continued overnight. Water and EtOAc were added to the cooled reaction mixture and the layers were separated. The aqueous layer was extracted with EtOAc, and the combined organic layers were dried over MgSO$_4$. The filtrate was concentrated under reduced pressure and the residue was triturated with EtOAc. The solid was filtered off and the title compound (15.34 g, 66.5 mmol, 80% yield) was isolated as a white solid. MS m/z=231 [M+H]$^+$. Calculated for $C_9H_8ClFN_2O_2$: 230.0

Step 2: 5-Fluoro-6-methoxy-8-oxo-5,6,7,8-tetrahydro-1,7-naphthyridine-3-carbonitrile A pressure bottle was charged with Pd(dba)$_3$ (Strem, 1.032 g, 1.127 mmol), 2-dicyclohexylphosphino-2',6'-dimethoxybiphenyl (Strem 1.157 g, 2.82 mmol), zinc cyanide (Alfa Aesar, 2.482 g, 21.14 mmol), 3-chloro-5-fluoro-6-methoxy-6,7-dihydro-1,7-naphthyridin-8(5H)-one (step 1, 3.25 g, 14.09 mmol) and DMF (70 ml). The bottle was purged with Argon and the reaction mixture was heated to 110° C. for 1 h. The crude reaction mixture was filtered through a pad of Celite and the filtercake was washed with MeOH. The combined filtrates were concentrated under reduced pressure. The residue was triturated with DCM. The solid was filtered off and washed with DCM. The title compound (2.27 g, 10.26 mmol, 72.8% yield) was obtained as an off white solid. MS m/z=222 [M+H]$^+$. Calculated for $C_{10}H_8FN_3O_2$: 221.1

Step 3: 8-Chloro-5-fluoro-1,7-naphthyridine-3-carbonitrile

A pressure bottle was charged with 5-fluoro-6-methoxy-8-oxo-5,6,7,8-tetrahydro-1,7-naphthyridine-3-carbonitrile (step 3, 2.27 g, 10.26 mmol), acetonitrile (41 ml) and phosphorus oxychloride (Aldrich, 3.35 ml, 35.9 mmol). The bottle was sealed and the reaction mixture was heated to 75° C. overnight. The reaction mixture was concentrated and the crude material was purified by silica gel chromatography (gradient 0-20% (10 MeOH in DCM)/DCM to afford the title compound (1.2 g, 5.78 mmol, 56.3% yield) as a white solid. MS m/z=208 [M+H]$^+$. Calculated for $C_9H_3ClFN_3$: 207.0

Intermediate 19 (Method R)

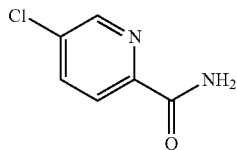

Synthesis of 5-chloropicolinamide

A 500-mL RBF was charged with 5-chloro-2-pyridinecarboxylic acid (Ark Pharm, 10.00 g, 63.5 mmol) and thionyl chloride (Aldrich, 100 ml, 1371 mmol). A catalytic amount of DMF (0.2 ml) was added and the reaction mixture was heated to 80° C. under Argon atmosphere for 4 hours. The reaction mixture was cooled to RT and concentrated under reduced pressure. The residue was diluted with DCM (100 ml) and added slowly to a stirred solution of ammonium hydroxide (131 ml, 3364 mmol) at 0° C. After completed addition, the reaction mixture was allowed to stir an additional 10 min. The reaction mixture was concentrated under reduced pressure and the precipitate was filtered off. The solid was washed with water and dried to give the title compound (8.686 g, 55.5 mmol, 87% yield) as an off-white solid. MS m/z=157 [M+H]$^+$. Calculated for $C_6H_5ClN_2O$: 156

Intermediate 20

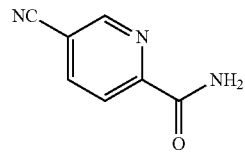 [SMILES: N#Cc1ccc(C(N)=O)nc1]

Synthesis of 5-cyanopicolinamide

The title compound was synthesized according to Method R starting from 5-cyanopicolinic acid (Aldrich). MS m/z=147.9 [M+H]$^+$. Calculated for $C_7H_5N_3O$: 147

Intermediate 21

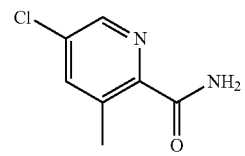

Synthesis of 5-chloro-3-methylpicolinamide

The title compound was synthesized according to Method R starting from 5-chloro-3-methylpicolinic acid (intermediate 17). MS m/z=171.1 [M+H]$^+$. Calculated for $C_7H_7ClN_2O$: 170

Intermediate 22

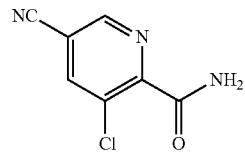 [SMILES: N#Cc1cnc(C(N)=O)c(Cl)c1]

Synthesis of 3-chloro-5-cyanopicolinamide

The title compound was synthesized according to Method R starting from 3-chloro-5-cyanopicolinic acid (Bionet Research). MS m/z=181.9 [M+H]$^+$. Calculated for $C_7H_4ClN_3O$: 181

Intermediate 23

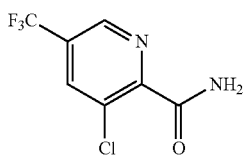

Synthesis of 3-chloro-5-(trifluoromethyl)picolinamide

The title compound was synthesized according to Method R starting from 3-chloro-5-(trifluoromethyl)picolinic acid (Ark Pharm). MS m/z=224.9 [M+H]+. Calculated for $C_7H_4ClF_3N_2O$: 224

Intermediate 24

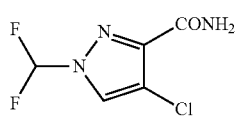

Synthesis of 4-chloro-1-(difluoromethyl)-1H-pyrazole-3-carboxamide

The title compound was prepared according to Method R starting from 4-chloro-1-(difluoromethyl)-1H-pyrazole-3-carboxylic acid (WO201169934). MS m/z=196 (M+H).

Intermediate 25

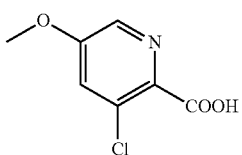

Synthesis of 3-chloro-5-methoxypicolinic acid

Step 1: methyl 3-chloro-5-methoxypicolinate

In a 1-L flask, methyl 3-chloro-5-hydroxypicolinate (Afferchem, 25.00 g, 133 mmol) and cesium carbonate (87 g, 267 mmol) were suspended in DMF (200 mL) and iodomethane (41.7 mL, 666 mmol) was added dropwise. A water-cooled condenser was attached, and the reaction vessel was heated in a 55° C. oil bath. After 3 h the reaction was concentrated under reduced pressure. The residue was taken up in 1.2 L of 80% EtOAc-hexane and 500 mL brine. The mixture was filtered through Celite. The filtrate was transferred into a separation funnel. The organic layer was separated, washed with brine (100 mL), dried over $MgSO_4$ and concentrated under reduced pressure. The residue was purified by silica gel chromatography eluting with 30% to 40% EtOAc-hexane, affording the title compound (19.1 g) as a tan solid. MS m/z=202 (M+H).

Step 2: 3-chloro-5-methoxypicolinic acid

Using an analogous reaction to that described for Intermediate 5, step 2 methyl 3-chloro-5-methoxypicolinate was converted to the title compound. MS m/z=188 (M+H).

Intermediate 26

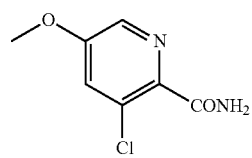

Synthesis of 3-chloro-5-methoxypicolinamide

The title compound was synthesized according to procedure R starting from 3-chloro-5-methoxypicolinic acid (intermediate 25). MS m/z=187 (M+H).

Intermediate 27

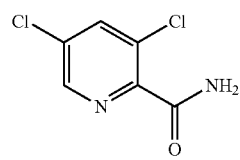 [SMILES: NC(=O)c1ncc(Cl)cc1Cl]

Synthesis of 3,5-dichloropicolinamide

The title compound was synthesized according to Method R, starting from 3,5-dichloropyridine-2-carboxylic acid (Matrix Scientific). MS m/z=190.9 [M+H]+. Calculated for $C_6H_4Cl_2N_2O$: 189.

Intermediate 28

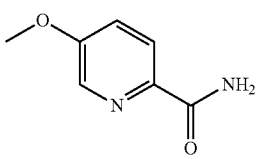

Synthesis of 5-methoxypicolinamide

Step 1: Sodium-5-methoxypicolinate

A microwave vial was charged with methyl 5-methoxypicolinate (9.700 g, 58.0 mmol, synthesized according to Tetrahedron Letters 2011, 52, 122-124) and sodium hydroxide solution (10 N; 58.0 ml, 580 mmol). The reaction mixture was stirred and heated in a CEM Voyager microwave (Large-Scale Unit) at 120° C. for 11 min (150 watts, Powermax feature on). Subsequently, the reaction mixture was allowed to stir for 10 minutes at ambient temperature. The precipitate was collected by filtration and the solid was rinsed with hexanes. The solid was dried to obtain sodium 5-methoxypicolinate (9.83 g, 56.1 mmol, 97% yield) as a light-yellow solid. MS m/z=175.9 [M+H]+. Calculated for $C_7H_6NNaO_3$: 175. $^1$H NMR (400 MHz, MeOH) d ppm 8.23 (d, J=2.93 Hz, 1H) 8.06 (d, J=8.61 Hz, 1H) 7.39 (dd, J=8.80, 2.93 Hz, 1H) 3.91 (s, 3H)

Step 2: 5-methoxypicolinamide

The title compound was synthesized according to Method R, starting from sodium-5-methoxypicolinate. MS m/z=153 [M+H]+. Calculated for $C_7H_8N_2O_2$: 152.

Intermediate 29

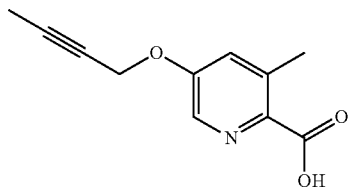

Step-1: Synthesis of 6-chloro-5-methylpyridine-3-amine

Iron (Fe) powder (9.75 g, 0.174 mol, Sigma-Aldrich) was added in portions over a period of 2 h to a stirred solution of 2-chloro-3-methyl-5-nitropyridine (10 g, 0.058 mol, Combi-blocks) in acetic acid/water (29 mL: 88 mL). After 3 h, the reaction mixture was filtered through celite and the filter cake was washed with ethyl acetate. The organic layer was separated and the aqueous layer was extracted with EtOAc. The combined organic layers were washed with aqueous sodium bicarbonate, brine and dried over Na2SO4. The solvent was removed under reduced pressure to yield 6-chloro-5-methylpyridine-3-amine as a brown solid (8.0 g; 97%). MS m/z=142.03 [M+H]+.

$^1$H-NMR (300 MHz, DMSO-d6): δ7.54 (d, J=30 Hz, 1H), 6.91-6.90 (dd, J=0.6 Hz & 2.7 Hz, 1H), 5.39 (s, 2H), 2.17 (s, 3H)

Step 2: Synthesis of 6-chloro-5-methylpyridine-3-ylacetate

In a 100 mL R.B. flask, Boron trifluoride diethyl etherate (1.8 mL, 0.0143 mol, Sigma Aldrich) was added drop wise to a cooled mixture (−15° C.) of 6-chloro-5-methylpyridine-3-amine (1.0 g, 0.0070 mol) in DME (7.5 mL) and dichloromethane (2.5 mL). Then tert-butyl nitrite (0.85 g, 0.0082 mol, Sigma-Aldrich) was added drop wise and the reaction mixture was stirred at −10° C. for 25 min. The reaction mixture was allowed to warm to 0° C. and stirred for additional 20 min. The reaction mixture was diluted with pentane (50 mL) and the tetrafluoroborate diazonium salt was collected by filtration. The salt was dissolved in acetic anhydride (10 mL) and heated at 95° C. for 2 h. The reaction mixture was cooled to ambient temperature and then partitioned between ethyl acetate (50 mL) and sat. aq. sodium bicarbonate solution (100 mL). The aqueous solution was separated and extracted with ethyl acetate (2×100 mL). The combined organic layers were washed with brine, dried over anhydrous sodium sulfate, filtered and concentrated to afford a brown oil. This oil was purified by column chromatography on silica gel, eluting with 5% ethyl acetate in petroleum ether to give 6-chloro-5-methylpyridine-3-yl acetate as pale yellow oil (780 mg, 62%). MS m/z=185.02 [M+H]+.

$^1$H-NMR (300 MHz, DMSO-d$_6$): δ 8.13 (d, J=2.4 Hz, 1H), 7.72 (d, J=2.7 Hz 1H), 2.34 (s, 3H), 2.30 (s, 3H)

Step-3: Synthesis of 6-chloro-5-methylpyridine-3-ol

Potassium carbonate (1.10 g, 0.0081 mol) was added to a stirred solution of 6-chloro-5-methylpyridine-3-yl acetate (750 mg, 0.004 mol) in MeOH (15 mL) at RT. The reaction mixture was stirred for 1 h at ambient temperature. The reaction mixture was concentrated under reduced pressure and the residue was diluted with minimum amounts of water and neutralized with 1N HCl (15 mL). After neutralization, the solution was extracted with ethyl acetate (2×100 mL). The combined organic layers were washed with brine, dried over anhydrous sodium sulfate and concentrated to give 6-chloro-5-methylpyridine-3-ol as a off white solid (500 mg, 89%). MS m/z=143.01 [M+H]+.

$^1$H-NMR (300 MHz, DMSO-d$_6$): δ 10.09 (s, 1H), 7.76 (d, J=3 Hz, 1H), 7.18 (d, J=3.6 Hz, 1H), 2.24 (s, 3H).

Step 4: Synthesis of 2-chloro-5-((4-methoxybenzyl)oxy)-3-methylpyridine

A mixture of 6-chloro-5-methylpyridin-3-ol (250 mg, 0.0017 mol), 1-(chloromethyl)-4-methoxybenzene (0.328 g, 0.0020 mol, Sigma Aldrich), and potassium carbonate (0.482 g, 0.0034 mol) in DMF (5 mL) was allowed to stir for 3 h at 60° C. After completion of the reaction, reaction mixture was cooled to ambient temperature and poured into ice cold water (25 mL). The obtained solid was filtered, washed with water (2×10 mL) and dried to obtain 2-chloro-5-((4-methoxybenzyl)oxy)-3-methylpyridine as an off white solid (400 mg, 87%).

MS m/z=263.9 [M+H]+.

$^1$H-NMR (300 MHz, CDCl$_3$): δ 7.96 (d, J=2.7 Hz, 1H), 7.34 (d, J=8.7 Hz, 2H), 7.15 (d, J=3 Hz, 1H), 6.94-6.89 (m, 2H), 4.99 (s, 2H), 3.81 (s, 3H), 2.33 (s, 3H).

Step 5: Synthesis of 5-((4-methoxybenzyl)oxy)-3-methyl-2-vinylpyridine

A 25 mL sealable tube was charged with a mixture of 2-chloro-5-(difluoromethoxy)-3-methylpyridine (330 mg, 0.0012 mmol), toluene (10 mL), and tributyl(vinyl)stannane (447 mg, 0.0015 mmol). The reaction mixture was purged with Argon gas for 10 min. Then Pd(PPh$_3$)$_4$ (144 mg, 0.00018 mol, Alfa-Aesar) was added and the reaction mixture was allowed to stir for 16 h at 100° C. The reaction mixture was cooled to ambient temperature and filtered through celite. The filter cake was washed with ethyl acetate and concentrated to get a crude residue. The residue was purified by column chromatography using silica and eluting with 5-10% ethyl acetate in petroleum ether to give 5-((4-methoxybenzyl)oxy)-3-methyl-2-vinylpyridine as an off white solid (250 mg, 65%). MS m/z=256.1 [M+H]+.

$^1$H-NMR (300 MHz, CDCl$_3$): δ 8.20 (d, J=2.7 Hz, 1H), 7.37-7.33 (m, 2H), 7.02 (d, J=2.7 Hz, 1H), 6.94-6.87 (m, 3H), 6.21 (dd, J=1.8 Hz & 16.8 Hz, 1H), 5.39 (dd, J=2.1 Hz & 10.5 Hz, 1H), 5.01 (s, 2H), 3.81 (s, 3H), 2.33 (s, 3H).

Step 6: Synthesis of 5-methyl-6-vinylpyridin-3-ol

Trifluoroacetic acid (1.25 mL, 5 times) was added to a stirred solution of 5-((4-methoxybenzyl)oxy)-3-methyl-2-vinylpyridine (250 mg, 0.00098 mmol) in anisole (0.5 mL). The reaction mixture was stirred for 2 h at ambient temperature. After completion of the reaction, the reaction mixture was concentrated and quenched with saturated NaHCO3 solution (2 ml). The reaction mixture was extracted with ethyl acetate (2×10 mL) and the combined organic layers were washed with brine, dried over anhydrous sodium sulfate and concentrated under reduced pressure. The crude residue was triturated with pentane to afford 5-methyl-6-vinylpyridin-3-ol as an off white solid (100 mg, 76%). MS m/z=136.15 [M+H]$^+$.

$^1$H-NMR (400 MHz, CDCl$_3$): δ 9.86 (s, 1H), 7.96 (d, J=2.8 Hz, 1H), 6.94-6.86 (m, 2H), 6.07 (dd, J=2.4 Hz & 16.8 Hz, 1H), 5.26 (dd, J=2.8 Hz & 10.4 Hz, 1H), 2.25 (s, 3H).

Step 7: Synthesis of 5-(but-2-yn-1-yloxy)-3-methyl-2-vinylpyridine

A reaction mixture of 5-methyl-6-vinylpyridin-3-ol (100 mg, 0.00074 mmol), sodium 1-bromobut-2-yne (118 mg, 0.00088 mol, Alfa-Aesar) and cesium carbonate (361 mg, 0.0011 mol) in DMF (2 mL) was stirred for 2 h at 80° C. After completion of the reaction, reaction mixture was cooled to ambient temperature, poured into ice-cold water (10 mL) and extracted with ethyl acetate (3×10 mL). The combined organic layers were washed with brine, dried over sodium sulfate and concentrated under reduced pressure. The crude residue was purified by column chromatography using silica gel and eluting with 0-10% ethyl acetate in petroleum ether to give 5-(but-2-yn-1-yloxy)-3-methyl-2-vinylpyridine as an off white solid (85 mg, 61.5%). MS m/z=188.3 [M+H]$^+$.

$^1$H-NMR (400 MHz, CDCl$_3$): δ 8.21 (d, J=2.8 Hz, 1H), 7.03 (d, J=2.4 Hz, 1H), 6.96-6.89 (m, 1H), 6.22 (dd, J=2.4 Hz & 17.2 Hz, 1H), 5.40 (dd, J=2 Hz & 10.8 Hz, 1H), 4.68-4.67 (m, 2H), 2.35 (s, 3H), 1.85 (t, J=2.4 Hz, 3H).

Step 8: Synthesis of 5-(but-2-yn-1-yloxy)-3-methylpicolinaldehyde

OsO$_4$ (2.5 wt. % sol. in tert-Butanol) (0.86 mL, 0.0027 mol) was added to a stirred solution of 5-(but-2-yn-1-yloxy)-3-methyl-2-vinylpyridine (5.1 g, 0.027 mol) in acetone/water (100:100 mL) at 0° C. The reaction mixture was allowed to stir for 30 min at ambient temperature. Then NaIO$_4$ (23.2 g, 0.108 mol) was added and the reaction mixture was allowed to stir for additional 4 h at ambient temperature. The reaction mixture was diluted with ice cold water (200 mL) and extracted with EtOAc (3×200 mL). The combined organic layers were washed with brine, dried over Na$_2$SO$_4$ and concentrated under reduced pressure. The crude residue was purified by flash column chromatography on silica gel, eluting with 5-10% EtOAc in pet ether to give 5-(but-2-yn-1-yloxy)-3-methylpicolinaldehyde as an off white solid (3.6 g, 69.9%). MS m/z=189.9 [M+H]$^+$.

$^1$H-NMR (400 MHz, CDCl$_3$): δ 10.10 (s, 1H), 8.37 (d, J=2.8 Hz, 1H), 7.13 (d, J=2.8 Hz, 1H), 4.77 (d, J=2.4 Hz, 2H), 2.67 (s, 3H), 1.86 (t, J=2 Hz, 3H).

Step 9: Synthesis of 5-(but-2-yn-1-yloxy)-3-methylpicolinic acid

A stirred solution of 5-(but-2-yn-1-yloxy)-3-methylpicolinaldehyde (3.6 g, 0.019 mol) in water (216 mL)/acetone (36 mL) was treated with sulphamic acid (2.5 g, 0.025 mol) and 85% sodium chlorite (2.65 g, 0.029 mol). The reaction mixture was allowed to stir for 2 h at ambient temperature. The reaction mixture was extracted with ethyl acetate (2×100 ml). The combined organic layer were washed with brine, dried over Na$_2$SO$_4$ and concentrated under reduced pressure. The crude residue was triturated with n-pentane to get 5-(but-2-yn-1-yloxy)-3-methylpicolinaldehyde as an off white solid (3.2 g, 82%).

MS m/z=206.3 [M+H]$^+$.

$^1$H-NMR (400 MHz, CD3OD): δ 8.16 (d, J=2.8 Hz, 1H), 7.38 (d, J=2.4 Hz, 1H), 4.84-4.82 (m, 2H), 2.63 (s, 3H), 1.83 (t, J=2 Hz, 3H).

Intermediate 30

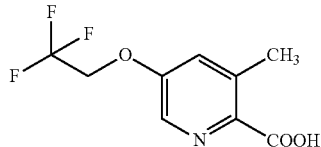 [SMILES: Cc1cc(OCC(F)(F)F)cnc1C(=O)O]

Step 1: Synthesis of 2-chloro-3-methyl-5-(2,2,2-trifluoroethoxy)pyridine

Tert-butyl nitrite (1.60 g, 0.0156 mol, Sigma-Aldrich) was added drop wise to a stirred solution of 6-chloro-5-methylpyridine-3-amine (2.0 g, 0.0140 mol) in trifluoroethanol (10.05 g, 0.100 mol) and TFA (2.42 g, 0.0212 mol) at ambient temperature, followed by slow addition of potassium carbonate (4.40 g). The reaction mixture was stirred at ambient temperature for 1 h. The reaction mixture was poured into ice-cold water and extracted with ethyl acetate (2×300 mL). The combined organic layer were washed with brine, dried over sodium sulfate and concentrated. The crude residue was purified by silica gel column chromatography, eluting with 5% ethyl acetate in petroleum ether to give 2-chloro-3-methyl-5-(2,2,2-trifluoroethoxy)pyridine (1.30 g, 41.13% yield) as a reddish oil. MS m/z=225.02 [M+H]$^+$.

$^1$H-NMR (400 MHz, CDCl$_3$): δ 7.96 (d, J=3.2 Hz, 1H), 7.19 (d, J=2.8 Hz, 1H), 7.87-4.41-4.35 (m, 2H), 2.37 (s, 3H),

Step 2: Synthesis of 3-methyl-5-(2,2,2-trifluoroethoxy)-2-vinylpyridine

Using an analogous reaction to that described for Intermediate 29, step 5 2-chloro-3-methyl-5-(2,2,2-trifluoroethoxy)pyridine was converted to 3-methyl-5-(2,2,2-trifluoroethoxy)-2-vinylpyridine. MS m/z=217.07 [M+H]$^+$ $^1$H-NMR (400 MHz, CDCl$_3$): δ 8.18 (d, J=2.8 Hz, 1H), 7.03 (d, 3.2 Hz, 1H), 6.96-6.89 (m, 2H), 6.26-6.21 (dd, J=2 Hz, 16.8 Hz, 1H), 5.45-5.42 (dd, J=2 Hz, 10.8 Hz, 1H), 4.42-4.36 (m, 2H), 2.36 (s, 3H).

Step 3: Synthesis of 3-methyl-5-(2,2,2-trifluoroethoxy) picolinaldehyde

Using an analogous reaction to that described for Intermediate 29, step 8 3-methyl-5-(2,2,2-trifluoroethoxy)-2-vinylpyridine was converted to 3-methyl-5-(2,2,2-trifluoroethoxy) picolinaldehyde. MS m/z=219.05 [M+H]$^+$ $^1$H-NMR (400 MHz, CDCl$_3$): δ 10.11 (s, 1H), 8.36 (dd, J=2.4 Hz, 1H), 7.11 (dd, J=2.8 Hz, 1H), 4.51-4.46 (m, 2H), 2.67 (s, 3H).

Step 4: Synthesis of 3-methyl-5-(2,2,2-trifluoroethoxy) picolinic acid

Using an analogous reaction to that described for Intermediate 34, step 9 3-methyl-5-(2,2,2-trifluoroethoxy) picolinaldehyde was converted to 3-methyl-5-(2,2,2-trifluoroethoxy) picolinic acid. MS m/z=235.05 [M+H]⁺

¹H-NMR (400 MHz, CD₃OD): δ 8.23 (d, J=2.4 Hz, 1H), 7.46 (d, J=2.4 Hz, 1H), 4.77-4.71 (m, 2H), 2.64 (s, 3H).

Intermediate 31

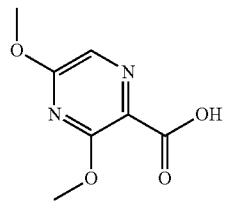

Synthesis of 3,5-dimethoxypyrazine-2-carboxylic acid

Step 1: 3,5-dichloropyrazine-2-carboxylic acid

To a solution of lithium diisopropylamide (2.0 M heptane/tetrahydrofuran/ethylbenzene, 11.10 mL, 22.20 mmol) in THF (75 mL) at −78° C. was added a solution of 2,6-dichloropyrazine (1.44 g, 9.67 mmol) in THF (20 mL) at room temperature over 20 min. The reaction mixture was stirred at −78° C. for 1.5 h and added via cannula to a 3-neck flask containing dry ice at −78° C. The reaction mixture was warmed from −78° C. to room temperature over 21 h and quenched with 5 M HCl. The mixture was partitioned between brine and EtOAc. The aqueous phase was acidified to pH 3.5 with 5 M HCl. The aqueous phase was extracted with EtOAc (6×) and the combined organic extracts were washed with brine (1×), dried over MgSO₄, filtered, and concentrated. Purification by flash column chromatography on silica gel (5% to 10% MeOH in DCM) gave 3,5-dichloropyrazine-2-carboxylic acid (0.408 g, 2.11 mmol, 22% yield) as a light brown solid. LC/MS (ESI⁺) m/z=193.0 (M+H)⁺.

Step 2: methyl 3,5-dichloropyrazine-2-carboxylate

To a solution of 3,5-dichloropyrazine-2-carboxylic acid (0.304 g, 1.58 mmol) in MeOH (5 mL) and diethyl ether (5 mL) at room temperature was added (trimethylsilyl)diazomethane (2.0 M solution in hexanes, 4.00 mL, 8.00 mmol). The reaction mixture was stirred at RT for 30 min and concentrated. Purification by flash column chromatography on silica gel (5% to 20% EtOAc in hexanes) gave methyl 3,5-dichloropyrazine-2-carboxylate (0.312 g, 1.51 mmol, 96% yield) as a white solid. LC/MS (ESI⁺) m/z=207.0 (M+H)⁺.

Step 3: ethyl 3,5-dimethoxypyrazine-2-carboxylate

To a solution of methyl 3,5-dichloropyrazine-2-carboxylate (0.312 g, 1.51 mmol) in THF (4.5 mL) at RT was added sodium hydride (60% wt. dispersion, 0.199 g, 4.98 mmol) and methanol (0.200 mL, 4.94 mmol). The reaction mixture was stirred at RT for 30 min, diluted with EtOAc, and quenched with saturated NH₄Cl. The aqueous phase was partitioned between brine and EtOAc. The aqueous phase was extracted with EtOAc (3×) and the combined organic extracts were washed with brine (1×), dried over MgSO₄, filtered, and concentrated. Purification by flash column chromatography on silica gel (10% to 50% EtOAc in hexanes) gave ethyl 3,5-dimethoxypyrazine-2-carboxylate (0.314 g, 1.48 mmol, 98% yield) as an off white solid. LC/MS (ESI⁺) m/z=199.1 (M+H)⁺.

Step 4: 3,5-dimethoxypyrazine-2-carboxylic acid

To a solution of ethyl 3,5-dimethoxypyrazine-2-carboxylate (0.314 g, 1.48 mmol) in MeOH (5 mL) at room temperature was added potassium hydroxide (0.135 g, 2.41 mmol). The reaction mixture was stirred at RT for 17 h, quenched with 5 M HCl (0.48 mL), and diluted with EtOAc. The solid was removed by filtration and the filtrate was concentrated. Purification by flash column chromatography on silica gel (10% MeOH in DCM) gave 3,5-dimethoxypyrazine-2-carboxylic acid (0.261 g, 1.42 mmol, 96% yield) as a white solid. LC/MS (ESI⁺) m/z=185.1 (M+H)⁺.

Intermediate 32

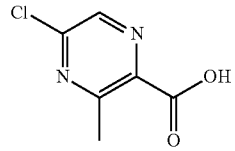

Synthesis of 5-chloro-3-methylpyrazine-2-carboxylic acid

A solution of methyl 5-chloro-3-methylpyrazine-2-carboxylate (0.117 g, 0.627 mmol) (Step 3 of Intermediate 24) and sodium hydroxide 5N (0.150 ml, 0.752 mmol) in dioxane (5 mL) was stirred at room temperature for 30 minutes. The reaction mixture was acidified with 2N HCl to pH 4 and extracted with EtOAc (2×). The combined organic extracts were dried over Na₂SO₄ and the filtrate was concentrated to afford the title compound (91.0 mg, 84%). MS m/z=172.9 (M+H)⁺.

Intermediate 33 (Method 5)

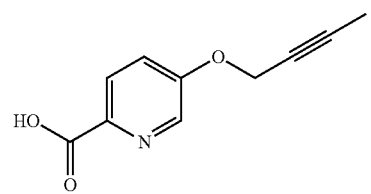

Synthesis of 5-(but-2-yn-1-yloxy)picolinic acid

Step 1: Methyl 5-(but-2-yn-1-yloxy)picolinate

A solution of methyl 5-hydroxypyridine-2-carboxylate (1.5 g, 9.8 mmol, Molbridge) in THF (39 ml) under argon was cooled to 0° C. and 2-butyn-1-ol (1.5 ml, 20 mmol, Aldrich), triphenyl phosphine (2.95 g, 11.2 mmol, Aldrich) and diisopropyl azodicarboxylate (2.2 ml, 11.2 mmol, Aldrich) were added consecutively. The reaction mixture was stirred at RT for 2 h. Additional diisopropyl azodicarboxylate (1 ml) was added and the reaction mixture was stirred at RT for another 1 h. The reaction mixture was diluted with $CH_2Cl_2$ and washed with saturated $NaHCO_3$ solution; the aqueous layer was back-extracted with $CH_2Cl_2$. The combined organic extracts were dried over $MgSO_4$ and concentrated in vacuo. Purification by silica gel chromatography (0% to 50% EtOAc/Hexanes) afforded the title compound as a light tan solid. MS m/z=206.0 [M+H]+.

Step 2: 5-(But-2-yn-1-yloxy)picolinic acid

Using an analogous reaction to that described for Intermediate 5, step 2 methyl 5-(but-2-yn-1-yloxy)picolinate was converted to 5-(But-2-yn-1-yloxy)picolinic acid MS m/z=192.1 [M+H]+.

Intermediate 34

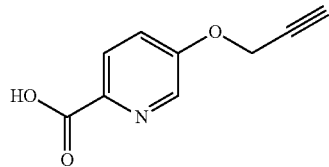

Synthesis of 5-(prop-2-yn-1-yloxy)picolinic acid

The title compound was synthesized analogously according to Method S starting from propargyl alcohol (Aldrich). MS m/z=178.1 [M+H]+.

Intermediate 35

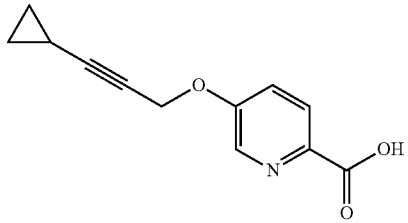 [SMILES: O=C(O)c1ccc(OCC#CC2CC2)cn1]

Synthesis of 5-((3-cyclopropylprop-2-yn-1-yl)oxy)picolinic acid

Step 1: 3-Cyclopropylprop-2-yn-1-ol

To a solution of cyclopropylacetylene (0.833 mL, 9.83 mmol, Aldrich) in THF (20 mL) at −78° C. under $N_2$ was added butyllithium (6.15 mL, 9.83 mmol, Aldrich) dropwise. After completed addition, the mixture was stirred at −78° C. for 30 min, followed by slow addition of a solution of paraformaldehyde powder (600 mg, 9.83 mmol, Aldrich) in THF (7 mL). The reaction mixture was then stirred at −78° C. for 2 h and allowed to warm up to room temperature overnight. The reaction mixture was quenched with saturated ammonium chloride (20 mL) at 0° C. The mixture was then extracted with diethyl ether (2×20 mL). The combined organic extracts were dried over $MgSO_4$ and concentrated to a volume of approximately 3 mL. The mixture was then purified by silica gel flash column chromatography, (0%-50% diethyl ether/pentane) to give 760 mg of the title compound as a colorless liquid containing diethyl ether, which was used in the next step. $^1$H NMR (MeOH) δ: 4.13 (d, J=2.0 Hz, 2H), 1.26-1.30 (m, 1H), 0.74-0.83 (m, 2H), 0.59-0.67 (m, 2H).

Step 2: 5-((3-Cyclopropylprop-2-yn-1-yl)oxy)picolinic acid

The title compound was synthesized analogously according to Method KS starting from methyl 5-hydroxypicolinate (Molbridge) and 3-cyclopropylprop-2-yn-1-ol. MS m/z: 218 (M+H).

Intermediate 36

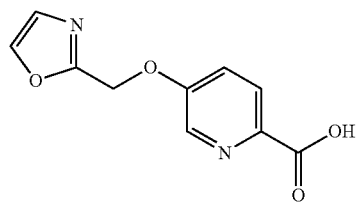 [SMILES: O=C(O)c1ccc(OCc2ncco2)cn1]

Synthesis of 5-(Oxazol-2-ylmethoxy)picolinic acid

The title compound was synthesized analogously according to Method S starting from methyl 5-hydroxypicolinate (Molbridge) and oxazol-2-ylmethanol (AstaTech). MS m/z=237.9 [M+H]+. Calculated for $C_9H_7N_3O_3S$. $^1$H NMR (400 MHz, DMSO-$d_6$) δ ppm 5.59 (s, 2H) 7.86 (d, J=1.96 Hz, 1H) 8.45 (d, J=1.17 Hz, 1H) 8.83 (d, J=1.37 Hz, 1H) 9.14 (d, J=1.96 Hz, 1H)

Intermediate 37

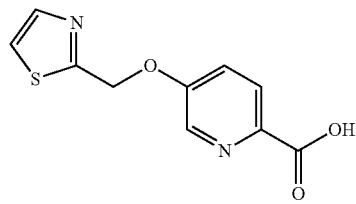 [SMILES: O=C(O)c1ccc(OCc2nccs2)cn1]

Synthesis of 5-(Thiazol-2-ylmethoxy)picolinic acid

The title compound was synthesized according to the above method S starting from 1,3-thiazol-2-ylmethanol (Maybridge Chemical Co., Ltd.). MS m/z=236.9 [M+H]+. Calculated for $C_{10}H_8N_2O_3S$: 293.084.

Intermediate 38

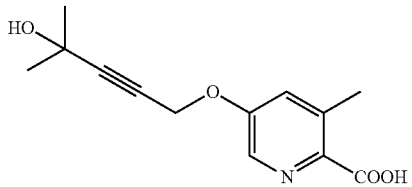 [SMILES: Cc1cc(OCC#CC(C)(C)O)cnc1C(=O)O]

Synthesis of 5-((4-hydroxy-4-methylpent-2-yn-1-yl)oxy)-3-methylpicolinic acid

Step 1: 5-hydroxy-3-methylpicolinonitrile

A resealable vessel was charged with $Pd_2dba_3$ (0.893 g, 0.975 mmol, Strem), dicyclohexyl(2',6'-dimethoxy-[1,1'-biphenyl]-2-yl)phosphine (0.858 g, 2.090 mmol, Strem), dicyanozinc (1.636 g, 13.93 mmol), and 6-chloro-5-methylpyridin-3-ol (2.00 g, 13.93 mmol, step 3 intermediate 34). The solids were taken up in DMF (45 mL) and the reaction mixture was purged with Argon. The vessel was sealed and heated in a 110° C. oil bath. After 21 h, the reaction was filtered through Celite and the filter cake was rinsed with 5% MeOH-DCM. The filtrate was concentrated and the residue was purified by silica gel chromatography, eluting with 40% to 50% EtOAc-hexane to afford the title compound (676 mg, 32%). MS m/z=135 $(M+H)^+$.

Step 2: 5-hydroxy-3-methylpicolinic acid

5-Hydroxy-3-methylpicolinonitrile (0.570 g, 4.25 mmol) was taken up in concentrated aqueous HCl (28.3 mL, 340 mmol). The reaction mixture was heated in a 110° C. oil bath. After 24 h, the reaction was concentrated to afford the title compound (650 mg). The residue was used as is. MS m/z=154 $(M+H)^+$.

Step 3: methyl 5-hydroxy-3-methylpicolinate

A sealable reaction vessel was charged with 5-hydroxy-3-methylpicolinic acid (0.651 g, 4.25 mmol) and MeOH (35 mL). The reaction vessel was placed in a water bath, and concentrated sulfuric acid (0.854 mL, 15.94 mmol) was added. The vessel was sealed and heated in a 95° C. oil bath. After 24 h, the reaction mixture was concentrated and the residue was taken up in 30 mL of 0.5M aqueous $Na_2CO_3$. The aqueous phase was extracted with 10% MeOH-EtOAc (100 mL). The aqueous layer was separated and saturated with NaCl. The aqueous phase was extracted with 10% MeOH-EtOAc (7×100 mL). The combined organic fractions were dried over $MgSO_4$ and concentrated. The residue was purified by silica gel chromatography, eluting with 3% to 4% MeOH-DCM to afford the title compound (593 mg). MS m/z=168 $(M+H)^+$.

Step 4: 4-methylpent-2-yne-1,4-diol

In a 1-L flask, potassium hydroxide (23.52 g, 419 mmol) was suspended in diethyl ether (338 mL). The suspension was cooled to 0° and propargyl alcohol (10.0 mL, 168 mmol, Aldrich) was added. After 1 h, acetone (36.9 mL, 503 mmol) was added and the mixture was stirred overnight at rt. The reaction mixture was cooled in an ice water bath and acidified with aqueous HCl (5M; 90 mL). The reaction mixture was diluted with 100 mL or water. The layers were separated. The aqueous layer was saturated with NaCl and extracted with EtOAc (2×100 mL). The combined organic extracts were dried over $MgSO_4$ and concentrated under reduced pressure. The residue was purified by silica gel chromatography, eluting with 70% to 80% EtOAc-hexane to afford the title compound (564 mg). $^1$H NMR (400 MHz, $CDCl_3$) δ ppm 4.29 (d, J=6.1 Hz, 2H), 2.05 (d, J=6.1 Hz, 1H), 1.73 (m, 1H), 1.53 (s, 6H).

Step 5: methyl 5-((4-hydroxy-4-methylpent-2-yn-1-yl)oxy)-3-methylpicolinate

The title compound was synthesized analogously according to Method S starting from methyl 5-hydroxy-3-methylpicolinate and 4-methylpent-2-yne-1,4-diol. MS m/z=264 $(M+H)^+$.

Step 6: 5-(4-hydroxy-4-methylpent-2-yn-1-yl)oxy)-3-methylpicolinic acid

Using an analogous reaction to that described for Intermediate 5, step 2 methyl 5-((4-hydroxy-4-methylpent-2-yn-1-yl)oxy)-3-methylpicolinate was coverted into the title compound. MS m/z=250 $(M+H)^+$.

Intermediate 39

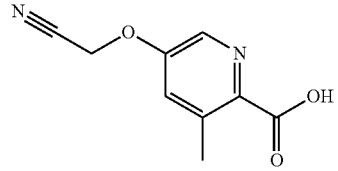

Synthesis of 5-(Cyanomethoxy)-3-methylpicolinic acid

Step 1: Methyl 5-(cyanomethoxy)-3-methylpicolinate

To a suspension of methyl 5-hydroxy-3-methylpicolinate (0.8063 g, 4.82 mmol, step 3 intermediate 38) and cesium carbonate (0.772 ml, 9.65 mmol, Alfa Aesar) in DMF (48.2 ml) was added bromoacetonitrile (0.336 ml, 4.82 mmol, Sigma-Aldrich Chemical Company, Inc.). The reaction mixture was stirred for 4 h at rt. The reaction mixture was diluted with aqueous, saturated sodium bicarbonate solution and extracted with EtOAc. The organic extract was washed with aqueous, saturated sodium bicarbonate solution, brine and dried over $MgSO_4$. The filtrate was concentrated in vacuo. MS m/z=207.1 $[M+H]^+$. Calculated for $C_{10}H_{10}N_2O_3$: 206.069. $^1$H NMR (400 MHz, CHLOROFORM-d) ppm 2.67 (s, 3H) 3.98 (s, 3H) 4.88 (s, 2H) 7.20 (d, J=2.35 Hz, 1H) 8.32 (br. s., 1H)

Step 2: 5-(Cyanomethoxy)-3-methylpicolinic acid

To a solution of methyl 5-(cyanomethoxy)-3-methylpicolinate (0.895 g, 4.34 mmol) and sodium iodide (0.354 ml, 8.68 mmol, Sigma-Aldrich Chemical Company, Inc.) in acetonitrile (4.34 ml) was added chlorotrimethylsilane (1.102 ml, 8.68 mmol, Strem Chemicals, Inc.). The reaction mixture was heated to 70° C. and allowed to stir overnight. The reaction mixture was concentrated under reduced pressure and the residue was diluted with water and extracted with EtOAc. The organic extract was washed with water, 10% sodium thio sulfate solution and dried over MgSO$_4$. The filtrate was concentrated in vacuo to give 5-(cyanomethoxy)-3-methylpicolinic acid which was used without further purification. MS m/z=192.9 [M+H]$^+$. Calculated for C$_9$H$_8$N$_2$O$_3$: 192.03

Intermediate 40 (Method T)

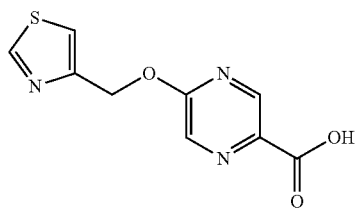 [SMILES: O=C(O)c1cnc(OCc2cscn2)cn1]

Synthesis of 5-(Thiazol-4-ylmethoxy)pyrazine-2-carboxylic acid

Step 1: Thiazol-4-ylmethanol

To a solution of thiazole-4-carboxaldehyde (0.810 ml, 9.67 mmol, Combi-Blocks Inc.) in MeOH (48.3 ml) at 0° C. was added sodium borohydride (0.341 ml, 9.67 mmol, Sigma-Aldrich Chemical Company, Inc.) in portions. The reaction mixture was allowed to stir for 1 hour. Saturated aqueous ammonium chloride solution was carefully added and the reaction mixture was filtered. The filtrate was concentrated in vacuo. The solid was taken up in 10% MeOH/DCM and filtered through a plug of silica gel to provide thiazol-4-ylmethanol (0.826 g, 7.18 mmol, 74.3% yield) as a yellow oil. MS m/z=116.0 [M+H]$^+$. Calculated for C$_4$H$_5$NOS: 115.009. $^1$H NMR (400 MHz, CHLOROFORM-d) δ ppm 2.58 (br. s., 1H) 4.86 (s, 2H) 7.27-7.30 (m, 1H) 8.83 (d, J=1.76 Hz, 1H)

Step 2: Methyl 5-(thiazol-4-ylmethoxy)pyrazine-2-carboxylate

A RBF was charged with methyl 5-chloropyrazine-2-carboxylate (1.239 g, 7.18 mmol, Ark Pharm), thiazol-4-ylmethanol (0.8266 g, 7.18 mmol), cesium carbonate (0.689 ml, 8.61 mmol, Alfa Aesar) and DMF (20.51 ml). The reaction mixture was stirred at 40° C. for 3 days. The reaction mixture was allowed to cool to rt and was diluted with water and extracted with EtOAc. The organic extract was washed with water, satd NaCl, dried over MgSO$_4$, and concentrated in vacuo. The crude product was adsorbed onto a plug of silica gel and purified by silica gel flash chromatography, eluting with a gradient of 10% to 100% EtOAc in hexane, to provide methyl 5-(thiazol-4-ylmethoxy)pyrazine-2-carboxylate (0.7606 g, 3.03 mmol, 42.2% yield). MS m/z=252.1 [M+H]$^+$. Calculated for C$_{10}$H$_9$N$_3$O$_3$S: 251.036. $^1$H NMR (400 MHz, DMSO-d$_6$) δ ppm 3.89 (s, 2H) 5.60 (s, 1H) 7.86 (d, J=1.96 Hz, 1H) 8.46 (d, J=1.37 Hz, 1H) 8.86 (d, J=1.37 Hz, 1H) 9.14 (d, J=1.96 Hz, 1H)

Step 3: 5-(Thiazol-4-ylmethoxy)pyrazine-2-carboxylic acid

To a solution of methyl 5-(thiazol-4-ylmethoxy)pyrazine-2-carboxylate (0.7606 g, 3.03 mmol) in 1,4-dioxane (15.14 ml) was added a 1 N solution of sodium hydroxide (4.54 ml, 4.54 mmol) at rt. The reaction mixture was allowed to stir for 16 hours. Hydrogen chloride (4.0M solution in 1,4-dioxane; 1.135 ml, 4.54 mmol, Sigma Aldrich) was added and after 10 minutes, the reaction mixture was concentrated in vacuo to give the title compound. MS m/z=237.9 [M+H]$^+$. Calculated for C$_9$H$_7$N$_3$O$_3$S: 237.021. $^1$H NMR (400 MHz, DMSO-d$_6$) δ ppm 5.59 (s, 2H) 7.86 (d, J=1.96 Hz, 1H) 8.45 (d, J=1.17 Hz, 1H) 8.83 (d, J=1.37 Hz, 1H) 9.14 (d, J=1.96 Hz, 1H)

Intermediate 41

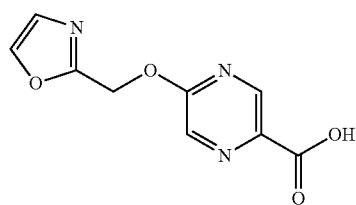 [SMILES: O=C(O)c1cnc(OCc2ncco2)cn1]

Synthesis of 5-(Oxazol-2-ylmethoxy)pyrazine-2-carboxylic acid

The title compound was synthesized according to the above method T starting from oxazol-2-ylmethanol (Asatech, Inc.). MS m/z=221.9 [M+H]$^+$. Calculated for C$_9$H$_7$N$_3$O$_4$: 221.044.

Intermediate 42

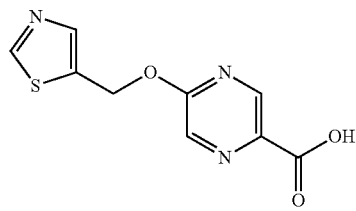 [SMILES: O=C(O)c1cnc(OCc2cncs2)cn1]

Synthesis of 5-(Thiazol-5-ylmethoxy)pyrazine-2-carboxylic acid

The title compound was synthesized according to the above method T starting from 5-(hydroxymethyl)thiazole (Oakwood Products, Inc.). MS m/z=237.9 [M+H]$^+$. Calculated for C$_9$H$_7$N$_3$O$_3$S: 237.02.

Intermediate 43

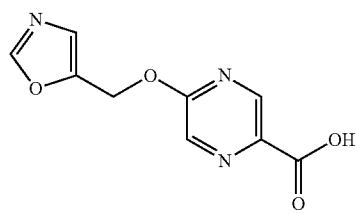 [SMILES: O=C(O)c1cnc(OCc2cnco2)cn1]

Synthesis of 5-(Oxazol-5-ylmethoxy)pyrazine-2-carboxylic acid

The title compound was synthesized according to the above method T starting from 1,3-oxazol-5-methanol (Combi-Blocks Inc.). MS m/z=222.1 [M+H]$^+$. Calculated for $C_9H_7N_3O_4$: 221.04.

Intermediate 44

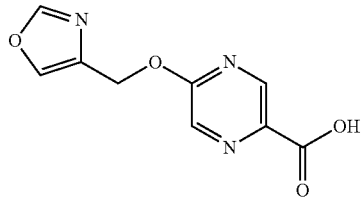 [SMILES: O=C(O)c1cnc(OCc2cocn2)cn1]

Synthesis of 5-(Oxazol-4-ylmethoxy)pyrazine-2-carboxylic acid

The title compound was synthesized according to the above method T starting from oxazol-4-ylmethanol (J&W Pharmlab). MS m/z=221.9 [M+H]$^+$. Calculated for $C_9H_7N_3O_4$: 221.04.

Intermediate 45

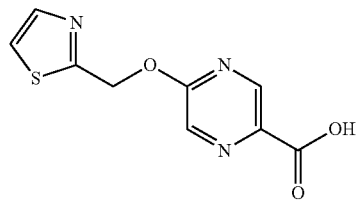 [SMILES: O=C(O)c1cnc(OCc2nccs2)cn1]

Synthesis of 5-(Thiazol-2-ylmethoxy)pyrazine-2-carboxylic acid

The title compound was synthesized according to the above method T starting from 1,3-thiazol-2-ylmethanol (Maybridge Chemical Co., Ltd.). MS m/z=237.9 [M+H]$^+$. Calculated for $C_9H_7N_3O_3S$: 237.02.

Intermediate 46

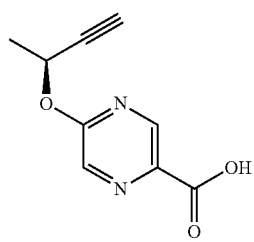

Synthesis of (S)-5-(But-3-yn-2-yloxy)pyrazine-2-carboxylic acid

The title compound was synthesized according to the above method T starting from (S)-(−)-3-butyn-2-ol (Alfa Aesar, A Johnson Matthey Company). MS m/z=192.9 [M+H]$^+$. Calculated for $C_9H_8N_2O_3$: 192.05

Intermediate 47

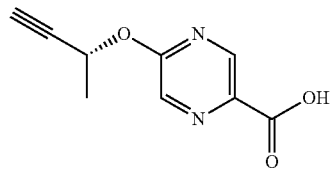

Synthesis of (R)-5-(But-3-yn-2-yloxy)pyrazine-2-carboxylic acid

The title compound was synthesized according to the above method T starting from (R)-(+)-3-butyn-2-ol (Aldrich). MS m/z=193 [M+H]$^+$. Calculated for $C_9H_8N_2O_3$: 192.05

Intermediate 48

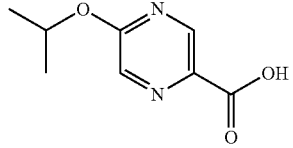

Synthesis of 5-isopropoxypyrazine-2-carboxylic acid

To a rt solution of sodium t-butoxide (1.41 g, 14.67 mmol) in THF (20 mL) was added 2-propanol (1.250 mL, 16.33 mmol) dropwise. After 10 min a solution of methyl 5-chloro-2-pyrazinecarboxylate (1.70 g, 9.85 mmol, Ark Pharm) in THF (10 mL) was added dropwise. After 1.5 h, the reaction was quenched with saturated aq $NH_4Cl$ and extracted with EtOAc (3×). The aqueous layer was concentrated under reduced pressure and the resulting solid was treated with aqueous HCl. The solution was extracted with DCM (3×) and the combined organic layers were purified by flash chromatography, eluting with 0.5% TFA in iPrOH:$CH_2Cl_2$ (0:1→1:9) to give a white crystalline solid. (497 mg, 2.7 mmol, 28%). MS m/z=183 [M+H]$^+$. Calculated for $C_8H_{10}N_2O_3$: 182.

Intermediate 49

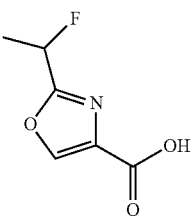

Synthesis of 2-(1-Fluoroethyl)oxazole-4-carboxylic acid

Step 1: Methyl 2-(2-fluoropropanamido)-3-hydroxypropanoate

A rbf was charged with DL-serine methyl ester hydrochloride (1.49 g, 9.57 mmol, Sigma-Aldrich Chemical Company, Inc.), HATU (4.37 g, 11.49 mmol, Sigma-Aldrich Chemical Company, Inc.) and DCM (22 mL). 2-Fluoropropionic acid (0.75 ml, 9.57 mmol, Alfa Aesar, A Johnson Matthey Company) and triethylamine (3.3 ml, 23.93 mmol, Sigma-Aldrich Chemical Company, Inc.) were added and the reaction mixture was allowed to stir at rt overnight. The reaction mixture was diluted with water and extracted with DCM. The organic extract was washed with water, aqueous saturated NaHCO$_3$ solution, brine, and dried over MgSO$_4$. The solution was concentrated in vacuo and the crude product was purified by silica gel chromatography, eluting with a gradient of 1% to 10% MeOH in DCM, to provide methyl 2-(2-fluoropropanamido)-3-hydroxypropanoate (0.69 g, 3.60 mmol, 38% yield).

$^1$H NMR (300 MHz, CHLOROFORM-d) δ ppm 1.40 (t, J=7.31 Hz, 5H) 1.50-1.77 (m, 3H) 3.23 (qd, J=7.31, 5.12 Hz, 3H) 3.82 (s, 3H) 3.88-4.15 (m, 2H) 4.69 (dt, J=7.53, 3.69 Hz, 1H) 4.87-5.21 (m, 1H)

Step 2: Methyl 2-(1-fluoroethyl)oxazole-4-carboxylate

A solution of methyl 2-(2-fluoropropanamido)-3-hydroxypropanoate (0.69 g, 3.60 mmol) in DCM (36.0 ml) was cooled to −20° C. and deoxo-fluor (50% in THF; 0.73 ml, 3.96 mmol, Fluka Chemie GmbH) was added dropwise. The reaction mixture was allowed to stir for 1 hour. Bromotrichloromethane (1.276 ml, 12.96 mmol, Sigma-Aldrich Chemical Company, Inc.) was added followed by addition of DBU (1.936 ml, 12.96 mmol, TCI). The reaction mixture was allowed to warm to 0° C. and stirred for 3 h. The reaction was quenched by the addition of aqueous, saturated NaHCO$_3$ solution and extracted with CH$_2$Cl$_2$. The organic extract was washed with water, brine and dried over MgSO$_4$. The solvent was removed in vacuo and the crude product was purified by silica gel chromatography, eluting with a gradient of 1% to 10% 2M NH3.MeOH in CH$_2$Cl$_2$, to provide methyl 2-(1-fluoroethyl)oxazole-4-carboxylate (0.2746 g, 1.586 mmol, 44.1% yield). MS m/z=173.9 [M]$^+$; Calculated for C$_7$H$_8$FNO$_3$: 173.049

Step 3: 2-(1-Fluoroethyl)oxazole-4-carboxylic acid

Using an analogous reaction to that described for Intermediate 5, step 2 methyl 2-(1-fluoroethyl)oxazole-4-carboxylate was coverted into the title compound. MS m/z=159.9 [M+H]$^+$. Calculated for C$_6$H$_6$FNO$_3$: 159.03

Intermediate 50

Synthesis of 4-Chloro-1-isopropyl-1H-pyrazole-3-carboxylic acid

Step 1: Methyl 1-isopropyl-1H-pyrazole-3-carboxylate

To a solution of 1-isopropyl-1 h-pyrazole-3-caboxylic acid (0.9757 g, 6.33 mmol, Matrix Scientific) in MeOH (31.6 ml) in a glass pressure vessel was added sulfuric acid (0.355 ml, 6.33 mmol Sigma Aldrich). The vessel was sealed and the rxn was brought to reflux to stir. (NOTE: A portable blast shield was used.) Rxn was allowed to stir for 5 hours. The rxn was concentrated in vacuo. The residue was diluted with water and extracted with EtOAc. The organic extract was washed with water, dried over MgSO$_4$, filtered and concentrated in vacuo to give methyl 1-isopropyl-1H-pyrazole-3-carboxylate (0.8073 g, 4.80 mmol, 76% yield) as a clear oil. MS m/z=168.9 [M+H]$^+$. Calculated for C$_8$H$_{12}$N$_2$O$_2$: 168.09. $^1$H NMR (400 MHz, CHLOROFORM-d) δ ppm 1.55 (d, J=6.85 Hz, 6H) 3.93 (s, 3H) 4.63 (dt, J=13.50, 6.75 Hz, 1H) 6.83 (d, J=2.35 Hz, 1H) 7.46 (d, J=2.35 Hz, 1H)

Step 2: Methyl 4-chloro-1-isopropyl-1H-pyrazole-3-carboxylate

To a solution of methyl 1-isopropyl-1H-pyrazole-3-carboxylate (0.8073 g, 4.80 mmol) in DMF (9.60 ml) was added n-chlorosuccinimide (3.20 g, 24.00 mmol, Sigma Aldrich). The reaction mixture was heated to 70° C. for 4.5 h. The reaction mixture was diluted with water and extracted with EtOAc. The organic extract was washed with water, brine, dried over MgSO$_4$, filtered and concentrated in vacuo. The crude product was purified by silica gel chromatography, eluting with a gradient of 10% to 30% EtOAc in hexane, to provide methyl 4-chloro-1-isopropyl-1H-pyrazole-3-carboxylate (0.2705 g, 1.335 mmol, 27.8% yield) as an off-white solid. MS m/z=203.0[M+H]$^+$. Calculated for C$_8$H$_{11}$ClN$_2$O$_2$: 202.051. $^1$H NMR (400 MHz, DMSO-d$_6$) δ ppm 1.42 (d, J=6.85 Hz, 6H) 3.80 (s, 3H) 4.55 (dt, J=13.30, 6.65 Hz, 1H) 8.23 (s, 1H)

Step 3: 4-chloro-1-isopropyl-1H-pyrazole-3-carboxylic acid

Using an analogous reaction to that described for Intermediate 5, step 2 methyl 4-chloro-1-isopropyl-1H-pyrazole-3-carboxylate was coverted into the title compound. MS m/z=188.9 [M+H]$^+$. Calculated for C$_7$H$_9$ClN$_2$O$_2$: 188.035. $^1$H NMR (400 MHz, DMSO-d$_6$) δ ppm 1.41 (d, J=6.65 Hz, 6H) 4.52 (quin, J=6.70 Hz, 1H) 8.17 (s, 1H) 12.89 (br. s., 1H)

Intermediate 51

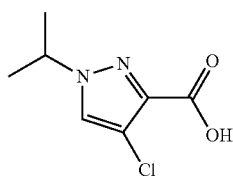

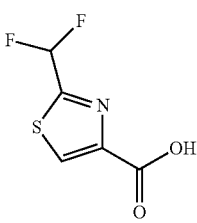 [SMILES: O=C(O)c1csc(C(F)F)n1]

Synthesis of 2-(difluoromethyl)thiazole-4-carboxylic acid

Step 1. 2,2-difluoroethanethioamide

To a solution of difluoroacetonitrile (0.650 ml, 9.45 mmol) in MeOH (20 mL) was added ammonium sulfide (40-48 wt. % solution in water; 2.00 ml, 11.74 mmol) dropwise at rt. After stirring over 2.5 days the reaction mixture was concentrated to dryness to give 1.023 g (97%) of an orange amorphous solid. The material was carried on to the next step without further purification. MS m/z=180 [M+H]$^+$. Calculated for $C_2H_3F_2NS$: 179.

Step 2. ethyl 2-(difluoromethyl)thiazole-4-carboxylate

A mixture of 2,2-difluoroethanethioamide (1.023 g, 9.21 mmol) and ethyl bromopyruvate (1.150 mL, 9.21 mmol) in EtOH (20 mL) was heated to 50° C. for 2 h.

The reaction mixture was cooled to rt and purified by silica gel flash chromatography, eluting with EtOAc:hexanes (0:1→1:1) to give 964 mg (51%) of a brown oil. MS m/z=208 [M+H]$^+$. Calculated for $C_7H_7F_2NO_2S$: 207.

Step 3. 2-(difluoromethyl)thiazole-4-carboxylic acid

Using an analogous reaction to that described for Intermediate 5, step 2 ethyl 2-(difluoromethyl)thiazole-4-carboxylate was converted into the title compound. MS m/z=180 [M+H]$^+$. Calculated for $C_5H_3F_2NO_2S$: 179.

Intermediate 52

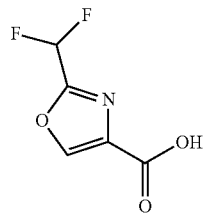 [SMILES: O=C(O)c1coc(C(F)F)n1]

Synthesis of 2-(difluoromethyl)oxazole-4-carboxylic acid

Step 1. methyl 2-(difluoromethyl)-4,5-dihydrooxazole-4-carboxylate

To a cooled (0° C.) solution of sodium methoxide (25 wt % solution in methanol; 0.230 mL, 1.032 mmol) and MeOH (20 mL) was added dropwise difluoroacetonitrile (0.690 mL, 10.03 mmol) while maintaining an internal temperature of <1° C. After 20 min DL-serine methyl ester hydrochloride (1.55 g, 9.96 mmol) was added followed by MeOH (20 mL) and the reaction was allowed to warm to rt overnight. Subsequently, the reaction was heated to 55° C. for 5 h. The reaction was cooled to rt and partitioned between DCM/water. The aqueous layer was extracted with DCM (3×) and the combined organic layers were washed with water and dried over MgSO$_4$. The filtrate was concentrated in vacuo to give 1.59 g (89%) of a light-brown oil. MS m/z=180 [M+H]$^+$. Calculated for $C_6H_7F_2NO_3$:179.

Step 2. methyl 2-(difluoromethyl)oxazole-4-carboxylate

To a cooled (0° C.) suspension of copper(II) bromide (5.95 g, 26.6 mmol) in DCM (50 ml) was added hexamethylenetetramine (3.73 g, 26.6 mmol, Aldrich) followed by 1,8-diazabicyclo[5.4.0]undec-7-ene (4.0 ml, 26.8 mmol, Aldrich). After 20 min a solution of methyl 2-(difluoromethyl)-4,5-dihydrooxazole-4-carboxylate (1.59 g, 8.88 mmol) in DCM (5 mL) was added and the reaction mixture was allowed to warm to rt and stirred for 2 h. The mixture was filtered and the filtrate was concentrated to dryness. The residue was partitioned between EtOAc and 1:1 satd NH$_4$Cl-conc NH$_4$OH. The aqueous layer was extracted with EtOAc (3×) and the combined organic layers were washed consecutively with 1:1 satd NH$_4$Cl-conc NH$_4$OH (1×), 10% citric acid (1×), satd NaHCO$_3$ (1×) and brine (1×). The organic layer was dried over MgSO4. The filtrate was purified by silica gel flash chromatography, eluting with 25% EtOH/EtOAc:hexanes (0:1→1:0) to give 708 mg (45%) of a white crystalline solid. MS m/z=178 [M+H]$^+$. Calculated for $C_6H_5F_2NO_3$:177.

Step 3. 2-(difluoromethyl)oxazole-4-carboxylic acid

Using an analogous reaction to that described for Intermediate 5, step 2 methyl 2-(difluoromethyl)oxazole-4-carboxylate was converted into the title compound. MS m/z=164 [M+H]$^+$. Calculated for $C_5H_3F_2NO_3$: 163.

Intermediate 53

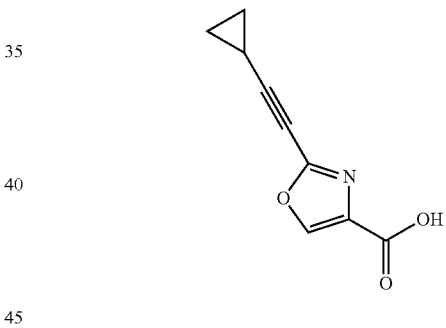

Synthesis of 2-(cyclopropylethynyl)oxazole-4-carboxylic acid

Step 1. ethyl 2-(cyclopropylethynyl)oxazole-4-carboxylate

A mixture of 2-bromo-oxazol-4-carboxylic ethyl ester (0.967 g, 4.40 mmol, Combi-Blocks), trans-dichlorobis (triphenylphosphine)palladium (II) (0.201 g, 0.286 mmol, Strem) and copper (I) iodide (0.165 g, 0.866 mmol, Aldrich) in toluene (15 ml) was purged with argon for 10 min. Ethynylcyclopropane (1.00 ml, 11.80 mmol) and triethylamine (1.70 ml, 12.22 mmol) were added. After 2.5 h, the reaction mixture was partitioned between CH$_2$Cl$_2$ and water. The aqueous layer was extracted with CH$_2$Cl$_2$ (3×). The combined organic layers were washed with brine. The solvent was removed under reduced pressure and the residue and was purified by silica gel flash chromatography, eluting with (EtOAc):hexanes (0:1→2:3) to give 452 mg (50%) of a light-orange oil. MS m/z=206 [M+H]$^+$. Calculated for $C_{11}H_{11}NO_3$: 205.

Step 2. 2-(cyclopropylethynyl)oxazole-4-carboxylic acid

Using an analogous reaction to that described for Intermediate 5, step 2 ethyl 2-(cyclopropylethynyl)oxazole-4-carboxylate was converted into the title compound. MS m/z=178 [M+H]$^+$. Calculated for $C_9H_7NO_3$: 177.

Intermediate 54

Synthesis of 7-bromo-2methyl-2H-pyrazolo[3,4-c]pyridine

Step 1. 7-bromo-1H-pyrazolo[3,4-c]pyridine

To a cooled (13° C.) mixture of 3-amino-2-bromo-4-picoline (4.5 g, 24.06 mmol, Combi-Blocks) and potassium acetate (3.09 g, 31.5 mmol) in AcOH (100 mL) was added a solution of sodium nitrite (2.01 g, 29.1 mmol) in water (10 mL) dropwise. Upon complete addition the reaction mixture was allowed to slowly warm to rt for 66 h. A solution of NaNO$_2$ (706 mg) in water (3 mL) was added to the reaction mixture and the reaction mixture was stirred for 5 h. The solvent was removed under reduced pressure and the residue was basified with saturated NaHCO$_3$. The aqueous layer was extracted with EtOAc (3×) and the combined organic layers were washed with water then brine, and dried over MgSO$_4$. The filtrate was purified by silica gel flash chromatography, eluting with EtOAc:hexanes (0:1→1:1) to give a white crystalline solid (1.38 g, 7.0 mmol, 29%). MS m/z=198 [M+H]$^+$. Calculated for $C_6H_4BrN_3$: 198. Step 2. 7-bromo-2-methyl-2H-pyrazolo[3,4-c]pyridine To a suspension of sodium hydride (57% in mineral oil; 0.052 g, 1.235 mmol) in DMF (4 mL) was added 7-bromo-1H-pyrazolo[3,4-c]pyridine (0.197 g, 0.995 mmol) in portions at room temperature. After 30 min iodomethane (0.070 mL, 1.127 mmol) was added. After 1.5 h the reaction was quenched with water (20 mL) and the solution was extracted with EtOAc (3×). The combined organic layers were purified by silica gel flash chromatography, eluting with MeOH (0:1→1:19) to give an off-white crystalline solid (19 mg, 0.09 mmol, 9%). MS m/z=214 [M+H]$^+$. Calculated for $C_7H_6BrN_3$: 212.

Intermediate 56

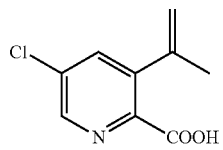

Synthesis of 5-chloro-3-(prop-1-en-2-yl)picolinic acid

A microwave glass vessel was charged with 3-bromo-5-chloropicolinonitrile (0.5 g, 2.3 mmol), tetrakis(triphenylphosphine)palladium(0) (0.13 g, 0.115 mmol) and sodium carbonate (0.731 g, 6.90 mmol). The vial was evacuated and back-filled with nitrogen. Dioxane (10 mL) and water (3 mL) were added. The reaction mixture was degassed and isopropenylboronic acid pinacol ester (0.474 ml, 2.53 mmol) was added. The reaction mixture was heated to 90° C. for 2 hs. The reaction mixture was partitioned between water and EtOAc. The organic phase was dried over MgSO$_4$ and concentrated in vacuo. The residue was dissolved in EtOH (7 mL) and NaOH (5M, 3 mL). The solution was heated to 115° C. for 1.5 hrs. The reaction mixture was partitioned between water and EtOAc. The organic phase was discarded and the aq. phase was acidified with aq. 2 M HCl and extracted with EtOAc. The organic phase was dried over MgSO$_4$ and concentrated under reduced pressure to obtain the title compound as a light-yellow solid (0.373 g, 82%). MS m/z=198.1 [M+H]$^+$. Calculated for $C_9H_8ClNO_2$: 197.024

Intermediate 57

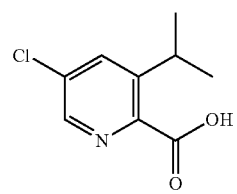

Synthesis of 5-chloro-3-isopropylpicolinic acid

A sealable vial was charged with 5-chloro-3-(prop-1-en-2-yl)picolinic acid (373 mg, 1.887 mmol) and EtOH (100 mL). The solution was purged with Nitrogen. Pt on activated carbon (479 mg, 0.245 mmol) was added, followed by glacial acetic acid (0.4 mL). The reaction mixture was evacuated, backfilled with hydrogen and stirred for 30 min at rt. The reaction mixture was filtered through a pad of celite to obtain the title compound as a white solid. The product contained minor amounts of dehalogenated product. The product was used in the next step without further purification.

MS m/z=200.1 [M+H]$^+$. Calculated for $C_9H_{10}ClNO_2$ 199.040

Intermediate 58

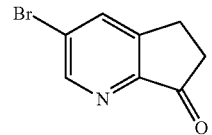

Synthesis of 3-bromo-5H-cyclopenta[b]pyridin-7(6H)-one

Step 1:

To a mixture of 3-bromo-6,7-dihydro-5H-cyclopenta[b]pyridine (1.83 g, 9.24 mmol) and potassium acetate (0.980 g, 9.99 mmol) in acetic acid (30 mL, 520 mmol) was added benzaldehyde (1.90 ml, 18.7 mmol). The reaction mixture was heated to 145° C. (oil bath temperature) in a sealed pressure tube for 3 d, cooled to room temperature and additional benzaldehyde (4 mL) and KOAc (1.83 g) were added. The reaction mixture was heated to 145° C. (oil bath temperature) in a sealed pressure tube for 2 d and cooled to room temperature. The reaction mixture was diluted with EtOAc. The organic phase was washed with 5 M NaOH, water and brine and dried over MgSO$_4$. The filtrate was concentrated under reduced pressure and the residue was purified by flash column chromatography on silica gel (5% to 10% EtOAc in heptane) to give (E)-7-benzylidene-3-bromo-6,7-dihydro-5H-cyclopenta[b]pyridine (1.57 g, 5.49 mmol, 59% yield) as a yellow solid. MS m/z=286.0 [M+H]+. Calculated for $C_{15}H_{12}BrN$ 285.0.

Step 2:

A solution of (E)-7-benzylidene-3-bromo-6,7-dihydro-5H-cyclopenta[b]pyridine (1.61 g, 5.63 mmol) in MeOH (75 mL) and DCM (75 mL) was cooled to −78° C. and a stream of ozone in oxygen was bubbled through the solution for 10 min until the solution turned light blue. Oxygen was pass through the solution for 10 min until the solution turned colorless. Triphenylphosphine (3.63 g, 13.8 mmol) was added and the reaction mixture was allowed to warm to room temperature. The reaction mixture was stirred at room temperature for 1.5 h and then concentrated under reduced pressure. The residue was purified by flash column chromatography on silica gel (80 g, 30% to 70% EtOAc in heptane) to give 3-bromo-5H-cyclopenta[b]pyridin-7(6H)-one (1.14 g, 5.38 mmol, 96% yield) as a yellow solid. MS m/z=211.9 [M+H]+. Calculated for $C_8H_6BrNO$ 211.0.

Intermediate 59

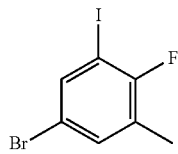

Synthesis of 5-bromo-2-fluoro-1-iodo-3-methylbenzene

A PFA plastic round bottom flask was charged with a solution of hydrogen fluoride pyridine (70 wt % HF, 100 ml, 1150 mmol). The solution was cooled to 0° C. and 4-bromo-2-iodo-6-methylaniline (9.2 g, 29.5 mmol, Organic Letters 2009, 11, 249-251) was added portion wise. After 15 minutes, sodium nitrite (1.032 ml, 32.4 mmol) was added and the reaction mixture was stirred at 0° C. for additional 15 minutes. The reaction mixture was allowed to warm to room temperature and stirred for 15 minutes, followed by heating at 90° C. for 3 hour. The reaction mixture was then cooled to room temperature and quenched with water and diethyl ether. The organic layer was separated, washed with brine and dried over magnesium sulfate. The filtrate was concentrated under reduced pressure. The crude material was purified via silica gel chromatography eluting with hexanes to afford the title compound (8.45 g, 26.8 mmol, 91% yield) as a brown solid. 1H NMR (300 MHz, CHLOROFORM-d) δ ppm 2.29 (s, 3H) 7.27-7.34 (m, 1H) 7.64-7.75 (m, 1H)

Intermediate 60

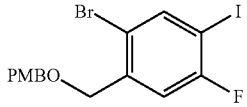

Synthesis of 1-bromo-4-fluoro-5-iodo-2-(((4-methoxybenzyl)-oxy)-methyl)-benzene

A solution of n-Butyllithium (2.5M in hexanes, 42.9 mL, 107 mmol) was added drop wise to a solution of freshly distilled 2,2,6,6-tetramethylpiperidine (18.11 mL, 107 mmol) in THF (220 mL) at −78° C. The solution was warmed to 0° C. for 30 minutes and then cooled again to −78° C. In a separate flask, a solution of 2-bromo-5-fluorobenzyl alcohol (10 g, 48.8 mmol) in THF (60 mL) was cooled to −78° C. and was transferred via cannula to the LiTMP solution. The resulting reaction mixture was stirred for 2 h at −78° C. Subsequently, a solution of iodine (14.86 g, 58.5 mmol) in THF (60 mL) was added dropwise and the reaction mixture was stirred 40 minutes before the reaction was quenched with saturated aqueous ammonium chloride at −78° C. After diluting with aqueous sodium thiosulfate and EtOAc, the layers were separated and the aqueous layer was extracted with EtOAc. The combined organic extracts were washed with saturated aqueous ammonium chloride, water, brine, and dried over sodium sulfate. The filtrate was concentrated in vacuo and the resulting crude product was taken up in THF (48 ml) and DMF (8 ml) and cooled to 0° C. Sodium hydride (60% in mineral oil, 0.341 g, 8.52 mmol) was added in one portion and after 15 minutes, 4-methoxybenzyl chloride (1.253 ml, 9.23 mmol) was added and the solution was stirred overnight at room temperature. The reaction mixture was cooled to 0° C. and quenched with 1N HCl. After dilution with water and EtOAc, the layers were separated and the aqueous layer was extracted with EtOAc. The combined organic extracts were washed with aqueous lithium bromide solution, brine, and dried over sodium sulfate. The filtrate was concentrated in vacuo to give the crude material. The crude material was purified by silica gel chromatography, eluting with 1:30 Et$_2$O in heptane, to afford 1-bromo-4-fluoro-5-iodo-2-(((4-methoxybenzyl)oxy)methyl)benzene as a ~2:1 mixture with 1-bromo-4-fluoro-2-(((4-methoxybenzyl)oxy)methyl)benzene. LC/MS (ESI+) m/z=472.9/474.8 (M+Na).

Intermediate 61

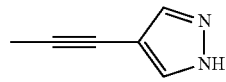

Synthesis of 4-(prop-1-yn-1-yl)-1H-pyrazole

A sealable vial was charged with a solution of tert-butyl 4-bromo-1H-pyrazole-1-carboxylate (1 g, 4.05 mmol) and triethylamine (2.81 mL, 20.24 mmol) in DMF (6.75 mL). The solution was purged with nitrogen for 10 minutes. Copper (I) iodide (0.077 g, 0.405 mmol) and tetrakis(triphenylphosphine)palladium (0.234 g, 0.202 mmol) were added and 1-propyne was bubbled through the solution for 2 min. The reaction mixture was heated at 70° C. overnight. The reaction was poured into a 9:1 mixture of aqueous saturated ammonium chloride/ammonium hydroxide and the mixture was extracted with EtOAc. The combined organic extracts were washed with a 9:1 mixture of aqueous saturated ammonium chloride/ammonium hydroxide, aqueous lithium bromide solution, brine, and dried over sodium sulfate. The filtrate was concentrated in vacuo and the residue was purified by silica gel chromatography, eluting with 1:9 EtOAc in heptane, to provide tert-butyl 4-(prop-1-yn-1-yl)-1H-pyrazole-1-carboxylate, which was taken up in MeOH and treated with excess solid K$_2$CO$_3$ for 15 minutes. The reaction mixture was filtered and the filtrate was concentrated under reduced pressure The crude material was partitioned between DCM and water. The layers were separated and the aqueous layer was extracted with DCM. The combined organic extracts were washed with brine and dried over sodium sulfate. The filtrate was concentrated in vacuo to afford 4-(prop-1-yn-1-yl)-1H-pyrazole. LC/MS (ESI$^-$) m/z=107.0 (M+H).

Intermediate 62

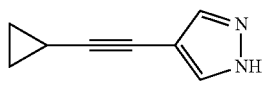

Synthesis of 4-(cyclopropylethynyl)-1H-pyrazole

The title compound was synthesized according to the procedure described for 4-(prop-1-yn-1-yl)-1H-pyrazole (intermediate 61) above, but using cyclopropylacetylene. LC/MS (ESI$^-$) m/z=133.1 (M+H).

The following carboxylic acid intermediates were synthesized according to existing literature procedures, as listed below:

| Intermediate # | Structure | Literature Reference |
|---|---|---|
| 63 | | WO2012095463 |
| 64 | | WO2012095463 |
| 65 | | WO2012095521 |
| 66 | | WO2012095521 |
| 67 | 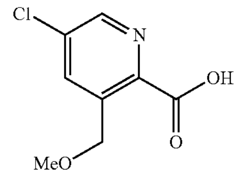 [SMILES: COCc1cc(Cl)cnc1C(=O)O] | WO2012954463 |
| 68 | 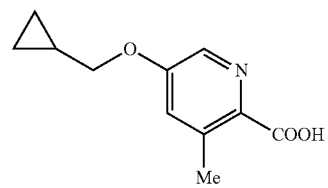 [SMILES: Cc1cc(OCC2CC2)cnc1C(=O)O] | WO2013061962 |
| 69 | 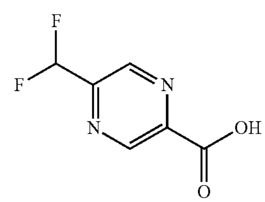 [SMILES: O=C(O)c1cnc(C(F)F)cn1] | WO2012138734 |
| 70 | 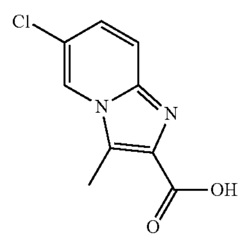 | WO2012078994 |
| 71 | 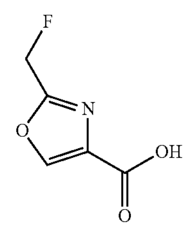 | WO2011069934 |
| 72 | 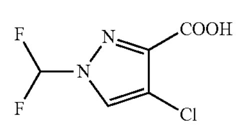 [SMILES: O=C(O)c1nn(C(F)F)cc1Cl] | WO2011069934 |
| 73 | 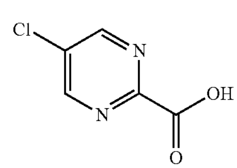 | WO2011044181 |
| 74 | 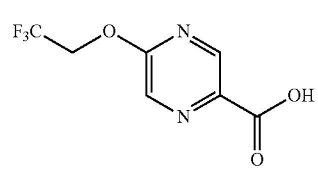 [SMILES: O=C(O)c1cnc(OCC(F)(F)F)cn1] | WO2011044181 |

| Intermediate # | Structure | Literature Reference |
|---|---|---|
| 75 | 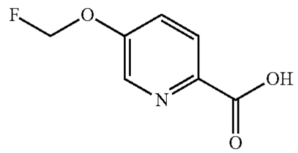 [SMILES: O=C(O)c1ccc(OCF)cn1] | WO 2011009898 |
| 76 | 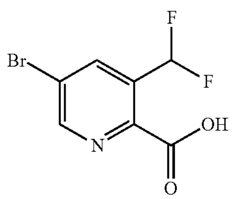 [SMILES: O=C(O)c1ncc(Br)cc1C(F)F] | WO 2012147763 |
| 77 | 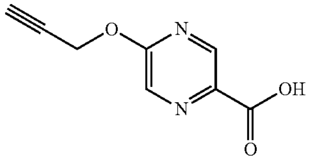 | J. Med. Chem. 2013, 56, 3980 |
| 78 | 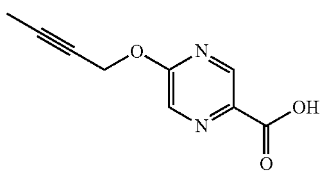 | J. Med. Chem. 2013, 56, 3980 |
| 79 | 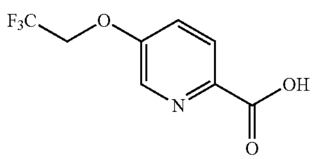 [SMILES: O=C(O)c1ccc(OCC(F)(F)F)cn1] | J. Med. Chem. 2013, 56, 3980 |
| 80 | 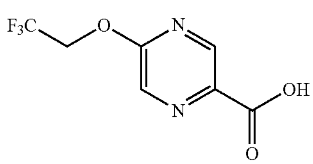 [SMILES: O=C(O)c1cnc(OCC(F)(F)F)cn1] | J. Med. Chem. 2013, 56, 3980 |

Intermediate 81

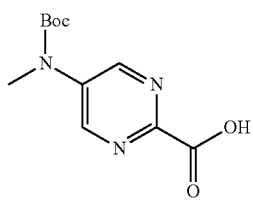 [SMILES: CN(C(=O)OC(C)(C)C)c1cnc(C(=O)O)nc1]

Synthesis of 5-((tert-butoxycarbonyl)(methyl)amino) pyrimidine-2-carboxylic acid Step 1: Methyl 5-aminopyrimidine-2-carboxylate A suspension of 5-aminopyrimidine-2-carboxylic acid (Goldenbridge Pharma, Inc.; 5.70 g, 41.0 mmol) in MeOH (120 mL) was cooled in an ice-water bath and treated dropwise with thionyl chloride (8.97 mL, 123 mmol). The resulting suspension was heated at reflux for 20 h and then concentrated to give a yellow solid. The solid was dissolved in saturated aqueous $NaHCO_3$ (60 mL) and extracted into EtOAc using a Gregar Extractor. The extract was concentrated to give methyl 5-aminopyrimidine-2-carboxylate (4.26 g, 68% yield) as an off-white solid. $^1$H NMR (400 MHz, $CDCl_3$): δ 8.32 (s, 2H), 4.35 (br s, 2H), 4.02 (s, 3H).

Step 2: Methyl 5-((tert-butoxycarbonyl)amino)pyrimidine-2-carboxylate

A solution of methyl 5-aminopyrimidine-2-carboxylate (1.37 g, 8.96 mmol) in DMF (15 mL) was treated with di-tert-butyl dicarbonate (2.15 g, 9.86 mmol) and stirred at ambient temperature for 5 min. DMAP (0.11 g, 0.90 mmol) was added and the solution was stirred at ambient temperature for 20 h. The resulting suspension was concentrated and purified by flash chromatography on silica gel eluting with a gradient of 0 to 40% EtOAc in DCM to give methyl 5-((tert-butoxycarbonyl)amino)pyrimidine-2-carboxylate (1.31 g, 58% yield) as a white crystalline solid. $^1$H NMR (400 MHz, $CDCl_3$): δ 9.01 (s, 2H), 6.78 (br. s, 1H), 4.05 (s, 3H), 1.54 (s, 9H).

Step 3: Methyl 5-((tert-butoxycarbonyl)(methyl) amino)pyrimidine-2-carboxylate

A solution of methyl 5-((tert-butoxycarbonyl)amino)pyrimidine-2-carboxylate (1.31 g, 5.16 mmol) in DMF (13 mL) was treated with cesium carbonate (2.19 g, 6.71 mmol) followed by iodomethane (0.64 mL, 10.32 mmol). The resulting suspension was stirred at ambient temperature for 5 h. The suspension was diluted with DCM (50 mL), filtered, concentrated, and purified by flash chromatography on silica gel eluting with a gradient of 0 to 40% EtOAc in DCM to give methyl 5-((tert-butoxycarbonyl)(methyl)amino)pyrimidine-2-carboxylate (1.16 g, 84% yield) as a white solid. $^1$H NMR (400 MHz, $CDCl_3$): δ 8.91 (s, 2H), 4.07 (s, 3H), 3.38 (s, 3H), 1.52 (s, 9H).

Step 4: 5-((tert-butoxycarbonyl)(methyl)amino)pyrimidine-2-carboxylate

A solution of methyl 5-((tert-butoxycarbonyl)(methyl) amino)pyrimidine-2-carboxylate (1.16 g, 4.35 mmol) in THF (15 mL) was treated with a 1.0 M aqueous solution of LiOH (4.6 mL, 4.6 mmol) and the solution was stirred at ambient temperature for 16 h. The mixture was concentrated and lyophilized from 1,4-dioxane to give lithium 5-((tert-butoxycarbonyl)(methyl)amino)pyrimidine-2-carboxylate (1.16 g, 100% yield) as a white powder. $^1$H NMR (400 MHz, DMSO-$d_6$): δ 8.63 (s, 2H), 3.24 (s, 3H), 1.43 (s, 9H).

Intermediate 82

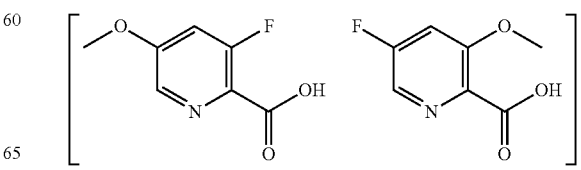

Synthesis of a mixture of 3-fluoro-5-methoxypicolinic acid and 5-fluoro-3-methoxypicolinic acid

Step 1: Mixture of 3-fluoro-5-hydroxypicolinic acid and 5-fluoro-3-hydroxypicolinic acid To a sealable tube was added 3,5-difluoropyridine-2-carboxylic acid (2.0 g, 12.57 mmol, Lancaster Synthesis Ltd.), lithium hydroxide hydrate (5.28 g, 126 mmol, Aldrich), and water (50 mL). The resulting mixture was stirred at 100° C. for 20 h. Then the mixture was cooled to RT and TFA (5.0 mL, 67.3 mmol, Aldrich) was added to the mixture. The mixture was concentrated and dried in vacuo overnight to provide 12.6 g of a crude product mixture of 3-fluoro-5-hydroxypicolinic acid and 5-fluoro-3-hydroxypicolinic acid, as a white solid, used directly in the next step. MS (ESI, positive ion) m/z: 158.1 (M+H) observed for both isomers.

Step 2: Mixture of methyl 3-fluoro-5-methoxypicolinate and methyl 5-fluoro-3-methoxypicolinate To a solution of 3-fluoro-5-hydroxypicolinic acid (1.98 g, 12.57 mmol) and 5-fluoro-3-hydroxypicolinic acid in DMF (100 mL, Aldrich) was added cesium carbonate (2.5 mL, 31.4 mmol, Aldrich) and iodomethane, stabilized (1.7 mL, 27.7 mmol, Alfa Aesar, A Johnson Matthey Company). The reaction was stirred at room temperature for 48 hours. Cesium carbonate (20.48 g, 62.8 mmol, Aldrich) and iodomethane, stabilized (3.4 mL, 55.4 mmol, Alfa Aesar) were added. The resulting mixture was stirred at room temperature for 16 hours. The mixture was diluted with $H_2O$ (500 mL) and extracted with EtOAc (2×500 mL). The combined extracts were washed with $H_2O$ (1×500 mL), dried over $MgSO_4$, concentrated, and dried in vacuo to give 1.18 g of products as a mixture of methyl 3-fluoro-5-methoxypicolinate and methyl 5-fluoro-3-methoxypicolinate as a light yellow solid. MS (ESI, positive ion) m/z: 186.1 (M+H) observed for both isomers.

Step 3: Mixture of 3-fluoro-5-methoxypicolinic acid and 5-fluoro-3-methoxypicolinic acid To a solution of methyl 3-fluoro-5-methoxypicolinate (1.18 g, 6.37 mmol) and methyl 5-fluoro-3-methoxypicolinate in MeOH (30 mL, Aldrich) and water (10 mL) at 0° C. was added lithium hydroxide hydrate (0.53 g, 12.74 mmol, Aldrich). After addition, the mixture was then stirred at room temperature for 1 h. The mixture was concentrated and $H_2O$ (25 mL) was added. The resulting mixture was adjusted to pH=5-6 by HCl (2N). The mixture was concentrated and dried. The residue was dissolved in MeOH (100 mL), adsorbed onto silica, and purified by silica gel flash chromatography using a gradient of 0%-40% MeOH in DCM to give 1.67 g (white solid) of products as a mixture of 3-fluoro-5-methoxypicolinic acid and 5-fluoro-3-methoxypicolinic acid. MS (ESI, positive ion) m/z: 172.1 (M+H) observed for both isomers.

Intermediate 83

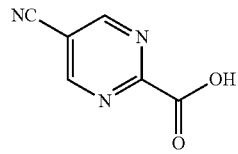 [SMILES: N#Cc1cnc(C(=O)O)nc1]

Synthesis of 5-cyanopyrimidine-2-carboxylic acid

Step 1: methyl 5-bromopyrimidine-2-carboxylate

To a solution of 5-bromopyrimidine-2-carboxylic acid (3.22 g, 15.9 mmol) in MeOH (50 mL) at room temperature was added acetyl chloride (4.0 mL, 56.3 mmol). The reaction mixture was heated to reflux for 15 min, cooled to room temperature and concentrated under reduced pressure. The reaction mixture was diluted with saturated $NaHCO_3$ (30 mL) and EtOAc, and transferred to a separatory funnel. The aqueous phase was extracted with EtOAc (4×) and the combined organic extracts were washed with brine (1×), dried over $MgSO_4$, filtered, and concentrated to give methyl 5-bromopyrimidine-2-carboxylate (2.30 g, 10.6 mmol, 67% yield) as a white solid. LC/MS (ESI$^+$) m/z=216.9 (M+H). Calculated for $C_6H_5BrN_2O_2$ 216.0.

Step 2: methyl 5-cyanopyrimidine-2-carboxylate

To a mixture of methyl 5-bromopyrimidine-2-carboxylate (2.30 g, 10.6 mmol) and copper (I) cyanide (1.92 g, 21.4 mmol) in a 100 mL round bottom flask was added DMA (21 mL). The reaction mixture was degassed by bubbling nitrogen through the solution for 5 min. The reaction mixture was heated to 110° C. for 2 d and cooled to room temperature. The reaction mixture was diluted with EtOAc and water and filtered through a glass frit (medium). The filtrate was transferred to a separatory funnel. The aqueous phase was extracted with EtOAc (4×) and the combined organic extracts were washed with brine (1×), dried over $MgSO_4$, filtered, concentrated to give a yellow oil. Purification by flash column chromatography on silica gel (80 g, 5% to 50% EtOAc in heptane) gave methyl 5-cyanopyrimidine-2-carboxylate (0.83 g, 5.08 mmol, 48% yield) as a white solid. LC/MS (ESI$^+$) m/z=164.0 (M+H). Calculated for $C_7H_5N_3O_2$ 163.0.

Step 3: 5-cyanopyrimidine-2-carboxylic acid

To a solution of methyl 5-cyanopyrimidine-2-carboxylate (0.11 g, 0.644 mmol) in THF (2.6 mL) at 0° C. was added a solution of lithium hydroxide monohydrate (30 mg, 0.715 mmol) in water (0.5 mL). The reaction mixture was stirred at 0° C. for 20 min and 1 M HCl (0.70 mL) was added. The reaction mixture was concentrated under reduced pressure and dried under high vacuum to give methyl 5-cyanopyrimidine-2-carboxylate (0.11 g, 0.644 mmol) as a white solid that was used without further purification. LC/MS (ESI$^+$) m/z=148.0 (M−H). Calculated for $C_6H_3N_3O_2$ 149.0.

Intermediate 84

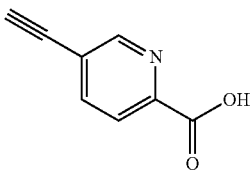

Synthesis of 5-ethynylpicolinic acid

Step 1: Methyl 5-((triethylsilyl)ethynyl)picolinate

A glass microwave reaction vessel was charged with methyl 5-bromopyridine-2-carboxylate (0.95 ml, 6.94 mmol, Alfa Aesar), (triethylsilyl) acetylene (3.73 ml, 20.81 mmol, Sigma-Aldrich), tetrakis(triphenylphosphine) palladium (0.61 g, 0.527 mmol, Strem Chemicals), triethylamine (4.82 ml, 34.7 mmol, Sigma-Aldrich Chemical), and copper (I) iodide (0.04 ml, 1.040 mmol, Sigma-Aldrich). The reaction mixture was stirred and heated in a Biotage Initiator microwave reactor at 70° C. for 30 min. The reaction mixture was filtered through celite and concentrated. The reaction mixture was diluted with saturated $NH_4Cl$ and extracted with EtOAc. The organic extract was washed with water and brine, dried over $MgSO_4$, filtered and concentrated in vacuo. The crude product was adsorbed onto a plug of silica gel and chromatographed through a silica gel column, eluting with a gradient of 0% to 40% EtOAc in hexane, to provide methyl 5-((triethylsilyl)ethynyl)picolinate (1.68 g, 6.09 mmol, 88% yield). MS m/z [M+H]$^+$=276.0. Calculated from $C_{15}H_{21}NO_2Si$: 275.418

Step 2: 5-Ethynylpicolinic acid

To a solution of methyl 5-((triethylsilyl)ethynyl)picolinate (1.68 g, 6.05 mmol) in THF (12.11 ml) was added TBAF, 1.0M in THF (6.68 ml, 6.68 mmol, Sigma Aldrich). The reaction was allowed to stir for 6 hours at RT. The reaction was concentrated. The crude product was adsorbed onto a plug of silica gel and chromatographed through silica gel column eluting with a gradient of 10% to 100% EtOAc in hexane followed by 1% AcOH in EtOAc, to afford 5-ethynylpicolinic acid (0.05 g, 0.37 mmol, 6.10% yield).

MS m/z [M+H]$^+$=147.9. Calculated from $C_8H_5NO_2$: 147.131

Intermediate 85

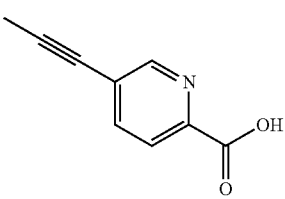

Synthesis of 5-(Prop-1-yn-1-yl)picolinic acid

Step 1: Methyl 5-bromopicolinate

To a suspension of 5-bromopicolinic acid (2.0 g, 9.94 mmol) in MeOH (2 ml)/toluene (20 ml) was added TMS-diazomethane (20M in diethyl ether; 5.47 ml, 10.94 mmol, Matrix Scientific) dropwise. The reaction was stirred at room temperature for 3 hours. An additional 0.2 eq (0.99 mL) of TMS-diazomethane was added and the reaction stirred for 1.5 hours. The reaction was concentrated and the brown solid was carried to next step without further work up. MS m/z [M+H]$^+$=217.9. Calculated from $C_7H_6BrNO_2$: 216.032

Step 2: Methyl 5-(prop-1-yn-1-yl)picolinate

To a solution of methyl 5-bromopicolinate (0.60 g, 2.77 mmol) in toluene (50 mL) was added tributyl(prop-1-yn-1-yl)stannane (1.01 mL, 3.32 mmol, Sigma Aldrich) and tetrakis(triphenylphosphine)palladium (0.04 g, 0.036 mmol, Strem Chemicals, Inc.). The reaction was stirred overnight at 100° C. The reaction was allowed to cool to rt and concentrated. The residue was adsorbed onto a plug of 10% w/w KF Silica and chromatographed with a silica gel column eluting with a gradient of 10% to 100% EtOAc in hexane, to provide methyl 5-(prop-1-yn-1-yl)picolinate (0.18, 1.05 mmol, 37.8% yield). MS m/z [M+H]$^+$=176.0. Calculated from $C_{10}H_9NO_2$: 175.184

Step 3: 5-(Prop-1-yn-1-yl)picolinic acid

To a solution of methyl 5-(prop-1-yn-1-yl)picolinate (0.18 g, 1.05 mmol) in tetrahydrofuran (3.48 ml) was added sodium hydroxide 1.0 N solution (1.05 mL, 1.045 mmol, Sigma). The reaction was stirred for 1.5 hours at room temperature. Hydrogen chloride (4.0M solution in 1,4-dioxane; 0.26 ml, 1.05 mmol, Sigma Aldrich) was added and the reaction stirred for an additional 10 minutes. The reaction was concentrated in vacuo to provide 5-(prop-1-yn-1-yl)picolinic acid as a light yellow solid. The material was used without further purification assuming theoretical yield. MS m/z [M+H]$^+$=162.1. Calculated from $C_9H_7NO_2$: 161.157

Intermediate 86

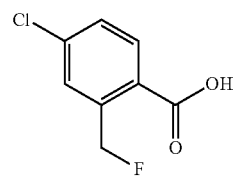 [SMILES: O=C(O)c1ccc(Cl)cc1CF]

Synthesis of 5-chloro-3-(fluoromethyl)picolinic acid

Step 1: Methyl 5-chloro-2-vinylnicotinate

A sealable vial was charged with methyl 2,5-dichloronicotinate (100 mg, 0.49 mmol, Bionet Research), tributyl(vinyl)stannane (156 µl, 0.53 mmol) and N,N-dimethylformamide (1 mL) at RT under nitrogen atmosphere. 2,6-Ditert-butyl-4-methylphenol (Aldrich, 5 mg) was added, followed by dichlorobis(triphenylphosphine)palladium(II) (Strem, 68 mg, 0.10 mmol) and the reaction mixture was heated to 80° C. for 1 hour. The reaction mixture was cooled to RT and partitioned between EtOAc (50 mL) and water (50 mL). The organic phase was separated and washed with water (2×25 mL) and brine (30 mL), The combined organic layers were dried over anhydrous magnesium sulfate and the filtrate was concentrated under reduced pressure. The crude product was purified by flash chromatography on silica gel (5-35% EtOAc/hexanes) to obtain the title compound as a colorless oil (96 mg).
¹H NMR (300 MHz, CHLOROFORM-d) δ ppm 3.95 (s, 3H) 3.97-4.00 (m, 1H) 5.55-5.69 (m, 1H) 6.43-6.58 (m, 1H) 7.51-7.67 (m, 1H) 8.12-8.23 (m, 1H) 8.59-8.69 (m, 1H)

Step 2: (5-Chloro-2-vinylpyridin-3-yl)methanol

A solution of methyl 5-chloro-2-vinylnicotinate (0.21 g, 1.06 mmol) in DCM (5 ml) was cooled to −45° C. A solution of diisobutylaluminum hydride (1M in hexane, 1.6 ml, 1.59 mmol, Aldrich) was added dropwise. After 15 min, the reaction mixture was quenched by the addition of a saturated aqueous solution of potassium sodium tartrate (3 mL). DCM was added, followed by water. The organic phase was separated, washed with water and dried over MgSO₄. The filtrate was concentrated under reduced pressure. The crude material was absorbed onto a plug of silica gel and purified by chromatography, eluting with a gradient of 5% to 55% EtOAc in hexane, to provide the title compound (77 mg) as a white solid. LC/MS m/z=170.1 [M+H]⁺.

Step 3: 5-Chloro-3-(fluoromethyl)-2-vinylpyridine

To a solution of triethylamine trihydrofluoride (Aldrich, 1.9 mL, 12 mmol) in DCM (30 mL) at −78° C., was added Xtalfluor-E (4.1 g, 18 mmol, Aldrich), followed by a solution of (5-chloro-2-vinylpyridin-3-yl)methanol (2 g, 12 mmol) in DCM (40 mL). The cold bath was removed and the reaction mixture was allowed to warm from −78° C. to rt over a period of 15 min. The reaction was quenched by the addition of aqueous saturated bicarbonate solution. After 15 min stirring at rt, the reaction mixture was diluted with EtOAc and water. The organic phase was separated and dried over MgSO₄. The filtrate was absorbed onto a plug of silica gel and purified by chromatography through, eluting with a gradient of 5% to 45% EtOAc in hexane, to provide the title compound as colorless oil (1.22 g). LC/MS m/z=172.1 [M+H]⁺.

Step 4: 5-chloro-3-(fluoromethyl)picolinaldehyde

To a solution of 5-chloro-3-(fluoromethyl)-2-vinylpyridine (65 mg, 0.38 mmol) in THF (2.3 mL) and water (3.5 mL) was added a solution of osmium tetroxide (2.5 wt % in 2-methyl-2-propanol, 80 μl, 0.038 mmol, Aldrich). After 5 min, sodium meta-periodate (122 mg, 0.568 mmol, Aldrich) was added in one portion and the reaction mixture was allowed to stir for 1 h. The reaction mixture was partitioned between brine and EtOAc. The organic phase was separated and dried over MgSO₄. The filtrate was absorbed onto a plug of silica gel and purified by chromatography, eluting with a gradient of 5% to 45% EtOAc in hexane, to provide the title compound as grey solid (55 mg).
¹H NMR (300 MHz, CHLOROFORM-d) δ ppm 5.81 (s, 1H) 5.97 (s, 1H) 8.02-8.21 (m, 1H) 8.63-8.82 (m, 1H) 10.03-10.19 (m, 1H)

Step 5: 5-chloro-3-(fluoromethyl)picolinic acid

To a solution of 5-chloro-3-(fluoromethyl)picolinaldehyde (55 mg, 0.32 mmol) in THF (2 mL) and water (4 mL) was added solid NaOH (13 mg) at 0° C. After 10 min, KMnO₄ (100 mg) was added in one portion. After additional 10 min, the reaction mixture was filtered through a pad of celite. The celite was washed with 1 M HCl (10 mL), water and EtOAc. The phases were separated and the aqueous phase was extracted with EtOAc. The combined organic layers were dried over MgSO₄ and the filtrate was concentrated under reduced pressure. The title compound was obtained as a yellow residue and taken onto the next step without further purification. LC/MS m/z=172.1 [M+H]⁺.

Intermediate 87

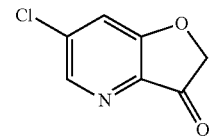 [SMILES: O=C1COc2cc(Cl)cnc21]

Synthesis of 6-chlorofuro[3,2-b]pyridin-3(2H)-one

Step 1: ethyl 2-((5-chloro-2-cyanopyridin-3-yl)oxy)acetate

To a mixture of cesium carbonate (1.63 g, 5.01 mmol) and 5-chloro-3-fluoropicolinonitrile (0.784 g, 5.01 mmol) was added NMP (5 mL) and ethyl glycolate (0.52 mL, 5.49 mmol). The reaction mixture was stirred at RT for 20 min, heated to 80° C. for 1 h and additional ethyl glycolate (0.10 mL) was added. Stirring was continued at 80° C. for 2 h and the reaction mixture was cooled to RT. The reaction was and diluted with EtOAc and water. The aqueous phase was extracted with EtOAc (2×) and the combined organic extracts were washed with brine (1×), dried over MgSO₄, filtered, and concentrated. Purification by flash column chromatography on silica gel eluting with a gradient of 0% to 15% EtOAc in DCM gave ethyl 2-((5-chloro-2-cyanopyridin-3-yl)oxy)acetate (0.83 g, 3.46 mmol, 69% yield) as a white solid. LC/MS (ESI⁺) m/z=240.9 (M+H). Calculated for C₁₀H₉ClN₂O₃ 240.0.

Step 2: ethyl 3-amino-6-chlorofuro[3,2-b]pyridine-2-carboxylate

The HCl salt of ethyl 2-((5-chloro-2-cyanopyridin-3-yl)oxy)acetate was formed by the addition of HCl (4 M in dioxane, 6.0 mL), 24 mmol) to a solution of ethyl 2-((5-chloro-2-cyanopyridin-3-yl)oxy)acetate in EtOH (15 mL). The solution was concentrated under reduced pressure. To a suspension of sodium hydride (60 wt % dispersion in mineral oil, 0.60 g, 14.9 mmol) in PhMe (45 mL) at RT was added ethanol (0.88 mL, 15.00 mmol). The mixture was stirred at room temperature for 20 min and added via cannula to ethyl 2-((5-chloro-2-cyanopyridin-3-yl)oxy) acetate hydrochloride (1.27 g, 4.58 mmol). The reaction mixture was stirred at RT for 40 min and quenched with saturated NH₄Cl. The reaction mixture was diluted with EtOAc and water. The aqueous phase was extracted with EtOAc (2×) and the combined organic extracts were washed with brine (1×), dried over MgSO₄, filtered, and concentrated to give ethyl 3-amino-6-chlorofuro[3,2-b]pyridine-2-carboxylate (0.84 g, 3.47 mmol, 76% yield) as a yellow solid which was used without further purification. LC/MS (ESI⁺) m/z=240.9 (M+H). Calculated for C₁₀H₉ClN₂O₃ 240.0.

Step 3: 6-chlorofuro[3,2-b]pyridin-3(2H)-one

A solution of ethyl 3-amino-6-chlorofuro[3,2-b]pyridine-2-carboxylate (0.81 g, 3.35 mmol) in hydrochloric acid (5.0 M in water, 50.0 mL, 3.35 mmol) was heated to reflux for 4 h and cooled to RT. The pH was adjusted to 7 with saturated NaHCO₃. The aqueous phase was extracted with EtOAc (3×) and the combined organic extracts were dried over MgSO₄, filtered, and concentrated. Purification by flash column chromatography on silica gel eluting with a gradient of 0% to 100% EtOAc in DCM gave 6-chlorofuro[3,2-b]pyridin-3 (2H)-one (0.12 g, 0.68 mmol, 20% yield) as a yellow solid. LC/MS (ESI⁺) m/z=170.0 (M+H). Calculated for C₇H₄ClNO₂ 169.0.

Intermediate 88

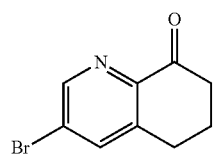 [SMILES: O=C1CCCc2cc(Br)cnc21]

Synthesis of 3-bromo-6,7-dihydroquinolin-8(5H)-one

Step 1: (E)-8-benzylidene-3-bromo-5,6,7,8-tetrahydroquinoline

To a mixture of 3-bromo-5,6,7,8-tetrahydroquinoline (0.58 g, 2.73 mmol) (prepared according to: *J. Am. Chem. Soc.* 2011, 133, 12285) and potassium acetate (2.94 g, 30.0 mmol) in acetic acid (9.50 mL, 165 mmol) in a pressure tube was added benzaldehyde (2.80 mL, 27.7 mmol). The reaction mixture was heated to 150° C. (oil bath temperature) for 8 d and cooled to room temperature. The reaction was diluted with EtOAc and washed with 5 M NaOH (1×), water (1×), brine (1×), dried over MgSO₄, filtered, and concentrated. Purification by flash column chromatography on silica gel eluting with a gradient of 0% to 10% EtOAc in heptane gave 1.29 g of a 2.5:1 mixture of (E)-8-benzylidene-3-bromo-5,6, 7,8-tetrahydroquinoline (1.29 g, 4.30 mmol) and benzaldehyde as a yellow oil that was used without further purification. LC/MS (ESI⁺) m/z=300.0 (M+H). Calculated for C₁₆H₁₄BrN 299.0.

Step 2: 3-bromo-6,7-dihydroquinolin-8(5H)-one

A solution of (E)-8-benzylidene-3-bromo-5,6,7,8-tetrahydroquinoline (0.82 g, 2.5:1 mixture with benzaldehyde) in MeOH (40 mL) and DCM (40 mL) was cooled to −78° C. and ozone was bubbled through the solution for 5 min until the solution turned light blue. Oxygen was passed through the solution for 10 min until the solution turned colorless and triphenylphosphine (1.03 g, 3.93 mmol) was added. The solution was removed from the dry ice/acetone bath and allowed to warm to RT. The reaction mixture was stirred at RT for 1 h. The reaction mixture was concentrated. Purification by flash column chromatography on silica gel eluting with 30% to 70% EtOAc in heptane) gave 3-bromo-6,7-dihydroquinolin-8(5H)-one (0.460 g, 2.04 mmol, 75% yield) as a white solid. LC/MS (ESI⁺) m/z=225.9 (M+H). Calculated for C₉H₈BrNO 225.0.

Intermediate 89

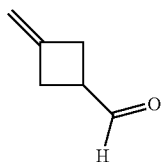

Synthesis of 3-Methylenecyclobutanecarbaldehyde

Step 1: N-methoxy-N-methyl-3-methylenecyclobutanecarboxamide

To a solution of 3-methylenecyclobutanecarboxylic acid (525 mg, 4.68 mmol, Frontiers Scientific Services) in DMF (5 mL, aldrich) was added a solution of N,O-dimethyl hydroxylamine hydrochloride (0.55 g, 5.62 mmol, Aldrich) and triethylamine (0.78 mL, 5.62 mmol, Aldrich) in DMF (5 mL, Aldrich). The reaction was cooled to 0° C. and propylphosphonic anhydride solution (50 wt. % in DMF; 4.47 mL, 7.02 mmol, Alfa Aesar) was added. The reaction was stirred at RT for 16 h. The reaction was quenched with saturated NaHCO₃ (10 mL) and stirred at RT for 5 min. The reaction was extracted with EtOAc (2×30 mL) and the combined organic extracts were washed with saturated ammonium chloride (2×40 mL), dried over MgSO₄, and concentrated. The residue was dissolved in diethyl ether (5 mL) and the solution mixture was washed with H₂O (2×10 mL), dried over MgSO₄, concentrated, and dried in vacuo to give 398 mg of the title compound as a light yellow liquid. MS (ESI, positive ion) m/z: 156.1 (M+H).

Step 2: 3-Methylenecyclobutanecarbaldehyde

To a solution of N-methoxy-N-methyl-3-methylenecyclobutanecarboxamide (0.11 g, 0.71 mmol) in diethyl ether (2 mL, Aldrich) at 0° C. under Ar(g) was added lithium aluminium hydride (1.0 M solution in THF; 0.851 mL, 0.851 mmol, Aldrich) dropwise. After completed addition, the reaction was stirred at 0° C. for 45 min. The reaction was quenched with a solution of KHSO₄ (1M, aq) at 0° C. and gradually warmed to room temperature and stirred for 30 min. The reaction was extracted with diethyl ether (2×10 mL) and the combined organic extracts were dried over MgSO₄, concentrated, and dried in vacuo to afford 68 mg of the title compound as a light yellow liquid, which was used directly in the next step without further purification. 1H NMR (CHLOROFORM-d) δ: 9.79 (d, J=2.3 Hz, 1H), 4.68-4.80 (m, 2H), 3.08-3.24 (m, 1H), 2.84-3.02 (m, 4H).

Intermediate 90

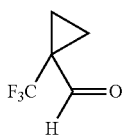

Synthesis of 1-(Trifluoromethyl)cyclopropanecarbaldehyde

Step 1: N-methoxy-N-methyl-1-(trifluoromethyl)cyclopropanecarboxamide

To a solution of N,O-dimethyl hydroxylamine hydrochloride (0.48 g, 4.87 mmol, Aldrich) in DMF (15 mL, Aldrich) was added triethylamine (0.68 mL, 4.87 mmol, Aldrich). After completed addition the reaction was stirred at RT for 5 min. 1-trifluoromethylcyclopropane-1-carboxylic acid (0.5 g, 3.24 mmol, Alfa Aesar, A Johnson Matthey Company) was added and the reaction was stirred at room temperature for 1 min. The reaction was cooled to 0° C. and propylphosphonic anhydride solution (50 wt. % in DMF; 3.10 mL, 4.87 mmol, Acros Organics) was added dropwise. The resulting mixture was stirred at room temperature for 5 days. The reaction was quenched with saturated NaHCO$_3$ and stirred at RT for 5 min. The reaction was extracted with diethyl ether (2×40 mL) and the combined organic extracts were washed with saturated ammonium chloride, water, dried over MgSO$_4$, and concentrated to give 229 mg of the title compound as a light yellow liquid. MS (ESI, positive ion) m/z: 198.1 (M+H).

Step 2: 1-(Trifluoromethyl)cyclopropanecarbaldehyde

To a solution of N-methoxy-N-methyl-1-(trifluoromethyl)cyclopropanecarboxamide (0.23 g, 1.162 mmol) in diethyl ether (3 mL, aldrich) at 0° C. under Ar(g) was added lithium aluminium hydride (1.0 M solution in THF; 1.39 mL, 1.39 mmol, aldrich) dropwise. After completed addition the reaction was then stirred at 0° C. for 45 min. The reaction was quenched with a solution of KHSO$_4$ (1M) at −78° C. and gradually warmed to RT and stirred for 30 min. The reaction was extracted with diethyl ether (2×10 mL). The combined organic extracts were dried over MgSO$_4$, concentrated, and dried in vacuo to afford 62 mg of the title compound as a light yellow liquid, which was used in the next step without further purification. 1H NMR (CHLOROFORM-d) δ: 9.69 (s, 1H), 1.43 (m, 2H), 1.21 (t, J=7.0 Hz, 2H)

Intermediate 91

Synthesis of 4-chloro-7-(trifluoromethyl)pyrido[3,2-d]pyrimidine

Step 1: 3-nitro-5-(trifluoromethyl)picolinonitrile

A microwave reaction vial was charged with 2-chloro-3-nitro-5-(trifluoromethyl)pyridine (2 g, 8.83 mmol), NMP (4.41 ml) and CuCN (0.830 g, 9.27 mmol). The vial was sealed and the mixture was irradiated in the MW at 175° C. for 15 min. Upon cooling to RT, the reaction mixture was poured onto ice and EtOAc was added. The mixture was filtered through Celite, washing with EtOAc and a small amount of MeOH. The layers of the filtrate were separated, and the aqueous portion was extracted again with EtOAc. The combined organic portions were dried with sodium sulfate, filtered and concentrated. The crude material was purified by silica gel chromatography, using a gradient of 0-30% EtOAc in heptane to provide 3-nitro-5-(trifluoromethyl)picolinonitrile (645 mg, 2.97 mmol, 33.7% yield) as a yellow oil that solidified upon standing. LC/MS (ESI$^+$) m/z=218.1 (M+H).

Step 2: 3-nitro-5-(trifluoromethyl)picolinamide

A round bottom flask was charged with 3-nitro-5-(trifluoromethyl)picolinonitrile (910 mg, 4.19 mmol) and sulfuric acid (4192 μl, 4.19 mmol), and the mixture was stirred at 60° C. for 16 h. Upon cooling to RT the crude mixture was poured onto ice, and the resulting solids were filtered, washed with water and dried. 3-nitro-5-(trifluoromethyl)picolinamide (850 mg, 3.62 mmol, 86% yield) was isolated as a light yellow solid. LC/MS (ESI$^+$) m/z=236.1 (M+H).

Step 3: 3-amino-5-(trifluoromethyl)picolinamide

A round bottom flask was charged with 3-nitro-5-(trifluoromethyl)picolinamide (850 mg, 3.62 mmol) and wet 5 wt. % Pd/C (769 mg, 0.362 mmol) and was purged with nitrogen. EtOAc (72300 and then MeOH (72300 were added, and the flask was evacuated and filled with hydrogen. The reaction was stirred at RT under hydrogen atmosphere for 17 h. The mixture was filtered through Celite and washed with EtOAc and MeOH. The filtrate was concentrated to provide 3-amino-5-(trifluoromethyl)picolinamide (720 mg, 3.51 mmol, 97% yield) as a white solid. LC/MS (ESI$^+$) m/z=206.1 (M+H).

Step 4: 7-(trifluoromethyl)pyrido[3,2-d]pyrimidin-4(3H)-one

A vial was charged with 3-amino-5-(trifluoromethyl)picolinamide (615 mg, 3.00 mmol) and triethyl orthoformate (2496 μl, 14.99 mmol). The vial was sealed and the mixture was heated at 120° C. for 17 h. Upon cooling, the heterogeneous mixture was filtered and the solids were washed with heptane. 7-(trifluoromethyl)pyrido[3,2-d]pyrimidin-4(3H)-one (540 mg, 2.51 mmol, 84% yield) was isolated as a tan solid. LC/MS (ESI$^+$) m/z=216.0 (M+H).

Step 5: 4-chloro-7-(trifluoromethyl)pyrido[3,2-d]pyrimidine

A pressure bottle was charged with 7-(trifluoromethyl)pyrido[3,2-d]pyrimidin-4(3H)-one (540 mg, 2.51 mmol), toluene (10.000 mL) and Hunig's base (1.315 mL, 7.53 mmol). POCl$_3$ (0.702 mL, 7.53 mmol) was added, and the bottle was sealed. The mixture was heated to 115° C. for 4 h. After cooling to RT, the mixture was diluted with EtOAc and water, and the layers were separated. The aqueous portion was extracted with additional EtOAc, and the combined organic portions were washed with saturated sodium bicarbonate, dried over sodium sulfate, filtered and concentrated. 4-chloro-7-(trifluoromethyl)pyrido[3,2-d]pyrimidine (560 mg, 2.397 mmol, 96% yield) was isolated as a brown solid. LC/MS (ESI$^+$) m/z=234.0 (M+H).

Methods to Synthesize Final Compounds

General Amidation Procedures:

The following four (4) methods were used to couple the aniline core intermediates to desired acid intermediates or other intermediates as presented herein, to prepare the final compounds of the invention.

Method A: Triphenylphosphine (T₃P) procedure

Example 28

Synthesis of N-(3-((1R,5S,6R)-3-amino-5-(difluoromethyl)-2-oxa-4-azabicyclo[4.1.0]hept-3-en-5-yl)-4-fluorophenyl)-5-chloro-3-methoxypicolinamide

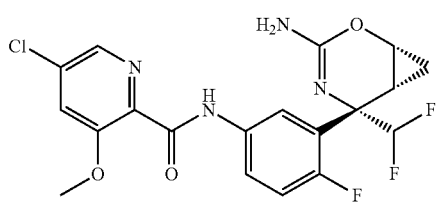 [SMILES: COc1cc(Cl)cnc1C(=O)Nc1ccc(F)c([C@@]2(C(F)F)N=C(N)O[C@@H]3C[C@@H]32)c1]

A solution of 1-propanephosphonic acid cyclic anhydride (50 wt % in EtOAc, 0.352 ml, 0.553 mmol) was added to a solution of (1R,5S,6R)-5-(5-amino-2-fluorophenyl)-5-(difluoromethyl)-2-oxa-4-azabicyclo[4.1.0]hept-3-en-3-amine (16g-B, 0.075 g, 0.277 mmol) and 5-chloro-3-methoxypicolinic acid (0.062 g, 0.332 mmol) in EtOAC (2 mL) at room temperature. The reaction mixture was stirred at rt for 12 h, diluted with aqueous saturated NaHCO₃ solution and extracted with EtOAC. The organic phase dried over MgSO₄ and the filtrate was concentrated under reduced pressure. The residue was purified by silica gel chromatography using (0-100% EtOAc/heptane) to give the title compound (0.082 g, 0.186 mmol, 67.3% yield). MS m/z=441.1 [M+H]⁺

1H NMR (400 MHz, DMSO-d6) δ ppm 10.51 (s, 1H), 8.26 (d, J=1.76 Hz, 1H), 7.71-7.91 (m, 3H), 7.20 (dd, J=11.64, 9.29 Hz, 1H), 5.99-6.37 (m, 1H), 5.86 (s, 2H), 3.98 (t, J=5.38 Hz, 1H), 3.89 (s, 3H), 1.63-1.76 (m, 1H), 1.12 (br. s., 1H), 0.82-0.96 (m, 1H)

Method B: DMTMM Procedure

Example 29

Synthesis of N-(3-([1(R,S),5(S,R),6(R,S)]-3-amino-5-methyl-2-oxa-4-azabicyclo[4.1.0]hept-3-en-5-yl)-4-fluorophenyl)-5-((4-hydroxy-4-methylpent-2-yn-1-yl)oxy)-3-methylpicolinamide

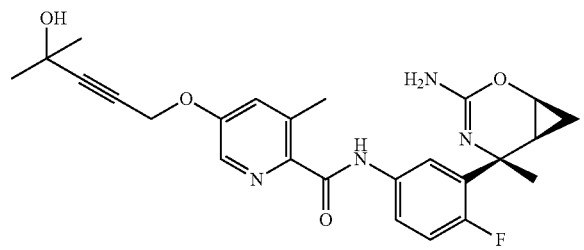 [SMILES: Cc1cc(OCC#CC(C)(C)O)cnc1C(=O)Nc1ccc(F)c([C@@]2(C)N=C(N)O[C@H]3C[C@H]32)c1]

4-(4,6-Dimethoxy-1,3,5-triazin-2-yl)-4-methylmorpholin-4-ium chloride (32.3 mg, 0.117 mmol) was added to a stirring solution of [1(S,R),5(S,R),6(S,R)]-5-(5-amino-2-fluorophenyl)-5-methyl-2-oxa-4-azabicyclo[4.1.0]hept-3-en-3-amine (1k-rac) (1k rac, 25 mg, 0.106 mmol), and 5-((4-hydroxy-4-methylpent-2-yn-1-yl)oxy)-3-methylpicolinic acid (intermediate 38, 27.8 mg, 0.112 mmol) in THF (1 mL) and MeOH (0.250 mL). The reaction mixture was stirred at RT for 2.5 hrs. The reaction mixture was concentrated under reduced pressure and the residue was purified via silica gel flash column chromatography eluting with 0 to 10% (2 M NH₃ in MeOH) in DCM to yield the title compound as a white solid. MS m/z=467.1 [M+H]⁺

1H NMR (400 MHz, CHLOROFORM-d) δ ppm 0.84 (dt, J=9.63, 6.63 Hz, 1H) 0.97 (td, J=6.90, 2.64 Hz, 1H) 1.51 (s, 6H) 1.64 (s, 3H) 1.74-1.83 (m, 1H) 2.76 (s, 3H) 3.31 (br. s., 3H) 3.89-3.96 (m, 1H) 4.78 (s, 2H) 7.04 (dd, J=11.54, 8.80 Hz, 1H) 7.13 (d, J=2.74 Hz, 1H) 7.41 (dd, J=7.14, 2.64 Hz, 1H) 7.90-7.96 (m, 1H) 8.10 (d, J=2.74 Hz, 1H) 9.98 (s, 1H)

Method C: DMTMM Procedure Followed by Deprotection of Benzoyl Group

Example 30

Synthesis of N-(3-([(1R,S),(5S,R),(6R,S)]-3-amino-5-(difluoromethyl)-2-oxa-4-azabicyclo[4.1.0]hept-3-en-5-yl)-4-fluoro-5-methylphenyl)-5-chloropicolinamide

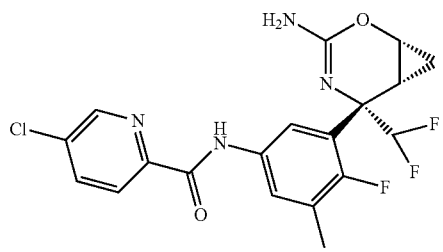 [SMILES: Cc1cc(NC(=O)c2ccc(Cl)cn2)cc([C@@]2(C(F)F)N=C(N)O[C@@H]3C[C@@H]32)c1F]

A solution of N-(((1R,S),(5S,R),(6R,S))-5-(5-amino-2-fluoro-3-methylphenyl)-5-(difluoromethyl)-2-oxa-4-azabicyclo[4.1.0]hept-3-en-3-yl)benzamide (21d-rac, 220 mg, 0.565 mmol) and 5-chloro-2-pyridinecarboxylic acid (134 mg, 0.848 mmol) in THF (1983 μl)/MeOH (991 μl) was cooled to 0° C. before adding 4-(4,6-dimethoxy-1,3,5-triazin-2-yl)-4-methylmorpholinium chloride (258 mg, 0.876 mmol). The reaction mixture was stirred at 0° C. for 15 minutes and then overnight at RT. The reaction was quenched with saturated sodium bicarbonate solution and diluted with water and EtOAc. The organic layer was washed with brine, dried over magnesium sulfate and the filtrate was concentrated under reduced pressure. The crude residue was taken up in MeOH (3 mL) and 1,8-diazabicyclo-[5.4.0]undec-7-ene (186 μl, 1.243 mmol) was added. The reaction mixture was heated to 50° C. for 6 hours and additional 12 h at rt. The precipitate was filtered off, suspended in water (5 mL) and MeOH (2 mL) and stirred vigorously for 10 minutes. The solid was filtered and dried under high vac to afford the title compound (155.6 mg, 0.366 mmol, 64.8% yield) as a white solid. MS m/z=424.9 [M+H]⁺

1H NMR (300 MHz, DMSO-d6) δ ppm 0.82-0.99 (m, 1H) 1.07-1.22 (m, 1H) 1.63-1.81 (m, 1H) 3.94-4.09 (m, 1H) 5.83 (s, 2H) 5.97-6.49 (m, 1H) 7.80 (d, J=4.82 Hz, 2H) 8.08-8.26 (m, 2H) 8.78 (d, J=1.61 Hz, 1H) 10.56 (s, 1H)

Method D: HATU Procedure

Example 31

Synthesis of N-(3-([(1R,S),(5S,R),(6R,S)]-3-amino-5-(fluoromethyl)-2-oxa-4-azabicyclo[4.1.0]hept-3-en-5-yl)-5-fluoro-4-methoxyphenyl)-5-chloropicolinamide

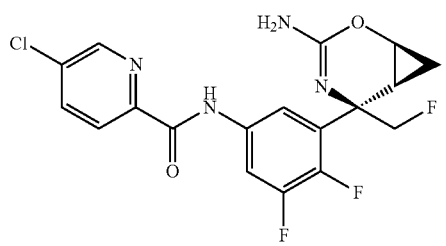 [SMILES: NC1=N[C@@](CF)(c2cc(NC(=O)c3ccc(Cl)cn3)cc(F)c2F)[C@@H]2C[C@@H]2O1]

To a solution of [(1R,S),(5S,R),(6R,S)]-5-(5-amino-3-fluoro-2-methoxyphenyl)-5-(fluoromethyl)-2-oxa-4-azabicyclo[4.1.0]hept-3-en-3-amine (12b rac, 80 mg, 0.282 mmol) and 5-chloropicolinic acid (102 mg, 0.650 mmol) in DMF (1 mL) was added 1-[bis(dimethylamino)methylene]-1H-1,2,3-triazolo[4,5-b]pyridinium 3-oxid hexafluorophosphate (247 mg, 0.650 mmol) and diisopropylethylamine (0.196 mL, 1.130 mmol). The reaction mixture was stirred at RT overnight and then quenched with aqueous, saturated $NaHCO_3$ solution. The reaction mixture was extracted with DCM and dried over $Na_2SO_4$. The filtrate was concentrated under reduced pressure and the residue was purified by flash column (DCM/EtOAc=4:1 to 3:1) to afford 5-chloro-N-([(1R,S), (5S,R),(6R,S)]-5-(5-(5-chloropicolinamido)-3-fluoro-2-methoxyphenyl)-5-(fluoromethyl)-2-oxa-4-azabicyclo[4.1.0]hept-3-en-3-yl)picolinamide (140 mg, 0.249 mmol). The product was dissolved 5 mL 2N $NH_3$/MeOH and heated to 60° C. overnight. The reaction mixture was cooled to rt, the solvent was evaporated under reduced pressure and the residue was purified by flash column (EtOAc/DCM=1:2 to 1:1 to EtOAc) to give the title compound as a light yellow solid (90 mg, 0.213 mmol, 75% yield). MS m/z=422.9 $[M+H]^+$ 1H NMR (400 MHz, CHLOROFORM-d) δ ppm=9.79 (br. s., 1H), 8.55 (s, 1H), 8.22 (d, J=8.4 Hz, 1H), 8.01 (d, J=13.5 Hz, 1H), 7.87 (d, J=8.6 Hz, 1H), 7.24 (br. s., 1H), 4.97-4.58 (m, 2H), 4.00 (s, 3H), 3.95 (br. s., 1H), 1.79 (q, J=7.7 Hz, 1H), 1.20-1.11 (m, 1H), 0.96-0.84 (m, 1H)

Examples 32-293

Using procedures analogous or similar to one of the general amidation procedures A-D described above, the appropriate aniline and carboxylic acid intermediates were reacted to provide the examples listed in Table 1.

TABLE 1

| Example # | Method | Compound Name | Structure | Analytical Data |
|---|---|---|---|---|
| 32 | D | N-(3-((1S,5R,6S)-3-amino-5-(fluoromethyl)-2-oxa-4-azabicyclo[4.1.0]hept-3-en-5-yl)-4,5-difluorophenyl)-5-chloropicolinamide | 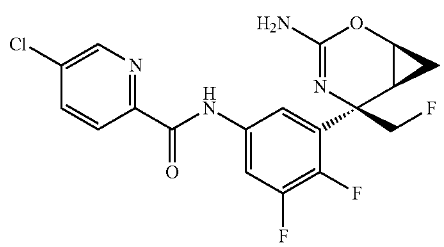 [SMILES: NC1=N[C@@](CF)(c2cc(NC(=O)c3ccc(Cl)cn3)cc(F)c2F)[C@@H]2C[C@@H]2O1] | MS m/z = 410.8 [M]+ <br> $^1$H NMR (400 MHz, CHLOROFORM-d) δ 9.59-9.79 (m, 1H), 8.48 (s, 1H), 8.11-8.23 (m, 1H), 7.96-8.07 (m, 1H), 7.86 (d, J = 8.41 Hz, 1H), 7.26 (br. s., 1H), 4.70-4.84 (m, 2H), 4.44-4.70 (m, 2H), 3.94 (br. s., 1H), 1.71 (br. s., 1H), 1.22 (br. s., 1H), 0.77-1.01 (m, 1H) |
| 33 | A | N-(3-((1R,5S,6R)-3-amino-5-(fluoromethyl)-2-oxa-4-azabicyclo[4.1.0]hept-3-en-5-yl)-4,5-difluorophenyl)-5-(prop-2-yn-1-yloxy)pyrazine-2-carboxamide | 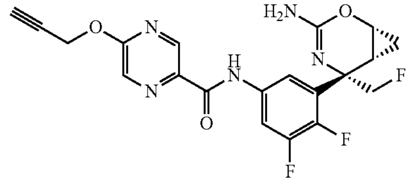 [SMILES: C#CCOc1cnc(C(=O)Nc2cc(F)c(F)c([C@@]3(CF)N=C(N)O[C@@H]4C[C@@H]43)c2)cn1] | MS m/z = 432.1 [M + H]+ <br> $^1$H NMR (400 MHz, DMSO-d6) d ppm 10.73 (s, 1 H), 8.91 (d, J = 1.17 Hz, 1 H), 8.49 (s, 1 H), 7.97 (ddd, J = 12.47, 6.80, 2.45 Hz, 1 H), 7.81-7.92 (m, 1 H), 5.66 (s, 2 H), 5.14 (d, J = 2.35 Hz, 2 H), 4.32-4.82 (m, 2 H), 4.00-4.15 (m, 1 H), 3.64 (t, J = 2.35 Hz, 1 H), 1.47-1.70 (m, 1 H), 0.99 (td, J = 6.50, 2.64 Hz, 1 H), 0.86 (dt, J = 9.49, 6.41 Hz, 1 H) |
| 34 | A | N-(3-((1S,5S,6S)-3-amino-5-(fluoromethyl)-2-oxa-4-azabicyclo[4.1.0]hept-3-en-5-yl)-4,5-difluorophenyl)-5-(prop-2-yn-1-yloxy)pyrazine-2-carboxamide | 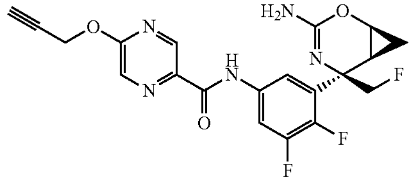 [SMILES: C#CCOc1cnc(C(=O)Nc2cc(F)c(F)c([C@]3(CF)N=C(N)O[C@H]4C[C@H]43)c2)cn1] | MS m/z = 432.1 [M + H]+ <br> $^1$H NMR (400 MHz, DMSO-d6) d ppm 10.73 (s, 1 H), 8.91 (d, J = 1.17 Hz, 1 H), 8.49 (d, J = 1.17 Hz, 1 H), 7.97 (ddd, J = 12.32, 6.85, 2.54 Hz, 1 H), 7.82-7.91 (m, 1 H), 5.66 (s, 2 H), 5.14 (d, J = 2.35 Hz, 2 H), 4.34-4.78 (m, 2 H), 3.97-4.17 (m, 1 H), 3.64 (d, J = 4.89 Hz, 1 H), 1.46-1.66 (m, 1 H), 0.99 (td, J = 6.46, 2.74 Hz, 1 H), 0.86 (dt, J = 9.49, 6.50 Hz, 1 H) |

TABLE 1-continued

| Example # | Method | Compound Name | Structure | Analytical Data |
|---|---|---|---|---|
| 35 | A | N-(3-((1R,5S,6R)-3-amino-5-(fluoromethyl)-2-oxa-4-azabicyclo[4.1.0]hept-3-en-5-yl)-4,5-difluorophenyl)-5-(but-2-yn-1-yloxy)pyrazine-2-carboxamide | 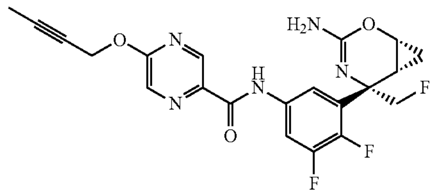 [SMILES: CC#CCOc1cnc(C(=O)Nc2cc(F)c(F)c([C@@]3(CF)N=C(N)O[C@@H]4C[C@@H]43)c2)cn1] | MS m/z = 446.1 [M + H]+<br>1H NMR (400 MHz, CHLOROFORM-d) d ppm 9.49 (br. s., 1 H), 8.99 (s, 1 H), 8.17 (s, 1 H), 7.97-8.11 (m, 1 H), 7.26 (s, 1 H), 5.04 (br. s., 2 H), 4.71-4.82 (m, 1 H), 4.57-4.69 (m, 1 H), 4.01 (br. s., 1 H), 1.89 (br. s., 3 H), 1.77 (q, J = 7.89 Hz, 1 H), 1.24 (br. s., 1 H), 0.97 (q, J = 7.37 Hz, 1 H). |
| 36 | A | N-(3-((1S,5S,6S)-3-amino-5-(fluoromethyl)-2-oxa-4-azabicyclo[4.1.0]hept-3-en-5-yl)-4,5-difluorophenyl)-5-(but-2-yn-1-yloxy)pyrazine-2-carboxamide | 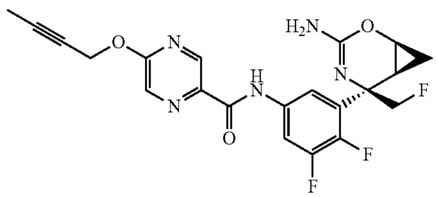 [SMILES: CC#CCOc1cnc(C(=O)Nc2cc(F)c(F)c([C@]3(CF)N=C(N)O[C@H]4C[C@H]43)c2)cn1] | MS m/z = 446.1 [M + H]+<br>1H NMR (400 MHz, CHLOROFORM-d) d ppm 9.49 (br. s., 1 H), 8.99 (s, 1 H), 8.17 (s, 1 H), 7.97-8.11 (m, 1 H), 7.26 (s, 1 H), 5.04 (br. s., 2 H), 4.71-4.82 (m, 1 H), 4.57-4.69 (m, 1 H), 4.01 (br. s., 1 H), 1.89 (br. s., 3 H), 1.77 (q, J = 7.89 Hz, 1 H), 1.24 (br. s., 1 H), 0.97 (q, J = 7.37 Hz, 1 H). |
| 37 | A | N-(3-((1R,5S,6R)-3-amino-5-(fluoromethyl)-2-oxa-4-azabicyclo[4.1.0]hept-3-en-5-yl)-4,5-difluorophenyl)-5-cyanopicolinamide | 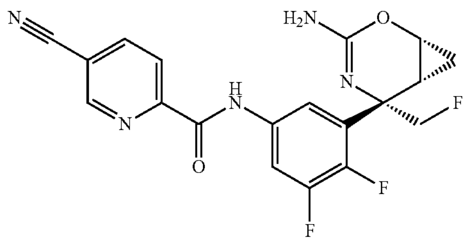 [SMILES: N#Cc1ccc(C(=O)Nc2cc(F)c(F)c([C@@]3(CF)N=C(N)O[C@@H]4C[C@@H]43)c2)nc1] | MS m/z = 402.2 [M + H]+<br>1H NMR (400 MHz, CHLOROFORM-d) d ppm 9.70 (br. s., 1 H), 8.82 (s, 1 H), 8.38 (s, 1 H), 8.19 (d, J = 8.02 Hz, 1 H), 7.86-8.06 (m, 1 H), 7.26 (br. s., 1 H), 4.53-4.89 (m, 4 H), 3.95 (br. s., 1 H), 1.71 (q, J = 7.63 Hz, 1 H), 1.22 (br. s., 1 H), 0.93 (q, J = 7.37 Hz, 1 H). |
| 38 | A | N-(3-((1S,5S,6S) 3-amino-5-(fluoromethyl)-2-oxa-4-azabicyclo[4.1.0]hept-3-en-5-yl)-4,5-difluorophenyl)-5-cyanopicolinamide | 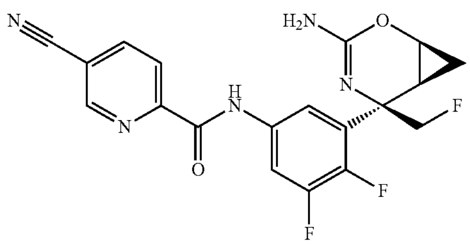 [SMILES: N#Cc1ccc(C(=O)Nc2cc(F)c(F)c([C@]3(CF)N=C(N)O[C@H]4C[C@H]43)c2)nc1] | MS m/z = 402 [M + H]+<br>$^1$H NMR (400 MHz, CHLOROFORM-d) 6 9.70 (br. s., 1H), 8.82 (s, 1H), 8.37 (d, J = 8.22 Hz, 1H), 8.19 (d, J = 8.02 Hz, 1H), 7.95-8.04 (m, 1H), 7.26 (br. s., 1 H), 4.55-4.82 (m, 4H), 3.95 (br. s., 1H), 1.71 (q, J = 7.63 Hz, 1H), 1.22 (br. s., 1H), 0.93 (q, J = 7.37 Hz, 1H). |
| 39 | A | N-(3-((1R,5S,6R)-3-amino-5-(fluoromethyl)-2-oxa-4-azabicyclo[4.1.0]hept-3-en-5-yl)-4,5-difluorophenyl)-5-bromopicolinamide | 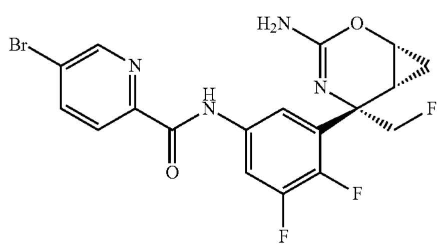 | MS m/z = 457 [M + H]+<br>1H NMR (400 MHz, CHLOROFORM-d) d ppm 9.78 (br. s., 1 H), 8.62 (d, J = 1.96 Hz, 1 H), 8.14 (s, 1 H), 7.90-8.08 (m, 2 H), 7.28 (d, J = 2.93 Hz, 1 H), 4.75 (s, 1 H), 4.63 (s, 1 H), 3.97 (t, J = 6.16 Hz, 1 H), 1.63-1.80 (m, 1 H), 1.21 (td, J = 6.94, 2.54 Hz, 1 H), 0.93 (dt, J = 9.34, 6.87 Hz, 1 H) |
| 40 | A | N-(3-((1S,5S,6S)-3-amino-5-(fluoromethyl)-2-oxa-4-azabicyclo[4.1.0]hept-3-en-5-yl)-4,5-difluorophenyl)-5-bromopicolinamide | 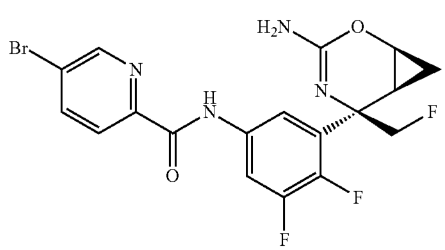 | MS m/z = 457 [M + H]+<br>1H NMR (400 MHz, CHLOROFORM-d) d ppm 9.76 (br. s., 1 H), 8.62 (d, J = 1.76 Hz, 1 H), 8.14 (s, 1 H), 7.97-8.07 (m, 2 H), 7.27 (br. s., 1 H), 4.74 (s, 1 H), 4.62 (s, 1 H), 4.50 (br. s., 2 H), 3.95 (t, J = 6.16 Hz, 1 H), 1.63-1.81 (m, 1 H), 1.20 (td, J = 6.85, 2.54 Hz, 1 H), 0.84-0.98 (m, 1 H) |

TABLE 1-continued

| Example # | Method | Compound Name | Structure | Analytical Data |
|---|---|---|---|---|
| 41 | A | N-(3-((1R,5S,6R)-3-amino-5-(fluoromethyl)-2-oxa-4-azabicyclo[4.1.0]hept-3-en-5-yl)-4,5-difluorophenyl)-5-methoxypicolinamide | 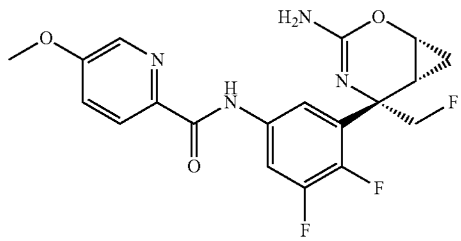 [SMILES: COc1ccc(C(=O)Nc2cc(F)c(F)c([C@@]3(CF)N=C(N)O[C@@H]4C[C@@H]43)c2)nc1] | MS m/z = 407.2 [M + H]+ 1H NMR (400 MHz, CHLOROFORM-d) d ppm 9.81 (s, 1 H), 8.15-8.25 (m, 2 H), 8.06 (ddd, J = 11.83, 6.94, 2.54 Hz, 1 H), 7.32 (dd, J = 8.61, 2.74 Hz, 1 H), 7.26 (s, 1 H), 4.51-4.90 (m, 2 H), 3.96-4.03 (m, 1 H), 3.94 (s, 3 H), 1.65-1.81 (m, 1 H), 1.15-1.30 (m, 1 H), 0.95 (dt, J = 9.49, 6.90 Hz, 1 H). NH2 is broad and not accounted for. |
| 42 | A | N-(3-((1R,5S,6R)-3-amino-5-(difluoromethyl)-2-oxa-4-azabicyclo[4.1.0]hept-3-en-5-yl)-4-fluorophenyl)-5-chloro-3-(methoxymethyl)picolinamide | 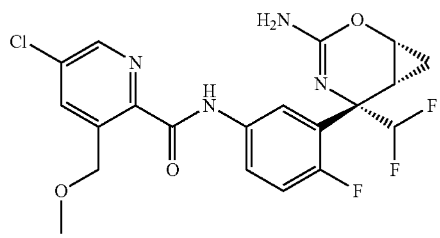 [SMILES: COCc1cc(Cl)cnc1C(=O)Nc1ccc(F)c([C@@]2(C(F)F)N=C(N)O[C@@H]3C[C@@H]32)c1] | MS m/z = 455.1 [M + H]+ 1H NMR (400 MHz, CHLOROFORM-d) d ppm 9.86 (br. s., 1 H), 8.27 (br. s., 1 H), 8.17 (br. s., 1 H), 7.92 (d, J = 6.06 Hz, 1 H), 7.49 (d, J = 6.26 Hz, 1 H), 7.00 (t, J = 10.07 Hz, 1 H), 6.03-6.42 (m, 1 H), 4.85-5.14 (m, 4 H), 3.91 (br. s., 1 H), 3.54 (s, 3 H), 1.83-1.96 (m, 1 H), 1.43 (br. s., 1 H), 0.95 (q, J = 7.30 Hz, 1 H) |
| 43 | A | N-(3-((1R,5S,6R)-3-amino-5-(difluoromethyl)-2-oxa-4-azabicyclo[4.1.0]hept-3-en-5-yl)-4-fluorophenyl)-5-chloro-3-methylpicolinamide | 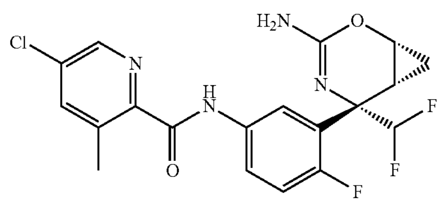 [SMILES: Cc1cc(Cl)cnc1C(=O)Nc1ccc(F)c([C@@]2(C(F)F)N=C(N)O[C@@H]3C[C@@H]32)c1] | MS m/z = 425.2 [M + H]+ 1H NMR (400 MHz, CHLOROFORM-d) d ppm 9.89 (s, 1 H), 8.24 (s, 1 H), 7.87-8.04 (m, 1 H), 7.61 (s, 1 H), 7.48 (dd, J = 6.65, 2.35 Hz, 1 H), 7.01 (dd, J = 11.35, 9.00 Hz, 1 H), 6.01-6.45 (m, 1 H), 4.96 (br. s., 2 H), 3.92 (t, J = 5.67 Hz, 1 H), 2.75 (s, 3 H), 1.82-1.97 (m, 1 H), 1.35-1.53 (m, 1 H), 0.86-1.03 (m, 1 H) |
| 44 | A | N-(3-((1R,5S,6R)-3-amino-5-(difluoromethyl)-2-oxa-4-azabicyclo[4.1.0]hept-3-en-5-yl)-4-fluorophenyl)-5-cyano-3-methylpicolinamide | 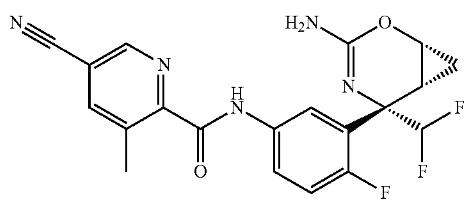 [SMILES: Cc1cc(C#N)cnc1C(=O)Nc1ccc(F)c([C@@]2(C(F)F)N=C(N)O[C@@H]3C[C@@H]32)c1] | MS m/z = 416.1 [M + H]+ 1H NMR (400 MHz, CHLOROFORM-d) d ppm 9.86 (s, 1 H), 8.54 (s, 1 H), 7.84-8.03 (m, 2 H), 7.49 (dd, J = 6.65, 2.54 Hz, 1 H), 7.00 (dd, J = 11.35, 8.80 Hz, 1 H), 6.02-6.48 (m, 1 H), 4.99 (br. s., 2 H), 3.79-3.99 (m, 1 H), 2.82 (s, 3 H), 1.82-1.93 (m, 1 H), 1.43 (t, J = 6.16 Hz, 1 H), 0.80-1.05 (m, 1 H) |
| 45 | A | N-(3-((1R,5S,6R)-3-amino-5-(difluoromethyl)-2-oxa-4-azabicyclo[4.1.0]hept-3-en-5-yl)-4-fluorophenyl)-5-cyano-3-methoxypicolinamide | 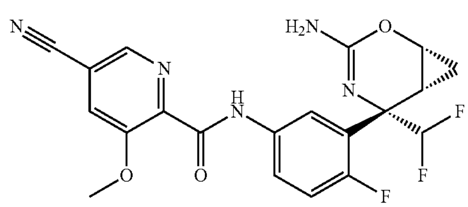 [SMILES: COc1cc(C#N)cnc1C(=O)Nc1ccc(F)c([C@@]2(C(F)F)N=C(N)O[C@@H]3C[C@@H]32)c1] | MS m/z = 432.2 [M + H]+ 1H NMR (400 MHz, CHLOROFORM-d) d ppm 9.59 (br. s., 1 H), 8.34 (s, 1 H), 8.01 (d, J = 8.02 Hz, 1 H), 7.49-7.67 (m, 2 H), 7.08 (t, J = 10.17 Hz, 1 H), 6.00-6.49 (m, 1 H), 4.97 (br. s., 2 H), 3.84-4.00 (m, 4 H), 1.82-1.94 (m, 1 H), 1.42 (br. s., 1 H), 0.96 (q, J = 7.63 Hz, 1 H) |
| 46 | A | N-(3-((1R,5S,6R)-3-amino-5-(fluoromethyl)-2-oxa-4-azabicyclo[4.1.0]hept-3-en-5-yl)-4,5-difluorophenyl)-4-chloro-1-(difluoromethyl)-1H-pyrazole-3-carboxamide | 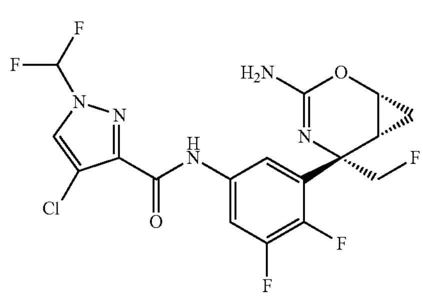 [SMILES: NC1=N[C@](CF)(c2cc(NC(=O)c3nn(C(F)F)cc3Cl)cc(F)c2F)[C@H]2C[C@H]2O1] | MS m/z = 450.1 [M + H]+ 1H NMR (400 MHz, CHLOROFORM-d) d ppm 8.45 (br. s., 1 H), 8.00 (ddd, J = 11.59, 6.99, 2.54 Hz, 1 H), 7.90 (s, 1 H), 7.25 (s, 1 H), 7.11-7.18 (m, 1 H), 4.48-4.84 (m, 2 H), 3.95 (t, J = 6.26 Hz, 1 H), 1.59-1.82 (m, 1 H), 1.20 (td, J = 6.94, 2.54 Hz, 1 H), 0.76-0.99 (m, 1 H). Note NH2 is broad from 5-3 ppm |

TABLE 1-continued

| Example # | Method | Compound Name | Structure | Analytical Data |
|---|---|---|---|---|
| 47 | A | N-(3-((1S,5S,6S)-3-amino-5-(fluoromethyl)-2-oxa-4-azabicyclo[4.1.0]hept-3-en-5-yl)-4,5-difluorophenyl)-4-chloro-1-(difluoromethyl)-1H-pyrazole-3-carboxamide | 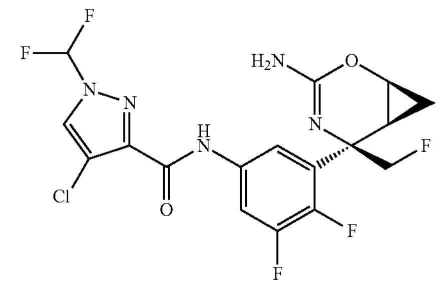 [SMILES: NC1=N[C@@](CF)(c2cc(NC(=O)c3nn(C(F)F)cc3Cl)cc(F)c2F)[C@@H]2C[C@@H]2O1] | MS m/z = 450.1 [M + H]+<br>¹H NMR (400 MHz, CHLOROFORM-d) δ 8.48 (br. s., 1H), 8.02 (dd, J = 6.94, 11.64 Hz, 1H), 8.01 (dd, J = 6.94, 11.64 Hz, 1H), 7.90 (s, 1H), 7.10-7.16 (m, 1H), 4.56-4.79 (m, 2H), 3.96 (t, J = 6.36 Hz, 1H), 1.68-1.76 (m, 1H), 1.21 (dt, J = 2.54, 6.85 Hz, 1H), 0.88-0.97 (m, 1H) |
| 48 | D | N-(3-((1S,5S,6S)-3-amino-5-(fluoromethyl)-2-oxa-4-azabicyclo[4.1.0]hept-3-en-5-yl)-4,5-difluorophenyl)-4-chloro-1-(difluoromethyl)-1H-pyrazole-3-carboxamide | 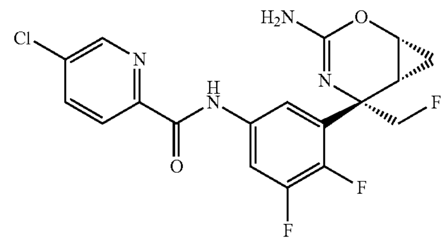 [SMILES: NC1=N[C@](CF)(c2cc(NC(=O)c3ccc(Cl)cn3)cc(F)c2F)[C@H]2C[C@H]2O1] | MS m/z = 410.8 [M]+<br>¹H NMR (400 MHz, CHLOROFORM-d) δ 8.48 (br. s., 1H), 8.02 (dd, J = 6.94, 11.64 Hz, 1H), 8.01 (dd, J = 6.94, 11.64 Hz, 1H), 7.90 (s, 1H), 7.10-7.16 (m, 1H), 4.56-4.79 (m, 2H), 3.96 (t, J = 6.36 Hz, 1H), 1.68-1.76 (m, 1H), 1.21 (dt, J = 2.54, 6.85 Hz, 1H), 0.88-0.97 (m, 1H) |
| 49 | A | N-(3-((1R,5S,6R)-3-amino-5-(fluoromethyl)-2-oxa-4-azabicyclo[4.1.0]hept-3-en-5-yl)-4,5-difluorophenyl)-5-chloropicolinamide | 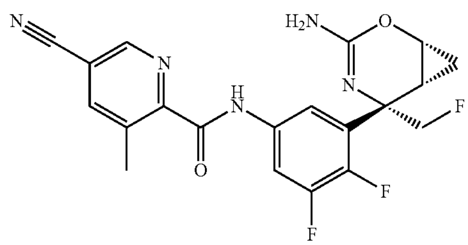 [SMILES: Cc1cc(C#N)cnc1C(=O)Nc1cc(F)c(F)c([C@@]2(CF)N=C(N)O[C@@H]3C[C@@H]32)c1] | MS m/z = 415.8 [M]+<br>1H NMR (400 MHz, CHLOROFORM-d) δ 9.70 (br. s., 1H), 8.47 (s, 1H), 8.14-8.19 (m, J = 8.41 Hz, 1H), 7.95-8.02 (m, 1H), 7.82-7.90 (m, J = 8.41 Hz, 1H), 7.26 (br. s., 1H), 4.49-4.92 (m, 4H), 3.94 (br. s., 1H), 1.72 (q, J = 7.69 Hz, 1H), 1.22 (t, J = 6.46 Hz, 1H), 0.91 (q, J = 7.37 Hz, 1H). |
| 50 | A | N-(3-((1R,5S,6R)-3-amino-5-(fluoromethyl)-2-oxa-4-azabicyclo[4.1.0]hept-3-en-5-yl)-4,5-difluorophenyl)-5-cyano-3-methylpicolinamide | 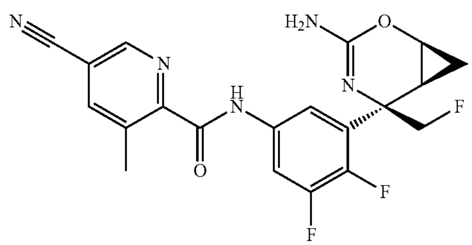 [SMILES: Cc1cc(C#N)cnc1C(=O)Nc1cc(F)c(F)c([C@]2(CF)N=C(N)O[C@H]3C[C@H]32)c1] | MS m/z = 415.8 [M]+<br>¹H NMR (400 MHz, CHLOROFORM-d) δ 9.90 (br. s., 1H), 8.63 (s, 1H), 7.99-8.07 (m, 1H), 7.94 (s, 1H), 7.14 (br. s., 1H), 4.56-4.81 (m, 4H), 3.95 (br. s., 1H), 2.84 (s, 3H), 1.73 (q, J = 7.96 Hz, 1H), 1.11-1.34 (m, 1H), 0.83-0.99 (m, 1H) |
| 51 | A | N-(3-((1R,5S,6R)-3-amino-5-(fluoromethyl)-2-oxa-4-azabicyclo[4.1.0]hept-3-en-5-yl)-4,5-difluorophenyl)-5-cyano-3-methylpicolinamide | 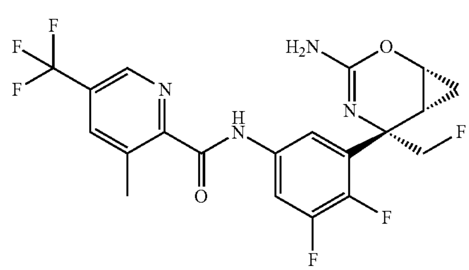 [SMILES: Cc1cc(C(F)(F)F)cnc1C(=O)Nc1cc(F)c(F)c([C@@]2(CF)N=C(N)O[C@@H]3C[C@@H]32)c1] | MS m/z = 458.9 [M]+<br>¹H NMR (400 MHz, CHLOROFORM-d) δ 9.90 (br. s., 1H), 8.63 (s, 1H), 7.99-8.07 (m, 1H), 7.94 (s, 1H), 7.14 (br. s., 1H), 4.56-4.81 (m, 4H), 3.95 (br. s., 1H), 2.84 (s, 3H), 1.73 (q, J = 7.96 Hz, 1H), 1.11-1.34 (m, 1H), 0.83-0.99 (m, 1H) |
| 52 | A | N-(3-((1R,5S,6R)-3-amino-5-(fluoromethyl)-2-oxa-4-azabicyclo[4.1.0]hept-3-en-5-yl)-4,5-difluorophenyl)-3-methyl-5-(trifluoromethyl)picolinamide | 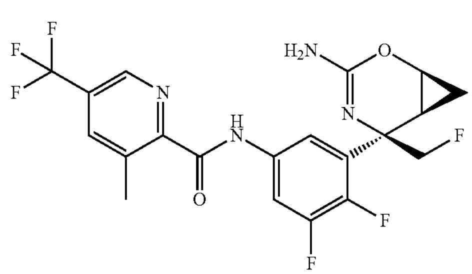 [SMILES: Cc1cc(C(F)(F)F)cnc1C(=O)Nc1cc(F)c(F)c([C@]2(CF)N=C(N)O[C@H]3C[C@H]32)c1] | MS m/z = 458.9 [M]+<br>1H NMR (400 MHz, CHLOROFORM-d) δ 9.91-10.10 (m, 1H), 8.53-8.68 (m, 1H), 7.98-8.10 (m, 1H), 7.82-7.93 (m, 1H), 7.10-7.21 (m, 1H), 4.26-5.17 (m, 3H), 3.74-4.08 (m, 1H), 2.86 (s, 4H), 1.57-1.91 (m, 1H), 1.09-1.38 (m, 1H), 0.79-1.06 (m, 1H). |

TABLE 1-continued

| Example # | Method | Compound Name | Structure | Analytical Data |
|---|---|---|---|---|
| 53 | A | N-(3-((1R,5S,6R)-3-amino-5-(difluoromethyl)-2-oxa-4-azabicyclo[4.1.0]hept-3-en-5-yl)-4-fluorophenyl)-5-chloro-3-methylpyrazine-2-carboxamide | 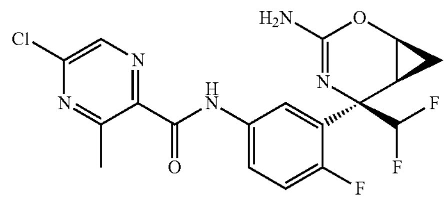 [SMILES: Cc1nc(Cl)cnc1C(=O)Nc1ccc(F)c([C@]2(C(F)F)N=C(N)O[C@H]3C[C@H]32)c1] | MS m/z = 425.9[M]+ 1H NMR (300 MHz, CHLOROFORM-d) d ppm 9.52 (s, 1 H), 8.25 (s, 1 H), 7.88-8.00 (m, 1 H), 7.45 (d, J = 4.97 Hz, 1 H), 6.89-7.06 (m, 1 H), 5.97-6.50 (m, 1 H), 4.78-5.40 (br. s., 2 H), 3.91 (br. s., 1 H), 3.00 (s, 3 H), 1.81-1.96 (m, 1 H), 1.43 (br. s., 1 H), 0.84-1.05 (m, 1 H) |
| 54 | A | N-(3-((1R,5S,6R)-3-amino-5-(difluoromethyl)-2-oxa-4-azabicyclo[4.1.0]hept-3-en-5-yl)-4-fluorophenyl)-6-chloro-3-methylpyrazine-2-carboxamide | 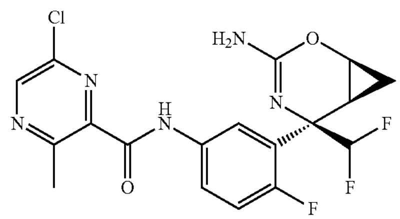 [SMILES: Cc1ncc(Cl)nc1C(=O)Nc1ccc(F)c([C@]2(C(F)F)N=C(N)O[C@H]3C[C@H]32)c1] | MS m/z = 425.9 [M]+ 1H NMR (300 MHz, CHLOROFORM-d) δ 9.42 (s, 1H), 8.64 (s, 1H), 7.93-8.01 (m, 1H), 7.51 (dd, J = 2.05, 6.43 Hz, 1H), 6.97-7.05 (m, 1H), 6.42-6.05 (t, 1H), 4.92 (br. s., 2H), 3.93 (m, 1H), 3.00 (s, 3H), 1.83-1.93 (m, 1H), 1.39-1.47 (m, 1H), 0.92-1.02 (m, 1H) |
| 55 | B | N-(3-([1(R,S),5(S,R),6(R,S)]-3-amino-5-(difluoromethyl)-2-oxa-4-azabicyclo[4.1.0]hept-3-en-5-yl)-4-fluorophenyl)-5-chloropicolinamide | 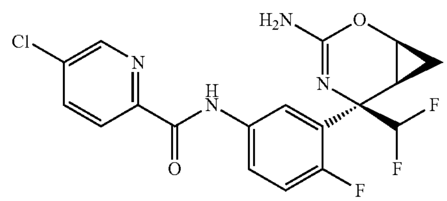 [SMILES: NC1=N[C@](c2cc(NC(=O)c3ccc(Cl)cn3)ccc2F)(C(F)F)[C@@H]2C[C@@H]2O1] | MS m/z = 411.0[M + H]+ 1H NMR (400 MHz, CHLOROFORM-d) δ ppm 0.93-1.01 (m, 1 H) 1.39-1.45 (m, 1 H) 1.83-1.91 (m, 1 H) 3.91-3.97 (m, 1 H) 4.67 (br. s., 2 H) 6.24 (t, J = 56.10 Hz, 1 H) 7.09 (dd, J = 11.54, 8.80 Hz, 1 H) 7.64 (dd, J = 6.85, 2.74 Hz, 1 H) 7.87 (dd, J = 8.41, 2.35 Hz, 1 H) 7.99 (ddd, J = 8.80, 4.11, 2.93 Hz, 1 H) 8.21 (d, J = 8.22 Hz, 1 H) 8.52 (d, J = 2.15 Hz, 1 H) 9.79 (s, 1 H) |
| 56 | B | N-(3-((1R,5S,6R)-3-amino-5-methyl-2-oxa-4-azabicyclo[4.1.0]hept-3-en-5-yl)-4-fluorophenyl)-5-(but-2-yn-1-yloxy)-3-methylpicolinamide | 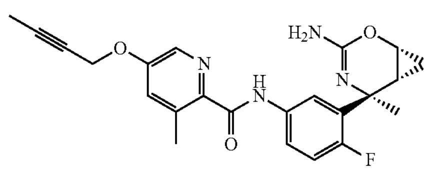 [SMILES: CC#CCOc1cnc(C(=O)Nc2ccc(F)c([C@@]3(C)N=C(N)O[C@@H]4C[C@@H]43)c2)c(C)c1] | MS m/z = 422.9 [M]+ 1H NMR (400 MHz, CHLOROFORM-d) δ ppm 0.89 (dt, J = 9.59, 6.65 Hz, 1 H) 1.01 (td, J = 6.99, 2.64 Hz, 1 H) 1.68 (s, 3 H) 1.83 (dt, J = 9.44, 7.31 Hz, 1 H) 1.88 (t, J = 2.25 Hz, 3 H) 2.78 (s, 3 H) 3.96-4.01 (m, 1 H) 4.40 (br. s., 2 H) 4.75 (q, J = 2.20 Hz, 2 H) 7.04 (dd, J = 11.64, 8.90 Hz, 1 H) 7.14 (d, J = 2.54 Hz, 1 H) 7.44 (dd, J = 7.14, 2.64 Hz, 1 H) 7.92 (ddd, J = 8.71, 4.11, 2.84 Hz, 1 H) 8.14 (d, J = 2.74 Hz, 1 H) 10.01 (s, 1 H) |
| 57 | B | N-(3-((1S,5R,6S)-3-amino-5-methyl-2-oxa-4-azabicyclo[4.1.0]hept-3-en-5-yl)-4-fluorophenyl)-5-(but-2-yn-1-yloxy)-3-methylpicolinamide | 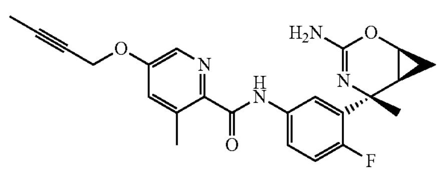 [SMILES: CC#CCOc1cnc(C(=O)Nc2ccc(F)c([C@]3(C)N=C(N)O[C@H]4C[C@H]43)c2)c(C)c1] | MS m/z = 422.9 [M]+ 1H NMR (400 MHz, CHLOROFORM-d) δ ppm 0.88 (dt, J = 9.73, 6.48 Hz, 1 H) 1.00 (td, J = 6.90, 2.64 Hz, 1 H) 1.67 (s, 3 H) 1.81 (dt, J = 9.98, 7.30 Hz, 1 H) 1.88 (t, J = 2.35 Hz, 3 H) 2.78 (s, 3 H) 3.97 (ddd, J = 7.48, 6.11, 2.64 Hz, 1 H) 4.09 (br. s., 2 H) 4.75 (q, J = 2.35 Hz, 2 H) 7.04 (dd, J = 11.74, 8.80 Hz, 1 H) 7.14 (d, J = 2.54 Hz, 1 H) 7.43 (dd, J = 7.04, 2.74 Hz, 1 H) 7.92 (ddd, J = 8.80, 4.11, 2.74 Hz, 1 H) 8.14 (d, J = 2.74 Hz, 1 H) 10.00 (s, 1 H) |
| 58 | B | N-(3-([1(R,S),5(S,R),6(R,S)]-3-amino-5-(difluoromethyl)-2-oxa-4-azabicyclo[4.1.0]hept-3-en-5-yl)-4-fluorophenyl)-5-methoxy-3-methylpyrazine-2-carboxamide | 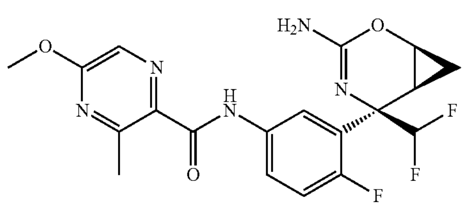 [SMILES: COc1cnc(C(=O)Nc2ccc(F)c([C@]3(C(F)F)N=C(N)O[C@H]4C[C@H]43)c2)c(C)n1] | MS m/z = 422.0[M + H]+ 1H NMR (400 MHz, DMSO-d6) δ ppm 0.92 (dt, J = 9.34, 6.48 Hz, 1 H) 1.12-1.18 (m, 1 H) 1.70-1.77 (m, 1 H) 2.76 (s, 3 H) 3.97-4.05 (m, 1 H) 4.00 (s, 3 H) 5.86 (s, 2 H) 6.19 (t, J = 56.10 Hz, 1 H) 7.20 (dd, J = 11.74, 8.80 Hz, 1 H) 7.82-7.87 (m, 1 H) 7.90 (dd, J = 7.04, 2.54 Hz, 1 H) 8.24 (s, 1 H) 10.45 (s, 1 H) |

TABLE 1-continued

| Example # | Method | Compound Name | Structure | Analytical Data |
|---|---|---|---|---|
| 59 | B | N-(3-([1(R,S),5(S,R),6(R,S)]-3-amino-5-(difluoromethyl)-2-oxa-4-azabicyclo[4.1.0]hept-3-en-5-yl)-4-fluorophenyl)-5-cyanopicolinamide compound | 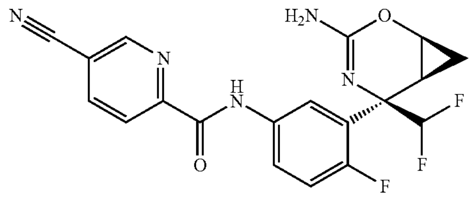 [SMILES: N#Cc1ccc(C(=O)Nc2ccc(F)c([C@]3(C(F)F)N=C(N)O[C@H]4C[C@H]43)c2)nc1] | MS m/z = 401.9[M]+<br>1H NMR (400 MHz, DMSO-d6) δ ppm 0.92 (dt, J = 9.34, 6.48 Hz, 1 H) 1.13-1.19 (m, 1 H) 1.74 (dt, J = 9.29, 7.09 Hz, 1 H) 4.00-4.06 (m, 1 H) 5.86 (s, 2 H) 6.20 (t, J = 55.90 Hz, 1 H) 7.24 (dd, J = 11.74, 8.80 Hz, 1 H) 7.89 (ddd, J = 8.80, 4.11, 2.93 Hz, 1 H) 8.06 (dd, J = 7.04, 2.74 Hz, 1 H) 8.29 (dd, J = 8.22, 0.59 Hz, 1 H) 8.58 (dd, J = 8.22, 1.96 Hz, 1 H) 9.20 (dd, J = 2.00, 0.78 Hz, 1 H) 10.86 (s, 1 H) |
| 60 | B | N-(3-((1S,5R,6S)-3-amino-5-(difluoromethyl)-2-oxa-4-azabicyclo[4.1.0]hept-3-en-5-yl)-4-fluorophenyl)-5-chloropicolinamide | 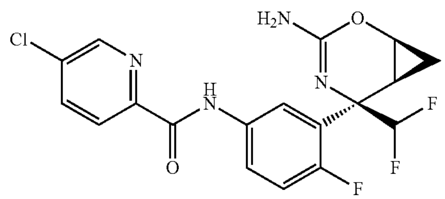 [SMILES: NC1=N[C@](c2cc(NC(=O)c3ccc(Cl)cn3)ccc2F)(C(F)F)[C@@H]2C[C@@H]2O1] | MS m/z = 410.9[M]+<br>1H NMR (400 MHz, CHLOROFORM-d) δ ppm 0.91-0.99 (m, 1 H) 1.40-1.46 (m, 1 H) 1.87 (dt, J = 9.44, 7.12 Hz, 1 H) 3.89-3.95 (m, 1 H) 4.85 (br. s., 2 H) 6.24 (t, J = 55.80 Hz, 1 H) 7.04 (dd, J = 11.54, 8.80 Hz, 1 H) 7.62 (dd, J = 6.65, 2.74 Hz, 1 H) 7.85 (dd, J = 8.41, 2.35 Hz, 1 H) 7.94 (ddd, J = 8.75, 4.16, 2.74 Hz, 1 H) 8.17 (d, J = 8.22 Hz, 1 H) 8.45 (d, J = 2.15 Hz, 1 H) 9.71 (s, 1 H) |
| 61 | B | N-(3-([1(R,S),5(S,R),6(R,S)]-3-amino-5-(difluoromethyl)-2-oxa-4-azabicyclo[4.1.0]hept-3-en-5-yl)-4-fluorophenyl)-6-chloro-3-methylimidazo[1,2-a]pyridine-2-carboxamide | 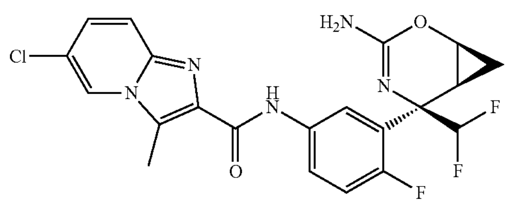 [SMILES: Cc1c(C(=O)Nc2ccc(F)c([C@]3(C(F)F)N=C(N)O[C@H]4C[C@H]43)c2)nc2ccc(Cl)cn12] | MS m/z = 463.9[M]+<br>1H NMR (400 MHz, DMSO-d6) δ ppm 0.86-0.98 (m, 1 H) 1.12-1.19 (m, 1 H) 1.73 (q, J = 7.56 Hz, 1 H) 2.81 (s, 3 H) 3.99-4.07 (m, 1 H) 5.85 (br. s., 2 H) 6.19 (t, J = 56.10 Hz, 1 H) 7.18 (dd, J = 11.15, 9.39 Hz, 1 H) 7.42 (d, J = 9.39 Hz, 1 H) 7.69 (d, J = 9.59 Hz, 1 H) 7.84-7.91 (m, 1 H) 7.96-8.02 (m, 1 H) 8.68 (s, 1 H) 10.24 (s, 1 H) |
| 62 | B | N-(3-([1(R,S),5(S,R),6(R,S)]-3-amino-5-(difluoromethyl)-2-oxa-4-azabicyclo[4.1.0]hept-3-en-5-yl)-4-fluorophenyl)-3-chloro-5-cyanopicolinamide | 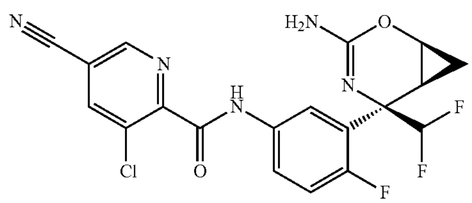 [SMILES: N#Cc1cnc(C(=O)Nc2ccc(F)c([C@]3(C(F)F)N=C(N)O[C@H]4C[C@H]43)c2)c(Cl)c1] | MS m/z = 435.8 [M + H]+<br>1H NMR (400 MHz, DMSO-d6) δ ppm 0.90 (dt, J = 9.15, 6.48 Hz, 1 H) 1.09-1.15 (m, 1 H) 1.66-1.75 (m, 1 H) 3.95-4.00 (m, 1 H) 5.93 (s, 2 H) 6.19 (t, J = 55.80 Hz, 1 H) 7.25 (dd, J = 11.74, 8.80 Hz, 1 H) 7.75 (dd, J = 6.94, 2.64 Hz, 1 H) 7.80-7.85 (m, 1 H) 8.81 (d, J = 1.76 Hz, 1 H) 9.11 (d, J = 1.76 Hz, 1 H) 10.95 (s, 1 H) |
| 63 | B | N-(3((1R,5S,6R)-3-amino-5-(difluoromethyl)-2-oxa-4-azabicyclo[4.1.0]hept-3-en-5-yl)-4-fluorophenyl)-5-methoxy-3-methylpyrazine-2-carboxamide | 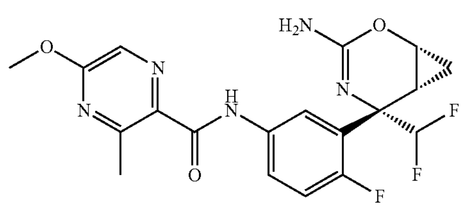 | MS m/z = 422.1 [M + H]+<br>1H NMR (400 MHz, CHLOROFORM-d) δ ppm 0.95 (q, J = 7.70 Hz, 1 H) 1.37-1.44 (m, 1 H) 1.86 (q, J = 7.76 Hz, 1 H) 2.91 (s, 3 H) 3.89-3.95 (m, 1 H) 4.04 (s, 3 H) 4.64 (br. s., 2 H) 6.22 (t, J = 55.80 Hz, 1 H) 7.05 (t, J = 10.30 Hz, 1 H) 7.48 (d, J = 6.26 Hz, 1 H) 7.91 (s, 1 H) 7.97-8.03 (m, 1 H) 9.70 (s, 1 H) |
| 64 | B | N-(3-((1S,5R,6S)-3-amino-5-(difluoromethyl)-2-oxa-4-azabicyclo[4.1.0]hept-3-en-5-yl)-4-fluorophenyl)-5-methoxy-3-methylpyrazine-2-carboxamide | 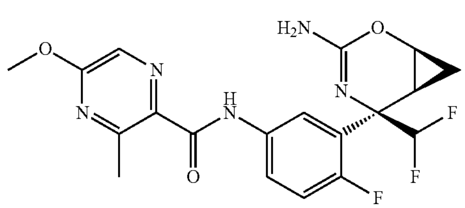 [SMILES: COc1cnc(C(=O)Nc2ccc(F)c([C@]3(C(F)F)N=C(N)O[C@H]4C[C@H]43)c2)c(C)n1] | MS m/z = 422.1 [M + H]+<br>1H NMR (400 MHz, CHLOROFORM-d) δ ppm 0.95 (q, J = 7.56 Hz, 1 H) 1.37-1.45 (m, 1 H) 1.86 (q, J = 7.56 Hz, 1 H) 2.91 (s, 3 H) 3.88-3.95 (m, 1 H) 4.04 (s, 3 H) 4.67 (br. s., 2 H) 6.22 (t, J = 55.90 Hz, 1 H) 7.04 (t, J = 10.60 Hz, 1 H) 7.48 (d, J = 6.26 Hz, 1 H) 7.90 (s, 1 H) 7.97-8.03 (m, 1 H) 9.69 (s, 1 H) |

TABLE 1-continued

| Example # | Method | Compound Name | Structure | Analytical Data |
|---|---|---|---|---|
| 65 | B | N-(3-((1S,5R,6S)-3-amino-5-(difluoromethyl)-2-oxa-4-azabicyclo[4.1.0]hept-3-en-5-yl)-4-fluorophenyl)-5-cyanopicolinamide | 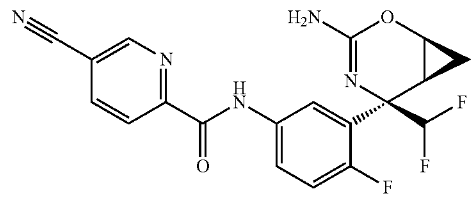 [SMILES: N#Cc1ccc(C(=O)Nc2ccc(F)c([C@]3(C(F)F)N=C(N)O[C@H]4C[C@H]43)c2)nc1] | MS m/z = 402.0 [M + H]+<br>1H NMR (400 MHz, DMSO-d6) δ ppm 0.92 (dt, J = 9.39, 6.46 Hz, 1 H) 1.12-1.18 (m, 1 H) 1.73 (dt, J = 9.15, 6.97 Hz, 1 H) 3.99-4.06 (m, 1 H) 5.88 (s, 2 H) 6.20 (t, J = 56.10 Hz, 1 H) 7.24 (dd, J = 11.93, 8.80 Hz, 1 H) 7.88 (ddd, J = 8.80, 4.11, 2.93 Hz, 1 H) 8.06 (dd, J = 7.04, 2.74 Hz, 1 H) 8.28 (dd, J = 8.22, 0.78 Hz, 1 H) 8.59 (dd, J = 8.22, 1.96 Hz, 1 H) 9.21 (dd, J = 2.05, 0.88 Hz, 1 H) 10.88 (s, 1 H) |
| 66 | B | N-(3-((1R,5S,6R)-3-amino-5-(difluoromethyl)-2-oxa-4-azabicyclo[4.1.0]hept-3-en-5-yl)-4-fluorophenyl)-3-chloro-5-cyanopicolinamide | 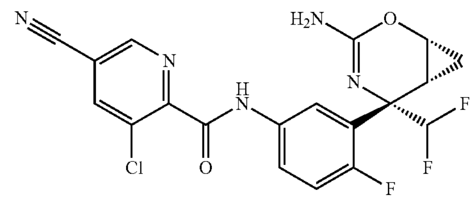 | MS m/z = 436.0 [M + H]+<br>1H NMR (400 MHz, DMSO-d6) δ ppm 0.90 (dt, J = 9.29, 6.50 Hz, 1 H) 1.10-1.15 (m, 1 H) 1.67-1.75 (m, 1 H) 3.95-4.01 (m, 1 H) 5.93 (s, 2 H) 6.19 (t, J = 55.90 Hz, 1 H) 7.26 (dd, J = 11.74, 8.80 Hz, 1 H) 7.75 (dd, J = 7.04, 2.74 Hz, 1 H) 7.83 (ddd, J = 8.75, 4.06, 2.84 Hz, 1 H) 8.81 (d, J = 1.57 Hz, 1 H) 9.11 (d, J = 1.57 Hz, 1 H) 10.95 (s, 1 H) |
| 67 | B | N-(3-((1S,5R,6S)-3-amino-5-(difluoromethyl)-2-oxa-4-azabicyclo[4.1.0]hept-3-en-5-yl)-4-fluorophenyl)-3-chloro-5-cyanopicolinamide | 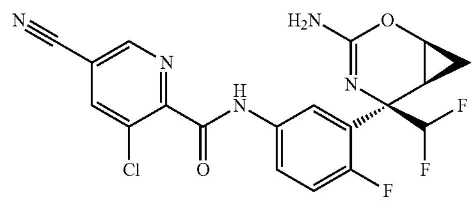 [SMILES: N#Cc1cnc(C(=O)Nc2ccc(F)c([C@]3(C(F)F)N=C(N)O[C@H]4C[C@H]43)c2)c(Cl)c1] | MS m/z = 436.0[M + H]+<br>1H NMR (400 MHz, DMSO-d6) δ ppm 0.90 (dt, J = 9.19, 6.46 Hz, 1 H) 1.09-1.15 (m, 1 H) 1.67-1.75 (m, 1 H) 3.95-4.02 (m, 1 H) 5.93 (s, 2 H) 6.19 (t, J = 55.90 Hz, 1 H) 7.26 (dd, J = 11.83, 8.90 Hz, 1 H) 7.75 (dd, J = 6.85, 2.74 Hz, 1 H) 7.83 (ddd, J = 8.75, 4.06, 2.84 Hz, 1 H) 8.81 (d, J = 1.76 Hz, 1 H) 9.11 (d, J = 1.56 Hz, 1 H) 10.95 (s, 1 H) |
| 68 | B | N-(3-(((1R,5S,6R)-3-amino-5-methyl-2-oxa-4-azabicyclo[4.1.0]hept-3-en-5-yl)-4-fluorophenyl)-5-chloropicolinamide | 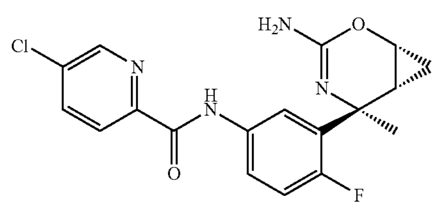 [SMILES: C[C@]1(c2cc(NC(=O)c3ccc(Cl)cn3)ccc2F)N=C(N)O[C@@H]2C[C@@H]21] | MS m/z = 375.0 [M]+<br>1H NMR (400 MHz, DMSO-d6) δ ppm 0.78 (dd, J = 8.02, 4.50 Hz, 2 H) 1.49 (s, 3 H) 1.58 (q, J = 7.82 Hz, 1 H) 3.88-3.97 (m, 1 H) 5.44 (br. s., 2 H) 7.14 (dd, J = 11.93, 8.80 Hz, 1 H) 7.75-7.80 (m, 1 H) 7.85 (dd, J = 7.43, 2.74 Hz, 1 H) 8.14 (d, J = 8.41 Hz, 1 H) 8.19 (dd, J = 8.41, 2.35 Hz, 1 H) 8.78 (d, J = 1.76 Hz, 1 H) 10.57 (s, 1 H) |
| 69 | B | N-(3-(((1R,5S,6R)-3-amino-5-(difluoromethyl)-2-oxa-4-azabicyclo[4.1.0]hept-3-en-5-yl)-4-fluorophenyl)-6-chloro-3-methylimidazo[1,2-a]pyridine-2-carboxamide | 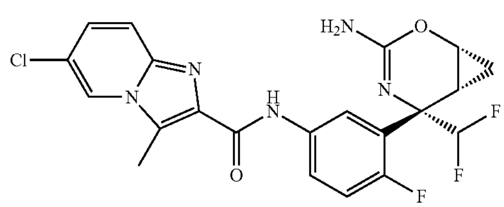 [SMILES: Cc1c(C(=O)Nc2ccc(F)c([C@@]3(C(F)F)N=C(N)O[C@@H]4C[C@@H]43)c2)nc2ccc(Cl)cn12] | MS m/z = 463.9 [M]+<br>1H NMR (400 MHz, DMSO-d6) δ ppm 0.92 (q, J = 6.80 Hz, 1 H) 1.10-1.21 (m, 1 H) 1.74 (q, J = 7.69 Hz, 1 H) 2.81 (s, 3 H) 3.99-4.07 (m, 1 H) 5.85 (s, 2 H) 6.19 (t, J = 55.90 Hz, 1 H) 7.18 (dd, J = 11.64, 9.10 Hz, 1 H) 7.42 (dd, J = 9.58, 1.37 Hz, 1 H) 7.69 (d, J = 9.59 Hz, 1 H) 7.84-7.92 (m, 1 H) 7.95-8.03 (m, 1 H) 8.68 (s, 1 H) 10.24 (s, 1 H) |
| 70 | B | N-(3-((1R,5S,6R)-3-amino-5-(difluoromethyl)-2-oxa-4-azabicyclo[4.1.0]hept-3-en-5-yl)-4-fluorophenyl)-3-chloro-5-methoxypicolinamide | 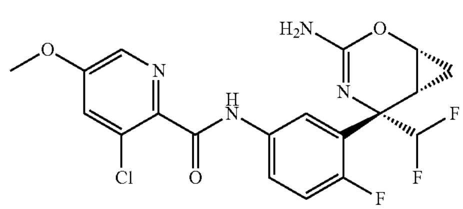 [SMILES: COc1cnc(C(=O)Nc2ccc(F)c([C@@]3(C(F)F)N=C(N)O[C@@H]4C[C@@H]43)c2)c(Cl)c1] | MS m/z = 440.8 [M]+<br>1H NMR (400 MHz, DMSO-d6) δ ppm 0.91 (dt, J = 9.24, 6.53 Hz, 1 H) 1.08-1.18 (m, 1 H) 1.67-1.76 (m, 1 H) 3.93 (s, 3 H) 3.96-4.03 (m, 1 H) 5.86 (s, 2 H) 6.19 (t, J = 56.10 Hz, 1 H) 7.17-7.24 (m, 1 H) 7.72 (d, J = 2.54 Hz, 1 H) 7.78-7.87 (m, 2 H) 8.34 (d, J = 2.54 Hz, 1 H) 10.57 (s, 1 H) |

TABLE 1-continued

| Example # | Method | Compound Name | Structure | Analytical Data |
|---|---|---|---|---|
| 71 | B | N-(3-((1R,5S,6R)-3-amino-5-(difluoromethyl)-2-oxa-4-azabicyclo[4.1.0]hept-3-en-5-yl)-4-fluorophenyl)-3,5-dichloropicolinamide | 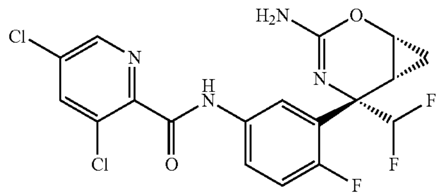 [SMILES: NC1=N[C@@](c2cc(NC(=O)c3ncc(Cl)cc3Cl)ccc2F)(C(F)F)[C@H]2C[C@H]2O1] | MS m/z = 444.8 [M]+ 1H NMR (400 MHz, DMSO-d6) δ ppm 0.90 (dt, J = 9.19, 6.46 Hz, 1 H) 1.10-1.16 (m, 1 H) 1.67-1.75 (m, 1 H) 3.96-4.01 (m, 1 H) 5.89 (s, 2 H) 6.19 (t, J = 56.10 Hz, 1 H) 7.23 (dd, J = 11.93, 8.80 Hz, 1 H) 7.77 (dd, J = 6.94, 2.64 Hz, 1 H) 7.79-7.84 (m, 1 H) 8.44 (d, J = 1.96 Hz, 1 H) 8.72 (d, J = 1.96 Hz, 1 H) 10.78 (s, 1 H) |
| 72 | B | N-(3-((1R,5S,6R)-3-amino-5-(difluoromethyl)-2-oxa-4-azabicyclo[4.1.0]hept-3-en-5-yl)-4-fluorophenyl)-5-methoxypyrazine-2-carboxamide | 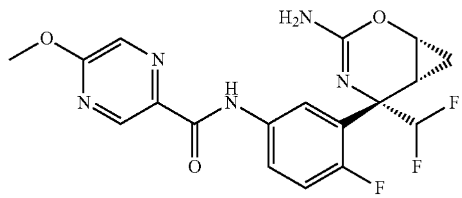 [SMILES: COc1cnc(C(=O)Nc2ccc(F)c([C@@]3(C(F)F)N=C(N)O[C@@H]4C[C@@H]43)c2)cn1] | MS m/z = 407.9 [M]+ 1H NMR (400 MHz, DMSO-d6) δ ppm 0.91 (dt, J = 9.29, 6.50 Hz, 1 H) 1.12-1.18 (m, 1 H) 1.69-1.76 (m, 1 H) 4.02 (s, 3 H) 3.99-4.05 (m, 1 H) 5.85 (s, 2 H) 6.19 (t, J = 56.10 Hz, 1 H) 7.21 (dd, J = 11.74, 8.80 Hz, 1 H) 7.85 (ddd, J = 8.80, 4.11, 2.93 Hz, 1 H) 8.03 (dd, J = 7.04, 2.74 Hz, 1 H) 8.41 (d, J = 1.37 Hz, 1 H) 8.89 (d, J = 1.17 Hz, 1 H) 10.52 (s, 1 H) |
| 73 | B | N-(5-([1(R,S),5(S,R),6(R,S)]-3-amino-5-(difluoromethyl)-2-oxa-4-azabicyclo[4.1.0]hept-3-en-5-yl)-6-fluoropyridin-3-yl)-5-chloropicolinamide | 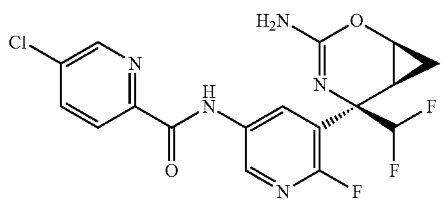 [SMILES: NC1=N[C@](c2cc(NC(=O)c3ccc(Cl)cn3)cnc2F)(C(F)F)[C@@H]2C[C@@H]2O1] | MS m/z = 411.8 [M]+ 1H NMR (400 MHz, CHLOROFORM-d) δ ppm 1.05 (dt, J = 9.44, 6.92 Hz, 1 H) 1.41-1.47 (m, 1 H) 1.92 (dt, J = 9.73, 7.16 Hz, 1 H) 4.02 (td, J = 6.75, 2.74 Hz, 1 H) 4.84 (br. s., 2 H) 6.19 (t, J = 55.40 Hz, 1 H) 7.90 (dd, J = 8.41, 2.35 Hz, 1 H) 8.24 (d, J = 8.41 Hz, 1 H) 8.37 (dd, J = 8.41, 2.60 Hz, 1 H) 8.58 (d, J = 1.96 Hz, 1 H) 8.71 (t, J = 2.15 Hz, 1 H) 9.89 (s, 1 H) |
| 74 | B | N-(3-((1R,5S,6R)-3-amino-5-(difluoromethyl)-2-oxa-4-azabicyclo[4.1.0]hept-3-en-5-yl)-4-fluorophenyl)-5-bromopicolinamide | 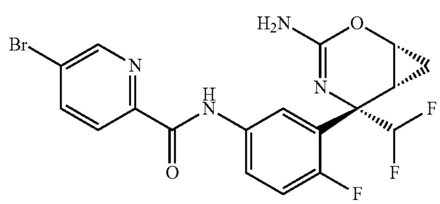 | MS m/z = 454.7 [M]+ 1H NMR (400 MHz, DMSO-d6) δ ppm 0.92 (dt, J = 9.24, 6.53 Hz, 1 H) 1.12-1.18 (m, 1 H) 1.69-1.78 (m, 1 H) 3.99-4.05 (m, 1 H) 5.86 (s, 2 H) 6.19 (t, J = 56.10 Hz, 1 H) 7.22 (dd, J = 11.84, 8.90 Hz, 1 H) 7.84-7.90 (m, 1 H) 8.03 (dd, J = 7.04, 2.74 Hz, 1 H) 8.08 (d, J = 8.22 Hz, 1 H) 8.32 (dd, J = 8.41, 2.35 Hz, 1 H) 8.86 (d, J = 2.15 Hz, 1 H) 10.69 (s, 1 H) |
| 75 | B | N-(5-([1(R,S),5(S,R),6(R,S)]-3-amino-5-(difluoromethyl)-2-oxa-4-azabicyclo[4.1.0]hept-3-en-5-yl)-6-fluoropyridin-3-yl)-5-cyanopicolinamide | 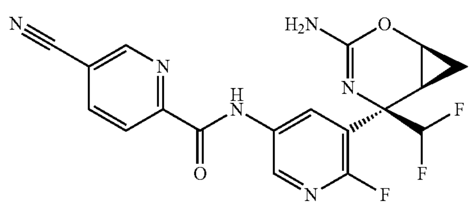 [SMILES: N#Cc1ccc(C(=O)Nc2cnc(F)c([C@]3(C(F)F)N=C(N)O[C@H]4C[C@H]43)c2)nc1] | MS m/z = 402.9 [M]+ 1H NMR (400 MHz, CHLOROFORM-d) δ ppm 1.03 (dt, J = 9.54, 6.97 Hz, 1 H) 1.40-1.46 (m, 1 H) 1.89 (dt, J = 9.68, 7.09 Hz, 2 H) 3.98 (td, J = 6.80, 2.54 Hz, 1 H) 4.71 (br. s., 2 H) 6.18 (t, J = 55.80 Hz, 1 H) 8.22 (dd, J = 8.22, 1.96 Hz, 1 H) 8.34 (dd, J = 8.41, 2.74 Hz, 1 H) 8.42 (dd, J = 8.10, 0.60 Hz, 1 H) 8.69-8.72 (m, 1 H) 8.90 (dd, J = 1.70, 0.70 Hz, 1 H) 9.87 (s, 1 H) |
| 76 | B | N-(3-((1R,5S,6R)-3-amino-5-(difluoromethyl)-2-oxa-4-azabicyclo[4.1.0]hept-3-en-5-yl)-4-fluorophenyl)-5-chloropicolinamide | 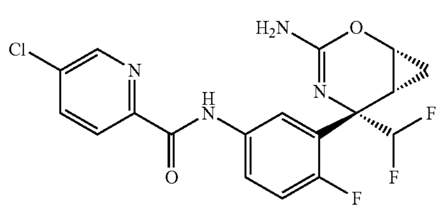 [SMILES: NC1=N[C@@](c2cc(NC(=O)c3ccc(Cl)cn3)ccc2F)(C(F)F)[C@H]2C[C@H]2O1] | MS m/z = 410.9 [M]+ 1H NMR (400 MHz, CHLOROFORM-d) δ ppm 0.92-1.00 (m, 1 H) 1.39-1.46 (m, 1 H) 1.87 (dt, J = 9.44, 7.12 Hz, 1 H) 3.90-3.95 (m, 1 H) 4.82 (br. s., 2 H) 6.24 (t, J = 56.10 Hz, 1 H) 7.04 (dd, J = 11.44, 8.90 Hz, 1 H) 7.63 (dd, J = 6.65, 2.74 Hz, 1 H) 7.85 (dd, J = 8.41, 2.35 Hz, 1 H) 7.95 (ddd, J = 8.80, 4.11, 2.93 Hz, 1 H) 8.18 (d, J = 8.41 Hz, 1 H) 8.46 (d, J = 2.15 Hz, 1 H) 9.72 (s, 1 H) |

TABLE 1-continued

| Example # | Method | Compound Name | Structure | Analytical Data |
|---|---|---|---|---|
| 77 | B | N-(3-((1R,5S,6R)-3-amino-5-(difluoromethyl)-2-oxa-4-azabicyclo[4.1.0]hept-3-en-5-yl)-4-fluorophenyl)-5-cyanopicolinamide | 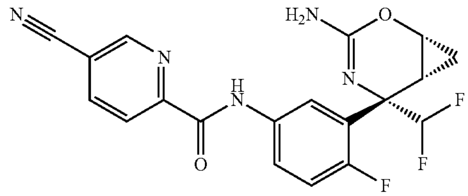 [SMILES: N#Cc1ccc(C(=O)Nc2ccc(F)c([C@@]3(C(F)F)N=C(N)O[C@@H]4C[C@@H]43)c2)nc1] | MS m/z = 402.0 [M + H]+<br>1H NMR (400 MHz, DMSO-d6) δ ppm 0.92 (dt, J = 9.19, 6.46 Hz, 1 H) 1.12-1.18 (m, 1 H) 1.73 (dt, J = 9.24, 6.92 Hz, 1 H) 3.99-4.06 (m, 1 H) 5.89 (s, 2 H) 6.20 (t, J = 55.90 Hz, 1 H) 7.24 (dd, J = 11.74, 8.80 Hz, 1 H) 7.88 (ddd, J = 8.80, 4.11, 2.74 Hz, 1 H) 8.06 (dd, J = 7.04, 2.74 Hz, 1 H) 8.28 (dd, J = 8.30, 0.80 Hz, 1 H) 8.59 (dd, J = 8.12, 2.05 Hz, 1 H) 9.21 (dd, J = 2.00, 0.78 Hz, 1 H) 10.88 (s, 1 H) |
| 78 | B | N-(3-((1S,5R,6S)-3-amino-5-(fluoromethyl)-2-oxa-4-azabicyclo[4.1.0]hept-3-en-5-yl)-2,4-difluorophenyl)-5-methoxypicolinamide | 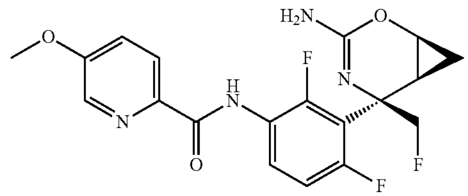 [SMILES: COc1ccc(C(=O)Nc2ccc(F)c([C@]3(CF)N=C(N)O[C@H]4C[C@H]43)c2F)nc1] | MS m/z = 406..9 [M]+<br>$^1$H NMR (300 MHz, DMSO-$d_6$) δ ppm 0.80-0.98 (m, 2 H) 1.50-1.61 (m, 1 H) 3.94 (s, 3 H) 4.09-4.15 (m, 1 H) 4.27-4.97 (m, 2 H) 5.55 (s, 2 H) 7.04-7.14 (m, 1 H) 7.63 (dd, J = 8.77, 2.92 Hz, 1 H) 8.03-8.10 (m, 1 H) 8.13 (d, J = 8.92 Hz, 1 H) 8.44 (d, J = 2.78 Hz, 1 H) 10.00-10.30 (m, 1 H) 10.14 (d, J = 2.19 Hz, 1 H). |
| 79 | A | N-(3-((1R,5S,6R)-3-amino-5-(fluoromethyl)-2-oxa-4-azabicyclo[4.1.0]hept-3-en-5-yl)-2,4-difluorophenyl)-5-methoxypicolinamide | 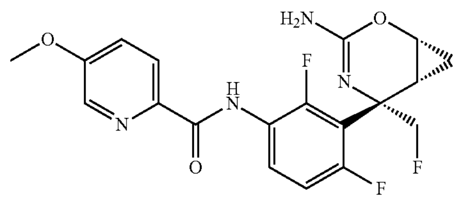 [SMILES: COc1ccc(C(=O)Nc2ccc(F)c([C@@]3(CF)N=C(N)O[C@@H]4C[C@@H]43)c2F)nc1] | MS m/z = 406.9 [M]+<br>$^1$H NMR (300 MHz, DMSO-$d_6$) δ ppm 0.81-0.98 (m, 2 H) 1.47-1.65 (m, 1 H) 3.94 (s, 3 H) 4.05-4.17 (m, 1 H) 4.28-4.97 (m, 2 H) 5.56 (s, 2 H) 7.04-7.14 (m, 1 H) 7.63 (dd, J = 8.77, 2.78 Hz, 1 H) 8.00-8.00 (m, 1 H) 8.02-8.11 (m, 1 H) 8.13 (d, J = 8.77 Hz, 1 H) 8.44 (d, J = 2.48 Hz, 1 H) 10.14 (s, 1 H). |
| 80 | A | N-(3-((1R,5S,6R)-3-amino-5-(methoxymethyl)-2-oxa-4-azabicyclo[4.1.0]hept-3-en-5-yl)-4-fluorophenyl)-5-methoxypyrazine-2-carboxamide | 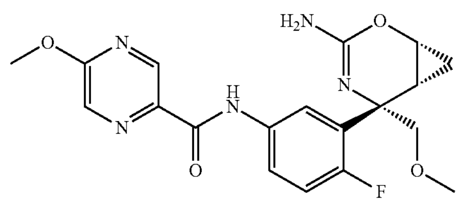 | MS m/z = 401.9 [M]+<br>$^1$H NMR (400 MHz, DMSO-$d_6$) δ ppm 0.78 (dt, J = 9.63, 6.33 Hz, 1 H) 0.88-0.96 (m, 1 H) 1.49-1.61 (m, 1 H) 3.23 (s, 3 H) 3.48-3.75 (m, 2 H) 3.98-4.04 (m, 4 H) 5.42 (s, 2 H) 7.08 (dd, J = 11.93, 8.80 Hz, 1 H) 7.76 (dt, J = 8.66, 3.40 Hz, 1 H) 7.95 (dd, J = 7.34, 2.64 Hz, 1 H) 8.41 (d, J = 1.37 Hz, 1 H) 8.89 (d, J = 1.17 Hz, 1 H) 10.43 (s, 1 H). |
| 81 | A | N-(3-((1S,5R,6S)-3-amino-5-(methoxymethyl)-2-oxa-4-azabicyclo[4.1.0]hept-3-en-5-yl)-4-fluorophenyl)-5-methoxypyrazine-2-carboxamide | 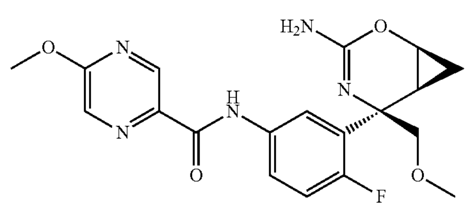 | MS m/z = 401.9 [M]+<br>$^1$H NMR (400 MHz, DMSO-$d_6$) δ ppm 0.80-0.89 (m, 1 H) 0.95-1.03 (m, 1 H) 1.56-1.69 (m, 1 H) 3.29 (s, 3 H) 3.54-3.82 (m, 2 H) 4.02-4.13 (m, 4 H) 5.48 (s, 2 H) 7.15 (dd, J = 11.93, 8.80 Hz, 1 H) 7.76-7.87 (m, 1 H) 8.01 (dd, J = 7.34, 2.64 Hz, 1 H) 8.47 (d, J = 1.37 Hz, 1 H) 8.95 (d, J = 1.17 Hz, 1 H) 10.49 (s, 1 H). |
| 82 | A | N-(3-((1R,5S,6R)-3-amino-5-(methoxymethyl)-2-oxa-4-azabicyclo[4.1.0]hept-3-en-5-yl)-4-fluorophenyl)-5-chloropicolinamide | 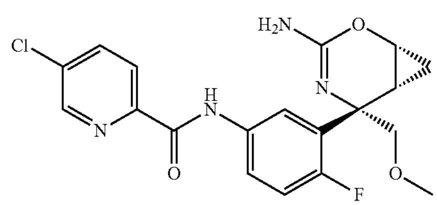 [SMILES: COC[C@]1(c2cc(NC(=O)c3ccc(Cl)cn3)ccc2F)N=C(N)O[C@@H]2C[C@@H]21] | MS m/z = 404.9 [M]+<br>$^1$H NMR (400 MHz, DMSO-$d_6$) δ ppm 0.71-0.86 (m, 1 H) 0.88-0.98 (m, 1 H) 1.51-1.65 (m, 1 H) 3.24 (s, 3 H) 3.53 (d, J = 9.78 Hz, 1 H) 3.72 (d, J = 9.19 Hz, 1 H) 4.02 (br. s., 1 H) 5.43 (br. s., 2 H) 7.10 (t, J = 10.37 Hz, 1 H) 7.79 (br. s., 1 H) 7.96 (d, J = 6.85 Hz, 1 H) 8.10-8.27 (m, 2 H) 8.79 (s, 1 H) 10.61 (s, 1 H). |

TABLE 1-continued

| Example # | Method | Compound Name | Structure | Analytical Data |
|---|---|---|---|---|
| 83 | A | N-(3-((1S,5R,6S)-3-amino-5-(methoxymethyl)-2-oxa-4-azabicyclo[4.1.0]hept-3-en-5-yl)-4-fluorophenyl)-5-chloropicolinamide | 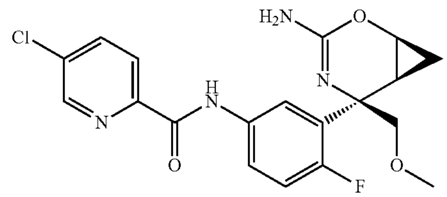 [SMILES: COC[C@@]1(c2cc(NC(=O)c3ccc(Cl)cn3)ccc2F)N=C(N)O[C@H]2C[C@H]21] | MS m/z = 404.9 [M]+<br>1H NMR (400 MHz, DMSO-d$_6$) δ ppm 0.73-0.98 (m, 2 H) 1.51-1.64 (m, 1 H) 3.24 (s, 3 H) 3.48-3.60 (m, 1 H) 3.72 (d, J = 8.80 Hz, 1 H) 4.02 (br. s., 1 H) 5.43 (br. s., 2 H) 7.10 (t, J = 9.78 Hz, 1 H) 7.78 (br. s., 1 H) 7.96 (d, J = 7.24 Hz, 1 H) 8.18 (q, J = 8.15 Hz, 2 H) 8.79 (s, 1 H) 10.61 (s, 1 H). |
| 84 | A | N-(3-((1R,5S,6R)-3-amino-5-(difluoromethyl)-2-oxa-4-azabicyclo[4.1.0]hept-3-en-5-yl)-4-fluorophenyl)-3,5-dimethoxypyrazine-2-carboxamide | 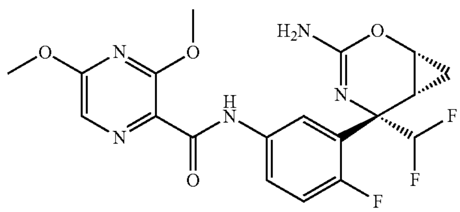 [SMILES: COc1cnc(C(=O)Nc2ccc(F)c([C@@]3(C(F)F)N=C(N)O[C@@H]4C[C@@H]43)c2)c(OC)n1] | MS m/z = 437.9 [M]+<br>$^1$H NMR (300 MHz, DMSO-d$_6$) δ ppm 0.90-1.03 (m, 1 H) 1.20 (br. s., 1 H) 1.72-1.84 (m, 1 H) 4.07 (d, J = 3.80 Hz, 7 H) 5.82 (s, 2 H) 6.25 (dt, J = 56.42, 1.00 Hz, 1 H) 7.25 (dd, J = 11.91, 8.70 Hz, 1 H) 7.82-7.94 (m, 1 H) 8.00 (s, 1 H) 10.36 (s, 1 H). |
| 85 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-methoxypyrazine-2-carboxamide | 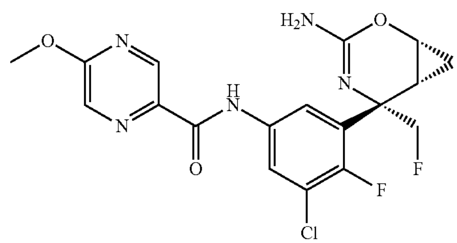 [SMILES: COc1cnc(C(=O)Nc2cc(Cl)c(F)c([C@@]3(CF)N=C(N)O[C@@H]4C[C@@H]43)c2)cn1] | MS m/z = 423.9 [M]+<br>$^1$H NMR (300 MHz, DMSO-d$_6$) δ ppm 0.77-0.93 (m, 1 H) 0.93-1.06 (m, 1 H) 1.47-1.66 (m, 1 H) 3.95-4.14 (m 4 H) 4.31-4.79 (m, 2 H) 5.67 (s, 2 H) 8.02 (d, J = 4.24 Hz, 1 H) 8.11 (d, J = 6.10 Hz, 1 H) 8.42 (s, 1 H) 8.90 (s, 1 H) 10.71 (s, 1 H). |
| 86 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-cyano-3-methoxypicolinamide | 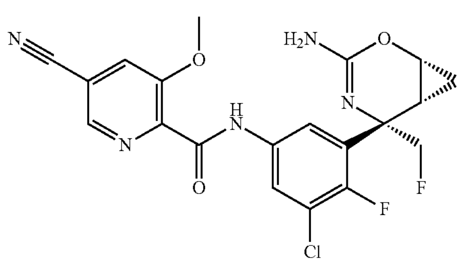 [SMILES: COc1cc(C#N)cnc1C(=O)Nc1cc(Cl)c(F)c([C@@]2(CF)N=C(N)O[C@@H]3C[C@@H]32)c1] | MS m/z = 447.8 [M]+<br>$^1$H NMR (300 MHz, DMSO-d$_6$) δ ppm 0.78-0.90 (m, 1 H) 0.93-1.03 (m, 1 H) 1.46-1.60 (m, 1 H) 3.93 (s, 3 H) 4.02 (br. s., 1 H) 4.38-4.71 (m, 2 H) 5.70 (s, 2 H) 7.67 (d, J = 5.99 Hz, 1 H) 8.07 (d, J = 4.82 Hz, 1 H) 8.23 (s, 1 H) 8.68 (s, 1 H) 10.86 (s, 1 H). |
| 87 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-(difluoromethoxy)-3-methylpicolinamide | 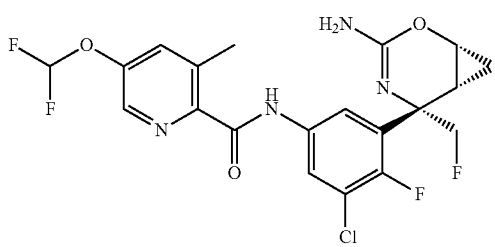 [SMILES: Cc1cc(OC(F)F)cnc1C(=O)Nc1cc(Cl)c(F)c([C@@]2(CF)N=C(N)O[C@@H]3C[C@@H]32)c1] | MS m/z = 472.8 [M]+<br>$^1$H NMR (300 MHz, DMSO-d$_6$) δ ppm 0.85-0.98 (m, 1 H) 0.99-1.11 (m, 1 H) 1.61 (q, J = 8.04 Hz, 1 H) 2.66 (s, 3 H) 4.11 (br. s., 1 H) 4.42-4.83 (m, 2 H) 5.74 (s, 2 H) 7.45 (t, J = 71.90 Hz, 1 H) 7.79 (s, 1 H) 7.90 (d, J = 3.80 Hz, 1 H) 8.19 (d, J = 6.14 Hz, 1 H) 8.50 (s, 1 H) 10.78 (s, 1 H). |
| 88 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-cyanopicolinamide | 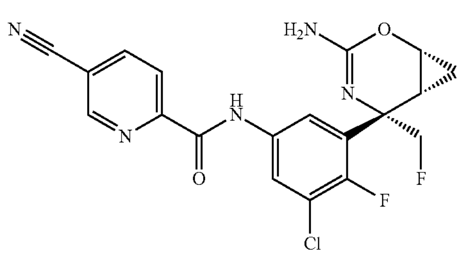 [SMILES: N#Cc1ccc(C(=O)Nc2cc(Cl)c(F)c([C@@]3(CF)N=C(N)O[C@@H]4C[C@@H]43)c2)nc1] | MS m/z = 417.9 [M]+<br>$^1$H NMR (300 MHz, DMSO-d$_6$) δ ppm 0.78-0.93 (m, 1 H) 0.93-1.05 (m, 1 H) 1.48-1.64 (m, 1 H) 4.00-4.13 (m, 1 H) 4.35-4.78 (m, 2 H) 5.68 (s, 2 H) 8.05 (d, J = 7.45 Hz, 1 H) 8.14 (d, J = 5.70 Hz, 1 H) 8.29 (d, J = 8.04 Hz, 1 H) 8.59 (d, J = 8.04 Hz, 1 H) 9.21 (s, 1 H) 11.03 (s, 1 H). |

TABLE 1-continued

| Example # | Method | Compound Name | Structure | Analytical Data |
|---|---|---|---|---|
| 89 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-methoxy-3-methylpyrazine-2-carboxamide | 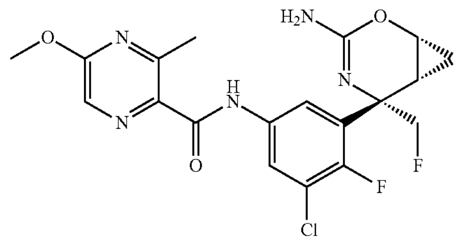 [SMILES: COc1cnc(C(=O)Nc2cc(Cl)c(F)c([C@@]3(CF)N=C(N)O[C@@H]4C[C@@H]43)c2)c(C)n1] | MS m/z = 437.9 [M]+ $^1$H NMR (300 MHz, DMSO-d$_6$) δ ppm 0.79-0.91 (m, 1 H) 0.92-1.06 (m, 1 H) 1.46-1.65 (m, 1 H) 4.00 (s, 3 H) 4.02-4.10 (m, 1 H) 4.36-4.76 (m, 2 H) 5.67 (s, 2 H) 7.86 (d, J = 5.70 Hz, 1 H) 8.12 (d, J = 6.58 Hz, 1 H) 8.25 (s, 1 H) 10.63 (s, 1 H). |
| 90 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-(2,2,2-trifluoroethoxy)pyrazine-2-carboxamide | 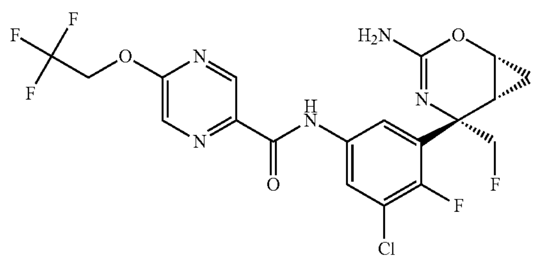 [SMILES: NC1=N[C@](CF)(c2cc(NC(=O)c3cnc(OCC(F)(F)F)cn3)cc(Cl)c2F)[C@H]2C[C@H]2O1] | MS m/z = 491.9 [M]+ $^1$H NMR (300 MHz, DMSO-d$_6$) δ ppm 0.79-0.92 (m, 1 H) 0.93-1.05 (m, 1 H) 1.48-1.63 (m, 1 H) 3.99-4.13 (m, 1 H) 4.36-4.79 (m, 2 H) 5.17 (q, J = 8.82 Hz, 2 H) 5.67 (s, 2 H) 8.04 (d, J = 5.99 Hz, 1 H) 8.12 (d, J = 5.70 Hz, 1 H) 8.63 (s, 1 H) 8.93 (s, 1 H) 10.80 (s, 1 H). |
| 91 | A | N-(3-((1R,5S,6R)-3-amino-5-(fluoromethyl)-2-oxa-4-azabicyclo[4.1.0]hept-3-en-5-yl)-5-chloro-4-fluorophenyl)-5-cyano-3-methylpicolinamide | 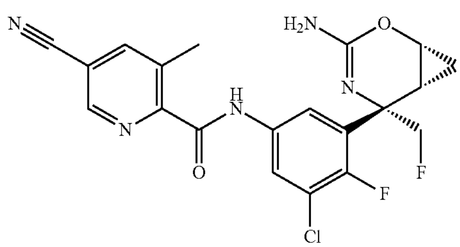 [SMILES: Cc1cc(C#N)cnc1C(=O)Nc1cc(Cl)c(F)c([C@@]2(CF)N=C(N)O[C@@H]3C[C@@H]32)c1] | MS m/z = 431.9 [M]+ $^1$H NMR (300 MHz, DMSO-d$_6$) δ ppm 0.79-0.92 (m, 1 H) 0.93-1.06 (m, 1 H) 1.46-1.63 (m, 1 H) 2.56 (s, 3 H) 3.98-4.10 (m, 1 H) 4.38-4.75 (m, 2 H) 5.69 (s, 2 H) 7.81 (br. s., 1 H) 8.11 (d, J = 4.38 Hz, 1 H) 8.41 (s, 1 H) 8.99 (s, 1 H) 10.91 (s, 1 H). |
| 92 | B | N-(3-((1S,5R,6S)-3-amino-5-(difluoromethyl)-2-oxa-4-azabicyclo[4.1.0]hept-3-en-5-yl)-4-chlorophenyl)-5-chloropicolinamide | 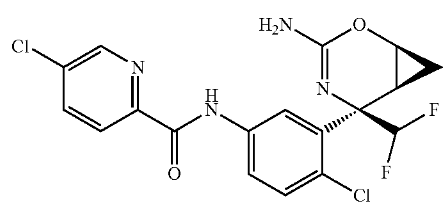 [SMILES: NC1=N[C@](c2cc(NC(=O)c3ccc(Cl)cn3)ccc2Cl)(C(F)F)[C@@H]2C[C@@H]2O1] | MS m/z = 427.0 [M + H]+ H NMR (400 MHz, DMSO-d6) d ppm 10.74 (br. s., 1 H) 8.78-8.80 (m, 1 H) 8.14-8.26 (m, 3 H) 7.92 (dd, J = 8.71, 2.64 Hz, 1 H) 7.44-7.50 (m, 1 H) 6.85-6.88 (m, 1 H) 6.70-6.75 (m, 1 H) 6.57-6.60 (m, 1 H) 5.81-5.89 (m, 2 H) 3.98 (t, J = 7.14 Hz, 1 H) 1.85-1.93 (m, 1 H) 1.07-1.15 (m, 1 H) 0.91-1.00 (m, 1 H) |
| 93 | B | N-(3-((1R,5S,6R)-3-amino-5-(difluoromethyl)-2-oxa-4-azabicyclo[4.1.0]hept-3-en-5-yl)-4-chlorophenyl)-5-cyanopicolinamide | 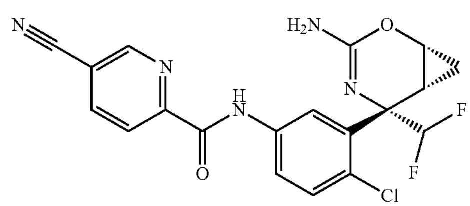 [SMILES: N#Cc1ccc(C(=O)Nc2ccc(Cl)c([C@@]3(C(F)F)N=C(N)O[C@@H]4C[C@@H]43)c2)nc1] | MS m/z = 418.0 [M + H]+ 1H NMR (400 MHz, CHLOROFORM-d) d ppm 9.64-9.71 (m, 1 H) 8.94-8.96 (m, 1 H) 8.94 (s, 1 H) 7.94-8.01 (m, 1 H) 7.69-7.74 (m, 1 H) 7.06-7.13 (m, 1 H) 6.38 (s, 1 H) 6.24 (s, 1 H) 6.10 (s, 1 H) 3.91-3.96 (m, 1 H) 1.83-1.91 (m, 1 H) 1.40-1.46 (m, 1 H) 0.93-1.01 (m, 1 H) |
| 94 | B | N-(3-((1S,5R,6S)-3-amino-5-(difluoromethyl)-2-oxa-4-azabicyclo[4.1.0]hept-3-en-5-yl)-4-chlorophenyl)-5-cyanopicolinamide | 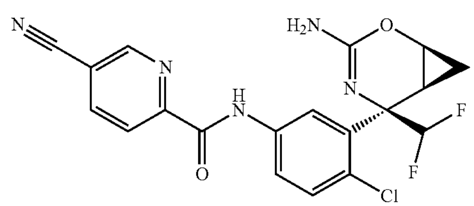 [SMILES: N#Cc1ccc(C(=O)Nc2ccc(Cl)c([C@]3(C(F)F)N=C(N)O[C@H]4C[C@H]43)c2)nc1] | MS m/z = 418.0 [M + H]+ 1H NMR (400 MHz, CHLOROFORM-d) d ppm 9.64-9.71 (m, 1 H) 8.94-8.96 (m, 1 H) 8.94 (s, 1 H) 7.94-8.01 (m, 1 H) 7.69-7.74 (m, 1 H) 7.06-7.13 (m, 1 H) 6.38 (s, 1 H) 6.24 (s, 1 H) 6.10 (s, 1 H) 3.91-3.96 (m, 1 H) 1.83-1.91 (m, 1 H) 1.40-1.46 (m, 1 H) 0.93-1.01 (m, 1 H) |

| Example # | Method | Compound Name | Structure | Analytical Data |
|---|---|---|---|---|
| 95 | B | N-(3-(((1R,5S,6R)-3-amino-5-(difluoromethyl)-2-oxa-4-azabicyclo[4.1.0]hept-3-en-5-yl)-4-fluorophenyl)-5-(prop-2-yn-1-yloxy)pyrazine-2-carboxamide trifluoroacetate | 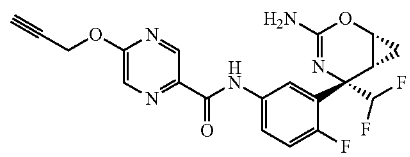 [SMILES: C#CCOc1cnc(C(=O)Nc2ccc(F)c([C@@]3(C(F)F)N=C(N)O[C@@H]4C[C@@H]43)c2)cn1] | MS m/z = 431.0 [M]+ <br> 1H NMR (400 MHz, DMSO-d6): δ 10.85 (s, 1 H), 10.70 (br s, 1 H), 9.47 (br s, 1 H), 8.93 (d, J = 1.4 Hz, 1 H), 8.52 (d, J = 1.4 Hz, 1 H), 8.24 (br s, 1 H), 8.18 (dd, J = 7.2, 2.5 Hz, 1 H), 7.96-8.07 (m, 1 H), 7.44 (dd, J = 11.9, 9.0 Hz, 1 H), 6.58-6.93 (m, 1 H), 5.12-5.22 (m, 2 H), 4.69 (br s, 1 H), 3.62-3.71 (m, 1 H), 2.04-2.19 (m, 1 H), 1.63 (br s, 1 H), 1.30 (q, J = 7.9 Hz, 1 H); 19F NMR (377 MHz, DMSO-d6): δ −73.76 (s, 3 F), −117.16 (s, 1 F), −126.50 (d, J = 279 Hz, 1 F), −128.54 (d, J = 279 Hz, 1 F). |
| 96 | B | N-(3-((1R,5S,6R)-3-amino-5-(difluoromethyl)-2-oxa-4-azabicyclo[4.1.0]hept-3-en-5-yl)-4-fluorophenyl)-5-(but-2-yn-1-yloxy)pyrazine-2-carboxamide trifluoroacetate | 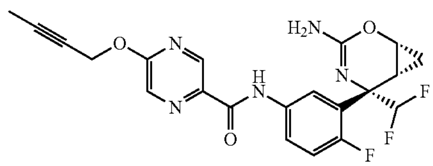 [SMILES: CC#CCOc1cnc(C(=O)Nc2ccc(F)c([C@@]3(C(F)F)N=C(N)O[C@@H]4C[C@@H]43)c2)cn1] | MS m/z = 446.0 [M + H]+ <br> 1H NMR (400 MHz, DMSO-d6): d 10.83 (s, 1 H), 10.77 (br s, 1 H), 9.45 (br s, 1 H), 8.92 (d, J = 1.2 Hz, 1 H), 8.49 (d, J = 1.2 Hz, 1 H), 8.37 (br s, 1 H), 8.18 (dd, J = 7.1, 2.4 Hz, 1 H), 8.02 (m, 1 H), 7.44 (dd, J = 11.9, 9.0 Hz, 1 H), 6.74 (t, J = 51 Hz, 1 H), 5.12 (q, J = 2.2 Hz, 2 H), 4.68 (br s, 1 H), 2.12 (q, J = 8.1 Hz, 1 H), 1.87 (t, J = 2.3 Hz, 3 H), 1.63 (t, J = 6.3 Hz, 1 H), 1.30 (q, J = 8.1 Hz, 1 H); 19F NMR (377 MHz, DMSO-d6): d −73.82 (s, 3 F), −117.20 (br s, 1 F), −126.48 (d, J = 287 Hz, 1 F), −128.55 (d, J = 287 Hz, 1 F). |
| 97 | B | N-(3-(((1R,S), (5S,R), (6R,S))-3-amino-5-(difluoromethyl)-2-oxa-4-azabicyclo[4.1.0]hept-3-en-5-yl)-4-chlorophenyl)-5-chloropicolinamide trifluoroacetate | 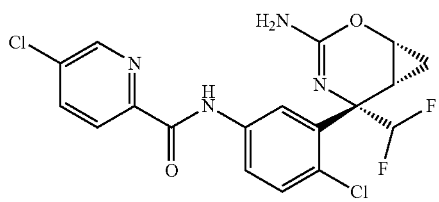 [SMILES: NC1=N[C@@](c2cc(NC(=O)c3ccc(Cl)cn3)ccc2Cl)(C(F)F)[C@H]2C[C@H]2O1] | MS m/z = 427.0 [M + H]+ <br> 1H NMR (400 MHz, CD3OD): d 8.75 (d, J = 2.2 Hz, 1 H), 8.43 (d, J = 2.3 Hz, 1 H), 8.24 (d, J = 8.4 Hz, 1 H), 8.12 (dd, J = 8.4, 2.3 Hz, 1 H), 7.87 (dd, J = 8.7, 2.4 Hz, 1 H), 7.64 (d, J = 8.8 Hz, 1 H), 7.11 (t, J = 54.8 Hz, 1 H), 4.61 (td, J = 6.7, 2.5 Hz, 1 H), 2.45 (dt, J = 9.8, 7.2 Hz, 1 H), 1.66 (t, J = 7.7 Hz, 1 H), 1.42 (ddd, J = 9.9, 8.3, 6.5 Hz, 1 H); 19F NMR (377 MHz, CD3OD): d −76.95 (br s, 3 F), −127.45 (d, J = 280.1 Hz, 1 F), −129.82 (d, J = 281.9 Hz, 1 F). |
| 98 | B | N-(3-(((1R,S), (5S,R), (6R,S))-3-amino-5-(difluoromethyl)-2-oxa-4-azabicyclo[4.1.0]hept-3-en-5-yl)-4-chlorophenyl)-5-cyanopicolinamide trifluoroacetate | 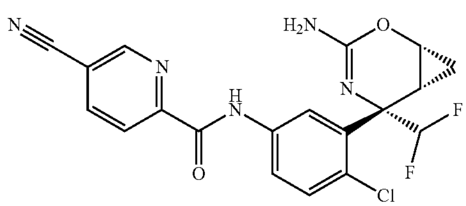 [SMILES: N#Cc1ccc(C(=O)Nc2ccc(Cl)c([C@@]3(C(F)F)N=C(N)O[C@@H]4C[C@@H]43)c2)nc1] | MS m/z = 418.0 [M + H]+ <br> 1H NMR (400 MHz, CD3OD): d 9.09 (dd, J = 2.0, 0.8 Hz, 1 H), 8.43-8.50 (m, 2 H), 8.37-8.42 (m, 1 H), 7.90 (dd, J = 8.6, 2.5 Hz, 1 H), 7.66 (d, J = 8.6 Hz, 1 H), 7.11 (t, J = 54.8 Hz, 1 H), 4.62 (td, J = 6.7, 2.7 Hz, 1 H), 2.45 (dt, J = 9.9, 7.2 Hz, 1 H), 1.66 (t, J = 7.7 Hz, 1 H), 1.43 (ddd, J = 9.9, 8.3, 6.3 Hz, 1 H); 19F NMR (377 MHz, CD3OD): d −76.97 (br s, 3 F), −127.42 (d, J = 283.1 Hz, 1 F), −129.82 (d, J = 284.3 Hz, 1 F). |
| 99 | B | N-(3-((1R,5S,6R)-3-amino-5-(difluoromethyl)-2-oxa-4-azabicyclo[4.1.0]hept-3-en-5-yl)-4-chlorophenyl)-5-chloropicolinamide | 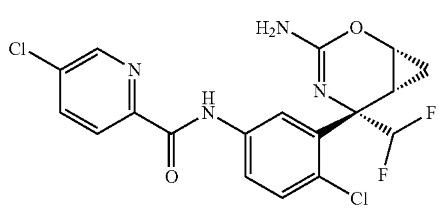 [SMILES: NC1=N[C@@](c2cc(NC(=O)c3ccc(Cl)cn3)ccc2Cl)(C(F)F)[C@H]2C[C@H]2O1] | MS m/z = 426.8 [M]+ <br> 1H NMR (400 MHz, DMSO-d6) d ppm 10.75 (s, 1 H) 8.78-8.80 (m, 1 H) 8.14-8.25 (m, 3 H) 7.91 (br. s., 1 H) 7.44-7.50 (m, 1 H) 6.87 (s, 1 H) 6.73 (s, 1 H) 6.57-6.60 (m, 1 H) 5.82-5.87 (m, 2 H) 3.95-4.02 (m, 1 H) 1.85-1.93 (m, 1 H) 1.07-1.14 (m, 1 H) 0.91-0.99 (m, 1 H) |

TABLE 1-continued

| Example # | Method | Compound Name | Structure | Analytical Data |
|---|---|---|---|---|
| 100 | A | N-(3-((1R,5S,6R)-3-amino-5-(difluoromethyl)-2-oxa-4-azabicyclo[4.1.0]hept-3-en-5-yl)-4-chlorophenyl)-5-methoxypicolinamide | 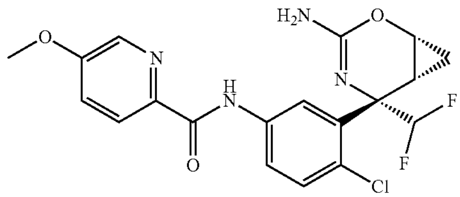 | MS m/z = 422.9 [M]+<br>1H NMR (400 MHz, CDCl3): δ 9.82 (s, 1H), 8.20 (s, 1H), 8.17-8.19 (m, 1H), 8.01 (dd, J = 2.74, 8.61 Hz, 1H), 7.78 (d, J = 2.74 Hz, 1H), 7.28-7.39 (m, 2H), 6.83 (t, J = 55.95 Hz, 1H), 4.70 (br. s., 2H), 3.94 (s, 3H), 3.82-3.90 (m, 1H), 2.08 (td, J = 7.14, 9.78 Hz, 1H), 1.38 (t, J = 7.04 Hz, 1H), 0.91-1.03 (m, 1H); 19F NMR (377 MHz, CDCl3): δ −126.39 (d, J = 278.35 Hz, 1F), −129.09 (d, J = 278.40 Hz, 1F). |
| 101 | A | N-(3-((1R,5S,6R)-3-amino-5-(difluoromethyl)-2-oxa-4-azabicyclo[4.1.0]hept-3-en-5-yl)-4-chlorophenyl)-5-methoxy-3-methylpicolinamide | 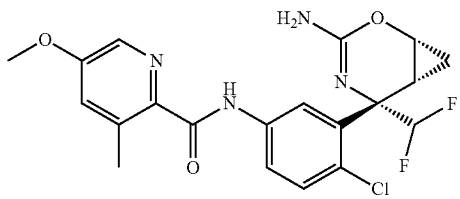 [SMILES: COc1cnc(C(=O)Nc2ccc(Cl)c([C@@]3(C(F)F)N=C(N)O[C@@H]4C[C@@H]43)c2)c(C)c1] | MS m/z = 437.0 [M + H]+<br>1H NMR (400 MHz, CDCl3): δ 10.04 (s, 1H), 8.04 (d, J = 8.79 Hz, 1H), 8.00 (s, 1H), 7.64 (d, J = 2.54 Hz, 1H), 7.30 (d, J = 8.80 Hz, 1H), 7.05 (d, J = 2.35 Hz, 1H), 6.82 (t, J = 55.95 Hz, 1H), 4.79 (br. s., 2H), 3.92 (s, 3H), 3.82-3.89 (m, 1H), 2.77 (s, 3H), 2.09 (td, J = 7.19, 9.68 Hz, 1H), 1.38 (t, J = 7.04 Hz, 1H), 0.97 (td, J = 6.82, 9.63 Hz, 1H); 19F NMR (377 MHz, CDCl3): δ −126.34 (d, J = 278.40 Hz, 1F), −129.10 (d, J = 278.30 Hz, 1F) |
| 102 | B | N-(3-((1R,5S,6R)-3-amino-5-(difluoromethyl)-2-oxa-4-azabicyclo[4.1.0]hept-3-en-5-yl)-4-chlorophenyl)-5-(oxazol-4-ylmethoxy)pyrazine-2-carboxamide | 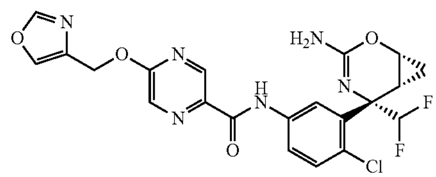 [SMILES: NC1=N[C@@](c2cc(NC(=O)c3cnc(OCc4cocn4)cn3)ccc2Cl)(C(F)F)[C@H]2C[C@H]2O1] | MS m/z = 490.9 [M + H]+<br>1H NMR (400 MHz, CDCl3): δ 9.42 (s, 1H), 8.98 (s, 1H), 8.13 (s, 1H), 7.99 (dd, J = 2.54, 8.61 Hz, 1H), 7.93 (s, 1H), 7.82 (s, 1H), 7.74 (d, J = 2.35 Hz, 1H), 7.31 (d, J = 8.61 Hz, 1H), 6.82 (t, J = 55.20 Hz, 1H), 5.46 (s, 2H), 4.88 (br s, 2H), 3.87 (t, J = 5.58 Hz, 1H), 2.05-2.14 (m, 1H), 1.39 (br s, 1H), 0.92-1.04 (m, 1H); 19F NMR (377 MHz, CDCl3): δ −126.1 (d, J = 278.40 Hz, 1F), −129.2 (d, J = 278.30 Hz, 1F). |
| 103 | A | N-(3-((1R,5S,6R)-3-amino-5-(difluoromethyl)-2-oxa-4-azabicyclo[4.1.0]hept-3-en-5-yl)-4-fluorophenyl)-5-methoxypyrimidine-2-carboxamide | 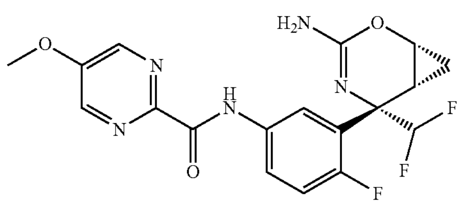 [SMILES: COc1cnc(C(=O)Nc2ccc(F)c([C@@]3(C(F)F)N=C(N)O[C@@H]4C[C@@H]43)c2)nc1] | MS m/z = 407.9 [M]+<br>1H NMR (400 MHz, CDCl3): δ 9.56-9.89 (m, 1H), 8.51 (s, 2H), 7.90-8.08 (m, 1H), 7.67-7.83 (m, 1H), 7.05-7.17 (m, 1H), 6.24 (t, J = 54.80 Hz, 1H), 4.49 (br s, 2H), 4.02 (s, 3H), 3.93-3.99 (m, 1H), 1.85-1.91 (m, 1H), 1.39-1.48 (m, 1H), 0.92-1.05 (m, 1H); 19F NMR (377 MHz, CDCl3): δ −115.77 (dd, J = 8.35, 10.73 Hz, 1F), −127.43 (d, J = 287.29 Hz, 1F), −129.55 (d, J = 275.96 Hz, 1F). |
| 104 | A | N-(3-((1R,5S,6R)-3-amino-5-(difluoromethyl)-2-oxa-4-azabicyclo[4.1.0]hept-3-en-5-yl)-4-chlorophenyl)-5-methoxypyrimidine-2-carboxamide | 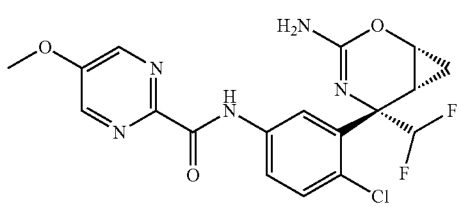 [SMILES: COc1cnc(C(=O)Nc2ccc(Cl)c([C@@]3(C(F)F)N=C(N)O[C@@H]4C[C@@H]43)c2)nc1] | MS m/z = 424.0 [M + H]+<br>1H NMR (400 MHz, CDCl3): δ 9.81 (s, 1H), 8.51 (s, 2H), 8.02 (dd, J = 2.54, 8.61 Hz, 1H), 7.91 (d, J = 2.54 Hz, 1H), 7.41 (d, J = 8.61 Hz, 1H), 6.84 (t, J = 55.40 Hz, 1H), 4.73 (br s, 2H), 4.03 (s, 3H), 3.89-3.93 (m, 1H), 2.11 (td, J = 7.24, 9.78 Hz, 1H), 1.40 (t, J = 7.24 Hz, 1H), 1.01 (td, J = 6.75, 9.78 Hz, 1H); 19F NMR (377 MHz, CDCl3): δ −126.31 (d, J = 278.95 Hz, 1F), −128.99 (d, J = 278.95 Hz, 1F). |
| 105 | C | N-(6-((1R,5S,6R)-3-amino-5-(fluoromethyl)-2-oxa-4-azabicyclo[4.1.0]hept-3-en-5-yl)-5-fluoropyridin-2-yl)-5-chloropicolinamide | 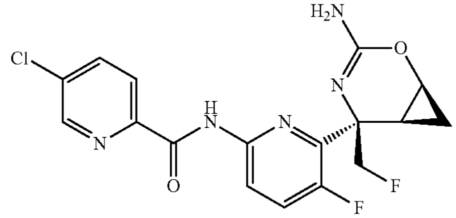 [SMILES: NC1=N[C@@](CF)(c2nc(NC(=O)c3ccc(Cl)cn3)ccc2F)[C@@H]2C[C@@H]2O1] | MS m/z = 394 [M + H]+<br>1H NMR (CHLOROFORM-d) Shift: 8.63 (d, J = 2.3 Hz, 1H), 8.34 (dd, J = 8.9, 3.0 Hz, 1H), 8.24 (d, J = 8.4 Hz, 1H), 7.91 (dd, J = 8.4, 2.3 Hz, 1H), 7.50 (dd, J = 10.5, 8.9 Hz, 1H), 5.11 (ddt, J = 46.6, 8.6, 1.0 Hz, 1H), 4.60 (dd, J = 46.9, 8.6 Hz, 1H), 4.12-4.21 (m, 1H), 2.1-2.25(br s, 3 H) 1.72-1.83 (m, 1H), 1.18 (td, J = 6.9, 2.3 Hz, 1H), 1.02 (dt, J = 9.8, 6.7 Hz, 1H) |

TABLE 1-continued

| Example # | Method | Compound Name | Structure | Analytical Data |
|---|---|---|---|---|
| 106 | C | N-(6-((1S,5R,6S)-3-amino-5-(fluoromethyl)-2-oxa-4-azabicyclo[4.1.0]hept-3-en-5-yl)-5-fluoropyridin-2-yl)-5-chloropicolinamide | 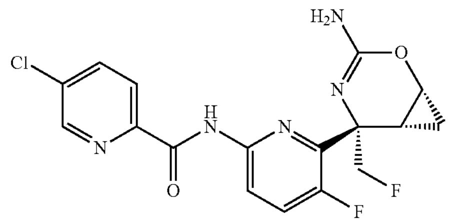 [SMILES: NC1=N[C@](CF)(c2nc(NC(=O)c3ccc(Cl)cn3)ccc2F)[C@H]2C[C@H]2O1] | MS m/z = 394 [M + H]+<br>1H NMR (CHLOROFORM-d) Shift: 8.63 (t, J = 2.2 Hz, 1H), 8.33 (dt, J = 8.8, 2.8 Hz, 1H), 8.25 (dd, J = 8.3, 2.2 Hz, 1H), 7.92 (dt, J = 8.3, 2.6 Hz, 1H), 7.46-7.55 (m, 1H), 5.10 (ddd, J = 46.8, 8.6, 2.0 Hz, 1H), 4.60 (ddd, J = 46.9, 8.6, 2.2 Hz, 1H), 4.10-4.22 (m, 1H), 1.57-1.83 (m, 3H), 1.10-1.22 (m, 1H), 0.96-1.06 (m, 1H) |
| 107 | B | N-(3-((1R,5S,6R)-3-amino-5-(difluoromethyl)-2-oxa-4-azabicyclo[4.1.0]hept-3-en-5-yl)-4,5-difluorophenyl)-5-chloropicolinamide | 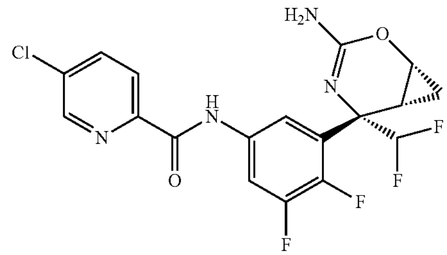 [SMILES: NC1=N[C@@](c2cc(NC(=O)c3ccc(Cl)cn3)cc(F)c2F)(C(F)F)[C@H]2C[C@H]2O1] | MS m/z = 428.9 [M]+<br>1H NMR (CHLOROFORM-d) Shift: 9.70 (br. s, 1H), 8.48 (dd, J = 1.8, 0.4 Hz, 1H), 8.19 (dd, J = 8.3, 0.4 Hz, 1H), 8.03 (ddd, J = 11.7, 6.9, 2.7 Hz, 1H), 7.87 (dd, J = 8.3, 2.3 Hz, 1H), 7.24-7.30 (m, 1H), 6.18 (td, J = 55.7, 1.0 Hz, 1H), 4.76 (br. s, 2H), 3.94 (td, J = 6.8, 2.8 Hz, 1H), 1.80-1.92 (m, 1H), 1.38-1.47 (m, 1H), 0.93-1.03 (m, 1H) |
| 108 | B | N-(3-((1S,5R,6S)-3-amino-5-(difluoromethyl)-2-oxa-4-azabicyclo[4.1.0]hept-3-en-5-yl)-4,5-difluorophenyl)-5-chloropicolinamide | 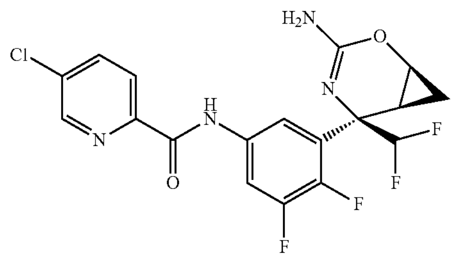 [SMILES: NC1=N[C@](c2cc(NC(=O)c3ccc(Cl)cn3)cc(F)c2F)(C(F)F)[C@@H]2C[C@@H]2O1] | MS m/z = 428.9 [M]+<br>1H NMR (CHLOROFORM-d) Shift: 9.69 (br. s, 1H), 8.48 (d, J = 2.0 Hz, 1H), 8.18 (d, J = 8.3 Hz, 1H), 8.03 (ddd, J = 11.7, 7.0, 2.8 Hz, 1H), 7.87 (dd, J = 8.3, 2.3 Hz, 1H), 6.18 (td, J = 55.8, 1.2 Hz, 1H), 4.82 (br. s., 2H), 3.93 (td, J = 6.8, 2.6 Hz, 1H), 3.49 (s, 1H), 1.79-1.93 (m, 1H), 1.38-1.47 (m, 1H), 0.92-1.03 (m, 1H) |
| 109 | B | N-(3-((1R,5S,6R)-3-amino-5-(difluoromethyl)-2-oxa-4-azabicyclo[4.1.0]hept-3-en-5-yl)-4,5-difluorophenyl)-5-cyanopicolinamide | 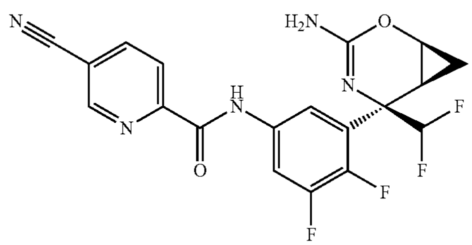 [SMILES: N#Cc1ccc(C(=O)Nc2cc(F)c(F)c([C@]3(C(F)F)N=C(N)O[C@H]4C[C@H]43)c2)nc1] | MS m/z = 419.9 [M]+<br>1H NMR (CHLOROFORM-d) Shift: 9.62 (br. s., 1H), 8.80 (dd, J = 2.0, 0.8 Hz, 1H), 8.37 (dd, J = 8.2, 0.7 Hz, 1H), 8.20 (dd, J = 8.1, 2.0 Hz, 1H), 8.02 (ddd, J = 11.5, 6.9, 2.8 Hz, 1H), 7.21-7.28 (m, 1H), 6.20 (td, J = 55.8, 1.3 Hz, 1H), 4.94 (br. s., 2H), 3.86-3.98 (m, 1H), 1.77-1.92 (m, 1H), 1.38-1.49 (m, 1H), 0.91-1.08 (m, 1H) |
| 110 | B | N-(3-((1R,5S,6R)-3-amino-5-(difluoromethyl)-2-oxa-4-azabicyclo[4.1.0]hept-3-en-5-yl)-4,5-difluorophenyl)-4-chloro-1-(difluoromethyl)-1H-pyrazole-3-carboxamide | 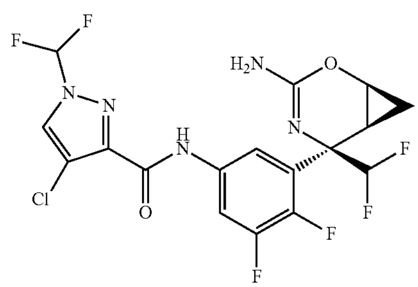 [SMILES: NC1=N[C@](c2cc(NC(=O)c3nn(C(F)F)cc3Cl)cc(F)c2F)(C(F)F)[C@@H]2C[C@@H]2O1] | MS m/z = 467.9 [M]+<br>1H NMR (MeOH) Shift: 8.40 (s, 1H), 7.93 (ddd, J = 11.8, 6.9, 2.7 Hz, 1H), 7.37-7.80 (m, 2H), 6.22 (t, J = 55.8 Hz, 1H), 4.04-4.14 (m, 1H), 1.84-1.95 (m, 1H), 1.28-1.41 (m, 1H), 0.95-1.06 (m, 1H) |
| 111 | B | N-(3-((1R,5S,6R)-3-amino-5-(difluoromethyl)-2-oxa-4-azabicyclo[4.1.0]hept-3-en-5-yl)-4,5-difluorophenyl)-5-(prop-2-yn-1-yloxy)pyrazine-2-carboxamide | 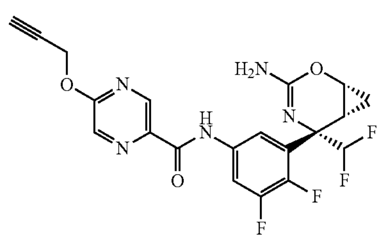 [SMILES: C#CCOc1cnc(C(=O)Nc2cc(F)c(F)c([C@@]3(C(F)F)N=C(N)O[C@@H]4C[C@@H]43)c2)cn1] | MS m/z = 449.9 [M + H]+<br>1H NMR (CHLOROFORM-d) Shift: 9.00 (d, J = 1.3 Hz, 1H), 8.22 (d, J = 1.3 Hz, 1H), 8.09 (ddd, J = 11.7, 6.9, 2.7 Hz, 1H), 7.23 (dt, J = 5.3, 2.4 Hz, 1H), 6.18 (td, J = 55.7, 0.9 Hz, 1H), 5.09 (d, J = 2.5 Hz, 2H), 3.91-4.00 (m, 1H), 2.58 (t, J = 2.4 Hz, 1H), 2.45 (br. s., 3H), 1.78-1.91 (m, 1H), 1.40 (t, J = 5.8 Hz, 1H), 0.93-1.04 (m, 1H) |

TABLE 1-continued

| Example # | Method | Compound Name | Structure | Analytical Data |
|---|---|---|---|---|
| 112 | B | N-(3-((1R,5S,6R)-3-amino-5-(difluoromethyl)-2-oxa-4-azabicyclo[4.1.0]hept-3-en-5-yl)-4,5-difluorophenyl)-5-methoxypyrazine-2-carboxamide | 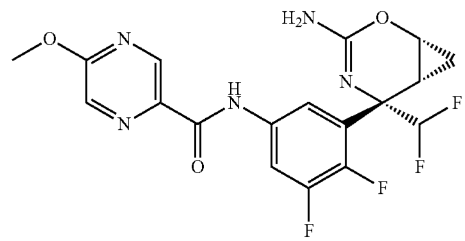 [SMILES: COc1cnc(C(=O)Nc2cc(F)c(F)c([C@@]3(C(F)F)N=C(N)O[C@@H]4C[C@@H]43)c2)cn1] | MS m/z = 425.9 [M + H]+ 1H NMR (CHLOROFORM-d) Shift: 9.32 (br. s, 1H), 8.95 (d, J = 1.3 Hz, 1H), 7.92-8.10 (m, 2H), 7.22 (dt, J = 5.2, 2.5 Hz, 1H), 6.18 (td, J = 55.7, 1.0 Hz, 1H), 4.88 (br. s., 2H), 4.07 (s, 3H), 3.86-3.98 (m, 1H), 1.79-1.91 (m, 1H), 1.42 (t, J = 6.4 Hz, 1H), 0.91-1.02 (m, 1H) |
| 113 | B | N-(3-((1R,5S,6R)-3-amino-5-(difluoromethyl)-2-oxa-4-azabicyclo[4.1.0]hept-3-en-5-yl)-4,5-difluorophenyl)-5-cyanopicolinamide | 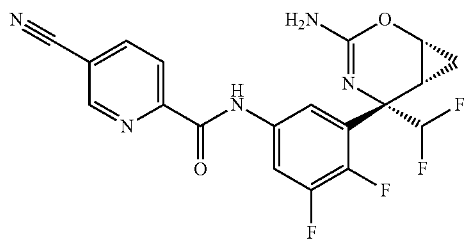 [SMILES: N#Cc1ccc(C(=O)Nc2cc(F)c(F)c([C@@]3(C(F)F)N=C(N)O[C@@H]4C[C@@H]43)c2)nc1] | MS m/z = 419.9 [M]+ 1H NMR (CHLOROFORM-d) Shift: 9.51 (br. s, 1H), 8.76 (d, J = 0.8 Hz, 1H), 8.35 (d, J = 8.2 Hz, 1H), 8.19 (dd, J = 8.2, 1.8 Hz, 1H), 7.98 (ddd, J = 11.4, 7.0, 2.5 Hz, 1H), 7.16-7.21 (m, 1H), 6.22 (t, J = 55.8 Hz, 1H), 5.20 (br. s., 2H), 3.88-3.95 (m, 1H), 1.80-1.89 (m, 1H), 1.42-1.49 (m, 1H), 0.81-1.08 (m, 1H) |
| 114 | B | N-(3-((1R,5S,6R)-3-amino-5-(difluoromethyl)-2-oxa-4-azabicyclo[4.1.0]hept-3-en-5-yl)-4,5-difluorophenyl)-4-chloro-1-(difluoromethyl)-1H-pyrazole-3-carboxamide | 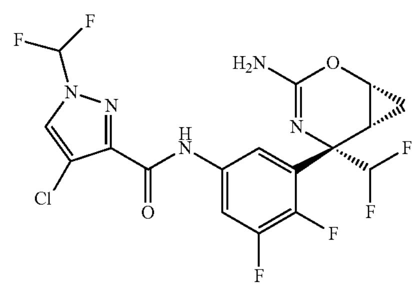 [SMILES: NC1=N[C@@](c2cc(NC(=O)c3nn(C(F)F)cc3Cl)cc(F)c2F)(C(F)F)[C@H]2C[C@H]2O1] | MS m/z = 467.8 [M]+ 1H NMR (CHLOROFORM-d) Shift: 8.46 (s, 1H), 8.00-8.11 (m, 1H), 7.90 (s, 1H), 6.87-7.31 (m, 2H), 6.16 (td, J = 55.7, 1.3 Hz, 1H), 4.96 (br. s., 1H), 3.88-3.97 (m, 1H), 1.79-1.90 (m, 1H), 1.37-1.45 (m, 1H), 0.91-1.03 (m, 1H) |
| 115 | B | N-(3-((1R,5S,6R)-3-amino-5-(difluoromethyl)-2-oxa-4-azabicyclo[4.1.0]hept-3-en-5-yl)-4,5-difluorophenyl)-5-(prop-2-yn-1-yloxy)pyrazine-2-carboxamide | 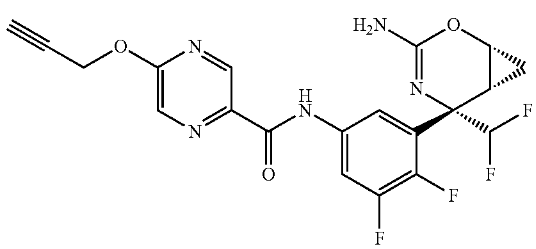 [SMILES: C#CCOc1cnc(C(=O)Nc2cc(F)c(F)c([C@@]3(C(F)F)N=C(N)O[C@@H]4C[C@@H]43)c2)cn1] | MS m/z = 449.9 [M]+ 1H NMR (CHLOROFORM-d) Shift: 9.00 (d, J = 1.3 Hz, 1H), 8.20 (d, J = 1.2 Hz, 1H), 8.07 (ddd, J = 11.7, 6.9, 2.6 Hz, 1H), 7.24 (dt, J = 5.3, 2.4 Hz, 1H), 6.17 (td, J = 55.5, 1.3 Hz, 1H), 5.09 (d, J = 2.3 Hz, 2H), 3.91-3.99 (m, 1H), 2.56 (t, J = 2.4 Hz, 1H), 1.80-1.90 (m, 2H), 1.61 (br. s., 2H), 1.40 (t, J = 6.3 Hz, 1H), 0.93-1.04 (m, 1H) |
| 116 | B | N-(3-((1R,5S,6R)-3-amino-5-(difluoromethyl)-2-oxa-4-azabicyclo[4.1.0]hept-3-en-5-yl)-4,5-difluorophenyl)-5-bromopicolinamide | 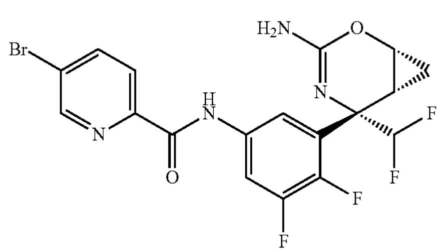 [SMILES: NC1=N[C@@](c2cc(NC(=O)c3ccc(Br)cn3)cc(F)c2F)(C(F)F)[C@H]2C[C@H]2O1] | MS m/z = 472.8 [M]+ 1H NMR (CHLOROFORM-d) Shift: 9.55 (br. s, 1H), 8.51 (d, J = 1.8 Hz, 1H), 7.91-8.12 (m, 3H), 7.15-7.24 (m, 1H), 6.22 (td, J = 56.0, 0.7 Hz, 1H), 5.23 (br. s, 2H), 3.86-3.95 (m, 1H), 1.80-1.90 (m, 1H), 1.40-1.49 (m, 1H), 0.91-1.02 (m, 1H) |
| 117 | B | N-(3-((1R,5S,6R)-3-amino-5-(fluoromethyl)-2-oxa-4-azabicyclo[4.1.0]hept-3-en-5-yl)-4-fluorophenyl)-5-chloropicolinamide | 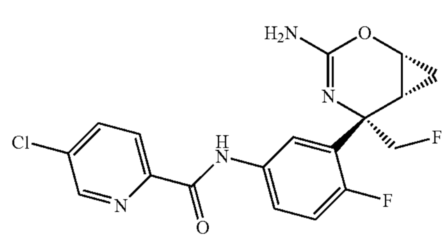 [SMILES: NC1=N[C@](CF)(c2cc(NC(=O)c3ccc(Cl)cn3)ccc2F)[C@H]2C[C@H]2O1] | MS m/z = 393 [M + H]+ 1H NMR (400 MHz, CDCl3) δ 0.87-0.95 (m, 1H), 1.19-1.27 (m, 1 H), 1.72-1.80 (m, 1 H), 3.95 (ddd, J = 6.11, 4.84, 1.37 Hz, 1 H), 4.35 (b br, 2H), 4.58-4.69 (m, 1H), 4.70-4.82 (m 1H), 7.07 (dd, J = 11.54, 8.80 Hz, 1H), 7.63 (dd, J = 6.85, 2.74 Hz, 1H), 7.84-7.92 (m, 1H), 7.92-7.96 (m, 1H), 8.20 (d, J = 8.41 Hz, 1H), 8.51 (d, J = 1.76 Hz, 1H), 9.77 (s, 1H) |

TABLE 1-continued

| Example # | Method | Compound Name | Structure | Analytical Data |
|---|---|---|---|---|
| 118 | B | N-(3-((1S,5R,6S)-3-amino-5-(fluoromethyl)-2-oxa-4-azabicyclo[4.1.0]hept-3-en-5-yl)-4-fluorophenyl)-5-chloropicolinamide | 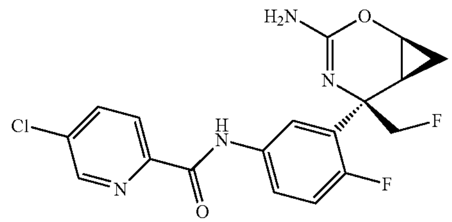 [SMILES: NC1=N[C@@](CF)(c2cc(NC(=O)c3ccc(Cl)cn3)ccc2F)[C@@H]2C[C@@H]2O1] | MS m/z = 393 [M + H]+ 1H NMR (400 MHz, CDCl3) δ 0.91 (d, J = 9.59 Hz, 1H), 1.21 (d, J = 2.54 Hz, 1H), 1.75 (d, J = 9.78 Hz, 1H), 3.90-4.00 (m, 1H), 4.36 (s br, 2H), 4.58-4.69 (m, 1H), 4.70-4.81 (m, 1H), 7.08 (dd, J = 11.54, 8.80 Hz, 1H), 7.63 (dd, J = 6.85, 2.74 Hz, 1H), 7.86 (dd, J = 8.41, 2.35 Hz, 1H), 7.95 (td, J = 4.40, 1.17 Hz, 1H), 8.22 (d, J = 8.41 Hz, 1H), 8.53 (d, J = 2.35 Hz, 1H), 9.79 (br s, 1H) |
| 119 | A | N-(3-((1R,5S,6R)-3-amino-5-(difluoromethyl)-2-oxa-4-azabicyclo[4.1.0]hept-3-en-5-yl)-4-fluorophenyl)-5-chloropyrimidine-2-carboxamide | 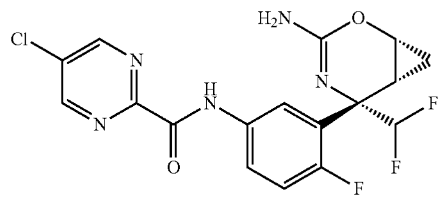 [SMILES: NC1=N[C@@](c2cc(NC(=O)c3ncc(Cl)cn3)ccc2F)(C(F)F)[C@H]2C[C@H]2O1] | MS m/z = 412.0 [M + H]+ 1H NMR (400MHz, CHLOROFORM-d) δ = 9.63 (s, 1 H), 8.82 (s, 2 H), 7.98 (ddd, J = 2.9, 4.1, 8.8 Hz, 1 H), 7.68 (dd, J = 2.7, 6.7 Hz, 1 H), 7.07 (dd, J = 8.8, 11.5 Hz, 1 H), 6.43-6.04 (m, 1 H), 4.76 (br. s., 2 H), 3.92 (br. s., 1 H), 1.86 (td, J = 7.1, 9.3 Hz, 1 H), 1.48-1.38 (m, 1 H), 1.01 - 0.90 (m, 1 H). |
| 120 | A | N-(3-((1R,5S,6R)-3-amino-5-(difluoromethyl)-2-oxa-4-azabicyclo[4.1.0]hept-3-en-5-yl)-4-fluorphenyl)-3-methyl-5-(2,2,2-trifluoroethoxy)pyrazine-2-carboxamide | 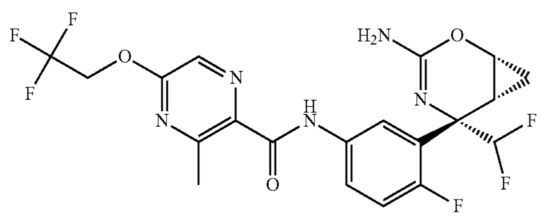 [SMILES: Cc1nc(OCC(F)(F)F)cnc1C(=O)Nc1ccc(F)c([C@@]2(C(F)F)N=C(N)O[C@@H]3C[C@@H]32)c1] | MS m/z = 490.1 [M + H]+ $^1$H NMR (400 MHz, CHLOROFORM-d) δ ppm 0.78-1.03 (m, 1 H) 1.39-1.54 (m, 1 H) 1.76-2.01 (m, 1 H) 2.89 (s, 3 H) 3.79-4.02 (m, 1 H) 4.67-5.08 (m, 2 H) 5.32 (br. s., 2 H) 6.25 (t, J = 57.51 Hz, 1 H) 6.93 (t, J = 10.07 Hz, 1 H) 7.42 (d, J = 6.26 Hz, 1 H) 7.90 (s, 2 H) 9.51 (s, 1 H) |
| 121 | B | N-(3-((1R,5S,6R)-3-amino-5-(difluoromethyl)-2-oxa-4-azabicyclo[4.1.0]hept-3-en-5-yl)-4-fluoro-5-methylphenyl)-5-chloropicolinamide | 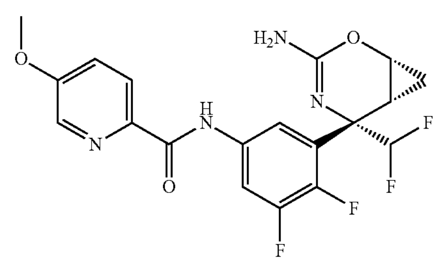 [SMILES: COc1ccc(C(=O)Nc2cc(F)c(F)c([C@@]3(C(F)F)N=C(N)O[C@@H]4C[C@@H]43)c2)nc1] | MS m/z = 424.9 [M + H]+ 1H NMR (300 MHz, CHLOROFORM-d) δ 0.92-1.05 (m, 1 H) 1.39-1.47 (m, 1 H) 1.84-1.94 (m, 1 H) 2.31 (d, J = 2.48 Hz, 3 H) 3.94-4.02 (m, 1 H) 6.06 - 6.48 (m, 2 H) 7.45 (dd, J = 6.14, 2.92 Hz, 1 H) 7.84-7.93 (m, 2 H) 8.19-8.24 (m, 1 H) 8.53 (d, J = 1.75 Hz, 1 H) 9.74 (s, 1 H) |
| 122 | C | N-(3-((1R,5S,6R)-3-amino-5-(fluoromethyl)-2-oxa-4-azabicyclo[4.1.0]hept-3-en-5-yl)-4-chlorophenyl)-5-(difluoromethyl)-3-methylpicolinamide | 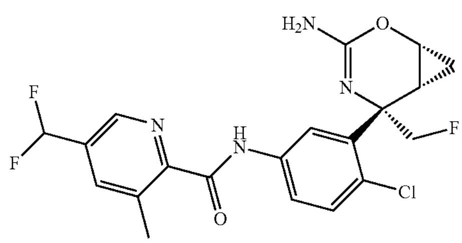 [SMILES: Cc1cc(C(F)F)cnc1C(=O)Nc1ccc(Cl)c([C@@]2(CF)N=C(N)O[C@@H]3C[C@@H]32)c1] | MS m/z = 439 [M + H]+ 1H NMR (400 MHz, CHLOROFORM-d) δ ppm 0.80-0.92 (m, 1 H) 0.95-1.05 (m, 1 H) 1.97-2.07 (m, 1 H) 2.86 (s, 3 H) 3.96 (d, J = 4.70 Hz, 1 H) 4.78-4.89 (m, 1 H) 4.90-5.00 (m, 1 H) 6.52-7.02 (m, 2 H) 7.40 (d, J = 8.80 Hz, 1 H) 7.76 (d, J = 14.08 Hz, 2 H) 8.04 (d, J = 9.00 Hz, 1 H) 8.58 (br. s., 1 H) 10.20 (br. s., 1 H) |
| 123 | C | N-(3-((1R,5S,6R)-3-amino-5-(difluoromethyl)-2-oxa-4-azabicyclo[4.1.0]hept-3-en-5-yl)-4-fluoro-5-methylphenyl)-5-chloropicolinamide | 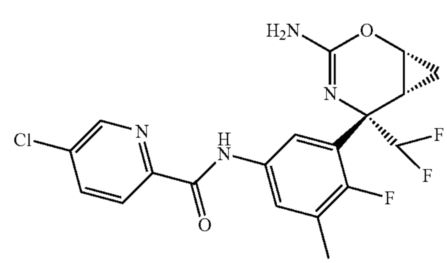 [SMILES: Cc1cc(NC(=O)c2ccc(Cl)cn2)cc([C@@]2(C(F)F)N=C(N)O[C@@H]3C[C@@H]32)c1F] | MS m/z = 424.9 [M]+ 1H NMR (300 MHz, CHLOROFORM-d) δ 0.92-1.05 (m, 1 H) 1.39-1.47 (m, 1 H) 1.84-1.94 (m, 1 H) 2.31 (d, J = 2.48 Hz, 3 H) 3.94-4.02 (m, 1 H) 6.06-6.48 (m, 2 H) 7.45 (dd, J = 6.14, 2.92 Hz, 1 H) 7.84-7.93 (m, 2 H) 8.19-8.24 (m, 1 H) 8.53 (d, J = 1.75 Hz, 1 H) 9.74 (s, 1 H) |

TABLE 1-continued

| Example # | Method | Compound Name | Structure | Analytical Data |
|---|---|---|---|---|
| 124 | C | N-(3-((1S,5R,6S)-3-amino-5-(difluoromethyl)-2-oxa-4-azabicyclo[4.1.0]hept-3-en-5-yl)-4-fluoro-5-methylphenyl)-5-chloropicolinamide | Chiral | MS m/z = 424.9 [M]+ 1H NMR (300 MHz, CHLOROFORM-d) δ ppm 0.92-1.05 (m, 1 H) 1.39-1.48 (m, 1 H) 1.87-1.94 (m, 1 H) 2.30 (d, J = 2.63 Hz, 3 H) 3.96 (t, J = 5.55 Hz, 1 H) 6.07-6.49 (m, 1 H) 7.44 (dd, J = 6.36, 2.70 Hz, 1 H) 7.83-7.94 (m, 2 H) 8.21 (d, J = 8.33 Hz, 1 H) 8.52 (d, J = 2.34 Hz, 1 H) 9.73 (s, 1 H) |
| 125 | C | N-(3-((1R,5S,6R)-3-amino-5-(fluoromethyl)-2-oxa-4-azabicyclo[4.1.0]hept-3-en-5-yl)-4-chlorophenyl)-3-methyl-5-(trifluoromethyl)picolinamide | 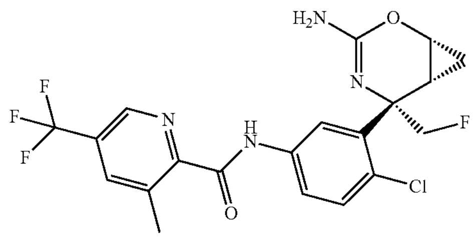 [SMILES: Cc1cc(C(F)(F)F)cnc1C(=O)Nc1ccc(Cl)c([C@@]2(CF)N=C(N)O[C@@H]3C[C@@H]32)c1] | MS m/z = 457 [M + H]+ 1H NMR (300 MHz, DMSO-d6) δ ppm 0.80-0.90 (m, 1 H) 0.93 (d, J = 3.80 Hz, 1 H) 1.60-1.74 (m, 1 H) 2.59 (s, 3 H) 3.90-4.00 (m, 1 H) 4.65 (s, 1 H) 4.80 (s, 1 H) 5.60 (s, 2 H) 7.43 (d, J = 8.48 Hz, 1 H) 7.86 (dd, J = 8.62, 2.48 Hz, 1 H) 8.01 (d, J = 2.34 Hz, 1 H) 8.29 (s, 1 H) 8.90 (s, 1 H) 10.75 (s, 1 H) |
| 126 | C | N-(3-((1R,5S,6R)-3-amino-5-(fluoromethyl)-2-oxa-4-azabicyclo[4.1.0]hept-3-en-5-yl)-4-chlorophenyl)-5-(difluoromethoxy)-3-methylpicolinamide | 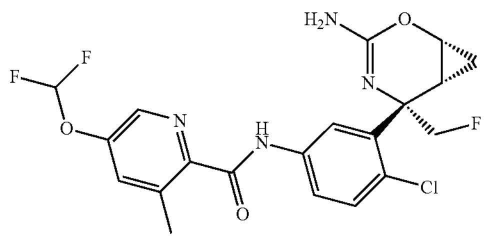 [SMILES: Cc1cc(OC(F)F)cnc1C(=O)Nc1ccc(Cl)c([C@@]2(CF)N=C(N)O[C@@H]3C[C@@H]32)c1] | MS m/z = 454.9 [M]+ 1H NMR (300 MHz, DMSO-d6) δ ppm 0.68-1.09 (m, 2 H) 1.67 (br. s., 1 H) 2.59 (br. s., 3 H) 3.97-4.16 (m, 1 H) 4.54-4.71 (m, 1 H) 4.72-4.90 (m, 1 H) 5.59 (br. s., 2 H) 7.00-7.53 (m, 2 H) 7.61-7.91 (m, 2 H) 7.92-8.17 (m, 1 H) 8.25-8.56 (m, 1 H) 10.58 (br. s., 1 H) |
| 127 | B | N-(34(1R,5S,6R)-3-amino-5-(fluoromethyl)-2-oxa-4-azabicyclo[4.1.0]hept-3-en-5-yl)-4-chlorophenyl)-3-chloro-5-cyanopicolinamide | 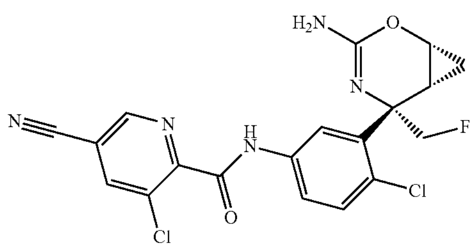 [SMILES: N#Cc1cnc(C(=O)Nc2ccc(Cl)c([C@@]3(CF)N=C(N)O[C@@H]4C[C@@H]43)c2)c(Cl)c1] | MS m/z = 433.8 [M]+ 1H NMR (300 MHz, CHLOROFORM-d) δ 0.94-1.06 (m, 1 H) 1.12-1.22 (m, 1 H) 1.96-2.10 (m, 1 H) 3.89-4.04 (m, 1 H) 4.71-4.89 (m, 1 H) 4.90-5.08 (m, 1 H) 7.40 (d, J = 7.89 Hz, 1 H) 7.69 (br. s., 1 H) 8.07 (d, J = 9.50 Hz, 1 H) 8.16 (br. s., 1 H) 8.74 (br. s., 1 H) 9.73 (br. s., 1 H) |
| 128 | C | N-(3-((1R,5S,6R)-3-amino-5-(fluoromethyl)-2-oxa-4-azabicyclo[4.1.0]hept-3-en-5-yl)-4-chlorophenyl)-5-chloro-3-(methoxymethyl)picolinamide | 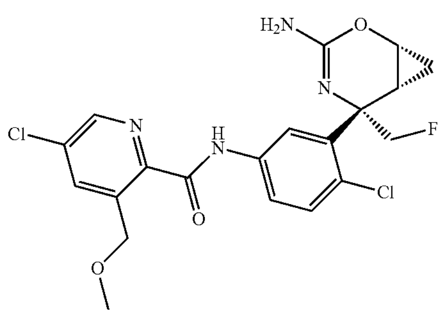 [SMILES: COCc1cc(Cl)cnc1C(=O)Nc1ccc(Cl)c([C@@]2(CF)N=C(N)O[C@@H]3C[C@@H]32)c1] | MS m/z = 452.9 [M]+ 1H NMR (300 MHz, CHLOROFORM-d) δ ppm 0.92-1.04 (m, 1 H) 1.17 (s, 1 H) 1.94-2.05 (m, 1 H) 3.56 (s, 3 H) 3.89-4.00 (m, 1 H) 4.73-4.86 (m, 1 H) 4.90-5.01 (m, 1 H) 5.10 (s, 1 H) 7.41 (d, J = 8.77 Hz, 1 H) 7.72 (s, 1 H) 8.01 (d, J = 7.45 Hz, 1 H) 8.22 (s, 1 H) 8.44 (s, 1 H) 10.06 (s, 1 H) |
| 129 | B | N-(34(1R,5S,6R)-3-amino-5-(difluoromethyl)-2-oxa-4-azabicyclo[4.1.0]hept-3-en-5-yl)-4-fluorophenyl)-5-chloro-3-fluoropicolinamide | 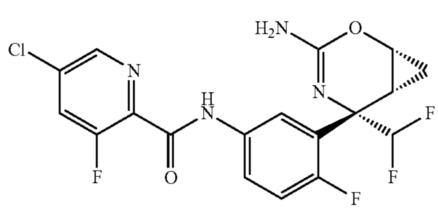 [SMILES: NC1=N[C@@](c2cc(NC(=O)c3ncc(Cl)cc3F)ccc2F)(C(F)F)[C@H]2C[C@H]2O1] | MS m/z = 428. [M]+ 1H NMR (300 MHz, CHLOROFORM-d) δ ppm 0.94-1.07 (m, 1 H) 1.44 (br. s., 1 H) 1.86-1.97 (m, 1 H) 4.00 (br. s., 1 H) 6.02-6.44 (m, 1 H) 7.03-7.18 (m, 1 H) 7.50-7.71 (m, 2 H) 7.97-8.06 (m, 1 H) 8.38 (s, 1 H) 9.64 (br. s., 1 H) |

TABLE 1-continued

| Example # | Method | Compound Name | Structure | Analytical Data |
|---|---|---|---|---|
| 130 | B | N-(3-((1R,5S,6R)-3-amino-5-(difluoromethyl)-2-oxa-4-azabicyclo[4.1.0]hept-3-en-5-yl)-4-fluorophenyl)-5-methoxypicolinamide | 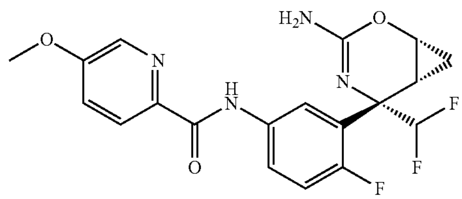 | MS m/z = 407 [M + H]+ 1H NMR (300 MHz, DMSO-d6) δ ppm 0.91-1.04 (m, 1 H) 1.22 (d, J = 6.28 Hz, 1 H) 1.74-1.86 (m, 1 H) 4.00 (s, 3 H) 4.08 (br. s., 1 H) 5.92 (s, 2 H) 6.03-6.51 (m, 1 H) 7.18-7.34 (m, 1 H) 7.68 (d, J = 8.92 Hz, 1 H) 7.94 (d, J = 8.62 Hz, 1 H) 8.07 (d, J = 6.58 Hz, 1 H) 8.19 (d, J = 8.77 Hz, 1 H) 8.45 (s, 1 H) 10.52 (s, 1 H) |
| 131 | B | N-(3-((1R,5S,6R)-3-amino-5-(difluoromethyl)-2-oxa-4-azabicyclo[4.1.0]hept-3-en-5-yl)-4-fluorophenyl)-5-methoxy-3-methylpicolinamide | 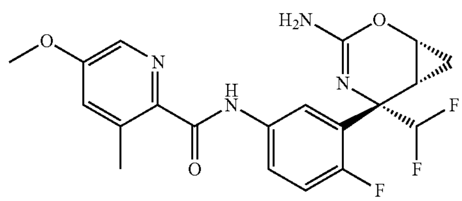 [SMILES: COc1cnc(C(=O)Nc2ccc(F)c([C@@]3(C(F)F)N=C(N)O[C@@H]4C[C@@H]43)c2)c(C)c1] | MS m/z = 421 [M + H]+ 1H NMR (300 MHz, DMSO-d6) δ ppm 0.84-0.98 (m, 1 H) 1.11-1.22 (m, 1 H) 1.67-1.81 (m, 1 H) 2.62 (s, 3 H) 3.91 (s, 3 H) 3.97-4.07 (m, 1 H) 5.86 (s, 2 H) 5.96-6.42 (m, 1 H) 7.13-7.25 (m, 1 H) 7.41 (s, 1 H) 7.87 (d, J = 6.14 Hz, 2 H) 8.22 (s, 1 H) 10.35-10.47 (m, 1 H) |
| 132 | B | N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methylpicolinamide | 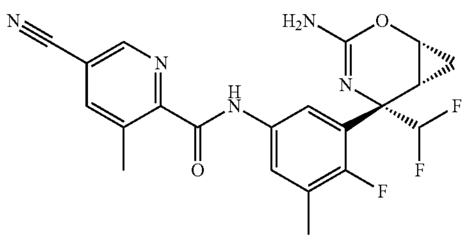 | MS m/z = 430 [M + H]+ 1H NMR (300 MHz, DMSO-d6) δ ppm 0.86-1.07 (m, 1 H) 1.08-1.26 (m, 1 H) 1.63-1.87 (m, 1 H) 2.32 (s, 3 H) 2.60 (s, 3 H) 4.04 (br. s., 1 H) 5.90 (s, 2 H) 6.05-6.55 (m, 1 H) 7.69 (d, J = 3.95 Hz, 1 H) 7.84 (d, J = 6.14 Hz, 1 H) 8.44 (s, 1 H) 9.03 (s, 1 H) 10.70 (s, 1 H) |
| 133 | B | N-(3(1R,5S,6R)-3-amino-5-(difluoromethyl)-2-oxa-4-azabicyclo[4.1.0]hept-3-en-5-yl)-4-fluoro-5-methylphenyl)-3-chloro-5-cyanopicolinamide | 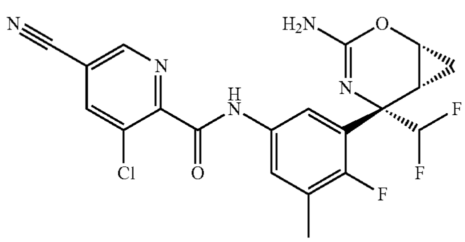 [SMILES: Cc1cc(NC(=O)c2ncc(C#N)cc2Cl)cc([C@@]2(C(F)F)N=C(N)O[C@@H]3C[C@@H]32)c1F] | MS m/z = 449.9 [M]+ 1H NMR (300 MHz, DMSO-d6) δ ppm 0.80-1.02 (m, 1 H) 1.11 (br. s., 1 H) 1.69 (q, J = 7.70 Hz, 1 H) 2.27 (s, 3 H) 3.83-4.05 (m, 1 H) 5.87 (s, 2 H) 5.99-6.44 (m, 1 H) 7.52 (d, J = 5.12 Hz, 1 H) 7.75 (d, J = 6.14 Hz, 1 H) 8.79 s, 1 H) 9.09 (s, 1 H) 10.83 (s, 1 H) |
| 134 | C | N-(3-((1R,5S,6R)-3-amino-5-(difluoromethyl)-2-oxa-4-azabicyclo[4.1.0]hept-3-en-5-yl)-4-fluoro-5-methylphenyl)-5-chloro-3-methoxypicolinamide | 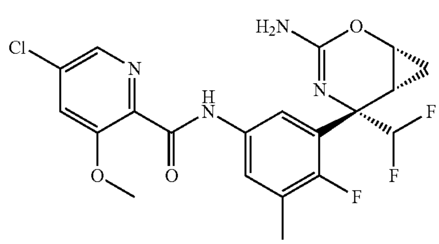 [SMILES: COc1cc(Cl)cnc1C(=O)Nc1cc(C)c(F)c([C@@]2(C(F)F)N=C(N)O[C@@H]3C[C@@H]32)c1] | MS m/z = 454.9 [M]+ 1H NMR (300 MHz, DMSO-d6) δ ppm 0.83-0.95 (m, 1 H) 1.06-1.15 (m, 1 H) 1.62-1.75 (m, 1 H) 2.25 (s, 3 H) 3.89 (s, 3 H) 3.93-4.01 (m, 1 H) 5.83 (s, 2 H) 6.01-6.41 (m, 1 H) 7.56 (d, J = 5.55 Hz, 1 H) 7.73 (d, J = 4.97 Hz, 1 H) 7.83 (s, 1 H) 8.25 (s, 1 H) 10.41 (s, 1 H) |
| 135 | C | N-(3-((1R,5S,6R)-3-amino-5-(difluoromethyl)-2-oxa-4-azabicyclo[4.1.0]hept-3-en-5-yl)-4-fluoro-5-methylphenyl)-3,5-dichloropicolinamide | 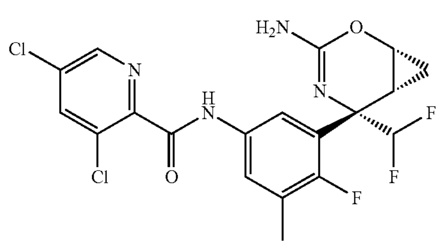 [SMILES: Cc1cc(NC(=O)c2ncc(Cl)cc2Cl)cc([C@@]2(C(F)F)N=C(N)O[C@@H]3C[C@@H]32)c1F] | MS m/z = 458.9 [M]+ 1H NMR (300 MHz, DMSO-d6) δ ppm 0.77-0.99 (m, 1 H) 1.03-1.21 (m, 1 H) 1.58-1.81 (m, 1 H) 2.26 (s, 3 H) 3.83-4.05 (m, 1 H) 5.86 (s, 2 H) 5.97-6.49 (m, 1 H) 7.54 (d, J = 4.97 Hz, 1 H) 7.75 (d, J = 5.99 Hz, 1 H) 8.43 (s, 1 H) 8.71 (s, 1 H) 10.69 (s, 1 H) |

TABLE 1-continued

| Example # | Method | Compound Name | Structure | Analytical Data |
|---|---|---|---|---|
| 136 | A | N-(3-((1R/S,5S/R,6R/S)-3-amino-5-(fluoromethyl)-2-oxa-4-azabicyclo[4.1.0]hept-3-en-5-yl)-4-chloro-5-fluorophenyl)-5-cyanopicolinamide | 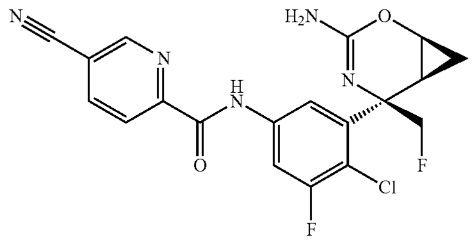 [SMILES: N#Cc1ccc(C(=O)Nc2cc(F)c(Cl)c([C@]3(CF)N=C(N)O[C@H]4C[C@H]43)c2)nc1] | MS m/z = 418 [M + H]+ <br> $^1$H NMR (400 MHz, DMSO-d$_6$) δ ppm 0.81-1.03 (m, 2 H), 1.62 (dt, J = 9.73, 6.97 Hz, 1 H), 3.94-4.06 (m, 1 H), 4.71 (dt, J = 47.8, 9.0 Hz, 2 H), 5.62 (s, 2 H), 8.03 (dd, J = 11.25, 2.45 Hz, 1 H), 8.09 (br. s., 1 H), 8.29 (dd, J = 8.22, 0.78 Hz, 1 H), 8.58 (dd, J = 8.2, 1.7 Hz, 1 H), 9.21 (d, J = 1.17 Hz, 1 H), 11.09 (s, 1 H). |
| 137 | B | N-(3-((1R/S,5S/R,6R/S)-3-amino-5-(fluoromethyl)-2-oxa-4-azabicyclo[4.1.0]hept-3-en-5-yl)-4-chloro-5-fluorophenyl)-5-cyano-3-methylpicolinamide | 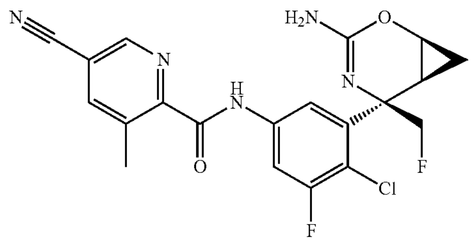 [SMILES: Cc1cc(C#N)cnc1C(=O)Nc1cc(F)c(Cl)c([C@]2(CF)N=C(N)O[C@H]3C[C@H]32)c1] | MS m/z = 431.9 [M]+ <br> $^1$H NMR (400 MHz, DMSO-d$_6$) δ ppm 0.83-0.98 (m, 2 H), 1.62 (q, J = 7.69 Hz, 1 H), 2.56 (s, 3 H), 3.98 (br. s., 1 H), 4.60-4.81 (m, 2 H), 5.63 (br. s., 2 H), 7.87 (s, 1 H), 7.99 (d, J = 11.15 Hz, 1 H), 8.41 (s, 1 H), 8.99 (s, 1 H), 11.00 (br. s., 1 H) |
| 138 | B | N-(3-((1R,5S,6R)-3-amino-5-(fluoromethyl)-2-oxa-4-azabicyclo[4.1.0]hept-3-en-5-yl)-4-chloro-5-fluorophenyl)-5-cyano-3-methylpicolinamide | 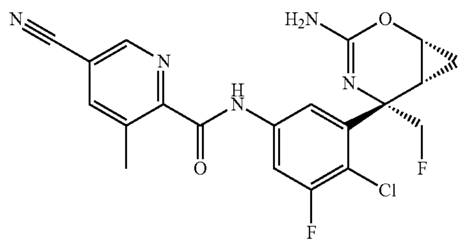 [SMILES: Cc1cc(C#N)cnc1C(=O)Nc1cc(F)c(Cl)c([C@@]2(CF)N=C(N)O[C@@H]3C[C@@H]32)c1] | MS m/z = 432 [M + H]+ <br> $^1$H NMR (400 MHz, DMSO-d$_6$) δ ppm 0.81-0.99 (m, 2 H), 1.62 (q, J = 7.70 Hz, 1 H), 2.56 (s, 3 H), 3.96 (br. s., 1 H), 4.71 (dq, J = 47.9, 9.0 Hz, 2 H), 5.63 (br. s., 2 H), 7.87 (s, 1 H), 7.99 (d, J = 11.15 Hz, 1 H), 8.41 (s, 1 H), 8.99 (s, 1 H), 11.01 (s, 1 H) |
| 139 | B | N-(3-((1S,5R,6S)-3-amino-5-(fluoromethyl)-2-oxa-4-azabicyclo[4.1.0]hept-3-en-5-yl)-4-chloro-5-fluorophenyl)-5-cyano-3-methylpicolinamide | 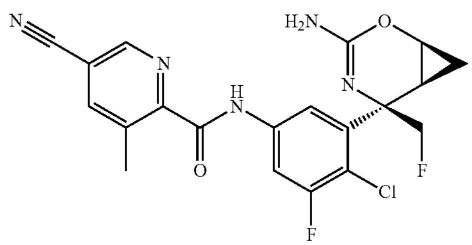 [SMILES: Cc1cc(C#N)cnc1C(=O)Nc1cc(F)c(Cl)c([C@]2(CF)N=C(N)O[C@H]3C[C@H]32)c1] | MS m/z = 431.9 [M]+ <br> $^1$H NMR (400 MHz, DMSO-d$_6$) δ ppm 0.81-0.99 (m, 2 H), 1.62 (q, J = 7.70 Hz, 1 H), 2.56 (s, 3 H), 3.96 (br. s., 1 H), 4.71 (dq, J = 47.9, 9.0 Hz, 2 H), 5.63 (br. s., 2 H), 7.87 (s, 1 H), 7.99 (d, J = 11.15 Hz, 1 H), 8.41 (s, 1 H), 8.99 (s, 1 H), 11.01 (s, 1 H) |
| 140 | B | N-(3-((1R/S,5S/R,6R/S)-3-amino-5-(fluoromethyl)-2-oxa-4-azabicyclo[4.1.0]hept-3-en-5-yl)-4-chloro-5-fluorophenyl)-5-(prop-2-yn-1-yloxy)pyrazine-2-carboxamide | 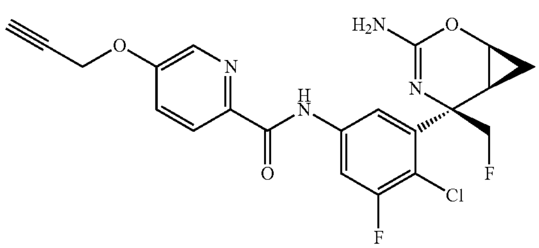 [SMILES: C#CCOc1ccc(C(=O)Nc2cc(F)c(Cl)c([C@]3(CF)N=C(N)O[C@H]4C[C@H]43)c2)nc1] | MS m/z = 448 [M + H]+ <br> $^1$H NMR (400 MHz, DMSO-d$_6$) δ ppm 0.85-1.01 (m, 2 H), 1.63 (dt, J = 9.73, 7.07 Hz, 1 H), 3.66 (t, J = 2.35 Hz, 1 H), 3.98-4.07 (m, 1 H), 4.55-4.88 (m, 2 H), 5.16 (d, J = 2.54 Hz, 2 H), 5.63 (s, 2 H), 8.02 (dd, J = 11.25, 2.45 Hz, 1 H), 8.10 (s, 1 H), 8.51 (d, J = 1.17 Hz, 1 H), 8.94 (d, J = 1.37 Hz, 1 H), 10.82 (s, 1 H) |
| 141 | B | N-(3-(((1S,R),(5S,R),(6R,S))-3-amino-5-(fluoromethyl)-2-oxa-4-azabicyclo[4.1.0]hept-3-en-5-yl)-5-fluoro-4-(methylthio)phenyl)-5-chloropicolinamide | 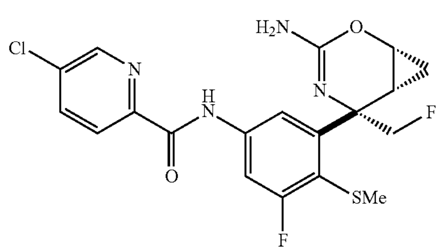 | MS m/z = 439 [M + H]+ <br> $^1$H NMR (400 MHz, DMSO-d$_6$) δ ppm 0.90-1.06 (m, 1 H) 1.14-1.33 (m, 1 H) 1.75 (m, 1 H) 3.40 (s, 3 H) 3.78-3.92 (m, 1 H) 4.55-4.76 (m, 1 H) 4.81 (m, 1 H) 5.67 (br. s., 2 H) 8.06 (d, J = 14.48 Hz) 8.15-8.26 (m, 2 H) 8.30 (s, 1 H) 8.82 (s, 1 H) 11.12 (br. s., 1 H) |

TABLE 1-continued

| Example # | Method | Compound Name | Structure | Analytical Data |
|---|---|---|---|---|
| 142 | B | N-(3-(((1R,S),(5S,R),(6R,S))-3-amino-5-(fluoromethyl)-2-oxa-4-azabicyclo[4.1.0]hept-3-en-5-yl)-4,5-difluorophenyl)-5-chloropicolinamide | 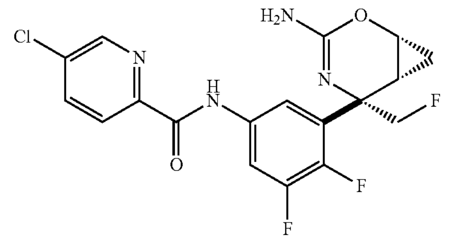 | MS m/z = 410 [M]+<br>1H NMR (400 MHz, CHLOROFORM-d) Shift = 10.00 (br. s., 1 H), 8.58 (s, 1 H), 8.23 (d, J = 8.6 Hz, 1 H), 8.11-8.00 (m, 1 H), 7.90 (d, J = 8.4 Hz, 1 H), 4.78-4.67 (m, 1 H), 4.69-4.58 (m, 1 H), 4.09-3.95 (m, 1 H), 1.80-1.74 (m, 1 H), 1.24 (t, J = 6.9 Hz, 1 H), 1.03-0.91 (m, 1 H) |
| 143 | D | N-(3-((1R,5S,6R)-3-amino-5-(fluoromethyl)-2-oxa-4-azabicyclo[4.1.0]hept-3-en-5-yl)-4,5-difluorophenyl)-5-methoxypyrazine-2-carboxamide | 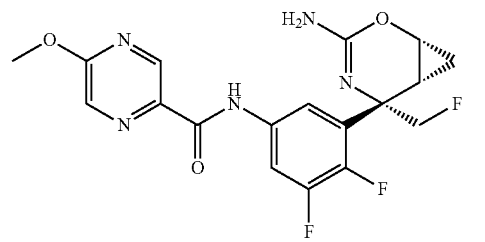 [SMILES: COc1cnc(C(=O)Nc2cc(F)c(F)c([C@@]3(CF)N=C(N)O[C@@H]4C[C@@H]43)c2)cn1] | MS m/z = 408 [M + H]+<br>1H NMR (400 MHz, CHLOROFORM-d) d = 9.51 (s, 1 H), 9.01 (s, 1 H), 8.15 (s, 1 H), 8.08 (ddd, J = 2.5, 6.8, 11.7 Hz, 1 H), 4.79-4.69 (m, 1 H), 4.67-4.57 (m, 1 H), 4.05 (s, 3H), 4.00 (t, J = 6.2 Hz, 1 H), 1.80-1.71 (m, 1 H), 1.21 (dt, J = 2.6, 7.0 Hz, 1 H), 1.01-0.92 (m, 1 H) |
| 144 | D | N-(3-((1S,5R,6S)-3-amino-5-(fluoromethyl)-2-oxa-4-azabicyclo[4.1.0]hept-3-en-5-yl)-4,5-difluorophenyl)-5-methoxypyrazine-2-carboxamide | 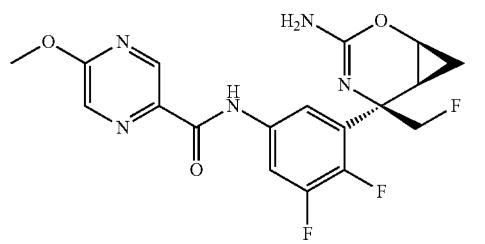 [SMILES: COc1cnc(C(=O)Nc2cc(F)c(F)c([C@]3(CF)N=C(N)O[C@H]4C[C@H]43)c2)cn1] | MS m/z = 407.9 [M]+<br>1H NMR (400 MHz, CHLOROFORM-d) d 9.47 (br. s., 1H), 8.99 (s, 1H), 8.12 (s, 1H), 7.99-8.09 (m, 1H), 4.55-4.82 (m, 2H), 4.07 (s, 3H), 3.98 (br. s., 1H), 1.74 (q, J = 7.69 Hz, 1H), 1.16-1.26 (m, 1H), 0.88-1.02 (m, 1H) |
| 145 | D | N-(3-((1R,5S,6R)-3-amino-5-(fluoromethyl)-2-oxa-4-azabicyclo[4.1.0]hept-3-en-5-yl)-5-fluoro-4-methoxyphenyl)-5-chloropicolinamide | 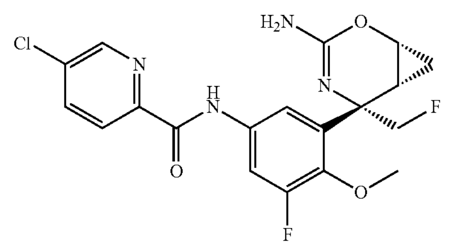 [SMILES: COc1c(F)cc(NC(=O)c2ccc(Cl)cn2)cc1[C@@]1(CF)N=C(N)O[C@@H]2C[C@@H]21] | MS m/z = 422.9 [M]+<br>1H NMR (400 MHz, CHLOROFORM-d) d 9.78 (br. s., 1H), 8.54 (s, 1H), 8.22 (d, J = 8.22 Hz 1H), 8.00 (d, J = 13.69 Hz, 1H), 7.87 (d, J = 8.41 Hz, 1H), 7.24 (br. s., 1H), 4.64-4.84 (m, 2H), 3.99 (s, 3H), 3.94 (br. s., 1H), 1.72-1.82 (m, 1H), 1.15 (t, J = 6.65 Hz, 1H), 0.89 (q, J = 7.63 Hz, 1H) |
| 146 | D | N-(3-((1S,5R,6S)-3-amino-5-(fluoromethyl)-2-oxa-4-azabicyclo[4.1.0]hept-3-en-5-yl)-5-fluoro-4-methoxyphenyl)-5-chloropicolinamide | 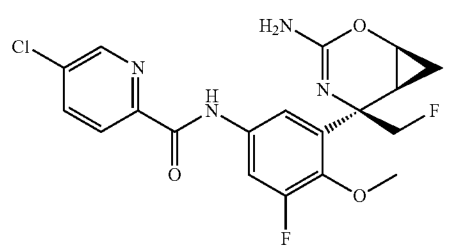 [SMILES: COc1c(F)cc(NC(=O)c2ccc(Cl)cn2)cc1[C@]1(CF)N=C(N)O[C@H]2C[C@H]21] | MS m/z = 422.9 [M]+<br>1H NMR (400 MHz, CHLOROFORM-d) d 9.77 (br. s., 1H), 8.53 (s, 1H), 8.22 (d, J = 8.41 Hz, 1H), 7.99 (d, J = 13.50 Hz, 1H), 7.87 (d, J = 8.22 Hz, 1H), 7.24 (br. s., 1H), 4.63-4.91 (m, 2H), 3.99 (s, 3H), 3.93 (br. s., 1H), 1.77 (q, J = 7.89 Hz, 1H), 1.15 (t, J = 6.85 Hz, 1H), 0.89 (q, J = 7.37 Hz, 1H) |
| 147 | B | N-(3-((1R,5S,6R)-3-amino-5-(difluoromethyl)-2-oxa-4-azabicyclo[4.1.0]hept-3-en-5-yl)-4-fluorophenyl)-5-isopropoxypyrazine-2-carboxamide | 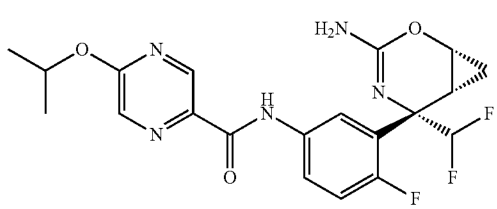 [SMILES: CC(C)Oc1cnc(C(=O)Nc2ccc(F)c([C@@]3(C(F)F)N=C(N)O[C@@H]4C[C@@H]43)c2)cn1] | MS m/z = 436 [M + H]+<br>1H NMR (300 MHz, DMSO-d6) d ppm 10.50 (s, 1 H), 8.86 (d, J = 1.32 Hz, 1 H), 8.33 (d, J = 1.32 Hz, 1 H), 8.03 (dd, J = 7.09, 2.56 Hz, 1 H), 7.77-7.93 (m, 1 H), 7.21 (dd, J = 11.84, 8.92 Hz, 1 H), 5.96-6.52 (m, 1 H), 5.85 (br. s., 2 H), 5.36 (spt, J = 6.16 Hz, 1 H), 4.03 (br. s., 1 H), 1.73 (d, J = 7.45 Hz, 1 H), 1.37 (d, J = 6.14 Hz, 6 H), 1.16 (d, J = 5.99 Hz, 1 H), 0.92 (d, J = 8.04 Hz, 1 H) |

TABLE 1-continued

| Example # | Method | Compound Name | Structure | Analytical Data |
|---|---|---|---|---|
| 148 | B | N-(3-((1R,5S,6R)-3-amino-5-(difluoromethyl)-2-oxa-4-azabicyclo[4.1.0]hept-3-en-5-yl)-4-fluorophenyl)-5-((R)-but-3-yn-2-yloxy)pyrazine-2-carboxamide | 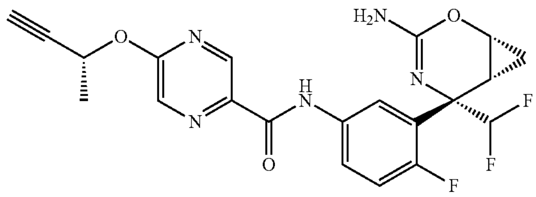 [SMILES: C#C[C@@H](C)Oc1cnc(C(=O)Nc2ccc(F)c([C@@]3(C(F)F)N=C(N)O[C@@H]4C[C@@H]43)c2)cn1] | MS m/z = 446 [M + H]+ 1H NMR (300 MHz, DMSO-d6) d ppm 10.55 (s, 1 H), 8.90 (d, J = 1.32 Hz, 1 H), 8.45 (d, J = 1.17 Hz, 1 H), 8.04 (dd, J = 7.02 2.63 Hz, 1 H), 7.76-7.93 (m, 1 H), 7.21 (dd, J = 11.84, 8.92 Hz, 1 H), 5.97-6.46 (m, 1 H), 5.72-5.92 (m, 3 H), 3.98-4.10 (m, 1 H), 3.59 (d, J = 2.05 Hz, 1 H), 1.67-1.81 (m, 1 H), 1.63 (d, J = 6.58 Hz, 3 H), 1.05-1.26 (m, 1 H), 0.92 (dt, J = 9.21, 6.50 Hz, 1 H) |
| 149 | B | N-(3-((1R,5S,6R)-3-amino-5-(difluoromethyl)-2-oxa-4-azabicyclo[4.1.0]hept-3-en-5-yl)-4-fluorophenyl)-2-(difluoromethyl)thiazole-4-carboxamide | 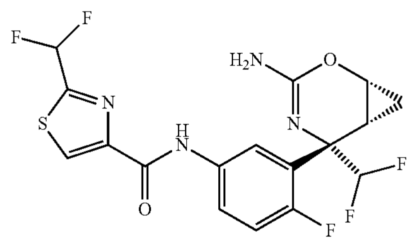 [SMILES: NC1=N[C@@](c2cc(NC(=O)c3csc(C(F)F)n3)ccc2F)(C(F)F)[C@H]2C[C@H]2O1] | MS m/z = 433 [M + H]+ 1H NMR (300 MHz, DMSO-d6) d ppm 10.47 (s, 1 H), 8.72 (s, 1 H), 7.96 (dd, J = 7.09, 2.70 Hz, 1 H), 7.79 (ddd, J = 8.84, 4.17, 2.78 Hz, 1 H), 7.43 (t, J = 54.08 Hz, 1 H), 7.21 (dd, J = 11.91, 8.84 Hz, 1 H), 6.19 (t, J = 55.83 Hz, 1 H), 5.85 (s, 2 H), 3.94-4.11 (m, 1 H), 1.72 (dt, J = 9.28, 6.83 Hz, 1 H), 1.07-1.26 (m, 1 H), 0.91 (dt, J = 9.32, 6.45 Hz, 1 H) |
| 150 | B | N-(3-((1R,5S,6R)-3-amino-5-(difluoromethyl)-2-oxa-4-azabicyclo[4.1.0]hept-3-en-5-yl)-4-fluorophenyl)-2-(difluoromethyl)oxazole-4-carboxamide 2,2,2-trifluoroacetate | 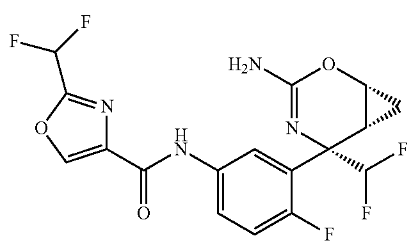 [SMILES: NC1=N[C@@](c2cc(NC(=O)c3coc(C(F)F)n3)ccc2F)(C(F)F)[C@H]2C[C@H]2O1] | MS m/z = 416.9 [M + H]+ 1H NMR (400 MHz, CD3OD) d ppm 8.75 (s, 1 H), 8.16 (dd, J = 7.04, 2.54 Hz, 1 H), 7.84 (ddd, J = 9.00, 4.30, 2.54 Hz, 1 H), 7.37 (dd, J = 11.84, 8.90 Hz, 1 H), 7.04 (t, J = 51.84 Hz, 1 H), 6.69 (t, J = 53.60 Hz, 1 H), 4.65 (td, J = 6.70, 2.84 Hz, 1 H), 2.26 (dt, J = 9.73, 7.07 Hz, 1 H), 1.70 (t, J = 7.63 Hz, 1 H), 1.41 (td, J = 9.05, 6.36 Hz, 1 H) |
| 151 | A | N-(3-((1R,5S,6R)-3-amino-5-(difluoromethyl)-2-oxa-4-azabicyclo[4.1.0]hept-3-en-5-yl)-4-fluorophenyl)-2-(cyclopropylethynyl)oxazole-4-carboxamide | 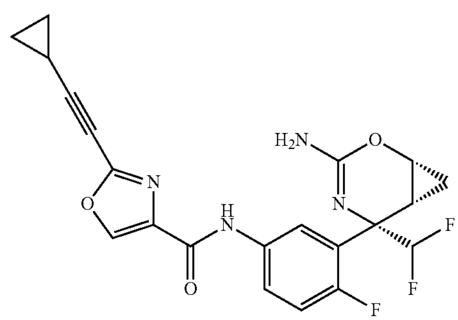 [SMILES: NC1=N[C@@](c2cc(NC(=O)c3coc(C#CC4CC4)n3)ccc2F)(C(F)F)[C@H]2C[C@H]2O1] | MS m/z = 431 [M + H]+ 1H NMR (400 MHz, DMSO-d6) d ppm 10.30 (s, 1 H), 8.75 (s, 1 H), 7.97 (dd, J = 7.04, 2.74 Hz, 1 H), 7.69-7.82 (m, 1 H), 7.18 (dd, J = 11.84, 8.90 Hz, 1 H), 6.18 (t, J = 56.14 Hz, 1 H), 5.83 (br. s., 2 H), 4.01 (t, J = 5.48 Hz, 1 H), 1.62-1.80 (m, 2 H), 1.09-1.19 (m, 1 H), 0.98-1.09 (m, 2 H), 0.81-0.95 (m, 3 H) |
| 152 | B | N-(3-([1(S,R),5(R,S),6(S,R)]-3-amino-5-(fluoromethyl)-2-oxa-4-azabicyclo[4.1.0]hept-3-en-5-yl)-4-chloro-5-fluorophenyl)-5-methoxypyrazine-2-carboxamide compound with N-(3-((1S,5R,6S)-3-amino-5-(fluoromethyl)-2-oxa-4-azabicyclo[4.1.0]hept-3-en-5-yl)-4-chloro-5-fluorophenyl)-5-methoxypyrazine-2-carboxamide (1:1) | 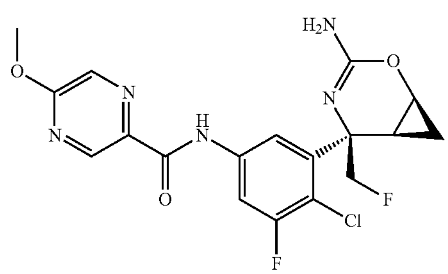 [SMILES: COc1cnc(C(=O)Nc2cc(F)c(Cl)c([C@]3(CF)N=C(N)O[C@H]4C[C@H]43)c2)cn1] | MS m/z = 424.9 [M + H]+ 1H NMR (400 MHz, DMSO-d6) δ ppm 10.77 (s, 1 H), 8.91 (d, J = 1.37 Hz, 1 H), 8.43 (d, J = 1.17 Hz, 1 H), 8.08 (s, 1 H), 8.00 (dd, J = 11.25, 2.45 Hz, 1 H), 5.62 (br. s., 2 H), 4.47-4.93 (m, 2 H), 3.94-4.11 (m, 1 H), 4.03 (s, 3H), 1.52-1.69 (m, 1 H), 0.81-1.04 (m, 2 H) |

| Example # | Method | Compound Name | Structure | Analytical Data |
|---|---|---|---|---|
| 153 | B | N-(3-([1(S,R),5(R,S),6(S,R)]-3-amino-5-(fluoromethyl)-2-oxa-4-azabicyclo[4.1.0]hept-3-en-5-yl)-4-chloro-5-fluorophenyl)-5-(difluoromethoxy)-3-methylpicolinamide compound with N-(3-((1S,5R,6S)-3-amino-5-(fluoromethyl)-2-oxa-4-azabicyclo[4.1.0]hept-3-en-5-yl)-4-chloro-5-fluorophenyl)-5-(difluoromethoxy)-3-methylpicolinamide (1:1) | 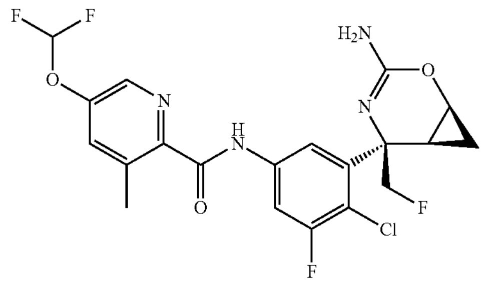 [SMILES: Cc1cc(OC(F)F)cnc1C(=O)Nc1cc(F)c(Cl)c([C@]2(CF)N=C(N)O[C@H]3C[C@H]32)c1] | MS m/z = 473[M + H]+<br>1H NMR (400 MHz, DMSO-d6) δ ppm 11.02 (s, 1 H), 10.36 (br. s., 1 H), 8.46 (d, J = 2.35 Hz, 1 H), 8.13 (dd, J = 11.35, 2.15 Hz, 1 H), 7.99 (s, 1 H), 7.76 (d, J = 2.15 Hz, 1 H), 7.46 (t, J = 73.00 Hz, 1 H), 5.21 (dd, J = 46.36, 9.19 Hz, 1 H), 4.98 (dd, J = 46.36, 10.17 Hz, 1 H), 4.61 (m, J = 6.46, 6.46 Hz, 1 H), 3.87 (br. s., 1 H), 2.62 (s, 3 H), 1.81-1.97 (m, 1 H), 1.51-1.68 (m, 1 H), 1.05-1.31 (m, 1 H) |
| 154 | B | N-(3-((1R,5S,6R)-3-amino-5-(difluoromethyl)-2-oxa-4-azabicyclo[4.1.0]hept-3-en-5-yl)-4-fluorophenyl)-3-(difluoromethyl)-1-methyl-1H-pyrazole-5-carboxamide | 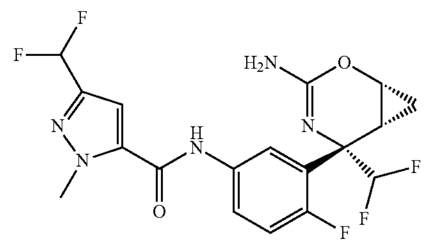 [SMILES: Cn1nc(C(F)F)cc1C(=O)Nc1ccc(F)c([C@@]2(C(F)F)N=C(N)O[C@@H]3C[C@@H]32)c1] | MS m/z = 430 [M + H]+<br>1H NMR (300 MHz, DMSO-d6) δ ppm 10.47 (s, 1 H), 7.81 (dd, J = 6.87, 2.19 Hz, 1 H), 7.73 (m, J = 8.48, 3.65 Hz, 1 H), 7.31 (s, 1 H), 7.22 (dd, J = 11.69, 8.92 Hz, 1 H), 7.07 (t, J = 54.52 Hz, 1 H), 6.18 (t, J = 55.98 Hz, 1 H), 5.86 (br. s, 2 H), 4.12 (s, 3 H), 4.00 (m, 1 H), 1.61-1.82 (m, 1 H), 1.13 (br. s., 1 H), 0.82-1.01 (m, 1 H) |
| 155 | B* | N-(3((1S,5R,6S)-3-amino-5-(fluoromethyl)-2-oxa-4-azabicyclo[4.1.0]hept-3-en-5-yl)-4-chloro-5-fluorophenyl)-5-methoxypyrazine-2-carboxamide | 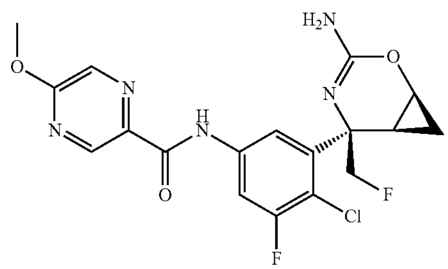 [SMILES: COc1cnc(C(=O)Nc2cc(F)c(Cl)c([C@]3(CF)N=C(N)O[C@H]4C[C@H]43)c2)cn1] | MS m/z = 424.1 [M + H]+<br>1H NMR (400 MHz, DMSO-d6) δ ppm 10.77 (s, 1 H), 8.91 (d, J = 1.17 Hz, 1 H), 8.43 (d, J = 1.37 Hz, 1 H), 8.08 (s, 1 H), 8.00 (dd, J = 11.25, 2.45 Hz, 1 H), 5.63 (br. s., 2 H), 4.46-4.92 (m, 2 H), 4.03 (s, 3 H), 3.96-4.02 (m, 1 H), 1.61 (dt, J = 9.68, 7.09 Hz, 1 H), 0.95 (td, J = 6.50, 2.64 Hz, 1 H), 0.83-0.92 (m, 1 H) |
| 156 | B | N-(3-((1R,5S,6R)-3-amino-5-(fluoromethyl)-2-oxa-4-azabicyclo[4.1.0]hept-3-en-5-yl)-4-chloro-5-fluorophenyl)-5-methoxypyrazine-2-carboxamide | 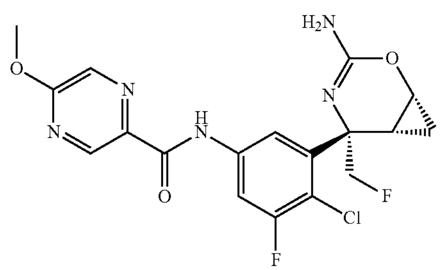 [SMILES: COc1cnc(C(=O)Nc2cc(F)c(Cl)c([C@@]3(CF)N=C(N)O[C@@H]4C[C@@H]43)c2)cn1] | MS m/z = 424. [M + H]+<br>1H NMR (400 MHz, DMSO-d6) δ ppm 10.76 (s, 1 H), 8.91 (d, J = 1.37 Hz, 1 H), 8.43 (d, J = 1.17 Hz, 1 H), 8.08 (s, 1 H), 8.00 (dd, J = 11.25, 2.45 Hz, 1 H), 5.62 (br. s., 2 H), 4.49-4.94 (m, 2 H), 4.03 (s, 3 H), 3.97-4.02 (m, 1 H), 1.61 (dt, J = 9.73, 7.07 Hz, 1 H), 0.95 (td, J = 6.60, 2.84 Hz, 1 H), 0.84-0.92 (m, 1 H) |
| 157 | B | N-(3-((1S,5R,6S)-3-amino-5-(fluoromethyl)-2-oxa-4-azabicyclo[4.1.0]hept-3-en-5-yl)-4-chloro-5-fluorophenyl)-5-(difluoromethoxy)-3-methylpicolinamide | 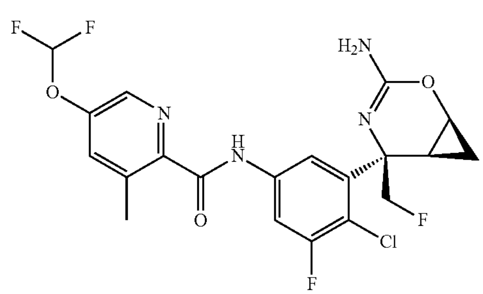 [SMILES: Cc1cc(OC(F)F)cnc1C(=O)Nc1cc(F)c(Cl)c([C@]2(CF)N=C(N)O[C@H]3C[C@H]32)c1] | MS m/z = 473.1 [M + H]+<br>1H NMR (400 MHz, DMSO-d6) δ ppm 10.80 (s, 1 H), 8.44 (s, 1 H), 8.01 (d, J = 11.15 Hz, 1 H), 7.90 (br. s, 1 H), 7.73 (s, 1 H), 7.44 (t, J = 72.97 Hz, 1 H), 5.63 (br. s., 2 H), 4.55-4.89 (m, 2 H), 3.93-4.07 (m, 1 H), 2.60 (s, 3 H), 1.62 (q, J = 7.69 Hz, 1 H), 0.81-1.03 (m, 2 H) |

TABLE 1-continued

| Example # | Method | Compound Name | Structure | Analytical Data |
|---|---|---|---|---|
| 158 | B | N-(3-((1R,5S,6R)-3-amino-5-(fluoromethyl)-2-oxa-4-azabicyclo[4.1.0]hept-3-en-5-yl)-4-chloro-5-fluorophenyl)-5-(difluoromethoxy)-3-methylpicolinamide | 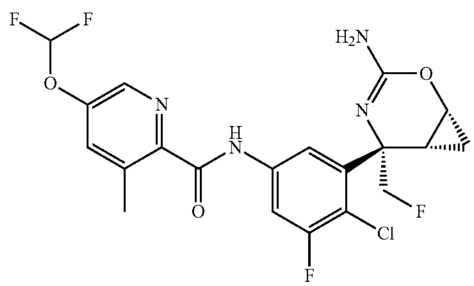 [SMILES: Cc1cc(OC(F)F)cnc1C(=O)Nc1cc(F)c(Cl)c([C@@]2(CF)N=C(N)O[C@@H]3C[C@@H]32)c1] | MS m/z = 473.1 [M + H]+ 1H NMR (400 MHz, DMSO-d6) δ ppm 10.80 (s, 1 H), 8.44 (s, 1 H), 8.00 (d, J = 11.15 Hz, 1 H), 7.90 (s, 1 H), 7.73 (s, 1 H), 7.44 (t, J = 73.16 Hz, 1 H), 5.62 (s, 2 H), 4.52-4.89 (m, 2 H), 3.89-4.06 (m, 1 H), 2.60 (s, 3 H), 1.62 (q, J = 7.69 Hz, 1 H), 0.81-1.01 (m, 2 H) |
| 159 | B | N-(3-([1(S,R),5(R,S),6(S,R)]-3-amino-5-(fluoromethyl)-2-oxa-4-azabicyclo[4.1.0]hept-3-en-5-yl)-4-chloro-5-fluorophenyl)-3-methyl-5-(2,2,2-trifluoroethoxy)pyrazine-2-carboxamide | 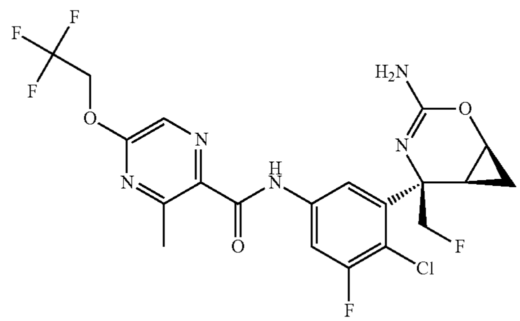 [SMILES: Cc1nc(OCC(F)(F)F)cnc1C(=O)Nc1cc(F)c(Cl)c([C@]2(CF)N=C(N)O[C@H]3C[C@H]32)c1] | MS m/z = 505.9 [M + H]+ 1H NMR (300 MHz, DMSO-d6) δ ppm 10.78 (s, 1 H), 8.44 (s, 1 H), 8.00 (d, J = 11.40 Hz, 1 H), 7.93 (s, 1 H), 5.63 (s, 2 H), 5.14 (q, J = 8.96 Hz, 2 H), 4.78 (dd, J = 28.79, 9.50 Hz, 1 H), 4.63 (dd, J = 28.65, 9.06 Hz, 1 H), 3.86-4.08 (m, 1 H), 2.77 (s, 3 H), 1.50-1.72 (m, 1 H), 0.76-1.05 (m, 2 H) |
| 160 | B | N-(3-((1R,5S,6R)-3-amino-5-(difluoromethyl)-2-oxa-4-azabicyclo[4.1.0]hept-3-en-5-yl)-4-fluorophenyl)-5-(2,2,2-trifluoroethoxy)pyrazine-2-carboxamide | 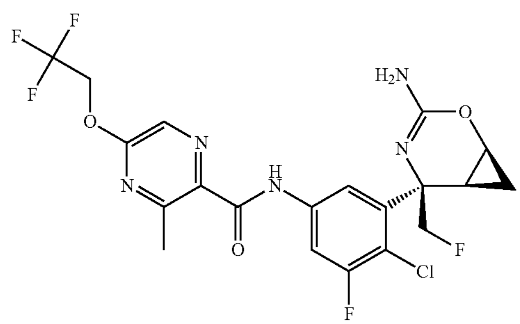 | MS m/z = 476.0 [M + H]+ 1H NMR (400 MHz, DMSO-d6) δ ppm 0.86-0.99 (m, 1 H) 1.15 (br. s., 1 H) 1.73 (q, J = 7.30 Hz, 1 H) 4.02 (br. s., 1 H) 5.16 (q, J = 8.93 Hz, 2 H) 5.85 (br. s., 2 H) 6.00-6.37 (m, 1 H) 7.22 (dd, J = 11.64, 8.90 Hz, 1 H) 7.85 (dt, J = 8.61, 3.42 Hz, 1 H) 8.04 (dd, J = 6.94, 2.64 Hz, 1 H) 8.62 (d, J = 1.17 Hz, 1 H) 8.92 (d, J = 1.17 Hz, 1 H) 10.62 (s, 1 H) |
| 161 | B | N-(3-((1R,5S,6R)-3-amino-5-(difluoromethyl)-2-oxa-4-azabicyclo[4.1.0]hept-3-en-5-yl)-4-fluorophenyl)-4-chloro-1-isopropyl-1H-pyrazole-3-carboxamide | 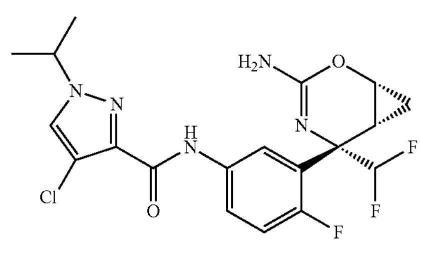 [SMILES: CC(C)n1cc(Cl)c(C(=O)Nc2ccc(F)c([C@@]3(C(F)F)N=C(N)O[C@@H]4C[C@@H]43)c2)n1] | MS m/z = 442.0 [M + H]+ 1H NMR (400 MHz, DMSO-d6) d ppm 0.91 (dt, J = 9.24, 6.53 Hz, 1 H) 1.09-1.19 (m, 1 H) 1.47 (d, J = 6.65 Hz, 5 H) 1.67-1.76 (m, 1 H) 3.97-4.04 (m, 1 H) 4.07 (q, J = 5.15 Hz, 1 H) 4.57 (quin, J = 6.70 Hz, 1 H) 5.84 (s, 1 H) 6.00-6.35 (m, 1 H) 7.18 (dd, J = 11.84, 8.90 Hz, 1 H) 7.68-7.79 (m, 1 H) 7.87 (dd, J = 7.04, 2.54 Hz, 1 H) 8.22 (s, 1 H) 10.06 (s, 1 H) |
| 162 | B | N-(3-((1R,5S,6R)-3-amino-5-(difluoromethyl)-2-oxa-4-azabicyclo[4.1.0]hept-3-en-5-yl)-4-fluorophenyl)-5-((S)-but-3-yn-2-yloxy)pyrazine-2-carboxamide | 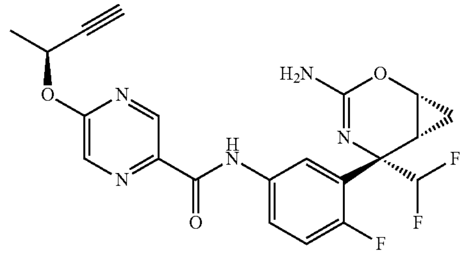 [SMILES: C#C[C@H](C)Oc1cnc(C(=O)Nc2ccc(F)c([C@@]3(C(F)F)N=C(N)O[C@@H]4C[C@@H]43)c2)cn1] | MS m/z = 446.0 [M + H]+ $^1$H NMR (400 MHz, DMSO-d$_6$) δ ppm 0.93 (br. s., 1 H) 1.73 (d, J = 5.87 Hz, 2 H) 3.59 (d, J = 2.15 Hz, 1 H) 5.73-5.91 (m, 3 H) 5.98-6.41 (m, 1 H) 7.22 (t, J = 10.37 Hz, 1 H) 7.86 (d, J = 8.02 Hz, 1 H) 8.04 (d, J = 4.89 Hz, 1 H) 8.45 (d, J = 1.37 Hz, 1 H) 8.90 (d, J = 1.17 Hz, 1 H) 10.55 (br. s., 1 H) |

TABLE 1-continued

| Example # | Method | Compound Name | Structure | Analytical Data |
|---|---|---|---|---|
| 163 | B | N-(3-((1R,5S,6R)-3-amino-5-(difluoromethyl)-2-oxa-4-azabicyclo[4.1.0]hept-3-en-5-yl)-4-fluorophenyl)-4-chloro-1-(difluoromethyl)-1H-pyrazole-3-carboxamide | 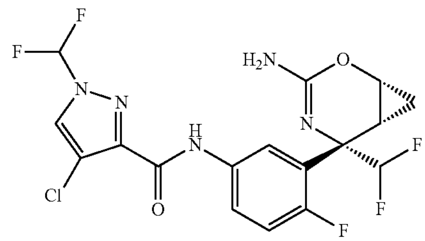 [SMILES: NC1=N[C@@](c2cc(NC(=O)c3nn(C(F)F)cc3Cl)ccc2F)(C(F)F)[C@H]2C[C@H]2O1] | MS m/z = 449.9 [M + H]$^+$ $^1$H NMR (400 MHz, DMSO-d$_6$) δ ppm 0.92 (br. s., 1 H) 1.14 (br. s., 1 H) 1.71 (br. s., 1 H) 4.01 (br. s., 1 H) 5.86 (br. s., 2 H) 5.97-6.40 (m, 1 H) 7.21 (t, J = 9.68 Hz, 1 H) 7.66-7.82 (m, 1 H) 7.88 (s, 2 H) 8.77 (s, 1 H) 10.57 (br. s., 1 H) |
| 164 | B | N-(3-((1R,5S,6R)-3-amino-5-(fluoromethyl)-2-oxa-4-azabicyclo[4.1.0]hept-3-en-5-yl)-4-fluorophenyl)-4-chloro-1-(difluoromethyl)-1H-pyrazole-3-carboxamide | 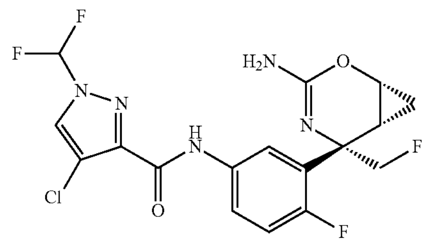 [SMILES: NC1=N[C@](CF)(c2cc(NC(=O)c3nn(C(F)F)cc3Cl)ccc2F)[C@H]2C[C@H]2O1] | MS m/z = 431.9 [M + H]$^+$ 1H NMR (400 MHz, DMSO-d6) d ppm 0.84 (dt, J = 9.5, 6.4 Hz, 1 H), 0.95-1.06 (m, 1 H), 1.50-1.62 (m, 1 H), 3.97-4.08 (m, 1 H), 4.41-4.73 (m, 2 H), 7.17 (dd, J = 11.9, 8.8 Hz, 1 H), 7.67-8.05 (m, 1 H), 7.84 (dd, J = 7.0, 2.5 Hz, 1 H), 7.88 (t, J = 58.5 Hz, 1 H), 8.76 (s, 1 H), 10.54 (s, 1 H) |
| 165 | B | N-(3-((1R,5S,6R)-3-amino-5-(difluoromethyl)-2-oxa-4-azabicyclo[4.1.0]hept-3-en-5-yl)-4-fluorophenyl)-5-(thiazol-2-ylmethoxy)pyrazine-2-carboxamide | 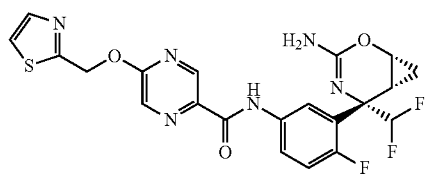 [SMILES: NC1=N[C@@](c2cc(NC(=O)c3cnc(OCc4nccs4)cn3)ccc2F)(C(F)F)[C@H]2C[C@H]2O1] | MS m/z = 491.0 [M + H]$^+$ 1H NMR (400 MHz, CHLOROFORM-d) d ppm 1.03-1.14 (m, 1 H) 1.26 (s, 1 H) 1.44-1.53 (m, 1 H) 1.90-2.03 (m, 1 H) 4.07 (br. s., 1 H) 5.81 (s, 1 H) 6.10-6.44 (m, 1 H) 7.16 (dd, J = 11.54, 9.00 Hz, 1 H) 7.42 (d, J = 3.13 Hz, 1 H) 7.69 (dd, J = 6.75, 2.64 Hz, 1 H) 7.85 (d, J = 3.13 Hz, 1 H) 7.98-8.06 (m, 1 H) 8.28 (d, J = 1.17 Hz, 1 H) 9.05 (d, J = 1.17 Hz, 1 H) 9.54 (s, 1 H) |
| 166 | B | N-(3-((1R,5S,6R)-3-amino-5-(difluoromethyl)-2-oxa-4-azabicyclo[4.1.0]hept-3-en-5-yl)-4-fluorophenyl)-2-methyloxazole-4-carboxamide | 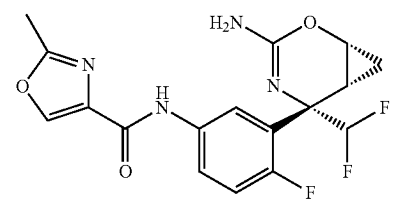 [SMILES: Cc1nc(C(=O)Nc2ccc(F)c([C@@]3(C(F)F)N=C(N)O[C@@H]4C[C@@H]43)c2)co1] | MS m/z = 380.9 [M + H]$^+$ 1H NMR (400 MHz, CHLOROFORM-d) d ppm 0.91-1.06 (m, 1 H) 1.43 (t, J = 6.75 Hz, 1 H) 1.88 (dt, J = 9.49, 7.09 Hz, 1 H) 2.50 (s, 3 H) 3.90-4.02 (m, 1 H) 6.05-6.42 (m, 1 H) 7.08 (dd, J = 11.54, 8.80 Hz, 1 H) 7.62 (dd, J = 6.75, 2.64 Hz, 1 H) 7.90 (ddd, J = 8.75, 4.06, 2.84 Hz, 1 H) 8.15 (s, 1 H) 8.65 (s, 1 H) |
| 167 | B | N-(3-((1R,5S,6R)-3-amino-5-(difluoromethyl)-2-oxa-4-azabicyclo[4.1.0]hept-3-en-5-yl)-4-fluorophenyl)-5-(oxazol-2-ylmethoxy)pyrazine-2-carboxamide | 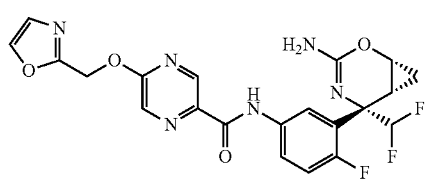 [SMILES: NC1=N[C@@](c2cc(NC(=O)c3cnc(OCc4ncco4)cn3)ccc2F)(C(F)F)[C@H]2C[C@H]2O1] | MS m/z = 475.0 [M + H]$^+$ 1H NMR (400 MHz, DMSO-d6) d ppm 0.86-0.97 (m, 1 H) 1.15 (br. s., 1 H) 1.67-1.78 (m, 1 H) 3.96-4.05 (m, 1 H) 5.61 (s, 2 H) 5.84 (s, 2 H) 6.01-6.36 (m, 1 H) 7.21 (dd, J = 11.83, 8.90 Hz, 1 H) 7.29 (d, J = 0.59 Hz, 1 H) 7.85 (dt, J = 7.29, 4.18 Hz, 1 H) 8.03 (dd, J = 7.14, 2.64 Hz, 1 H) 8.19 (d, J = 0.78 Hz, 1 H) 8.53 (d, J = 1.37 Hz, 1 H) 8.88 (d, J = 1.37 Hz, 1 H) 10.56 (s, 1 H) |
| 168 | B | N-(3-((1R,5S,6R)-3-amino-5-(difluoromethyl)-2-oxa-4-azabicyclo[4.1.0]hept-3-en-5-yl)-4-fluorophenyl)-2-(fluoromethyl)oxazole-4-carboxamide | 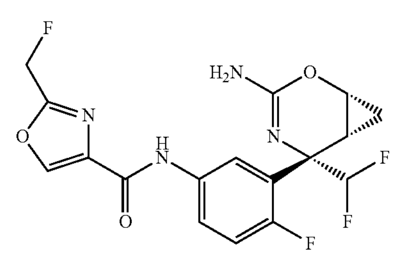 [SMILES: NC1=N[C@@](c2cc(NC(=O)c3coc(CF)n3)ccc2F)(C(F)F)[C@H]2C[C@H]2O1] | MS m/z = 398.9 [M + H]$^+$ 1H NMR (400 MHz, DMSO-d6) d ppm 0.91 (dt, J = 9.39, 6.46 Hz, 1 H) 1.07-1.19 (m, 1 H) 1.64-1.77 (m, 1 H) 3.96-4.06 (m, 1 H) 5.48-5.71 (m, 2 H) 5.84 (s, 2 H) 6.00-6.37 (m, 1 H) 7.19 (dd, J = 11.74, 8.80 Hz, 1 H) 7.73-7.82 (m, 1 H) 7.96 (dd, J = 7.14, 2.64 Hz, 1 H) 8.88 (d, J = 1.56 Hz, 1 H) 10.34 (s, 1 H) |

TABLE 1-continued

| Example # | Method | Compound Name | Structure | Analytical Data |
|---|---|---|---|---|
| 169 | A | N-(3-((1R,5S,6R)-3-amino-5-(difluoromethyl)-2-oxa-4-azabicyclo[4.1.0]hept-3-en-5-yl)-4-fluorophenyl)-5-(thiazol-4-ylmethoxy)pyrazine-2-carboxamide | 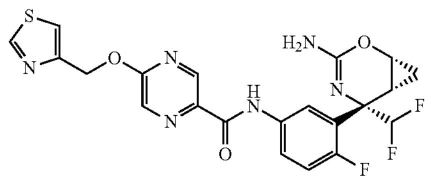 [SMILES: NC1=N[C@@](c2cc(NC(=O)c3cnc(OCc4cscn4)cn3)ccc2F)(C(F)F)[C@H]2C[C@H]2O1] | MS m/z = 490.9 [M + H]+<br>1H NMR (400 MHz, DMSO-d6) d ppm 0.91 (dt, J = 9.39, 6.36 Hz, 1 H) 1.15 (t, J = 4.89 Hz, 1 H) 1.64-1.78 (m, 1 H) 4.02 (t, J = 5.38 Hz, 1 H) 5.62 (s, 2 H) 5.85 (s, 2 H) 6.02-6.37 (m, 1 H) 7.21 (dd, J = 11.84, 8.90 Hz, 1 H) 7.80-7.87 (m, 1 H) 7.88 (d, J = 1.76 Hz, 1 H) 8.03 (dd, J = 7.04, 2.74 Hz, 1 H) 8.47 (d, J = 1.17 Hz, 1 H) 8.91 (d, J = 1.17 Hz, 1 H) 9.15 (d, J = 1.96 Hz, 1 H) 10.54 (s, 1 H) |
| 170 | B | N-(3-((1R,5S,6R)-3-amino-5-(difluoromethyl)-2-oxa-4-azabicyclo[4.1.0]hept-3-en-5-yl)-4-fluorophenyl)-5-(thiazol-5-ylmethoxy)pyrazine-2-carboxamide | 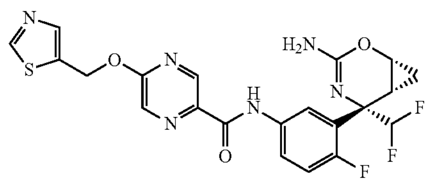 [SMILES: NC1=N[C@@](c2cc(NC(=O)c3cnc(OCc4cncs4)cn3)ccc2F)(C(F)F)[C@H]2C[C@H]2O1] | MS m/z = 490.9 [M + H]+<br>1H NMR (400 MHz, DMSO-d6) d ppm 0.86-1.00 (m, 1 H) 1.15 (br. s., 1 H) 1.65-1.79 (m, 1 H) 3.96-4.08 (m, 1 H) 5.78 (s, 2 H) 5.84 (s, 2 H) 6.01-6.37 (m, 1 H) 7.21 (dd, J = 11.83, 8.71 Hz, 1 H) 7.85 (dt, J = 7.29, 4.18 Hz, 1 H) 8.03 (dd, J = 7.14, 2.64 Hz, 1 H) 8.10 (d, J = 0.59 Hz, 1 H) 8.46 (d, J = 1.37 Hz, 1 H) 8.93 (d, J = 1.37 Hz, 1 H) 9.15 (s, 1 H) 10.55 (s, 1 H) |
| 171 | B | N-(3-((1R,5S,6R)-3-amino-5-(difluoromethyl)-2-oxa-4-azabicyclo[4.1.0]hept-3-en-5-yl)-4-fluorophenyl)-5-(oxazol-5-ylmethoxy)pyrazine-2-carboxamide | 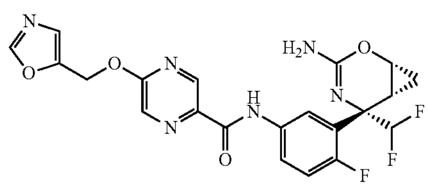 [SMILES: NC1=N[C@@](c2cc(NC(=O)c3cnc(OCc4cnco4)cn3)ccc2F)(C(F)F)[C@H]2C[C@H]2O1] | MS m/z = 475.0 [M + H]+<br>1H NMR (400 MHz, CHLOROFORM-d) d ppm 1.12-1.23 (m, 1 H) 1.53-1.67 (m, 1 H) 2.01-2.17 (m, 1 H) 4.15-4.29 (m, 1 H) 5.54 (s, 2 H) 6.15-6.51 (m, 1 H) 7.18 (dd, J = 11.54, 9.00 Hz, 1 H) 7.76 (dd, J = 6.65, 2.54 Hz, 1 H) 7.93 (s, 1 H) 7.98 (dt, J = 8.80, 3.42 Hz, 1 H) 8.21 (d, J = 1.17 Hz, 1 H) 9.03 (d, J = 1.17 Hz, 1 H) 9.56 (s, 1 H) |
| 172 | B | N-(3-((1R,5S,6R)-3-amino-5-(difluoromethyl)-2-oxa-4-azabicyclo[4.1.0]hept-3-en-5-yl)-4-fluorophenyl)-5-(thiazol-2-ylmethoxy)picolinamide | 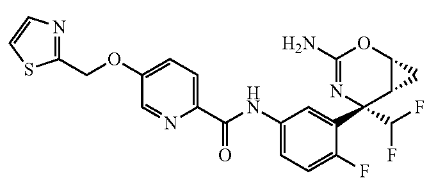 [SMILES: NC1=N[C@@](c2cc(NC(=O)c3ccc(OCc4nccs4)cn3)ccc2F)(C(F)F)[C@H]2C[C@H]2O1] | MS m/z = 490.0 [M + H]+<br>1H NMR (400 MHz, CHLOROFORM-d) d ppm 0.99 (q, J = 7.69 Hz, 1 H) 1.44 (br. s., 1 H) 1.89 (q, J = 7.69 Hz, 1 H) 3.97 (br. s., 1 H) 5.52 (s, 2 H) 6.09-6.43 (m, 1 H) 7.10 (t, J = 10.17 Hz, 1 H) 7.45 (br. s., 1 H) 7.48 (d, J = 8.80 Hz, 1 H) 7.65 (d, J = 6.65 Hz, 1 H) 7.86 (br. s., 1 H) 8.01 (d, J = 7.82 Hz, 1 H) 8.22 (d, J = 8.80 Hz, 1 H) 8.35 (s, 1 H) 9.81 (s, 1 H) |
| 173 | B | N-(3-((1R,5S,6R)-3-amino-5-(difluoromethyl)-2-oxa-4-azabicyclo[4.1.0]hept-3-en-5-yl)-4-fluorophenyl)-5-(oxazol-2-ylmethoxy)picolinamide | 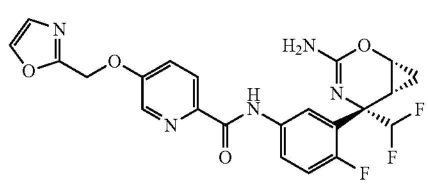 [SMILES: NC1=N[C@@](c2cc(NC(=O)c3ccc(OCc4ncco4)cn3)ccc2F)(C(F)F)[C@H]2C[C@H]2O1] | MS m/z = 474.0 [M + H]+<br>1H NMR (400 MHz, CHLOROFORM-d) d ppm 0.89-1.05 (m, 1 H) 1.44 (br. s., 1 H) 1.88 (q, J = 7.76 Hz, 1 H) 3.91-4.15 (m, 3 H) 5.29 (s, 2 H) 6.08-6.44 (m, 1 H) 7.10 (t, J = 10.47 Hz, 1 H) 7.21 (s, 1 H) 7.50 (d, J = 8.61 Hz, 1 H) 7.66 (d, J = 6.46 Hz, 1 H) 7.74 (s, 1 H) 7.94-8.05 (m, 1 H) 8.23 (d, J = 8.61 Hz, 1 H) 8.35 (s, 1 H) 9.81 (s, 1 H) |
| 174 | B | N-(3-((1R,5S,6R)-3-amino-5-(difluoromethyl)-2-oxa-4-azabicyclo[4.1.0]hept-3-en-5-yl)-4-fluorophenyl)-5-(oxazol-4-ylmethoxy)pyrazine-2-carboxamide | 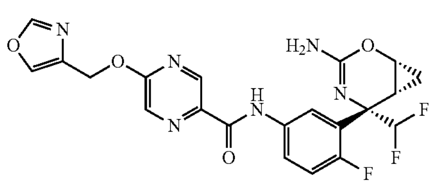 [SMILES: NC1=N[C@@](c2cc(NC(=O)c3cnc(OCc4cocn4)cn3)ccc2F)(C(F)F)[C@H]2C[C@H]2O1] | MS m/z = 475.0 [M + H]+<br>1H NMR (400 MHz, CHLOROFORM-d) d ppm 0.94-1.06 (m, 1 H) 1.38-1.48 (m, 1 H) 1.82-1.98 (m, 1 H) 3.93-4.05 (m, 1 H) 5.47 (s, 2 H) 6.06-6.42 (m, 1 H) 7.12 (dd, J = 11.54, 9.00 Hz, 1 H) 7.65 (dd, J = 6.65, 2.54 Hz, 1 H) 7.82 (s, 1 H) 7.94 (s, 1 H) 7.99 (dt, J = 8.51, 3.47 Hz, 1 H) 8.19 (s, 1 H) 9.02 (s, 1 H) 9.48 (s, 1 H) |

TABLE 1-continued

| Example # | Method | Compound Name | Structure | Analytical Data |
|---|---|---|---|---|
| 175 | B | N-(3-((1R,5S,6R)-3-amino-5-(difluoromethyl)-2-oxa-4-azabicyclo[4.1.0]hept-3-en-5-yl)-4-fluorophenyl)-2-(1-fluoroethyl)oxazole-4-carboxamide 2,2,2-trifluoroacetate | 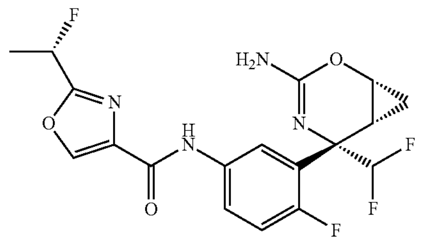 [SMILES: C[C@H](F)c1nc(C(=O)Nc2ccc(F)c([C@@]3(C(F)F)N=C(N)O[C@@H]4C[C@@H]43)c2)co1] | MS m/z = 413.0 [M + H]⁺<br>1H NMR (400 MHz, CHLOROFORM-d) d ppm 1.31-1.44 (m, 1 H) 1.72 (br. s., 1 H) 1.77-1.92 (m, 2 H) 2.16-2.30 (m, 1 H) 4.42 (br. s., 1 H) 5.58-5.82 (m, 1 H) 6.23-6.59 (m, 1 H) 7.21 (t, J = 10.27 Hz, 1 H) 7.83 (d, J = 7.04 Hz, 1 H) 8.33 (s, 1 H) 8.84 (br. s., 1 H) 120768-50-1 |
| 176 | B | N-(3-((1R,5S,6R)-3-amino-5-(difluoromethyl)-2-oxa-4-azabicyclo[4.1.0]hept-3-en-5-yl)-4-fluorophenyl)-4-methylthiophene-2-carboxamide | 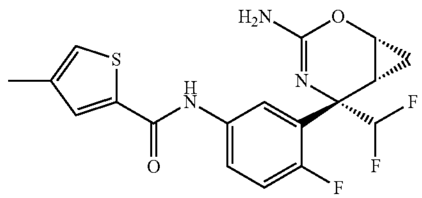 [SMILES: Cc1csc(C(=O)Nc2ccc(F)c([C@@]3(C(F)F)N=C(N)O[C@@H]4C[C@@H]43)c2)c1] | MS m/z = 395.9 [M + H]⁺<br>1H NMR (400 MHz, DMSO-d6) d ppm 0.90 (q, J = 6.91 Hz, 1 H) 1.13 (br. s., 1 H) 1.64-1.79 (m, 1 H) 2.27 (s, 3 H) 4.00 (br. s., 1 H) 5.84 (s, 2 H) 5.97-6.37 (m, 1 H) 7.19 (t, J = 10.27 Hz, 1 H) 7.44 (s, 1 H) 7.69 (d, J = 7.04 Hz, 1 H) 7.83 (br. s., 2 H) 10.27 (s, 1 H) |
| 177 | B | N-(3-((1R,5S,6R)-3-amino-5-(difluoromethyl)-2-oxa-4-azabicyclo[4.1.0]hept-3-en-5-yl)-4-fluorophenyl)-4-chlorothiophene-2-carboxamide | 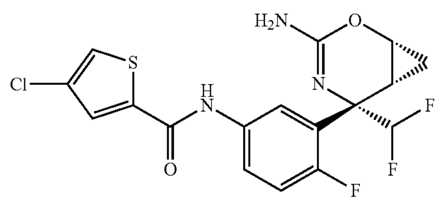 [SMILES: NC1=N[C@@](c2cc(NC(=O)c3cc(Cl)cs3)ccc2F)(C(F)F)[C@H]2C[C@H]2O1] | MS m/z = 415.9 [M + H]⁺<br>1H NMR (400 MHz, DMSO-d6) d ppm 0.90 (dt, J = 9.29, 6.50 Hz, 1 H) 1.08-1.18 (m, 1 H) 1.72 (dt, J = 9.34, 6.87 Hz, 1 H) 3.95-4.04 (m, 1 H) 5.86 (s, 2 H) 6.00-6.35 (m, 1 H) 7.22 (dd, J = 11.74, 8.80 Hz, 1 H) 7.64-7.74 (m, 1 H) 7.82 (dd, J = 6.94, 2.64 Hz, 1 H) 7.91 (d, J = 1.37 Hz, 1 H) 8.03 (d, J = 1.37 Hz, 1 H) 10.42 (s, 1 H) |
| 178 | B | N-(3-((1R,5S,6R)-3-amino-5-(difluoromethyl)-2-oxa-4-azabicyclo[4.1.0]hept-3-en-5-yl)-4-fluorophenyl)-4-cyanothiophene-2-carboxamide | 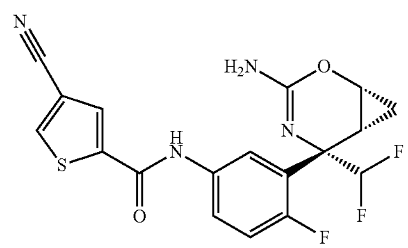 [SMILES: N#Cc1csc(C(=O)Nc2ccc(F)c([C@@]3(C(F)F)N=C(N)O[C@@H]4C[C@@H]43)c2)c1] | MS m/z = 406.9 [M + H]⁺<br>1H NMR (400 MHz, DMSO-d6) d ppm 0.82-0.98 (m, 1 H) 1.13 (br. s., 1 H) 1.64-1.79 (m, 1 H) 3.99 (br. s., 1 H) 5.86 (s, 2 H) 5.99-6.35 (m, 1 H) 7.23 (t, J = 10.66 Hz, 1 H) 7.69 (br. s., 1 H) 7.80 (d, J = 6.65 Hz, 1 H) 8.32 (s, 1 H) 8.80 (s, 1 H) 10.54 (s, 1 H) |
| 179 | B | N-(3-((1R,5S,6R)-3-amino-5-(difluoromethyl)-2-oxa-4-azabicyclo[4.1.0]hept-3-en-5-yl)-4-fluorophenyl)-5-chlorothiophene-2-carboxamide | 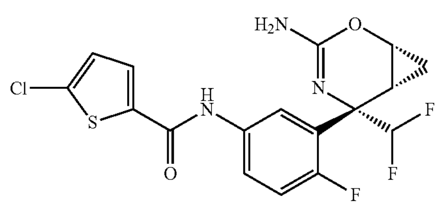 [SMILES: NC1=N[C@@](c2cc(NC(=O)c3ccc(Cl)s3)ccc2F)(C(F)F)[C@H]2C[C@H]2O1] | MS m/z = 415.9 [M + H]⁺<br>1H NMR (400 MHz, DMSO-d6) d ppm 1.28 (d, J = 5.48 Hz, 1 H) 1.62 (br. s., 1 H) 2.09 (d, J = 6.46 Hz, 1 H) 3.43 (br. s., 1 H) 4.67 (br. s., 1 H) 6.55-6.92 (m, 1 H) 7.30 (br. s., 1 H) 7.42 (t, J = 10.07 Hz, 1 H) 7.81 (br. s., 1 H) 8.05 (br. s., 2 H) 10.70 (br. s., 2 H) |
| 180 | B | N-(3-((1R,5S,6R)-3-amino-5-(difluoromethyl)-2-oxa-4-azabicyclo[4.1.0]hept-3-en-5-yl)-4-fluorophenyl)-5-(fluoromethoxy)picolinamide | 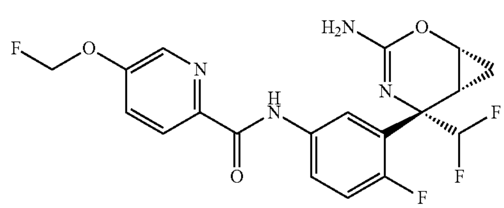 [SMILES: NC1=N[C@@](c2cc(NC(=O)c3ccc(OCF)cn3)ccc2F)(C(F)F)[C@H]2C[C@H]2O1] | MS m/z = 425.0 [M + H]⁺<br>1H NMR (400 MHz, CHLOROFORM-d) d ppm 0.96-1.10 (m, 1 H) 1.46 (br. s., 1 H) 1.93 (q, J = 8.09 Hz, 1 H) 4.02 (br. s., 1 H) 5.69-5.94 (m, 2 H) 6.07-6.44 (m, 1 H) 7.13 (t, J = 10.27 Hz, 1 H) 7.57 (d, J = 8.80 Hz, 1 H) 7.69 (d, J = 7.04 Hz, 1 H) 8.02 (d, J = 7.63 Hz, 1 H) 8.28 (d, J = 8.41 Hz, 1 H) 8.41 (s, 1 H) 9.85 (br. s., 1 H) |
| 181 | B | N-(3-((1R,5S,6R)-3-amino-5-(difluoromethyl)-2-oxa-4-azabicyclo[4.1.0]hept-3-en-5-yl)-4-fluorophenyl)-5-chlorothiophene-3-carboxamide | 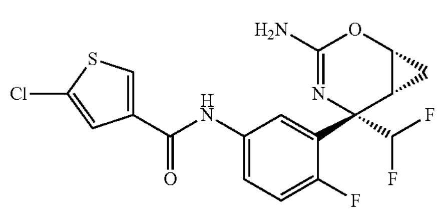 [SMILES: NC1=N[C@@](c2cc(NC(=O)c3csc(Cl)c3)ccc2F)(C(F)F)[C@H]2C[C@H]2O1] | MS m/z = 416.0 [M + H]⁺<br>1H NMR (400 MHz, CHLOROFORM-d) d ppm 0.99 (d, J = 7.43 Hz, 1 H) 1.36 (br. s., 1 H) 1.87 (q, J = 7.76 Hz, 1 H) 3.93 (br. s., 1 H) 6.02-6.39 (m, 1 H) 7.01-7.11 (m, 1 H) 7.14 (d, J = 6.26 Hz, 1 H) 7.46 (s, 1 H) 7.94 (s, 1 H) 8.13 (br. s., 1 H) |

TABLE 1-continued

| Example # | Method | Compound Name | Structure | Analytical Data |
|---|---|---|---|---|
| 182 | B | N-(3-((1R,5S,6R)-3-amino-5-(difluoromethyl)-2-oxa-4-azabicyclo[4.1.0]hept-3-en-5-yl)-4-fluorophenyl)-5-(methylsulfonyl)picolinamide | 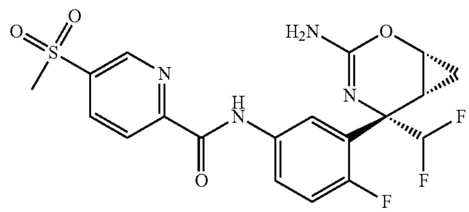 [SMILES: CS(=O)(=O)c1ccc(C(=O)Nc2ccc(F)c([C@@]3(C(F)F)N=C(N)O[C@@H]4C[C@@H]43)c2)nc1] | MS m/z = 455.1 [M + H]+<br>1H NMR (400 MHz, CHLOROFORM-d) d ppm 0.96-1.07 (m, 1 H) 1.45 (br. s., 1 H) 1.85-1.97 (m, 1 H) 3.18 (s, 3 H) 3.94-4.02 (m, 1 H) 6.07-6.42 (m, 1 H) 7.13 (dd, J = 11.15, 9.00 Hz, 1 H) 7.72 (dd, J = 6.55, 2.25 Hz, 1 H) 7.97-8.06 (m, 1 H) 8.41-8.52 (m, 2 H) 9.13 (s, 1 H) 9.90 (s, 1 H) |
| 183 | C | N-(3-((1R,5S,6R)-3-amino-5-(fluoromethyl)-2-oxa-4-azabicyclo[4.1.0]hept-3-en-5-yl)-4-chlorophenyl)-5-(fluoromethoxy)picolinamide | 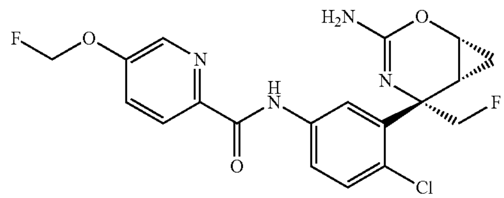 [SMILES: NC1=N[C@](CF)(c2cc(NC(=O)c3ccc(OCF)cn3)ccc2Cl)[C@H]2C[C@H]2O1] | MS m/z = 422.9 [M + H]+<br>1H NMR (400 MHz, CHLOROFORM-d) d ppm 0.98 (dt, J = 9.78, 6.65 Hz, 1 H) 1.17 (td, J = 7.04, 2.74 Hz, 1 H) 1.99 (dt, J = 9.88, 7.19 Hz, 1 H) 3.89-3.99 (m, 1 H) 4.75-5.01 (m, 2 H) 5.69-5.93 (m, 2 H) 7.42 (d, J = 8.80 Hz, 1 H) 7.58 (dd, J = 8.61, 2.74 Hz, 1 H) 7.83 (d, J = 2.74 Hz, 1 H) 8.01 (dd, J = 8.61, 2.54 Hz, 1 H) 8.28 (d, J = 8.80 Hz, 1 H) 8.41 (d, J = 2.74 Hz, 1 H) 9.88 (s, 1 H) |
| 184 | B | N-(3-((1R,5S,6R)-3-amino-5-(difluoromethyl)-2-oxa-4-azabicyclo[4.1.0]hept-3-en-5-yl)-4-fluorophenyl)-5-(cyanomethoxy)-3-methylpicolinamide | 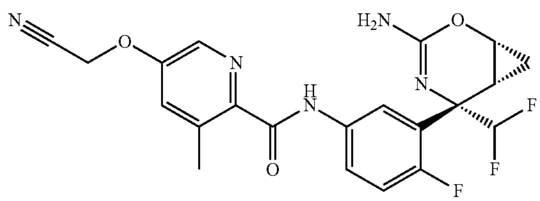 [SMILES: Cc1cc(OCC#N)cnc1C(=O)Nc1ccc(F)c([C@@]2(C(F)F)N=C(N)O[C@@H]3C[C@@H]32)c1] | MS m/z = 446.0 [M + H]+<br>1H NMR (400 MHz, ACETONITRILE-d3) d ppm 1.18-1.31 (m, 1 H) 1.57 (br. s., 1 H) 2.04-2.12 (m, 2 H) 2.73 (s, 3 H) 3.28 (s, 1 H) 4.39 (br. s., 1 H) 5.02 (s, 2 H) 6.26-6.65 (m, 1 H) 7.25 (t, J = 10.47 Hz, 1 H) 7.38 (br. s., 1 H) 7.84 (d, J = 7.04 Hz, 1 H) 7.94 (br. s., 1 H) 8.25 (br. s., 1 H) 10.10 (br. s., 1 H) |
| 185 | B | N-(3-((1R,5S,6R)-3-amino-5-(difluoromethyl)-2-oxa-4-azabicyclo[4.1.0]hept-3-en-5-yl)-4-fluorophenyl)-3,5-dimethylpicolinamide | 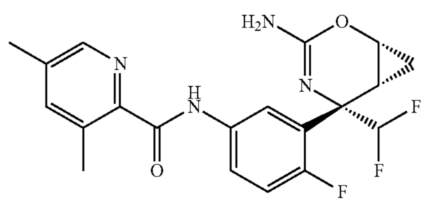 [SMILES: Cc1cnc(C(=O)Nc2ccc(F)c([C@@]3(C(F)F)N=C(N)O[C@@H]4C[C@@H]43)c2)c(C)c1] | MS m/z = 405.0 [M + H]+<br>1H NMR (400 MHz, CHLOROFORM-d) d ppm 0.99 (q, J = 7.50 Hz, 1 H) 1.43 (br. s., 1 H) 1.91 (q, J = 7.82 Hz, 1 H) 2.39 (s, 3 H) 2.76 (s, 3 H) 3.98 (br. s., 1 H) 6.05-6.45 (m, 1 H) 7.10 (t, J = 10.27 Hz, 1 H) 7.43 (s, 1 H) 7.54 (d, J = 6.85 Hz, 1 H) 8.08 (d, J = 8.22 Hz, 1 H) 8.24 (s, 1 H) 10.19 (br. s., 1 H) |
| 186 | B | N-(3-((1R,5S,6R)-3-amino-5-(difluoromethyl)-2-oxa-4-azabicyclo[4.1.0]hept-3-en-5-yl)-4-fluorophenyl)-5-(difluoromethyl)-3-methylpicolinamide | 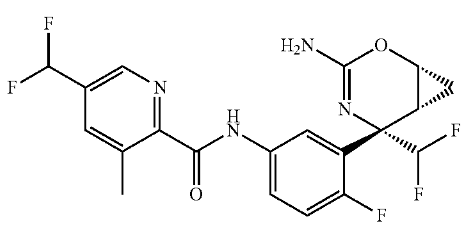 [SMILES: Cc1cc(C(F)F)cnc1C(=O)Nc1ccc(F)c([C@@]2(C(F)F)N=C(N)O[C@@H]3C[C@@H]32)c1] | MS m/z = 440.9 [M + H]+<br>1H NMR (400 MHz, CHLOROFORM-d) d ppm 0.95-1.07 (m, 1 H) 1.39-1.52 (m, 1 H) 1.85-1.99 (m, 1 H) 2.85 (s, 3 H) 3.98 (t, J = 5.38 Hz, 1 H) 6.04-6.43 (m, 1 H) 6.55-6.95 (m, 1 H) 7.09 (dd, J = 11.35, 9.00 Hz, 1 H) 7.57 (dd, J = 6.55, 2.45 Hz, 1 H) 7.78 (s, 1 H) 8.04 (dd, J = 7.82, 3.72 Hz, 1 H) 8.54 (s, 1 H) 10.11 (s, 1 H) |
| 187 | B | N-(3-((1R,5S,6R)-3-amino-5-(difluoromethyl)-2-oxa-4-azabicyclo[4.1.0]hept-3-en-5-yl)-4-fluorophenyl)-6-methoxypyridazine-3-carboxamide | 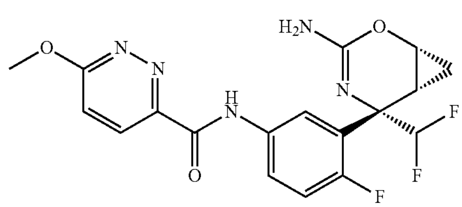 [SMILES: COc1ccc(C(=O)Nc2ccc(F)c([C@@]3(C(F)F)N=C(N)O[C@@H]4C[C@@H]43)c2)nn1] | MS m/z = 408.0 [M + H]+<br>1H NMR (400 MHz, CHLOROFORM-d) d ppm 1.02 (q, J = 7.82 Hz, 1 H) 1.46 (br. s., 1 H) 1.89 (q, J = 7.82 Hz, 1 H) 3.95-4.07 (m, 1 H) 4.24 (s, 3 H) 6.07-6.45 (m, 1 H) 7.09-7.21 (m, 2 H) 7.69 (d, J = 6.26 Hz, 1 H) 8.01 (d, J = 8.61 Hz, 1 H) 8.28 (d, J = 9.00 Hz, 1 H) 9.89 (br. s., 1 H) |

TABLE 1-continued

| Example # | Method | Compound Name | Structure | Analytical Data |
|---|---|---|---|---|
| 188 | B | N-(3-((1R,5S,6R)-3-amino-5-(difluoromethyl)-2-oxa-4-azabicyclo[4.1.0]hept-3-en-5-yl)-4-fluorophenyl)-3-methyl-5-(trifluoromethyl)picolinamide | 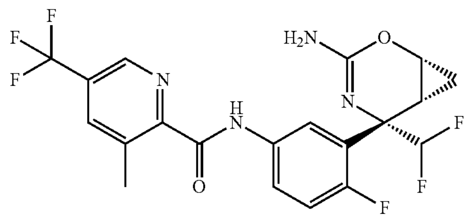 [SMILES: Cc1cc(C(F)(F)F)cnc1C(=O)Nc1ccc(F)c([C@@]2(C(F)F)N=C(N)O[C@@H]3C[C@@H]32)c1] | MS m/z = 459.0 [M + H]+<br>1H NMR (300 MHz, CHLOROFORM-d) δ ppm 0.93-1.08 (m, 1 H) 1.45 (br. s., 1 H) 1.84-2.00 (m, 1 H) 2.87 (s, 3 H) 3.98 (br. s., 1 H) 5.99-6.47 (m, 1 H) 6.99-7.16 (m, 1 H) 7.57 (d, J = 6.87 Hz, 1 H) 7.89 (s, 1 H) 7.95-8.10 (m, 1 H) 8.65 (s, 1 H) 10.07 (s, 1 H) |
| 189 | B | N-(3-((1R,5S,6R)-3-amino-5-(difluoromethyl)-2-oxa-4-azabicyclo[4.1.0]hept-3-en-5-yl)-4-fluorophenyl)-3-methyl-5-(2,2,2-trifluoroethoxy)picolinamide | 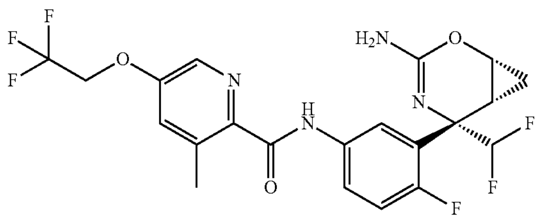 [SMILES: Cc1cc(OCC(F)(F)F)cnc1C(=O)Nc1ccc(F)c([C@@]2(C(F)F)N=C(N)O[C@@H]3C[C@@H]32)c1] | MS m/z = 489.0 [M + H]+<br>1H NMR (300 MHz, CHLOROFORM-d) δ ppm 0.88-1.11 (m, 1 H) 1.43 (br. s., 1 H) 1.79-2.00 (m, 1 H) 2.80 (s, 3 H) 3.96 (br. s., 1 H) 4.47 (q, J = 7.80 Hz, 2 H) 5.98-6.50 (m, 1 H) 7.03-7.12 (m, 1 H) 7.15 (br. s., 1 H) 7.52 (d, J = 5.99 Hz, 1 H) 7.97-8.10 (m, 1 H) 8.12 (br. s., 1 H) 9.98 (br. s., 1 H) |
| 190 | B | N-(3-((1R,5S,6R)-3-amino-5-(difluoromethyl)-2-oxa-4-azabicyclo[4.1.0]hept-3-en-5-yl)-4-fluorophenyl)-5-methylpicolinamide | 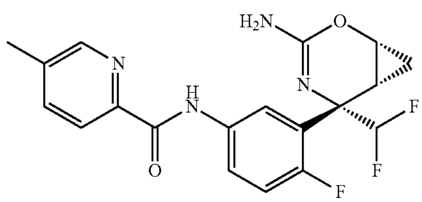 [SMILES: Cc1ccc(C(=O)Nc2ccc(F)c([C@@]3(C(F)F)N=C(N)O[C@@H]4C[C@@H]43)c2)nc1] | MS m/z = 391 0 [M + H]+<br>1H NMR (400 MHz, CHLOROFORM-d) δ ppm 0.98 (q, J = 7.76 Hz, 1 H) 1.43 (br. s., 1 H) 1.89 (q, J = 7.69 Hz, 2 H) 2.44 (s, 3 H) 3.97 (br. s., 1 H) 4.56 (br. s., 2 H) 6.05-6.44 (m, 1 H) 7.11 (t, J = 10.17 Hz, 1 H) 7.69 (d, J = 6.65 Hz, 2 H) 8.02 (d, J = 6.26 Hz, 1 H) 8.16 (d, J = 7.82 Hz, 1 H) 8.41 (s, 1 H) 9.96 (br. s., 1 H) |
| 191 | B | N-(3-((1R,5S,6R)-3-amino-5-(difluoromethyl)-2-oxa-4-azabicyclo[4.1.0]hept-3-en-5-yl)-4-fluorophenyl)-5-(1,1-difluoroethoxy)picolinamide | 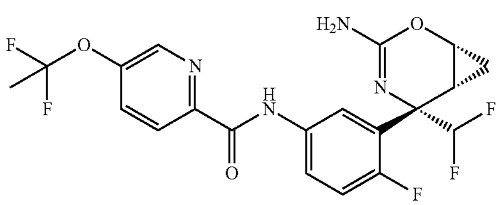 [SMILES: CC(F)(F)Oc1ccc(C(=O)Nc2ccc(F)c([C@@]3(C(F)F)N=C(N)O[C@@H]4C[C@@H]43)c2)nc1] | MS m/z = 457.0 [M + H]+<br>1H NMR (400 MHz, CHLOROFORM-d) δ ppm 0.95-1.10 (m, 1 H) 1.38-1.54 (m, 1 H) 1.92 (dt, J = 9.54, 7.16 Hz, 1 H) 2.02 (t, J = 13.60 Hz, 3 H) 3.91-4.10 (m, 1 H) 5.02 (br. s., 1 H) 6.03-6.47 (m, 1 H) 7.11 (dd, J = 11.54, 8.80 Hz, 1 H) 7.67 (dd, J = 6.75, 2.64 Hz, 1 H) 7.69-7.73 (m, 1 H) 8.27 (d, J = 8.61 Hz, 1 H) 8.44 (d, J = 1.96 Hz, 1 H) 9.85 (s, 1 H) |
| 192 | B | N-(3-((1R,5S,6R)-3-amino-5-(fluoromethyl)-2-oxa-4-azabicyclo[4.1.0]hept-3-en-5-yl)-4-fluorophenyl)-5-cyanopicolinamide | 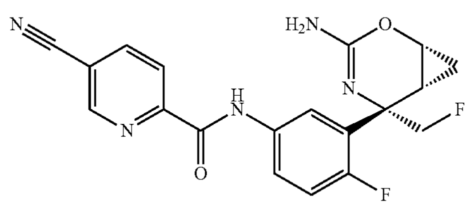 [SMILES: N#Cc1ccc(C(=O)Nc2ccc(F)c([C@@]3(CF)N=C(N)O[C@@H]4C[C@@H]43)c2)nc1] | MS m/z = 384 [M + H]+<br>1H NMR (400 MHz, DMSO-d6) d ppm 10.82 (s, 1 H), 9.20 (s, 1 H) 8.58 (d, J = 8.22 Hz, 1 H), 8.28 (d, J = 8.22 Hz, 1 H), 8.01 (d, J = 6.85 Hz, 1 H), 7.85 (d, J = 7.63 Hz, 1 H), 7.19 (t, J = 10.37 Hz, 1 H), 5.65 (br. s., 2 H), 4.40-4.75 (m, 2 H), 4.04 (br. s., 1 H), 1.58 (q, J = 7.63 Hz, 1 H), 1.00 (br. s., 1 H), 0.75-0.90 (m, 1 H). |
| 193 | B | N-(34(1R,5S,6R)-3-amino-5-(fluoromethyl)-2-oxa-4-azabicyclo[4.1.0]hept-3-en-5-yl)-4-fluorophenyl)-3,5-dichloropicolinamide | 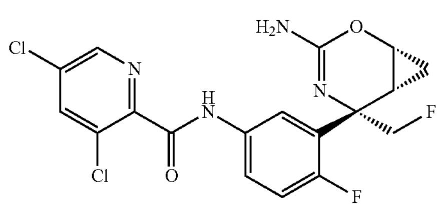 [SMILES: NC1=N[C@](CF)(c2cc(NC(=O)c3ncc(Cl)cc3Cl)ccc2F)[C@H]2C[C@H]2O1] | MS m/z = 427.1 [M + H]+<br>1H NMR (400 MHz, DMSO-d6) d ppm 10.75 (s, 1 H), 8.72 (d, J = 1.96 Hz, 1 H), 8.43 (d, J = 2.15 Hz, 1 H), 7.68-7.82 (m, 2 H), 7.19 (dd, J = 11.74, 8.80 Hz, 1 H), 5.73 (br. s., 2 H), 4.37-4.76 (m, 2 H), 4.00 (t, J = 5.48 Hz, 1 H), 1.48-1.63 (m, 1 H), 1.00 (td, J = 6.46, 2.54 Hz, 1 H), 0.83 (dt, J = 9.39, 6.36 Hz, 1 H). |

TABLE 1-continued

| Example # | Method | Compound Name | Structure | Analytical Data |
|---|---|---|---|---|
| 194 | B | N-(3-((1R,5S,6R)-3-amino-5-(fluoromethyl)-2-oxa-4-azabicyclo[4.1.0]hept-3-en-5-yl)-4-fluorophenyl)-5-methoxypyrazine-2-carboxamide | 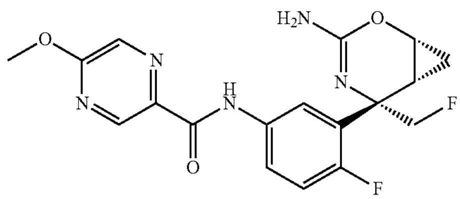 [SMILES: COc1cnc(C(=O)Nc2ccc(F)c([C@@]3(CF)N=C(N)O[C@@H]4C[C@@H]43)c2)cn1] | MS m/z = 390.2 [M + H]⁺ 1H NMR (400 MHz, DMSO-d6) d ppm 10.50 (s, 1 H), 8.89 (d, J = 1.17 Hz, 1 H), 8.41 (d, J = 1.17 Hz, 1 H), 7.99 (dd, J = 7.34, 2.64 Hz, 1 H), 7.76-7.87 (m, 1 H), 7.17 (dd, J = 11.93, 8.80 Hz, 1 H), 5.79 (br. s., 2 H), 4.39-4.77 (m, 2 H), 3.94-4.12 (m, 4 H), 1.43-1.70 (m, 1 H), 1.02 (td, J = 6.41, 2.64 Hz, 1 H), 0.85 (dt, J = 9.44, 6.43 Hz, 1 H). |
| 195 | B | N-(3-((1R,5S,6R)-3-amino-5-(fluoromethyl)-2-oxa-4-azabicyclo[4.1.0]hept-3-en-5-yl)-4-fluorophenyl)-5-methoxypicolinamide | 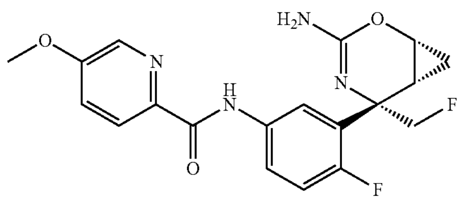 [SMILES: COc1ccc(C(=O)Nc2ccc(F)c([C@@]3(CF)N=C(N)O[C@@H]4C[C@@H]43)c2)nc1] | MS m/z = 389.2 [M + H]⁺ 1H NMR (400 MHz, DMSO-d6) d ppm 10.44 (s, 1 H), 8.39 (d, J = 2.74 Hz, 1 H), 8.12 (d, J = 8.80 Hz, 1 H), 7.96 (dd, J = 7.24, 2.74 Hz, 1 H), 7.81-7.88 (m, 1 H), 7.61 (dd, J = 8.70, 2.84 Hz, 1 H), 7.16 (dd, J = 11.74, 8.80 Hz, 1 H), 5.64 (br. s., 2 H), 4.34-4.75 (m, 2 H), 4.03 (t, J = 5.28 Hz, 1 H), 3.93 (s, 3 H), 1.49-1.65 (m, 1 H), 0.96-1.04 (m, 1 H), 0.83 (dt, J = 9.34, 6.28 Hz, 1 H). |
| 196 | B | N-(3-((1R,5S,6R)-3-amino-5-(fluoromethyl)-2-oxa-4-azabicyclo[4.1.0]hept-3-en-5-yl)-4-fluorophenyl)-5-cyano-3-methylpicolinamide | 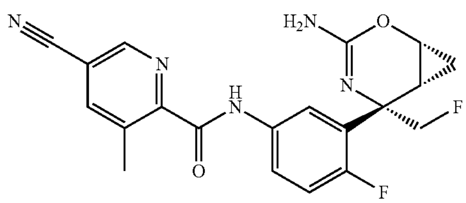 [SMILES: Cc1cc(C#N)cnc1C(=O)Nc1ccc(F)c([C@@]2(CF)N=C(N)O[C@@H]3C[C@@H]32)c1] | MS m/z = 397.9 [M + H]⁺ 1H NMR (400 MHz, DMSO-d6) d ppm 10.71 (s, 1 H), 8.97 (d, J = 1.37 Hz, 1 H), 8.39 (d, J = 1.17 Hz, 1 H), 7.78-7.86 (m, 2 H), 7.18 (dd, J = 11.74, 8.80 Hz, 1 H), 5.70 (br. s., 2 H), 4.32-4.73 (m, 2 H), 3.97-4.05 (m, 1 H), 2.54 (s, 3 H), 1.49-1.62 (m, 1 H), 1.00 (td, J = 6.46, 2.54 Hz, 1 H), 0.78-0.89 (m, 1 H). |
| 197 | B | N-(3-((1R,5S,6R)-3-amino-5-(fluoromethyl)-2-oxa-4-azabicyclo[4.1.0]hept-3-en-5-yl)-4-fluorophenyl)-5-(prop-2-yn-1-yloxy)pyrazine-2-carboxamide | 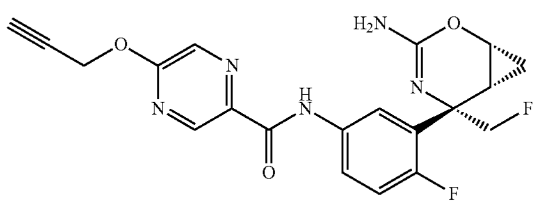 [SMILES: C#CCOc1cnc(C(=O)Nc2ccc(F)c([C@@]3(CF)N=C(N)O[C@@H]4C[C@@H]43)c2)cn1] | MS m/z = 414.1 [M + H]⁺ 1H NMR (400 MHz, DMSO-d6) d ppm 10.53 (s, 1 H), 8.90 (s, 1 H), 8.48 (s, 1 H), 7.99 (dd, J = 7.24, 2.35 Hz, 1 H), 7.72-7.89 (m, 1 H), 7.17 (dd, J = 11.74, 8.80 Hz, 1 H), 5.69 (br. s., 2H), 5.14 (d, J = 2.35 Hz, 2 H), 4.36-4.80 (m, 2 H), 3.90-4.12 (m, 1 H), 1.50-1.64 (m, 1H), 1.24 (s, 1H), 0.92-1.06 (m, 1H), 0.84 (dt, J = 9.44, 6.43 Hz, 1 H). |
| 198 | B | N-(3-((1R,5S,6R)-3-amino-5-(fluoromethyl)-2-oxa-4-azabicyclo[4.1.0]hept-3-en-5-yl)-4-fluorophenyl)-5-chloro-3-methylpicolinamide | 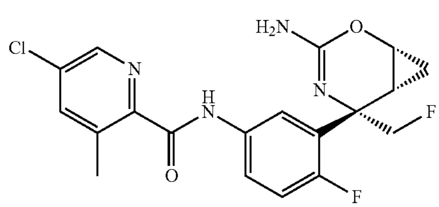 [SMILES: Cc1cc(Cl)cnc1C(=O)Nc1ccc(F)c([C@@]2(CF)N=C(N)O[C@@H]3C[C@@H]32)c1] | MS m/z = 407.1 [M + H]⁺ 1H NMR (400 MHz, DMSO-d6) d ppm 10.55 (s, 1 H), 8.57 (d, J = 1.56 Hz, 1 H), 8.01 (d, J = 0.78 Hz, 1 H), 7.77-7.86 (m, 2 H), 7.16 (dd, J = 11.74, 8.80 Hz, 1 H), 5.63 (br. s., 2 H), 4.40-4.71 (m, 2 H), 4.00 (t, J = 5.28 Hz, 1 H), 2.55 (s, 3 H), 1.51-1.61 (m, 1 H), 0.95-1.02 (m, 1 H), 0.78-0.88 (m, 1 H). |
| 199 | B | N-(3-((1R,5S,6R)-3-amino-5-(fluoromethyl)-2-oxa-4-azabicyclo[4.1.0]hept-3-en-5-yl)-4-fluorophenyl)-5-(but-2-yn-1-yloxy)pyrazine-2-carboxamide | 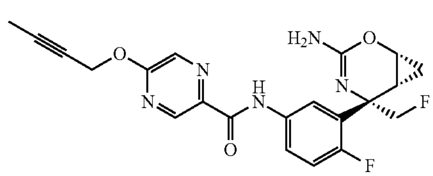 [SMILES: CC#CCOc1cnc(C(=O)Nc2ccc(F)c([C@@]3(CF)N=C(N)O[C@@H]4C[C@@H]43)c2)cn1] | MS m/z = 428.1 [M + H]+ 1H NMR (400 MHz, DMSO-d6) d ppm 10.51 (s, 1 H), 8.89 (d, J = 1.17 Hz, 1 H), 8.45 (d, J = 1.37 Hz, 1 H), 7.99 (dd, J = 7.34, 2.64 Hz, 1 H), 7.78-7.85 (m, 1 H), 7.17 (dd, J = 11.74, 8.80 Hz, 1 H), 5.63 (br. s., 2 H), 5.09 (d, J = 2.35 Hz, 2 H), 4.39-4.74 (m, 2 H), 4.00-4.08 (m, 1 H), 1.86 (t, J = 2.35 Hz, 3 H), 1.53-1.62 (m, 1 H), 0.93-1.03 (m, 1 H), 0.83 (dt, J = 9.39, 6.36 Hz, 1 H). |

TABLE 1-continued

| Example # | Method | Compound Name | Structure | Analytical Data |
|---|---|---|---|---|
| 200 | B | N-(3-((1R,5S,6R)-3-amino-5-(fluoromethyl)-2-oxa-4-azabicyclo[4.1.0]hept-3-en-5-yl)-4-fluorophenyl)-6-chloro-3-methylimidazo[1,2-a]pyridine-2-carboxamide | 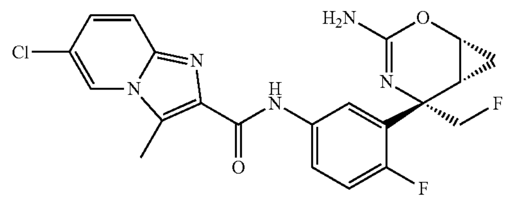 [SMILES: Cc1c(C(=O)Nc2ccc(F)c([C@@]3(CF)N=C(N)O[C@@H]4C[C@@H]43)c2)nc2ccc(Cl)cn12] | MS m/z = 446.1 [M + H]+ 1H NMR (400 MHz, DMSO-d6) d ppm 10.21 (s, 1 H), 8.68 (d, J = 1.17 Hz, 1 H), 7.94 (dd, J = 7.24, 2.54 Hz, 1 H), 7.84 (dt, J = 8.51, 3.47 Hz, 1 H), 7.69 (d, J = 9.59 Hz, 1 H), 7.42 (dd, J = 9.59, 1.96 Hz, 1 H), 7.14 (dd, J = 11.84, 8.90 Hz, 1 H), 5.64 (br. s., 2 H), 4.39-4.75 (m, 2 H), 4.05 (d, J = 5.28 Hz, 1 H), 2.81 (s, 3 H), 1.53-1.63 (m, 1 H), 0.96-1.04 (m, 1 H), 0.84 (dt, J = 9.29, 6.41 Hz, 1 H). |
| 201 | B | N-(3-((1R,5S,6R)-3-amino-5-(fluoromethyl)-2-oxa-4-azabicyclo[4.1.0]hept-3-en-5-yl)-4-fluorophenyl)-5-(difluoromethyl)-3-methylpicolinamide | 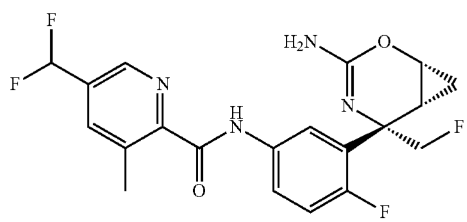 [SMILES: Cc1cc(C(F)F)cnc1C(=O)Nc1ccc(F)c([C@@]2(CF)N=C(N)O[C@@H]3C[C@@H]32)c1] | MS m/z = 423 [M + H]+ 1H NMR (400 MHz, DMSO-d6) d ppm 10.62 (s, 1 H), 8.71 (s, 1 H) 8.04 (s, 1 H), 7.79-7.87 (m, 2 H), 7.07-7.37 (m, 2 H), 5.63 (br. s., 2 H), 4.42-4.71 (m, 2 H), 3.96-4.04 (m, 1 H), 2.58 (s, 3 H), 1.51-1.61 (m, 1 H), 0.98 (td, J = 6.50, 2.45 Hz, 1 H), 0.83 (dt, J = 9.49, 6.41 Hz, 1 H). |
| 202 | A | N-(3-((1R,5S,6R)-3-amino-5-(fluoromethyl)-2-oxa-4-azabicyclo[4.1.0]hept-3-en-5-yl)-4-fluorophenyl)isoquinoline-3-carboxamide | 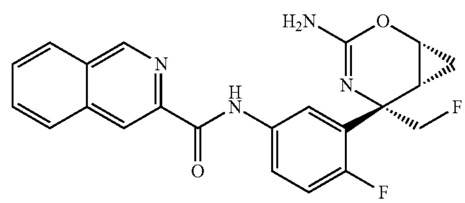 [SMILES: NC1=N[C@](CF)(c2cc(NC(=O)c3cc4ccccc4cn3)ccc2F)[C@H]2C[C@H]2O1] | MS m/z = 409.1 [M + H]+ 1H NMR (400 MHz, DMSO-d6) d ppm 10.75 (s, 1 H), 9.48 (s, 1 H), 8.71 (s, 1 H), 8.21-8.34 (m, 2 H), 8.04 (dd, J = 7.24, 2.74 Hz, 1 H), 7.89-7.96 (m, 2 H), 7.82-7.89 (m, 1 H), 7.20 (dd, J = 11.93, 8.80 Hz, 1 H), 5.67 (br. s., 2 H), 4.41-4.76 (m, 2 H), 4.05 (d, J = 5.09 Hz, 1 H), 1.53-1.67 (m, 1 H), 0.95-1.07 (m, 1 H), 0.85 (dt, J = 9.24, 6.33 Hz, 1 H). |
| 203 | B | N-(3-((1R,5S,6R)-3-amino-5-(fluoromethyl)-2-oxa-4-azabicyclo[4.1.0]hept-3-en-5-yl)-4-fluorophenyl)-5-(but-2-yn-1-yloxy)picolinamide | 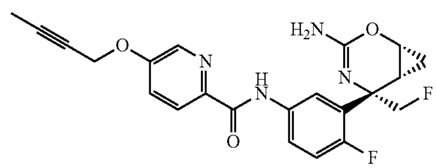 [SMILES: CC#CCOc1ccc(C(=O)Nc2ccc(F)c([C@@]3(CF)N=C(N)O[C@@H]4C[C@@H]43)c2)nc1] | MS m/z = 427.1 [M + H]+ 1H NMR (400 MHz, DMSO-d6) d ppm 10.46 (s, 1 H), 8.42 (d, J = 2.74 Hz, 1 H), 8.13 (d, J = 8.80 Hz, 1 H), 7.97 (dd, J = 7.24, 2.54 Hz, 1 H), 7.79-7.89 (m, 1 H), 7.63 (dd, J = 8.71, 2.84 Hz, 1 H), 7.16 (dd, J = 11.74, 8.80 Hz, 1 H), 5.68 (br. s., 2 H), 4.96 (d, J = 2.15 Hz, 2 H), 4.39-4.75 (m, 2 H), 4.04 (t, J = 5.58 Hz, 1 H), 1.85 (t, J = 2.25 Hz, 3 H), 1.52-1.63 (m, 1 H), 1.00 (td, J = 6.26, 2.35 Hz, 1 H), 0.84 (dt, J = 9.49, 6.31 Hz, 1 H). |
| 204 | A | N-(5-((1R,5S,6R)-3-amino-5-(fluoromethyl)-2-oxa-4-azabicyclo[4.1.0]hept-3-en-5-yl)-6-fluoropyridin-3-yl)-5-cyanopicolinamide | 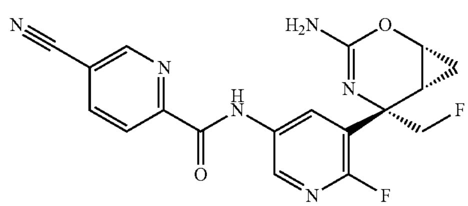 [SMILES: N#Cc1ccc(C(=O)Nc2cnc(F)c([C@@]3(CF)N=C(N)O[C@@H]4C[C@@H]43)c2)nc1] | MS m/z = 385 [M + H]+ 1H NMR (400 MHz, DMSO-d6) d ppm 11.21 (s, 1 H), 9.17-9.26 (m, 1 H), 8.64 (s, 1 H), 8.58 (ddd, J = 16.38, 8.56, 2.05 Hz, 2 H), 8.30 (d, J = 8.22 Hz, 1 H), 5.72 (s, 2 H), 4.44-4.71 (m, 2 H), 4.01-4.10 (m, 1 H), 1.49-1.62 (m, 1 H), 1.00 (td, J = 6.46, 2.54 Hz, 1 H), 0.86 (dt, J = 9.54, 6.38 Hz, 1 H). |

TABLE 1-continued

| Example # | Method | Compound Name | Structure | Analytical Data |
|---|---|---|---|---|
| 205 | B | N-(3-((1R,5S,6R)-3-amino-5-(fluoromethyl)-2-oxa-4-azabicyclo[4.1.0]hept-3-en-5-yl)-4-fluorophenyl)-5-(prop-2-yn-1-yloxy)picolinamide | 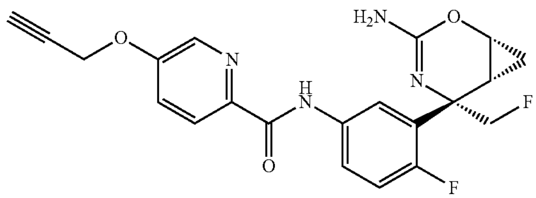 [SMILES: C#CCOc1ccc(C(=O)Nc2ccc(F)c([C@@]3(CF)N=C(N)O[C@@H]4C[C@@H]43)c2)nc1] | MS m/z = 413 [M + H]+ 1H NMR (400 MHz, DMSO-d6) d ppm 10.46 (s, 1 H), 8.44 (d, J = 2.74 Hz, 1 H), 8.14 (d, J = 8.61 Hz, 1 H), 7.97 (dd, J = 7.24, 2.54 Hz, 1 H), 7.79-7.88 (m, 1 H), 7.66 (dd, J = 8.70, 2.84 Hz, 1 H), 7.16 (dd, J = 11.74, 8.80 Hz, 1 H), 5.63 (br. s., 2 H), 5.03 (d, J = 2.35 Hz, 2 H), 4.39-4.74 (m, 2 H), 4.03 (t, J = 5.38 Hz, 1 H), 3.70 (t, J = 2.35 Hz, 1 H), 1.53-1.62 (m, 1 H), 0.99 (td, J = 6.36, 2.54 Hz, 1 H), 0.83 (dt, J = 9.49, 6.41 Hz, 1 H). |
| 206 | A | N-(5-((1R,5S,6R)-3-amino-5-(fluoromethyl)-2-oxa-4-azabicyclo[4.1.0]hept-3-en-5-yl)-6-fluoropyridin-3-yl)-5-(prop-2-yn-1-yloxy)pyrazine-2-carboxamide | 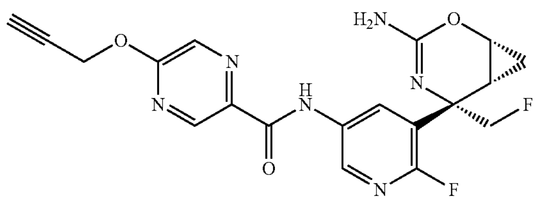 [SMILES: C#CCOc1cnc(C(=O)Nc2cnc(F)c([C@@]3(CF)N=C(N)O[C@@H]4C[C@@H]43)c2)cn1] | MS m/z = 415.1 [M + H]+ 1H NMR (400 MHz, DMSO-d6) d ppm 10.92 (s, 1 H), 8.92 (d, J = 1.37 Hz, 1 H), 8.59-8.62 (m, 1 H), 8.54 (dd, J = 9.10, 2.64 Hz, 1 H), 8.50 (d, J = 1.37 Hz, 1 H), 5.72 (s, 2 H), 5.14 (d, J = 2.35 Hz, 2 H), 4.45-4.70 (m, 2 H), 4.07 (d, J = 2.54 Hz, 1 H), 3.64 (t, J = 2.35 Hz, 1 H), 1.55 (dt, J = 9.19, 6.94 Hz, 1 H), 1.00 (td, J = 6.46, 2.54 Hz, 1 H), 0.86 (dt, J = 9.49, 6.50 Hz, 1 H). |
| 207 | A | N-(5-((1R,5S,6R)-3-amino-5-(fluoromethyl)-2-oxa-4-azabicyclo[4.1.0]hept-3-en-5-yl)-6-fluoropyridin-3-yl)-4-chloro-1-(difluoromethyl)-1H-pyrazole-3-carboxamide | 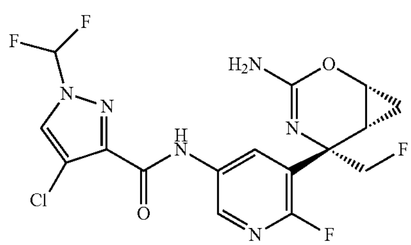 [SMILES: NC1=N[C@](CF)(c2cc(NC(=O)c3nn(C(F)F)cc3Cl)cnc2F)[C@H]2C[C@H]2O1] | MS m/z = 433 [M + H]+ 1H NMR (400 MHz, DMSO-d6) d ppm 10.84 (s, 1 H), 8.78 (s, 1 H) 8.53 (s, 1 H), 8.38 (dd, J = 9.10, 2.45 Hz, 1 H), 7.72-8.07 (m, 1 H), 5.74 (br. s., 2 H), 4.44-4.69 (m, 2 H), 4.04 (t, J = 5.38 Hz, 1 H), 1.48-1.60 (m, 1 H), 0.94-1.04 (m, 1 H), 0.86 (dt, J = 9.44, 6.43 Hz, 1 H). |
| 208 | B | N-(3-([1(R,S),5(S,R),6(R,S)]-3-amino-5-(trifluoromethyl)-2-oxa-4-azabicyclo[4.1.0]hept-3-en-5-yl)phenyl)-5-chloropicolinamide | 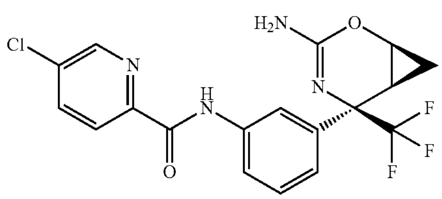 [SMILES: NC1=N[C@](c2cccc(NC(=O)c3ccc(Cl)cn3)c2)(C(F)(F)F)[C@@H]2C[C@@H]2O1] | MS m/z = 410.9 [M + H]+ 1H NMR (300 MHz, CHLOROFORM-d) d = 9.88 (s, 1 H), 8.58 (d, J = 2.0 Hz, 1 H), 8.26 (d, J = 8.3 Hz, 1 H), 7.98 (s, 1 H), 7.93-7.79 (m, 2 H), 7.48-7.39 (m, 2 H), 4.53 (br. s., 2 H), 4.03-3.98 (m, 1 H), 1.91 (td, J = 7.0, 9.7 Hz, 1 H), 1.53 (t, J = 6.4 Hz, 1 H), 1.12-0.99 (m, 1 H). |
| 209 | A | N-(3-([1(R,S),5(S,R),6(R,S)]-3-amino-5-(difluoromethyl)-2-oxa-4-azabicyclo[4.1.0]hept-3-en-5-yl)-4-chlorophenyl)-5-(difluoromethoxy)-3-methylpicolinamide | 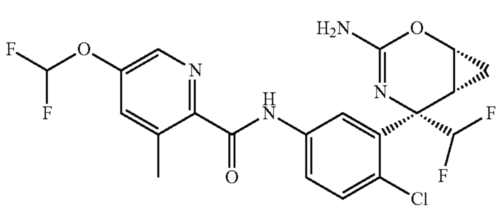 [SMILES: Cc1cc(OC(F)F)cnc1C(=O)Nc1ccc(Cl)c([C@]2(C(F)F)N=C(N)O[C@@H]3C[C@@H]32)c1] | MS m/z = 472.9 [M + H]+ 1H NMR (300 MHz ,DMSO-d6) d = 10.61 (s, 1 H), 8.43 (d, J = 2.5 Hz, 1 H), 8.07 (d, J = 2.5 Hz, 1 H), 7.89 (dd, J = 2.6, 8.6 Hz, 1 H), 7.72 (d, J = 2.3 Hz, 1 H), 7.69-7.12 (m, 2 H), 6.95-6.48 (m, 1 H), 5.84 (s, 2 H), 4.03-3.88 (m, 1 H), 2.59 (s, 3 H), 1.87 (td, J = 7.0, 9.6 Hz, 1 H), 1.08 (br. s., 1 H), 0.94 (td, J = 6.4, 9.5 Hz, 1 H). |
| 210 | A | N-(3-([1(R,S),5(S,R),6(R,S)]-3-amino-5-(difluoromethyl)-2-oxa-4-azabicyclo[4.1.0]hept-3-en-5-yl)-4-chlorophenyl)-5-(but-2-yn-1-yloxy)pyrazine-2-carboxamide | 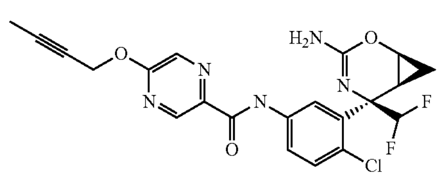 [SMILES: CC#CCOc1cnc(C(=O)Nc2ccc(Cl)c([C@]3(C(F)F)N=C(N)O[C@H]4C[C@H]43)c2)cn1] | MS m/z = 461.8 [M + H]+ 1H NMR (300 MHz, DMSO-d6) d = 10.59 (s, 1 H), 8.89 (d, J = 1.2 Hz, 1 H), 8.46 (d, J = 1.3 Hz, 1 H), 8.22 (d, J = 2.6 Hz, 1 H), 7.89 (dd, J = 2.6, 8.6 Hz, 1 H), 7.45 (d, J = 8.6 Hz, 1 H), 6.96-6.43 (m, 1 H), 5.91-5.75 (m, 2 H), 5.09 (q, J = 2.2 Hz, 2 H), 4.04-3.89 (m, 1 H), 1.94-1.77 (m, 4 H), 1.10 (s, 1 H), 0.94 (td, J = 6.4, 9.5 Hz, 1 H). |

TABLE 1-continued

| Example # | Method | Compound Name | Structure | Analytical Data |
|---|---|---|---|---|
| 211 | B | N-(3-((1R,5S,6R)-3-amino-5-(difluoromethyl)-2-oxa-4-azabicyclo[4.1.0]hept-3-en-5-yl)-4-chlorophenyl)-3,5-dichloropicolinamide | 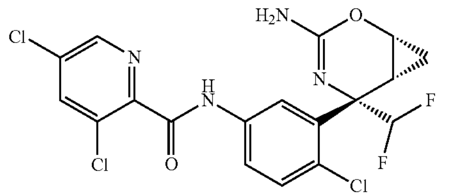 [SMILES: NC1=N[C@@](c2cc(NC(=O)c3ncc(Cl)cc3Cl)ccc2Cl)(C(F)F)[C@H]2C[C@H]2O1] | MS m/z = 460.8 [M + H]$^+$<br>1H NMR (300 MHz, DMSO-d6) d = 10.88 (br. s., 1 H), 8.73 (d, J = 1.9 Hz, 1 H), 8.45 (d, J = 2.0 Hz, 1 H), 7.97 (d, J = 2.6 Hz, 1 H), 7.86 (dd, J = 2.6, 8.6 Hz, 1 H), 7.48 (d, J = 8.6 Hz, 1 H), 6.93-6.50 (m, 1 H), 5.87 (s, 2 H), 4.01-3.87 (m, 1 H), 1.87 (td, J = 6.9, 9.6 Hz, 1 H), 1.06 (br. s., 1 H), 0.94 (td, J = 6.4, 9.4 Hz, 1 H). |
| 212 | A | N-(3-((1R,5S,6R)-3-amino-5-(difluoromethyl)-2-oxa-4-azabicyclo[4.1.0]hept-3-en-5-yl)-4-chlorophenyl)-5-(difluoromethoxy)-3-methylpicolinamide | 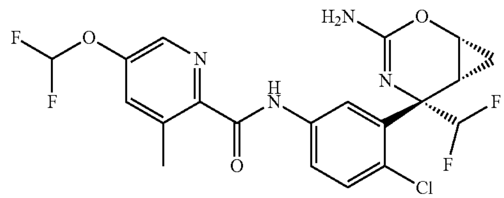 [SMILES: Cc1cc(OC(F)F)cnc1C(=O)Nc1ccc(Cl)c([C@@]2(C(F)F)N=C(N)O[C@@H]3C[C@@H]32)c1] | MS m/z = 472.9 [M + H]$^+$<br>1H NMR (300 MHz, DMSO-d6) d = 10.61 (s, 1 H), 8.43 (d, J = 2.5 Hz, 1 H), 8.07 (d, J = 2.5 Hz, 1 H), 7.89 (dd, J = 2.6, 8.6 Hz, 1 H), 7.72 (d, J = 2.2 Hz, 1 H), 7.69-7.11 (m, 2 H), 6.97-6.45 (m, 1 H), 5.84 (s, 2 H), 4.02-3.87 (m, 1 H), 2.59 (s, 3 H), 1.87 (td, J = 7.0, 9.5 Hz, 1 H), 1.14-1.02 (m, 1 H), 0.94 (td, J = 6.4, 9.5 Hz, 1 H). |
| 213 | A | N-(3-((1S,5R,6S)-3-amino-5-(difluoromethyl)-2-oxa-4-azabicyclo[4.1.0]hept-3-en-5-yl)-4-chlorophenyl)-5-(difluoromethoxy)-3-methylpicolinamide | 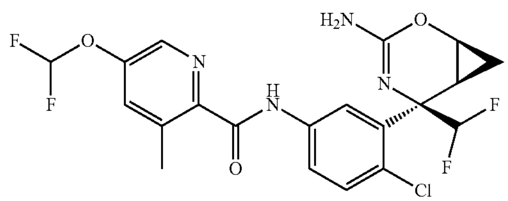 [SMILES: Cc1cc(OC(F)F)cnc1C(=O)Nc1ccc(Cl)c([C@]2(C(F)F)N=C(N)O[C@H]3C[C@H]32)c1] | MS m/z = 472.9 [M + H]$^+$<br>1H NMR (300 MHz, DMSO-d6) d = 10.61 (s, 1 H), 8.43 (d, J = 2.5 Hz, 1 H), 8.07 (d, J = 2.5 Hz, 1 H), 7.89 (dd, J = 2.6, 8.7 Hz, 1 H), 7.72 (d, J = 2.3 Hz, 1 H), 7.69-7.09 (m, 2 H), 6.96-6.44 (m, 1 H), 5.84 (s, 2 H), 4.02-3.86 (m, 1 H), 2.59 (s, 3 H), 1.87 (td, J = 7.0, 9.6 Hz, 1 H), 1.15-1.02 (m, 1 H), 0.94 (td, J = 6.4, 9.5 Hz, 1 H). |
| 214 | B | N-(3-((1R,5S,6R)-3-amino-5-(difluoromethyl)-2-oxa-4-azabicyclo[4.1.0]hept-3-en-5-yl)-4-chlorophenyl)-5-bromopicolinamide | 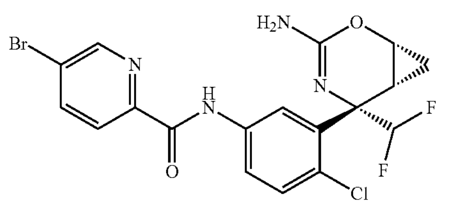 | MS m/z = 470.7 [M + H]$^+$<br>1H NMR (300 MHz, DMSO-d6) d = 10.74 (s, 1 H), 8.87 (dd, J = 0.7, 2.3 Hz, 1 H), 8.33 (dd, J = 2.3, 8.4 Hz, 1 H), 8.22 (d, J = 2.6 Hz, 1 H), 8.08 (dd, J = 0.6, 8.5 Hz, 1 H), 7.91 (dd, J = 2.6, 8.6 Hz, 1 H), 7.46 (d, J = 8.6 Hz, 1 H), 6.95-6.46 (m, 1 H), 5.84 (s, 2 H), 4.02-3.91 (m, 1 H), 1.88 (td, J = 6.8, 9.7 Hz, 1 H), 1.14-1.04 (m, 1 H), 0.94 (td, J = 6.4, 9.5 Hz, 1 H). |
| 215 | A | N-(3-((1R,5S,6R)-3-amino-5-(difluoromethyl)-2-oxa-4-azabicyclo[4.1.0]hept-3-en-5-yl)-4-chlorophenyl)-5-(but-2-yn-1-yloxy)pyrazine-2-carboxamide | 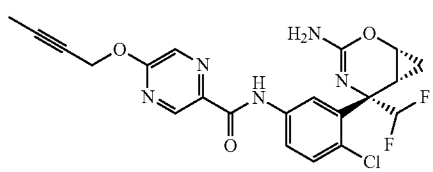 [SMILES: CC#CCOc1cnc(C(=O)Nc2ccc(Cl)c([C@@]3(C(F)F)N=C(N)O[C@@H]4C[C@@H]43)c2)cn1] | MS m/z = 461.9 [M + H]$^+$<br>1H NMR (300 MHz, DMSO-d6) d = 10.59 (s, 1 H), 8.89 (d, J = 1.3 Hz, 1 H), 8.46 (d, J = 1.3 Hz, 1 H), 8.22 (d, J = 2.5 Hz, 1 H), 7.89 (dd, J = 2.6, 8.6 Hz, 1 H), 7.45 (d, J = 8.6 Hz, 1 H), 6.98-6.41 (m, 1 H), 5.83 (s, 2 H), 5.09 (q, J = 2.2 Hz, 2 H), 4.05-3.88 (m, 1 H), 1.95-1.74 (m, 4 H), 1.09 (br. s., 1 H), 0.94 (td, J = 6.4, 9.5 Hz, 1 H). |
| 216 | A | N-(3-((1S,5R,6S)-3-amino-5-(difluoromethyl)-2-oxa-4-azabicyclo[4.1.0]hept-3-en-5-yl)-4-chlorophenyl)-5-(but-2-yn-1-yloxy)pyrazine-2-carboxamide | 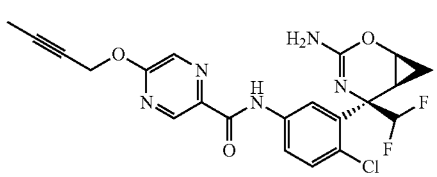 [SMILES: CC#CCOc1cnc(C(=O)Nc2ccc(Cl)c([C@]3(C(F)F)N=C(N)O[C@H]4C[C@H]43)c2)cn1] | MS m/z = 461.8 [M + H]$^+$<br>H NMR (300 MHz, DMSO-d6) d = 10.59 (s, 1 H), 8.89 (d, J = 1.2 Hz, 1 H), 8.46 (d, J = 1.3 Hz, 1 H), 8.22 (d, J = 2.6 Hz, 1 H), 7.89 (dd, J = 2.6, 8.6 Hz, 1 H), 7.45 (d, J = 8.6 Hz, 1 H), 6.96-6.47 (m, 1 H), 5.83 (s, 2 H), 5.09 (q, J = 2.3 Hz, 2 H), 4.04-3.84 (m, 1 H), 1.94-1.76 (m, 4 H), 1.09 (br. s., 1 H), 0.94 (td, J = 6.5, 9.4 Hz, 1 H). |

TABLE 1-continued

| Example # | Method | Compound Name | Structure | Analytical Data |
|---|---|---|---|---|
| 217 | B | N-(3-((1R,5S,6R)-3-amino-5-(difluoromethyl)-2-oxa-4-azabicyclo[4.1.0]hept-3-en-5-yl)-4-chlorophenyl)-3-methyl-5-(trifluoromethyl)picolinamide | 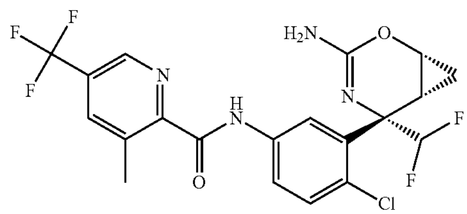 [SMILES: Cc1cc(C(F)(F)F)cnc1C(=O)Nc1ccc(Cl)c([C@@]2(C(F)F)N=C(N)O[C@@H]3C[C@@H]32)c1] | MS m/z = 474.9 [M + H]+ 1H NMR (300 MHz ,DMSO-d6) d = 10.79 (s, 1 H), 8.90 (s, 1 H), 8.30 (s, 1 H), 8.05 (d, J = 2.6 Hz, 1 H), 7.89 (dd, J = 2.6, 8.6 Hz, 1 H), 7.47 (d, J = 8.6 Hz, 1 H), 6.98-6.42 (m, 1 H), 5.85 (s, 2 H), 3.95 (t, J = 5.5 Hz, 1 H), 2.59 (s, 3 H), 1.94-1.78 (m, 1 H), 1.07 (br. s., 1 H), 1.00-0.82 (m, 1 H). |
| 218 | B | N-(3-((1(R,S),5(S,R),6(R,S))-3-amino-5-(trifluoromethyl)-2-oxa-4-azabicyclo[4.1.0]hept-3-en-5-yl)-4-fluorophenyl)-5-chloropicolinamide compound | 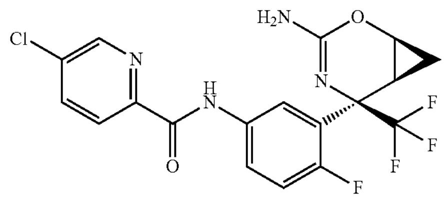 [SMILES: NC1=N[C@](c2cc(NC(=O)c3ccc(Cl)cn3)ccc2F)(C(F)(F)F)[C@@H]2C[C@@H]2O1] | MS m/z = 428.9 [M + H]+ 1H NMR (300 MHz, CHLOROFORM-d) d = 9.78 (s, 1 H), 8.51 (dd, J = 0.6, 2.3 Hz, 1 H), 8.22 (dd, J = 0.7, 8.4 Hz, 1 H), 8.09-8.00 (m, 1 H), 7.87 (dd, J = 2.4, 8.4 Hz, 1 H), 7.80-7.74 (m, 1 H), 7.11 (dd, J = 8.8, 11.9 Hz, 1 H), 4.70 (br. s., 2 H), 4.02-3.93 (m, 1 H), 2.41-2.30 (m, 1 H), 1.50 (t, J = 6.4 Hz, 1 H), 1.10 - 0.98 (m, 1 H). |
| 219 | A | N-(3-((1(S,R),5(R,S),6(S,R))-3-amino-5-(difluoromethyl)-2-oxa-4-azabicyclo[4.1.0]hept-3-en-5-yl)-4-chlorophenyl)-5-(prop-2-yn-1-yloxy)pyrazine-2-carboxamide | 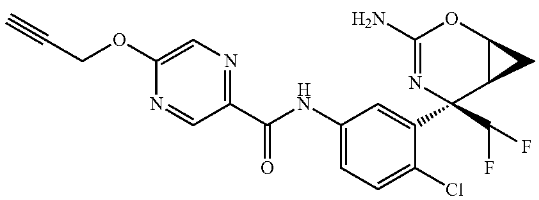 [SMILES: C#CCOc1cnc(C(=O)Nc2ccc(Cl)c([C@]3(C(F)F)N=C(N)O[C@H]4C[C@H]43)c2)cn1] | MS m/z = 447.9 [M + H]+ 1H NMR (300 MHz, DMSO-d6) d = 10.61 (br. s., 1 H), 8.90 (s, 1 H), 8.49 (s, 1 H), 8.23 (br. s., 1 H), 7.89 (d, J = 8.5 Hz, 1 H), 7.46 (d, J = 8.2 Hz, 1 H), 6.97-6.43 (m, 1 H), 5.83 (br. s., 2 H), 5.14 (br. s., 2 H), 3.97 (br. s., 1 H), 3.64 (br. s., 1 H), 1.87 (d, J = 7.2 Hz, 1 H), 1.24-0.77 (m, 2 H). |
| 220 | A | N-(3-((1(R,S),5(S,R),6(R,S))-3-amino-5-(difluoromethyl)-2-oxa-4-azabicyclo[4.1.0]hept-3-en-5-yl)-4-chlorophenyl)-4-chloro-1-(difluoromethyl)-1H-pyrazole-3-carboxamide | 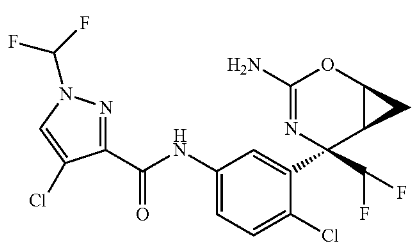 [SMILES: NC1=N[C@](c2cc(NC(=O)c3nn(C(F)F)cc3Cl)ccc2Cl)(C(F)F)[C@@H]2C[C@@H]2O1] | MS m/z = 465.8 [M + H]+ 1H NMR (300 MHz, DMSO-d6) d = 10.66 (s, 1 H), 8.77 (s, 1 H), 8.14-7.66 (m, 3 H), 7.45 (d, J = 8.6 Hz, 1 H), 6.96-6.47 (m, 1 H), 5.84 (s, 2 H), 3.96 (br. s., 1 H), 1.93-1.79 (m, 1 H), 1.08 (br. s., 1 H), 1.00-0.88 (m, 1 H). |
| 221 | A | N-(3-((1R,5S,6R)-3-amino-5-(difluoromethyl)-2-oxa-4-azabicyclo[4.1.0]hept-3-en-5-yl)-4-chlorophenyl)-5-(prop-2-yn-1-yloxy)pyrazine-2-carboxamide | 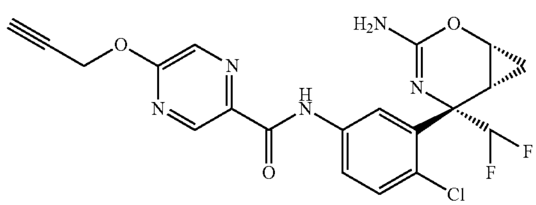 [SMILES: C#CCOc1cnc(C(=O)Nc2ccc(Cl)c([C@@]3(C(F)F)N=C(N)O[C@@H]4C[C@@H]43)c2)cn1] | MS m/z = 447.9 [M + H]+ 1H NMR (300 MHz, DMSO-d6) d = 10.61 (s, 1 H), 8.91 (d, J = 1.3 Hz, 1 H), 8.49 (d, J = 1.3 Hz, 1 H), 8.23 (d, J = 2.6 Hz, 1 H), 7.89 (dd, J = 2.6, 8.6 Hz, 1 H), 7.46 (d, J = 8.6 Hz, 1 H), 6.97-6.48 (m, 1 H), 5.83 (s, 2 H), 5.14 (d, J = 2.3 Hz, 2 H), 4.03-3.93 (m, 1 H), 3.64 (t, J = 2.3 Hz, 1 H), 1.88 (td, J = 7.0, 9.6 Hz, 1 H), 1.09 (br. s., 1 H), 0.95 (td, J = 6.4, 9.5 Hz, 1 H) |
| 222 | A | N-(3-((1S,5R,6S)-3-amino-5-(difluoromethyl)-2-oxa-4-azabicyclo[4.1.0]hept-3-en-5-yl)-4-chlorophenyl)-5-(prop-2-yn-1-yloxy)pyrazine-2-carboxamide | 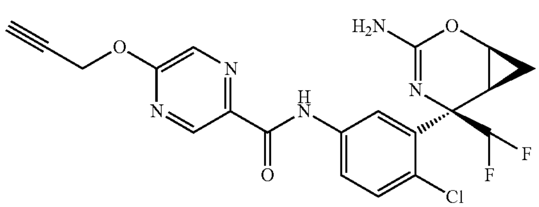 [SMILES: C#CCOc1cnc(C(=O)Nc2ccc(Cl)c([C@]3(C(F)F)N=C(N)O[C@H]4C[C@H]43)c2)cn1] | MS m/z = 447.8 [M + H]+ 1H NMR (300 MHz, DMSO-d6) d = 10.67 (s, 1 H), 8.96 (d, J = 1.3 Hz, 1 H), 8.55 (d, J = 1.3 Hz, 1 H), 8.29 (d, J = 2.6 Hz, 1 H), 7.95 (dd, J = 2.6, 8.7 Hz, 1 H), 7.52 (d, J = 8.5 Hz, 1 H), 7.02-6.56 (m, 1 H), 5.89 (br. s., 2 H), 5.20 (d, J = 2.3 Hz, 2 H), 4.04 (br. s., 1 H), 3.70 (t, J = 2.4 Hz, 1 H), 2.00-1.87 (m, 1 H), 1.16 (br. s., 1 H), 1.07-0.95 (m, 1 H). |

TABLE 1-continued

| Example # | Method | Compound Name | Analytical Data |
|---|---|---|---|
| 223 | A | N-(3-((1R,5S,6R)-3-amino-5-(difluoromethyl)-2-oxa-4-azabicyclo[4.1.0]hept-3-en-5-yl)-4-chlorophenyl)-5-cyano-3-methylpicolinamide | MS m/z = 431.9 [M + H]+ 1H NMR (300 MHz, DMSO-d6) d = 10.82 (s, 1 H), 8.98 (d, J = 1.5 Hz, 1 H), 8.40 (d, J = 1.2 Hz, 1 H), 8.05 (d, J = 2.6 Hz, 1 H), 7.88 (dd, J = 2.6, 8.6 Hz, 1 H), 7.47 (d, J = 8.6 Hz, 1 H), 6.96-6.50 (m, 1 H), 5.85 (s, 2 H), 3.95 (t, J = 5.4 Hz, 1 H), 2.55 (s, 3 H), 1.87 (td, J = 6.9, 9.9 Hz, 1 H), 1.08 (br. s., 1 H), 0.94 (td, J = 6.3, 9.5 Hz, 1 H). |
| 224 | A | N-(3-((1R,5S,6R)-3-amino-5-(difluoromethyl)-2-oxa-4-azabicyclo[4.1.0]hept-3-en-5-yl)-4-chlorophenyl)-4-chloro-1-(difluoromethyl)-1H-pyrazole-3-carboxamide | MS m/z = 465.8 [M + H]+ 1H NMR (300 MHz, METHANOL-d4) d = 8.28 (s, 1 H), 7.86 (d, J = 2.6 Hz, 1 H), 7.73 (dd, J = 2.6, 8.6 Hz, 1 H), 7.68-7.24 (m, 2 H), 6.95-6.50 (m, 1 H), 3.96-3.85 (m, 1 H), 2.05-1.91 (m, 1 H), 1.18 (t, J = 6.9 Hz, 1 H), 0.90 (td, J = 6.8, 9.3 Hz, 1 H). |
| 225 | A | N-(3-((1S,5R,6S)-3-amino-5-(difluoromethyl)-2-oxa-4-azabicyclo[4.1.0]hept-3-en-5-yl)-4-chlorophenyl)-4-chloro-1-(difluoromethyl)-1H-pyrazole-3-carboxamide | MS m/z = 465.8 [M + H]+ 1H NMR (300 MHz, METHANOL-d4) d = 8.40 (s, 1 H), 7.98 (d, J = 2.5 Hz, 1 H), 7.84 (dd, J = 2.6, 8.6 Hz, 1 H), 7.80-7.36 (m, 2 H), 7.08-6.60 (m, 1 H), 4.08-3.97 (m, 1 H), 2.17-2.01 (m, 1 H), 1.35-1.26 (m, 1 H), 1.01 (td, J = 6.8, 9.4 Hz, 1 H) |
| 226 | A | N-(3-((1R,5S,6R)-3-amino-5-(difluoromethyl)-2-oxa-4-azabicyclo[4.1.0]hept-3-en-5-yl)-4-chlorophenyl)-5-methoxypyrazine-2-carboxamide | MS m/z = 423.8 [M + H]+ 1H NMR (400 MHz ,DMSO-d6) d = 10.50 (s, 1 H), 8.82 (s, 1 H), 8.35 (s, 1 H), 8.15 (br. s., 1 H), 7.82 (d, J = 8.6 Hz, 1 H), 7.39 (s, 1 H), 6.85-6.46 (m, 1 H), 5.76 (br. s., 2 H), 3.96 (s, 3 H), 3.90 (br. s., 1 H), 1.80 (q, J = 7.6 Hz, 1 H), 1.02 (br. s., 1 H), 0.87 (q, J = 6.9 Hz, 1 H). |
| 227 | B | N-(3-((1(R,S),5(S,R),6(R,S))-3-amino-5-(fluoromethyl)-2-oxa-4-azabicyclo[4.1.0]hept-3-en-5-yl)-4-fluorophenyl)-3-chloro-5-cyanopicolinamide | MS m/z = 417.8, [M + H]+ 1H NMR (MeOH) d: 8.95 (d, J = 1.8 Hz, 1H), 8.54 (d, J = 1.8 Hz, 1H), 7.80-7.91 (m, 1H), 7.76 (dd, J = 7.0, 2.7 Hz, 1H), 7.19 (dd, J = 11.9, 8.8 Hz, 1H), 4.77 (d, J = 3.7 Hz, 1H), 4.66 (d, J = 2.5 Hz, 1H), 3.99-4.24 (m, 1H), 1.66-1.90 (m, 1H), 1.11-1.25 (m, 1H), 0.83-1.02 (m, 1H) |
| 228 | B | N-(3-((1R,5S,6R)-3-amino-5-(fluoromethyl)-2-oxa-4-azabicyclo[4.1.0]hept-3-en-5-yl)-4-fluorophenyl)-3-chloro-5-cyanopicolinamide | MS m/z = 418.0, [M + H]+ 1H NMR (MeOH) d: 8.94 (d, J = 1.6 Hz, 1H), 8.52 (d, J = 1.8 Hz, 1H), 7.83 (dt, J = 8.8, 3.4 Hz, 1H), 7.75 (dd, J = 6.9, 2.6 Hz, 1H), 7.18 (dd, J = 11.7, 8.8 Hz, 1H), 4.76 (d, J = 6.7 Hz, 1H), 4.64 (d, J = 6.5 Hz, 1H), 4.07 (br. s., 1H), 1.77 (d, J = 9.6 Hz, 1H), 1.12-1.22 (m, 1H), 0.84-1.00 (m, 1H) |
| 229 | B | N-(3-((1R,5S,6R)-3-amino-5-(fluoromethyl)-2-oxa-4-azabicyclo[4.1.0]hept-3-en-5-yl)-4-fluorophenyl)-3-chloro-5-methoxypicolinamide | MS m/z = 422.9 [M + H]+ 1H NMR (MeOH) d: 8.32 (d, J = 2.5 Hz, 1H), 7.83 (dt, J = 8.7, 3.4 Hz, 1H), 7.73-7.80 (m, 1H), 7.62 (d, J = 2.3 Hz, 1H), 7.17 (dd, J = 11.8, 8.9 Hz, 1H), 4.72-4.84 (m, 1H), 4.59-4.71 (m, 1H), 4.10 (br. s., 1H), 3.99 (s, 3H), 1.68-1.91 (m, 1H), 1.12-1.27 (m, 1H), 0.82-1.05 (m, 1H) |

TABLE 1-continued

| Example # | Method | Compound Name | Structure | Analytical Data |
|---|---|---|---|---|
| 230 | B | N-(5-((1S,5R,6S)-3-amino-5-(fluoromethyl)-2-oxa-4-azabicyclo[4.1.0]hept-3-en-5-yl)-6-fluoropyridin-3-yl)-5-chloropicolinamide | 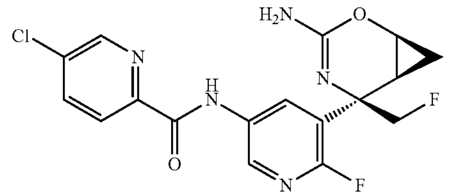 [SMILES: NC1=N[C@@](CF)(c2cc(NC(=O)c3ccc(Cl)cn3)cnc2F)[C@@H]2C[C@@H]2O1] | MS m/z = 394.1 [M + H]+ 1H NMR (MeOH) d: 8.70-8.75 (m, 1H), 8.63-8.67 (m, 1H), 8.42-8.50 (m, 1H), 8.19-8.25 (m, 1H), 8.05-8.10 (m, 1H), 4.70-4.80 (m, 1H), 4.56-4.67 (m, 1H), 4.05-4.19 (m, 1H), 1.67-1.79 (m, 1H), 1.10-1.24 (m, 1H), 0.86-1.01 (m, 1H) |
| 231 | B | N-(5-((1R,5S,6R)-3-amino-5-(fluoromethyl)-2-oxa-4-azabicyclo[4.1.0]hept-3-en-5-yl)-6-fluoropyridin-3-yl)-5-chloropicolinamide | 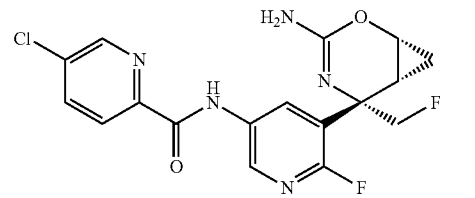 [SMILES: NC1=N[C@](CF)(c2cc(NC(=O)c3ccc(Cl)cn3)cnc2F)[C@H]2C[C@H]2O1] | MS m/z = 394.1 [M + H]+ 1H NMR (MeOH) d: 8.74 (d, J = 2.2 Hz, 1H), 8.64-8.70 (m, 1H), 8.49 (dd, J = 8.8, 2.5 Hz, 1H), 8.24 (d, J = 8.4 Hz, 1H), 8.10 (dd, J = 8.4, 2.3 Hz, 1H), 4.78 (s, 1H), 4.66 (s, 1H), 4.13 (br. s., 1H), 1.75 (d, J = 9.6 Hz, 1H), 1.12-1.23 (m, 1H), 0.90-1.04 (m, 1H) |
| 232 | A | N-(3-((1R,5S,6R)-3-amino-5-(difluoromethyl)-2-oxa-4-azabicyclo[4.1.0]hept-3-en-5-yl)-4-fluorophenyl)-5-(prop-2-yn-1-yloxy)picolinamide | 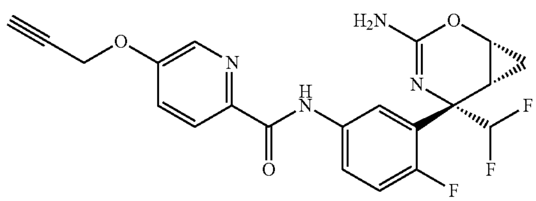 [SMILES: C#CCOc1ccc(C(=O)Nc2ccc(F)c([C@@]3(C(F)F)N=C(N)O[C@@H]4C[C@@H]43)c2)nc1] | MS m/z = 431[M + H]+ 1H NMR (MeOH) d: 8.41 (d, J = 2.7 Hz, 1H), 8.17 (d, J = 8.8 Hz, 1H), 7.86 (dd, J = 6.7, 2.9 Hz, 2H), 7.61 (dd, J = 8.7, 2.8 Hz, 1H), 7.16 (dd, J = 11.7, 9.6 Hz, 1H), 5.91-6.54 (m, 1H), 4.94 (s, 2H), 3.91-4.16 (m, 1H), 3.08 (t, J = 2.3 Hz, 1H), 1.74-2.00 (m, 1H), 1.33 (br. s., 1H), 0.83-1.07 (m, 1H) |
| 233 | A | N-(3-((1R,5S,6R)-3-amino-5-(difluoromethyl)-2-oxa-4-azabicyclo[4.1.0]hept-3-en-5-yl)-4-fluorophenyl)-5-(but-2-yn-1-yloxy)picolinamide | 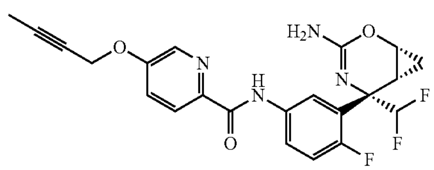 [SMILES: CC#CCOc1ccc(C(=O)Nc2ccc(F)c([C@@]3(C(F)F)N=C(N)O[C@@H]4C[C@@H]43)c2)nc1] | MS m/z = 445.1 [M + H]+ 1H NMR (MeOH) d: 8.38 (d, J = 2.7 Hz, 1H), 8.16 (d, J = 8.6 Hz, 1H), 7.86 (dd, J = 6.5, 3.3 Hz, 2H), 7.58 (dd, J = 8.6, 2.7 Hz, 1H), 7.16 (dd, J = 11.7, 9.6 Hz, 1H), 6.07-6.49 (m, 1H), 4.86 (d, J = 2.3 Hz, 2H), 4.01-4.11 (m, 1H), 1.78-1.98 (m, 4H), 1.33 (br. s., 1H), 0.98 (d, J = 9.4 Hz, 1H) |
| 234 | A | N-(5-((1R,5S,6R)-3-amino-5-(fluoromethyl)-2-oxa-4-azabicyclo[4.1.0]hept-3-en-5-yl)-6-fluoropyridin-3-yl)-5-(difluoromethyl)-3-methylpicolinamide | 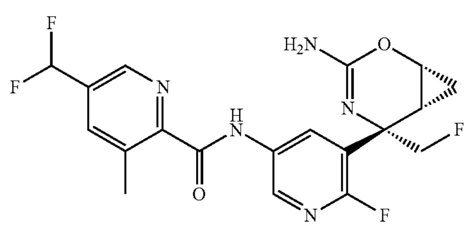 [SMILES: Cc1cc(C(F)F)cnc1C(=O)Nc1cnc(F)c([C@@]2(CF)N=C(N)O[C@@H]3C[C@@H]32)c1] | MS m/z = 424[M + H]+ 1H NMR (MeOH) d: 8.69 (s, 1H), 8.63 (s, 1H), 8.41 (dd, J = 8.8, 2.5 Hz, 1H), 7.96 (s, 1H), 6.76-7.15 (m, 1H), 4.76 (br. s., 1H), 4.64 (d, J = 2.2 Hz, 1H), 4.11 (t, J = 5.4 Hz, 1H), 2.74 (s, 3H), 1.60-1.81 (m, 1H), 1.09-1.22 (m, 1H), 0.84-1.01 (m, 1H) |
| 235 | A | N-(5-((1R,5S,6R)-3-amino-5-(fluoromethyl)-2-oxa-4-azabicyclo[4.1.0]hept-3-en-5-yl)-6-fluoropyridin-3-yl)-5-bromopicolinamide | 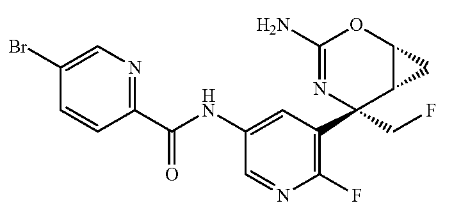 [SMILES: NC1=N[C@](CF)(c2cc(NC(=O)c3ccc(Br)cn3)cnc2F)[C@H]2C[C@H]2O1] | MS m/z = 437.9 [M + H]+ 1H NMR (MeOH) d: 8.81 (d, J = 2.0 Hz, 1H), 8.64 (s, 1H), 8.46 (dd, J = 8.8, 2.5 Hz, 1H), 8.23 (dd, J = 8.4, 2.2 Hz, 1H), 8.07-8.18 (m, 1H), 4.75 (d, J = 1.8 Hz, 1H), 4.63 (d, J = 2.5 Hz, 1H), 4.10 (t, J = 5.7 Hz, 1H), 1.61-1.80 (m, 1H), 1.16 (td, J = 6.8, 2.4 Hz, 1H), 0.95 (dt, J = 9.6, 6.7 Hz, 1H) |
| 236 | A | N-(3-((1R,5S,6R)-3-amino-5-(difluoromethyl)-2-oxa-4-azabicyclo[4.1.0]hept-3-en-5-yl)-4-fluorophenyl)-5-(2,2,2-trifluoroethoxy)picolinamide | 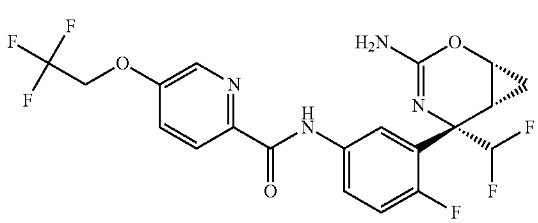 [SMILES: NC1=N[C@@](c2cc(NC(=O)c3ccc(OCC(F)(F)F)cn3)ccc2F)(C(F)F)[C@H]2C[C@H]2O1] | MS m/z = 475[M + H]+ 1H NMR (MeOH) Shift: 8.49 (d, J = 2.7 Hz, 1H), 8.23 (d, J = 8.8 Hz, 1H), 7.85-7.93 (m, 2H), 7.69 (dd, J = 8.7, 2.8 Hz, 1H), 7.21 (dd, J = 11.6, 8.7 Hz, 1H), 6.16-6.49 (m, 1H), 4.80 (q, J = 8.2 Hz, 2H), 4.12 (t, J = 5.4 Hz, 1H), 1.89-1.99 (m, 1H), 1.38 (t, J = 5.8 Hz, 1H), 0.98-1.10 (m, 1H) |

TABLE 1-continued

| Example # | Method | Compound Name | Structure | Analytical Data |
|---|---|---|---|---|
| 237 | A | N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)-3-methylpicolinamide | 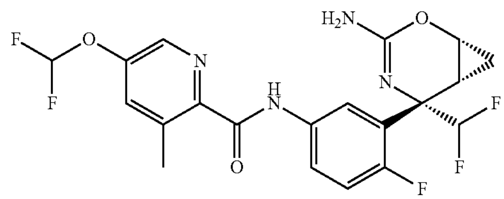 [SMILES: Cc1cc(OC(F)F)cnc1C(=O)Nc1ccc(F)c([C@@]2(C(F)F)N=C(N)O[C@@H]3C[C@@H]32)c1] | MS m/z = 457.1 [M + H]+<br>1H NMR (MeOH) d: 8.40 (d, J = 2.5 Hz, 1H), 7.88 (ddd, J = 8.8, 4.3, 2.8 Hz, 1H), 7.82 (dd, J = 6.9, 2.6 Hz, 1H), 7.61 (s, 1H), 7.18-7.27 (m, 1H), 6.86-7.17 (m, 1H), 6.11-6.48 (m, 1H), 3.99-4.17 (m, 1H), 2.73 (s, 3H), 1.83-2.01 (m, 1H), 1.36 (br. s., 1H), 0.91-1.09 (m, 1H) |
| 238 | A | N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)pyrazine-2-carboxamide | 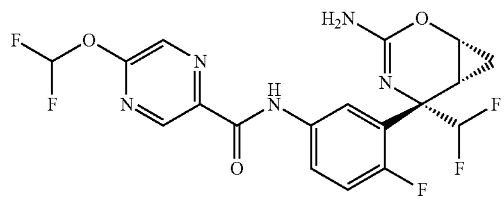 [SMILES: NC1=N[C@@](c2cc(NC(=O)c3cnc(OC(F)F)cn3)ccc2F)(C(F)F)[C@H]2C[C@H]2O1] | MS m/z = 444 [M + H]+<br>1H NMR (MeOH) d: 8.97 (s, 1H), 8.49 (s, 1H), 7.80-7.93 (m, 2H), 7.41-7.70 (m, 1H), 7.17 (t, J = 10.1 Hz, 1H), 6.07-6.44 (m, 1H), 3.93-4.12 (m, 1H), 1.88 (q, J = 7.9 Hz, 1H), 1.32 (br. s., 1H), 0.97 (q, J = 7.7 Hz, 1H) |
| 239 | A | N-(3-((1R,5S,6R)-3-amino-5-(difluoromethyl)-2-oxa-4-azabicyclo[4.1.0]hept-3-en-5-yl)-4-fluorophenyl)cyclohexanecarboxamide | 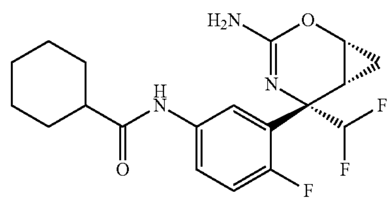 [SMILES: NC1=N[C@@](c2cc(NC(=O)C3CCCCC3)ccc2F)(C(F)F)[C@H]2C[C@H]2O1] | MS m/z = 382.1 [M + H]+<br>1H NMR (MeOH) ?: 7.66 (br. s., 1H), 7.58 (d, J = 6.8 Hz, 1H), 7.07 (t, J = 10.0 Hz, 1H), 6.06-6.41 (m, 1H), 4.01 (br. s., 1H), 2.35 (t, J = 11.4 Hz, 1H), 1.78-1.91 (m, 5H), 1.72 (d, J = 11.2 Hz, 1H), 1.44-1.58 (m, 2H), 1.20-1.41 (m, 4H), 0.90-1.01 (m, 1H) |
| 240 | | N-(3-((1R,5S,6R)-3-amino-5-(difluoromethyl)-2-oxa-4-azabicyclo[4.1.0]hept-3-en-5-yl)-4-fluorophenyl)-2-methoxyacetamide | 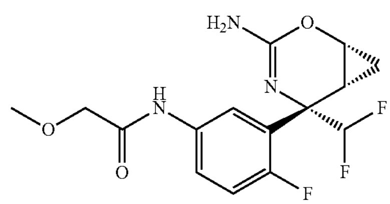 [SMILES: COCC(=O)Nc1ccc(F)c([C@@]2(C(F)F)N=C(N)O[C@@H]3C[C@@H]32)c1] | MS m/z = 344.1 [M + H]+<br>1H NMR (MeOH) ?: 7.29-7.74 (m, 2H), 7.11 (t, J = 10.2 Hz, 1H), 6.07-6.41 (m, 1H), 4.02 (s, 3H), 3.47 (s, 3H), 1.84 (q, J = 7.5 Hz, 1H), 1.30 (br. s., 1H), 0.88-1.01 (m, 1H) |
| 241 | A | N-(3-((1R,5S,6R)-3-amino-5-(difluoromethyl)-2-oxa-4-azabicyclo[4.1.0]hept-3-en-5-yl)-4-fluorophenyl)-2-cyclohexylacetamide | 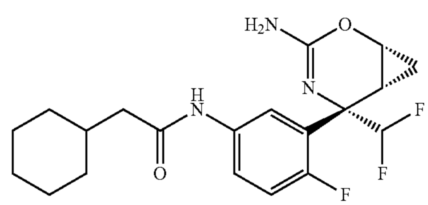 [SMILES: NC1=N[C@@](c2cc(NC(=O)CC3CCCCC3)ccc2F)(C(F)F)[C@H]2C[C@H]2O1] | MS m/z = 396.1 [M + H]+<br>1H NMR (MeOH) ?: 7.67 (br. s., 1H), 7.57 (d, J = 6.8 Hz, 1H), 7.08 (t, J = 10.6 Hz, 1H), 6.06-6.41 (m, 1H), 4.01 (br. s., 1H), 2.22 (d, J = 7.2 Hz, 2H), 1.64-1.88 (m, 7H), 1.13-1.40 (m, 4H), 0.89-1.11 (m, 3H) |
| 242 | A | N-(3-((1R,5S,6R)-3-amino-5-(difluoromethyl)-2-oxa-4-azabicyclo[4.1.0]hept-fluorophenyl)tetrahydro-2H-pyran-4-carboxamide | 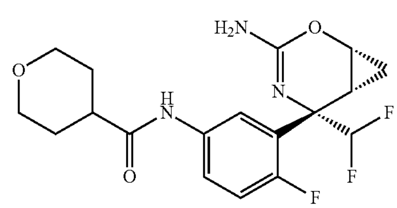 [SMILES: NC1=N[C@@](c2cc(NC(=O)C3CCOCC3)ccc2F)(C(F)F)[C@H]2C[C@H]2O1] | MS m/z = 384.1 [M + H]+<br>1H NMR (MeOH) ?: 7.31-7.71 (m, 2H), 7.02-7.21 (m, 1H), 6.06-6.41 (m, 1H), 4.00 (d, J = 8.6 Hz, 3H), 3.48 (t, J = 11.7 Hz, 2H), 2.62 (t, J = 11.6 Hz 1H), 1.68-1.93 (m, 5H), 1.29 (br. s., 1H), 0.86-1.01 (m, 1H) |
| 243 | A | N-(3-((1R,5S,6R)-3-amino-5-(difluoromethyl)-2-oxa-4-azabicyclo[4.1.0]hept-3-en-5-yl)-4-fluorophenyl)cyclohex-1-enecarboxamide | 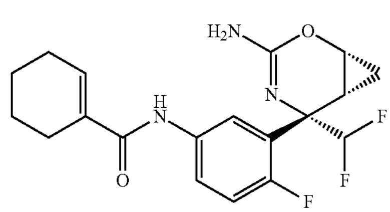 [SMILES: NC1=N[C@@](c2cc(NC(=O)C3=CCCCC3)ccc2F)(C(F)F)[C@H]2C[C@H]2O1] | MS m/z = 380.1 [M + H]+<br>1H NMR (MeOH) ?: 7.63-7.72 (m, 2H), 7.12 (dd, J = 11.8, 8.7 Hz, 1H), 6.70 (dt, J = 3.7, 2.1 Hz, 1H), 6.11-6.45 (m, 1H), 3.99-4.09 (m, 1H), 2.32-2.40 (m, 2H), 2.27 (dd, J = 6.2, 2.6 Hz, 2H), 1.82-1.93 (m, 1H), 1.65-1.79 (m, 4H), 1.33 (d, J = 4.5 Hz, 1H), 0.99 (dt, J = 9.4, 6.7 Hz, 1H) |

TABLE 1-continued

| Example # | Method | Compound Name | Structure | Analytical Data |
|---|---|---|---|---|
| 244 | A | (S,R)-N-(3-((1R,5S,6R)-3-amino-5-(difluoromethyl)-2-oxa-4-azabicyclo[4.1.0]hept-3-en-5-yl)-4-fluorophenyl) tetrahydrofuran-2-carboxamide | 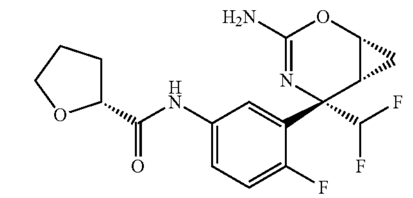 [SMILES: NC1=N[C@@](c2cc(NC(=O)[C@H]3CCCO3)ccc2F)(C(F)F)[C@H]2C[C@H]2O1] | MS m/z = 370.1 [M + H]+<br>1H NMR (MeOH) ?: 7.67-7.76 (m, 2H), 7.14 (dd, J = 11.7, 8.8 Hz, 1H), 6.08-6.45 (m, 1H), 4.44 (dd, J = 7.8, 6.3 Hz, 1H), 4.08-4.15 (m, 1H), 4.02-4.07 (m, 1H), 3.92-3.98 (m, 1H), 2.36 (dq, J = 12.4, 7.5 Hz, 1H), 2.10 (dq, J = 13.1, 6.6 Hz, 1H), 1.94-2.03 (m, 2H), 1.83-1.91 (m, 1H), 1.33 (t, J = 6.0 Hz, 1H), 0.99 (dt, J = 9.4, 6.7 Hz, 1H) |
| 245 | A | N-(3-((1R,5S,6R)-3-amino-5-(difluoromethyl)-2-oxa-4-azabicyclo[4.1.0]hept-3-en-5-yl)-4-fluorophenyl)-1-(4-chlorophenyl) cyclopropanecarboxamide | 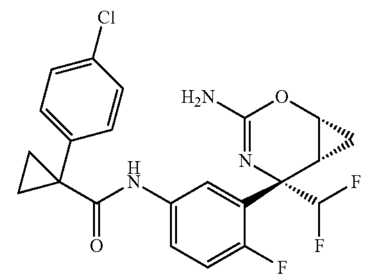 [SMILES: NC1=N[C@@](c2cc(NC(=O)C3(c4ccc(Cl)cc4)CC3)ccc2F)(C(F)F)[C@H]2C[C@H]2O1] | MS m/z = 450 [M + H]+<br>1H NMR (MeOH) ?: 7.46-7.52 (m, 4H), 7.38-7.45 (m, 2H), 7.04-7.13 (m, 1H), 6.05-6.39 (m, 1H), 3.97-4.05 (m, 1H), 1.84 (dt, J = 9.4, 6.9 Hz, 1H), 1.60 (q, J = 3.7 Hz, 2H), 1.30 (t, J = 6.5 Hz, 1H), 1.20 (q, J = 3.7 Hz, 2H), 0.96 (dt, J = 9.4, 6.7 Hz, 1H) |
| 246 | A | N-(3-((1R,5S,6R)-3-amino-5-(difluoromethyl)-2-oxa-4-azabicyclo[4.1.0]hept-3-en-5-yl)-4-fluorophenyl)-1-(4-chlorophenyl) cyclobutanecarboxamide | 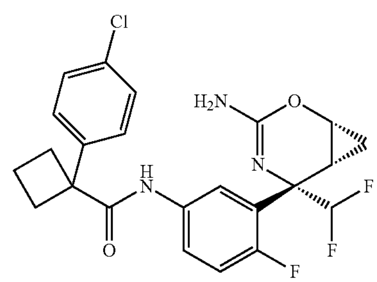 [SMILES: NC1=N[C@@](c2cc(NC(=O)C3(c4ccc(Cl)cc4)CCC3)ccc2F)(C(F)F)[C@H]2C[C@H]2O1] | MS m/z = 464.1 [M + H]+<br>1H NMR (MeOH) ?: 7.53-7.62 (m, 2H), 7.43-7.49 (m, 2H), 7.33-7.39 (m, 2H), 7.07 (dd, J = 11.7, 8.8 Hz, 1H), 6.03-6.39 (m, 1H), 3.93-4.04 (m, 1H), 2.82-2.94 (m, 2H), 2.54 (d, J = 7.2 Hz, 2H), 1.86-2.03 (m, 2H), 1.75-1.86 (m, 1H), 1.23-1.34 (m, 1H), 0.89-1.01 (m, 1H) |
| 247 | A | N-(3-((1R,5S,6R)-3-amino-5-(difluoromethyl)-2-oxa-4-azabicyclo[4.1.0]hept-3-en-5-yl)-4-fluorophenyl)-3-methoxypropanamide | 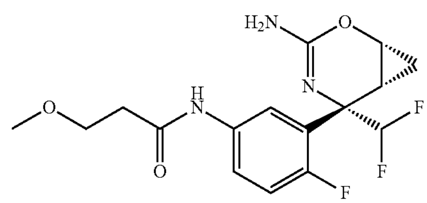 [SMILES: COCCC(=O)Nc1ccc(F)c([C@@]2(C(F)F)N=C(N)O[C@@H]3C[C@@H]32)c1] | MS m/z = 358.1 [M + H]+<br>1H NMR (MeOH) ?: 7.31-7.76 (m, 2H), 7.04-7.22 (m, 1H), 6.01-6.44 (m, 1H), 3.92-4.07 (m, 1H), 3.72 (t, J = 6.1 Hz, 2H), 3.36 (s, 3H), 2.61 (t, J = 6.2 Hz, 2H), 1.75-1.90 (m, 1H), 1.31 (br. s., 1H), 0.96 (dt, J = 9.5, 6.7 Hz, 1H) |
| 248 | A | N-(3-((1R,5S,6R)-3-amino-5-(difluoromethyl)-2-oxa-4-azabicyclo[4.1.0]hept-3-en-5-yl)-4-fluorophenyl)-1-methyl-6-oxo-1,6-dihydropyridine-3-carboxamide | 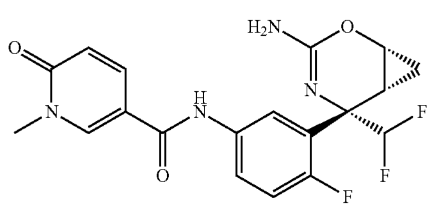 [SMILES: Cn1cc(C(=O)Nc2ccc(F)c([C@@]3(C(F)F)N=C(N)O[C@@H]4C[C@@H]43)c2)ccc1=O] | MS m/z = 407 [M + H]+<br>1H NMR (MeOH) ?: 8.46 (d, J = 2.5 Hz, 1H), 8.06 (dd, J = 9.4, 2.7 Hz, 1H), 7.78 (ddd, J = 8.8, 4.2, 2.8 Hz, 1H), 7.71 (dd, J = 6.8, 2.7 Hz, 1H), 7.17 (dd, J = 11.7, 8.8 Hz, 1H), 6.61 (d, J = 9.4 Hz, 1H), 6.09-6.45 (m, 1H), 3.98-4.11 (m, 1H), 3.67 (s, 3H), 1.80-1.93 (m, 1H), 1.34 (t, J = 6.6 Hz, 1H), 1.00 (dt, J = 9.6, 6.7 Hz, 1H) |
| 249 | A | N-(3-((1R,5S,6R)-3-amino-5-(difluoromethyl)-2-oxa-4-azabicyclo[4.1.0]hept-3-en-5-yl)-4-fluorophenyl)-1-methyl-2-oxo-1,2-dihydropyridine-4-carboxamide | 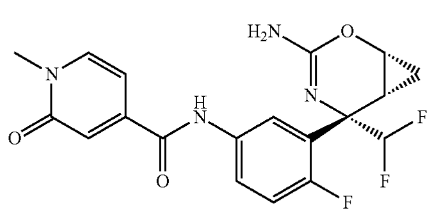 [SMILES: Cn1ccc(C(=O)Nc2ccc(F)c([C@@]3(C(F)F)N=C(N)O[C@@H]4C[C@@H]43)c2)cc1=O] | MS m/z = 407 [M + H]+<br>1H NMR (MeOH) ?: 7.80 (d, J = 6.3 Hz, 3H), 7.20 (dd, J = 11.7, 9.0 Hz, 1H), 7.03 (s, 1H), 6.78 (dd, J = 6.9, 1.9 Hz, 1H), 6.07-6.50 (m, 1H), 4.09 (br. s., 1H), 3.64 (s, 3H), 1.79-1.97 (m, 1H), 1.36 (br. s., 1H), 0.95-1.09 (m, 1H) |

TABLE 1-continued

| Example # | Method | Compound Name | Structure | Analytical Data |
|---|---|---|---|---|
| 250 | A | N-(3-((1R,5S,6R)-3-amino-5-(difluoromethyl)-2-oxa-4-azabicyclo[4.1.0]hept-3-en-5-yl)-4-fluorophenyl)-5-((3-cyclopropylprop-2-yn-1-yl)oxy)picolinamide | 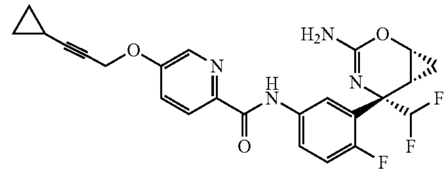 [SMILES: NC1=N[C@@](c2cc(NC(=O)c3ccc(OCC#CC4CC4)cn3)ccc2F)(C(F)F)[C@H]2C[C@H]2O1] | MS m/z = 471.1 [M + H]<sup>+</sup><br>1H NMR (MeOH) ?: 8.37 (br. s., 1H), 8.15 (d, J = 8.6 Hz, 1H), 7.85 (d, J = 5.9 Hz, 2H), 7.56 (d, J = 8.4 Hz, 1H), 7.16 (t, J = 10.5 Hz, 1H), 6.06-6.43 (m, 1H), 4.85 (s, 2H), 4.05 (br. s., 1H), 1.83-1.95 (m, 1H), 1.19-1.40 (m, 3H), 0.97 (d, J = 7.8 Hz, 1H), 0.79 (d, J = 7.2 Hz, 2H), 0.62 (br. s., 2H) |
| 251 | A | N-(3-((1R,5S,6R)-3-amino-5-(difluoromethyl)-2-oxa-4-azabicyclo[4.1.0]hept-3-en-5-yl)-4-fluorophenyl)-3,3,3-trifluoropropanamide | 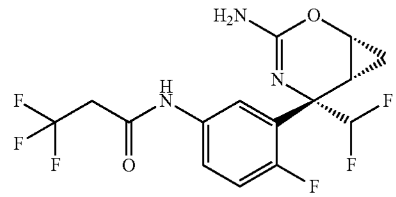 [SMILES: NC1=N[C@@](c2cc(NC(=O)CC(F)(F)F)ccc2F)(C(F)F)[C@H]2C[C@H]2O1] | MS m/z = 382 [M + H]<sup>+</sup><br>1H NMR (MeOH) ?: 7.70 (d, J = 8.4 Hz, 1H), 7.60 (d, J = 6.5 Hz, 1H), 7.12 (t, J = 10.3 Hz, 1H), 6.05-6.43 (m, 1H), 4.03 (br. s., 1H), 3.34 (s, 2H), 1.84 (q, J = 7.5 Hz, 1H), 1.30 (br. s., 1H), 0.96 (q, J = 7.5 Hz, 1H) |
| 252 | A | N-(3-((1R,5S,6R)-3-amino-5-(difluoromethyl)-2-oxa-4-azabicyclo[4.1.0]hept-3-en-5-yl)-4-fluorophenyl)-2-(4-chlorophenyl)propanamide | 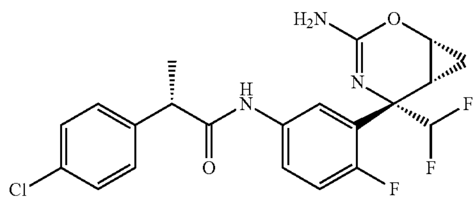 [SMILES: C[C@H](C(=O)Nc1ccc(F)c([C@@]2(C(F)F)N=C(N)O[C@@H]3C[C@@H]32)c1)c1ccc(Cl)cc1] | MS m/z = 438 [M + H]<sup>+</sup><br>1H NMR (MeOH) ?: 7.66 (br. s., 1H), 7.56 (t, J = 7.7 Hz, 1H), 7.35-7.41 (m, 2H), 7.28-7.35 (m, 2H), 7.07 (t, J = 10.4 Hz, 1H), 6.03-6.40 (m, 1H), 3.99 (br. s., 1H), 3.80 (q, J = 7.1 Hz, 1H), 1.81 (d, J = 7.2 Hz, 1H), 1.49 (d, J = 6.8 Hz, 3H), 1.17-1.34 (m, 1H), 0.88-1.01 (m, 1H) |
| 253 | A | (R,S)-N-(3-((1R,5S,6R)-3-amino-5-(difluoromethyl)-2-oxa-4-azabicyclo[4.1.0]hept-3-en-5-yl)-4-fluorophenyl)tetrahydrofuran-3-carboxamide | 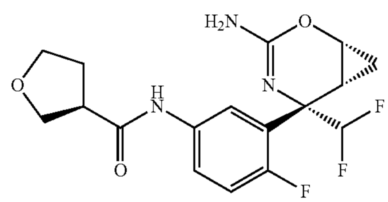 [SMILES: NC1=N[C@@](c2cc(NC(=O)[C@@H]3CCOC3)ccc2F)(C(F)F)[C@H]2C[C@H]2O1] | MS m/z = 370.1 [M + H]<sup>+</sup><br>1H NMR (MeOH) ?: 7.66-7.97 (m, 1H), 7.43-7.62 (m, 1H), 7.09 (t, J = 10.5 Hz, 1H), 6.00-6.44 (m, 1H), 3.75-4.05 (m, 4H), 3.34 (s, 1H), 3.17 (quin, J = 7.3 Hz, 1H), 2.14-2.25 (m, 2H), 1.83 (q, J = 7.4 Hz, 1H), 1.29 (br. s., 1H), 0.86-1.01 (m, 1H) |
| 254 | A | N-(3-((1R,5S,6R)-3-amino-5-(difluoromethyl)-2-oxa-4-azabicyclo[4.1.0]hept-3-en-5-yl)-4-fluorophenyl)-2-(tert-butoxy)acetamide | 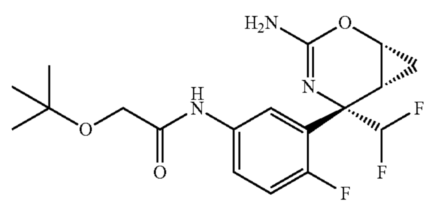 [SMILES: CC(C)(C)OCC(=O)Nc1ccc(F)c([C@@]2(C(F)F)N=C(N)O[C@@H]3C[C@@H]32)c1] | MS m/z = 386.1 [M + H]<sup>+</sup><br>1H NMR (MeOH) ?: 7.65 (d, J = 6.3 Hz, 2H), 7.11 (t, J = 10.3 Hz, 1H), 6.01-6.42 (m, 1H), 3.85-4.14 (m, 3H), 1.85 (q, J = 7.5 Hz, 1H), 1.29 (s, 9H), 1.17-1.28 (m, 1H), 0.95 (q, J = 7.6 Hz, 1H) |
| 255 | A | N-(3-((1R,5S,6R)-3-amino-5-(difluoromethyl)-2-oxa-4-azabicyclo[4.1.0]hept-3-en-5-yl)-4-fluorophenyl)-2-(2-methoxyethoxy)acetamide | 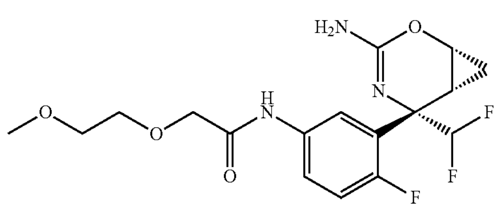 [SMILES: COCCOCC(=O)Nc1ccc(F)c([C@@]2(C(F)F)N=C(N)O[C@@H]3C[C@@H]32)c1] | MS m/z = 388.1 [M + H]<sup>+</sup><br>1H NMR (MeOH) ?: 7.69 (d, J = 5.9 Hz, 2H), 7.12 (t, J = 10.1 Hz, 1H), 6.03-6.42 (m, 1H), 4.11 (s, 2H), 4.02 (br. s., 1H), 3.75 (d, J = 2.2 Hz, 2H), 3.63 (br. s., 2H), 3.43 (s, 3H), 1.78-1.88 (m, 1H), 1.30 (br. s., 1H), 0.91-1.00 (m, 1H) |
| 256 | A | N-(3-((1R,5S,6R)-3-amino-5-(difluoromethyl)-2-oxa-4-azabicyclo[4.1.0]hept-3-en-5-yl)-4-fluorophenyl)-2-phenoxyacetamide | 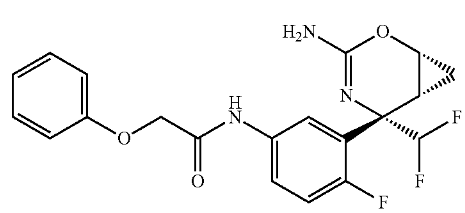 [SMILES: NC1=N[C@@](c2cc(NC(=O)COc3ccccc3)ccc2F)(C(F)F)[C@H]2C[C@H]2O1] | MS m/z = 406.1 [M + H]+<br>1H NMR (MeOH) ?: 7.67-7.74 (m, 2H), 7.31 (t, J = 7.7 Hz, 2H), 7.13 (t, J = 10.3 Hz, 1H), 6.95-7.07 (m, 3H), 6.11-6.44 (m, 1H), 4.65 (s, 2H), 4.05 (br. s., 1H), 1.87 (q, J = 7.6 Hz, 1H), 1.32 (m, 1H), 1.28-1.37 (m, 1H), 0.98 (q, J = 7.4 Hz, 1H) |

TABLE 1-continued

| Example # | Method | Compound Name | Structure | Analytical Data |
|---|---|---|---|---|
| 257 | A | (R,S)-N-(3-((1R,5S,6R)-3-amino-5-(difluoromethyl)-2-oxa-4-azabicyclo[4.1.0]hept-3-en-5-yl)-4-fluorophenyl)-2-methoxypropanamide | 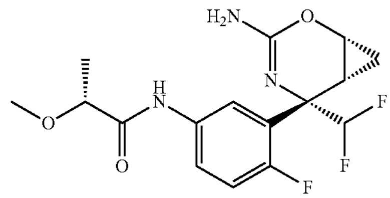 [SMILES: CO[C@H](C)C(=O)Nc1ccc(F)c([C@@]2(C(F)F)N=C(N)O[C@@H]3C[C@@H]32)c1] | MS m/z = 358 [M + H]+<br>1H NMR (MeOH) ?: 7.70 (d, J = 6.8 Hz, 2H), 7.12 (t, J = 10.4 Hz, 1H), 6.00-6.45 (m, 1H), 4.04 (br. s., 1H), 3.87 (q, J = 6.8 Hz, 1H), 3.42 (s, 3H), 1.86 (q, J = 7.5 Hz, 1H), 1.40 (d, J = 6.8 Hz, 3H), 1.32 (br. s., 1H), 0.91-1.02 (m, 1H) |
| 258 | A | N-(3-((1R,5S,6R)-3-amino-5-(difluoromethyl)-2-oxa-4-azabicyclo[4.1.0]hept-3-en-5-yl)-4-fluorophenyl)-3-oxocyclobutane-carboxamide | 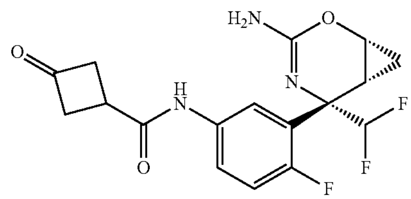 [SMILES: NC1=N[C@@](c2cc(NC(=O)C3CC(=O)C3)ccc2F)(C(F)F)[C@H]2C[C@H]2O1] | MS m/z = 368 [M + H]+<br>1H NMR (MeOH) ?: 7.54-7.85 (m, 2H), 7.12 (t, J = 10.2 Hz, 1H), 5.91-6.46 (m, 1H), 4.05 (br. s., 1H), 3.35 (d, J = 5.7 Hz, 3H), 1.76-1.95 (m, 1H), 1.32 (br. s., 1H), 0.75-1.08 (m, 1H) |
| 259 | A | N-(3-((1R,5S,6R)-3-amino-5-(difluoromethyl)-2-oxa-4-azabicyclo[4.1.0]hept-3-en-5-yl)-4-fluorophenyl)-5-((R,S))-1-cyanoethoxy)picolinamide | 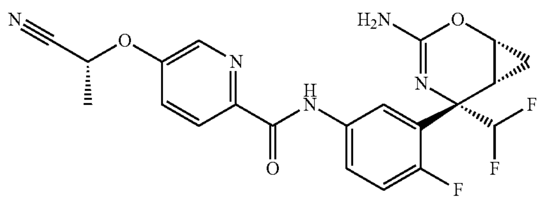 [SMILES: C[C@H](C#N)Oc1ccc(C(=O)Nc2ccc(F)c([C@@]3(C(F)F)N=C(N)O[C@@H]4C[C@@H]43)c2)nc1] | MS m/z = 446.1 [M + H]+<br>1H NMR (MeOH) ?: 8.51 (d, J = 2.7 Hz, 1H), 8.26 (d, J = 8.8 Hz, 1H), 7.87-7.93 (m, 2H), 7.74 (dd, J = 8.7, 2.8 Hz, 1H), 7.20 (dd, J = 11.7, 9.2 Hz, 1H), 6.11-6.48 (m, 1H), 5.49 (q, J = 6.7 Hz, 1H), 4.07-4.12 (m, 1H), 1.88-1.96 (m, 1H), 1.85 (d, J = 6.7 Hz, 3H), 1.34-1.40 (m, 1H), 1.01 (dt, J = 9.5, 6.8 Hz, 1H) |
| 260 | A | N-(3-((1R,5S,6R)-3-amino-5-(difluoromethyl)-2-oxa-4-azabicyclo[4.1.0]hept-3-en-5-yl)-4-fluorophenyl)cyclopropanecarboxamide | 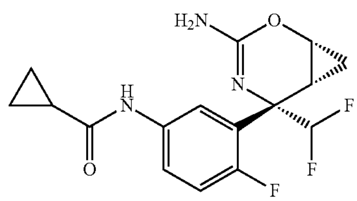 [SMILES: NC1=N[C@@](c2cc(NC(=O)C3CC3)ccc2F)(C(F)F)[C@H]2C[C@H]2O1] | MS m/z = 340 [M + H]+<br>1H NMR (MeOH) ?: 7.67 (dd, J = 5.2, 3.6 Hz, 1H), 7.59 (dd, J = 6.9, 2.6 Hz, 1H), 7.09 (dd, J = 11.7, 8.8 Hz, 1H), 6.06-6.42 (m, 1H), 3.98-4.07 (m, 1H), 1.81-1.90 (m, 1H), 1.72-1.79 (m, 1H), 1.31 (t, J = 5.8 Hz, 1H), 0.92-1.00 (m, 3H), 0.86 (dt, J = 7.8, 3.1 Hz, 2H) |
| 261 | A | N-(3-((1R,5S,6R)-3-amino-5-(difluoromethyl)-2-oxa-4-azabicyclo[4.1.0]hept-3-en-5-yl)-4-fluorophenyl)-5-chloropyrazine-2-carboxamide | 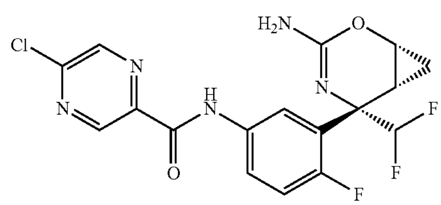 [SMILES: NC1=N[C@@](c2cc(NC(=O)c3cnc(Cl)cn3)ccc2F)(C(F)F)[C@H]2C[C@H]2O1] | MS m/z = 412.0 [M + H]+<br>$^1$H NMR (MeOH): 9.16 (d, J = 1.2 Hz, 1H), 8.80 (d, J = 1.4 Hz, 1H), 7.81-8.02 (m, 2H), 7.21 (dd, J = 11.8, 9.3 Hz, 1H), 6.00-6.54 (m, 1H), 4.08 (br. s., 1H), 1.91 (d, J = 9.4 Hz, 1H), 1.36 (br. s., 1H), 0.93-1.08 (m, 1H) |
| 262 | A | N-(3-((1R,5S,6R)-3-amino-5-(difluoromethyl)-2-oxa-4-azabicyclo[4.1.0]hept-3-en-5-yl)-4-fluorophenyl)-3-phenylpropiolamide | 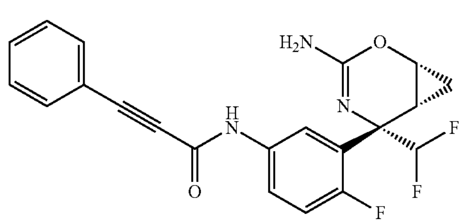 [SMILES: NC1=N[C@@](c2cc(NC(=O)C#Cc3ccccc3)ccc2F)(C(F)F)[C@H]2C[C@H]2O1] | MS m/z = 400.1 [M + H]+<br>1H NMR (MeOH) ?: 7.71-7.80 (m, 2H), 7.63-7.69 (m, 2H), 7.45-7.56 (m, 3H), 7.17 (dd, J = 11.7, 8.8 Hz, 1H), 6.13-6.47 (m, 1H), 4.04-4.10 (m, 1H), 1.85-1.92 (m, 1H), 1.33-1.37 (m, 1H), 0.97-1.05 (m, 1H) |
| 263 | C | N-(3-([(1R,S),(5S,R),(6R,S)]-3-amino-5-(difluoromethyl)-2-oxa-4-azabicyclo[4.1.0]hept-3-en-5-yl)phenyl)-5-chloropicolinamide | 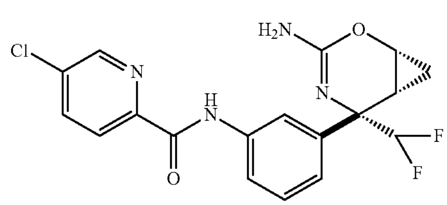 | MS m/z = 392.9 [M + H]+.<br>$^1$H NMR (400 MHz, CHLOROFORM-d) d ppm 9.83-9.88 (m, 1 H) 8.55 (s, 1 H) 8.22-8.27 (m, 1 H) 7.85-7.93 (m, 2 H) 7.81 (d, J = 7.43 Hz, 1 H) 7.35-7.44 (m, 2 H) 5.78 (s, 1 H) 3.94-4.01 (m, 1 H) 1.72-1.81 (m, 1 H) 1.38-1.43 (m, 1 H) 0.94-1.02 (m, 1 H) |

TABLE 1-continued

| Example # | Method | Compound Name | Structure | Analytical Data |
|---|---|---|---|---|
| 264 | C | N-(3-((1S,5R,6S)-3-amino-5-(difluoromethyl)-2-oxa-4-azabicyclo[4.1.0]hept-3-en-5-yl)phenyl)-5-chloropicolinamide | 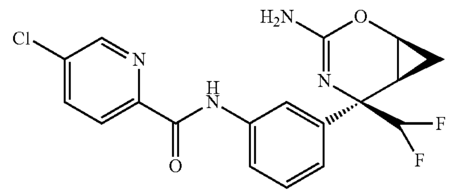 [SMILES: NC1=N[C@](c2cccc(NC(=O)c3ccc(Cl)cn3)c2)(C(F)F)[C@@H]2C[C@@H]2O1] | MS m/z = 392.9 [M + H]$^+$. $^1$H NMR (400 MHz, CHLOROFORM-d) d ppm 9.84 (br. s., 1 H) 8.50-8.56 (m, 1 H) 8.22 (br. s., 1 H) 7.77-7.95 (m, 4 H) 7.34-7.43 (m, 3 H) 5.78 (br. s., 1 H) 3.94-4.02 (m, 2 H) 1.74-1.81 (m, 1 H) 1.42 (t, J = 7.63 Hz, 1 H) 0.94-1.01 (m, 1 H) |
| 265 | C | N-(3-((1R,5S,6R)-3-amino-5-(difluoromethyl)-2-oxa-4-azabicyclo[4.1.0]hept-3-en-5-yl)phenyl)-5-chloropicolinamide | 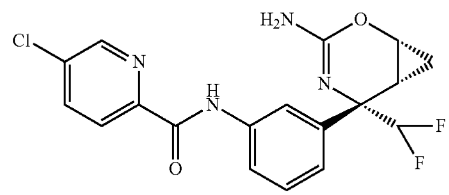 [SMILES: NC1=N[C@@](c2cccc(NC(=O)c3ccc(Cl)cn3)c2)(C(F)F)[C@H]2C[C@H]2O1] | MS m/z = 392.9 [M + H]$^+$. $^1$H NMR (400 MHz, CHLOROFORM-d) d ppm 9.76 (br. s., 1 H) 8.41-8.50 (m, 1 H) 8.15 (d, J = 8.41 Hz, 1 H) 7.82-7.87 (m, 1 H) 7.75-7.82 (m, 1 H) 7.66-7.75 (m, 1 H) 7.26-7.35 (m, 2 H) 5.68-5.73 (m, 1 H) 3.85-3.93 (m, 1 H) 1.65-1.74 (m, 1 H) 1.29-1.36 (m, 1 H) 0.85-0.95 (m, 1 H) |
| 266 | B | N-(3-((1R,5S,6R)-3-amino-5-(difluoromethyl)-2-oxa-4-azabicyclo[4.1.0]hept-3-en-5-yl)-4-fluorophenyl)-5-methylpyrazine-2-carboxamide | 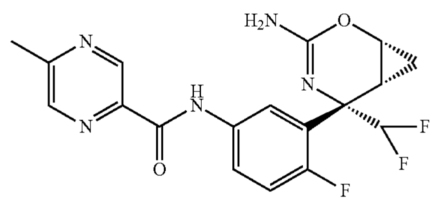 [SMILES: Cc1cnc(C(=O)Nc2ccc(F)c([C@@]3(C(F)F)N=C(N)O[C@@H]4C[C@@H]43)c2)cn1] | MS m/zm/z = 392 [M + H]$^+$. $^1$H NMR (400 MHz, CHLOROFORM-d) d ppm 9.59-9.63 (m, 1 H) 9.33-9.36 (m, 1 H) 8.42 (s, 1 H) 7.97 (br. s., 1 H) 7.67 (br. s., 1 H) 7.08-7.15 (m, 1 H) 6.24 (s, 1 H) 3.99 (t, J = 7.92 Hz, 1 H) 2.66-2.71 (m, 3 H) 1.86-1.94 (m, 1 H) 1.44 (t, J = 7.73 Hz, 1 H) 0.97-1.04 (m, 1 H) |
| 267 | B | N-(3-((1R,5S,6R)-3-amino-5-(difluoromethyl)-2-oxa-4-azabicyclo[4.1.0]hept-3-en-5-yl)-4-fluorophenyl)-5-bromopyrimidine-2-carboxamide | 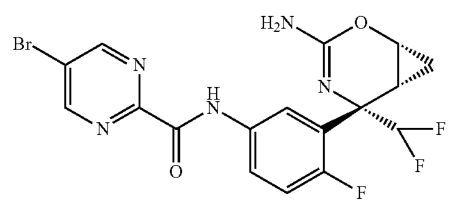 [SMILES: NC1=N[C@@](c2cc(NC(=O)c3ncc(Br)cn3)ccc2F)(C(F)F)[C@H]2C[C@H]2O1] | MS m/z = 456.9 [M + H]$^+$. $^1$H NMR (400 MHz, CHLOROFORM-d) d ppm 9.64-9.71 (m, 1 H) 8.94-8.96 (m, 1 H) 8.94 (s, 1 H) 7.94-8.01 (m, 1 H) 7.69-7.74 (m, 1 H) 7.06-7.13 (m, 1 H) 6.24 (s, 1 H) 3.91-3.96 (m, 1 H) 1.83-1.91 (m, 1 H) 1.40-1.46 (m, 1 H) 0.93-1.01 (m, 1 H) |
| 268 | B | N-(3-((1R,5S,6R)-3-amino-5-(difluoromethyl)-2-oxa-4-azabicyclo[4.1.0]hept-3-en-5-yl)-4-fluorophenyl)-5-(trifluoromethyl)pyrazine-2-carboxamide | 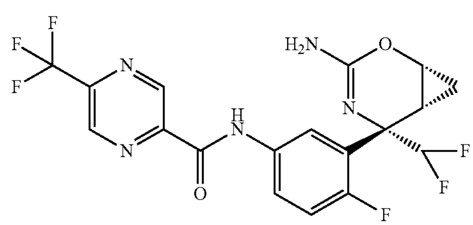 [SMILES: NC1=N[C@@](c2cc(NC(=O)c3cnc(C(F)(F)F)cn3)ccc2F)(C(F)F)[C@H]2C[C@H]2O1] | MS m/z = 446 [M + H]$^+$. $^1$H NMR (400 MHz, CHLOROFORM-d) d ppm 9.55-9.59 (m, 2 H) 8.93 (s, 1 H) 7.98 (br. s., 1 H) 7.69 (d, J = 7.24 Hz, 1 H) 7.08-7.13 (m, 1 H) 6.22-6.25 (m, 1 H) 4.00 (t, J = 8.02 Hz, 1 H) 1.91 (br. s., 1 H) 1.45 (t, J = 8.22 Hz, 1 H) 1.02 (br. s., 1 H) |
| 269 | B | N-(3-((1R,5S,6R)-3-amino-5-(difluoromethyl)-2-oxa-4-azabicyclo[4.1.0]hept-3-en-5-yl)-4-methylphenyl)-5-cyanopicolinamide | 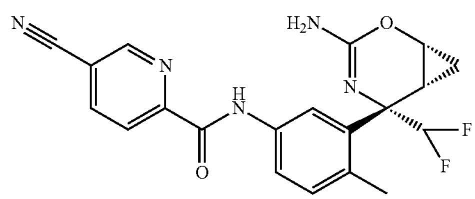 [SMILES: Cc1ccc(NC(=O)c2ccc(C#N)cn2)cc1[C@@]1(C(F)F)N=C(N)O[C@@H]2C[C@@H]21] | MS m/z = 398 [M + H]$^+$. $^1$H NMR (300 MHz, CHLOROFORM-d) 6 ppm 9.83 (br. s., 1 H) 8.88 (s, 1 H) 8.42 (d, J = 8.04 Hz, 1 H) 8.19 (d, J = 8.04 Hz, 1 H) 8.08 (s, 1 H) 7.70 (d, J = 7.89 Hz, 1 H) 7.18-7.24 (m, 1 H) 6.19 (t, J = 56.20 Hz, 1 H) 4.06 (br. s., 1 H) 2.59 (s, 3 H) 1.87 (d, J = 8.48 Hz, 1 H) 1.47 (br. s., 1 H) 1.01 (d, J = 8.62 Hz, 1 H) |
| 270 | C | N-(3-((1R,5S,6R)-3-amino-5-(fluoromethyl)-2-oxa-4-azabicyclo[4.1.0]hept-3-en-5-yl)-4-chlorophenyl)-5-chloropicolinamide | 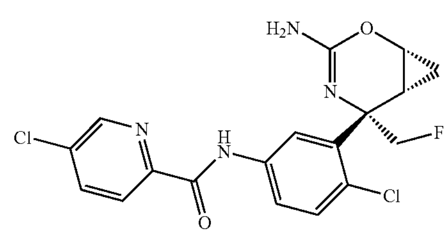 [SMILES: NC1=N[C@](CF)(c2cc(NC(=O)c3ccc(Cl)cn3)ccc2Cl)[C@H]2C[C@H]2O1] | MS m/z = 409.1 [M + H]$^+$. $^1$H NMR (300 MHz, DMSO-d$_6$) ppm 0.68-1.14 (m, 2 H) 1.52-1.83 (m, 1 H) 3.76-4.14 (m, 1 H) 4.46-5.02 (m, 2 H) 5.44-5.70 (m, 2 H) 7.14-7.55 (m, 1 H) 7.79-7.99 (m, 1 H) 8.17 (s, 3 H) 8.65-9.03 (m, 1 H) 10.53-10.96 (m, 1 H) |

TABLE 1-continued

| Example # | Method | Compound Name | Analytical Data |
|---|---|---|---|
| 271 | C | N-(34(1S,5R,6S)-3-amino-5-(fluoromethyl)-2-oxa-4-azabicyclo[4.1.0]hept-3-en-5-yl)-4-chlorophenyl)-5-chloropicolinamide | MS m/z = 409.1 [M + H]+.<br>$^1$H NMR (300 MHz, DMSO-d$_6$) ppm 0.74-1.07 (m, 2 H) 1.52-1.84 (m, 1 H) 3.97 (br. s., 1 H) 4.46-4.98 (m, 2 H) 7.42 (d, J = 8.62 Hz, 1 H) 7.88 (dd, J = 8.55, 2.27 Hz, 1 H) 8.04-8.30 (m, 3 H) 8.79 (d, J = 1.75 Hz, 1 H) 10.70 (s, 1 H) |
| 272 | C | N-(34(1R,5S,6R)-3-amino-5-(fluoromethyl)-2-oxa-4-azabicyclo[4.1.0]hept-3-en-5-yl)-4-chlorophenyl)-5-methoxypyrazine-2-carboxamide | MS m/z = 406.1 [M + H]+.<br>$^1$H NMR (300 MHz, DMSO-d$_6$) ppm 0.68-1.04 (m, 2 H) 1.58-1.78 (m, 1 H) 3.97 (br. s., 1 H) 4.03 (s, 3 H) 4.51-4.94 (m, 2 H) 5.59 (s, 2 H) 7.41 (d, J = 8.62 Hz, 1 H) 7.86 (dd, J = 8.62, 2.63 Hz, 1 H) 8.16 (d, J = 2.63 Hz, 1 H) 8.42 (d, J = 1.17 Hz, 1 H) 8.89 (d, J = 1.32 Hz, 1 H) 10.53 (s, 1 H) |
| 273 | C | N-(34(1S,5R,6S)-3-amino-5-(fluoromethyl)-2-oxa-4-azabicyclo[4.1.0]hept-3-en-5-yl)-4-chlorophenyl)-5-methoxypyrazine-2-carboxamide | MS m/z = 406.1 [M + H]+.<br>$^1$H NMR (300 MHz, DMSO-d$_6$) ppm 0.78-1.01 (m, 2 H) 1.67 (dt, J = 9.76, 6.96 Hz, 1 H) 3.93-4.00 (m, 1 H) 4.02 (s, 3 H) 4.54-4.95 (m, 2 H) 5.59 (s, 2 H) 7.41 (d, J = 8.62 Hz, 1 H) 7.86 (dd, J = 8.62, 2.63 Hz, 1 H) 8.16 (d, J = 2.63 Hz, 1 H) 8.42 (d, J = 1.32 Hz, 1 H) 8.89 (d, J = 1.32 Hz, 1 H) 10.53 (s, 1 H) |
| 274 | C | N-(3-((1R,5S,6R)-3-amino-5-(fluoromethyl)-2-oxa-4-azabicyclo[4.1.0]hept-3-en-5-yl)-4-chlorophenyl)-5-bromopicolinamide | MS m/z = 452.9 [M]+.<br>1H NMR (300 MHz, DMSO-d$_6$) ppm 0.81-0.99 (m, 2 H) 1.67 (dt, J = 9.57, 7.05 Hz, 1 H) 3.97 (br. s., 1 H) 4.57-4.89 (m, 2 H) 5.59 (s, 2 H) 7.42 (d, J = 8.62 Hz, 1 H) 7.88 (dd, J = 8.62, 2.63 Hz, 1 H) 8.08 (d, J = 8.33 Hz, 1 H) 8.16 (d, J = 2.48 Hz, 1 H) 8.33 (dd, J = 8.40, 2.27 Hz, 1 H) 8.87 (d, J = 2.19 Hz, 1 H) 10.70 (s, 1 H) |
| 275 | C | N-(3-((1S,5R,6S)-3-amino-5-(fluoromethyl)-2-oxa-4-azabicyclo[4.1.0]hept-3-en-5-yl)-4-chlorophenyl)-5-bromopicolinamide | MS m/z = 452.9 [M]+.<br>$^1$H NMR (300 MHz, DMSO-d$_6$) ppm 0.81-1.00 (m, 2 H) 1.67 (dt, J = 9.65, 7.02 Hz, 1 H) 3.96 (br. s., 1 H) 4.56-4.89 (m, 2 H) 5.60 (s, 2 H) 7.42 (d, J = 8.62 Hz, 1 H) 7.88 (dd, J = 8.62, 2.48 Hz, 1 H) 8.08 (d, J = 8.33 Hz, 1 H) 8.16 (d, J = 2.48 Hz, 1 H) 8.33 (dd, J = 8.33, 2.19 Hz, 1 H) 8.87 (d, J = 2.19 Hz, 1 H) 10.70 (s, 1 H) |
| 276 | C | N-(3-(((1R,S), (5S,R), (6R,S))-3-amino-5-(fluoromethyl)-2-oxa-4-azabicyclo[4.1.0]hept-3-en-5-yl)-4-chlorophenyl)-5-chloropicolinamide | MS m/z = 409.1 [M + H]+.<br>$^1$H NMR (300 MHz, DMSO-d$_6$) ppm 0.78-1.05 (m, 2 H) 1.43-1.61 (m, 1 H) 1.62-1.83 (m, 1 H) 3.97 (br. s., 1 H) 4.46-4.99 (m, 2 H) 5.60 (br. s., 2 H) 7.42 (d, J = 8.62 Hz, 1 H) 7.88 (d, J = 7.60 Hz, 1 H) 8.08-8.34 (m, 3 H) 8.79 (s, 1 H) 10.69 (br. s., 1 H) |

TABLE 1-continued

| Example # | Method | Compound Name | Structure | Analytical Data |
|---|---|---|---|---|
| 277 | B | N-(3-((1R,5S,6R)-3-amino-5-(fluoromethyl)-2-oxa-4-azabicyclo[4.1.0]hept-3-en-5-yl)-4-chlorophenyl)-5-cyanopicolinamide | 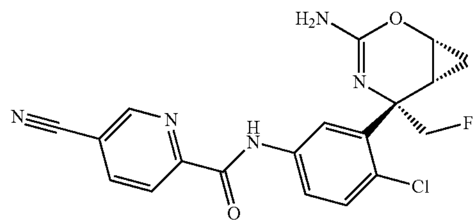 [SMILES: N#Cc1ccc(C(=O)Nc2ccc(Cl)c([C@@]3(CF)N=C(N)O[C@@H]4C[C@@H]43)c2)nc1] | MS m/z = 400.1 [M + H]⁺. ¹H NMR (300 MHz, DMSO-d₆) ppm 0.95 (br. s., 2 H) 1.73 (br. s., 1 H) 4.11 (br. s., 1 H) 4.62-5.04 (m, 2 H) 7.49 (d, J = 8.48 Hz, 1 H) 7.94 (d, J = 9.21 Hz, 1 H) 8.21 (d, J = 2.19 Hz, 1 H) 8.26-8.32 (m, 1 H) 8.59 (dd, J = 8.11, 1.97 Hz, 1 H) 9.21 (d, J = 1.17 Hz, 1 H) 10.95 (br. s., 1 H) |
| 278 | B | N-(3-((1S,5R,6S)-3-amino-5-(fluoromethyl)-2-oxa-4-azabicyclo[4.1.0]hept-3-en-5-yl)-4-chlorophenyl)-5-cyanopicolinamide | 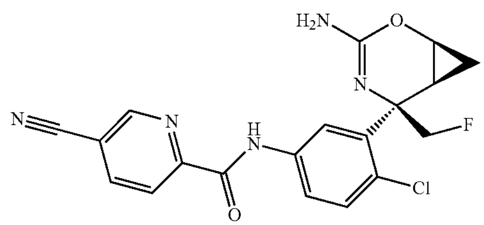 [SMILES: N#Cc1ccc(C(=O)Nc2ccc(Cl)c([C@]3(CF)N=C(N)O[C@H]4C[C@H]43)c2)nc1] | MS m/z = 400.1 [M + H]⁺. ¹H NMR (300 MHz, DMSO-d₆) ppm 0.71-1.13 (m, 2 H) 1.53-1.83 (m, 1 H) 4.00 (br. s., 1 H) 4.53-4.95 (m, 13 H) 5.39-5.90 (m, 2 H) 7.45 (d, J = 8.62 Hz, 1 H) 7.90 (dd, J = 8.62, 2.63 Hz, 1 H) 8.11-8.38 (m, 2 H) 8.58 (dd, J = 8.18, 2.05 Hz, 1 H) 9.21 (d, J = 1.17 Hz, 1 H) 10.88 (s, 7 H) |
| 279 | B | N-(3-((1R,5S,6R)-3-amino-5-(fluoromethyl)-2-oxa-4-azabicyclo[4.1.0]hept-3-en-5-yl)-4-chlorophenyl)-5-(prop-2-yn-1-yloxy)pyrazine-2-carboxamide | 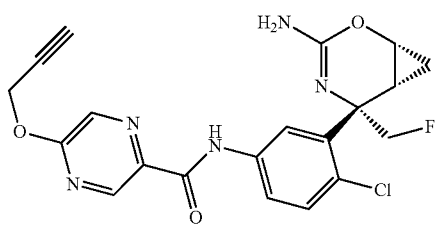 [SMILES: C#CCOc1cnc(C(=O)Nc2ccc(Cl)c([C@@]3(CF)N=C(N)O[C@@H]4C[C@@H]43)c2)cn1] | MS m/z = 430.1 [M + H]⁺. ¹H NMR (300 MHz, DMSO-d₆) ppm 0.93 (br. s., 2 H) 1.71 (br. s., 1 H) 3.64 (t, J = 2.41 Hz, 1 H) 3.92-4.23 (m, 1 H) 4.58-4.96 (m, 2 H) 5.14 (d, J = 2.34 Hz, 2 H) 5.75 (s, 1 H) 7.45 (d, J = 8.48 Hz, 1 H) 7.89 (d, J = 7.45 Hz, 1 H) 8.18 (d, J = 2.34 Hz, 1 H) 8.49 (d, J = 1.32 Hz, 1 H) 8.91 (d, J = 1.32 Hz, 1 H) 10.61 (br. s., 1 H) |
| 280 | B | N-(3-((1S,5R,6S)-3-amino-5-(fluoromethyl)-2-oxa-4-azabicyclo[4.1.0]hept-3-en-5-yl)-4-chlorophenyl)-5-(prop-2-yn-1-yloxy)pyrazine-2-carboxamide | 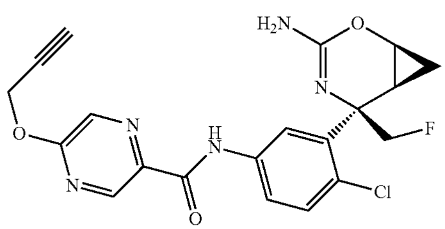 [SMILES: C#CCOc1cnc(C(=O)Nc2ccc(Cl)c([C@]3(CF)N=C(N)O[C@H]4C[C@H]43)c2)cn1] | MS m/z = 430.1 [M + H]⁺. ¹H NMR (300 MHz, DMSO-d₆) ppm 0.77-1.04 (m, 2 H) 1.55-1.78 (m, 1 H) 3.64 (t, J = 2.34 Hz, 1 H) 3.98 (br. s., 1 H) 4.55-4.89 (m, 2 H) 5.14 (d, J = 2.48 Hz, 2 H) 5.60 (br. s., 2 H) 7.42 (d, J = 8.62 Hz, 1 H) 7.86 (dd, J = 8.62, 2.48 Hz, 1 H) 8.17 (d, J = 2.48 Hz, 1 H) 8.49 (d, J = 1.32 Hz, 1 H) 8.90 (d, J = 1.17 Hz, 1 H) 10.57 (s, 6 H) |
| 281 | B | N-(3-((1R,5S,6R)-3-amino-5-(fluoromethyl)-2-oxa-4-azabicyclo[4.1.0]hept-3-en-5-yl)-4-chlorophenyl)-3,5-dichloropicolinamide | 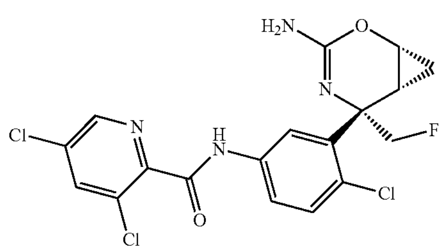 [SMILES: NC1=N[C@](CF)(c2cc(NC(=O)c3ncc(Cl)cc3Cl)ccc2Cl)[C@H]2C[C@H]2O1] | MS m/z = 443.0 [M + H]⁺. ¹H NMR (300 MHz, DMSO-d₆) ppm 0.71-1.07 (m, 2 H) 1.58-1.81 (m, 1 H) 3.94 (br. s., 1 H) 4.56-4.72 (m, 1 H) 4.74-4.89 (m, 1 H) 5.62 (br. s., 2 H) 7.44 (d, J = 8.62 Hz, 1 H) 7.81 (dd, J = 8.55, 2.56 Hz, 1 H) 7.92 (d, J = 2.48 Hz, 1 H) 8.44 (d, J = 2.05 Hz, 1 H) 8.73 (d, J = 2.05 Hz, 1 H) 10.83 (s, 1 H) |
| 282 | B | N-(3-((1R,5S,6R)-3-amino-5-(fluoromethyl)-2-oxa-4-azabicyclo[4.1.0]hept-3-en-5-yl)-4-chlorophenyl)-5-methoxypicolinamide | 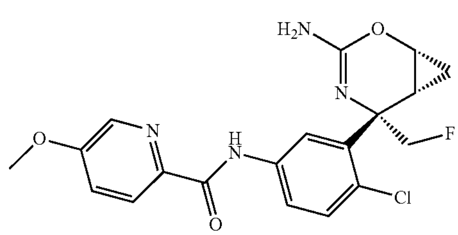 [SMILES: COc1ccc(C(=O)Nc2ccc(Cl)c([C@@]3(CF)N=C(N)O[C@@H]4C[C@@H]43)c2)nc1] | MS m/z = 405.0 [M + H]⁺. ¹H NMR (300 MHz, DMSO-d₆) ppm 0.80-1.01 (m, 2 H) 1.68 (dt, J = 9.76, 6.96 Hz, 1 H) 3.88-4.04 (m, 4 H) 4.51-4.92 (m, 2 H) 5.61 (br. s., 2 H) 7.41 (d, J = 8.62 Hz, 1 H) 7.62 (dd, J = 8.77, 2.92 Hz, 1 H) 7.90 (dd, J = 8.62, 2.63 Hz, 1 H) 8.07-8.23 (m, 2 H) 8.40 (d, J = 2.78 Hz, 1 H) 10.48 (s, 1 H) |

TABLE 1-continued

| Example # | Method | Compound Name | Structure | Analytical Data |
|---|---|---|---|---|
| 283 | B | N-(3-((1R,5S,6R)-3-amino-5-(fluoromethyl)-2-oxa-4-azabicyclo[4.1.0]hept-3-en-5-yl)-4-chlorophenyl)-5-cyano-3-methylpicolinamide | 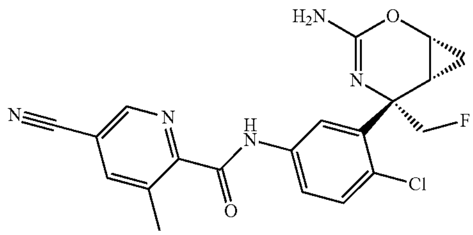 [SMILES: Cc1cc(C#N)cnc1C(=O)Nc1ccc(Cl)c([C@@]2(CF)N=C(N)O[C@@H]3C[C@@H]32)c1] | MS m/z = 414.1 [M + H]$^+$.<br>$^1$H NMR (300 MHz, DMSO-d$_6$) ppm 0.76-1.02 (m, 2 H) 1.57-1.77 (m, 1 H) 2.55 (s, 3 H) 3.95 (br. s., 1 H) 4.51-4.92 (m, 2 H) 5.60 (br. s., 2 H) 7.43 (d, J = 8.62 Hz, 1 H) 7.84 (dd, J = 8.62, 2.48 Hz, 1 H) 8.01 (d, J = 2.34 Hz, 1 H) 8.39 (d, J = 1.17 Hz, 1 H) 8.98 (d, J = 1.46 Hz, 1 H) 10.77 (s, 1 H) |
| 284 | B | N-(3-((1R,5S,6R)-3-amino-5-(fluoromethyl)-2-oxa-4-azabicyclo[4.1.0]hept-3-en-5-yl)-4-chlorophenyl)-3-chloro-5-methoxypicolinamide | 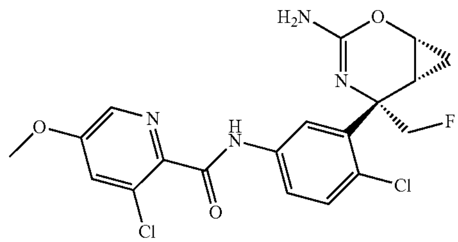 [SMILES: COc1cnc(C(=O)Nc2ccc(Cl)c([C@@]3(CF)N=C(N)O[C@@H]4C[C@@H]43)c2)c(Cl)c1] | MS m/z = 439.1 [M + H]$^+$.<br>$^1$H NMR (300 MHz, DMSO-d$_6$) ppm 0.79-0.98 (m, 2 H) 1.60-1.73 (m, 1 H) 3.93 (s, 4 H) 4.64 (s, 1 H) 4.80 (s, 1 H) 5.59 (br. s., 2 H) 7.41 (d, J = 8.62 Hz, 1 H) 7.73 (d, J = 2.48 Hz, 1 H) 7.82 (dd, J = 8.55, 2.56 Hz, 1 H) 7.97 (d, J = 2.48 Hz, 1 H) 8.35 (d, J = 2.48 Hz, 1 H) 10.62 (s, 1 H) |
| 285 | B | N-(3-((1R,5S,6R)-3-amino-5-(fluoromethyl)-2-oxa-4-azabicyclo[4.1.0]hept-3-en-5-yl)-4-chlorophenyl)-5-(but-2-yn-1-yloxy)pyrazine-2-carboxamide | 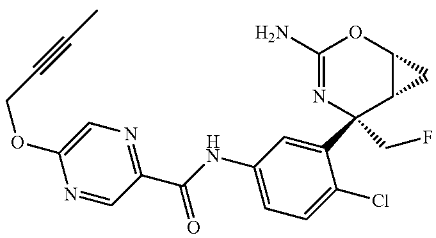 [SMILES: CC#CCOc1cnc(C(=O)Nc2ccc(Cl)c([C@@]3(CF)N=C(N)O[C@@H]4C[C@@H]43)c2)cn1] | MS m/z = 444 [M + H]$^+$.<br>$^1$H NMR (300 MHz, DMSO-d$_6$) ppm 0.70-1.07 (m, 2 H) 1.57-1.75 (m, 1 H) 1.85 (t, J = 2.27 Hz, 3 H) 4.00 (d, J = 14.76 Hz, 1 H) 4.51-4.90 (m, 2 H) 5.09 (d, J = 2.34 Hz, 2 H) 5.60 (br. s., 2 H) 7.42 (d, J = 8.62 Hz, 1 H) 7.86 (dd, J = 8.70, 2.56 Hz, 1 H) 8.16 (d, J = 2.48 Hz, 1 H) 8.46 (d, J = 1.17 Hz, 1 H) 8.89 (d, J = 1.17 Hz, 1 H) 10.55 (s, 1 H) |
| 286 | B | N-(3-((1R,5S,6R)-3-amino-5-(difluoromethyl)-2-oxa-4-azabicyclo[4.1.0]hept-3-en-5-yl)-4-fluorophenyl)-6-chloropicolinamide | 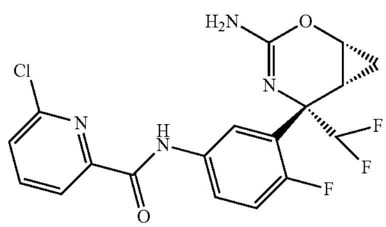 [SMILES: NC1=N[C@@](c2cc(NC(=O)c3cccc(Cl)n3)ccc2F)(C(F)F)[C@H]2C[C@H]2O1] | MS m/z = 411.1 [M + H]$^+$.<br>$^1$H NMR (300 MHz, DMSO-d$_6$) ppm 0.83-1.00 (m, 1 H) 1.15 (br. s., 1 H) 1.68-1.84 (m, 1 H) 3.90-4.10 (m, 1 H) 5.86 (s, 2 H) 5.96-6.46 (m, 1 H) 7.22 (dd, J = 11.84, 8.92 Hz, 1 H) 7.74-7.89 (m, 2 H) 7.98 (dd, J = 7.09, 2.70 Hz, 1 H) 8.06-8.15 (m, 2 H) 10.50 (s, 1 H) |
| 287 | B | N-(3-((1R,5S,6R)-3-amino-5-(difluoromethyl)-2-oxa-4-azabicyclo[4.1.0]hept-3-en-5-yl)-4-fluorophenyl)-4-chloropicolinamide | 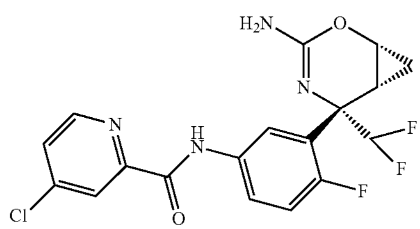 [SMILES: NC1=N[C@@](c2cc(NC(=O)c3cc(Cl)ccn3)ccc2F)(C(F)F)[C@H]2C[C@H]2O1] | MS m/z = 411.1 [M + H]$^+$.<br>$^1$H NMR (400 MHz, DMSO-d$_6$) ppm 0.74-1.04 (m, 1 H) 1.15 (br. s., 1 H) 1.58-1.86 (m, 1 H) 4.03 (br. s., 1 H) 5.85 (br. s., 2 H) 6.00-6.42 (m, 1 H) 7.22 (dd, J = 11.84, 8.90 Hz, 1 H) 7.79-7.95 (m, 2 H) 8.04 (dd, J = 7.04, 2.74 Hz, 1 H) 8.15 (d, J = 1.96 Hz, 1 H) 8.72 (d, J = 5.28 Hz, 1 H) 10.73 (s, 1 H) |
| 288 | B | N-(3-((1R,5S,6R)-3-amino-5-(difluoromethyl)-2-oxa-4-azabicyclo[4.1.0]hept-3-en-5-yl)-4-fluorophenyl)-3-isopropylpicolinamide | 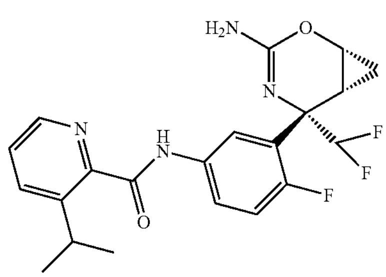 [SMILES: CC(C)c1cccnc1C(=O)Nc1ccc(F)c([C@@]2(C(F)F)N=C(N)O[C@@H]3C[C@@H]32)c1] | MS m/z = 419.1 [M + H]$^+$.<br>$^1$H NMR (300 MHz, DMSO-d$_6$) ppm 0.85-0.98 (m, 1 H) 1.07 (s, 1 H) 1.10-1.20 (m, 2 H) 1.23 (dd, J = 6.87, 0.88 Hz, 5 H) 1.64-1.78 (m, 1 H) 1.99 (s, 1 H) 3.57 (quin, J = 6.87 Hz, 1 H) 3.89-4.09 (m, 2 H) 5.86 (br. s., 2 H) 5.98-6.46 (m, 1 H) 7.12-7.29 (m, 1 H) 7.53 (dd, J = 8.04, 4.68 Hz, 1 H) 7.82-7.89 (m, 1 H) 7.95 (dd, J = 7.97, 1.39 Hz, 1 H) 8.49 (dd, J = 4.68, 1.46 Hz, 1 H) 10.59 (s, 1 H) |

TABLE 1-continued

| Example # | Method | Compound Name | Structure | Analytical Data |
|---|---|---|---|---|
| 289 | B | N-(3-((1R,5S,6R)-3-amino-5-(difluoromethyl)-2-oxa-4-azabicyclo[4.1.0]hept-3-en-5-yl)-4-fluorophenyl)-5-chloro-3-isopropylpicolinamide | 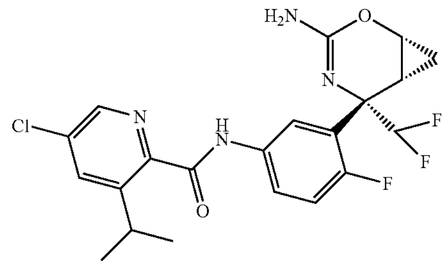 [SMILES: CC(C)c1cc(Cl)cnc1C(=O)Nc1ccc(F)c([C@@]2(C(F)F)N=C(N)O[C@@H]3C[C@@H]32)c1] | MS m/z = 453.2 [M + H]$^+$.<br>$^1$H NMR (300 MHz, DMSO-d$_6$) ppm 0.79-1.01 (m, 1 H) 1.09-1.18 (m, 2 H) 1.24 (d, J = 6.87 Hz, 6 H) 1.62-1.82 (m, 1 H) 3.51 (quin, J = 6.87 Hz, 1 H) 3.85-4.13 (m, 2 H) 5.87 (s, 2 H) 5.99-6.43 (m, 1 H) 7.21 (dd, J = 11.62, 8.55 Hz, 1 H) 7.73-7.92 (m, 2 H) 8.09 (d, J = 2.19 Hz, 1 H) 8.54 (d, J = 2.19 Hz, 1 H) 10.63 (s, 1 H) |
| 290 | B | N-(3-((1R,5S,6R)-3-amino-5-(difluoromethyl)-2-oxa-4-azabicyclo[4.1.0]hept-3-en-5-yl)-4-fluorophenyl)-5-bromo-3-(difluoromethyl)picolinamide | 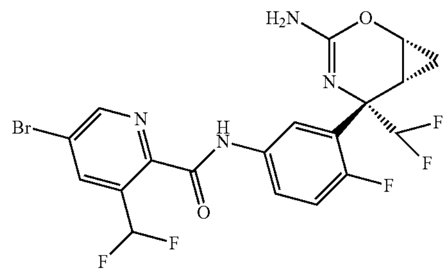 [SMILES: NC1=N[C@@](c2cc(NC(=O)c3ncc(Br)cc3C(F)F)ccc2F)(C(F)F)[C@H]2C[C@H]2O1] | MS m/z = 505 [M + H]$^+$.<br>$^1$H NMR (400 MHz, DMSO-d$_6$) δ ppm 0.81-1.02 (m, 1 H) 1.08-1.22 (m, 2 H) 1.14 (br. s., 1 H) 1.66-1.79 (m, 1 H) 3.94-4.10 (m, 1 H) 5.82-5.89 (m, 2 H) 5.86 (br. s., 2 H) 6.00-6.41 (m, 1 H) 7.16-7.29 (m, 1 H) 7.53-7.98 (m, 3 H) 8.51 (s, 1 H) 9.02 (s, 1 H) 10.85 (s, 1 H) |
| 291 | B | N-(3-((1R,5S,6R)-3-amino-5-(difluoromethyl)-2-oxa-4-azabicyclo[4.1.0]hept-3-en-5-yl)-4-fluorophenyl)-5-phenylpicolinamide | 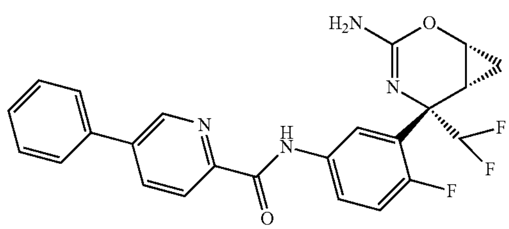 [SMILES: NC1=N[C@@](c2cc(NC(=O)c3ccc(-c4ccccc4)cn3)ccc2F)(C(F)F)[C@H]2C[C@H]2O1] | MS m/z = 453.2 [M + H]$^+$.<br>$^1$H NMR (300 MHz, DMSO-d$_6$) δ ppm 0.77-1.05 (m, 1 H) 1.10-1.34 (m, 1 H) 1.60-1.86 (m, 1 H) 3.92-4.12 (m, 1 H) 5.87 (s, 2 H) 5.98-6.44 (m, 1 H) 7.10-7.35 (m, 1 H) 7.41-7.72 (m, 3 H) 7.84 (d, J = 7.60 Hz, 2 H) 7.89-7.97 (m, 1 H) 8.02-8.12 (m, 1 H) 8.24 (s, 1 H) 8.34 (s, 1 H) 8.89-9.15 (m, 1 H) 10.56-10.83 (m, 1 H) |
| 292 | B | N-(3-((1R,5S,6R)-3-amino-5-(difluoromethyl)-2-oxa-4-azabicyclo[4.1.0]hept-3-en-5-yl)-4-fluorophenyl)picolinamide | 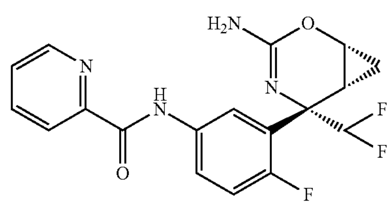 [SMILES: NC1=N[C@@](c2cc(NC(=O)c3ccccn3)ccc2F)(C(F)F)[C@H]2C[C@H]2O1] | MS m/z = 377.1 [M + H]$^+$.<br>$^1$H NMR (300 MHz, DMSO-d$_6$) δ ppm 0.86-0.99 (m, 1 H) 1.09-1.23 (m, 1 H) 1.65-1.81 (m, 1 H) 3.17 (d, J = 5.12 Hz, 2 H) 3.97-4.13 (m, 1H + 1 H) 5.86 (s, 2 H) 5.98-6.43 (m, 1 H) 7.14-7.31 (m, 1H) 7.61-7.75 (m, 1 H) 7.84-7.95 (m, 1 H) 8.00-8.20 (m, 3 H) 8.62-8.84 (m, 1 H) 10.57-10.77 (m, 1 H) (traces of methanol) |
| 293 | B | N-(3-((1R,5S,6R)-3-amino-5-(difluoromethyl)-2-oxa-4-azabicyclo[4.1.0]hept-fluorophenyl)-3-methylpicolinamide | 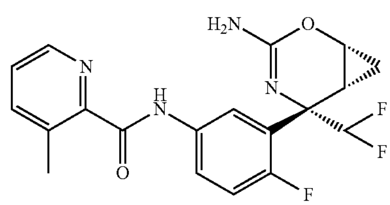 [SMILES: Cc1cccnc1C(=O)Nc1ccc(F)c([C@@]2(C(F)F)N=C(N)O[C@@H]3C[C@@H]32)c1] | MS m/z = 391.1 [M + H]$^+$.<br>$^1$H NMR (300 MHz, DMSO-d$_6$) δ ppm 0.76-1.01 (m, H) 1.06-1.25 (m, 1 H) 1.59-1.83 (m, 1 H) 2.56 (s, 3 H) 3.86-4.10 (m, 1 H) 5.85 (s, 2 H) 5.96-6.45 (m, 1 H) 7.08-7.30 (m, 1 H) 7.46-7.58 (m, 1 H) 7.88 (br. s., 3 H) 8.41-8.63 (m, 1 H) 10.57 (s, 1 H) |
| 294 | A | N-(3-((1R,5S,6R)-3-amino-5-(difluoromethyl)-2-oxa-4-azabicyclo[4.1.0]hept-3-en-5-yl)-4-methylphenyl)-5-methoxypyrazine-2-carboxamide | 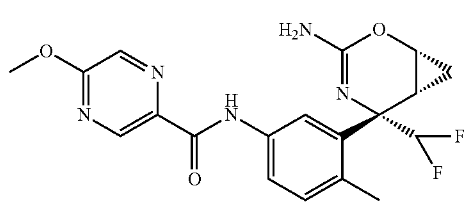 [SMILES: COc1cnc(C(=O)Nc2ccc(C)c([C@@]3(C(F)F)N=C(N)O[C@@H]4C[C@@H]43)c2)cn1] | MS m/z = 404.0 [M + H]$^+$<br>$^1$H NMR (400 MHz, CHLOROFORM-d) δ ppm 9.51 (br. s., 1 H) 9.01 (s, 1 H) 8.15 (s, 1 H) 8.08 (s, 1 H) 7.64 (s, 1 H) 7.19 (d, J = 8.41 Hz, 1 H) 6.00-6.41 (m, 1 H) 4.04-4.13 (m, 4 H) 2.58 (s, 3 H) 1.65-1.78 (m, 1 H) 1.45-1.55 (m, 1 H) 0.99-1.06 (m, 1 H) |

| Example # | Method | Compound Name | Structure | Analytical Data |
|---|---|---|---|---|
| 295 | A | N-(3-((1R,5S,6R)-3-amino-5-(difluoromethyl)-2-oxa-4-azabicyclo[4.1.0]hept-3-en-5-yl)-4-methylphenyl)-5-chloropicolinamide | 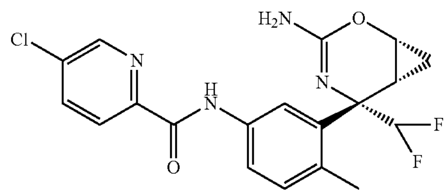 [SMILES: Cc1ccc(NC(=O)c2ccc(Cl)cn2)cc1[C@@]1(C(F)F)N=C(N)O[C@@H]2C[C@@H]21] | MS m/z = 407.0 [M + H]+<br>1H NMR (400 MHz, CHLOROFORM-d) δ ppm 9.81 (br. s., 1 H) 8.55 (s, 1 H) 8.24 (d, J = 8.22 Hz, 1 H) 8.08 (s, 1 H) 7.83-7.92 (m, 1 H) 7.68 (d, J = 7.82 Hz, 1 H) 7.20 (d, J = 8.22 Hz, 1 H) 6.20 (t, J = 56.24 Hz, 1 H) 4.07 (br. s., 1 H) 2.59 (s, 3 H) 1.73-1.98 (m, 1 H) 1.48 (t, J = 5.87 Hz, 1 H) 0.83-1.08 (m, 1 H) |
| 296 | A | N-(3-((1S,5R,6S)-3-amino-5-(difluoromethyl)-2-oxa-4-azabicyclo[4.1.0]hept-3-en-5-yl)-4-fluorophenyl)-5-bromopicolinamide | 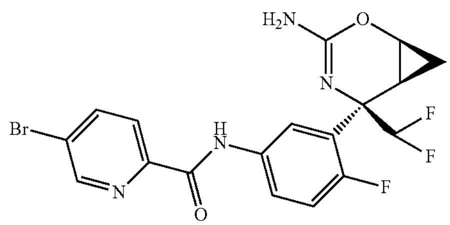 [SMILES: NC1=N[C@](c2cc(NC(=O)c3ccc(Br)cn3)ccc2F)(C(F)F)[C@@H]2C[C@@H]2O1] | MS m/z = 455.0 [M + H]+<br>1H NMR (400 MHz, CHLOROFORM-d) δ ppm 0.95 (dd, J = 16.04, 6.85 Hz, 1 H) 1.42 (br. s., 1 H) 1.86 (dd, J = 15.85, 8.61 Hz, 1 H) 3.89-3.95 (m, 1 H) 4.63 (br. s., 2 H) 6.23 (t, J = 55.90 Hz, 1 H) 7.06 (t, J = 10.20 Hz, 1 H) 7.63 (d, J = 6.43 Hz, 1 H) 7.93-8.00 (m, 1 H) 8.01 (d, J = 8.57 Hz, 1 H) 8.12 (d, J = 8.41 Hz, 1 H) 8.59 (s, 1 H) 9.74 (br. s., 1 H) |
| 297 | C | N-(3-((1R,5S,6R)-3-amino-5-(fluoromethyl)-2-oxa-4-azabicyclo[4.1.0]hept-3-en-5-yl)-4-chlorophenyl)-5-chloro-3-methoxypicolinamide | 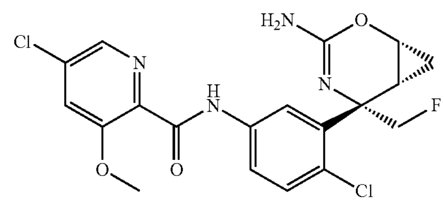 [SMILES: COc1cc(Cl)cnc1C(=O)Nc1ccc(Cl)c([C@@]2(CF)N=C(N)O[C@@H]3C[C@@H]32)c1] | MS m/z = 439.0 [M + H]+<br>1H NMR (300 MHz, DMSO) Shift = 10.56 (s, 1H), 8.27 (s, 1H), 7.94 (s, 1H), 7.85 (s, 1H), 7.81 (d, J = 8.8 Hz, 1H), 7.40 (d, J = 8.5 Hz, 1H), 5.59 (s, 2H), 4.80 (s, 1H), 4.64 (s, 1H), 3.99-3.87 (m, 4H), 1.72-1.62 (m, 1H), 0.93 (d, J = 4.8 Hz, 1H), 0.90-0.80 (m, 1H) |
| 298 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-cyanopyrimidine-2-carboxamide | 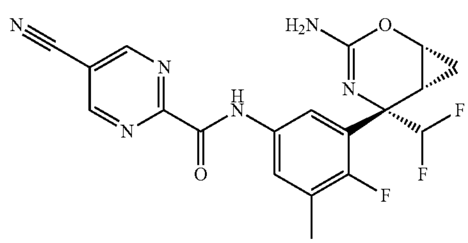 [SMILES: Cc1cc(NC(=O)c2ncc(C#N)cn2)cc([C@@]2(C(F)F)N=C(N)O[C@@H]3C[C@@H]32)c1F] | MS m/z = 416.9 [M + H]+<br>1H NMR (300 MHz, DMSO) Shift = 10.86 (s, 1H), 9.52 (s, 2H), 7.84-7.69 (m, 2H), 6.44-6.01 (m, 2H), 5.84 (s, 2H), 4.00 (br. s., 1H), 2.27 (s, 3H), 1.77-1.65 (m, 1H), 1.13 (br. s., 1H), 0.90 (d, J = 7.9 Hz, 1H) |
| 299 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-methoxypyrazine-2-carboxamide | 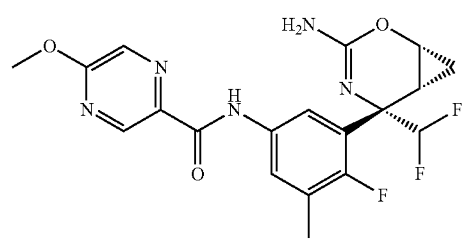 [SMILES: COc1cnc(C(=O)Nc2cc(C)c(F)c([C@@]3(C(F)F)N=C(N)O[C@@H]4C[C@@H]43)c2)cn1] | MS m/z = 422.1 [M + H]+<br>1H NMR (300 MHz, DMSO) Shift = 10.39 (s, 1H), 8.88 (d, J = 1.3 Hz, 1H), 8.41 (d, J = 1.3 Hz, 1H), 7.96-7.55 (m, 2H), 6.49-5.98 (m, 2H), 5.82 (s, 2H), 4.02 (s, 3H), 2.26 (d, J = 2.2 Hz, 3H), 1.83-1.63 (m, 1H), 1.13 (br. s., 1H), 1.01-0.80 (m, 1H) |
| 300 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-methoxy-3-methylpyrazine-2-carboxamide | 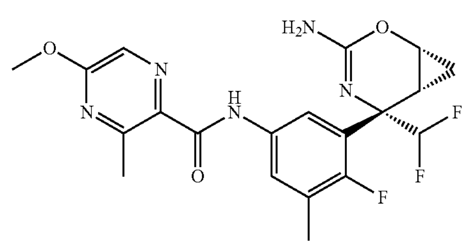 | MS m/z = 436.1 [M + H]+<br>1H NMR (300 MHz, DMSO) Shift = 10.35 (s, 1H), 8.23 (s, 1H), 7.84-7.76 (m, 1H), 7.71-7.62 (m, 1H), 6.43-6.02 (m, 2H), 5.83 (s, 2H), 4.07-3.90 (m, 4H), 2.74 (s, 3H), 2.26 (s, 3H), 1.77-1.65 (m, 1H), 1.18-1.07 (m, J = 3.7 Hz, 1H), 0.98-0.84 (m, 1H) |

| Example # | Method | Compound Name | Structure | Analytical Data |
|---|---|---|---|---|
| 301 | A | N-(3-((1R,5S,6R)-3-amino-5-(fluoromethyl)-2-oxa-4-azabicyclo[4.1.0]hept-3-en-5-yl)-4-chlorophenyl)-5-methoxy-3-methylpyrazine-2-carboxamide | 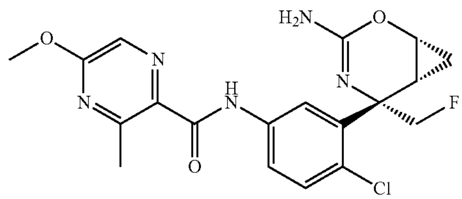 [SMILES: COc1cnc(C(=O)Nc2ccc(Cl)c([C@@]3(CF)N=C(N)O[C@@H]4C[C@@H]43)c2)c(C)n1] | MS m/z = 420 [M + H]+<br>1H NMR (300 MHz, DMSO) Shift = 10.88 (br. s., 1H), 8.22 (s, 1H), 8.08-7.95 (m, 2H), 7.49 (d, J = 8.8 Hz, 1H), 4.98 (d, J = 13.2 Hz, 1H), 4.82 (d, J = 12.9 Hz, 1H), 4.25 (br. s., 1H), 3.99 (s, 3H), 2.74 (s, 3H), 1.91 (br. s., 1H), 1.10-0.88 (m, 2H) |
| 302 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-chloro-3-fluoropicolinamide | 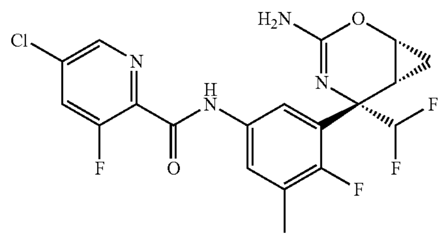 [SMILES: Cc1cc(NC(=O)c2ncc(Cl)cc2F)cc([C@@]2(C(F)F)N=C(N)O[C@@H]3C[C@@H]32)c1F] | MS m/z = 443 [M + H]+<br>1H NMR (300 MHz, DMSO) Shift = 10.60 (s, 1H), 8.73-8.60 (m, 1H), 8.32 (dd, J = 1.9, 10.2 Hz, 1H), 7.79-7.61 (m, 2H), 6.47-5.98 (m, 1H), 5.85 (s, 2H), 4.08-3.91 (m, 1H), 2.26 (d, J = 2.2 Hz, 3H), 1.75-1.65 (m, 1H), 1.16-1.08 (m, 1H), 0.96-0.85 (m, 1H) |
| 303 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-chloro-3-methylpicolinamide | 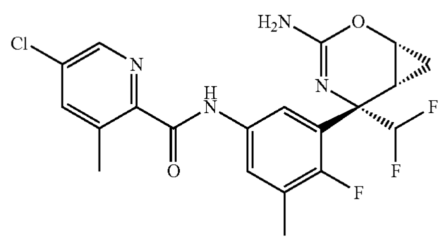 [SMILES: Cc1cc(Cl)cnc1C(=O)Nc1cc(C)c(F)c([C@@]2(C(F)F)N=C(N)O[C@@H]3C[C@@H]32)c1] | MS m/z = 439.1 [M + H]+<br>1H NMR (300 MHz, DMSO) Shift = 10.52 (s, 1H), 8.57 (d, J = 2.0 Hz, 1H), 8.02 (d, J = 1.8 Hz, 1H), 7.80 (d, J = 3.8 Hz, 1H), 7.65 (dd, J = 2.8, 6.6 Hz, 1H), 6.52-5.75 (m, 3H), 4.04 (br. s., 1H), 3.96-3.90 (m, 1H), 2.55 (s, 3H), 2.26 (d, J = 2.0 Hz, 3H), 1.79-1.68 (m, 1H), 1.21-1.11 (m, 1H), 0.99-0.90 (m, 1H) |
| 304 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-methoxypicolinamide | 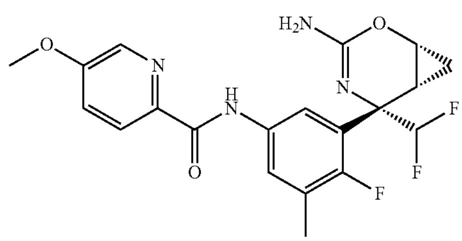 | MS m/z = 421.1 [M + H]+<br>1H NMR (300 MHz, DMSO) Shift = 10.34 (s, 1H), 8.39 (d, J = 2.8 Hz, 1H), 8.12 (d, J = 8.8 Hz, 1H), 7.79 (t, J = 5.8 Hz, 2H), 7.62 (dd, J = 2.9, 8.8 Hz, 1H), 6.45-6.00 (m, 1H), 5.83 (s, 2H), 4.05-3.97 (m, 1H), 3.94 (s, 3H), 2.26 (d, J = 2.2 Hz, 3H), 1.78-1.66 (m, 1H), 1.14 (br. s., 1H), 0.97-0.86 (m, 1H) |
| 305 | A | N-(3-((1R,5S,6R)-3-amino-5-(difluoromethyl)-2-oxa-4-azabicyclo[4.1.0]hept-3-en-5-yl)-4-fluoro-5-methylphenyl)-5-methoxy-3-methylpicolinamide | 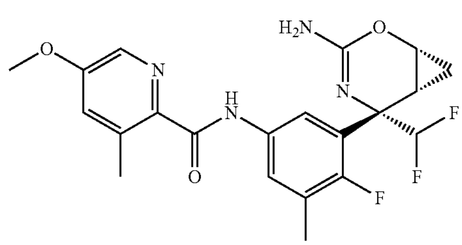 [SMILES: COc1cnc(C(=O)Nc2cc(C)c(F)c([C@@]3(C(F)F)N=C(N)O[C@@H]4C[C@@H]43)c2)c(C)c1] | MS m/z = 435 [M + H]+<br>1H NMR (300 MHz, DMSO) Shift = 10.31 (s, 1H), 8.22 (d, J = 2.6 Hz, 1H), 7.92-7.74 (m, 1H), 7.68-7.57 (m, 1H), 7.41 (d, J = 2.6 Hz, 1H), 6.41 - 6.01 (m, 1H), 5.84 (s, 2H), 4.04-3.95 (m, 1H), 3.91 (s, 3H), 2.62 (s, 3H), 2.26 (d, J = 2.0 Hz, 3H), 1.77-1.66 (m, 1H), 1.17-1.09 (m, 1H), 0.96-0.84 (m, 1H) |
| 306 | A | N-(3-((1R,5S,6R)-3-amino-5-(difluoromethyl)-2-oxa-4-azabicyclo[4.1.0]hept-3-en-5-yl)-4-fluorophenyl)-3-fluoro-5-methoxypicolinamide | 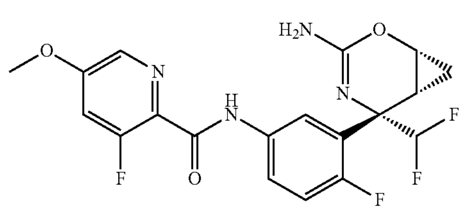 | MS m/z = 425.1 [M + H]+ δ:<br>1H NMR (400 MHz, MeOH-d4) δ: 8.26 (d, J = 1.6 Hz, 1H), 7.82-7.89 (m, 2H), 7.41 (dd, J = 12.7, 2.3 Hz, 1H), 7.18 (dd, J = 11.8, 9.3 Hz, 1H), 6.12-6.46 (m, 1H), 4.03-4.11 (m, 1H), 4.00 (s, 3H), 1.84-1.97 (m, 1H), 1.35 (t, J = 5.8 Hz, 1H), 1.00 (dt, J = 9.5, 6.8 Hz, 1H) |

| Example # | Method | Compound Name | Analytical Data |
|---|---|---|---|
| 307 | A | N-(3-((1R,5S,6R)-3-amino-5-(difluoromethyl)-2-oxa-4-azabicyclo[4.1.0]hept-3-en-5-yl)-4-fluorophenyl)-5-fluoro-3-methoxypicolinamide | MS m/z = 425.1 [M + H]+<br>1H NMR (400 MHz, MeOH-d4) δ: 8.18 (d, J = 2.2 Hz, 1H), 7.85-7.91 (m, 1H), 7.80 (dd, J = 6.9, 2.6 Hz, 1H), 7.76-7.82 (m, 1H), 7.59 (dd, J = 10.7, 2.2 Hz, 1H), 7.18 (dd, J = 11.7, 8.8 Hz, 1H), 6.12-6.45 (m, 1H), 4.03-4.10 (m, 1H), 4.00 (s, 3H), 1.87-1.93 (m, 1H), 1.35 (t, J = 6.7 Hz, 1H), 1.00 (dt, J = 9.4, 6.7 Hz, 1H) |
| 308 | A | N-(3-((1R,5S,6R)-3-amino-5-(difluoromethyl)-2-oxa-4-azabicyclo[4.1.0]hept-3-en-5-yl)-4-fluorophenyl)-5-chloro-3-(fluoromethyl)picolinamide | MS m/z = 442.9 [M + H]+<br>1H NMR (300 MHz, DMSO-d6) δ ppm 0.85-0.97 (m, 1 H) 1.10-1.27 (m, 3 H, contains EtOAc) 1.66-1.81 (m, 1 H) 3.96-4.09 (m, 2 H, contains EtOAc) 5.80-6.41 (m, 5 H) 7.15-7.27 (m, 1 H) 7.79-7.87 (m, 1 H) 7.90-7.97 (m, 1 H) 8.16 (d, J = 2.19 Hz, 1 H) 8.76 (d, J = 2.19 Hz, 1 H) 10.73 (s, 1 H) |
| 309 | A | N-(3-(((1R,S),(5S,R),(6R.S))-3-amino-5-(difluoromethyl)-2-oxa-4-azabicyclo[4.1.0]hept-3-en-5-yl)-5-fluoro-4-methylphenyl)-5-cyano-3-methylpicolinamide | MS m/z = 430.0 [M + H]+<br>1H NMR (400 MHz, CHLOROFORM-d) δ 10.03 (s, 1H), 8.69 (s, 1H), 7.94 (s, 1H), 7.79 (d, J = 11.54 Hz, 1H), 7.63 (s, 1H), 5.91-6.42 (m, 1H), 4.45 (br. s., 2H), 4.00-4.10 (m, 1H), 2.87 (s, 3H), 2.48 (d, J = 2.74 Hz, 3H), 1.75-1.93 (m, 1H), 1.48 (t, J = 5.97 Hz, 1H), 0.97-1.13 (m, 1H) |
| 310 | A | N-(3-((1R,5S,6R)-3-amino-5-(difluoromethyl)-2-oxa-4-azabicyclo[4.1.0]hept-3-en-5-yl)-5-fluoro-4-methylphenyl)-5-cyano-3-methylpicolinamide | MS m/z = 430.0 [M + H]+<br>1H NMR (400 MHz, CHLOROFORM-d) δ 10.04 (s, 1H), 8.69 (d, J = 1.56 Hz, 1H), 7.94 (s, 1H), 7.80 (dd, J = 1.86, 11.44 Hz, 1H), 7.63 (s, 1H), 7.58-7.68 (m, 1H), 5.92-6.43 (m, 1H), 4.65 (br. s., 2H), 4.08 (t, J = 5.67 Hz, 1H), 2.86 (s, 3H), 2.78-2.96 (m, 3H), 2.78-2.96 (m, 3H), 2.48 (d, J = 3.13 Hz, 3H), 1.85 (td, J = 7.04, 9.78 Hz, 1H), 1.43-1.57 (m, 1H), 0.99-1.12 (m, 1H). |
| 311 | A | N-(3-((1S,5R,6S)-3-amino-5-(difluoromethyl)-2-oxa-4-azabicyclo[4.1.0]hept-3-en-5-yl)-5-fluoro-4-methylphenyl)-5-cyano-3-methylpicolinamide | MS m/z = 430.0 [M + H]+<br>1H NMR (400 MHz, CHLOROFORM-d) δ 10.02 (s, 1H), 8.67 (d, J = 1.56 Hz, 1H), 7.94 (s, 1H), 7.79 (dd, J = 1.96, 11.35 Hz, 1H), 7.61 (s, 1H), 5.99-6.47 (m, 1H), 4.62 (br. s., 2H), 4.07 (t, J = 5.48 Hz, 1H), 2.86 (s, 3H), 2.48 (d, J = 3.13 Hz, 3H), 1.84 (td, J = 7.04, 9.78 Hz, 1H), 1.41-1.58 (m, 1H), 0.95-1.14 (m, 1H). |
| 312 | B | N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)picolinamide | MS m/z = 442.9 [M + H]+<br>1H NMR (300 MHz, CHLOROFORM-d) δ ppm 0.98-1.14 (m, 1 H) 1.49 (br. s., 1 H) 1.96 (q, J = 8.14 Hz, 1 H) 4.05 (br. s., 1 H) 6.03-6.92 (m, 2 H) 7.06-7.21 (m, 1 H) 7.66 (d, J = 8.18 Hz, 1 H) 7.72 (d, J = 6.72 Hz, 1 H) 7.93-8.06 (m, 1 H) 8.30 (d, J = 8.62 Hz, 1 H) 8.45 (s, 1 H) 9.84 (br. s., 1 H) |

TABLE 1-continued

| Example # | Method | Compound Name | Structure | Analytical Data |
|---|---|---|---|---|
| 313 | B | N-(3-((1R,5S,6R)-3-amino-5-(difluoromethyl)-2-oxa-4-azabicyclo[4.1.0]hept-3-en-5-yl)-4-fluorophenyl)-5-ethynylpicolinamide | 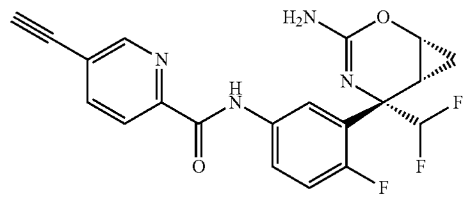 [SMILES: C#Cc1ccc(C(=O)Nc2ccc(F)c([C@@]3(C(F)F)N=C(N)O[C@@H]4C[C@@H]43)c2)nc1] | MS m/z = 401 [M + H]+<br>1H NMR (300 MHz, CHLOROFORM-d) δ ppm 0.92-1.10 (m, 1 H) 1.45 (t, J = 6.65 Hz, 1 H) 1.91 (dt, J = 9.61, 7.11 Hz, 1 H) 3.90-4.08 (m, 1 H) 4.84 (br. s., 1 H) 6.01-6.48 (m, 1 H) 7.11 (dd, J = 11.55, 8.92 Hz, 1 H) 7.69 (dd, J = 6.72, 2.78 Hz, 1 H) 7.91-8.06 (m, 2 H) 8.24 (dd, J = 8.04, 0.73 Hz, 1 H) 8.67 (d, J = 1.32 Hz, 1 H) 9.90 (s, 1 H) |
| 314 | B | N-(3-((1R,5S,6R)-3-amino-5-(difluoromethyl)-2-oxa-4-azabicyclo[4.1.0]hept-3-en-5-yl)-4-fluorophenyl)-5-(prop-1-yn-1-yl)picolinamide | 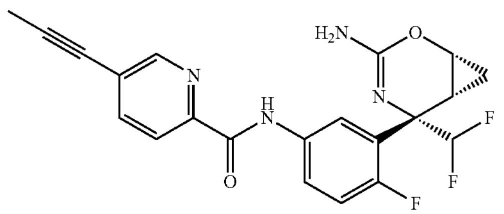 [SMILES: CC#Cc1ccc(C(=O)Nc2ccc(F)c([C@@]3(C(F)F)N=C(N)O[C@@H]4C[C@@H]43)c2)nc1] | MS m/z = 415 [M + H]+<br>1H NMR (400 MHz, CHLOROFORM-d) δ ppm 0.92-1.07 (m, 1 H) 1.44 (t, J = 6.65 Hz, 1 H) 1.83-1.96 (m, 1 H) 2.13 (s, 3 H) 3.93-4.03 (m, 1 H) 4.67 (br. s., 2 H) 6.05-6.46 (m, 1 H) 7.12 (dd, J = 11.54, 8.80 Hz, 1 H) 7.69 (dd, J = 6.75, 2.64 Hz, 1 H) 7.85 (dd, J = 8.12, 1.86 Hz, 1 H) 8.01 (dt, J = 8.80, 3.42 Hz, 1 H) 8.19 (d, J = 8.02 Hz, 1 H) 8.57 (d, J = 1.37 Hz, 1 H) 9.91 (s, 1 H) |
| 315 | B | N-(3-((1R,5S,6R)-3-amino-5-(fluoromethyl)-2-oxa-4-azabicyclo[4.1.0]hept-3-en-5-yl)-4-chloro-5-fluorophenyl)-3-methyl-5-(2,2,2-trifluoroethoxy)pyrazine-2-carboxamide | 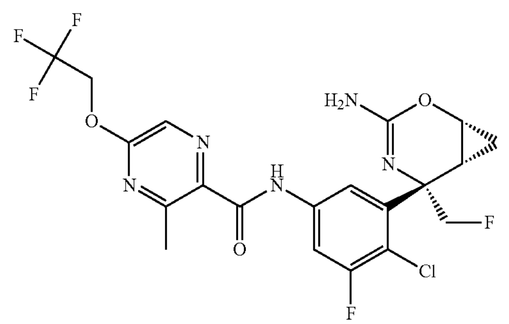 [SMILES: Cc1nc(OCC(F)(F)F)cnc1C(=O)Nc1cc(F)c(Cl)c([C@@]2(CF)N=C(N)O[C@@H]3C[C@@H]32)c1] | MS m/z = 505.9 [M + H]+<br>1H NMR (400 MHz, DMSO-d6) δ ppm 10.78 (s, 1 H), 8.44 (s, 1 H), 8.00 (dd, J = 11.15, 2.35 Hz, 1 H), 7.92 (s, 1 H), 5.62 (s, 2 H), 5.14 (q, J = 9.00 Hz, 2 H), 4.51-4.89 (m, 2 H), 4.00 (m, J = 5.67, 5.67 Hz, 1 H), 2.77 (s, 3 H), 1.61 (dt, J = 9.83, 7.02 Hz, 1 H), 0.95 (td, J = 6.55, 2.74 Hz, 1 H), 0.84-0.92 (m, 1 H) |
| 316 | B | N-(3-((1S,5R,6S)-3-amino-5-(fluoromethyl)-2-oxa-4-azabicyclo[4.1.0]hept-3-en-5-yl)-4-chloro-5-fluorophenyl)-3-methyl-5-(2,2,2-trifluoroethoxy)pyrazine-2-carboxamide | 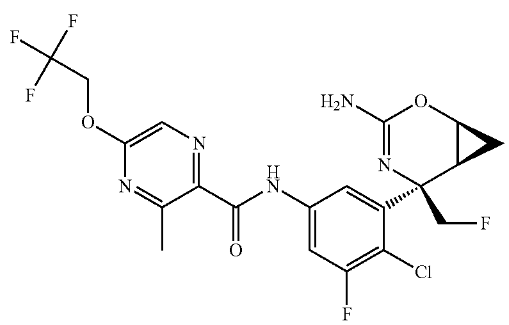 [SMILES: Cc1nc(OCC(F)(F)F)cnc1C(=O)Nc1cc(F)c(Cl)c([C@]2(CF)N=C(N)O[C@H]3C[C@H]32)c1] | MS m/z = 505.9 [M + H]+<br>1H NMR (400 MHz, DMSO-d6) δ ppm 10.78 (s, 1 H), 8.44 (s, 1 H), 8.00 (dd, J = 11.15, 2.35 Hz, 1 H), 7.92 (s, 1 H), 5.62 (s, 2 H), 5.14 (q, J = 9.00 Hz, 2 H), 4.51-4.89 (m, 2 H), 4.00 (m, J = 5.67, 5.67 Hz, 1 H), 2.77 (s, 3 H), 1.61 (dt, J = 9.83, 7.02 Hz, 1 H), 0.95 (td, J = 6.55, 2.74 Hz, 1 H), 0.84-0.92 (m, 1 H) |
| 317 | B | N-(3-((1R,5S,6R)-3-amino-5-(fluoromethyl)-2-oxa-4-azabicyclo[4.1.0]hept-3-en-5-yl)-4-chloro-5-fluorophenyl)-5-(prop-2-yn-1-yloxy)pyrazine-2-carboxamide | 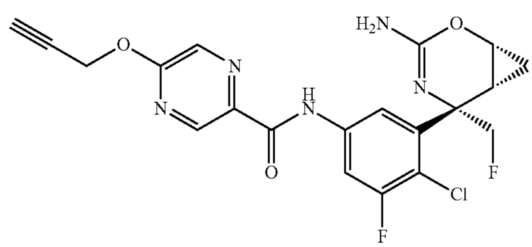 [SMILES: C#CCOc1cnc(C(=O)Nc2cc(F)c(Cl)c([C@@]3(CF)N=C(N)O[C@@H]4C[C@@H]43)c2)cn1] | MS m/z = 448 [M + H]+<br>1H NMR (400 MHz, DMSO-d6) δ ppm 0.82-1.01 (m, 2 H), 1.57-1.66 (m, 1 H), 3.64 (t, J = 2.35 Hz, 1 H), 4.01 (t, J = 5.67 Hz, 1 H), 4.53-4.88 (m, 2 H), 5.14 (d, J = 2.35 Hz, 2 H), 5.62 (br s, 2 H), 8.00 (dd, J = 11.15, 2.35 Hz, 1 H), 8.08 (s, 1 H), 8.50 (d, J = 1.17 Hz, 1 H), 8.92 (d, J = 1.17 Hz, 1 H), 10.80 (s, 1 H) |

TABLE 1-continued

| Example # | Method | Compound Name | Structure | Analytical Data |
|---|---|---|---|---|
| 318 | B | N-(34(1 S,5R,6S)-3-amino-5-(fluoromethyl)-2-oxa-4-azabicyclo[4.1.0]hept-3-en-5-yl)-4-chloro-5-fluorophenyl)-5-(prop-2-yn-1-yloxy)pyrazine-2-carboxamide | 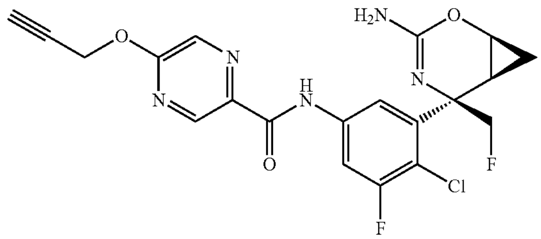 [SMILES: C#CCOc1cnc(C(=O)Nc2cc(F)c(Cl)c([C@]3(CF)N=C(N)O[C@H]4C[C@H]43)c2)cn1] | MS m/z = 448 [M + H]+ 1H NMR (400 MHz, DMSO-d6) δ ppm 0.82-1.01 (m, 2 H), 1.57-1.66 (m, 1 H), 3.64 (t, J = 2.35 Hz, 1 H), 4.01 (t, J = 5.67 Hz, 1 H), 4.53-4.88 (m, 2 H), 5.14 (d, J = 2.35 Hz, 2 H), 5.62 (br s, 2 H), 8.00 (dd, J = 11.15, 2.35 Hz, 1 H), 8.08 (s, 1 H), 8.50 (d, J = 1.17 Hz, 1 H), 8.92 (d, J = 1.17 Hz, 1 H), 10.80 (s, 1 H) |
| 441 | A | N-(3-((1R,5S,6R)-3-amino-5-(fluoromethyl)-2-oxa-4-azabicyclo[4.1.0]hept-3-en-5-yl)-4-chlorophenyl)-5-chloro-3-(fluoromethyl)picolinamide | 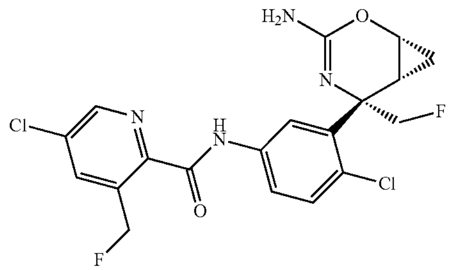 [SMILES: NC1=N[C@](CF)(c2cc(NC(=O)c3ncc(Cl)cc3CF)ccc2Cl)[C@H]2C[C@H]2O1] | MS m/z = 441 [M]+ 1H NMR (400 MHz, DMSO-d6) δ ppm 0.81-0.90 (m, 1 H) 0.91-0.99 (m, 1 H) 1.62-1.71 (m, 1 H) 3.29-3.32 (m, 2 H) 3.93-3.99 (m, 1 H) 4.59-4.86 (m, 2 H) 5.54-5.65 (m, 2 H) 5.84-5.93 (m, 1 H) 5.97-6.04 (m, 1 H) 7.36-7.50 (m, 1 H) 7.79-7.87 (m, 1H) 8.05-8.11 (m, 1 H) 8.13-8.19 (m, 1 H) 8.74-8.82 (m, 1 H) 10.70-10.82 (m, 1 H) |
| 442 | A | N-(3-((1R,5S,6R)-3-amino-5-(fluoromethyl)-2-oxa-4-azabicyclo[4.1.0]hept-3-en-5-yl)-4-chlorophenyl)-5-chloro-3-fluoropicolinamide | 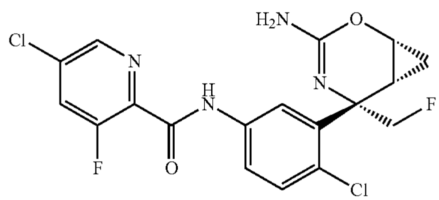 | MS m/z = 427 [M]+ 1H NMR (300 MHz, DMSO) Shift = 10.74 (s, 1H), 10.82-10.63 (m, 1H), 8.74-8.57 (m, 1H), 8.33 (dd, J = 1.9, 10.4 Hz, 1H), 8.04 (d, J = 2.5 Hz, 1H), 7.82 (dd, J = 2.6, 8.6 Hz, 1H), 7.43 (d, J = 8.5 Hz, 1H), 5.83-5.43 (m, 2H), 4.81 (s, 1H), 4.65 (s, 1H), 3.97 (br. s., 1H), 1.67 (td, J = 6.9, 9.5 Hz, 1H), 0.95 (d, J = 4.2 Hz, 1H), 0.86 (td, J = 6.3, 9.5 Hz, 1H) |
| 443 | A | N-(3-((1R,5S,6R)-3-amino-5-(fluoromethyl)-2-oxa-4-azabicyclo[4.1.0]hept-3-en-5-yl)-4-chlorophenyl)-5-chloro-3-methylpicolinamide | 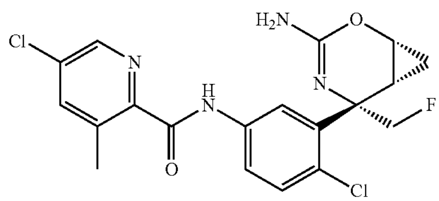 | MS m/z = 423 [M]+ 1H NMR (300 MHz, DMSO) Shift = 10.65 (s, 1H), 8.59 (d, J = 2.2 Hz, 1H), 8.05-8.03 (m, 1H), 8.02 (d, J = 2.6 Hz, 1H), 7.85 (dd, J = 2.6, 8.7 Hz, 1H), 7.41 (d, J = 8.6 Hz, 1H), 5.62 (s, 2H), 4.88-4.74 (m, 1H), 4.71-4.60 (m, 1H), 3.95 (br. s., 1H), 2.56 (s, 3H), 1.73-1.61 (m, 1H), 0.96-0.90 (m, 1H), 0.85 (td, J = 6.2, 9.4 Hz, 1H) |
| 444 | A | N-(3-((1R,5S,6R)-3-amino-5-(difluoromethyl)-2-oxa-4-azabicyclo[4.1.0]hept-3-en-5-yl)-4-fluoro-5-methylphenyl)-4-chloro-2-(fluoromethyl)benzamide | 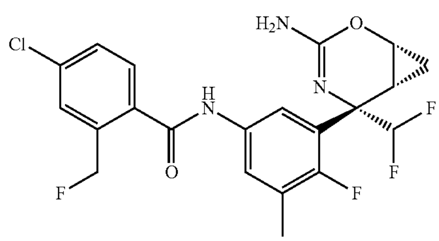 [SMILES: Cc1cc(NC(=O)c2ccc(Cl)cc2CF)cc([C@@]2(C(F)F)N=C(N)O[C@@H]3C[C@@H]32)c1F] | MS m/z = 457 [M + H]+ 1H NMR (300 MHz, DMSO) Shift = 10.65 (s, 1H), 8.77 (d, J = 2.3 Hz, 1H), 8.16 (d, J = 2.3 Hz, 1H), 7.85-7.75 (m, 1H), 7.70 (dd, J = 2.6, 6.4 Hz, 1H), 6.42-6.03 (m, 1H), 6.02 (s, 1H), 5.89-5.84 (m, 3H), 4.06-3.96 (m, 1H), 2.26 (d, J = 2.0 Hz, 3H), 1.70 (dd, J = 7.2, 16.6 Hz, 1H), 1.14 (d, J = 5.8 Hz, 1H), 0.97-0.85 (m, 1H) |
| 445 | A | N-(3-((1R,5S,6R)-3-amino-5-(fluoromethyl)-2-oxa-4-azabicyclo[4.1.0]hept-3-en-5-yl)-4-chlorophenyl)-5-fluoropicolinamide | 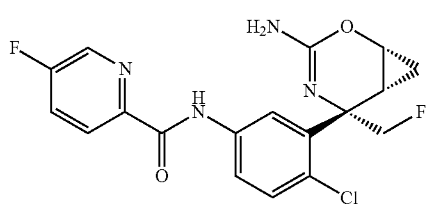 [SMILES: NC1=N[C@](CF)(c2cc(NC(=O)c3ccc(F)cn3)ccc2Cl)[C@H]2C[C@H]2O1] | MS m/z = 393 [M + H]+ 1H NMR (300 MHz, DMSO) Shift = 10.94 (br. s., 1H), 8.73 (d, J = 2.6 Hz, 1H), 8.36-8.14 (m, 2H), 8.09-7.91 (m, 2H), 7.49 (d, J = 8.8 Hz, 1H), 5.10-4.72 (m, 2H), 4.22 (br. s., 1H), 1.98-1.78 (m, 1H), 1.22 (d, J = 13.3 Hz, 1H), 1.01 (d, J = 8.0 Hz, 1H) |

Examples 319 and 320

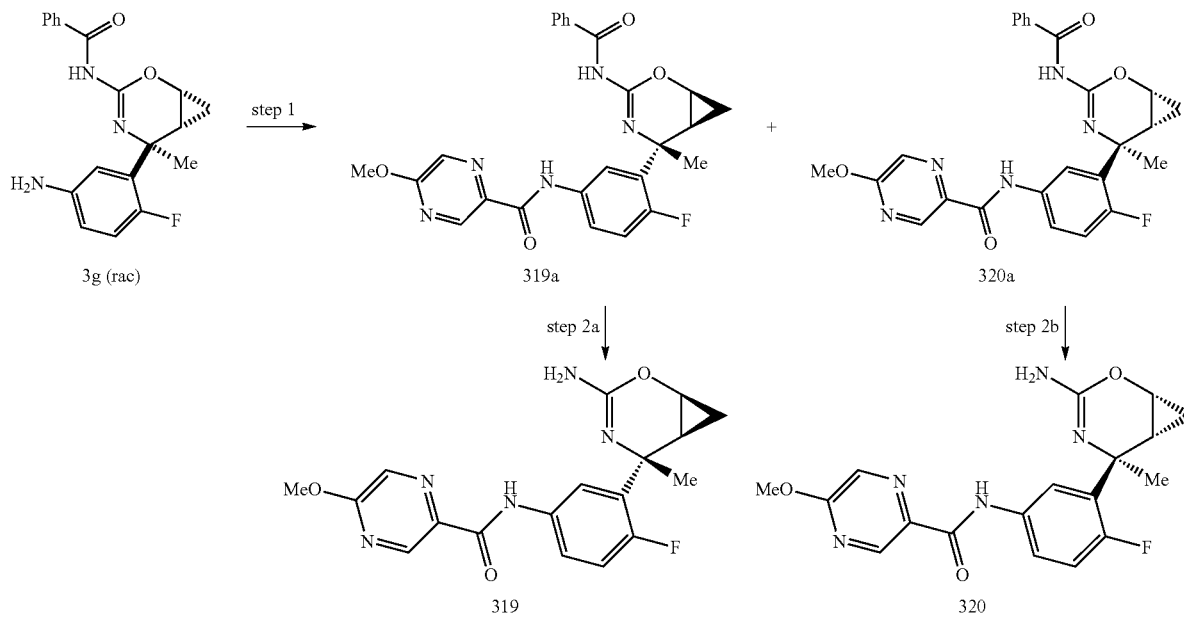

Step 1: N-(3-((1S,5R,6S)-3-benzamido-5-methyl-2-oxa-4-azabicyclo[4.1.0]hept-3-en-5-yl)-4-fluorophenyl)-5-methoxypyrazine-2-carboxamide (319a) and N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide (320a)

N-[3-[(1(S,R),5(R,S),6(S,R)]-3-benzamido-5-methyl-2-oxa-4-azabicyclo[4.1.0]hept-3-en-5-yl]-4-fluorophenyl]-5-methoxypyrazine-2-carboxamide (912 mg, 1.92 mmol) was prepared by a similar procedure to that described in step 1 for the synthesis of 2a rac, but using N-[[1(S,R),5(R,S),6(S,R)]-5-(5-amino-2-fluorophenyl)-5-methyl-2-oxa-4-azabicyclo[4.1.0]hept-3-en-3-yl]benzamide (3g-rac). The product was subsequently subjected to chromatography using supercritical $CO_2$ (additives: 20% iPrOH with 20 mM Ammonia in MeOH) on a OJ-H column (250×30 mm, 5 μm) eluting at a flow rate of 120 ml/min (100 bar pressure, 40° C. column temperature). The first peak (retention time=3.62 min) provided N-(3-((1S,5R,6S)-3-benzamido-5-methyl-2-oxa-4-azabicyclo[4.1.0]hept-3-en-5-yl)-4-fluorophenyl)-5-methoxypyrazine-2-carboxamide (319a) (0.341 g, 0.717 mmol, 39.3% yield; 99% de; 99% ee) as a white solid. The second peak (retention time=4.38 min) provided N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide (320a) (0.343 g, 0.722 mmol, 39.5% yield; 99% de; 99% ee) as a white solid. MS m/z=476 [M+H]$^+$ (for both enantiomers). Calculated for $C_{25}H_{22}FN_5O_4$: 475.47

Step 2a: N-(3-((1S,5R,6S)-3-amino-5-methyl-2-oxa-4-azabicyclo[4.1.0]hept-3-en-5-yl)-4-fluorophenyl)-5-methoxypyrazine-2-carboxamide (Example 319)

A sealed vial was charged with N-(3-((1S,5R,6S)-3-benzamido-5-methyl-2-oxa-4-azabicyclo[4.1.0]hept-3-en-5-yl)-4-fluorophenyl)-5-methoxypyrazine-2-carboxamide (319a, 0.341 g, 0.717 mmol) and ammonia (2.0M solution in methanol; 7.17 ml, 14.34 mmol, Aldrich). The reaction mixture was heated to 80° C. for 24 h. The reaction was concentrated under reduced pressure and purified via silica gel flash chromatography using a gradient of 0-10% (2M ammonia in MeOH)/DCM to afford the title compound as a white solid. (0.129 g, 0.347 mmol, 48.4% yield).

MS m/z=372 [M+H]$^+$. Calculated for $C_{18}H_{18}FN_5O_3$: 371.366

$^1$H NMR (300 MHz, CHLOROFORM-d) δ ppm 0.87 (dt, J=9.61, 6.60 Hz, 1H) 1.00 (td, J=6.91, 2.70 Hz, 1H) 1.66 (d, J=1.02 Hz, 3H) 1.75-1.85 (m, 1H) 3.95 (td, J=6.80, 2.63 Hz, 1H) 4.07 (s, 3H) 7.07 (dd, J=11.55, 8.77 Hz, 1H) 7.53 (dd, J=7.02, 2.78 Hz, 1H) 7.86-7.93 (m, 1H) 8.15 (d, J=1.32 Hz, 1H) 9.01 (d, J=1.32 Hz, 1H) 9.46 (br. s., 1H)

Step 2b: N-(3-((1R,5S,6R)-3-amino-5-methyl-2-oxa-4-azabicyclo[4.1.0]hept-3-en-5-yl)-4-fluorophenyl)-5-methoxypyrazine-2-carboxamide (Example 320)

The title compound was prepared by steps and procedures similar to those described in step 2a for the synthesis of 319, but starting with N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide (320a). MS m/z=372 [M+H]$^+$. Calculated for $C_{18}H_{18}FN_5O_3$: 371.366.

$^1$H NMR (300 MHz, CHLOROFORM-d) δ ppm 0.86-0.96 (m, 1H) 0.98-1.07 (m, 1H) 1.69 (d, J=1.17 Hz, 3H) 1.77-1.88 (m, 1H) 3.96-4.04 (m, 1H) 4.08 (s, 3H) 7.09 (dd, J=11.55, 8.77 Hz, 1H) 7.55 (dd, J=7.02, 2.78 Hz, 1H) 7.86-7.95 (m, 1H) 8.16 (d, J=1.32 Hz, 1H) 9.02 (d, J=1.32 Hz, 1H) 9.48 (br. s., 1H)

General Metal-Catalyzed Amidation Procedures:

The following three (3) methods were used to couple the bromide core intermediates with corresponding amides to prepare compounds of the invention.

Method E: Copper (Cu) Catalyzed Amidation Procedure

Example 321

Synthesis of rac N-(6-((1R,5S,6R)-3-amino-5-(difluoromethyl)-2-oxa-4-azabicyclo[4.1.0]hept-3-en-5-yl)-5-fluoropyridin-2-yl)-5-chloropicolinamide

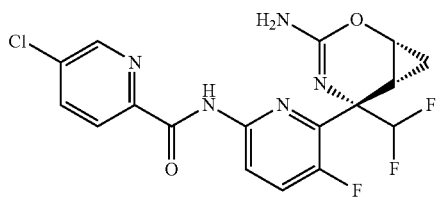 [SMILES: NC1=N[C@@](c2nc(NC(=O)c3ccc(Cl)cn3)ccc2F)(C(F)F)[C@H]2C[C@H]2O1]

A sealable tube was charged with mixture of 17d rac (55 mg, 0.164 mmol), 5-chloropicolinamide (38.4 mg, 0.245 mmol), potassium carbonate (90 mg, 0.655 mmol) and copper (I) iodide (9.35 mg, 0.049 mmol). The vial was evacuated and backfilled with nitrogen gas. Dioxane (1 mL) was added, followed by (1R,2R)-(−)-N,N''-dimethylcyclohexane-1,2-diamine (7.74 µl, 0.049 mmol). The reaction vial was sealed and heated to 100° C. for 2 h. The reaction mixture was cooled and purified by silica gel flash chromatography, eluting with a gradient of DCM/EtOAc=4:1 to 3:1 to 2:1 to 1:1 to 1:2. The title compound was obtained as an offwhite solid (30 mg, 0.073 mmol, 44.5% yield). MS m/z=412 [M+H]⁺

1H NMR (400 MHz, CHLOROFORM-d) d=10.29 (br. s., 1H), 8.62 (d, J=2.0 Hz, 1H), 8.38 (dd, J=3.0, 8.9 Hz, 1H), 8.25 (d, J=8.4 Hz, 1H), 7.90 (dd, J=2.2, 8.3 Hz, 1H), 7.51 (t, J=9.7 Hz, 1H), 6.77-6.35 (m, 1H), 4.24-4.06 (m, 1H), 1.93-1.77 (m, 1H), 1.53 (br. s., 1H), 1.16-0.99 (m, 1H).

Method F: Palladium (Pd) Catalyzed Amidation Procedure

Examples 322 & 323

Synthesis of N-(6-((1R,5S,6R)-3-amino-5-methyl-2-oxa-4-azabicyclo[4.1.0]hept-3-en-5-yl)-5-fluoropyridin-2-yl)-5-methoxypyrazine-2-carboxamide (Eg 322)

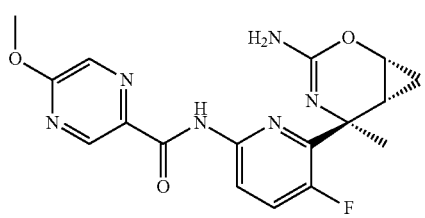 [SMILES: COc1cnc(C(=O)Nc2ccc(F)c([C@@]3(C)N=C(N)O[C@@H]4C[C@@H]43)n2)cn1]

and N-(6-((1S,5R,6S)-3-amino-5-methyl-2-oxa-4-azabicyclo[4.1.0]hept-3-en-5-yl)-5-fluoropyridin-2-yl)-5-methoxypyrazine-2-carboxamide (eg 323)

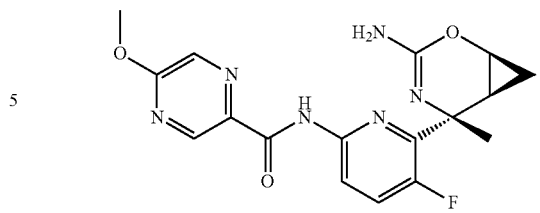

A sealable vial was charged with 4d rac (0.2 g, 0.666 mmol), 5-methoxypyrazine-2-carboxamide (0.148 g, 0.966 mmol), (9,9-dimethyl-9H-xanthene-4,5-diyl)bis(diphenylphosphine) (0.116 g, 0.200 mmol), Pd2(dba)3 (0.046 g, 0.050 mmol), and cesium carbonate (0.543 g, 1.666 mmol). The vial was evacuated and backfilled with N₂ gas. 1,4-Dioxane (2.5 mL) was added and the reaction mixture was stirred in a pre-heated 100° C. oil bath for 15.5 hours. The reaction mixture was cooled to RT and diluted with water and EtOAc. The organic layer was washed with water, brine and dried over magnesium sulfate. The filtrate was concentrated under reduced pressure. The crude residue was triturated with EtOAc and the solid was collected by filtration. The material was taken up in EtOAc and washed with water and brine. The organic layer was dried over magnesium sulfate and the filtrate was concentrated under reduced pressure to afford N-(6-(((1R,S),(5S,R),(6R,S))-3-amino-5-methyl-2-oxa-4-azabicyclo[4.1.0]hept-3-en-5-yl)-5-fluoropyridin-2-yl)-5-methoxypyrazine-2-carboxamide (0.164 g, 0.440 mmol, 66% yield). This material was subjected to chromatography using supercritical CO₂ (additives 20% MeOH with 20 mM NH₃) on a CHIRALPAK AS-H SFC column (21×250 mm, 5 µm) eluting at a flow rate 75 ml/min (100 bar pressure, 40° C. column temperature). The first peak (retention time=1.16 min) provided (N-(6-((1R,5S,6R)-3-amino-5-methyl-2-oxa-4-azabicyclo[4.1.0]hept-3-en-5-yl)-5-fluoropyridin-2-yl)-5-methoxypyrazine-2-carboxamide (Example 322, 32.1 mg, 0.086 mmol, 32.1% yield, 99% de; 99% ee). The second peak (retention time=3.43 min) provided N-(6-((1S,5R,6S)-3-amino-5-methyl-2-oxa-4-azabicyclo[4.1.0]hept-3-en-5-yl)-5-fluoropyridin-2-yl)-5-methoxypyrazine-2-carboxamide (Example 323, 33.4 mg, 0.090 mmol, 33.4% yield; 99% de; 99% ee). MS m/z=373 [M+H]⁺. (for both enantiomers)

Peak 1: 1H NMR (300 MHz, DMSO-d6) δ ppm 0.73 (d, J=5.70 Hz, 1H) 0.82 (dt, J=9.72, 6.18 Hz, 1H) 1.43-1.51 (m, 1H) 1.54 (s, 3H) 4.01-4.07 (m, 4H) 5.26 (br. s., 2H) 7.72 (dd, J=10.96, 8.77 Hz, 1H) 8.14 (dd, J=8.84, 2.85 Hz, 1H) 8.47 (d, J=1.32 Hz, 1H) 8.95 (d, J=1.17 Hz, 1H) 9.96 (s, 1H)

Peak 2: 1H NMR (300 MHz, DMSO-d6) δ ppm 0.67-0.77 (m, 1H) 0.77-0.87 (m, 1H) 1.47 (d, J=9.65 Hz, 1H) 1.53 (s, 3H) 4.00-4.13 (m, 4H) 5.24 (br. s., 2H) 7.72 (dd, J=11.04, 8.84 Hz, 1H) 8.14 (dd, J=8.70, 2.85 Hz, 1H) 8.46 (d, J=1.17 Hz, 1H) 8.95 (d, J=1.32 Hz, 1H) 9.96 (br. s., 1H)

Synthesis of N-(6-((1R,5S,6R)-3-amino-5-methyl-2-oxa-4-azabicyclo[4.1.0]hept-3-en-5-yl)-5-fluoropyridin-2-yl)-5-cyanopicolinamide (Example 324) and

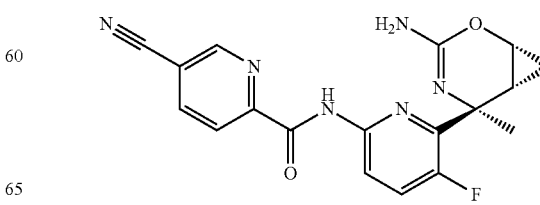

N-(6-((1S,5R,6S)-3-amino-5-methyl-2-oxa-4-azabicyclo[4.1.0]hept-3-en-5-yl)-5-fluoropyridin-2-yl)-5-cyanopicolinamide (Example 325)

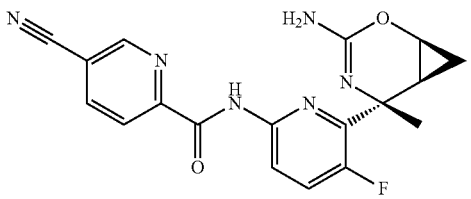 [SMILES: C[C@@]1(c2nc(NC(=O)c3ccc(C#N)cn3)ccc2F)N=C(N)O[C@H]2C[C@H]21]

The title compounds were synthesized according to procedure F, but using 5-cyanopicolinamide.

MS m/z=367 [M+H]+. (for both enantiomers)

Eg 324: 1H NMR (300 MHz, DMSO-d6) δ ppm 0.67-0.78 (m, 1H) 0.78-0.87 (m, 1H) 1.43-1.52 (m, 1H) 1.54 (s, 3H) 4.02-4.08 (m, 1H) 5.25 (br. s., 2H) 7.74 (dd, J=10.96, 8.77 Hz, 1H) 8.33-8.37 (m, 1H) 8.63 (dd, J=8.18, 1.90 Hz, 1H) 9.22-9.27 (m, 1H) 10.29 (br. s., 1H)

Eg 325: 1H NMR (300 MHz, DMSO-d6) δ ppm 0.69-0.77 (m, 1H) 0.78-0.90 (m, 1H) 1.43-1.52 (m, 1H) 1.54 (s, 3H) 4.01-4.09 (m, 1H) 5.25 (br. s., 2H) 7.74 (dd, J=10.89, 8.84 Hz, 1H) 8.16 (dd, J=8.84, 3.00 Hz, 1H) 8.32-8.37 (m, 1H) 8.60-8.66 (m, 1H) 9.22-9.27 (m, 1H) 10.30 (br. s., 1H)

Method G: Pd-Catalyzed Amidation Followed by Deprotection of Benzoyl Group

Examples 326 & 327

Synthesis of N-(6-((1R,5S,6R)-3-amino-5-methyl-2-oxa-4-azabicyclo[4.1.0]hept-3-en-5-yl)-5-fluoropyridin-2-yl)-5-chloropicolinamide (Eg 326)

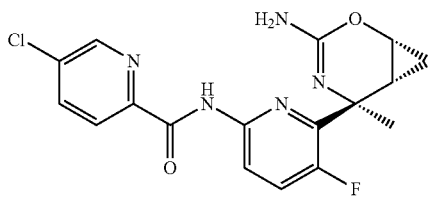

And N-(6-((1S,5R,6S)-3-amino-5-methyl-2-oxa-4-azabicyclo[4.1.0]hept-3-en-5-yl)-5-fluoropyridin-2-yl)-5-chloropicolinamide (Eg 327)

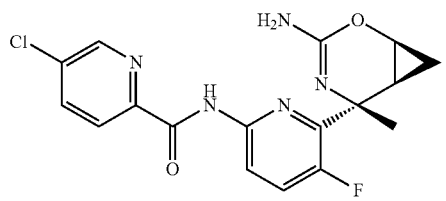 [SMILES: C[C@@]1(c2nc(NC(=O)c3ccc(Cl)cn3)ccc2F)N=C(N)O[C@H]2C[C@H]21]

Step 1:
A sealable vial was charged with N-[(1R,S),(5S,R),(6R,S)]-5-(6-bromo-3-fluoropyridin-2-yl)-5-methyl-2-oxa-4-azabicyclo[4.1.0]hept-3-en-3-yl)benzamide 4c rac (0.57 g, 1.410 mmol), 5-chloropicolinamide (0.320 g, 2.045 mmol), (9,9-dimethyl-9H-xanthene-4,5-diyl)bis(diphenylphosphine) (0.245 g, 0.423 mmol), Pd2(dba)3 (0.097 g, 0.106 mmol), and cesium carbonate (1.149 g, 3.53 mmol). The vial was evacuated and backfilled with $N_2$ gas. 1,4-Dioxane (5 mL) was added and the reaction mixture was stirred in a pre-heated 100° C. oil bath over for 15.5 hours. The reaction mixture was cooled to RT and diluted with water and EtOAc. The organic layer was washed with water, brine and dried over magnesium sulfate. The filtrate was concentrated under reduced pressure. The crude residue was purified via silica gel column chromatography (5-60% EtOAc:Hexanes) to afford N-(6-(((1R,S),(5S,R),(6R,S)]-3-benzamido-5-methyl-2-oxa-4-azabicyclo[4.1.0]hept-3-en-5-yl)-5-fluoropyridin-2-yl)-5-chloropicolinamide (0.554 g, 1.154 mmol, 82% yield). MS m/z=479.9 [M]

Step 2:
A microwave vial was charged with N-(6-(((1R,S),(5S,R),(6R,S)]-3-benzamido-5-methyl-2-oxa-4-azabicyclo[4.1.0]hept-3-en-5-yl)-5-fluoropyridin-2-yl)-5-chloropicolinamide (0.554 g, 1.154 mmol), MeOH (4.62 ml) and DBU (0.696 ml, 4.62 mmol). The reaction mixture was heated to 75° C. for 3 h in the microwave. The solid was collected by vacuum filtration to afford N-(6-(((1R,S),(5S,R),(6R,S))-3-amino-5-methyl-2-oxa-4-azabicyclo[4.1.0]hept-3-en-5-yl)-5-fluoropyridin-2-yl)-5-chloropicolinamide (0.309 g, 0.822 mmol, 71.2% yield). This material was subjected to chromatography using supercritical $CO_2$ (additives 20% MeOH with 20 mM $NH_3$) on a CHIRALPAK AS-H SFC column (21×250 mm, 5 μm) eluting at a flow rate 75 ml/min (100 bar pressure, 40° C. column temperature). The first peak (retention time=1.26 min) provided (N-(6-((1R,5S,6R)-3-amino-5-methyl-2-oxa-4-azabicyclo[4.1.0]hept-3-en-5-yl)-5-fluoropyridin-2-yl)-5-chloropicolinamide ((Example 326, 115 mg, 0.306 mmol, 38.1% yield, 99% de; 99% ee). The second peak (retention time=1.95 min) provided N-(6-((1S,5R,6S)-3-amino-5-methyl-2-oxa-4-azabicyclo[4.1.0]hept-3-en-5-yl)-5-fluoropyridin-2-yl)-5-chloropicolinamide (N-(6-((1S,5R,6S)-3-amino-5-methyl-2-oxa-4-azabicyclo[4.1.0]hept-3-en-5-yl)-5-fluoropyridin-2-yl)-5-chloropicolinamide (Example 327, 123.1 mg, 0.328 mmol, 40.8% yield; 99% de; 99% ee)

MS m/z=375.9 [M+H]+. (for both enantiomers)

Peak 1: 1H NMR (300 MHz, CHLOROFORM-d) δ ppm 0.97 (dt, J=9.83, 6.70 Hz, 1H) 1.05-1.13 (m, 1H) 1.67-1.74 (m, 1H) 1.77 (s, 3H) 4.10-4.17 (m, 1H) 7.46 (dd, J=10.60, 8.84 Hz, 1H) 7.89 (dd, J=8.33, 2.34 Hz, 1H) 8.25 (d, J=8.33 Hz, 1H) 8.31 (dd, J=8.77, 3.07 Hz, 1H) 8.62 (d, J=1.90 Hz, 1H) 10.24 (br. s., 1H)

Peak 2: 1H NMR (300 MHz, CHLOROFORM-d) δ ppm 0.88-0.98 (m, 1H) 1.03 (td, J=6.94, 2.92 Hz, 1H) 1.66 (dt, J=9.79, 7.23 Hz, 1H) 1.73 (s, 3H) 4.06-4.14 (m, 1H) 7.45 (dd, J=10.60, 8.84 Hz, 1H) 7.89 (dd, J=8.33, 2.34 Hz, 1H) 8.25 (d, J=8.33 Hz, 1H) 8.30 (dd, J=8.77, 2.92 Hz, 1H) 8.61 (d, J=2.19 Hz, 1H) 10.24 (br. s., 1H)

Synthesis of N-(6-((1R,5S,6R)-3-amino-5-methyl-2-oxa-4-azabicyclo[4.1.0]hept-3-en-5-yl)-5-fluoropyridin-2-yl)-3,5-dichloropicolinamide (Example 328)

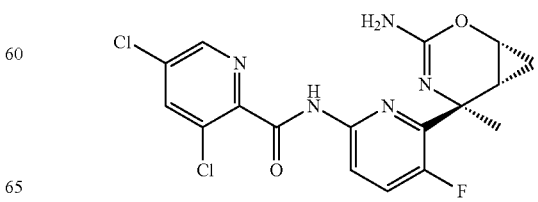

And N-(6-((1S,5R,6S)-3-amino-5-methyl-2-oxa-4-azabicyclo[4.1.0]hept-3-en-5-yl)-5-fluoropyridin-2-yl)-3,5-dichloropicolinamide (Example 329)

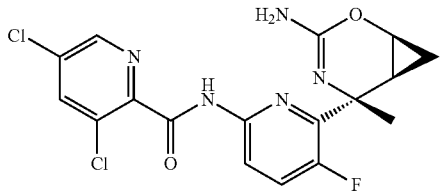 [SMILES: C[C@@]1(c2nc(NC(=O)c3ncc(Cl)cc3Cl)ccc2F)N=C(N)O[C@H]2C[C@H]21]

The title compounds were synthesized according to procedure G, but using 3,5-dichloropicolinamide.
MS m/z=409.9 [M+H]⁺. (for both enantiomers)

Peak 1: 1H NMR (300 MHz, CHLOROFORM-d) δ ppm 0.98-1.09 (m, 1H) 1.11-1.20 (m, 1H) 1.72-1.85 (m, 4H) 4.14-4.22 (m, 1H) 7.49 (dd, J=10.45, 8.84 Hz, 1H) 7.92 (d, J=2.05 Hz, 1H) 8.35 (dd, J=8.92, 3.07 Hz, 1H) 8.56 (d, J=2.05 Hz, 1H)

Peak 2: 1H NMR (300 MHz, CHLOROFORM-d) δ ppm 0.91-1.00 (m, 1H) 1.03-1.11 (m, 1H) 1.65-1.73 (m, 1H) 1.74 (s, 3H) 4.08-4.15 (m, 1H) 7.46 (dd, J=10.52, 8.77 Hz, 1H) 7.92 (d, J=2.05 Hz, 1H) 8.32 (dd, J=8.84, 3.00 Hz, 1H) 8.54 (d, J=2.05 Hz, 1H)

Examples 330-336

Using procedures similar to one of the general metal-catalyzed amidation procedures described above, the appropriate bromide and amide were combined to prepare the examples listed in Table 2:

TABLE 2

| Example # | Method | Compound Name | Compound Structure | Analytical Data |
|---|---|---|---|---|
| 330 | E | N-(6-9((1RS),(5S,R),(6R,S))-3-amino-5-(difluoromethyl)-2-oxa-4-azabicyclo[4.1.0]hept-3-en-5-yl)-5-fluoropyridin-2-yl)-5-cyanopicolinamide | 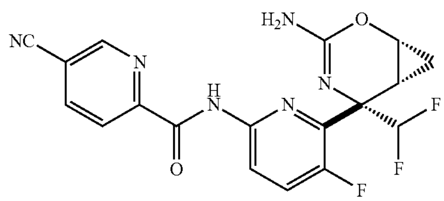 | MS m/z = 403 [M + H]+ 1H NMR (400 MHz, CHLOROFORM-d) d = 10.28 (s, 1 H), 8.94 (d, J = 1.2 Hz, 1 H), 8.43 (d, J = 8.2 Hz, 1 H), 8.37 (dd, J = 2.9, 8.8 Hz, 1 H), 8.22 (dd, J = 2.1, 8.1 Hz, 1 H), 7.52 (dd, J = 9.0, 10.2 Hz, 1 H), 6.72-6.32 (m, 1 H), 4.11 (t, J = 5.3 Hz, 1 H), 1.89-1.74 (m, 1 H), 1.51 (t, J = 6.5 Hz, 1 H), 1.13-1.00 (m, 1 H) |
| 331 | E | N-(6-((1R,5S,6R)-3-amino-5-(difluoromethyl)-2-oxa-4-azabicyclo[4.1.0]hept-3-en-5-yl)-5-fluoropyridin-2-yl)-5-cyanopicolinamide | 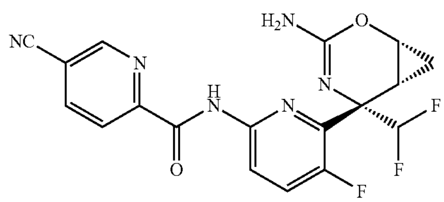 [SMILES: N#Cc1ccc(C(=O)Nc2ccc(F)c([C@@]3(C(F)F)N=C(N)O[C@@H]4C[C@@H]43)n2)nc1] | MS m/z = 403 [M + H]+ 1H NMR (400 MHz, CHLOROFORM-d) d = 10.28 (s, 1 H), 8.94 (d, J = 1.2 Hz, 1 H), 8.43 (d, J = 8.2 Hz, 1 H), 8.37 (dd, J = 2.9, 8.8 Hz, 1 H), 8.22 (dd, J = 2.1, 8.1 Hz, 1 H), 7.52 (dd, J = 9.0, 10.2 Hz, 1 H), 6.72-6.32 (m, 1 H), 4.11 (t, J = 5.3 Hz, 1 H), 1.89-1.74 (m, 1 H), 1.51 (t, J = 6.5 Hz, 1 H), 1.13-1.00 (m, 1 H) |
| 332 | E | (1R,5S,6R)-5-(5-((3-(5-chloropyridin-2-yl)oxetan-3-yl)amino)-2-fluorophenyl)-5-(difluoromethyl)-2-oxa-4-azabicyclo[4.1.0]hept-3-en-3-amine | 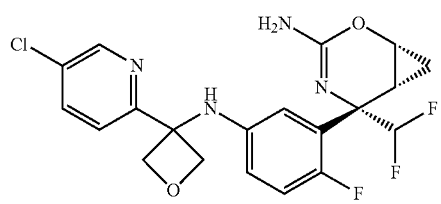 [SMILES: NC1=N[C@@](c2cc(NC3(c4ccc(Cl)cn4)COC3)ccc2F)(C(F)F)[C@H]2C[C@H]2O1] | MS m/z = 438.8 [M]+ 1H NMR (400 MHz, CHLOROFORM-d) d = 8.65 (d, J = 2.3 Hz, 1 H), 7.58 (dd, J = 2.5, 8.4 Hz, 1 H), 7.43 (d, J = 8.6 Hz, 1 H), 6.82 (dd, J = 8.7, 11.6 Hz, 1 H), 6.51 (dd, J = 2.8, 6.4 Hz, 1 H), 6.37-5.98 (m, 2 H), 5.26 (d, J = 6.1 Hz, 1 H), 5.15 (d, J = 6.3 Hz, 1 H), 4.80 (d, J = 6.1 Hz, 2 H), 3.88 (t, J = 5.3 Hz, 1 H), 1.86-1.75 (m, 1 H), 1.38 (t, J = 7.1 Hz, 1 H), 1.00-0.89 (m, 1 H) |
| 333 | E | N-(5-((1(R,S),5(S,R),6(R,S)-3-amino-5-methyl-2-oxa-4-azabicyclo[4.1.0]hept-3-en-5-yl)-6-fluoropyridin-3-yl)-5-chloropicolinamide | 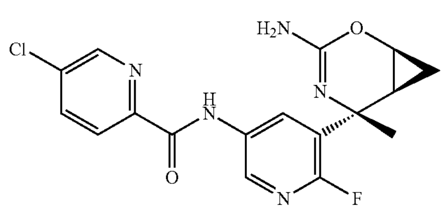 [SMILES: C[C@@]1(c2cc(NC(=O)c3ccc(Cl)cn3)cnc2F)N=C(N)O[C@H]2C[C@H]21] | m/z = 376.4 [M + H]+ 1H NMR (MeOH) d: 8.73 (d, J = 2.2 Hz, 1H), 8.58-8.66 (m, 1H), 8.43 (dd, J = 9.0, 2.5 Hz, 1H), 8.22 (d, J = 8.4 Hz, 1H), 8.09 (dd, J = 8.4, 2.3 Hz, 1H), 4.02-4.25 (m, 1H), 1.76-1.89 (m, 1H), 1.70 (s, 3H), 1.31 (s, 1H), 1.06 (dt, J = 6.8, 3.3 Hz, 1H), 0.93-1.02 (m, 1H) |

TABLE 2-continued

| Example # | Method | Compound Name | Compound Structure | Analytical Data |
|---|---|---|---|---|
| 334 | E | N-(5-((1R,5S,6R)-3-amino-5-methyl-2-oxa-4-azabicyclo[4.1.0]hept-3-en-5-yl)-6-fluoropyridin-3-yl)-5-chloropicolinamide | 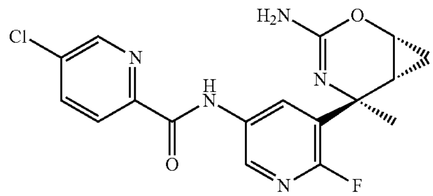 [SMILES: C[C@]1(c2cc(NC(=O)c3ccc(Cl)cn3)cnc2F)N=C(N)O[C@@H]2C[C@@H]21] | MS m/z = 376.4 [M + H]+ 1H NMR (MeOH) d: 8.74 (d, J = 2.0 Hz, 1H), 8.63 (s, 1H), 8.43 (dd, J = 8.9, 2.4 Hz, 1H), 8.23 (d, J = 8.4 Hz, 1H), 8.11 (dd, J = 8.4, 2.3 Hz, 1H), 4.14 (t, J = 5.3 Hz, 1H), 1.82 (d, J = 9.6 Hz, 1H), 1.70 (s, 3H), 1.02-1.17 (m, 1H), 0.98 (dd, J = 9.7, 6.4 Hz, 1H) |
| 335 | E | N-(5-((1S,5R,6S)-3-amino-5-methyl-2-oxa-4-azabicyclo[4.1.0]hept-3-en-5-yl)-6-fluoropyridin-3-yl)-5-chloropicolinamide | 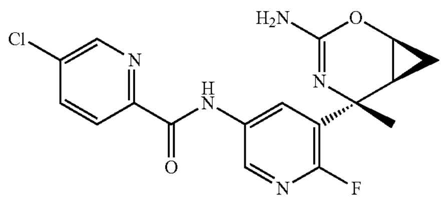 [SMILES: C[C@@]1(c2cc(NC(=O)c3ccc(Cl)cn3)cnc2F)N=C(N)O[C@H]2C[C@H]21] | MS m/z = 376.4 [M + H]+ 1H NMR (MeOH) d: 8.74 (d, J = 2.0 Hz, 1H), 8.63 (s, 1H), 8.42 (dd, J = 9.0, 2.5 Hz, 1H), 8.23 (d, J = 8.2 Hz, 1H), 8.11 (dd, J = 8.4, 2.3 Hz, 1H), 4.12 (t, J = 5.4 Hz, 1H), 1.81 (d, J = 9.6 Hz, 1H), 1.69 (s, 3H), 1.01-1.09 (m, 1H), 0.90-1.00 (m, 1H) |
| 336 | E | N-(5-((1(R,S),5(S,R),6(R,S))-3-amino-5-methyl-2-oxa-4-azabicyclo[4.1.0]hept-3-en-5-yl)-6-fluoropyridin-3-yl)-5-methoxypyrazine-2-carboxamide | 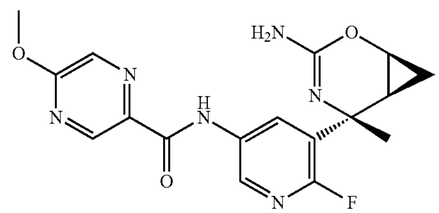 [SMILES: COc1cnc(C(=O)Nc2cnc(F)c([C@]3(C)N=C(N)O[C@H]4C[C@H]43)c2)cn1] | MS m/z = 373 [M + H]+ 1H NMR (MeOH) d: 8.97 (s, 1H), 8.57-8.74 (m, 2H), 8.35 (s, 1H), 4.63 (d, J = 3.7 Hz, 1H), 4.12 (s, 3H), 2.07 (d, J = 9.8 Hz, 1H), 1.93 (s, 3H), 1.37-1.46 (m, 1H), 1.24-1.34 (m, 1H) |

Method H:

Examples 337 & 338

Synthesis of (1S,5S,6S)-5-(2-fluoro-5-((3-methoxy-1,7-naphthyridin-8-yl)amino)phenyl)-5-methyl-2-oxa-4-azabicyclo[4.1.0]hept-3-en-3-amine (Eg 337)

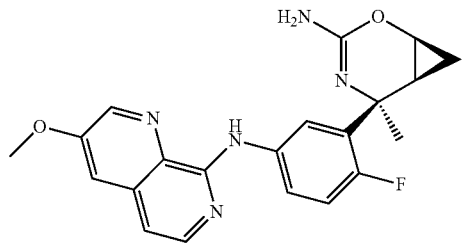 [SMILES: COc1cnc2c(Nc3ccc(F)c([C@@]4(C)N=C(N)O[C@H]5C[C@H]54)c3)nccc2c1]

and (1R,5R,6R)-5-(2-fluoro-5-((3-methoxy-1,7-naphthyridin-8-yl)amino)phenyl)-5-methyl-2-oxa-4-azabicyclo[4.1.0]hept-3-en-3-amine (Eg 338)

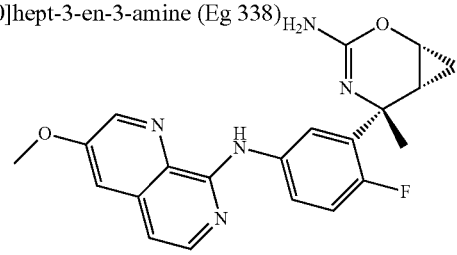

A sealable vial was charged with and [1(S,R),5(S,R),6(S,R)]-5-(5-amino-2-fluorophenyl)-5-methyl-2-oxa-4-azabicyclo[4.1.0]hept-3-en-3-amine (1k rac; 350 mg, 1.488 mmol) and 8-chloro-3-methoxy-1,7-naphthyridine (Intermediate 2; 304 mg, 1.56 mmol). Iso-propanol (6.8 mL) and sulfuric acid (103 μl, 1.93 mmol) were added and the mixture was heated to 55° C. for 20 min. The cooled reaction mixture was diluted with water and extracted with EtOAc. The aqueous phase was neutralized with aqueous saturated sodium bicarbonate solution. The solution was extracted three times with EtOAc. The combined organic phases were separated and dried over MgSO₄. The solvent was removed under reduced pressure. The residue was washed with Et₂O to obtain [1(S,R),5(S,R),6(S,R)]-5-(2-fluoro-5-((3-methoxy-1,7-naphthyridin-8-yl)amino)phenyl)-5-methyl-2-oxa-4-azabicyclo[4.1.0]hept-3-en-3-amine as a beige solid (290 mg). The solid was subjected to chromatography using supercritical CO₂ (additives 50% MeOH with 20 mM NH₃) on a AD-H column (21×250 mm, 5 μm) eluting at a flow rate 50 ml/min (100 bar pressure, 40° C. column temperature). The first peak (retention time=1.24 min) provided (1S,5S,6S)-5-(2-fluoro-5-((3-methoxy-1,7-naphthyridin-8-yl)amino)phenyl)-5-methyl-2-oxa-4-azabicyclo[4.1.0]hept-3-en-3-amine (Example 337, 122 mg, 0.310 mmol, 20.84% yield; 99% de; 99% ee) as a light-yellow powder. The second peak (retention time=2.33 min) provided (1R,5R,6R)-5-(2-fluoro-5-((3-methoxy-1,7-naphthyridin-8-yl)amino)phenyl)-5-methyl-2-oxa-4-azabicyclo[4.1.0]hept-3-en-3-amine (Example 338; 110 mg, 0.280 mmol, 18.79% yield; 99% de; 99% ee) as a light-yellow powder.

MS m/z=394.1 [M+H]⁺. Calculated for $C_{21}H_{20}FN_5O_2$: 393.41 (for both enantiomers)

¹H NMR (312; 300 MHz, DMSO-d₆) δ ppm 0.38 (td, J=6.36, 2.92 Hz, 1H) 0.61 (dt, J=9.50, 6.21 Hz, 1H) 1.59 (s, 3H) 1.64-1.80 (m, 1H) 3.97 (s, 3H) 3.99-4.08 (m, 1H) 5.40 (s, 2H) 7.02-7.15 (m, 2H) 7.70 (d, J=2.78 Hz, 1H) 7.92 (dd, J=7.09, 2.85 Hz, 1H) 8.02 (d, J=5.70 Hz, 1H) 8.11-8.27 (m, 1H) 8.61 (d, J=2.78 Hz, 1H) 9.19 (s, 1H) ¹H NMR (313; 300 MHz, DMSO-d₆) δ ppm 0.39 (td, J=6.43, 2.92 Hz, 1H) 0.61 (dt, J=9.57, 6.25 Hz, 1H) 1.59 (s, 3H) 1.64-1.77 (m, 1H) 3.97

(s, 3H) 4.00-4.10 (m, 1H) 5.41 (s, 2H) 7.00-7.18 (m, 2H) 7.70 (d, J=2.78 Hz, 1H) 7.93 (dd, J=7.16, 2.92 Hz, 1H) 8.03 (d, J=5.70 Hz, 1H) 8.12-8.26 (m, 1H) 8.61 (d, J=2.78 Hz, 1H) 9.19 (s, 1H)

Examples 339-365

The examples in Table 3 were synthesized following a procedure analogous to Method H

TABLE 3

| Example No | Compound Name | Compound Structure | Analytical Data |
|---|---|---|---|
| 339 | (1S,5R,6S)-5-(2-fluoro-5-((3-methoxy-1,7-naphthyridin-8-yl)amino)phenyl)-5-methyl-2-oxa-4-azabicyclo[4.1.0]hept-3-en-3-amine | 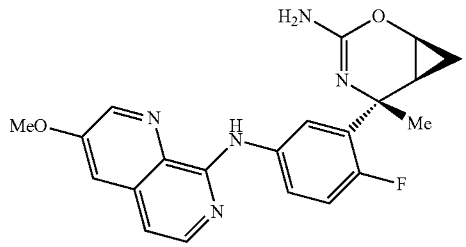 [SMILES: COc1cnc2c(Nc3ccc(F)c([C@]4(C)N=C(N)O[C@H]5C[C@H]54)c3)nccc2c1] | MS m/z = 394.0 [M + H]+. 1H NMR (300 MHz, CHLOROFORM-d) δ ppm 0.81-0.92 (m, 1 H) 0.96-1.05 (m, 1 H) 1.68 (s, 3 H) 1.78-1.88 (m, 1 H) 3.92-4.00 (m, 4 H) 6.91 (d, J = 5.85 Hz, 1 H) 7.08 (dd, J = 11.77, 8.84 Hz, 1 H) 7.23 (d, J = 2.63 Hz, 1 H) 7.69 (dd, J = 7.23, 2.56 Hz, 1 H) 8.01-8.13 (m, 2 H) 8.50 (d, J = 2.48 Hz, 1 H) 8.86 (s, 1 H) |
| 340 | (1R,5S,6R)-5-(2-fluoro-5-((3-methoxy-1,7-naphthyridin-8-yl)amino)phenyl)-5-methyl-2-oxa-4-azabicyclo[4.1.0]hept-3-en-3-amine | 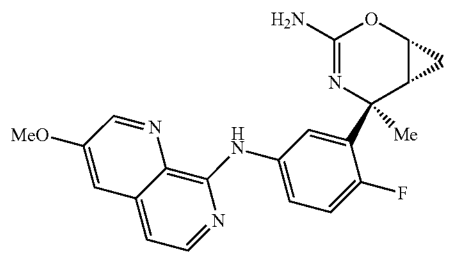 [SMILES: COc1cnc2c(Nc3ccc(F)c([C@@]4(C)N=C(N)O[C@@H]5C[C@@H]54)c3)nccc2c1] | MS m/z = 394.0 [M + H]+. 1H NMR (300 MHz, CHLOROFORM-d) δ ppm 0.85 (dt, J = 9.61, 6.60 Hz, 1 H) 1.00 (td, J = 6.91, 2.41 Hz, 1 H) 1.67 (s, 3 H) 1.77-1.87 (m, 1 H) 3.90-4.01 (m, 4 H) 6.90 (d, J = 5.85 Hz, 1 H) 7.07 (dd, J = 11.69, 8.77 Hz, 1 H) 7.22 (d, J = 2.63 Hz, 1 H) 7.67 (dd, J = 7.16, 2.63 Hz, 1 H) 8.02-8.12 (m, 2 H) 8.49 (d, J = 2.63 Hz, 1 H) 8.85 (s, 1 H) |
| 341 | (1S,5S,6S)-5-(5-((3-chloro-1,7-naphthyridin-8-yl)amino)-2,3-difluorophenyl)-5-(fluoromethyl)-2-oxa-4-azabicyclo[4.1.0]hept-3-en-3-amine | 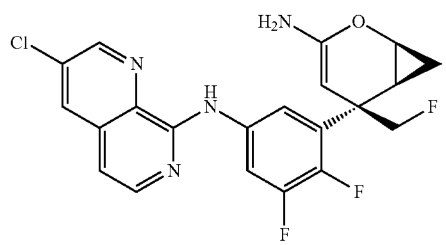 [SMILES: NC1=C[C@@](CF)(c2cc(Nc3nccc4cc(Cl)cnc34)cc(F)c2F)[C@@H]2C[C@@H]2O1] | MS m/z = 434.2 [M + H]+ 1H NMR (400 MHz, CHLOROFORM-d) d ppm 8.87 (s, 1 H), 8.60 (s, 1 H), 8.32 (ddd, J = 12.42, 6.94, 2.35 Hz, 1 H), 8.07 (d, J = 5.67 Hz, 1 H), 7.96 (d, J = 2.15 Hz, 1 H), 7.32-7.45 (m, 1 H), 6.90 (s, 1 H), 4.79 (s, 1 H), 4.67 (s, 1 H), 3.97 (br. s., 1 H), 1.70-1.85 (m, 1 H), 1.17-1.34 (m, 2 H), 0.77-1.01 (m, 2 H) |
| 342 | (1R,5S,6R)-5-(5-((3-chloro-1,7-naphthyridin-8-yl)amino)-2,3-difluorophenyl)-5-(fluoromethyl)-2-oxa-4-azabicyclo[4.1.0]hept-3-en-3-amine | 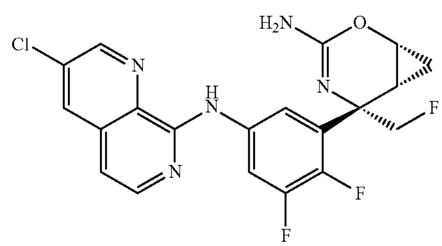 [SMILES: NC1=N[C@](CF)(c2cc(Nc3nccc4cc(Cl)cnc34)cc(F)c2F)[C@H]2C[C@H]2O1] | MS m/z = 434.2 [M + H]+ 1H NMR (400 MHz, CHLOROFORM-d) d ppm 8.86 (br. s., 1 H), 8.59 (s, 1 H), 8.28-8.38 (m, 1 H), 8.07 (d, J = 5.67 Hz, 1 H), 7.96 (s, 1 H), 7.35 (br. s., 1 H), 6.89 (d, J = 5.67 Hz, 1 H), 4.78 (s, 1 H), 4.66 (s, 1 H), 3.96 (br. s., 1 H), 1.76 (q, J = 7.69 Hz, 1 H), 1.16-1.33 (m, 1 H), 0.92 (q, J = 7.50 Hz, 1 H). Note NH2 is very broad around 5.5 to 4 ppm |
| 343 | 8-((3-(((1R,5S,6R)-3-amino-5-(fluoromethyl)-2-oxa-4-azabicyclo[4.1.0]hept-3-en-5-yl)-4-fluorophenyl)amino)-5-fluoro-1,7-naphthyridine-3-carbonitrile | 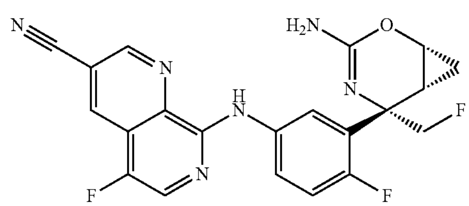 [SMILES: N#Cc1cnc2c(Nc3ccc(F)c([C@@]4(CF)N=C(N)O[C@@H]5C[C@@H]54)c3)ncc(F)c2c1] | MS m/z = 425.2 [M + H]+ 1H NMR (400 MHz, DMSO-d6) d ppm 9.71 (s, 1 H), 9.32 (d, J = 1.96 Hz, 1 H), 9.13 (d, J = 1.76 Hz, 1 H), 8.32 (dd, J = 7.34, 2.64 Hz, 1 H), 8.25 (s, 1 H), 7.93 (dt, J = 8.66, 3.50 Hz, 1 H), 7.15 (dd, J = 11.83, 8.90 Hz, 1 H), 5.69 (br. s, 2 H), 4.43-4.73 (m, 2 H), 4.01 (t, J = 5.77 Hz, 1 H), 1.49-1.66 (m, 1 H), 1.03 (td, J = 6.21, 2.25 Hz, 1 H), 0.82 (dt, J = 9.24, 6.43 Hz, 1 H). |

TABLE 3-continued

| Example No | Compound Name | Compound Structure | Analytical Data |
|---|---|---|---|
| 344 | (1R,5S,6R)-5-(2-fluoro-5-((5-fluoro-3-methoxy-1,7-naphthyridin-8-yl)amino)phenyl)-5-(fluoromethyl)-2-oxa-4-azabicyclo[4.1.0]hept-3-en-3-amine | 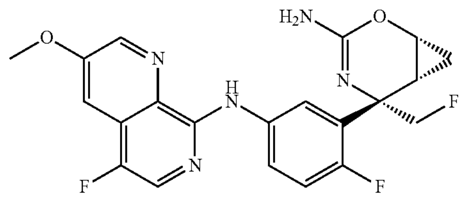 [SMILES: COc1cnc2c(Nc3ccc(F)c([C@@]4(CF)N=C(N)O[C@@H]5C[C@@H]54)c3)ncc(F)c2c1] | MS m/z = 430 [M + H]+<br>1H NMR (400 MHz, DMSO-d6)<br>d ppm 9.35 (s, 1 H), 8.71 (d, J = 2.93 Hz, 1 H), 8.22 (dd, J = 7.43, 2.74 Hz, 1 H), 8.09 (d, J = 1.56 Hz, 1 H), 7.93-8.00 (m, 1 H), 7.71 (d, J = 2.74 Hz, 1 H), 7.12 (dd, J = 11.74, 8.80 Hz, 1 H), 5.68 (s, 2 H), 4.43-4.73 (m, 2 H), 3.97-4.07 (m, 4 H), 1.56-1.66 (m, 1 H), 1.02 (td, J = 6.41, 2.64 Hz, 1 H), 0.81 (dt, J = 9.29, 6.41 Hz, 1 H). |
| 345 | (1R,5S,6R)-5-(5-((3-chloro-1,7-naphthyridin-8-yl)amino)-2-fluorophenyl)-5-(fluoromethyl)-2-oxa-4-azabicyclo[4.1.0]hept-3-en-3-amine | 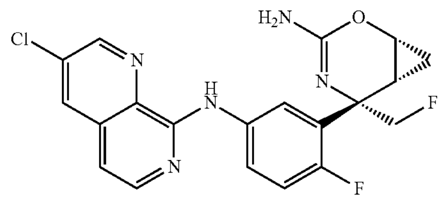 [SMILES: NC1=N[C@](CF)(c2cc(Nc3nccc4cc(Cl)cnc34)ccc2F)[C@H]2C[C@H]2O1] | MS m/z = 416 [M + H]+<br>1H NMR (400 MHz, DMSO-d6)<br>d ppm 9.58 (s, 1 H), 8.90 (d, J = 2.35 Hz, 1 H), 8.51 (d, J = 2.35 Hz, 1 H), 8.22 (dd, J = 7.24, 2.74 Hz, 1 H), 8.14 (d, J = 5.67 Hz, 1 H), 8.03 (dt, J = 8.36, 3.64 Hz, 1 H), 7.10-7.19 (m, 2 H), 5.68 (br. s., 2 H), 4.41-4.74 (m, 2 H), 4.02 (t, J = 5.58 Hz, 1 H), 1.56-1.66 (m, 1 H), 1.02 (td, J = 6.16, 2.35 Hz, 1 H), 0.82 (dt, J = 9.34, 6.48 Hz, 1 H). |
| 346 | 8-((3-((1R,5S,6R)-3-amino-5-(fluoromethyl)-2-oxa-4-azabicyclo[4.1.0]hept-3-en-5-yl)-4-fluorophenyl)amino)-1,7-naphthyridine-3-carbonitrile | 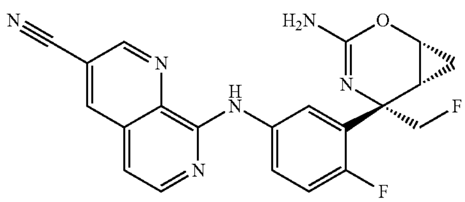 | MS m/z = 407 [M + H]+<br>1H NMR (400 MHz, DMSO-d6)<br>d ppm 9.72 (s, 1 H), 9.21 (d, J = 1.76 Hz, 1 H), 8.87-9.06 (m, 1 H), 8.25 (dd, J = 7.34, 2.64 Hz, 1 H), 8.22 (d, J = 5.87 Hz, 1 H), 8.02 (dt, J = 8.56, 3.55 Hz, 1 H), 7.22 (d, J = 5.67 Hz, 1H), 7.16 (dd, J = 8.80, 11.74 Hz, 1H), 5.75 (s, 2 H), 4.39-4.75 (m, 2 H), 3.90-4.10 (m, 1 H), 1.49-1.69 (m, 1 H), 1.03 (d, J = 1.96 Hz, 1 H), 0.83 (dt, J = 9.24, 6.33 Hz, 1 H). |
| 347 | (1R,5S,6R)-5-(5-((7-chloropyrido[3,2-d]pyrimidin-4-yl)amino)-2-fluorophenyl)-5-(fluoromethyl)-2-oxa-4-azabicyclo[4.1.0]hept-3-en-3-amine | 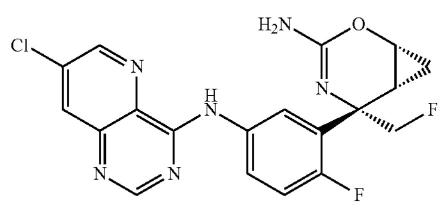 [SMILES: NC1=N[C@](CF)(c2cc(Nc3ncnc4cc(Cl)cnc34)ccc2F)[C@H]2C[C@H]2O1] | MS m/z = 417 [M + H]+<br>1H NMR (400 MHz, DMSO-d6)<br>d ppm 10.42 (s, 1 H), 8.93 (d, J = 2.35 Hz, 1 H), 8.67 (s, 1 H), 8.39 (d, J = 2.15 Hz, 1 H), 8.27 (dd, J = 7.43, 2.74 Hz, 1 H), 7.90 (dt, J = 8.17, 3.64 Hz, 1 H), 7.20 (dd, J = 11.83, 8.90 Hz, 1 H), 5.67 (br. s., 2 H), 4.40-4.75 (m, 2 H), 4.03 (t, J = 5.67 Hz, 1 H), 1.54-1.66 (m, 1 H), 1.02 (td, J = 6.11, 2.25 Hz, 1 H), 0.83 (dt, J = 9.44, 6.43 Hz, 1 H). |
| 348 | (1R,5S,6R)-5-(difluoromethyl)-5-(2-fluoro-5-((3-methoxy-1,7-naphthyridin-8-yl)amino)phenyl)-2-oxa-4-azabicyclo[4.1.0]hept-3-en-3-amine | 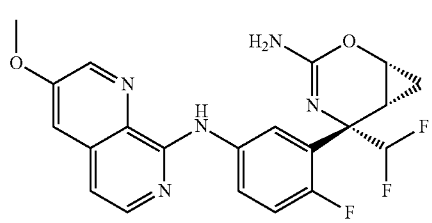 [SMILES: COc1cnc2c(Nc3ccc(F)c([C@@]4(C(F)F)N=C(N)O[C@@H]5C[C@@H]54)c3)nccc2c1] | MS m/z = 430[M + H]+<br>1H NMR (MeOH) d: 8.57 (d, J = 2.7 Hz, 1H), 8.03 (dd, J = 6.9, 2.8 Hz, 1H), 7.99 (d, J = 5.9 Hz, 1H), 7.95 (ddd, J = 8.8, 4.2, 2.8 Hz, 1H), 7.56 (d, J = 2.7 Hz, 1H), 7.16 (dd, J = 11.9, 8.8 Hz, 1H), 7.08 (d, J = 5.9 Hz, 1H), 6.16-6.51 (m, 1H), 4.06-4.13 (m, 1H), 4.02 (s, 3H), 1.86-2.01 (m, 1H), 1.32-1.43 (m, 1H), 1.00 (dt, J = 9.3, 6.7 Hz, 1H) |

TABLE 3-continued

| Example No | Compound Name | Compound Structure | Analytical Data |
|---|---|---|---|
| 349 | 8-((3-((1(R,S),5(S,R),6(R,S))-3-amino-5-(difluoromethyl)-2-oxa-4-azabicyclo[4.1.0]hept-3-en-5-yl)-4-chlorophenyl)amino)-5-fluoro-1,7-naphthyridine-3-carbonitrile | 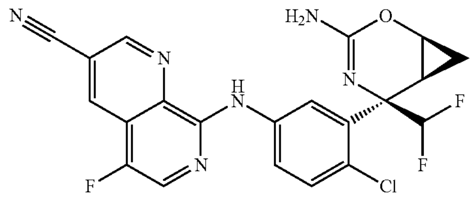 [SMILES: N#Cc1cnc2c(Nc3ccc(Cl)c([C@]4(C(F)F)N=C(N)O[C@H]5C[C@H]54)c3)ncc(F)c2c1] | MS m/z = 458.9 [M + H]+<br>1H NMR (300 MHz, DMSO-d6) d = 9.84 (s, 1 H), 9.34 (d, J = 1.9 Hz, 1 H), 9.17 (d, J = 1.9 Hz, 1 H), 8.74 (d, J = 2.5 Hz, 1 H), 8.33 (s, 1 H), 7.95 (dd, J = 2.4, 8.8 Hz, 1 H), 7.42 (d, J = 8.5 Hz, 1 H), 7.02-6.51 (m, 1 H), 5.94 (s, 2 H), 3.95 (br. s., 1 H), 2.05-1.88 (m, 1 H), 1.12 (br. s., 1 H), 1.01-0.85 (m, 1 H). |
| 350 | 8-((3-((1R,5S,6R)-3-amino-5-(difluoromethyl)-2-oxa-4-azabicyclo[4.1.0]hept-3-en-5-yl)-4-chlorophenyl)amino)-5-fluoro-1,7-naphthyridine-3-carbonitrile | 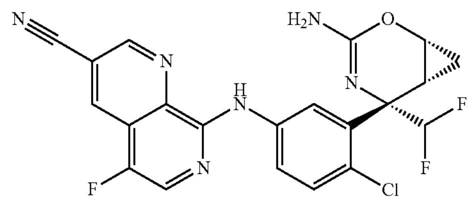 | MS m/z = 458.9 [M + H]+<br>1H NMR (400 MHz, DMSO-d6) d = 9.76 (s, 1 H), 9.27 (s, 1 H), 9.09 (s, 1 H), 8.66 (br. s., 1 H), 8.26 (s, 1 H), 7.88 (d, J = 8.8 Hz, 1 H), 7.35 (d, J = 8.4 Hz, 1 H), 6.90-6.52 (m, 1 H), 5.87 (br. s., 2 H), 3.88 (br. s., 1 H), 1.97-1.85 (m, 1 H), 1.05 (br. s., 1 H), 0.85 (d, J = 7.6 Hz, 1 H). |
| 351 | 8-((3-((1S,5R,6S)-3-amino-5-(difluoromethyl)-2-oxa-4-azabicyclo[4.1.0]hept-3-en-5-yl)-4-chlorophenyl)amino)-5-fluoro-1,7-naphthyridine-3-carbonitrile | 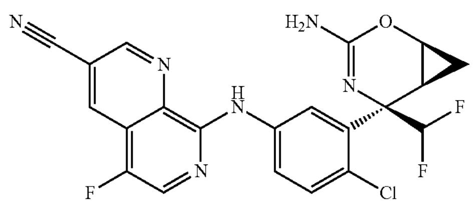 [SMILES: N#Cc1cnc2c(Nc3ccc(Cl)c([C@]4(C(F)F)N=C(N)O[C@H]5C[C@H]54)c3)ncc(F)c2c1] | MS m/z = 458.9 [M + H]+<br>1H NMR (400 MHz, DMSO-d6) d = 9.83 (br. s., 1 H), 9.34 (s, 1 H), 9.17 (s, 1 H), 8.74 (br. s., 1 H), 8.33 (s, 1 H), 7.96 (d, J = 8.6 Hz, 1 H), 7.42 (d, J = 8.6 Hz, 1 H), 6.97-6.58 (m, 1 H), 5.95 (br. s., 2 H), 3.96 (br. s., 1 H), 2.04-1.91 (m, 1 H), 1.13 (br. s., 1 H), 0.93 (d, J = 7.4 Hz, 1 H). |
| 352 | 8-((3-((1R,5S,6R)-3-amino-5-(difluoromethyl)-2-oxa-4-azabicyclo[4.1.0]hept-3-en-5-yl)-4-fluorophenyl)amino)-5-fluoro-1,7-naphthyridine-3-carbonitrile | 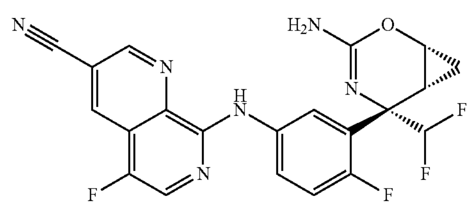 [SMILES: N#Cc1cnc2c(Nc3ccc(F)c([C@@]4(C(F)F)N=C(N)O[C@@H]5C[C@@H]54)c3)ncc(F)c2c1] | MS m/z = 442.9 [M + H]+<br>1H NMR (400 MHz, DMSO-d6) δ ppm 0.87-0.94 (m, 1 H) 1.15-1.21 (m, 1 H) 1.71-1.81 (m, 1 H) 3.97-4.06 (m, 1 H) 5.92 (s, 2 H) 6.21 (t, J = 56.10 Hz, 1 H) 7.19 (dd, J = 11.64, 8.90 Hz, 1 H) 7.94 (dt, J = 8.46, 3.59 Hz, 1 H) 8.26 (s, 1 H) 8.43 (dd, J = 7.24, 2.74 Hz, 1 H) 9.14 (d, J = 1.96 Hz, 1 H) 9.32 (d, J = 1.96 Hz, 1 H) 9.75 (s, 1 H) |
| 353 | (1R,5S,6R)-5-(5-((7-chloropyrido[3,2-d]pyrimidin-4-yl)amino)-2-fluorophenyl)-5-(difluoromethyl)-2-oxa-4-azabicyclo[4.1.0]hept-3-en-3-amine | 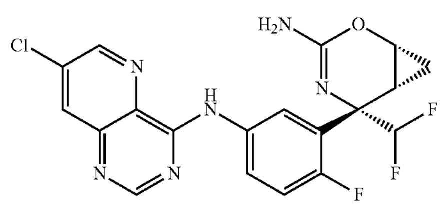 [SMILES: NC1=N[C@@](c2cc(Nc3ncnc4cc(Cl)cnc34)ccc2F)(C(F)F)[C@H]2C[C@H]2O1] | MS m/z = 434.9 [M + H]+<br>1H NMR (400 MHz, DMSO-d6) δ ppm 0.87-0.95 (m, 1 H) 1.14-1.21 (m, 1 H) 1.72-1.80 (m, 1 H) 3.99-4.07 (m, 1 H) 5.90 (s, 2 H) 6.21 (t, J = 55.90 Hz, 1 H) 7.24 (dd, J = 11.64, 8.90 Hz, 1 H) 7.92 (dt, J = 8.46, 3.50 Hz, 1 H) 8.37 (dd, J = 7.24, 2.74 Hz, 1 H) 8.40 (d, J = 2.35 Hz, 1 H) 8.68 (s, 1 H) 8.93 (d, J = 2.15 Hz, 1 H) 10.45 (s, 1 H) |
| 354 | (1S,5R,6S)-5-(2,6-difluoro-3-((2-methoxypyrido[3,4-b]pyrazin-5-yl)amino)phenyl)-5-(fluoromethyl)-2-oxa-4-azabicyclo[4.1.0]hept-3-en-3-amine | 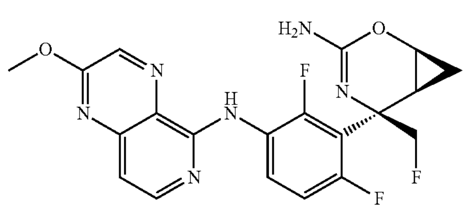 [SMILES: COc1cnc2c(Nc3ccc(F)c([C@]4(CF)N=C(N)O[C@H]5C[C@H]54)c3F)nccc2n1] | MS m/z = 430.9 [M + H]+<br>$^1$H NMR (300 MHz, DMSO-d$_6$) δ ppm 0.81-0.96 (m, 2 H) 1.50-1.64 (m, 1 H) 4.04-4.16 (m, 4 H) 4.29-4.97 (m, 2 H) 5.54 (s, 2 H) 7.03-7.15 (m, 2 H) 8.21 (d, J = 5.85 Hz, 1 H) 8.33-8.46 (m, 1 H) 8.60 (s, 1 H) 9.01 (d, J = 3.07 Hz, 1 H). |

TABLE 3-continued

| Example No | Compound Name | Compound Structure | Analytical Data |
|---|---|---|---|
| 355 | (1R,5S,6R)-5-(2,6-difluoro-3-((2-methoxypyrido[3,4-b]pyrazin-5-yl)amino)phenyl)-5-(fluoromethyl)-2-oxa-4-azabicyclo[4.1.0]hept-3-en-3-amine | 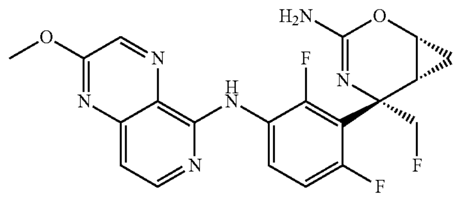 [SMILES: COc1cnc2c(Nc3ccc(F)c([C@@]4(CF)N=C(N)O[C@@H]5C[C@@H]54)c3F)nccc2n1] | MS m/z = 430.9 [M + H]+ $^1$H NMR (300 MHz, DMSO-d$_6$) δ ppm 0.82-0.97 (m, 2 H) 1.51-1.64 (m, 1 H) 4.04-4.17 (m, 4 H) 4.29-4.97 (m, 2 H) 5.54 (s, 2 H) 7.02-7.16 (m, 2 H) 8.21 (d, J = 5.85 Hz, 1 H) 8.33-8.46 (m, 1 H) 8.60 (s, 1 H) 9.01 (d, J = 3.22 Hz, 1 H). |
| 356 | (1R,5S,6R)-5-(3-chloro-2-fluoro-5-((2-methoxypyrido[3,4-b]pyrazin-5-yl)amino)phenyl)-5-(fluoromethyl)-2-oxa-4-azabicyclo[4.1.0]hept-3-en-amine | 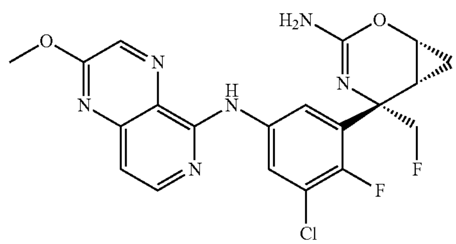 [SMILES: COc1cnc2c(Nc3cc(Cl)c(F)c([C@@]4(CF)N=C(N)O[C@@H]5C[C@@H]54)c3)nccc2n1] | MS m/z = 446.9 [M + H]+ $^1$H NMR (300 MHz, DMSO-d$_6$) δ ppm 0.79-0.92 (m, 1 H) 0.96-1.06 (m, 1 H) 1.51-1.65 (m, 1 H) 4.08 (s, 4 H) 4.38-4.79 (m, 2 H) 5.70 (s, 2 H) 7.13 (d, J = 5.85 Hz, 1 H) 8.17-8.26 (m, 1 H) 8.29 (d, J = 5.99 Hz, 1 H) 8.33-8.41 (m, 1 H) 8.57 (s, 1 H) 9.69 (s, 1 H). |
| 357 | (1R,5S,6R)-5-(3-chloro-2-fluoro-5-((2-isopropoxypyrido[3,4-b]pyrazin-5-yl)amino)phenyl)-5-(fluoromethyl)-2-oxa-4-azabicyclo[4.1.0]hept-3-en-3-amine | 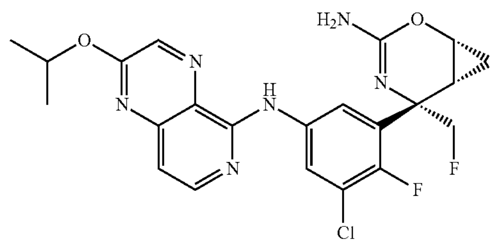 [SMILES: CC(C)Oc1cnc2c(Nc3cc(Cl)c(F)c([C@@]4(CF)N=C(N)O[C@@H]5C[C@@H]54)c3)nccc2n1] | MS m/z = 474.9 [M + H]+ $^1$H NMR (300 MHz, DMSO-d$_6$) δ ppm 0.85-0.97 (m, 1 H) 1.02-1.12 (m, 1 H) 1.48 (d, J = 6.14 Hz, 6 H) 1.58-1.72 (m, 1 H) 4.08-4.17 (m, 1 H) 4.46-4.84 (m, 2 H) 5.54 (s, 1 H) 5.76 (s, 2 H) 7.15 (d, J = 5.99 Hz, 1 H) 8.28 (d, J = 6.58 Hz, 1 H) 8.34 (d, J = 5.85 Hz, 1 H) 8.44 (d, J = 4.68 Hz, 1 H) 8.55 (s, 1 H) 9.73 (s, 1 H). |
| 358 | (1R,5S,6R)-5-difluoromethyl)-5-(2-fluoro-5-((2-methyl-2H-pyrazolo[3,4-c]pyridin-7-yl)amino)phenyl)-2-oxa-4-azabicyclo[4.1.0]hept-3-en-3-amine 2,2,2-trifluoroacetate | 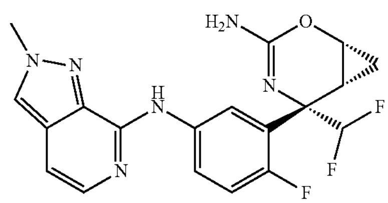 [SMILES: Cn1cc2ccnc(Nc3ccc(F)c([C@@]4(C(F)F)N=C(N)O[C@@H]5C[C@@H]54)c3)c2n1] | MS m/z = 403 [M + H]+ 1H NMR (300 MHz, CD3CN) d ppm 8.21 (s, 1 H), 7.54-7.69 (m, 2 H), 7.39-7.53 (m, 1 H), 7.10-7.26 (m, 2 H), 6.52 (t, J = 54.52 Hz, 1 H), 4.48 (td, J = 6.80, 2.78 Hz, 1 H), 4.21 (s, 3 H), 2.16 (dt, J = 9.83, 7.07 Hz, 1 H), 1.63 (t, J = 7.53 Hz, 1 H), 1.30 (td, J = 9.03, 6.50 Hz, 1 H) |
| 359 | (1R,5S,6R)-5-(2-chloro-5-((3-chloro-1,7-naphthyridin-8-yl)amino)phenyl)-5-(fluoromethyl)-2-oxa-4-azabicyclo[4.1.0]hept-3-en-3-amine | 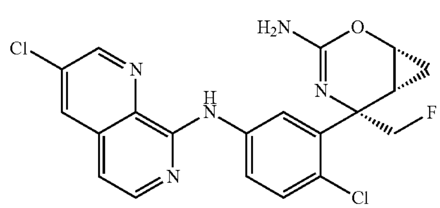 [SMILES: NC1=N[C@](CF)(c2cc(Nc3nccc4cc(Cl)cnc34)ccc2Cl)[C@H]2C[C@H]2O1] | MS m/z = 431.9 [M]+ 1H NMR (300 MHz, MeOD-d4) δ ppm 0.88-1.01 (m, 1 H) 1.08-1.18 (m, 1 H) 1.96-2.10 (m, 1 H) 3.96-4.06 (m, 1 H) 4.77-4.82 (m, 1 H) 4.92-5.04 (m, 1 H) 7.08 (d, J = 5.85 Hz, 1 H) 7.40 (d, J = 8.77 Hz, 1 H) 7.96 (dd, J = 8.62, 2.63 Hz, 1 H) 8.11 (d, J = 5.85 Hz, 1 H) 8.23-8.30 (m, 2 H) 8.81 (d, J = 2.19 Hz, 1 H) |
| 360 | (1R,5S,6R)-5-(2-chloro-5-((3-methoxy-1,7-naphthyridin-8-yl)amino)phenyl)-5-(fluoromethyl)-2-oxa-4-azabicyclo[4.1.0]hept-3-en-3-amine | 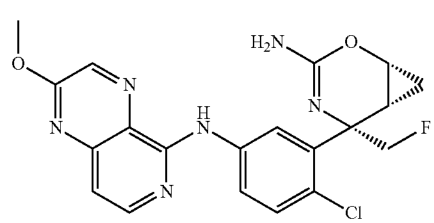 [SMILES: COc1cnc2c(Nc3ccc(Cl)c([C@@]4(CF)N=C(N)O[C@@H]5C[C@@H]54)c3)nccc2n1] | MS m/z = 428.0 [M + H]+ 1H NMR (300 MHz, Solvent) δ ppm 0.93-1.01 (m, 1 H) 1.13-1.19 (m, 1 H) 1.99-2.07 (m, 1 H) 4.01 (s, 3 H) 4.02-4.08 (m, 1 H) 4.83-4.84 (m, 1 H) 4.95-5.02 (m, 1 H) 7.06-7.12 (m, 1 H) 7.40 (d, J = 8.62 Hz, 1 H) 7.56 (s, 1 H) 7.97 (dd, J = 8.62, 2.78 Hz, 1 H) 8.02 (d, J = 5.85 Hz, 1 H) 8.22 (d, J = 2.78 Hz, 1 H) 8.57 (d, J = 2.78 Hz, 1 H) |

TABLE 3-continued

| Example No | Compound Name | Compound Structure | Analytical Data |
|---|---|---|---|
| 361 | (1R,5S,6R)-5-(5-((3-chloro-5-fluoro-1,7-naphthyridin-8-yl)amino)-2-fluorophenyl)-5-(difluoromethyl)-2-oxa-4-azabicyclo[4.1.0]hept-3-en-3-amine | 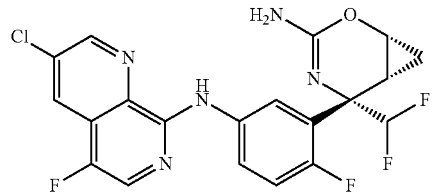 [SMILES: NC1=N[C@@](c2cc(Nc3ncc(F)c4cc(Cl)cnc34)ccc2F)(C(F)F)[C@H]2C[C@H]2O1] | MS m/z = 452.0 [M + H]+ <br> $^1$H NMR (300 MHz, DMSO-d$_6$) ppm 0.80-0.98 (m, 1 H) 1.17 (br. s., 1 H) 1.66-1.86 (m, 1 H) 4.01 (t, J = 5.55 Hz, 1 H) 5.91 (s, 2 H) 6.00-6.50 (m, 1 H) 7.17 (dd, J = 11.77, 8.84 Hz, 1 H) 7.84-8.02 (m, 1 H) 8.19 (d, J = 1.32 Hz, 1 H) 8.40 (dd, J = 7.09, 2.85 Hz, 1 H) 8.59 (d, J = 2.34 Hz, 1 H) 9.01 (d, J = 2.34 Hz, 1 H) 9.61 (s, 1 H) |
| 362 | (1R,5S,6R)-5-(5-((3-chloro-1,7-naphthyridin-8-yl)amino)-2-fluorophenyl)-5-(difluoromethyl)-2-oxa-4-azabicyclo[4.1.0]hept-3-en-3-amine | 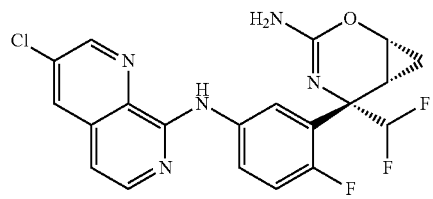 [SMILES: NC1=N[C@@](c2cc(Nc3nccc4cc(Cl)cnc34)ccc2F)(C(F)F)[C@H]2C[C@H]2O1] | MS m/z = 434.0 [M + H]+ <br> $^1$H NMR (300 MHz, DMSO-d$_6$) ppm 0.91 (d, J = 9.21 Hz, 1 H) 1.17 (br. s., 1 H) 1.76 (d, J = 9.21 Hz, 1 H) 4.03 (t, J = 5.19 Hz, 1 H) 5.90 (s, 2 H) 5.99-6.43 (m, 1 H) 7.10-7.26 (m, 2 H) 7.96-8.09 (m, 1 H) 8.15 (d, J = 5.70 Hz, 1 H) 8.32 (dd, J = 7.02, 2.63 Hz, 1 H) 8.51 (d, J = 2.34 Hz, 1 H) 8.90 (d, J = 2.34 Hz, 1 H) 9.61 (s, 1 H) |
| 363 | 8-((3-((1R,5S,6R)-3-amino-5-(fluoromethyl)-2-oxa-4-azabicyclo[4.1.0]hept-3-en-5-yl)-4-chlorophenyl)amino)-5-fluoro-1,7-naphthyridine-3-carbonitrile | 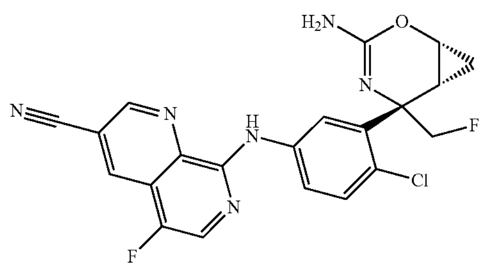 [SMILES: N#Cc1cnc2c(Nc3ccc(Cl)c([C@@]4(CF)N=C(N)O[C@@H]5C[C@@H]54)c3)ncc(F)c2c1] | MS m/z = 441.0 [M + H]+ <br> $^1$H NMR (300 MHz, DMSO-d$_6$) ppm 0.84 (dt, J = 9.57, 6.39 Hz, 1 H) 1.00 (td, J = 6.43, 2.63 Hz, 1 H) 1.78 (dt, J = 9.46, 7.03 Hz, 1 H) 3.84-4.01 (m, 1 H) 4.70 (d, J = 2.48 Hz, 1 H) 4.87 (s, 1 H) 5.69 (s, 2 H) 7.38 (d, J = 8.77 Hz, 1 H) 7.96 (dd, J = 8.70, 2.70 Hz, 1 H) 8.31 (d, J = 1.02 Hz, 1 H) 8.58 (d, J = 2.63 Hz, 1 H) 9.15 (d, J = 2.05 Hz, 1 H) 9.33 (d, J = 1.90 Hz, 1 H) 9.78 (s, 1 H) |
| 364 | (1R,5S,6R)-5-(difluoromethyl)-5-(2-fluoro-5-((7-methoxypyrido[3,2-d]pyrimidin-4-yl)amino)phenyl)-2-oxa-4-azabicyclo[4.1.0]hept-3-en-3-amine | 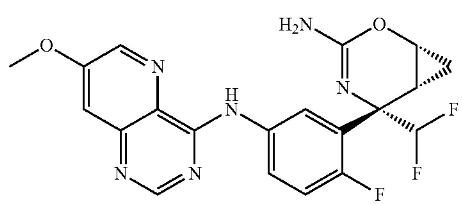 | MS m/z = 431.1 [M + H]+ <br> 1H NMR (400 MHz, MeOH-d4) δ: 8.59-8.63 (m, 2H), 8.41 (dd, J = 7.0, 2.5 Hz, 1H), 7.87-7.93 (m, 1H), 7.47 (d, J = 2.7 Hz, 1H), 7.30 (dd, J = 11.7, 8.8 Hz, 1H), 6.41-6.71 (m, 1H), 4.42 (t, J = 5.3 Hz, 1H), 4.03 (s, 3H), 2.10-2.18 (m, 1H), 1.54-1.60 (m, 1H), 1.19-1.28 (m, 1H) |
| 365 | (1R,5S,6R)-5-(difluoromethyl)-5-(2-fluoro-5-((2-(trifluoromethyl)pyrido[3,4-b]pyrazin-5-yl)amino)phenyl)-2-oxa-4-azabicyclo[4.1.0]hept-3-en-3-amine | 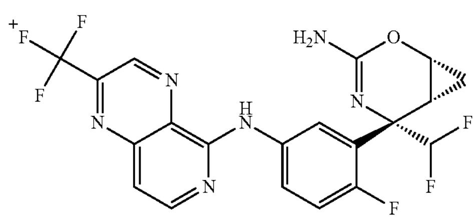 | MS m/z = 469.1 [M + H]+ <br> 1H NMR (400 MHz, MeOH-d4) δ: 9.21 (s, 1H), 8.38 (d, J = 6.1 Hz, 1H), 8.21 (dd, J = 7.0, 2.7 Hz, 1H), 7.90-7.99 (m, 1H), 7.31 (d, J = 6.1 Hz, 1H), 7.18 (dd, J = 11.6, 8.9 Hz, 1H), 6.16-6.50 (m, 1H), 4.07 (t, J = 5.5 Hz, 1H), 1.88-1.96 (m, 1H), 1.36 (br. s., 1H), 0.94-1.04 (m, 1H) |
| 446 | 8-((3-((1R,5S,6R)-3-amino-5-(difluoromethyl)-2-oxa-4-azabicyclo[4.1.0]hept-3-en-5-yl)-4-fluorophenyl)amino)-1,7-naphthyridine-3-carbonitrile | 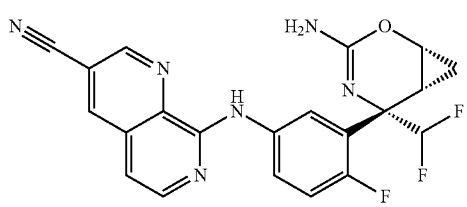 | MS m/z = 425.1 [M + H]+ <br> 1H NMR (MeOH) δ: 9.09 (d, J = 2.0 Hz, 1H), 8.74 (d, J = 2.0 Hz, 1H), 8.63 (dd, J = 7.0, 2.5 Hz, 1H), 8.21 (d, J = 5.9 Hz, 1H), 7.90 (dt, J = 8.9, 3.4 Hz, 1H), 7.29-7.37 (m, 1H), 7.23 (d, J = 5.9 Hz, 1H), 6.51-6.87 (m, 1H), 4.61 (td, J = 6.7, 2.5 Hz, 1H), 2.20-2.32 (m, 1H), 1.69 (t, J = 7.2 Hz, 1H), 1.30-1.44 (m, 1H) |

TABLE 3-continued

| Example No | Compound Name | Compound Structure | Analytical Data |
|---|---|---|---|
| 447 | (1R,5S,6R)-5-(difluoromethyl)-5-(2-fluoro-5-((2-methoxypyrido[3,4-b]pyrazin-5-yl)amino)phenyl)-2-oxa-4-azabicyclo[4.1.0]hept-3-en-3-amine | 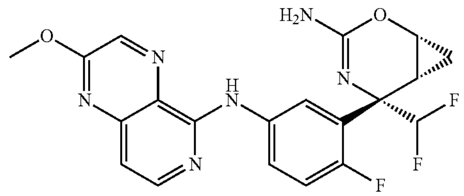 [SMILES: COc1cnc2c(Nc3ccc(F)c([C@@]4(C(F)F)N=C(N)O[C@@H]5C[C@@H]54)c3)nccc2n1] | MS m/z = 431.1 [M + H]+ 1H NMR (MeOH) δ: 8.44 (s, 1H), 8.20 (d, J = 6.1 Hz, 2H), 7.89 (dt, J = 8.8, 3.4 Hz, 1H), 7.20 (dd, J = 11.7, 8.8 Hz, 1H), 7.09 (d, J = 5.9 Hz, 1H), 6.21-6.61 (m, 1H), 4.22 (t, J = 5.6 Hz, 1H), 4.15 (s, 3H), 1.97-2.08 (m, 1H), 1.45 (t, J = 6.7 Hz, 1H), 1.06-1.14 (m, 1H) |
| 448 | (1R,5S,6R)-5-(difluoromethyl)-5-(2-fluoro-5-((5-fluoro-3-methoxy-1,7-naphthyridin-8-yl)amino)phenyl)-2-oxa-4-azabicyclo[4.1.0]hept-3-en-3-amine | 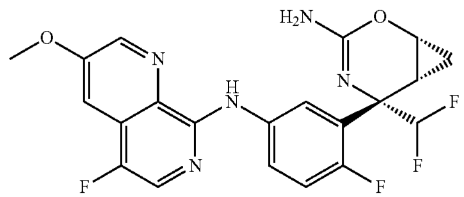 [SMILES: COc1cnc2c(Nc3ccc(F)c([C@@]4(C(F)F)N=C(N)O[C@@H]5C[C@@H]54)c3)ncc(F)c2c1] | MS m/z = 448.1 [M + H]+ 1H NMR (DMSO-d6) δ: 9.39 (s, 1H), 8.71 (d, J = 2.5 Hz, 1H), 8.34 (d, J = 4.9 Hz, 1H), 8.10 (s, 1H), 7.98 (d, J = 8.6 Hz, 1H), 7.71 (d, J = 2.3 Hz, 1H), 7.08-7.21 (m, 1H), 6.05-6.39 (m, 1H), 5.91 (s, 2H), 4.01-4.07 (m, 4H), 1.71-1.81 (m, 1H), 1.17 (br. s., 1H), 0.85-0.94 (m, 1H) |
| 449 | (1R,5S,6R)-5-(difluoromethyl)-5-(2-fluoro-5-((7-(trifluoromethyl)pyrido[3,2-d]pyrimidin-4-yl)amino)phenyl)-2-oxa-4-azabicyclo[4.1.0]hept-3-en-3-amine | 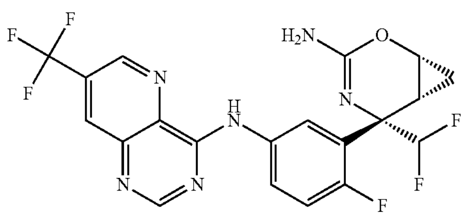 [SMILES: NC1=N[C@@](c2cc(Nc3ncnc4cc(C(F)(F)F)cnc34)ccc2F)(C(F)F)[C@H]2C[C@H]2O1] | MS m/z = 469.1 [M + H]+ 1H NMR (DMSO-d6) δ: 10.62 (s, 1H), 9.22 (d, J = 2.0 Hz, 1H), 8.77 (s, 1H), 8.66 (s, 1H), 8.40 (dd, J = 7.2, 2.7 Hz, 1H), 7.91-7.98 (m, 1H), 7.26 (dd, J = 11.7, 8.8 Hz, 1H), 6.04-6.39 (m, 1H), 5.92 (s, 2H), 3.94-4.10 (m, 1H), 1.70-1.85 (m, 1H), 1.18 (br. s., 1H), 0.80-0.99 (m, 1H) |

Method I

Example 366

Synthesis of 8-((3-((1S,5R,6S)-3-amino-5-(difluoromethyl)-2-oxa-4-azabicyclo[4.1.0]hept-3-en-5-yl)-4,5-difluorophenyl)amino)-5-fluoro-1,7-naphthyridine-3-carbonitrile

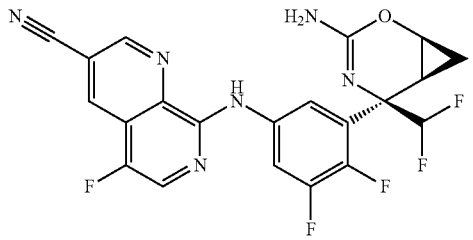 [SMILES: N#Cc1cnc2c(Nc3cc(F)c(F)c([C@]4(C(F)F)N=C(N)O[C@H]5C[C@H]54)c3)ncc(F)c2c1]

A sealable vial was charged with (1S,5R,6S)-5-(5-amino-2,3-difluorophenyl)-5-(difluoromethyl)-2-oxa-4-azabicyclo[4.1.0]hept-3-en-3-amine (20f-A, 0.100 g, 0.346 mmol), chloro[2-(dicyclohexylphosphino)-3,6-dimethoxy-2',4',6'-triisopropyl-1,1'-biphenyl][2-(2-aminoethyl)phenyl]palladium(II) (0.025 g, 0.031 mmol), 8-chloro-5-fluoro-1,7-naphthyridine-3-carbonitrile (0.080 g, 0.385 mmol), and potassium bis(trimethylsilyl)amide (0.075 g, 0.376 mmol). The vial was evacuated and backfilled with nitrogen. Dioxane (0.4 mL) was added and the reaction mixture was heated to 70° C. for 1 hour. The reaction mixture was partitioned between water (40 mL), aqueous saturated sodium bicarbonate solution (10 mL) and ethyl acetate (100 mL). The organic phase was separated and was dried over magnesium sulfate. The filtrate was concentrated under reduced pressure and the residue was purified by reverse-phase preparative HPLC using a Phenomenex Gemini column, 10 micron, C18, 100 Å, 150×30 mm, 0.1% TFA in CH₃CN/H₂O, gradient 30% to 70% over 15 min to provide the purified product as the TFA salt. The product was partitioned between DCM and aq. 10% Na₂CO₃. The layers were separated and the aqueous layer was extracted with DCM. The combined organic extracts were washed with brine and dried over sodium sulfate. The filtrate was concentrated in vacuo to afford the title compound as the free base (0.0576 g, 0.125 mmol, 36.2% yield). MS m/z=461 [M+H]+

1H NMR (CHLOROFORM-d) Shift: 8.92 (d, J=1.9 Hz, 1H), 8.71 (br. s, 1H), 8.66 (d, J=1.9 Hz, 1H), 8.20 (ddd, J=12.4, 6.9, 2.8 Hz, 1H), 8.06 (d, J=1.0 Hz, 1H), 7.34 (dt, J=5.1, 2.6 Hz, 1H), 6.23 (td, J=56.0, 0.9 Hz, 1H), 3.89-3.99 (m, 1H), 1.82-1.93 (m, 1H), 1.60 (br. s., 2H), 1.40-1.48 (m, 1H), 0.94-1.05 (m, 1H)

Example 367

Synthesis of 8-((3-((1R,5S,6R)-3-amino-5-(difluoromethyl)-2-oxa-4-azabicyclo[4.1.0]hept-3-en-5-yl)-4,5-difluorophenyl)amino)-5-fluoro-1,7-naphthyridine-3-carbonitrile

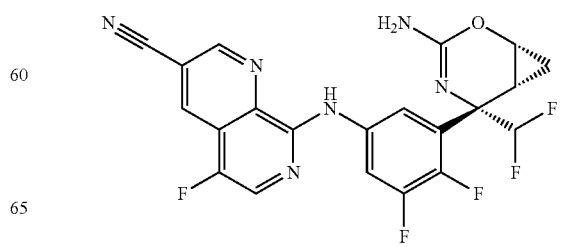

The titled compound was synthesized according to Method I, but using (1R,5S,6R)-5-(5-amino-2,3-difluorophenyl)-5-(difluoromethyl)-2-oxa-4-azabicyclo[4.1.0]hept-3-en-3-amine (20f-B). MS m/z=461 [M+H]⁺

1H NMR (CHLOROFORM-d) Shift: 8.91 (d, J=1.9 Hz, 1H), 8.71 (br. s, 1H), 8.65 (d, J=1.9 Hz, 1H), 8.20 (ddd, J=12.4, 6.9, 2.8 Hz, 1H), 8.06 (d, J=1.0 Hz, 1H), 7.34 (dt, J=5.1, 2.6 Hz, 1H), 6.23 (td, J=55.9, 1.0 Hz, 1H), 3.87-3.99 (m, 1H), 1.83-1.95 (m, 1H), 1.61 (br. s., 2H), 1.41-1.48 (m, 1H), 0.94-1.05 (m, 1H)

Method K:

Example 368

Synthesis of (1R,5S,6R)-5-(5-(((cyclobutylmethyl)amino)-2-fluorophenyl)-5-(difluoromethyl)-2-oxa-4-azabicyclo[4.1.0]hept-3-en-3-amine

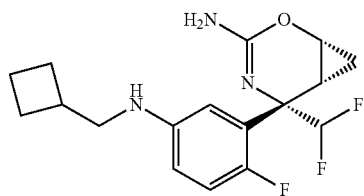 [SMILES: NC1=N[C@@](c2cc(NCC3CCC3)ccc2F)(C(F)F)[C@H]2C[C@H]2O1]

To a solution of (1R,5S,6R)-5-(5-amino-2-fluorophenyl)-5-(difluoromethyl)-2-oxa-4-azabicyclo[4.1.0]hept-3-en-3-amine (16g-B, 50 mg, 0.184 mmol) in 1,2-dichloroethane (1.2 mL) was added cyclobutanecarbaldehyde (15.51 mg, 0.184 mmol) and sodium triacetoxyborohydride (0.033 mL, 0.221 mmol). After addition, the mixture was then stirred at room temperature for 3 h. Additional cyclobutanecarbaldehyde (15.51 mg, 0.184 mmol) was added and the mixture was stirred at room temperature for additional 30 min. The mixture was quenched with saturated NaHCO3 and extracted with DCM (1×6 mL). The organic layer was collected, dried over MgSO4, and concentrated. The residue was then dissolved in MeOH and solution mixture was purified by preparative HPLC (0%-100% MeCN 0.1% TFA/H2O 0.1% TFA) to give a desired product, which was dissolved in MeOH. The solution was loaded onto a PL-HCO₃ MP SPE 200 mg/6 mL column and eluted with MeOH (2×2 mL). The combined eluates were concentrated and dried in vacuo to give 30 mg of the title compound as a light yellow solid. MS m/z=340.1 [M+H]⁺

1H NMR (MeOH) δ: 6.91 (t, J=10.3 Hz, 1H), 6.64 (d, J=6.3 Hz, 1H), 6.58 (d, J=7.8 Hz, 1H), 6.16-6.48 (m, 1H), 4.12 (br. s., 1H), 3.05 (d, J=7.0 Hz, 2H), 2.59 (dt, J=15.0, 7.4 Hz, 1H), 2.10 (br. s., 2H), 1.85-1.99 (m, 3H), 1.70-1.81 (m, 2H), 1.36 (br. s., 1H), 1.01 (q, J=7.6 Hz, 1H)

Examples 369-376 listed in Table 4 were synthesized according to Method K using the appropriate aniline and aldehyde or ketone:

TABLE 4

| Example No | Compound Name | Compound Structure | Analytical Data |
| --- | --- | --- | --- |
| 369 | (1R,5S,6R)-5-(difluoromethyl)-5-(2-fluoro-5-((3-phenylprop-2-yn-1-yl)amino)phenyl)-2-oxa-4-azabicyclo[4.1.0]hept-3-en-3-amine | 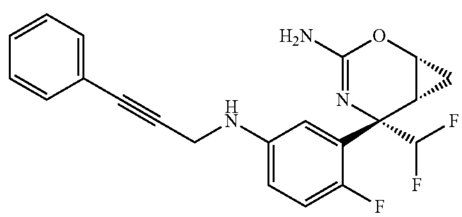 [SMILES: NC1=N[C@@](c2cc(NCC#Cc3ccccc3)ccc2F)(C(F)F)[C@H]2C[C@H]2O1] | MS m/z = 386.1 [M + H]+ 1H NMR (MeOH) δ: 7.35-7.40 (m, 2H), 7.28-7.33 (m, 3H), 7.05 (dd, J = 12.0, 8.7 Hz, 1H), 6.78-6.87 (m, 2H), 6.24-6.55 (m, 1H), 4.17-4.22 (m, 1H), 4.14 (s, 2H), 1.94-2.03 (m, 1H), 1.43 (t, J = 6.9 Hz, 1H), 1.05-1.13 (m, 1H) |
| 370 | (1R,5S,6R)-5-(5-(((1-(4-chlorophenyl)cyclopropyl)methyl)amino)-2-fluorophenyl)-5-(difluoromethyl)-2-oxa-4-azabicyclo[4.1.0]hept-3-en-3-amine | 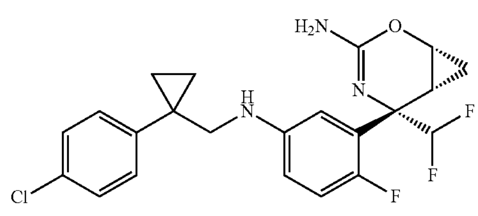 [SMILES: NC1=N[C@@](c2cc(NCC3(c4ccc(Cl)cc4)CC3)ccc2F)(C(F)F)[C@H]2C[C@H]2O1] | MS m/z = 436.1 [M + H]+ 1H NMR (MeOH) δ: 7.33-7.38 (m, 2H), 7.25-7.29 (m, 2H), 6.88 (dd, J = 11.9, 8.8 Hz, 1H), 6.65 (dd, J = 6.7, 2.9 Hz, 1H), 6.54 (dt, J = 8.9, 3.4 Hz, 1H), 6.13-6.44 (m, 1H), 4.07 (br. s., 1H), 3.30 (d, J = 9.2 Hz, 2H), 1.81-1.90 (m, 1H), 1.33 (d, J = 4.3 Hz, 1H), 0.92-1.04 (m, 3H), 0.84-0.90 (m, 2H) |
| 371 | (1R,5S,6R)-5-(difluoromethyl)-5-(2-fluoro-5-(((((1(S,R),2(S,R))-2-phenylcyclopropyl)methyl)amino)phenyl)-2-oxa-4-azabicyclo[4.1.0]hept-3-en-3-amine | 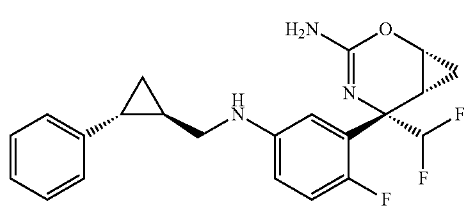 [SMILES: NC1=N[C@@](c2cc(NC[C@@H]3C[C@H]3c3ccccc3)ccc2F)(C(F)F)[C@H]2C[C@H]2O1] | MS m/z = 402 [M + H]+ 1H NMR (MeOH) δ: 7.20-7.28 (m, 2H), 7.05-7.17 (m, 4H), 6.45-6.83 (m, 3H), 4.58 (dt, J = 6.7, 3.6 Hz, 1H), 3.17 (dt, J = 6.3, 3.0 Hz, 2H), 2.19 (dt, J = 9.8, 7.0 Hz, 1H), 1.84-1.92 (m, 1H), 1.60-1.68 (m, 1H), 1.38-1.47 (m, 1H), 1.31-1.38 (m, 1H), 0.95-1.02 (m, 2H) |

TABLE 4-continued

| Example No | Compound Name | Compound Structure | Analytical Data |
|---|---|---|---|
| 372 | (1R,5S,6R)-5-(difluoromethyl)-5-(2-fluoro-5-(((((1(S,R),2(R,S))-2-phenylcyclopropyl)methyl)amino)phenyl)-2-oxa-4-azabicyclo[4.1.0]hept-3-en-3-amine | 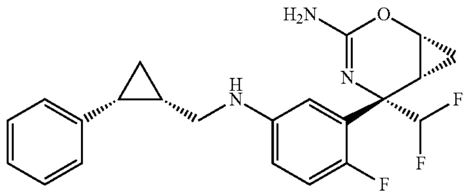 [SMILES: NC1=N[C@@](c2cc(NC[C@H]3C[C@H]3c3ccccc3)ccc2F)(C(F)F)[C@H]2C[C@H]2O1] | MS m/z = 402 [M + H]+ 1H NMR (MeOH) δ: 7.17-7.33 (m, 5H), 6.98 (dd, J = 12.1, 9.0 Hz, 1H), 6.37-6.69 (m, 3H), 4.49 (br. s., 1H), 2.70-2.83 (m, 2H), 2.29-2.36 (m, 1H), 2.05-2.14 (m, 1H), 1.58 (br. s., 1H), 1.45-1.53 (m, 1H), 1.24-1.32 (m, 1H), 1.08-1.15 (m, 1H), 0.95 (q, J = 5.7 Hz, 1H) |
| 373 | (1R,5S,6R)-5-(5-(((4-chloro-1-(difluoromethyl)-1H-pyrazol-3-yl)methyl)amino)-2-fluorophenyl)-5-(fluoromethyl)-2-oxa-4-azabicyclo[4.1.0]hept-3-en-3-amine | 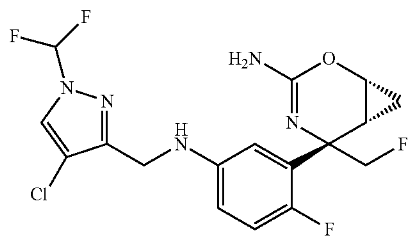 [SMILES: NC1=N[C@](CF)(c2cc(NCc3nn(C(F)F)cc3Cl)ccc2F)[C@H]2C[C@H]2O1] | MS m/z = 418 [M + H]+ (300 MHz, CHLOROFORM-d) d: 0.86 (m, 1 H), 1.18 (m, 1 H), 1.71 (m, 1 H), 3.88 (m, 1 H), 4.20 (m, 1 H), 4.31 (d, J = 5.7 Hz, 2 H), 4.60 (dd, J = 47.1, 10.2 Hz, 1 H), 4.69 (dd, J = 49.1, 10.2 Hz, 1 H), 6.59 (dt, J = 8.7, 3.4, 3.4 Hz, 1 H), 6.83 (dd, J = 6.7, 2.9 Hz, 1 H), 6.91 (dd, J = 11.7, 8.7 Hz, 1 H), 7.09 (t, J = 60.5 Hz, 1 H), 7.78 (s, 1 H). |
| 374 | (1R,5R,6R)-5-(5-(((4-chloro-1-(difluoromethyl)-1H-pyrazol-3-yl)methyl)amino)-2-fluorophenyl)-5-(difluoromethyl)-2-oxa-4-azabicyclo[4.1.0]hept-3-en-3-amine | 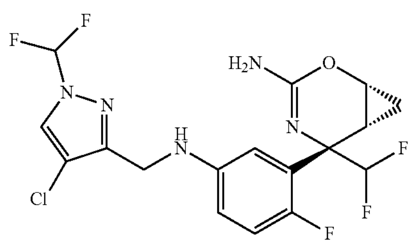 [SMILES: NC1=N[C@@](c2cc(NCc3nn(C(F)F)cc3Cl)ccc2F)(C(F)F)[C@H]2C[C@H]2O1] | MS m/z = 435.8 [M + H]+ (300 MHz, CHOROFORM-d) d: 0.90 (m, 1 H), 1.36 (m, 1 H), 1.80 (m, 1 H), 3.87 (m, 1 H), 4.21 (br, 1 H), 4.30 (d, J = 5.7 Hz, 2 H), 6.21 (t, J = 55.8 Hz, 1 H), 6.62 (m, 1 H), 6.84 (dd, J = 6.5, 2.9 Hz, 1 H), 6.92 (dd, J = 11.7, 8.6 Hz, 1 H), 7.09 (t, J = 60.5 Hz, 1 H), 7.78 (s, 1 H). |
| 375 | (1R,5S,6R)-5-(difluoromethyl)-5-(2-fluoro-5-(((3-methylenecyclobutyl)methyl)amino)phenyl)-2-oxa-4-azabicyclo[4.1.0]hept-3-en-3-amine | 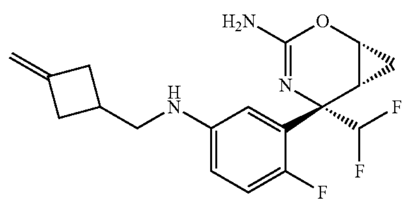 [SMILES: C=C1CC(CNc2ccc(F)c([C@@]3(C(F)F)N=C(N)O[C@@H]4C[C@@H]43)c2)C1] | MS m/z = 352.1 [M + H]+ 1H NMR (400 MHz, MeOH-d4) δ: 6.92 (dd, J = 12.0, 8.7 Hz, 1H), 6.71 (dd, J = 6.5, 2.9 Hz, 1H), 6.60 (dt, J = 8.8, 3.4 Hz, 1H), 6.13-6.44 (m, 1H), 4.77 (t, J = 2.3 Hz, 2H), 4.01-4.07 (m, 1H), 3.14 (d, J = 7.2 Hz, 2H), 2.79-2.88 (m, 2H), 2.53-2.64 (m, 1H), 2.40-2.48 (m, 2H), 1.82-1.91 (m, 1H), 1.30-1.36 (m, 1H), 0.96 (dt, J = 9.2, 6.7 Hz, 1H) |
| 376 | (1R,5S,6R)-5-(difluoromethyl)-5-(2-fluoro-5-(((1-(trifluoromethyl)cyclopropyl)methyl)amino)phenyl)-2-oxa-4-azabicyclo[4.1.0]hept-3-en-3-amine | 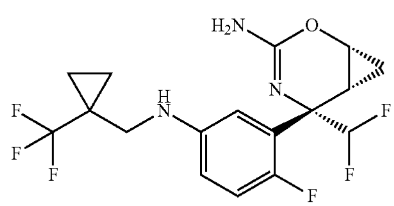 [SMILES: NC1=N[C@@](c2cc(NCC3(C(F)(F)F)CC3)ccc2F)(C(F)F)[C@H]2C[C@H]2O1] | MS m/z = 394.1 [M + H]+ 1H NMR (400 MHz, MeOH-d4) δ: 6.93 (dd, J = 11.9, 8.8 Hz, 1H), 6.71 (dd, J = 6.6, 3.0 Hz, 1H), 6.58 (dt, J = 8.7, 3.4 Hz, 1H), 6.10-6.41 (m, 1H), 3.97-4.03 (m, 1H), 1.80-1.87 (m, 1H), 1.30 (t, J = 6.4 Hz, 1H), 0.91-0.99 (m, 3H), 0.81 (br. s., 2H) |

Method L:

Example 377

Synthesis of (1R,5S,6R)-5-(5-(((5-chloropyridin-2-yl)methyl)amino)-2-fluorophenyl)-5-(difluoromethyl)-2-oxa-4-azabicyclo[4.1.0]hept-3-en-3-amine

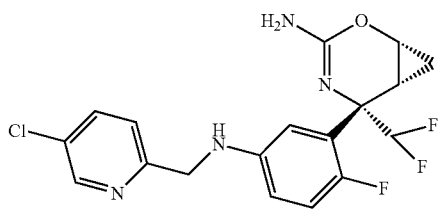 [SMILES: NC1=N[C@@](c2cc(NCc3ccc(Cl)cn3)ccc2F)(C(F)F)[C@H]2C[C@H]2O1]

To a solution of tert-butyl((1R,5S,6R)-5-(5-amino-2-fluorophenyl)-5-(difluoromethyl)-2-oxa-4-azabicyclo[4.1.0]hept-3-en-3-yl)carbamate (16i-B, 0.072 g, 0.194 mmol) and 5-chloropicolinaldehyde (0.028 g, 0.198 mmol) in DCE (1 mL) at RT was added HOAc (0.011 ml, 0.194 mmol) and sodium triacetoxyborohydride (0.050 g, 0.236 mmol). The reaction mixture was stirred at RT for 1.5 h. Trifluoroacetic acid (2.0 ml, 26.9 mmol) was added and after 15 min, and the reaction mixture was diluted with EtOAc and water. The pH was adjusted to 9 with 10 M NaOH. The aqueous phase was extracted with EtOAc and the combined organic extracts were washed with brine and dried over $MgSO_4$. The filtrate was concentrated under reduced pressure and the residue was purified by flash column chromatography on silica gel (60% to 100% EtOAc in heptane) to give the title compound (0.064 g, 0.161 mmol, 83% yield) as a white solid.

MS m/z=397.1 [M+H]+

1H NMR (400 MHz, CDCl3) δ 0.83-0.92 (m, 1H), 1.39 (t, J=6.85 Hz, 1H), 1.66-1.89 (m, 1H), 3.79-3.87 (m, 1H), 4.24 (d, J=4.50 Hz, 2H), 4.63 (br s, 1H), 4.99 (br s, 2H), 6.23 (t, J=56.1 Hz, 1H), 6.41 (dt, J=8.51, 3.37 Hz, 1H), 6.77-6.87 (m, 2H), 7.14 (d, J=8.41 Hz, 1H), 7.56 (dd, J=8.41, 2.35 Hz, 1H), 8.48 (d, J=2.35 Hz, 1H)

Examples 378-385 listed in Table 5 were synthesized according to Method L using the appropriate Boc-protected aniline and aldehyde or ketone:

TABLE 5

| Example No | Compound Name | Compound Structure | Analytical Data |
|---|---|---|---|
| 378 | (1R,5S,6R)-5-(5-(((R)-1-(5-chloropyridin-2-yl)ethyl)amino)-2-fluorophenyl)-5-(difluoromethyl)-2-oxa-4-azabicyclo[4.1.0]hept-3-en-3-amine and (1R,5S,6R)-5-(5-(((S)-1-(5-chloropyridin-2-yl)ethyl)amino)-2-fluorophenyl)-5-(difluoromethyl)-2-oxa-4-azabicyclo[4.1.0]hept-3-en-3-amine | 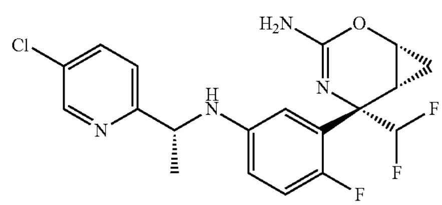 [SMILES: C[C@@H](Nc1ccc(F)c([C@@]2(C(F)F)N=C(N)O[C@@H]3C[C@@H]32)c1)c1ccc(Cl)cn1] | MS m/z = 411 [M + H]+ 1H NMR (400 MHz, CDCl3) δ 0.86-0.95 (m, 1H), 1.31-1.41 (m, 1H), 1.44-1.49 (m, 3H), 1.72-1.82 (m, 1H), 3.78-3.89 (m, 1H), 4.31 (br s, 1H), 4.43-4.54 (m, 1H), 4.69 (s br, 2H), 6.19 (t, J = 56.14 Hz, 1H), 6.30-6.38 (m, 1H), 6.64-6.74 (m, 1H), 6.81 (ddd, J = 11.74, 8.61, 3.33 Hz, 1H), 7.24-7.28 (m, 1H), 7.56 (ddd, J = 8.61, 6.46, 2.54 Hz, 1H), 8.50 (dd, J = 7.92, 2.05 Hz, 1H) |
| 379 | (1R,5S,6R)-5-(5-((cyclopropylmethyl)amino)-2-fluorophenyl)-5-(difluoromethyl)-2-oxa-4-azabicyclo[4.1.0]hept-3-en-3-amine | 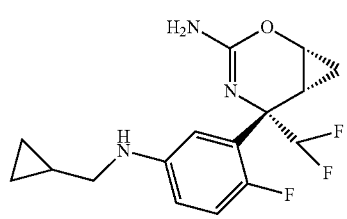 [SMILES: NC1=N[C@@](c2cc(NCC3CC3)ccc2F)(C(F)F)[C@H]2C[C@H]2O1] | MS m/z = 326[M + H]+ 1H NMR (400 MHz, CDCl3) δ 0.15-0.23 (m, 2H), 0.48-0.55 (m, 2H), 0.84-0.95 (m, 1H), 0.97-1.09 (m, 1H), 1.37 (t, J = 6.26 Hz, 1H), 1.76-1.86 (m, 1H), 2.87 (d, J = 6.85 Hz, 2H), 3.70 (s br, 1H), 3.84-3.88 (m, 1H), 4.52 (s br, 2H), 6.22 (t, J = 56.10 Hz, 1H), 6.47 (dt, J = 8.61, 3.42 Hz, 1H), 6.72 (dd, J = 6.46, 2.93 Hz, 1H), 6.90 (dd, J = 11.74, 8.80 Hz, 1H) |

TABLE 5-continued

| Example No | Compound Name | Compound Structure | Analytical Data |
|---|---|---|---|
| 380 | (1R,5S,6R)-5-(5-(((R)-3-bromo-6,7-dihydro-5H-cyclopenta[b]pyridin-7-yl)amino)-2-fluorophenyl)-5-(difluoromethyl)-2-oxa-4-azabicyclo[4.1.0]hept-3-en-3-amine or (1R,5S,6R)-5-(5-(((S)-3-bromo-6,7-dihydro-5H-cyclopenta[b]pyridin-7-yl)amino)-2-fluorophenyl)-5-(difluoromethyl)-2-oxa-4-azabicyclo[4.1.0]hept-3-en-3-amine | | MS m/z = 467.0 [M + H]+. $^1$H NMR (400 MHz, CDCl$_3$) δ 0.87-0.94 (m, 1H), 1.38 (t, J = 6.70 Hz, 1H), 1.77-1.83 (m, 1H), 1.89-1.98 (m, 1H), 2.71-2.81 (m, 1H), 2.85-2.93 (m, 2H), 3.87 (t, J = 5.48 Hz, 1H), 4.40 (br s, 1H), 4.48 (s br, 2H), 4.62-4.68 (m, 1H), 6.24 (t, J = 55.90 Hz, 1H), 6.64 (dt, J = 8.61, 3.10 Hz, 1H), 6.88 (dd, J = 6.46, 2.93 Hz, 1H), 6.93 (dd, J = 11.54, 8.61 Hz, 1H), 7.68 (s, 1H), 8.47 (s, 1H). or $^1$H NMR (400 MHz, CDCl$_3$) δ 0.85-0.94 (m, 1H), 1.38 (t, J = 6.75 Hz, 1H), 1.72-1.93 (m, 2H), 2.72-2.97 (m, 3H), 3.83-3.88 (m, 1H), 4.41 (s br, 1H), 4.52-4.73 (m, 3H), 6.24 (t, J = 55.80 Hz, 1H), 6.61 (dt, J = 8.61, 3.42 Hz, 1H), 6.82 (dd, J = 6.46, 2.93 Hz, 1H), 6.89 (dd, J = 11.54, 8.61 Hz, 1H), 7.68 (s, 1H), 8.49 (s, 1H). |
| 381 | (1R,5S,6R)-5-(5-(((S)-3-bromo-6,7-dihydro-5H-cyclopenta[b]pyridin-7-yl)amino)-2-fluorophenyl)-5-(difluoromethyl)-2-oxa-4-azabicyclo[4.1.0]hept-3-en-3-amine or (1R,5S,6R)-5-(5-(((R)-3-bromo-6,7-dihydro-5H-cyclopenta[b]pyridin-7-yl)amino)-2-fluorophenyl)-5-(difluoromethyl)-2-oxa-4-azabicyclo[4.1.0]hept-3-en-3-amine | | MS m/z = 467.0 [M + H]+. $^1$H NMR (400 MHz, CDCl$_3$) δ 0.85-0.94 (m, 1H), 1.38 (t, J = 6.75 Hz, 1H), 1.72-1.93 (m, 2H), 2.72-2.97 (m, 3H), 3.83-3.88 (m, 1H), 4.41 (s br, 1H), 4.52-4.73 (m, 3H), 6.24 (t, J = 55.80 Hz, 1H), 6.61 (dt, J = 8.61, 3.42 Hz, 1H), 6.82 (dd, J = 6.46, 2.93 Hz, 1H), 6.89 (dd, J = 11.54, 8.61 Hz, 1H), 7.68 (s, 1H), 8.49 (s, 1H). or $^1$H NMR (400 MHz, CDCl$_3$) δ 0.87-0.94 (m, 1H), 1.38 (t, J = 6.70 Hz, 1H), 1.77-1.83 (m, 1H), 1.89-1.98 (m, 1H), 2.71-2.81 (m, 1H), 2.85-2.93 (m, 2H), 3.87 (t, J = 5.48 Hz, 1H), 4.40 (br s, 1H), 4.48 (s br, 2H), 4.62-4.68 (m, 1H), 6.24 (t, J = 55.90 Hz, 1H), 6.64 (dt, J = 8.61, 3.10 Hz, 1H), 6.88 (dd, J = 6.46, 2.93 Hz, 1H), 6.93 (dd, J = 11.54, 8.61 Hz, 1H), 7.68 (s, 1H), 8.47 (s, 1H). |
| 382 | (1R,5S,6R)-5-(5-(((R)-3-bromo-5,6,7,8-tetrahydroquinolin-8-yl)amino)-2-fluorophenyl)-5-(difluoromethyl)-2-oxa-4-azabicyclo[4.1.0]hept-3-en-3-amine and (1R,5S,6R)-5-(5-(((S)-3-bromo-5,6,7,8-tetrahydroquinolin-8-yl)amino)-2-fluorophenyl)-5-(difluoromethyl)-2-oxa-4-azabicyclo[4.1.0]hept-3-en-3-amine | 1:1 mixture of diastereomers | MS m/z = 483.0 [M + H]+. 1H NMR (400 MHz, CHLOROFORM-d) δ ppm 0.90 (dd, J = 16.24, 8.61 Hz, 1 H) 1.37 (t, J = 7.20 Hz, 1 H) 1.72-1.97 (m, 4 H) 2.20-2.36 (m, 1 H) 2.72-2.87 (m, 2 H) 3.86 (t, J = 5.38 Hz, 1 H) 4.24-4.43 (m, 3 H) 4.61-4.81 (m, 1 H) 6.24 (t, J = 56.50 Hz, 1 H) 6.60-6.69 (m, 1 H) 6.78-6.96 (m, 2 H) 7.58 (s, 1 H) 8.46-8.49 (m, 1 H) |

TABLE 5-continued

| Example No | Compound Name | Compound Structure | Analytical Data |
|---|---|---|---|
| 383 | (R)-4-((3-((1R,5S,6R)-3-amino-5-(difluoromethyl)-2-oxa-4-azabicyclo[4.1.0]hept-3-en-5-yl)-4-fluorophenyl)amino)chroman-7-carbonitrile and (S)-4-((3-((1R,5S,6R)-3-amino-5-(difluoromethyl)-2-oxa-4-azabicyclo[4.1.0]hept-3-en-5-yl)-4-fluorophenyl)amino)chroman-7-carbonitrile | 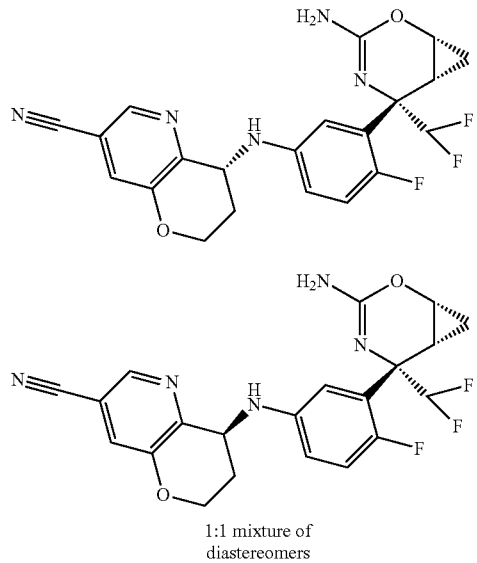<br>1:1 mixture of diastereomers | MS m/z = 429.0 [M + H]+. 1H NMR (400 MHz, CHLOROFORM-d) δ ppm 0.88-0.98 (m, 1 H) 1.37 (br. s., 1 H) 1.76-1.86 (m, 1 H) 2.08-2.18 (m, 2 H) 3.80 (d, J = 7.24 Hz, 1 H) 3.89 (t, J = 6.75 Hz, 1 H) 4.17-4.36 (m, 4 H) 4.53-4.63 (m, 1 H) 6.22 (t, J = 57.10 Hz, 1 H) 6.55-6.61 (m, 1 H) 6.79 (td, J = 5.97, 3.13 Hz, 1 H) 6.96 (dd, J = 11.54, 8.80 Hz, 1 H) 7.13 (s, 1 H) 7.16 (d, J = 8.02 Hz, 1 H) 7.41 (d, J = 7.82 Hz, 1 H) |
| 384 | (1R,5S,6R)-5-(5-(((R)-5-bromo-2,3-dihydro-1H-inden-1-yl)amino)-2-fluorophenyl)-5-(difluoromethyl)-2-oxa-4-azabicyclo[4.1.0]hept-3-en-3-amine and (1R,5S,6R)-5-(5-(((S)-5-bromo-2,3-dihydro-1H-inden-1-yl)amino)-2-fluorophenyl)-5-(difluoromethyl)-2-oxa-4-azabicyclo[4.1.0]hept-3-en-3-amine | 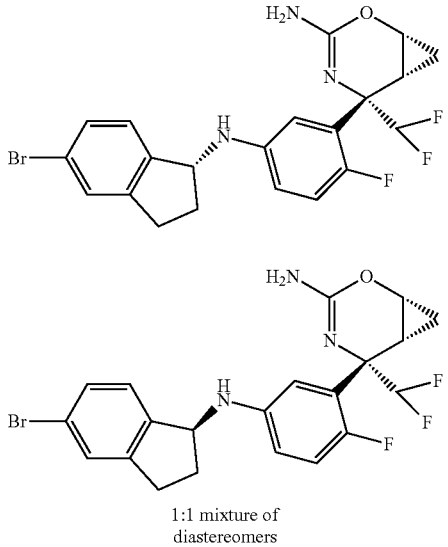<br>1:1 mixture of diastereomers | MS m/z = 467.0 [M + H]+. 1H NMR (400 MHz, CHLOROFORM-d) δ ppm 0.85-0.98 (m, 1 H) 1.34-1.41 (m, 1 H) 1.77-1.95 (m, 2 H) 2.53 (d, J = 7.24 Hz, 1 H) 2.80-2.90 (m, 1 H) 2.93-3.03 (m, 1 H) 3.76 (br. s., 1 H) 3.84-3.92 (m, 1 H) 4.35 (br. s., 2 H) 4.83-4.91 (m, 1 H) 6.22 (t, J = 56.30 Hz, 1 H) 6.54-6.61 (m, 1 H) 6.79 (td, J = 6.70, 3.10 Hz, 1 H) 6.92 (dd, J = 11.74, 8.61 Hz, 1 H) 7.20 (d, J = 7.82 Hz, 1 H) 7.31 (br. s., 1 H) 7.39 (s, 1 H) |
| 385 | N-(3-((1R,5S,6R)-3-amino-5-(difluoromethyl)-2-oxa-4-azabicyclo[4.1.0]hept-3-en-5-yl)-4-fluorophenyl)-6-chlorofuro[3,2-b]pyridin-3-amine | 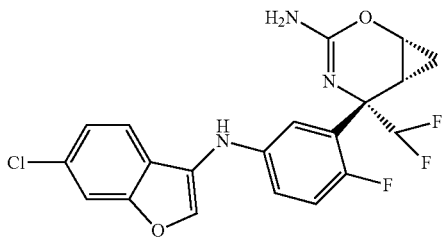 [SMILES: NC1=N[C@@](c2cc(Nc3coc4cc(Cl)ccc34)ccc2F)(C(F)F)[C@H]2C[C@H]2O1] | MS m/z = 423 [M + H]+. 1H NMR (400 MHz, CHLOROFORM-d) δ ppm 0.93 (dd, J = 15.06, 6.85 Hz, 1 H) 1.42 (t, J = 6.10 Hz, 1 H) 1.83 (dd, J = 16.43, 7.24 Hz, 1 H) 3.89 (t, J = 7.20 Hz, 1 H) 4.64-4.85 (m, 2 H) 6.16 (s, 1H), 6.25 (t, J = 55.90 Hz, 1 H) 6.78-6.84 (m, 1 H) 6.99 (dd, J = 11.44, 8.70 Hz, 1 H) 7.17 (dd, J = 6.46, 2.93 Hz, 1 H) 7.66 (d, J = 1.76 Hz, 1 H) 7.87 (s, 1 H) 8.44-8.47 (m, 1 H) |

Method M:

Example 386

Synthesis of N-(3-((1R,5S,6R)-3-amino-5-(fluoromethyl)-2-oxa-4-azabicyclo[4.1.0]hept-3-en-5-yl)-4-chlorophenyl)-5-cyano-3-(methoxymethyl)picolinamide

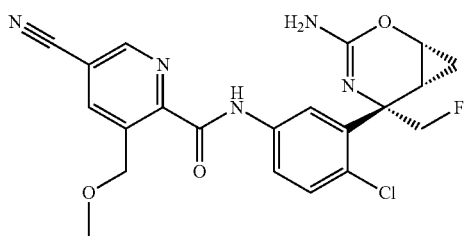 [SMILES: COCc1cc(C#N)cnc1C(=O)Nc1ccc(Cl)c([C@@]2(CF)N=C(N)O[C@@H]3C[C@@H]32)c1]

A microwave vial was charged with N-(3-((1R,5S,6R)-3-amino-5-(fluoromethyl)-2-oxa-4-azabicyclo[4.1.0]hept-3-en-5-yl)-4-chlorophenyl)-5-chloro-3-(methoxymethyl)picolinamide (Example 128, 0.139 g, 0.307 mmol), tris(dibenzylideneacetone) dipalladium (0) (0.028 g, 0.031 mmol), 2-dicyclohexylphosphino-2',6'-dimethoxy-1'1'-biphenyl (0.025 g, 0.061 mmol), and zinc cyanide (0.023 ml, 0.368 mmol). The vial was evacuated and backfilled with $N_2$ gas. A solvent mixture of 99:1 DMF: water (1.5 mL) was added and the reaction mixture was heated to 120° C. for 20 minutes in the microwave. The reaction mixture was cooled to rt and diluted with water and EtOAc. The organic layer was separated and sequentially washed with water, 1M LiCl (aq), and brine before drying over magnesium sulfate. The filtrate was concentrated under reduced pressure. The residue was triturated with DCM:ether ~1:1 to afford a white solid which was collected by filtration, dried under high vacuum and identified as the title compound (0.0931 g, 0.210 mmol, 68.4% yield). MS m/z=443.9 [M+H]+

1H NMR (400 MHz, DMSO-d6) δ ppm 0.88 (dt, J=9.63, 6.33 Hz, 1H) 0.96 (td, J=6.50, 2.64 Hz, 1H) 1.69 (dt, J=9.88, 7.09 Hz, 1H) 3.42 (s, 3H) 3.94-4.01 (m, 1H) 4.63-4.72 (m, 1H) 4.75-4.84 (m, 1H) 4.86 (s, 2H) 5.62 (s, 2H) 7.45 (d, J=8.61 Hz, 1H) 7.86 (dd, J=8.61, 2.54 Hz, 1H) 8.05 (d, J=2.54 Hz, 1H 8.45-8.52 (m, 1H) 9.11 (d, J=1.96 Hz, 1H) 10.85 (s, 1H)

Table 6 includes compound examples prepared wherein the appropriate halogenated intermediate (also a compound example) was converted into the corresponding cyano-compound (Examples 387-400 in Table 6) according to Method M:

TABLE 6

| Example No | Compound Name | Compound Structure | Analytical Data |
| --- | --- | --- | --- |
| 387 | N-(3-((1R,5S,6R)-3-amino-5-(fluoromethyl)-2-oxa-4-azabicyclo[4.1.0]hept-3-en-5-yl)-4-chlorophenyl)-5-cyano-3-(hydroxymethyl)picolinamide | 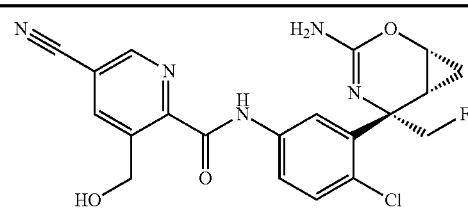 | MS m/z = 430 [M + H]+ 1H NMR (300 MHz, DMSO-d6) δ ppm 0.77-1.00 (m, 2 H) 1.61-1.75 (m, 1 H) 3.89-4.00 (m, 1 H) 4.55-4.71 (m, 1 H) 4.74-4.86 (m, 1 H) 4.92 (s, 2 H) 5.60 (s, 2 H) 7.43 (d, J = 8.48 Hz, 1 H) 7.85 (d, J = 8.77 Hz, 1 H) 8.05 (s, 1 H) 8.54 (s, 1 H) 9.06 (s, 1 H) 10.84 (br. s., 1 H) |
| 388 | N-(3-((1R,5S,6R)-3-amino-5-(difluoromethyl)-2-oxa-4-azabicyclo[4.1.0]hept-3-en-5-yl)-4-fluorophenyl)-5-cyano-3-fluoropicolinamide | 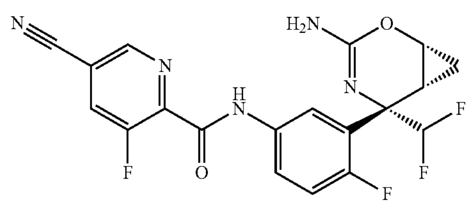 [SMILES: N#Cc1cnc(C(=O)Nc2ccc(F)c([C@@]3(C(F)F)N=C(N)O[C@@H]4C[C@@H]43)c2)c(F)c1] | MS m/z = 419.9 [M]+ 1H NMR (300 MHz, DMSO-d6) δ 0.82-0.98 (m, 1 H) 1.14 (br. s., 1 H) 1.62-1.79 (m, 1 H) 3.92-4.05 (m, 1 H) 5.88 (s, 2 H) 5.98-6.40 (m, 1 H) 7.08-7.39 (m, 1 H) 7.70-8.02 (m, 2 H) 8.66 (d, J = 10.23 Hz, 1 H) 9.04 (s, 1 H) 10.88 (s, 1 H) |
| 389 | N-(3-((1R,5S,6R)-3-amino-5-(difluoromethyl)-2-oxa-4-azabicyclo[4.1.0]hept-3-en-5-yl)-4-fluorophenyl)-5-cyano-3-(dimethylamino)picolinamide | 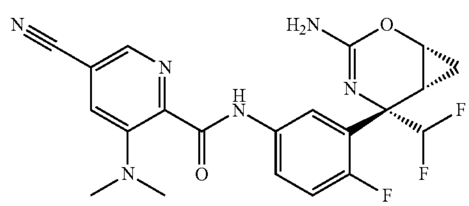 [SMILES: CN(C)c1cc(C#N)cnc1C(=O)Nc1ccc(F)c([C@@]2(C(F)F)N=C(N)O[C@@H]3C[C@@H]32)c1] | MS m/z = 445 [M + H]+ 1H NMR (300 MHz, DMSO-d6) δ ppm 0.90 (d, J = 5.99 Hz, 1 H) 1.13-1.27 (m, 1 H) 1.70 (d, J = 4.53 Hz, 1 H) 2.92 (br. s., 6 H) 3.98 (br. s., 1 H) 5.87 (br. s., 2 H) 5.97-6.46 (m, 1 H) 7.19-7.34 (m, 1 H) 7.72-7.90 (m, 3 H) 8.35 (br. s., 1 H) 10.72 (br. s., 1 H) |
| 390 | N-(3-((1R,5S,6R)-3-amino-5-(difluoromethyl)-2-oxa-4-azabicyclo[4.1.0]hept-3-en-5-yl)-4-fluoro-5-methylphenyl)-5-cyanopicolinamide | 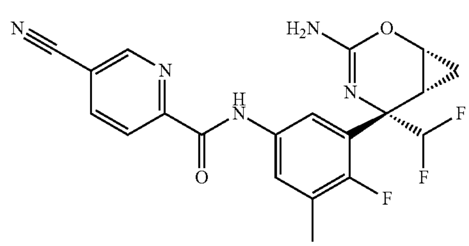 [SMILES: Cc1cc(NC(=O)c2ccc(C#N)cn2)cc([C@@]2(C(F)F)N=C(N)O[C@@H]3C[C@@H]32)c1F] | MS m/z = 416 [M + H]+ 1H NMR (300 MHz, DMSO-d6) δ ppm 0.82-1.01 (m, 1 H) 1.14 (br. s., 1 H) 1.71 (q, J = 7.70 Hz, 1 H) 2.26 (s, 3 H) 4.01 (br. s., 1 H) 5.83 (s, 2 H) 6.00-6.48 (m, 1 H) 7.82 (t, J = 6.87 Hz, 2 H) 8.27 (d, J = 8.18 Hz, 1 H) 8.58 (d, J = 7.89 Hz, 1 H) 9.19 (s, 1 H) 10.73 (s, 1 H) |

TABLE 6-continued

| Example No | Compound Name | Compound Structure | Analytical Data |
|---|---|---|---|
| 391 | N-(3-((1R,5S,6R)-3-amino-5-(difluoromethyl)-2-oxa-4-azabicyclo[4.1.0]hept-3-en-5-yl)-4-fluorophenyl)-5-cyano-3-(methoxymethyl)picolinamide | 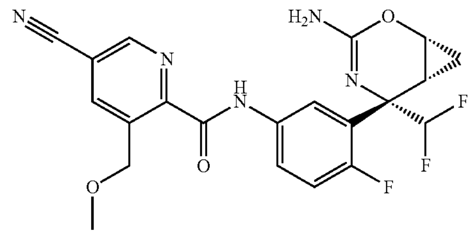 [SMILES: COCc1cc(C#N)cnc1C(=O)Nc1ccc(F)c([C@@]2(C(F)F)N=C(N)O[C@@H]3C[C@@H]32)c1] | MS m/z = 446 [M + H]+<br>1H NMR (300 MHz, CHLOROFORM-d) d ppm 9.84 (s, 1 H), 8.56 (s, 1 H), 8.50 (s, 1 H), 7.82-7.98 (m, 1 H), 7.50 (dd, J = 6.50, 2.12 Hz, 1 H), 6.91-7.04 (m, 1 H), 6.03-6.46 (m, 1 H), 4.97-5.28 (m, 4 H), 3.91 (t, J = 5.70 Hz, 1 H), 3.56 (s, 3 H), 1.81-1.96 (m, 1 H), 1.38-1.55 (m, 1 H), 0.92-1.05 (m, 1 H). |
| 392 | 8-((3-((1R,5S,6R)-3-amino-5-(fluoromethyl)-2-oxa-4-azabicyclo[4.1.0]hept-3-en-5-yl)-4-fluorophenyl)amino)-1,7-naphthyridine-3-carbonitrile | 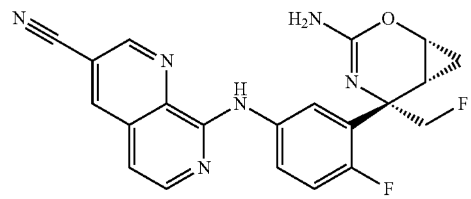 [SMILES: N#Cc1cnc2c(Nc3ccc(F)c([C@@]4(CF)N=C(N)O[C@@H]5C[C@@H]54)c3)nccc2c1] | MS m/z = 407.2 [M + H]+<br>1H NMR (400 MHz, DMSO-d6) d ppm 9.72 (s, 1 H), 9.21 (d, J = 1.76 Hz, 1 H), 8.87-9.06 (m, 1 H), 8.25 (dd, J = 7.34, 2.64 Hz, 1 H), 8.22 (d, J = 5.87 Hz, 1 H), 8.02 (dt, J = 8.56, 3.55 Hz, 1 H), 7.22 (d, J = 5.67 Hz, 1H), 7.16 (dd, J = 8.80, 11.74 Hz, 1H), 5.75 (s, 2 H), 4.39-4.75 (m, 2 H), 3.90-4.10 (m, 1 H), 1.49-1.69 (m, 1 H), 1.03 (d, J = 1.96 Hz, 1 H), 0.83 (dt, J = 9.24, 6.33 Hz, 1 H). |
| 393 | 4-((3-((1R,5S,6R)-3-amino-5-(fluoromethyl)-2-oxa-4-azabicyclo[4.1.0]hept-3-en-5-yl)-4-fluorophenyl)amino)pyrido[3,2-d]pyrimidine-7-carbonitrile | 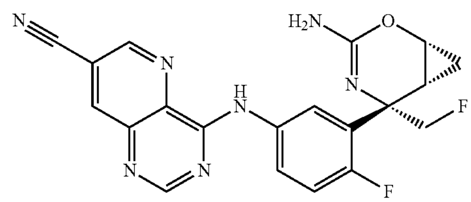 [SMILES: N#Cc1cnc2c(Nc3ccc(F)c([C@@]4(CF)N=C(N)O[C@@H]5C[C@@H]54)c3)ncnc2c1] | MS m/z = 408 [M + H]+<br>1H NMR (400 MHz, DMSO-d6) d ppm 10.58 (s, 1 H), 9.24 (d, J = 1.76 Hz, 1 H), 8.87 (d, J = 1.96 Hz, 1 H), 8.74 (s, 1 H), 8.29 (dd, J = 7.43, 2.74 Hz, 1 H), 7.84-7.95 (m, 1 H), 7.22 (dd, J = 11.74, 8.80 Hz, 1 H), 5.69 (br. s., 2 H), 4.44-4.76 (m, 2 H), 4.03 (t, J = 5.28 Hz, 1 H), 1.54-1.69 (m, 1 H), 0.97-1.08 (m, 1 H), 0.78-0.89 (m, 1 H). |
| 394 | N-(3-((1R,5S,6R)-3-amino-5-(difluoromethyl)-2-oxa-4-azabicyclo[4.1.0]hept-3-en-5-yl)-4-fluorophenyl)-5-cyano-3-isopropylpicolinamide | 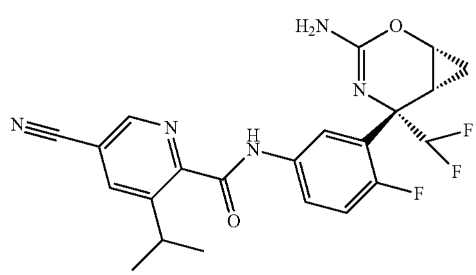 [SMILES: CC(C)c1cc(C#N)cnc1C(=O)Nc1ccc(F)c([C@@]2(C(F)F)N=C(N)O[C@@H]3C[C@@H]32)c1] | MS m/z = 444 [M + H]+<br>$^1$H NMR (300 MHz, DMSO-d$_6$) ppm 0.83-0.98 (m, 1 H) 1.09-1.17 (m, 1 H) 1.25 (d, J = 6.87 Hz, 6 H) 1.63-1.82 (m, 1 H) 3.40 (quin, J = 6.83 Hz, 1 H) 3.92-4.03 (m, 1 H) 5.88 (s, 2 H) 5.97-6.56 (m, 1 H) 7.23 (dd, J = 11.77, 8.84 Hz, 1 H) 7.70-7.90 (m, 2 H) 8.53 (d, J = 1.90 Hz, 1 H) 8.95 (d, J = 1.90 Hz, 1 H) 10.78 (s, 1 H) |
| 395 | N-(3-((1R,5S,6R)-3-amino-5-(difluoromethyl)-2-oxa-4-azabicyclo[4.1.0]hept-3-en-5-yl)-4-fluorophenyl)-5-cyano-3-(difluoromethyl)picolinamide | 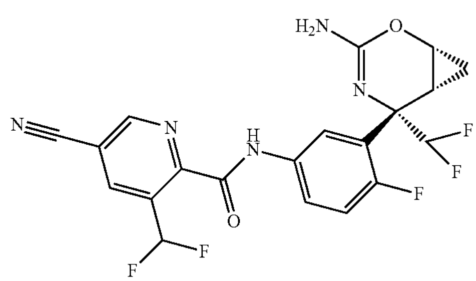 [SMILES: N#Cc1cnc(C(=O)Nc2ccc(F)c([C@@]3(C(F)F)N=C(N)O[C@@H]4C[C@@H]43)c2)c(C(F)F)c1] | MS m/z = 452.1 [M + H]+<br>$^1$H NMR (300 MHz, DMSO-d$_6$) δ ppm 0.77-0.96 (m, 4 H) 1.07-1.54 (m, 12 H) 1.73 (d, J = 9.50 Hz, 2 H) 4.00 (br. s., 1 H) 5.74-5.93 (m, 2 H) 5.96-6.42 (m, 1 H) 7.14-7.31 (m, 1 H) 7.49-8.00 (m, 3 H) 8.78-8.96 (m, 1 H) 9.28-9.42 (m, 1 H) 10.94-11.09 (m, 1 H) |

TABLE 6-continued

| Example No | Compound Name | Compound Structure | Analytical Data |
|---|---|---|---|
| 396 | N-(3-((1R,5S,6R)-3-amino-5-(difluoromethyl)-2-oxa-4-azabicyclo[4.1.0]hept-3-en-5-yl)-4-fluorophenyl)-5-cyano-3-(hydroxymethyl)picolinamide | 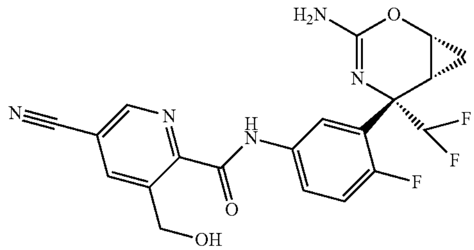 [SMILES: N#Cc1cnc(C(=O)Nc2ccc(F)c([C@@]3(C(F)F)N=C(N)O[C@@H]4C[C@@H]43)c2)c(CO)c1] | MS m/z = 432 [M + H]+<br>¹H NMR (300 MHz, DMSO-d₆) δ ppm 0.85-0.99 (m, 1 H) 1.09-1.22 (m, 1 H) 1.64-1.80 (m, 1 H) 3.17 (d, J = 5.26 Hz, 1 H) 3.94-4.05 (m, 1 H) 4.83-4.99 (m, 2 H) 5.52-5.65 (m, 1 H) 5.80-5.91 (m, 2 H) 5.96-6.42 (m, 1 H) 7.13-7.29 (m, 1 H) 7.74-7.97 (m, 2 H) 8.47-8.64 (m, 1 H) 8.99-9.12 (m, 1 H) 10.72-10.88 (m, 1 H) |
| 397 | N-(3-((1R,5S,6R)-3-amino-5-(fluoromethyl)-2-oxa-4-azabicyclo[4.1.0]hept-3-en-5-yl)-4-chlorophenyl)-5-cyano-3-methoxypicolinamide | 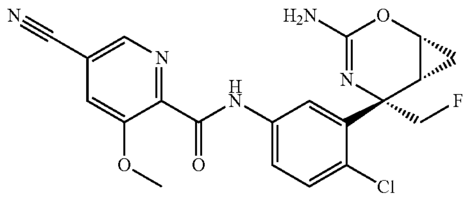 [SMILES: COc1cc(C#N)cnc1C(=O)Nc1ccc(Cl)c([C@@]2(CF)N=C(N)O[C@@H]3C[C@@H]32)c1] | MS m/z = 430.1 [M + H]+<br>1H NMR (300 MHz, DMSO) Shift = 10.73 (s, 1H), 8.67 (d, J = 1.6 Hz, 1H), 8.22 (d, J = 1.5 Hz, 1H), 7.91 (d, J = 2.5 Hz, 1H), 7.81 (dd, J = 2.5, 8.6 Hz, 1H), 7.42 (d, J = 8.6 Hz, 1H), 5.60 (s, 2H), 4.87-4.73 (m, 1H), 4.70-4.59 (m, 1H), 3.99-3.80 (m, 4H), 1.67 (td, J = 6.9, 9.7 Hz, 1H), 0.94 (dt, J = 2.8, 6.6 Hz, 1H), 0.85 (td, J = 6.3, 9.6 Hz, 1H) |
| 398 | N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-fluoropicolinamide | 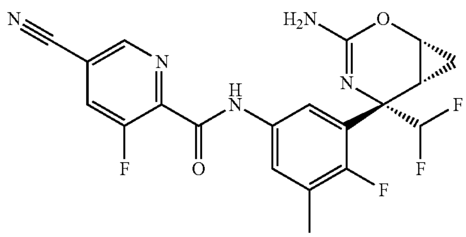 | MS m/z = 434.0 [M + H]+<br>1H NMR (300 MHz, DMSO) Shift = 10.79 (s, 1H), 9.09-8.97 (m, 1H), 8.66 (dd, J = 1.5, 10.2 Hz, 1H), 7.75 (dd, J = 2.6, 6.2 Hz, 1H), 7.65 (dd, J = 2.7, 6.4 Hz, 1H), 6.44-5.99 (m, 1H), 5.86 (s, 2H), 4.03-3.94 (m, 1H), 2.27 (d, J = 2.2 Hz, 3H), 1.76-1.64 (m, 1H), 1.17-1.07 (m, 1H), 0.96-0.84 (m, 1H) |
| 399 | N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methoxypicolinamide | 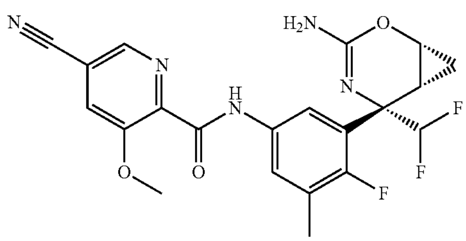 [SMILES: COc1cc(C#N)cnc1C(=O)Nc1cc(C)c(F)c([C@@]2(C(F)F)N=C(N)O[C@@H]3C[C@@H]32)c1] | MS m/z = 446.1 [M + H]+<br>¹H NMR (300 MHz, DMSO-d₆) δ ppm 0.80-0.95 (m, 1 H) 1.04-1.15 (m, 1 H) 1.62-1.75 (m, 1 H) 2.26 (s, 3 H) 3.91 (s, 3 H) 3.93-4.01 (m, 1 H) 5.85 (s, 2 H) 6.00-6.52 (m, 1 H) 7.53 (d, J = 4.97 Hz, 1 H) 7.74 (d, J = 4.68 Hz, 1 H) 8.20 (s, 1 H) 8.66 (s, 1 H) 10.58 (s, 1 H) |
| 400 | 4-((3-((1R,5S,6R)-3-amino-5-(difluoromethyl)-2-oxa-4-azabicyclo[4.1.0]hept-3-en-5-yl)-4-fluorophenyl)amino)pyrido[3,2-d]pyrimidine-7-carbonitrile | 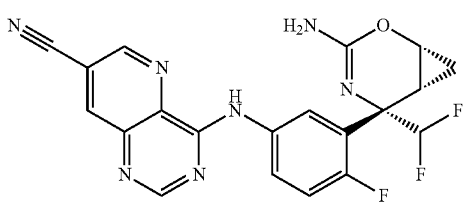 [SMILES: N#Cc1cnc2c(Nc3ccc(F)c([C@@]4(C(F)F)N=C(N)O[C@@H]5C[C@@H]54)c3)ncnc2c1] | MS m/z = 425.9 [M + H]+<br>1H NMR (400 MHz, DMSO-d6) δ ppm 0.91 (dt, J = 9.19, 6.55 Hz, 1 H) 1.18 (t, J = 7.14 Hz, 1 H) 1.73-1.80 (m, 1 H) 4.00-4.06 (m, 1 H) 5.91 (s, 2 H) 6.21 (t, J = 56.10 Hz, 1 H) 7.26 (dd, J = 11.74, 8.80 Hz, 1 H) 7.93 (ddd, J = 8.80, 3.91, 2.93 Hz, 1 H) 8.39 (dd, J = 4.31 Hz, 1 H) 8.75 (s, 1 H) 8.88 (d, J = 1.96 Hz, 1 H) 9.24 (d, J = 1.96 Hz, 1 H) 10.61 (s, 1 H) |
| 450 | N-(3-((1R,5S,6R)-3-amino-5-(fluoromethyl)-2-oxa-4-azabicyclo[4.1.0]hept-3-en-5-yl)-4-chlorophenyl)-5-cyano-3-fluoropicolinamide | 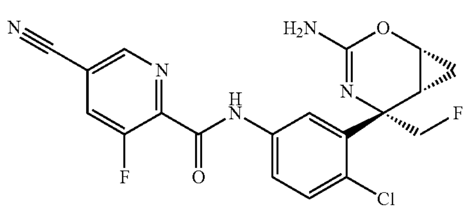 [SMILES: N#Cc1cnc(C(=O)Nc2ccc(Cl)c([C@@]3(CF)N=C(N)O[C@@H]4C[C@@H]43)c2)c(F)c1] | MS m/z = 418.1 [M + H]+<br>1H NMR (300 MHz, DMSO) δ = 10.95 (s, 1H), 9.05 (s, 1H), 8.68 (dd, J = 1.5, 10.2 Hz, 1H), 8.02 (d, J = 2.5 Hz, 1H), 7.82 (dd, J = 2.6, 8.7 Hz, 1H), 7.45 (d, J = 8.6 Hz, 1H), 5.64 (s, 2H), 4.80 (s, 1H), 4.65 (s, 1H), 4.01-3.90 (m, 1H), 1.66 (td, J = 6.9, 9.8 Hz, 1H), 0.94 (dt, J = 2.7, 6.5 Hz, 1H), 0.85 (td, J = 6.2, 9.5 Hz, 1H) |

Method N

Example 401

Synthesis of (R)-7-((3-(((1R,5S,6R)-3-amino-5-(difluoromethyl)-2-oxa-4-azabicyclo[4.1.0]hept-3-en-5-yl)-4-fluorophenyl)amino)-6,7-dihydro-5H-cyclopenta[b]pyridine-3-carbonitrile

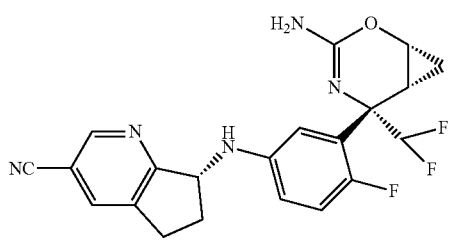 [SMILES: N#Cc1cnc2c(c1)CC[C@H]2Nc1ccc(F)c([C@@]2(C(F)F)N=C(N)O[C@@H]3C[C@@H]32)c1]

A sealable vial was charged with a mixture of potassium ferrocyanide trihydrate (0.056 g, 0.13 mmol), chloro(2-dicyclohexylphosphino-2',4',6'-triisopropyl-1,1'-biphenyl)[2-(2'-amino-1,1'-biphenyl)]palladium(II) (0.010 g, 0.013 mmol), 2-(dicyclohexylphosphino)-2',4',6'-tri-isopropyl-1,1'-biphenyl (0.0069 g, 0.014 mmol), and (1R,5S,6R)-5-(5-(((R)-3-bromo-6,7-dihydro-5H-cyclopenta[b]pyridin-7-yl)amino)-2-fluorophenyl)-5-(difluoromethyl)-2-oxa-4-azabicyclo[4.1.0]hept-3-en-3-amine (Example 351, 0.115 g, 0.246 mmol). Dioxane (0.65 mL) was added, followed by 0.65 mL of a solution of 30 mg of KOAc in 6.5 mL of water. The reaction mixture was purged with Nitrogen for 5 min. The reaction mixture was heated to 80° C. for 18 h, heated to 100° C. for 2 h and then cooled to room temperature. The reaction mixture was diluted with EtOAc, brine, and water. The aqueous phase was extracted with EtOAc (2×) and the combined organic extracts were washed with brine and dried over $MgSO_4$. The filtrate was concentrated under reduced pressure. The residue was purified by flash column chromatography on silica gel (20% to 80% EtOAc in DCM) to give the title compound (0.074 g, 0.18 mmol, 73% yield) as a pale yellow solid.

MS m/z=414.0 $[M+H]^+$. Calculated for $C_{21}H_{18}F_3N_5O$ 413.1.

$^1$H NMR (400 MHz, $CDCl_3$) δ 0.88-0.94 (m, 1H), 1.38 (t, J=6.80 Hz, 1H), 1.76-1.83 (m, 1H), 1.89-2.00 (m, 1H), 2.77-2.99 (m, 3H), 3.84-3.90 (m, 1H), 4.43 (d br, J=3.33 Hz, 1H), 4.54 (br s, 2H), 4.74 (td, J=8.00, 2.93 Hz, 1H), 6.24 (t, J=55.90 Hz, 1H), 6.65 (dt, J=8.61, 3.50 Hz, 1H), 6.89-6.98 (m, 2H), 7.79 (s, 1H), 8.70 (s, 1H).

The relative stereochemistry at the benzylic carbon was not determined. The compound may have either R or S stereochemistry at the benzylic carbon. It was isolated as a single diastereomer.

Table 7 includes compound examples prepared wherein the appropriate halogenated intermediate (also a compound example) was converted into the corresponding cyano-compound (Examples 402-404) according to Method N

TABLE 7

| Example No | Compound Name | Compound Structure | Analytical Data |
|---|---|---|---|
| 402 | (S)-7-((3-(((1R,5S,6R)-3-amino-5-(difluoromethyl)-2-oxa-4-azabicyclo[4.1.0]hept-3-en-5-yl)-4-fluorophenyl)amino)-6,7-dihydro-5H-cyclopenta[b]pyridine-3-carbonitrile (Example 365) | 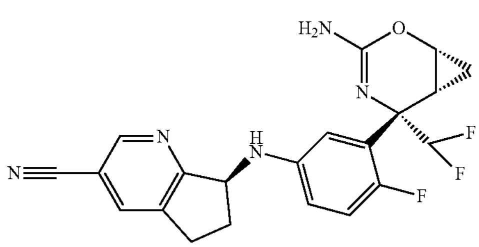 [SMILES: N#Cc1cnc2c(c1)CC[C@@H]2Nc1ccc(F)c([C@@]2(C(F)F)N=C(N)O[C@@H]3C[C@@H]32)c1] | MS m/z = 414.0 [M + H]+. $^1$H NMR (400 MHz, $CDCl_3$) δ 0.86-0.94 (m, 1H), 1.39 (t, J = 6.70 Hz, 1H), 1.74-1.82 (m, 1H), 1.83-1.96 (m, 1H), 2.76-3.05 (m, 3H), 3.83-3.90 (m, 1H), 4.45 (d br, J = 3.52 Hz, 1H), 4.60-4.82 (m, 3H), 6.24 (t, J = 55.80 Hz, 1H), 6.60 (dt, J = 8.66, 3.30 Hz, 1H), 6.83 (dd, J = 6.46, 2.93 Hz, 1H), 6.88 (dd, J = 11.54, 8.80 Hz, 1H), 7.79 (s, 1H), 8.72 (s, 1 H). The relative stereochemistry at the benzylic carbon was not determined. The compound may have either R or S stereochemistry at the benzylic carbon. It was isolated as a single diastereomer. |

TABLE 7-continued

| Example No | Compound Name | Compound Structure | Analytical Data |
|---|---|---|---|
| 403 | (R)-8-((3-((1R,5S,6R)-3-amino-5-(difluoromethyl)-2-oxa-4-azabicyclo[4.1.0]hept-3-en-5-yl)-4-fluorophenyl)amino)-5,6,7,8-tetrahydroquinoline-3-carbonitrile and (S)-8-((3-((1R,5S,6R)-3-amino-5-(difluoromethyl)-2-oxa-4-azabicyclo[4.1.0]hept-3-en-5-yl)-4-fluorophenyl)amino)-5,6,7,8-tetrahydroquinoline-3-carbonitrile | and<br><br>1:1 mixture of diastereomers | MS m/z = 428.1 [M + H]+. 1H NMR (400 MHz, CHLOROFORM-d) δ ppm 0.91 (dd, J = 15.85, 8.61 Hz, 1 H) 1.37 (br. s., 1 H) 1.75-2.00 (m, 4 H) 2.30-2.43 (m, 1 H) 2.77-2.93 (m, 2 H) 3.87 (t, J = 5.58 Hz, 1 H) 4.26-4.50 (m, 3 H) 4.78 (br. s., 1 H) 6.24 (t, J = 56.30 Hz, 1 H) 6.62-6.70 (m, 1 H) 6.79-6.97 (m, 2 H) 7.70 (s, 1 H) 8.68 (d, J = 6.06 Hz, 1 H) |
| 404 | (R)-1-((3-((1R,5S,6R)-3-amino-5-(difluoromethyl)-2-oxa-4-azabicyclo[4.1.0]hept-3-en-5-yl)-4-fluorophenyl)amino)-2,3-dihydro-1H-indene-5-carbonitrile and (S)-1-((3-((1R,5S,6R)-3-amino-5-(difluoromethyl)-2-oxa-4-azabicyclo[4.1.0]hept-3-en-5-yl)-4-fluorophenyl)amino)-2,3-dihydro-1H-indene-5-carbonitrile | and<br><br>1:1 mixture of diastereomers | MS m/z = 413.1 [M + H]+. 1H NMR (400 MHz, CHLOROFORM-d) δ ppm 0.88-0.95 (m, 1 H) 1.33-1.41 (m, 1 H) 1.77-1.95 (m, 2 H) 2.61 (d, J = 6.65 Hz, 1 H) 2.82-2.94 (m, 1 H) 2.96-3.06 (m, 1 H) 3.72-3.92 (m, 2 H) 4.43 (br. s., 2 H) 4.95 (br. s., 1 H) 6.21 (t, J = 56.10 Hz, 1 H) 6.54-6.60 (m, 1 H) 6.81 (dd, J = 6.36, 3.03 Hz, 1 H) 6.92 (dd, J = 11.54, 8.61 Hz, 1 H) 7.37-7.45 (m, 1 H) 7.46-7.56 (m, 2 H) |

Method O:

Example 405

Synthesis of N-(3-((1R,5S,6R)-3-amino-5-(difluoromethyl)-2-oxa-4-azabicyclo[4.1.0]hept-3-en-5-yl)-4-fluorophenyl)-5-(cyclopropylethynyl)picolinamide

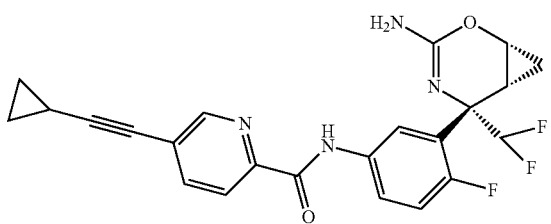 [SMILES: NC1=N[C@@](c2cc(NC(=O)c3ccc(C#CC4CC4)cn3)ccc2F)(C(F)F)[C@H]2C[C@H]2O1]

A sealable vial was evacuated and backfilled with nitrogen and then charged under a positive pressure of nitrogen with N-(3-((1R,5S,6R)-3-amino-5-(difluoromethyl)-2-oxa-4-azabicyclo[4.1.0]hept-3-en-5-yl)-4-fluorophenyl)-5-chloropicolinamide (Example 76, 200 mg, 0.487 mmol), 2-(dicyclohexylphosphino)-2',4',6',-tri-isopropyl-1,1'-biphenyl (69.6 mg, 0.146 mmol) bis(acetonitrile)palladium(II) dichloride (12.63 mg, 0.049 mmol) and cesium carbonate (555 mg, 1.704 mmol), followed by anhydrous MeCN (1.5 mL). The suspension was stirred for 25 min. Then cyclopropylacetylene (0.083 mL, 0.974 mmol) was added and the reaction mixture was heated to 90° C. for 1.5 h. The reaction mixture was cooled to rt and partitioned between water and EtOAc. The organic extract was washed with brine and dried over MgSO4. The filtrate was concentrated in vacuo to give the crude material which was treated with MeOH. A solid precipitated which was filtered off and discarded. The filtrate was absorbed onto a plug of silica gel and purified by silica gel flash chromatography, eluting with a gradient of 15% to 90% EtOAc in hexane, to provide the title compound (116 mg, 0.263 mmol, 54.1% yield) as light-yellow solid. MS m/z=441 [M+H]$^+$ $^1$H NMR (300 MHz, DMSO-d$_6$) δ ppm 0.78-1.05 (m, 5H) 1.07-1.26 (m, 2H) 1.58-1.82 (m, 2H) 3.98-4.08 (m, 2H) 5.94-6.46 (m, 1H) 7.21 (dd, J=11.84, 8.92 Hz, 1H) 7.75-7.94 (m, 1H) 7.97-8.16 (m, 3H) 8.69 (d, J=1.32 Hz, 1H) 10.66 (s, 1H)

Table 8 includes compound examples prepared wherein the appropriate halogenated intermediate was reacted with the corresponding alkyne (Examples 406-410) according to Method O:

TABLE 8

| Example No | Compound Name | Compound Structure | Analytical Data |
|---|---|---|---|
| 406 | (1R,5S,6R)-5-(5-((3-(cyclopropylethynyl)-1,7-naphthyridin-8-yl)amino)-2-fluorophenyl)-5-(difluoromethyl)-2-oxa-4-azabicyclo[4.1.0]hept-3-en-3-amine | 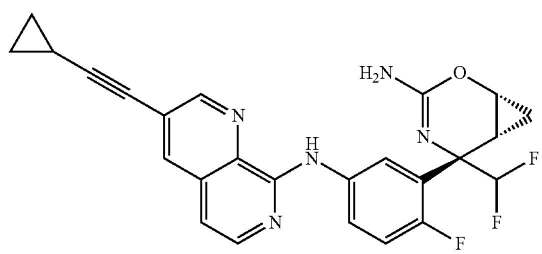 [SMILES: NC1=N[C@@](c2cc(Nc3nccc4cc(C#CC5CC5)cnc34)ccc2F)(C(F)F)[C@H]2C[C@H]2O1] | MS m/z = 464.1 [M + H]+<br>$^1$H NMR (300 MHz, DMSO-d$_6$) ppm 0.78-1.05 (m, 6 H) 1.13-1.29 (m, 2 H) 1.60-1.71 (m, 1 H) 1.71-1.83 (m, 1 H) 3.93-4.21 (m, 1 H) 5.90 (br. s., 2 H) 5.99-6.49 (m, 1 H) 7.04-7.28 (m, 2 H) 7.99-8.17 (m, 2 H) 8.27-8.40 (m, 2 H) 8.82 (d, J = 2.05 Hz, 1 H) 9.56 (s, 4 H) |
| 407 | N-(3-((1R,5S,6R)-3-amino-5-(difluoromethyl)-2-oxa-4-azabicyclo[4.1.0]hept-3-en-5-yl)-4-fluorophenyl)-5-(cyclopropylethynyl)pyrazine-2-carboxamide | 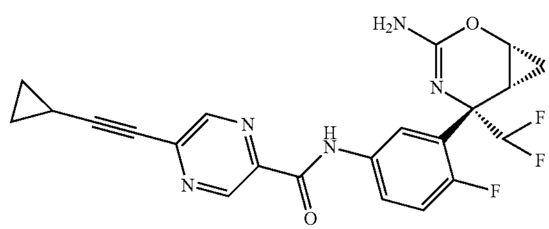 [SMILES: NC1=N[C@@](c2cc(NC(=O)c3cnc(C#CC4CC4)cn3)ccc2F)(C(F)F)[C@H]2C[C@H]2O1] | MS m/z = 442.1 [M + H]+<br>$^1$H NMR (300 MHz, DMSO-d$_6$) ppm 0.86-0.97 (m, 3 H) 0.99-1.09 (m, 2 H) 1.15 (br. s., 1 H) 1.58-1.83 (m, 2 H) 4.02 (br. s., 1 H) 5.85 (br. s., 2 H) 5.97-6.52 (m, 1 H) 7.22 (dd, J = 11.84, 9.06 Hz, 1 H) 7.86 (dd, J = 7.89, 3.51 Hz, 1 H) 8.04 (dd, J = 7.02, 2.78 Hz, 1 H) 8.77 (d, J = 1.32 Hz, 1 H) 9.17 (d, J = 1.46 Hz, 1 H) 10.78 (s, 1 H) |
| 408 | (1R,5S,6R)-5-(5-((3-(cyclopropylethynyl)-5-fluoro-1,7-naphthyridin-8-yl)amino)-2-fluorophenyl)-5-(difluoromethyl)-2-oxa-4-azabicyclo[4.1.0]hept-3-en-3-amine | 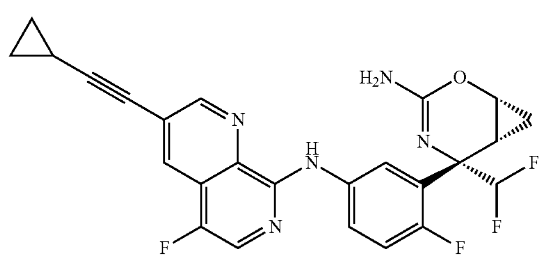 [SMILES: NC1=N[C@@](c2cc(Nc3ncc(F)c4cc(C#CC5CC5)cnc34)ccc2F)(C(F)F)[C@H]2C[C@H]2O1] | MS m/z = 482.1 [M + H]+<br>$^1$H NMR (300 MHz, DMSO-d$_6$) ppm 0.84-0.94 (m, 3 H) 0.96-1.05 (m, 2 H) 1.12-1.21 (m, 2 H) 1.63-1.84 (m, 3 H) 3.82-4.12 (m, 1 H) 5.73-6.54 (m, 3 H) 7.05-7.28 (m, 1 H) 7.86-8.06 (m, 1 H) 8.14 (s, 1 H) 8.36 (d, J = 2.05 Hz, 2 H) 8.92 (d, J = 1.90 Hz, 1 H) 9.56 (s, 1 H) |

TABLE 8-continued

| Example No | Compound Name | Compound Structure | Analytical Data |
|---|---|---|---|
| 409 | N-(3-((1R,5S,6R)-3-amino-5-(difluoromethyl)-2-oxa-4-azabicyclo[4.1.0]hept-3-en-5-yl)-4-fluorophenyl)-5-((3-methyloxetan-3-yl)ethynyl)picolinamide | 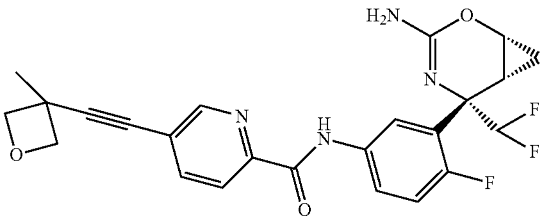 [SMILES: CC1(C#Cc2ccc(C(=O)Nc3ccc(F)c([C@@]4(C(F)F)N=C(N)O[C@@H]5C[C@@H]54)c3)nc2)COC1] | MS m/z = 471 [M + H]+<br>$^1$H NMR (300 MHz, DMSO-d$_6$) δ ppm 0.82-1.00 (m, 1 H) 1.09-1.20 (m, 1 H) 1.68 (s, 3 H) 1.70-1.79 (m, 1 H) 3.96-4.10 (m, 1 H) 4.48 (d, J = 5.70 Hz, 2 H) 4.80 (d, J = 5.41 Hz, 2 H) 5.86 (s, 2 H) 5.96-6.43 (m, 1 H) 7.21 (dd, J = 11.84, 8.77 Hz, 1 H) 7.89 (ddd, J = 8.81, 4.06, 2.78 Hz, 1 H) 8.00-8.19 (m, 3 H) 8.77 (dd, J = 1.75, 1.02 Hz, 1 H) 10.71 (s, 1 H) |
| 410 | N-(3-((1R,5S,6R)-3-amino-5-(difluoromethyl)-2-oxa-4-azabicyclo[4.1.0]hept-3-en-5-yl)-4,5-difluorophenyl)-5-(cyclopropylethynyl)picolinamide | 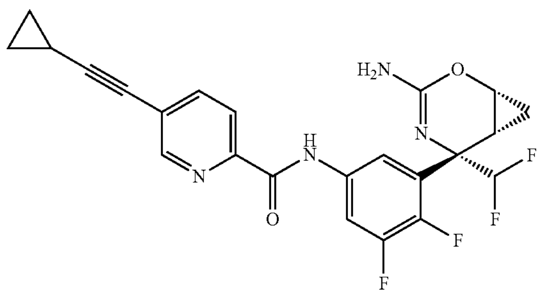 [SMILES: NC1=N[C@@](c2cc(NC(=O)c3ccc(C#CC4CC4)cn3)cc(F)c2F)(C(F)F)[C@H]2C[C@H]2O1] | MS m/z = 458.9 [M + H]+<br>1H NMR (CHLOROFORM-d) δ 9.63 (br. s, 1H), 8.38 (d, J = 1.5 Hz, 1H), 7.92-8.12 (m, 2H), 7.79 (dd, J = 8.1, 2.0 Hz, 1H), 7.22 (dt, J = 5.2, 2.4 Hz, 1H), 6.22 (td, J = 55.9, 0.9 Hz, 1H), 5.22 (br. s., 2H), 3.86-3.95 (m, 1H), 1.79-1.90 (m, 2H), 1.39-1.57 (m, 2H), 0.84-1.01 (m, 5H) |

Method P:

Synthesis of N-(3-((1R,5S,6R)-3-amino-5-(difluoromethyl)-2-oxa-4-azabicyclo[4.1.0]hept-3-en-5-yl)-4-fluorophenyl)-5-((3-cyclopropylprop-2-yn-1-yl)oxy)pyrazine-2-carboxamide (Example 411)

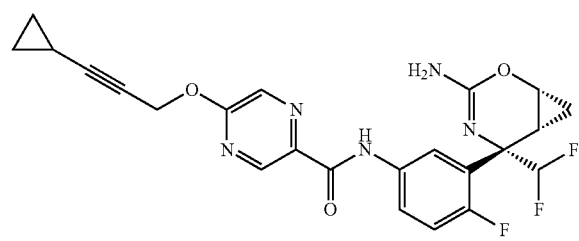 [SMILES: NC1=N[C@@](c2cc(NC(=O)c3cnc(OCC#CC4CC4)cn3)ccc2F)(C(F)F)[C@H]2C[C@H]2O1]

To a solution of 3-cyclopropylprop-2-yn-1-ol (205 mg, 2.137 mmol) in DMF (1 mL) was added sodium hydride (60% dispersion in mineral oil; 8.6 mg, 0.214 mmol) at rt. After 15 min N-(3-((1R,5S,6R)-3-amino-5-(difluoromethyl)-2-oxa-4-azabicyclo[4.1.0]hept-3-en-5-yl)-4-fluorophenyl)-5-chloropyrazine-2-carboxamide (Example 261, 88 mg, 0.214 mmol) was added and the reaction mixture was stirred at 60° C. for 50 min. Water (1.0 mL) and aqueous, saturated NaHCO$_3$ solution (1 mL) were added. The resulting mixture was then extracted with EtOAc (2×10 mL). The combined organic extracts were washed with water and dried over MgSO$_4$. The filtrate was concentrated under reduced pressure and the residue was purified by silica gel flash column chromatography (0%-20% MeOH/DCM) to give 58 mg of the title compound as an off-white solid. MS m/z=472 [M+H]$^+$ 1H NMR (MeOH) d: 8.90 (s, 1H), 8.29 (s, 1H), 7.86 (d, J=5.7 Hz, 2H), 7.17 (t, J=10.1 Hz, 1H), 6.04-6.49 (m, 1H), 5.05 (s, 2H), 4.05 (br. s., 1H), 1.80-2.00 (m, 1H), 1.25-1.40 (m, 2H), 0.90-1.02 (m, 1H), 0.79 (d, J=7.6 Hz, 2H), 0.63 (br. s., 2H)

Table 9 includes compound examples prepared wherein the appropriate halogenated intermediate was reacted with the corresponding alcohol (Examples 412-418) according to Method P:

TABLE 9

| Example No. | Compound Name | Compound Structure | Analytical Data |
|---|---|---|---|
| 412 | N-(3-((1R,5S,6R)-3-amino-5-(difluoromethyl)-2-oxa-4-azabicyclo[4.1.0]hept-3-en-5-yl)-4-fluorophenyl)-5-((tetrahydro-2H-pyran-4-yl)methoxy)pyrazine-2-carboxamide | 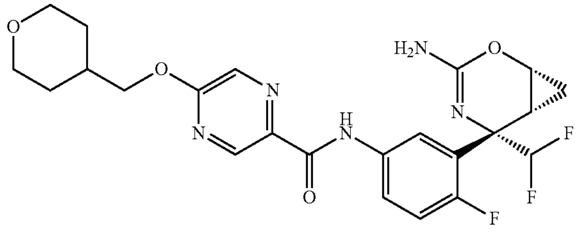 [SMILES: NC1=N[C@@](c2cc(NC(=O)c3cnc(OCC4CCOCC4)cn3)ccc2F)(C(F)F)[C@H]2C[C@H]2O1] | MS m/z = 492.1 [M + H]+<br>1H NMR (MeOH) d: 8.90 (d, J = 1.2 Hz, 1H), 8.30 (d, J = 1.2 Hz, 1H), 7.79-7.92 (m, 2H), 7.06-7.28 (m, 1H), 6.04-6.54 (m, 1H), 4.34 (d, J = 6.5 Hz, 2H), 4.04-4.11 (m, 1H), 4.00 (dd, J = 11.2, 3.9 Hz, 2H), 3.41-3.53 (m, 2H), 2.07-2.26 (m, 1H), 1.83-1.98 (m, 1H), 1.78 (d, J = 12.9 Hz, 2H), 1.40-1.57 (m, 2H), 1.33 (br. s., 1H), 0.89-1.06 (m, 1H) |

TABLE 9-continued

| Example No. | Compound Name | Compound Structure | Analytical Data |
|---|---|---|---|
| 413 | N-(3-((1R,5S,6R)-3-amino-5-(difluoromethyl)-2-oxa-4-azabicyclo[4.1.0]hept-3-en-5-yl)-4-fluorophenyl)-5-(((R,S))-tetrahydrofuran-3-yl)methoxy)pyrazine-2-carboxamide | 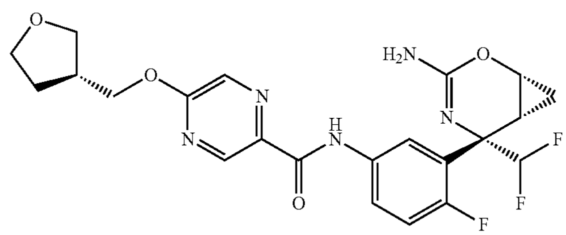 | MS m/z = 478.1 [M + H]+ 1H NMR (MeOH) d: 8.81-9.01 (m, 1H), 8.20-8.37 (m, 1H), 7.77-7.92 (m, 2H), 7.09-7.24 (m, 1H), 6.07-6.48 (m, 1H), 4.44-4.50 (m, 2H), 4.33-4.41 (m, 1H), 4.01-4.11 (m, 1H), 3.87-3.96 (m, 2H), 3.67-3.82 (m, 2H), 2.75-2.91 (m, 1H), 2.08-2.25 (m, 1H), 1.84-1.97 (m, 1H), 1.73-1.84 (m, 1H), 1.31-1.36 (m, 1H), 0.94-1.04 (m, 1H) |
| 414 | 5-(allyloxy)-N-(3-((1R,5S,6R)-3-amino-5-(difluoromethyl)-2-oxa-4-azabicyclo[4.1.0]hept-3-en-5-yl)-4-fluorophenyl)pyrazine-2-carboxamide | 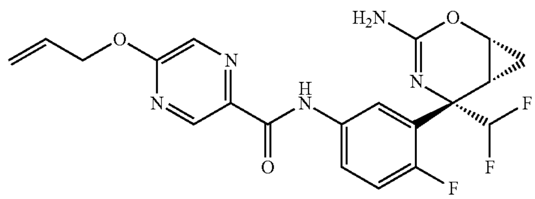 [SMILES: C=CCOc1cnc(C(=O)Nc2ccc(F)c([C@@]3(C(F)F)N=C(N)O[C@@H]4C[C@@H]43)c2)cn1] | MS m/z = 434.1 [M + H]+ 1H NMR (MeOH) d: 8.89 (s, 1H), 8.29 (s, 1H), 7.86 (d, J = 5.9 Hz, 2H), 7.17 (t, J = 9.9 Hz, 1H), 6.00-6.48 (m, 2H), 5.44 (d, J = 17.2 Hz, 1H), 5.30 (d, J = 11.2 Hz, 1H), 4.98 (d, J = 5.5 Hz, 2H), 4.05 (br. s., 1H), 1.88 (d, J = 7.6 Hz, 1H), 1.33 (br. s., 1H), 0.98 (d, J = 8.0 Hz, 1H) |
| 415 | N-(3-((1R,5S,6R)-3-amino-5-(difluoromethyl)-2-oxa-4-azabicyclo[4.1.0]hept-3-en-5-yl)-4-fluorophenyl)-5-(cyclopropylmethoxy)pyrazine-2-carboxamide | 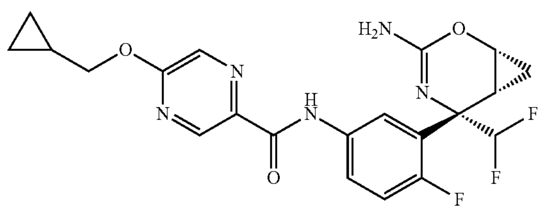 [SMILES: NC1=N[C@@](c2cc(NC(=O)c3cnc(OCC4CC4)cn3)ccc2F)(C(F)F)[C@H]2C[C@H]2O1] | MS m/z = 448.1 [M + H]+ NMR (MeOH) d: 8.87 (s, 1H), 8.26 (s, 1H), 7.85 (br. s., 1H), 7.04-7.30 (m, 1H), 6.05-6.50 (m, 1H), 4.30 (d, J = 7.0 Hz, 2H), 4.06 (br. s., 1H), 1.89 (d, J = 6.8 Hz, 1H), 1.34 (br. s., 2H), 0.99 (d, J = 7.4 Hz, 1H), 0.64 (d, J = 8.0 Hz, 2H), 0.40 (d, J = 3.7 Hz, 2H) |
| 416 | N-(3-((1R,5S,6R)-3-amino-5-(difluoromethyl)-2-oxa-4-azabicyclo[4.1.0]hept-3-en-5-yl)-4-fluorophenyl)-5-(cyclohexylmethoxy)pyrazine-2-carboxamide | 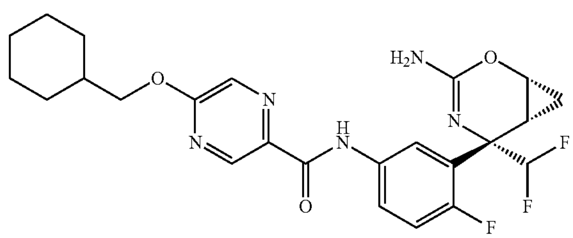 [SMILES: NC1=N[C@@](c2cc(NC(=O)c3cnc(OCC4CCCCC4)cn3)ccc2F)(C(F)F)[C@H]2C[C@H]2O1] | MS m/z = 490.1 [M + H]+ 1H NMR (MeOH) d: 8.91 (d, J = 1.2 Hz, 1H), 8.29 (d, J = 1.2 Hz, 1H), 7.83-7.92 (m, 2H), 7.20 (dd, J = 11.7, 9.4 Hz, 1H), 6.09-6.48 (m, 1H), 4.29 (d, J = 6.1 Hz, 2H), 4.04-4.13 (m, 1H), 1.88-1.97 (m, 4H), 1.72-1.86 (m, 3H), 1.26-1.43 (m, 4H), 1.11-1.22 (m, 2H), 0.95-1.05 (m, 1H) |
| 417 | N-(3-((1R,5S,6R)-3-amino-5-(difluoromethyl)-2-oxa-4-azabicyclo[4.1.0]hept-3-en-5-yl)-4-fluorophenyl)-5-ethoxypyrazine-2-carboxamide | 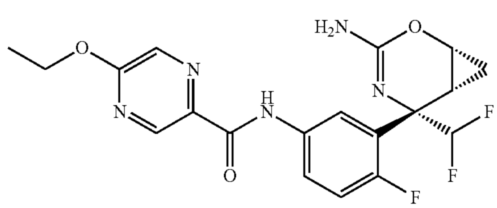 [SMILES: CCOc1cnc(C(=O)Nc2ccc(F)c([C@@]3(C(F)F)N=C(N)O[C@@H]4C[C@@H]43)c2)cn1] | MS m/z = 422.1 [M + H]+ 1H NMR (MeOH) d: 8.91 (d, J = 1.4 Hz, 1H), 8.28 (d, J = 1.4 Hz, 1H), 7.78-7.92 (m, 2H), 7.11-7.26 (m, 1H), 6.06-6.52 (m, 1H), 4.46-4.62 (m, 2H), 4.00-4.14 (m, 1H), 1.82-1.98 (m, 1H), 1.47 (d, J = 14.3 Hz, 3H), 1.36 (br. s., 1H), 0.89-1.06 (m, 1H) |
| 418 | N-(3-((1R,5S,6R)-3-amino-5-(difluoromethyl)-2-oxa-4-azabicyclo[4.1.0]hept-3-en-5-yl)-4-fluorophenyl)-5-(cyclopentylmethoxy)pyrazine-2-carboxamide | 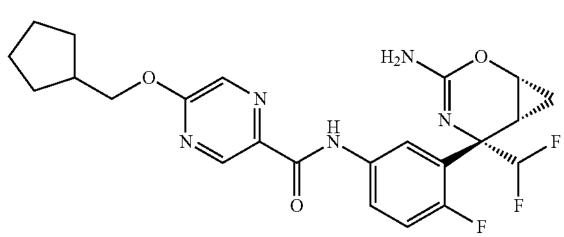 [SMILES: NC1=N[C@@](c2cc(NC(=O)c3cnc(OCC4CCCC4)cn3)ccc2F)(C(F)F)[C@H]2C[C@H]2O1] | MS m/z = 476.1 [M + H]+ 1H NMR (MeOH) d: 8.91 (d, J = 1.2 Hz, 1H), 8.29 (d, J = 1.2 Hz, 1H), 7.79-7.95 (m, 2H), 7.19 (dd, J = 11.7, 9.6 Hz, 1H), 6.06-6.50 (m, 1H), 4.37 (d, J = 7.0 Hz, 2H), 4.07 (t, J = 5.5 Hz, 1H), 2.35-2.56 (m, 1H), 1.83-1.97 (m, 3H), 1.57-1.78 (m, 4H), 1.29-1.52 (m, 3H), 0.91-1.09 (m, 1H) |

Method Q:

Example 419

Synthesis of N-(3-((1R,5S,6R)-3-amino-5-(difluoromethyl)-2-oxa-4-azabicyclo-[4.1.0]hept-3-en-5-yl)-4-fluorophenyl)-5-chloro-3-(hydroxymethyl)picolinamide

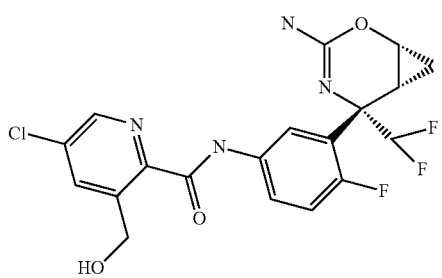 [SMILES: NC1=N[C@@](c2cc(NC(=O)c3ncc(Cl)cc3CO)ccc2F)(C(F)F)[C@H]2C[C@H]2O1]

A solution of N-(3-((1R,5S,6R)-3-amino-5-(difluoromethyl)-2-oxa-4-azabicyclo[4.1.0]hept-3-en-5-yl)-4-fluorophenyl)-5-chloro-3-(methoxymethyl) picolinamide (Example 42, 140 mg, 0.308 mmol) in DCM was cooled to 0° C. Boron tribromide (0.062 mL, 0.646 mmol) was added dropwise and the reaction mixture was allowed to warm to rt. After 3 hs, the reaction was quenched by the addition of water. The aq. phase was neutralized by the addition of aq. sat bicarbonate solution and extracted with EtOAc. The organic phase was over MgSO4. The filtrate material was absorbed onto a plug of silica gel and purified by chromatography eluting with a gradient of 15% to 100% EtOAc in hexane, to provide the title compound (62 mg, 0.141 mmol, 45.7% yield) as a whit solid. MS m/z=441 [M+H]+

$^1$H NMR (300 MHz, DMSO-d$_6$) δ ppm 0.79-1.02 (m, 1H) 1.15 (br. s., 1H) 1.61-1.84 (m, 1H) 4.01 (br. s., 1H) 4.93 (d, J=5.55 Hz, 2H) 5.54 (t, J=5.55 Hz, 1H) 5.87 (br. s., 2H) 5.98-6.46 (m, 1H) 7.21 (dd, J=11.84, 8.92 Hz, 1H) 7.78-7.97 (m, 2H) 8.20 (d, J=2.19 Hz, 1H) 8.64 (d, J=2.34 Hz, 1H) 10.63 (s, 1H)

Table 10 includes compound examples prepared wherein the appropriate methoxy compound was converted into the corresponding hydroxy-compound according to Method Q (Examples 420, Table 10):

Example 421

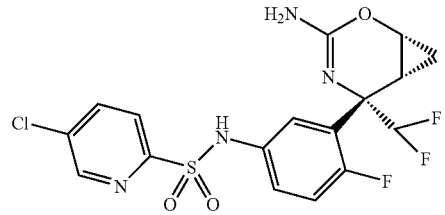 [SMILES: NC1=N[C@@](c2cc(NS(=O)(=O)c3ccc(Cl)cn3)ccc2F)(C(F)F)[C@H]2C[C@H]2O1]

Synthesis of N-(3-((1R,5S,6R)-3-amino-5-(difluoromethyl)-2-oxa-4-azabicyclo[4.1.0]hept-3-en-5-yl)-4-fluorophenyl)-5-chloropyridine-2-sulfonamide Step 1: 2-(benzylthio)-5-chloropyridine To a suspension of cesium carbonate (3.76 g, 11.5 mmol) in DMF (20 mL) at room temperature was added 5-chloro-2-fluoropyridine (1.00 mL, 9.96 mmol) and benzylmercaptan (1.15 mL, 9.80 mmol). The reaction mixture was stirred at room temperature for 16 h and heated to 60° C. for 6 h. The reaction mixture was diluted with Et$_2$O. The organic phase was washed with water (2×), brine and dried over MgSO$_4$. The filtrate was concentrated under reduced pressure and the residue was purified by flash column chromatography on silica gel (5% to 10% EtOAc in heptane) to give the title compound (2.33 g, 9.88 mmol, 101% yield) as a colorless oil that was used without further purification in the next step. MS) m/z=236.1 [M+H]+. Calculated for C$_{12}$H$_{10}$ClNS 235.0.

Step 2: 5-chloropyridine-2-sulfonyl chloride

Chlorine gas was bubbled through a solution of 2-(benzylthio)-5-chloropyridine (2.33 g, 9.88 mmol) in DCM (65 mL) and water (13 mL) at 0° C. for 20 min, followed by purging with Nitrogen for 15 min. The reaction mixture was transferred to a separatory funnel and diluted with water. The aqueous was discarded and the organic phase was washed with brine and dried over MgSO$_4$. The filtrate was concentrated under reduced pressure to give a colorless oil that was used without further purification in the next step. LC/MS (ESI$^+$) m/z=211.9 (M+H). Calculated for C$_5$H$_3$Cl$_2$NO$_2$S 210.9.

TABLE 10

| Example No | Compound Name | Compound Structure | Analytical Data |
|---|---|---|---|
| 420 | N-(3-((1R,5S,6R)-3-amino-5-(fluoromethyl)-2-oxa-4-azabicyclo[4.1.0]hept-3-en-5-yl)-4-chlorophenyl)-5-chloro-3-(hydroxymethyl)picolinamide | 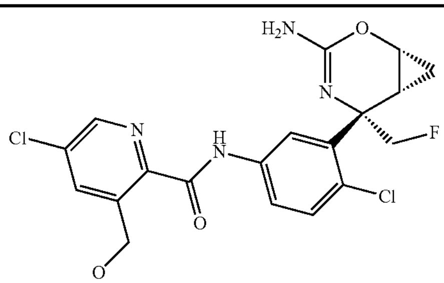 | MS m/z = 439 [M]+ 1H NMR (300 MHz, DMSO-d6) δ ppm 0.74-0.99 (m, 2 H) 1.57-1.75 (m, 1 H) 3.96 (br. s., 1 H) 4.57-4.71 (m, 1 H) 4.73-4.86 (m, 1 H) 4.94 (br. s., 2 H) 5.43-5.64 (m, 3 H) 7.41 (d, J = 7.89 Hz, 1 H) 7.85 (d, J = 8.62 Hz, 1 H) 8.04 (br. s., 1 H) 8.21 (br. s., 1 H) 8.65 (s, 1 H) 10.66 (br. s., 1 H) |

337

Step 3: tert-butyl((1R,5S,6R)-5-(5-(5-chloropyridine-2-sulfonamido)-2-fluorophenyl)-5-(difluoromethyl)-2-oxa-4-azabicyclo[4.1.0]hept-3-en-3-yl)carbamate To a solution of tert-butyl((1R,5S,6R)-5-(5-amino-2-fluorophenyl)-5-(difluoromethyl)-2-oxa-4-azabicyclo[4.1.0]hept-3-en-3-yl)carbamate (16i-B, 0.059 g, 0.16 mmol) in DCM (1.5 mL) at 0° C. were added triethylamine (0.070 mL, 0.50 mmol) and 5-chloropyridine-2-sulfonyl chloride (0.034 g, 0.16 mmol). The reaction mixture was allowed to warm up to room temperature over a period of 2 h and then diluted with EtOAc and water. The aqueous phase was extracted with EtOAc (2×). The combined organic extracts were washed with brine and dried over MgSO$_4$. The filtrate was concentrated under reduced pressure and the residue was purified by flash column chromatography on silica gel (10% to 50% EtOAc in heptane) to give the title compound (0.061 g, 0.11 mmol, 70% yield) as a colorless oil. MS m/z=547.0 [M+H]+. Calculated for C$_{22}$H$_{22}$ClF$_3$N$_4$O$_5$S 546.1.

Step 4: N-(3-((1R,5S,6R)-3-amino-5-(difluoromethyl)-2-oxa-4-azabicyclo[4.1.0]hept-3-en-5-yl)-4-fluorophenyl)-5-chloropyridine-2-sulfonamide To a solution of tert-butyl((1R,5S,6R)-5-(5-(5-chloropyridine-2-sulfonamido)-2-fluorophenyl)-5-(difluoromethyl)-2-oxa-4-azabicyclo[4.1.0]hept-3-en-3-yl)carbamate (0.061 g, 0.11 mmol) in DCM (2 mL) at room temperature was added trifluoroacetic acid (2.0 mL). The reaction mixture was stirred at room temperature for 30 min and concentrated under reduced pressure. The residue was partitioned between saturated NaHCO$_3$ and EtOAc. The aqueous phase was extracted with EtOAc (2×). The combined organic extracts were washed with brine and dried over MgSO$_4$. The filtrate was concentrated under reduced pressure and the residue was purified by flash column chromatography on silica gel (30% to 70% EtOAc in heptane) to give the title compound (0.045 g, 0.10 mmol, 90% yield) as a white solid. MS m/z=446.9 [M+H]+. Calculated for C$_{17}$H$_{14}$ClF$_3$N$_4$O$_3$S 446.0. $^1$H NMR (400 MHz, CDCl$_3$) δ 0.80-0.90 (m, 1H), 1.33 (t, J=6.85 Hz, 1H), 1.69-1.78 (m, 2H), 3.65-3.70 (m, 1H), 5.70 (s br, 2H), 6.06 (t, J=56.10 Hz, 1H), 6.95 (dd, J=6.75, 2.64 Hz, 1H), 7.06 (dd, J=11.44, 8.71 Hz, 1H), 7.45 (ddd, J=8.56, 4.25, 2.84 Hz, 1H), 7.72 (s, 2H), 8.33 (s, 1H).

Example 422

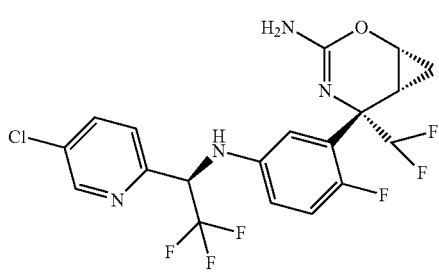

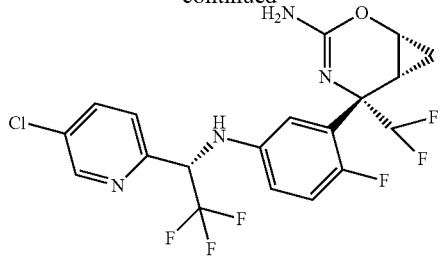

Synthesis of a 1:1 mixture of (1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-amine and (1R,5S,6R)-5-(5-(((S)-1-(5-chloropyridin-2-yl)-2,2,2-trifluoroethyl)amino-2-fluorophenyl)-5-(difluoromethyl)-2-oxa-4-azabicyclo[4.1.0]hept-3-en-3-amine Step 1: 1-(5-chloropyridin-2-yl)-2,2,2-trifluoroethanol To a solution of 5-chloropicolinaldehyde (0.505 g, 3.57 mmol) in THF (7 mL) at 0° C. were added (trifluoromethyl)trimethylsilane (0.685 mL, 4.63 mmol) and tetra-N-butylammonium fluoride (1 M in THF, 0.036 mL, 0.036 mmol). The reaction mixture was stirred at 0° C. for 15 min and diluted with water (10 mL) and additional tetra-N-butylammonium fluoride (1 M in THF, 2.0 mL, 2.0 mmol). The reaction mixture was allowed to warm to room temperature and stirred for 30 min. The reaction mixture was diluted with EtOAc, the organic phase was separated and washed with water, brine and dried over MgSO$_4$. The filtrate was concentrated under reduced pressure and the residue was purified by flash column chromatography on silica gel (5% to 20% EtOAc in heptane) to give the title compound (0.643 g, 3.04 mmol, 85% yield) as a yellow oil. MS m/z=211.9 [M+H]+. Calculated for C$_7$H$_5$ClF$_3$NO 211.0.

Step 2: 1-(5-chloropyridin-2-yl)-2,2,2-trifluoroethanone

To a solution of 1-(5-chloropyridin-2-yl)-2,2,2-trifluoroethanol (0.643 g, 3.04 mmol) in DCM (9 mL) at 0° C. was added 1,1,1-tris(acetyloxy)-1,1-dihydro-1,2-benziodoxol-3-(1H)-one (1.55 g, 3.65 mmol). The reaction mixture was allowed to warm to room temperature and stirred for 20 h before quenching with saturated NaHCO$_3$ (10 mL) and saturated sodium thiosulfate solution. The reaction mixture was stirred for 20 min and transferred to a separatory funnel. The aqueous phase was discarded and the organic phase was washed with brine and dried over MgSO$_4$ The filtrate was concentrated under reduced pressure and the residue was purified by flash column chromatography on silica gel (5% to 30% EtOAc in heptane) to afford the title compound (0.545 g, 2.60 mmol, 86% yield) as a pale yellow oil. LC/MS (ESI$^+$) m/z=209.9 (M+H). Calculated for C$_7$H$_3$ClF$_3$NO 209.0.

Step 3: tert-butyl((1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-yl)carbamate and tert-butyl((1R,5S,6R)-5-(5-(((S)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-yl)carbamate To a solution of tert-butyl((1R,5S,6R)-5-(5-amino-2-fluorophenyl)-5-(difluoromethyl)-2-oxa-4-azabicyclo[4.1.0]

hept-3-en-3-yl)carbamate (16i-B, 0.121, 0.326 mmol) and 1-(5-chloropyridin-2-yl)-2,2,2-trifluoroethanone (0.070 g, 0.33 mmol) in DCM (1.5 mL) at −78° C. were added triethylamine (0.135 mL, 0.969 mmol) and titanium chloride (1 M in DCM, 0.360 mL, 0.360 mmol). The cold bath was removed and the reaction mixture was allowed to stir at room temperature over 10 min. The reaction mixture was again cooled to −78° C. and lithium aluminium hydride (1.0 M in THF, 0.660 mL, 0.660 mmol) was added. The reaction mixture was stirred at −78° C. for 20 min and quenched with EtOAc. Saturated aqueous sodium potassium tartrate (5 mL) was added. The mixture was warmed to room temperature and stirred for 45 min. The mixture was transferred to a separatory funnel. The aqueous phase was extracted with EtOAc (2×). The combined organic extracts were washed with brine and dried over $MgSO_4$. The filtrate was concentrated under reduced pressure and the residue was purified by flash column chromatography on silica gel (10% to 50% EtOAc in heptane) to give a 1:1 mixture of tert-butyl((1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0] hept-3-en-3-yl)carbamate and tert-butyl((1R,5S,6R)-5-(5-(((S)-1-(5-chloropyridin-2-yl)-2,2,2-trifluoroethyl)amino)-2-fluorophenyl)-5-(difluoromethyl)-2-oxa-4-azabicyclo [4.1.0]hept-3-en-3-yl)carbamate (0.070 g, 0.124 mmol, 38% yield combined yield) as a white solid. MS m/z=565.1 (M+H). Calculated for $C_{24}H_{23}ClF_6N_4O_3$ 564.1.

Step 4: (1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-amine and (1R,5S,6R)-5-(5-(((S)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-amine To a solution of tert-butyl((1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0] hept-3-en-3-yl)carbamate and tert-butyl((1R,5S,6R)-5-(5-(((S)-1-(5-chloropyridin-2-yl)-2,2,2-trifluoroethyl)amino)-2-fluorophenyl)-5-(difluoromethyl)-2-oxa-4-azabicyclo [4.1.0]hept-3-en-3-yl)carbamate (1:1 mixture of diastereomers, 0.070 g, 0.12 mmol) in DCM (2 mL) at room temperature was added trifluoroacetic acid (2.00 mL, 0.124 mmol). The reaction mixture was stirred at room temperature for 30 min and concentrated. The concentrate was partitioned between saturated $NaHCO_3$ and EtOAc. The aqueous phase was discarded. The organic phase was washed with brine and dried over $MgSO_4$. The filtrate was concentrated under reduced pressure and the residue was purified by flash column chromatography on silica gel (12 g, 20% to 60% EtOAc in heptane) to give (1R,5S,6R)-5-(5-(((R)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-amine and (1R,5S,6R)-5-(5-(((S)-1-(5-chloropyridin-2-yl)-2,2,2-trifluoroethyl)amino)-2-fluorophenyl)-5-(difluoromethyl)-2-oxa-4-azabicyclo[4.1.0]hept-3-en-3-amine (1:1 mixture of diastereomers, 0.056 g, 0.120 mmol, 97% yield) as a white solid. MS m/z=465.0 [M+H]+. Calculated for $C_{19}H_{15}ClF_6N_4O$ 464.1. $^1$H NMR (400 MHz, $CDCl_3$) δ 0.86-0.95 (m, 1H), 1.32-1.41 (m, 1H), 1.73-1.85 (m, 1H), 3.83-3.90 (m, 1H), 4.50 (br s, 2H), 4.87-4.97 (m, 1H), 5.33 (dd, J=11.93, 7.63 Hz, 1H), 6.02-6.34 (m, 1H), 6.60-6.66 (m, 1H), 6.87-6.96 (m, 2H) 7.27-7.35 (m, 1H), 7.65-7.70 (m, 1H), 8.57-8.59 (m, 1H).

Example 423

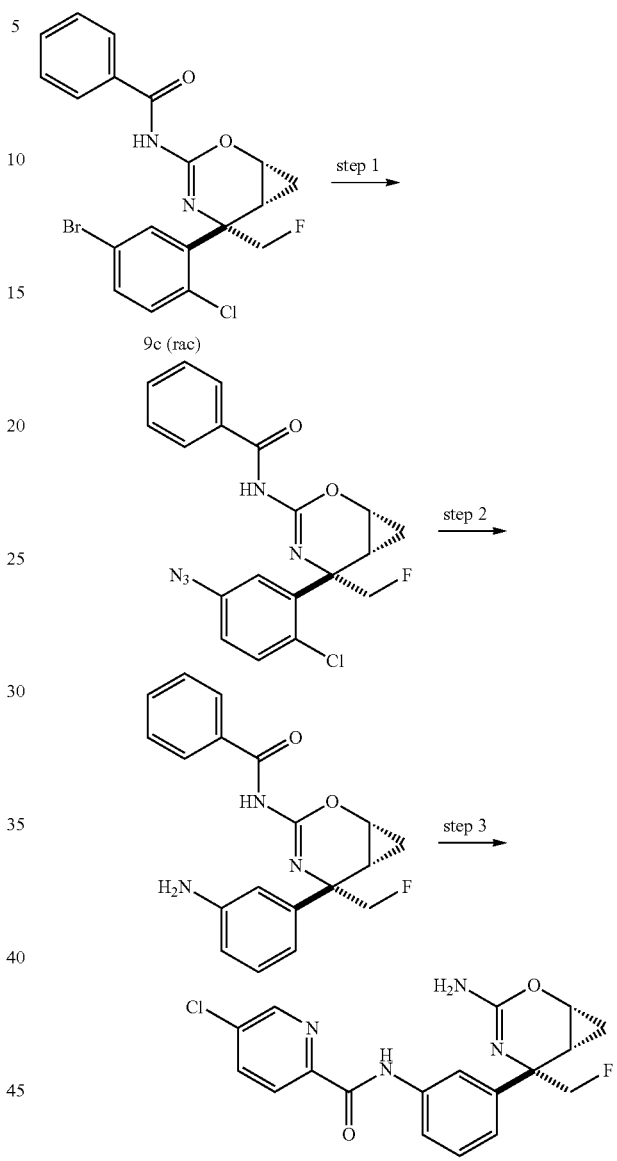

Synthesis of N-(3-(((1R,S),(5S,R),(6R,S))-3-amino-5-(fluoromethyl)-2-oxa-4-azabicyclo[4.1.0]hept-3-en-5-yl)phenyl)-5-chloropicolinamide Step 1: N-(((1RS),(5S,R),(6R,S))-5-(5-azido-2-chlorophenyl)-5-(fluoromethyl)-2-oxa-4-azabicyclo[4.1.0]hept-3-en-3-yl)benzamide The title compound was isolated as a byproduct from the reaction described in step 4 for the conversion of 6c-rac into 6d-rac. MS m/z=400.0 [M+H]+. Calculated for $C_{19}H_{15}ClFN_5O_2$: 399.8

Step 2: N-(((1R,S),(5S,R),(6R,S))-5-(3-aminophenyl)-5-(fluoromethyl)-2-oxa-4-azabicyclo[4.1.0]hept-3-en-3-yl)benzamide A sealable vial was charged with N-(((1RS),(5S,R),(6R,S))-5-(5-azido-2-chlorophenyl)-5-(fluoromethyl)-2-oxa-4- azabicyclo[4.1.0]hept-3-en-3-yl)benzamide (0.25 g, 0.625 mmol), 1,1-bis[(di-t-butyl-p-methylaminophenyl]palladium (H) chloride (0.089 g, 0.125 mmol), and sodium formate (0.255 g, 3.75 mmol). The vial was evacuated and backfilled with $N_2$ gas. DMF (3 ml) was added and the reaction was stirred in a pre-heated 90° C. oil bath for 48 hours. The reaction was cooled to ambient temperature and additional sodium formate (0.255 g, 3.75 mmol) and 1,1-bis[(di-t-butyl-p-methylaminophenyl]palladium(II) chloride (0.089 g, 0.125 mmol) were added. The reaction mixture was purged with nitrogen and heated to 130° C. for an additional 72 hours. The reaction was cooled to ambient temperature and diluted with water and EtOAc. The organic layer was separated and washed sequentially with water, 1M LiCl aqueous solution, and brine before being dried over magnesium sulfate. The filtrate was concentrated under reduced pressure and the crude residue was purified via silica gel flash chromatography using a gradient of 10-70% EtOAc in hexanes to afford the title compound as a light yellow oil (0.04 g, 0.118 mmol, 18.85% yield)

MS m/z=340.0 [M+H]$^+$. Calculated for $C_{19}H_{18}FN_3O_2$: 339.4

Step 3: N-(3-(((1R,S),(5S,R),(6R,S))-3-amino-5-(fluoromethyl)-2-oxa-4-azabicyclo[4.1.0]hept-3-en-5-yl)phenyl)-5-chloropicolinamide The title compound was prepared using a procedure similar to that described in step 4 for the synthesis of 4d rac, but using N-(((1R,S),(5S,R),(6R,S))-5-(3-aminophenyl)-5-(fluoromethyl)-2-oxa-4-azabicyclo[4.1.0]hept-3-en-3-yl)benzamide MS m/z=374.9 M$^+$. Calculated for $C_{18}H_{16}ClFN_4O_2$: 374.8

1H NMR (300 MHz, CHLOROFORM-d) δ ppm 0.95-1.05 (m, 1H) 1.27-1.31 (m, 1H) 1.68-1.77 (m, 1H) 4.07-4.15 (m, 1H) 4.40-4.59 (m, 1H) 4.60-4.79 (m, 1H) 7.31-7.37 (m, 1H) 7.38-7.46 (m, 1H) 7.73-7.79 (m, 1H) 7.87-7.94 (m, 2H) 8.24-8.29 (m, 1H) 8.57-8.60 (m, 1H) 9.87 (s, 1H)

Example 424

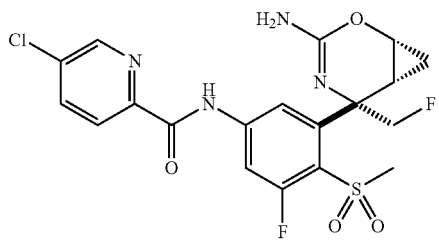 [SMILES: CS(=O)(=O)c1c(F)cc(NC(=O)c2ccc(Cl)cn2)cc1[C@@]1(CF)N=C(N)O[C@@H]2C[C@@H]21]

Synthesis of N-(3-(((1RS),(5S,R),(6R,S))-3-amino-5-(fluoromethyl)-2-oxa-4-azabicyclo[4.1.0]hept-3-en-5-yl)-5-fluoro-4-(methylsulfonyl)phenyl)-5-chloropicolinamide To a solution of N-(3-(((1S,R),(5S,R),(6R,S))-3-amino-5-(fluoromethyl)-2-oxa-4-azabicyclo[4.1.0]hept-3-en-5-yl)-5-fluoro-4-(methylthio)phenyl)-5-chloropicolinamide (0.019 g, 0.043 mmol, Example 141) in MeCN (0.1 mL), water (0.15 mL) and EtAc (0.1 mL) was added sodium (meta)periodate (0.037 g, 0.173 mmol) and ruthenium(III) chloride (0.5 mg, 2.165 μmol). The reaction mixture was stirred at RT for 30 min, then diluted with DCM and filtered through a cotton plug. Water was added to the filtrate and the phases were separated. The aqueous layer was extracted with DCM (3×) times and the combined organic layers were dried over sodium sulfate. The filtrate was concentrated under reduced pressure and the crude material was purified by column chromatography, eluting with 1-10% 2M ammonia in MeOH/DCM, to give the title compound (0.012 g, 0.025 mmol, 58.9% yield).

MS m/z=471.0 [M+H]$^+$. Calculated for $C_{19}H_{17}ClF_2N_4O_4S$: 470.9.

$^1$H NMR (400 MHz, DMSO-d$_6$) δ ppm 0.90-1.06 (m, 1H) 1.14-1.33 (m, 1H) 1.75 (m, 1H) 3.40 (s, 3H) 3.78-3.92 (m, 1H) 4.55-4.76 (m, 1H) 4.81 (m, 1H) 5.67 (br. s., 2H) 8.06 (d, J=14.48 Hz, 1H) 8.15-8.26 (m, 2H) 8.30 (s, 1H) 8.82 (s, 1H) 11.12 (br. s., 1H)

Example 425

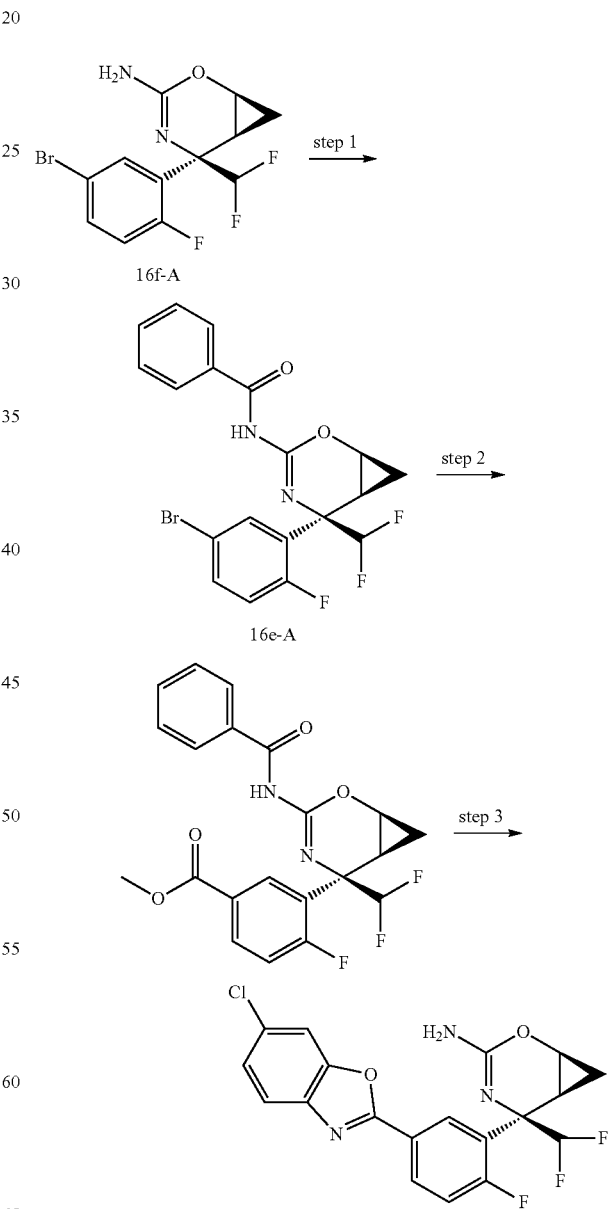

Synthesis of (1S,5R,6S)-5-(5-(6-chlorobenzo[d]oxazol-2-yl)-2-fluorophenyl)-5-(difluoromethyl)-2-oxa-4-azabicyclo[4.1.0]hept-3-en-3-amine Step 1:

To a solution of (1S,5R,6S)-5-(5-bromo-2-fluorophenyl)-5-(difluoromethyl)-2-oxa-4-azabicyclo[4.1.0]hept-3-en-3-amine (16f-A, 2.20 g, 6.56 mmol) in DMF (20 mL) under nitrogen was added TEA (1.37 mL, 9.85 mmol) and benzoic anhydride (1.66 g, 7.35 mmol). The reaction mixture was stirred at RT overnight, then diluted with aqueous saturated $Na_2CO_3$ solution and extracted with EtOAc twice. The organic phase was washed with water, brine and dried over $Na_2SO_4$. The filtrate was concentrated in vacuo and the crude was purified by silica gel chromatography (0-50% EtOAc-hexane) to obtain N-((1S,5R,6S)-5-(5-bromo-2-fluorophenyl)-5-(difluoromethyl)-2-oxa-4-azabicyclo[4.1.0]hept-3-en-3-yl)benzamide (16e-A) as a white solid (2.88 g, 100% yield). MS m/z=439, 441 [M+H]$^+$. Calculated for $C_{19}H_{14}BrF_3N_2O_2$: 439.2.

Step 2:

A sealable vial was charged with -((1S,5R,6S)-5-(5-bromo-2-fluorophenyl)-5-(difluoromethyl)-2-oxa-4-azabicyclo[4.1.0]hept-3-en-3-yl)benzamide (16e-A, 1.05 g, 2.39 mmol), (9,9-dimethyl-9H-xanthene-4,5-diyl)bis(diphenylphosphine) (0.15 g, 0.26 mmol), palladium (II) acetate (0.029 g, 0.13 mmol), methanol (0.97 ml, 23.86 mmol) and triethylamine (4.99 ml, 35.8 mmol). The vial was evacuated and backfilled with CO gas. The reaction mixture was stirred at 65° C. overnight, then diluted with EtOAc and filtered through a pad of celite. The filtrate was washed with water, brine and dried over $Na_2SO_4$. The filtrate was concentrated in vacuo and the crude was purified by silica gel chromatography (0-100% EtOAc-DCM) to obtain methyl 3-((1S,5R,6S)-3-benzamido-5-(difluoromethyl)-2-oxa-4-azabicyclo[4.1.0]hept-3-en-5-yl)-4-fluorobenzoate as a yellow solid (0.69 g, 69% yield). MS m/z=419 [M+H]$^+$. Calculated for $C_{21}H_{17}F_3N_2O_4$: 418.4.

Step 3:

A sealable vial was charged with methyl 3-((1S,5R,6S)-3-benzamido-5-(difluoromethyl)-2-oxa-4-azabicyclo[4.1.0]hept-3-en-5-yl)-4-fluorobenzoate (0.100 g, 0.24 mmol), 2-amino-5-chlorophenol (0.086 g, 0.60 mmol) and polyphosphoric acid (0.50 mL). The reaction mixture was purged with nitrogen for 1 min and then heated to 170° C. for 1 h. The reaction mixture was allowed to cool to rt, neutralized with aqueous, saturated $Na_2CO_3$ solution and 1 N NaOH. The mixture was extracted three times with a solvent mixture of $CHCl_3$:i-PrOH (3:1). The combined organic extracts were dried over $Na_2SO_4$, and concentrated in vacuo. The crude was purified first by silica gel chromatography 0-100% EtOAc-hexane. The collected fractions were further purified by reverse-phase preparative HPLC using a Phenomenex Gemini column, 10 micron, C18, 100 Å, 150×30 mm, 0.1% TFA in $CH_3CN/H_2O$, gradient 10% to 100% over 16 min. The fractions containing the desired product were combined and neutralized with solid $Na_2CO_3$. The aqueous phase was extracted with DCM and dried over $Na_2SO_4$. The filtrate was concentrated in vacuo to obtain the title compound as a beige solid (10.5 mg, 11% yield). MS m/z=408 [M+H]$^+$. Calculated for $C_{19}H_{13}ClF_3N_3O_2$: 407.8.

$^1$H NMR (400 MHz, CHLOROFORM-d) δ=8.44 (dd, J=2.3, 7.4 Hz, 1H), 8.07 (ddd, J=2.3, 4.6, 8.5 Hz, 1H), 7.57 (d, J=8.4 Hz, 1H), 7.36 (d, J=1.8 Hz, 1H), 7.29 (dd, J=2.0, 8.4 Hz, 1H), 7.20 (dd, J=8.4, 11.5 Hz, 1H), 6.41-6.07 (m, 1H), 4.90 (br. s., 2H), 4.03-3.90 (m, 1H), 1.91 (td, J=7.1, 9.5 Hz, 1H), 1.51-1.43 (m, 1H), 1.07-0.95 (m, 1H).

Example 426

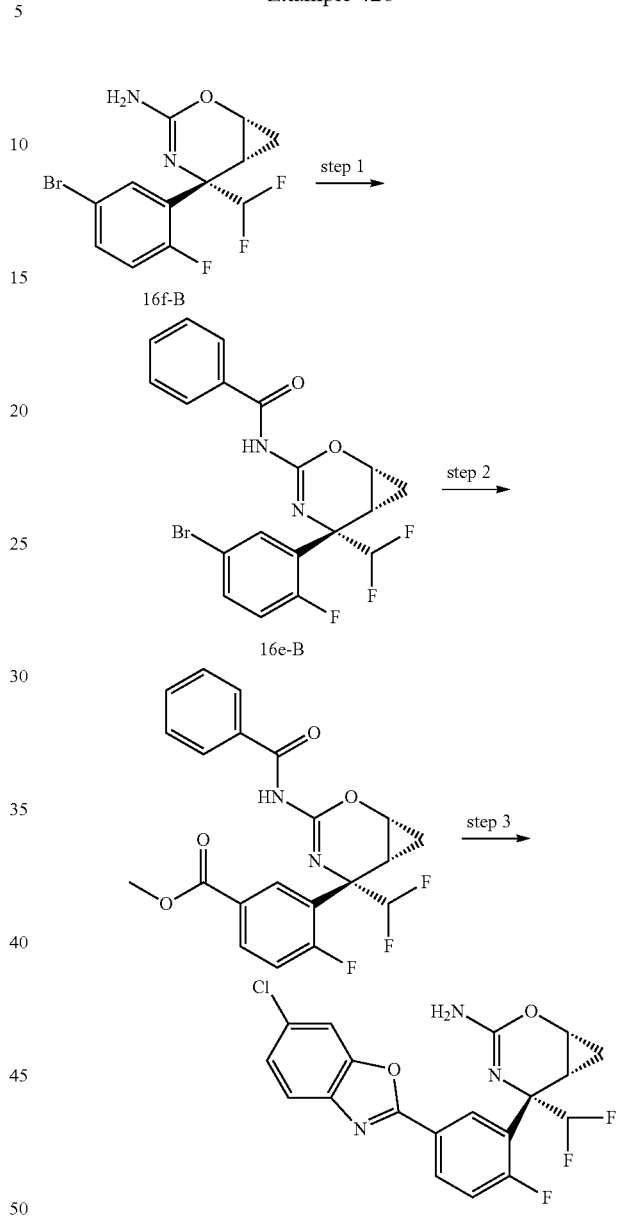

Synthesis of (1R,5S,6R)-5-(5-(6-chlorobenzo[d]oxazol-2-yl)-2-fluorophenyl)-5-(difluoromethyl)-2-oxa-4-azabicyclo[4.1.0]hept-3-en-3-amine The title compound was synthesized according to procedures and steps analogous to those described for Example 423 above, but using (1R,5S,6R)-5-(5-bromo-2-fluorophenyl)-5-(difluoromethyl)-2-oxa-4-azabicyclo[4.1.0]hept-3-en-3-amine (16f-B) in step 1. MS m/z=408 [M+H]$^+$. Calculated for $C_{19}H_{13}ClF_3N_3O_2$: 407.8.

$^1$H NMR (400 MHz, CHLOROFORM-d) δ=8.43 (dd, J=2.2, 7.4 Hz, 1H), 8.04 (ddd, J=2.3, 4.7, 8.4 Hz, 1H), 7.55 (d, J=8.4 Hz, 1H), 7.32 (d, J=1.6 Hz, 1H), 7.28 (dd, J=2.0, 8.4 Hz, 1H), 7.19 (dd, J=8.4, 11.5 Hz, 1H), 6.42-6.07 (m, 1H), 5.01

(br. s., 2H), 4.03-3.91 (m, 1H), 1.98-1.86 (m, 1H), 1.48 (t, J=5.9 Hz, 1H), 1.08-0.94 (m, 1H).

Example 427

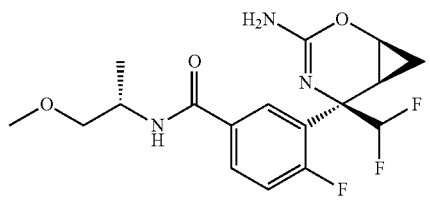 [SMILES: COC[C@H](C)NC(=O)c1ccc(F)c([C@]2(C(F)F)N=C(N)O[C@H]3C[C@H]32)c1]

Synthesis of 3-((1S,5R,6S)-3-Amino-5-(difluoromethyl)-2-oxa-4-azabicyclo[4.1.0]hept-3-en-5-yl)-4-fluoro-N—((S)-1-methoxypropan-2-yl)benzamide Step 1:
A sealable vial was charged with N-((1S,5R,6S)-5-(5-bromo-2-fluorophenyl)-5-(difluoromethyl)-2-oxa-4-azabicyclo[4.1.0]hept-3-en-3-yl)benzamide (16e-A, 0.4060 g, 0.924 mmol), palladium acetate (9.34 mg, 0.042 mmol), 9,9-dimethyl-4,5-bis(diphenylphosphino)xanthene ((0.029 g, 0.051 mmol), sodium carbonate (0.058 ml, 1.387 mmol) and toluene (1.849 ml). (S)-(+)-1-Methoxy-2-propylamine (0.195 ml, 1.849 mmol) was added and CO gas was bubbled through the reaction mixture for 10 minutes. The reaction mixture was heated to 80° C. for 3 hours. The reaction mixture was cooled to rt, adsorbed onto a plug of silica gel and purified by flash chromatography, eluting with a gradient of 5% to 80% EtOAc in hexane, to provide 3-((1S,5R,6S)-3-benzamido-5-(difluoromethyl)-2-oxa-4-azabicyclo[4.1.0]hept-3-en-5-yl)-4-fluoro-N—((S)-1-methoxypropan-2-yl)benzamide (0.3780 g, 0.795 mmol, 86% yield).

MS m/z=476.0 [M+H]$^+$ Calculated from $C_{24}H_{24}F_3N_3O_4$: 475.172

$^1$H NMR (300 MHz, CHLOROFORM-d) δ ppm 1.18 (d, J=6.58 Hz, 3H) 1.73 (br. s., 1H) 2.18 (dt, J=9.46, 7.03 Hz, 1H) 3.14 (s, 3H) 3.26 (d, J=3.65 Hz, 2H) 3.37 (d, J=3.80 Hz, 1H) 4.24 (br. s., 2H) 6.10-6.57 (m, 1H) 7.16-7.26 (m, 1H) 7.37-7.61 (m, 4H) 7.88-8.05 (m, 1H) 8.22 (br. s., 1H)

Step 2:
A flask was charged with 3-((1S,5R,6S)-3-benzamido-5-(difluoromethyl)-2-oxa-4-azabicyclo[4.1.0]hept-3-en-5-yl)-4-fluoro-N—((S)-1-methoxypropan-2-yl)benzamide (0.3780 g, 0.795 mmol), 1,8-diazabicyclo-[5.4.0]undec-7-ene (0.143 ml, 0.954 mmol) and MeOH (7.95 ml). The reaction mixture was heated to 65° C. for 4 hours. The crude product was adsorbed onto a plug of silica gel and purified by flash chromatography, eluting with a gradient of 10% to 100% EtOAc:EtOH (75:25) in hexane, to provide the title compound (0.0563 g, 0.152 mmol, 19.07% yield).

MS m/z=372.0 [M+H]$^+$ Calculated for $C_{17}H_{20}F_3N_3O_3$: 371.146

$^1$H NMR (400 MHz, DMSO-d$_6$) δ ppm 0.85-0.98 (m, 1H) 1.15 (d, J=6.85 Hz, 4H) 1.71-1.85 (m, 1H) 3.22-3.35 (m, 6H) 3.42 (dd, J=9.59, 6.46 Hz, 1H) 4.00 (t, J=5.38 Hz, 1H) 4.13-4.25 (m, 1H) 5.94 (s, 2H) 6.00-6.36 (m, 1H) 7.32 (dd, J=11.93, 8.61 Hz, 1H) 7.86 (ddd, J=8.36, 4.55, 2.35 Hz, 1H) 8.07 (dd, J=7.82, 2.35 Hz, 1H) 8.21 (1H, J=8.02 Hz, 1H)

$^1$H NMR (400 MHz, CHLOROFORM-d) δ ppm 2.24 (dt, J=9.39, 6.46 Hz, 1H) 2.44-2.55 (m, 3H) 3.11 (dt, J=9.24, 6.92 Hz, 1H) 3.80-3.89 (m, 3H) 4.58-4.68 (m, 5H) 4.75 (dd, J=9.59, 6.46 Hz, 1H) 5.28-5.36 (m, 1H) 5.45-5.59 (m, 1H) 7.34-7.69 (m, 1H) 8.64 (dd, J=11.93, 8.41 Hz, 1H) 9.19 (ddd, J=8.41, 4.50, 2.35 Hz, 1H) 9.40 (dd, J=7.82, 2.35 Hz, 1H) 9.53 (d, J=8.02 Hz, 1H)

Example 428

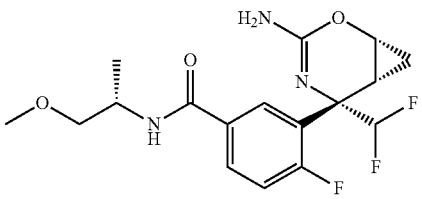 [SMILES: COC[C@H](C)NC(=O)c1ccc(F)c([C@@]2(C(F)F)N=C(N)O[C@@H]3C[C@@H]32)c1]

Synthesis of 3-((1R,5S,6R)-3-Amino-5-(difluoromethyl)-2-oxa-4-azabicyclo[4.1.0]hept-3-en-5-yl)-4-fluoro-N—((S)-1-methoxypropan-2-yl)benzamide The title compound was synthesized by procedures and steps analogous to those described for Example 427 above, but using N-((1R,5S,6R)-5-(5-bromo-2-fluorophenyl)-5-(difluoromethyl)-2-oxa-4-azabicyclo[4.1.0]hept-3-en-3-yl)benzamide (16e-B), in step 1. MS m/z=372.0 [M+H]$^+$. Calculated for $C_{17}H_{20}F_3N_3O_3$: 371.146

$^1$H NMR (400 MHz, CHLOROFORM-d) δ ppm 0.92-1.06 (m, 1H) 1.28 (d, J=6.65 Hz, 3H) 1.42 (br. s., 1H) 1.85 (q, J=7.76 Hz, 1H) 3.38 (s, 3H) 3.45 (br. s., 2H) 3.50 (s, 1H) 3.94 (br. s., 1H) 4.35 (br. s., 1H) 6.02-6.36 (m, 1H) 6.39 (d, J=6.46 Hz, 1H) 7.16 (t, J=9.98 Hz, 1H) 7.81 (br. s., 1H) 7.94 (d, J=7.24 Hz, 1H)

Example 429

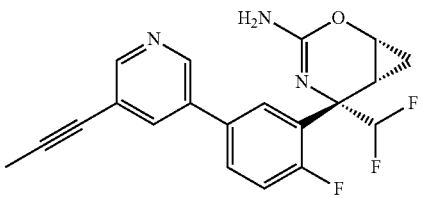 [SMILES: CC#Cc1cncc(-c2ccc(F)c([C@@]3(C(F)F)N=C(N)O[C@@H]4C[C@@H]43)c2)c1]

Synthesis of (1R,5S,6R)-5-(difluoromethyl)-5-(2-fluoro-5-(5-(prop-1-yn-1-yl)pyridin-3-yl)phenyl)-2-oxa-4-azabicyclo[4.1.0]hept-3-en-3-amine A microwave vial was charged with mixture of potassium phosphate (0.19 g, 0.90 mmol), (1R,5S,6R)-5-(5-bromo-2-fluorophenyl)-5-(difluoromethyl)-2-oxa-4-azabicyclo[4.1.0]hept-3-en-3-amine (16f-B, 0.10 g, 0.30 mmol), (5-(prop-1-yn-1-yl)pyridin-3-yl)boronic acid (0.12 g, 0.75 mmol) and 1,1-bis[(di-t-butyl-p-methylaminophenyl]palladium(II) chloride (10.56 mg, 0.015 mmol) in dioxane/water (2.0/0.5 mL). The reaction mixture was heated to 110° C. for 30 min in the microwave. The reaction mixture was then diluted with water and extracted with DCM three times. The combined organic extracts were washed with brine and dried over sodium sulfate. The filtrate was concentrated in vacuo and the crude material was purified by silica gel chromatography (0-100% EtOAc-DCM) to obtain the title compound as a white solid (82.3 mg, 74% yield). MS m/z=372 [M+H]+. Calculated for C20H16F3N3O: 371.4.

1H NMR (400 MHz, CHLOROFORM-d) δ=8.65 (d, J=2.3 Hz, 1H), 8.55 (d, J=1.8 Hz, 1H), 7.80 (t, J=2.1 Hz, 1H), 7.73 (dd, J=2.3, 7.4 Hz, 1H), 7.49 (ddd, J=2.4, 4.6, 8.4 Hz, 1H), 7.19 (dd, J=8.4, 11.7 Hz, 1H), 6.40-6.04 (m, 1H), 4.44 (br. s., 2H), 3.99-3.88 (m, 1H), 2.08 (s, 3H), 1.93-1.82 (m, 1H), 1.48-1.38 (m, 1H), 1.03-0.93 (m, 1H).

Example 430

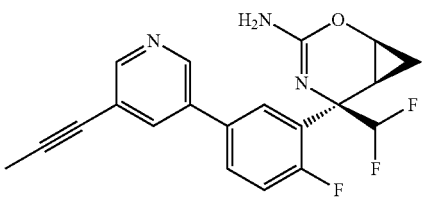 [SMILES: CC#Cc1cncc(-c2ccc(F)c([C@]3(C(F)F)N=C(N)O[C@H]4C[C@H]43)c2)c1]

Synthesis of (1S,5R,6S)-5-(difluoromethyl)-5-(2-fluoro-5-(prop-1-yn-1-yl)pyridin-3-yl)phenyl)-2-oxa-4-azabicyclo[4.1.0]hept-3-en-3-amine The title compound was synthesized according to the procedure described for Example 429 above, but using (1S,5R,6S)-5-(5-bromo-2-fluorophenyl)-5-(difluoromethyl)-2-oxa-4-azabicyclo[4.1.0]hept-3-en-3-amine (16f-A). MS m/z=372 [M+H]+. Calculated for C20H16F3N3O: 371.4.

1H NMR (400 MHz, CHLOROFORM-d)=8.64 (d, J=2.2 Hz, 1H), 8.53 (d, J=1.8 Hz, 1H), 7.78 (t, J=2.1 Hz, 1H), 7.73 (dd, J=2.4, 7.3 Hz, 1H), 7.49 (ddd, J=2.5, 4.5, 8.4 Hz, 1H), 7.19 (dd, J=8.5, 11.6 Hz, 1H), 6.41-6.02 (m, 1H), 4.53 (br. s., 2H), 4.01-3.86 (m, 1H), 2.06 (s, 3H), 1.87 (td, J=7.0, 9.5 Hz, 1H), 1.48-1.37 (m, 1H), 0.97 (td, J=6.7, 9.2 Hz, 1H).

Example 431

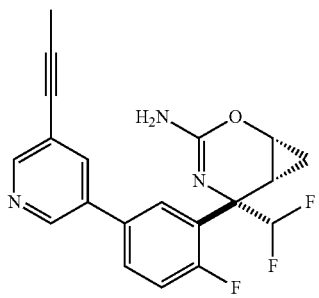 [SMILES: CC#Cc1cncc(-c2ccc(F)c([C@@]3(C(F)F)N=C(N)O[C@@H]4C[C@@H]43)c2)c1]

Synthesis of 2946459 (1(S,R),5(R,S),6(S,R))-5-(2-fluoro-5-(5-(prop-1-yn-1-yl)pyridin-3-yl)phenyl)-5-(fluoromethyl)-2-oxa-4-azabicyclo[4.1.0]hept-3-en-3-amine Step 1:
N-(((1R,S),(5R,S),(6R,S))-5-(2-fluoro-5-(5-(prop-1-yn-1-yl)pyridin-3-yl)phenyl)-5-(fluoromethyl)-2-oxa-4-azabicyclo[4.1.0]hept-3-en-3-yl)benzamide was synthesized according to the procedure described for Example 429 above, but using (6f-rac). MS m/z=458 [M+H]+.

Step 2:
A solution of N-(((1R,S),(5R,S),(6R,S))-5-(2-fluoro-5-(5-(prop-1-yn-1-yl)pyridin-3-yl)phenyl)-5-(fluoromethyl)-2-oxa-4-azabicyclo[4.1.0]hept-3-en-3-yl)benzamide (0.253 g, 0.277 mmol) in MeOH (3.5 mL) under argon atmosphere was treated with 1,8-diazabicyclo-[5.4.0]undec-7-ene (0.4 ml, 2.68 mmol). The reaction mixture was heated at 60° C. for 3 h. The reaction mixture was cooled to room temperature, and the suspension was filtered. The solid was rinsed with MeOH to give the title compound (0.0944 g) as a white solid. MS m/z=354.3 [M]+.

1H NMR (400 MHz, DMSO-d6) δ ppm 8.75 (d, J=2.15 Hz, 1H), 8.58 (d, J=1.57 Hz, 1H), 7.99 (s, 1H), 7.78 (dd, J=7.53, 2.25 Hz, 1H), 7.69-7.75 (m, 1H), 7.32 (dd, J=11.93, 8.41 Hz, 1H), 5.77 (s, 2H), 4.46-4.75 (m, 2H), 4.01 (t, J=5.67 Hz, 1H), 2.11 (s, 3H), 1.51-1.75 (m, 1H), 1.03 (td, J=6.26, 2.35 Hz, 1H), 0.82 (dt, J=9.39, 6.46 Hz, 1H).

Example 432

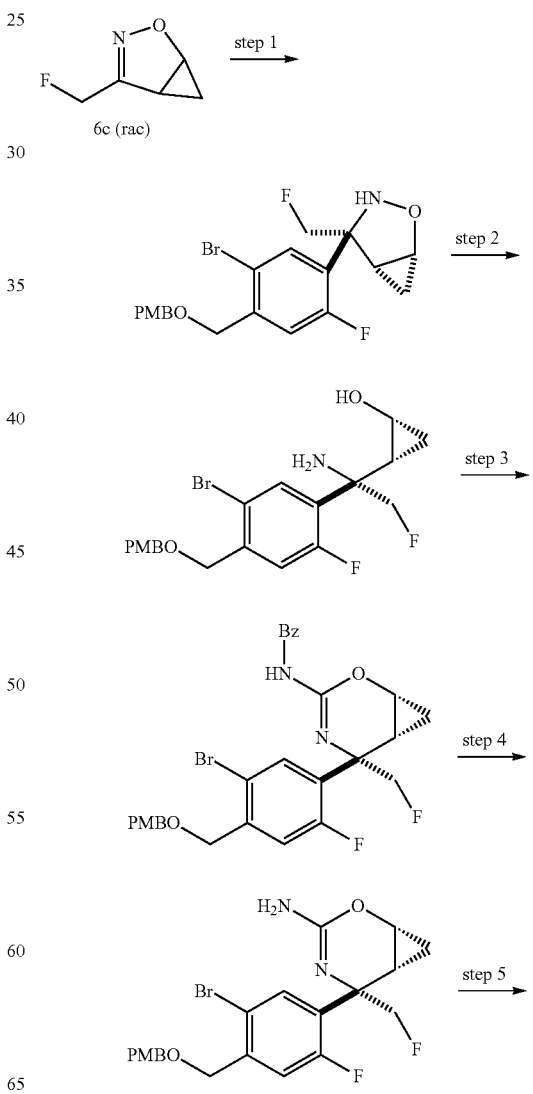

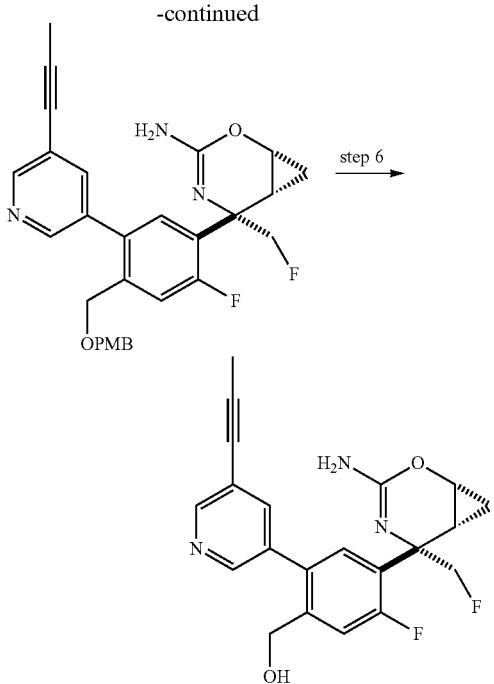

Synthesis of (4-(((1S,R),(5R,S),(6S,R))-3-amino-5-(fluoromethyl)-2-oxa-4-azabicyclo[4.1.0]hept-3-en-5-yl)-5-fluoro-2-(5-(prop-1-yn-1-yl)pyridin-3-yl)phenyl)methanol Step 1:

To a solution of 1-bromo-4-fluoro-5-iodo-2-(((4-methoxybenzyl)oxy)methyl)benzene (intermediate 60, 0.766 g, 1.291 mmol) in Et₂O (3.7 mL) at −78° C. was added a solution of n-butyllithium (2.5M in hexanes, 0.516 mL, 1.291 mmol) dropwise. The solution was stirred at −78° C. for 15 min. In a separate flask, a solution of 4-(fluoromethyl)-2-oxa-3-azabicyclo[3.1.0]hex-3-ene (6c rac, 0.114 g, 0.993 mmol) in toluene (4.5 mL) was treated with boron fluoride diethyl etherate at −78° C. This solution was added via cannula to the aryl lithium solution and the resulting reaction mixture was stirred at −78° C. for 1 h. The reaction was quenched with saturated aqueous ammonium chloride at −78° C. and diluted with water and EtOAc. The layers were separated and the aqueous layer was extracted with EtOAc. The combined organic extracts were washed with water, brine, and dried over sodium sulfate. The filtrate was concentrated in vacuo and the crude material was purified by silica gel chromatography, eluting with 1:9 EtOAc in heptane, to provide [(1S,R),(4R,S),(5S,R)]-4-(5-bromo-2-fluoro-4-(((4-methoxybenzyl)oxy)methyl)phenyl)-4-(fluoromethyl)-2-oxa-3-azabicyclo[3.1.0]hexane. MS m/z=440.2/442.0 (M+H).

Steps 2-4: [(1R,S),(5S,R),(6R,S)]-5-(5-bromo-2-fluoro-4-(((4-methoxybenzyl)oxy)methyl)phenyl)-5-(fluoromethyl)-2-oxa-4-azabicyclo[4.1.0]hept-3-en-3-amine The title compound was synthesized using procedures similar to those described in steps 2-4 for the synthesis of 4d rac, but using [(1S,R),(4R,S),(5S,R)]-4-(5-bromo-2-fluoro-4-(((4-methoxybenzyl)oxy)methyl)phenyl)-4-(fluoromethyl)-2-oxa-3-azabicyclo[3.1.0]hexane. MS m/z=467.0/469.0 (M+H).

Step 5:

[(1R,S),(5S,R),(6R,S)]-5-(2-fluoro-4-(((4-methoxybenzyl)oxy)methyl)-5-(5-(prop-1-yn-1-yl)pyridin-3-yl)phenyl)-5-(fluoromethyl)-2-oxa-4-azabicyclo[4.1.0]hept-3-en-3-amine was synthesized in an analogous manner as Example 390, but using [(1R,S), (5S,R),(6R,S)]-5-(5-bromo-2-fluoro-4-(((4-methoxybenzyl)oxy)methyl)phenyl)-5-(fluoromethyl)-2-oxa-4-azabicyclo[4.1.0]hept-3-en-3-amine and (5-(prop-1-yn-1-yl)pyridin-3-yl)boronic acid. MS m/z=504.2 (M+H).

Step 6:

2,3-Dichloro-5,6-dicyano-p-benzoquinone (0.040 g, 0.178 mmol) was added in one portion to a solution of [(1R,S),(5S,R),(6R,S)]-5-(2-fluoro-4-(((4-methoxybenzyl)oxy)methyl)-5-(5-(prop-1-yn-1-yl)pyridin-3-yl)phenyl)-5-(fluoromethyl)-2-oxa-4-azabicyclo[4.1.0]hept-3-en-3-amine (0.069 g, 0.137 mmol) in DCM (1.3 ml) and water (0.065 ml) at room temperature. After 40 minutes, an additional amount of 2,3-dichloro-5,6-dicyano-p-benzoquinone (0.040 g, 0.178 mmol) was added. After 40 minutes, the reaction was partitioned between EtOAc and 1N NaOH. The layers were separated and the aqueous layer was extracted with EtOAc. The combined organic extracts were washed with 1N NaOH, brine, and dried over sodium sulfate. The filtrate was concentrated in vacuo to give the crude material which was purified by silica gel chromatography, eluting with 1:20 2M $NH_3$.MeOH in $CH_2CL_2$, to afford the title compound. MS m/z=384.0 (M+H).

1H NMR (400 MHz, METHANOL-d4) δ ppm 0.84-0.96 (m, 1H) 1.12-1.22 (m, 1H) 1.24-1.38 (m, 1H) 1.72-1.84 (m, 1H) 2.08 (s, 3H) 3.97-4.08 (m, 1H) 4.46 (s, 2H) 4.69 (d, J=47.30 Hz, 2H) 7.31 (d, J=7.63 Hz, 1H) 7.38 (d, J=13.11 Hz, 1H) 7.80 (s, 1H) 8.41 (s, 1H) 8.52 (s, 1H)

Example 433

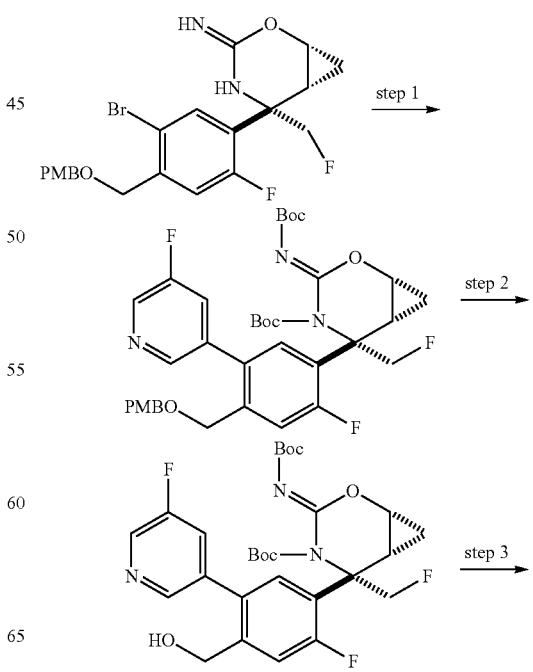

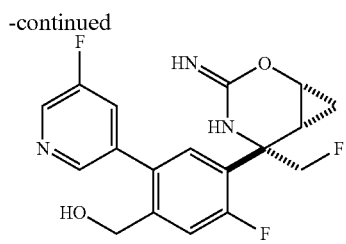

Synthesis of (5-fluoro-4-([(1R,S),(5S,R),(6R,S)]-5-(fluoromethyl)-3-imino-2-oxa-4-azabicyclo[4.1.0]heptan-5-yl)-2-(5-fluoropyridin-3-yl)phenyl)methanol Step 1:

A glass microwave reaction vessel was charged with the [(1R,S),(5S,R),(6R,S)]-5-(5-bromo-2-fluoro-4-(((4-methoxybenzyl)oxy)methyl)phenyl)-5-(fluoromethyl)-2-oxa-4-azabicyclo[4.1.0]hept-3-en-3-amine (step 4 in Example 393, 0.0709 g, 0.152 mmol), sodium carbonate (0.096 g, 0.910 mmol), and 5-fluoropyridine-3-boronic acid (0.034 g, 0.243 mmol) in 1,4-dioxane (1.2 ml) and water (0.4 ml). The vessel was capped and the solution was degassed by bubbling nitrogen gas through the solution for 10 minutes. Next, Aphos-PdCl$_2$ (10.74 mg, 0.015 mmol) was added and the vessel was sealed. The reaction mixture was stirred and heated in a Initiator microwave reactor (Personal Chemistry, Biotage AB, Inc., Upssala, Sweden) at 120° C. for 20 minutes. The reaction was poured into water and the mixture was extracted with EtOAc. The combined organic extracts were washed with water, saturated aqueous sodium chloride, and dried over sodium sulfate. The solution was filtered and concentrated in vacuo to give the crude material. The crude material was taken up in MeCN (1.6 mL) and 4-(dimethylamino)pyridine (0.037 g, 0.303 mmol) and di-tert-butyl dicarbonate (0.073 g, 0.334 mmol) were added. After 2.5 hours, the reaction was concentrated and purified by silica gel chromatography by eluting with 1:2 EtOAc/Heptanes, to provide [(1R,S), (5S,R), (6R,S),Z]-tert-butyl 3-((tert-butoxycarbonyl)imino)-5-(2-fluoro-5-(5-fluoropyridin-3-yl)-4-(((4-methoxybenzyl)oxy)methyl)phenyl)-5-(fluoromethyl)-2-oxa-4-azabicyclo[4.1.0]heptane-4-carboxylate. MS m/z=684.2 (M+H).

Step 2:

2,3-Dichloro-5,6-dicyano-p-benzoquinone (0.027 g, 0.121 mmol) was added in one portion to a solution of [(1R, S),(5S,R),(6R,S),Z]-tert-butyl 3-((tert-butoxycarbonyl)imino)-5-(2-fluoro-5-(5-fluoropyridin-3-yl)-4-(((4-methoxybenzyl)oxy)methyl)phenyl)-5-(fluoromethyl)-2-oxa-4-azabicyclo[4.1.0]heptane-4-carboxylate in DCM (0.9 ml) and water (0.045 ml) at room temperature. After 2 hours, the reaction is filtered through a plug of aluminum oxide (activated, neutral, Brockmann I) with 1:9 MeOH/DCM. Removal of the solvents in vacuo to afford [(1R,S),(5S,R),(6R,S),Z]-tert-butyl 3-((tert-butoxycarbonyl)imino)-5-(2-fluoro-5-(5-fluoropyridin-3-yl)-4-(hydroxymethyl)phenyl)-5-(fluoromethyl)-2-oxa-4-azabicyclo[4.1.0]heptane-4-carboxylate which is used directly in the next step without further purification. LC/MS (ESI⁻) m/z=586 (M+Na) 564.2 (M+H).

Step 3:

Trifluoroacetic acid (1 mL, 13.46 mmol) was added in one portion to a solution of [(1R,S),(5S,R),(6R,S),Z]-tert-butyl 3-((tert-butoxycarbonyl)imino)-5-(2-fluoro-5-(5-fluoropyridin-3-yl)-4-(hydroxymethyl)phenyl)-5-(fluoromethyl)-2-oxa-4-azabicyclo[4.1.0]heptane-4-carboxylate (0.052 g, 0.092 mmol) in DCM (2 mL) at RT. After 45 minutes, the reaction was concentrated and the crude material was partitioned between DCM and 10% Na$_2$CO$_3$. The layers were separated and the aqueous layer was extracted with DCM. The combined organic extracts were washed with saturated aqueous sodium chloride and dried over sodium sulfate. The solution was filtered and concentrated in vacuo to give the crude material. The crude material was purified by silica gel chromatography by eluting with 1:20 2M NH$_3$.MeOH in CH$_2$CL$_2$, to provide the title compound. LC/MS (ESI⁻) m/z=364.1 (M+H).

1H NMR (400 MHz, METHANOL-d4) δ ppm 0.86-0.96 (m, 1H) 1.13-1.21 (m, 1H) 1.72-1.84 (m, 1H) 3.97-4.07 (m, 1H) 4.48 (s, 2H) 4.69 (d, J=48.12 Hz, 2H) 5.49 (s, 1H) 7.29-7.46 (m, 2H) 7.71 (d, J=9.59 Hz, 1H) 8.40 (s, 1H) 8.49 (s, 1H)

Example 434

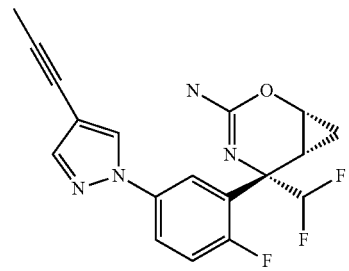 [SMILES: CC#Cc1cnn(-c2ccc(F)c([C@@]3(C(F)F)N=C(N)O[C@@H]4C[C@@H]43)c2)c1]

Synthesis of (1R,5S,6R)-5-(difluoromethyl)-5-(2-fluoro-5-(4-(prop-1-yn-1-yl)-1H pyrazol-1-yl)phenyl)-2-oxa-4-azabicyclo[4.1.0]hept-3-en-3-amine A sealable vial was charged with potassium carbonate, (0.095 g, 0.686 mmol), (1R,5S,6R)-5-(5-bromo-2-fluorophenyl)-5-(difluoromethyl)-2-oxa-4-azabicyclo[4.1.0]hept-3-en-3-amine (16f-B, 0.100 g, 0.298 mmol), and 4-(prop-1-yn-1-yl)-1H-pyrazole (intermediate 61, 0.041 g, 0.388 mmol). The vial was evacuated and backfilled with nitrogen twice before adding toluene (3 ml) and 0.1 mL of a premixed stock solution of copper(I) iodide (55 mg) and trans-N,N'-dimethylcyclohexane-1,2-diamine (0.2 mL) in toluene (1 mL). The reaction mixture was heated at 110° C. overnight. The reaction was poured into a 9:1 mixture of aqueous saturated ammonium chloride/ammonium hydroxide and the mixture was extracted with EtOAc. The combined organic extracts were washed with a 9:1 mixture of aqueous saturated ammonium chloride/ammonium hydroxide, brine, and dried over sodium sulfate. The filtrate was concentrated in vacuo to give the crude material which was purified by reverse-phase preparative HPLC using a Phenomenex Gemini column, 10 micron, C18, 100 Å, 150×30 mm, 0.1% TFA in CH$_3$CN/H$_2$O, gradient 10% to 95% over 15 min to provide the purified product as the TFA salt. The product was partitioned between DCM and aq. 10% Na$_2$CO$_3$. The layers were separated and the aqueous layer was extracted with DCM. The combined organic extracts were washed with brine and dried over sodium sulfate. The filtrate was concentrated in vacuo to afford the title compound as the free base.

MS m/z=361.1 [M+H]⁺.

¹H NMR (400 MHz, CHLOROFORM-d) δ ppm 0.96-1.05 (m, 1H) 1.36-1.48 (m, 1H) 1.80-1.93 (m, 1H) 2.03 (s, 3H) 3.86-4.01 (m, 1H) 6.20 (t, J=56.34 Hz, 1H) 7.10-7.23 (m, 1H) 7.26 (s, 1H) 7.66 (s, 1H) 7.76 (m, 1H) 7.88 (s, 1H)

Example 435

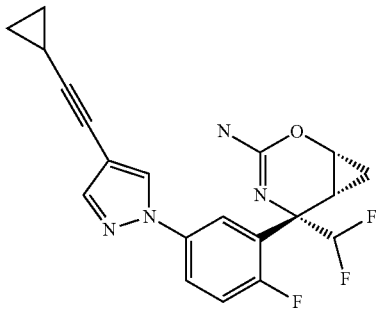 [SMILES: NC1=N[C@@](c2cc(-n3cc(C#CC4CC4)cn3)ccc2F)(C(F)F)[C@H]2C[C@H]2O1]

Synthesis of (1R,5S,6R)-5-(difluoromethyl)-5-(2-fluoro-5-(4-(prop-1-yn-1-yl)-1H pyrazol-1-yl)phenyl)-2-oxa-4-azabicyclo[4.1.0]hept-3-en-3-amine The title compound was synthesized according to the procedure described for Example 432, above, but using 4-(cyclopropylethynyl)-1H-pyrazole (Intermediate 62). MS m/z=387.0 [M+H]⁺.

¹H NMR (400 MHz, METHANOL-d4) δ ppm 0.64-0.75 (m, 2H) 0.79-0.91 (m, 2H) 0.91-1.02 (m, 1H) 1.20-1.37 (m, 1H) 1.38-1.48 (m, 1H) 1.87-1.96 (m, 1H) 3.35 (s, 1H) 4.01-4.09 (m, 1H) 6.17 (t, J=56.14 Hz, 1H) 7.27 (dd, J=11.35, 9.00 Hz, 1H) 7.66 (s, 1H) 7.67-7.74 (m, 1H) 7.84 (dd, J=6.46, 2.74 Hz, 1H) 8.20 (s, 1H).

Example 436

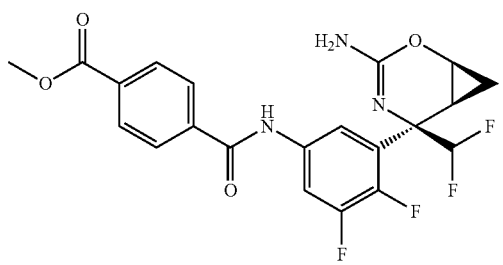 [SMILES: COC(=O)c1ccc(C(=O)Nc2cc(F)c(F)c([C@]3(C(F)F)N=C(N)O[C@H]4C[C@H]43)c2)cc1]

Synthesis of methyl 6-((3-((1S,5R,6S)-3-amino-5-(difluoromethyl)-2-oxa-4-azabicyclo[4.1.0]hept-3-en-5-yl)-4,5-difluorophenyl)carbamoyl)nicotinate Step 1:
Methyl 6-((3-((1S,5R,6S)-3-amino-5-(difluoromethyl)-2-oxa-4-azabicyclo[4.1.0]hept-3-en-5-yl)-4,5-difluorophenyl)carbamoyl)nicotinimidate was isolated as a by-product in the coupling of (1S,5R,6S)-5-(5-amino-2,3-difluorophenyl)-5-(difluoromethyl)-2-oxa-4-azabicyclo[4.1.0]hept-3-en-3-amine (20f-A) with 5-cyano-2-pyridinecarboxylic acid according to method B.

Step 2:
Methyl 6-((3-((1R,5S,6R)-3-amino-5-(difluoromethyl)-2-oxa-4-azabicyclo[4.1.0]hept-3-en-5-yl)-4,5-difluorophenyl)carbamoyl)nicotinimidate (0.050 g, 0.111 mmol) was dissolved in hydrochloric acid (2N, 5 mL, 10.00 mmol) and stirred at room temperature. After 15 minutes, the reaction mixture was neutralized with 1 N sodium hydroxide (10 mL). A solution of aqueous saturated sodium bicarbonate (5 mL) was added and the mixture stirred for 10 minutes. The suspension was filtered and the solid was washed with water (10 mL). The solid was further purified by silica gel chromatography [10-90% (2% NH4OH in 3:1 ethyl acetate: ethanol) in hexane] to give the title compound (0.0298 g, 0.066 mmol, 59.5% yield). MS m/z=452.9 [M+H]⁺. 1H NMR (CHLOROFORM-d) Shift: 9.75 (s, 1H), 9.04 (dd, J=2.0, 0.7 Hz, 1H), 8.48 (dd, J=8.0, 2.0 Hz, 1H), 8.26 (dd, J=8.1, 0.7 Hz, 1H), 7.99 (ddd, J=11.7, 7.0, 2.8 Hz, 1H), 7.22-7.28 (m, 1H), 6.23 (td, J=55.8, 0.9 Hz, 1H), 5.17 (br. s., 2H), 4.01 (s, 3H), 3.92 (td, J=6.8, 2.6 Hz, 1H), 1.80-1.92 (m, 1H), 1.40-1.49 (m, 1H), 0.90-1.03 (m, 1H)

Example 437

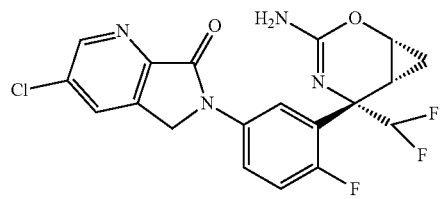 [SMILES: NC1=N[C@@](c2cc(N3Cc4cc(Cl)cnc4C3=O)ccc2F)(C(F)F)[C@H]2C[C@H]2O1]

Synthesis of 6-(3-((1R,5S,6R)-3-amino-5-(difluoromethyl)-2-oxa-4-azabicyclo[4.1.0]hept-3-en-5-yl)-4-fluorophenyl)-3-chloro-5H-pyrrolo[3,4-b]pyridin-7(6H)-one A solution of N-(3-((1R,5S,6R)-3-amino-5-(difluoromethyl)-2-oxa-4-azabicyclo[4.1.0]hept-3-en-5-yl)-4-fluorophenyl)-5-chloro-3-(hydroxymethyl)picolinamide (Example 420, 60 mg, 0.136 mmol) in DCM (2 mL) was cooled 0° C. under nitrogen atmosphere. A solution of Deoxo-fluor, (50 w % in THF, 0.150 mL, 0.408 mmol) was added dropwise and the reaction mixture was allowed to stir at rt for 25 min. The reaction mixture was poured into aqueous saturated bicarbonate solution and extracted with EtOAc. The crude material was absorbed onto a plug of silica gel and purified by chromatography, eluting with a gradient of 20% to 100% EtOAc in hexane, to provide the title compound as white solid. MS m/z=423 [M+H]⁺.

¹H NMR (300 MHz, DMSO-d₆) δ ppm 0.80-0.98 (m, 1H) 1.16 (br. s., 1H) 1.66-1.88 (m, 1H) 3.99 (t, J=5.41 Hz, 1H) 5.52 (s, 2H) 5.84-6.47 (m, 3H) 7.19 (dd, J=11.84, 8.62 Hz, 1H) 7.33 (ddd, J=8.62, 4.38, 2.78 Hz, 1H) 7.47 (dd, J=7.31, 2.63 Hz, 1H) 8.27 (d, J=2.19 Hz, 1H) 8.82 (d, J=2.19 Hz, 1H)

Example 438

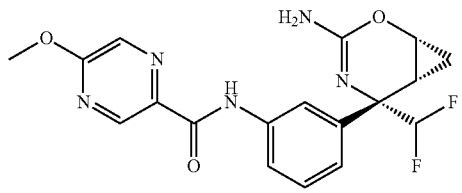 [SMILES: COc1cnc(C(=O)Nc2cccc([C@@]3(C(F)F)N=C(N)O[C@@H]4C[C@@H]43)c2)cn1]

Synthesis of N-(3-((1R,5S,6R)-3-amino-5-(difluoromethyl)-2-oxa-4-azabicyclo[4.1.0]hept-3-en-5-yl)phenyl)-5-methoxypyrazine-2-carboxamide The title compound was isolated as a byproduct during the synthesis of the methyl derivative N-(3-((1R,5S,6R)-3-amino-5-(difluoromethyl)-2-oxa-4-azabicyclo[4.1.0]hept-3-en-5-yl)-4-methylphenyl)-5-chloropicolinamide (Example 295) described above.

1H NMR (300 MHz, CHLOROFORM-d) δ ppm 9.54 (br. s., 1H) 9.01 (br. s., 1H) 8.14 (br. s., 1H) 7.92 (br. s., 1H) 7.78 (d, J=4.97 Hz, 1H) 7.38 (br. s., 2H) 5.80 (t, J=56.42 Hz, 1H) 3.96-4.15 (m, 4H) 1.80 (d, J=7.31 Hz, 1H) 1.43 (br. s., 1H) 1.01 (d, J=6.58 Hz, 1H). MS m/z=390 [M+H]+.

Example 439

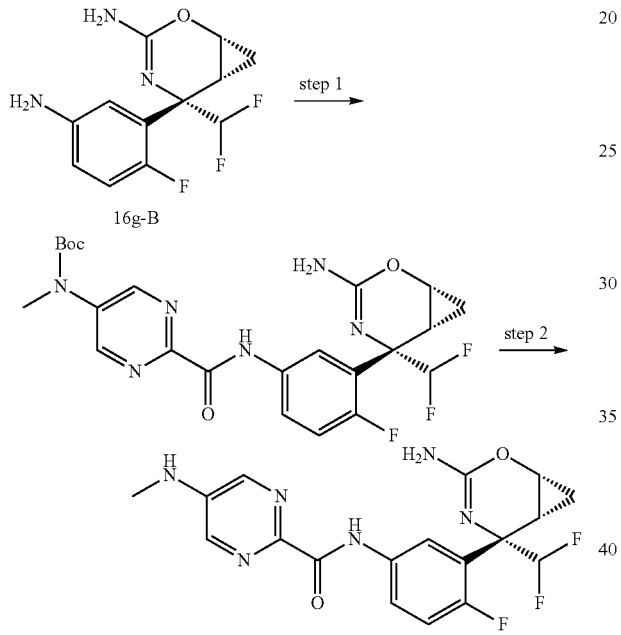

Synthesis of N-(3-((1R,5S,6R)-3-amino-5-(difluoromethyl)-2-oxa-4-azabicyclo[4.1.0]hept-3-en-5-yl)-4-fluorophenyl)-5-(methylamino)pyrimidine-2-carboxamide dihydrochloride Step 1: Tert-butyl(2-((3-((1R,5S,6R)-3-amino-5-(difluoromethyl)-2-oxa-4-azabicyclo[4.1.0]hept-3-en-5-yl)-4-fluorophenyl)carbamoyl)pyrimidin-5-yl)(methyl)carbamate The title compound was prepared using the procedure described in Method A above but using 5-((tert-butoxycarbonyl)(methyl)amino)pyrimidine-2-carboxylate, Intermediate 81. MS m/z=507.0 [M+H]+.

Step 2: N-(3-((1R,5S,6R)-3-amino-5-(difluoromethyl)-2-oxa-4-azabicyclo[4.1.0]hept-3-en-5-yl)-4-fluorophenyl)-5-(methylamino)pyrimidine-2-carboxamide dihydrochloride A solution of tert-butyl(2-((3-((1R,5S,6R)-3-amino-5-(difluoromethyl)-2-oxa-4-azabicyclo[4.1.0]hept-3-en-5-yl)-4-fluorophenyl)carbamoyl)pyrimidin-5-yl)(methyl)carbamate (0.06 g, 0.11 mmol) in 1,4-dioxane (2 mL) was treated with HCl (4.0M in 1,4-dioxane; 1 mL). The resulting suspension was treated with water (0.1 mL) resulting in a pale-yellow biphasic solution. The solution was stirred for 2 h, concentrated, and lyophilized from 1,4-dioxane to give N-(3-((1R,5S,6R)-3-amino-5-(difluoromethyl)-2-oxa-4-azabicyclo[4.1.0]hept-3-en-5-yl)-4-fluorophenyl)-5-(methylamino)pyrimidine-2-carboxamide dihydrochloride (0.05 g, 0.105 mmol, 93% yield) as a pale-yellow solid.

1H NMR (400 MHz, DMSO-d6): δ 10.61-10.78 (m, 2H), 9.54 (br. s, 1H), 8.37 (br. s., 1H), 8.25 (s, 2H), 8.14 (dd, J=2.54, 7.24 Hz, 1H), 7.98-8.05 (m, 1H), 7.41 (dd, J=9.00, 11.93 Hz, 1H), 6.76 (t, J=53 Hz, 1H), 4.83-5.56 (br. s, 2H), 4.69 (dt, J=2.74, 6.65 Hz, 1H), 2.86 (s, 3H), 2.12 (td, J=7.09, 9.49 Hz, 1H), 1.63 (t, J=6.26 Hz, 1H), 1.25-1.38 (m, 1H). MS m/z=407.0 [M+H]+.

Example 440

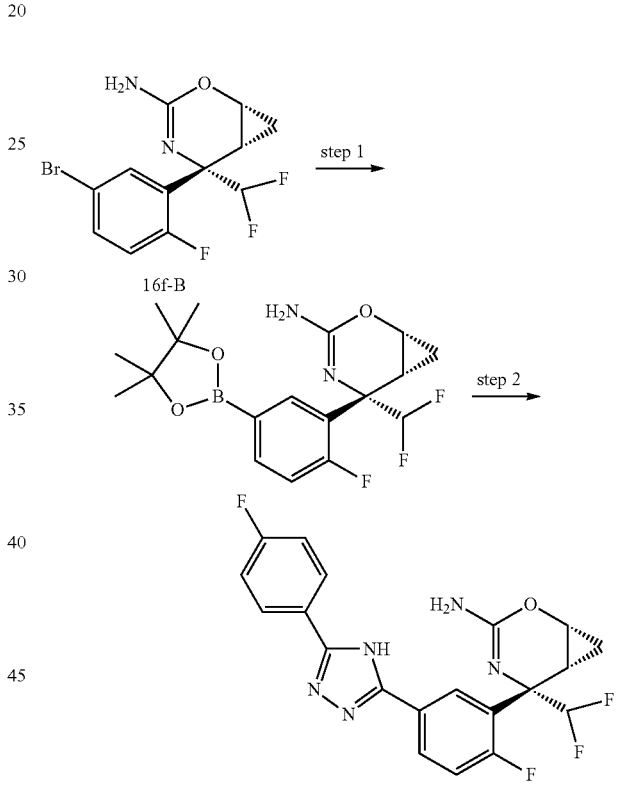

Step 1: (1R,5S,6R)-5-(difluoromethyl)-5-(2-fluoro-5-(4,4,5,5-tetramethyl-1,3,2-dioxaborolan-2-yl)phenyl)-2-oxa-4-azabicyclo[4.1.0]hept-3-en-3-amine A glass microwave reaction vessel was charged with (1R,5S,6R)-5-(5-bromo-2-fluorophenyl)-5-(difluoromethyl)-2-oxa-4-azabicyclo[4.1.0]hept-3-en-3-amine (0.11 g, 0.32 mmol), potassium acetate (0.095 g, 0.967 mmol), (1,1'-bis(diphenylphosphino)ferrocene)dichloropalladium(II) (0.024 g, 0.032 mmol), and bis(pinacolato) diboron (0.098 g, 0.387 mmol). The vessel was evacuated and flushed with nitrogen twice. Next, degassed DMSO (1.5 ml) was added and the reaction mixture was heated in an oil bath at 80° C. After two hours, the reaction was poured into water and the mixture was extracted with EtOAc. The combined organic extracts were washed with water, saturated aqueous sodium chloride, and dried over sodium sulfate. The solution was filtered and concentrated in vacuo to give the intermediate (1R,5S,6R)-5-(difluoromethyl)-5-(2-fluoro-5-(4,4,5,5-tetramethyl-1,3,2-dioxaborolan-2-yl)phenyl)-2-oxa-4-azabicyclo[4.1.0]hept-3-en-3-amine which was used without further purification. LC/MS (ESI⁻) m/z=383.1 (M+H).

Step 2. (1R,5S,6R)-5-(difluoromethyl)-5-(2-fluoro-5-(5-(4-fluorophenyl)-4H-1,2,4-triazol-3-yl)phenyl)-2-oxa-4-azabicyclo[4.1.0]hept-3-en-3-amine A glass microwave reaction vessel was charged with sodium carbonate (0.171 g, 1.609 mmol), 3-bromo-5-(4-fluorophenyl)-4H-1,2,4-triazole (0.078 g, 0.322 mmol, US20130184248 A1), (1R,5S,6R)-5-(difluoromethyl)-5-(2-fluoro-5-(4,4,5,5-tetramethyl-1,3,2-dioxaborolan-2-yl)phenyl)-2-oxa-4-azabicyclo[4.1.0]hept-3-en-3-amine, 1,4-dioxane (2.5 ml) and water (0.83 ml). The vessel was capped and the solution was degassed by bubbling nitrogen gas through the solution for 10 minutes. Next, 1,1-bis[(di-t-butyl-p-methylaminophenyl]palladium(II) chloride (0.023 g, 0.032 mmol) was added and the vessel was sealed. The reaction mixture was stirred and heated in a Initiator microwave reactor (Personal Chemistry, Biotage AB, Inc., Upssala, Sweden) at 120° C. for 20 minutes. The reaction was poured into water and the mixture was extracted with EtOAc. The combined organic extracts were washed with a 9:1 mixture of aqueous saturated ammonium chloride/ammonium hydroxide, saturated aqueous sodium chloride, and then stirred with activated carbon. The solution was filtered through a pad of celite and concentrated in vacuo to give the crude material. The crude material was purified by silica gel chromatography by eluting with 1:40 2M NH₃.MeOH in CH₂CL₂, and then repurified by preparative TLC by eluting with 1:30 2M NH₃.MeOH in CH₂CL₂ to provide the titled compound as a white solid after concentration with MeOH.

LC/MS (ESI⁻) m/z=418.1 (M+H)⁺.

1H NMR (400 MHz, MeOH-d4) δ ppm 0.95-1.04 (m, 1H) 1.36 (m, 1H) 1.90-1.99 (m, 1H) 4.05-4.13 (m, 1H) 6.28 (t, J=56.34 Hz, 1H) 7.23-7.29 (m, 2H) 7.27-7.34 (m, 1H) 8.03-8.16 (m, 3H) 8.28 (dd, J=7.53, 1.86 Hz, 1H)

Example 451

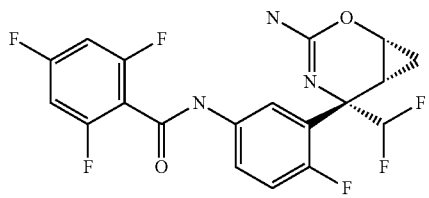 [SMILES: NC1=N[C@@](c2cc(NC(=O)c3c(F)cc(F)cc3F)ccc2F)(C(F)F)[C@H]2C[C@H]2O1]

Synthesis of N-(3-((1R,5S,6R)-3-amino-5-(difluoromethyl)-2-oxa-4-azabicyclo[4.1.0]hept-3-en-5-yl)-4-fluorophenyl)-2,4,6-trifluorobenzamide To a solution of 2,4,6-trifluorobenzoic acid (120 mg, 0.681 mmol, Aldrich) in dichloromethane (2 mL) was added oxalyl chloride (0.242 mL, 2.73 mmol, Aldrich), followed by catalytic amounts of DMF (20 μL). The reaction mixture was stirred at room temperature for 3 h. The reaction mixture was concentrated under reduced pressure and the residue was dissolved in DCM (2 mL). This solution was added dropwise to a separate solution of (1R,5S,6R)-5-(5-amino-2-fluorophenyl)-5-(difluoromethyl)-2-oxa-4-azabicyclo[4.1.0]hept-3-en-3-amine (185 mg, 0.682 mmol) and diisopropylethylamine (0.12 mL, 0.682 mmol) in dichloromethane (2.5 mL) cooled to 0° C. After completed addition, the reaction mixture was stirred for 20 min at 0° C. The reaction mixture was quenched with aqueous saturated sodium bicarbonate solution and extracted with DCM (2×3 mL). The combined organic extracts were dried over MgSO4 and concentrated under reduced pressure. The residue was dissolved in MeOH (1.5 mL) and cooled to 0° C. H₂O (4 mL) was added to the solution and the mixture was stirred at 0° C. for 1 h. The white solid was filtered off, washed with H₂O and dried in under reduced pressure to give 203 mg of the title compound as a white solid.

LC/MS (ESI-) m/z=430.1 [M+H]+.

1H NMR (MeOH) δ: 7.80-7.88 (m, 1H), 7.75 (dd, J=6.9, 2.6 Hz, 1H), 7.20 (dd, J=11.7, 8.8 Hz, 1H), 7.04 (t, J=8.4 Hz, 2H), 6.12-6.48 (m, 1H), 4.07 (t, J=5.5 Hz, 1H), 1.83-1.94 (m, 1H), 1.34 (br. s., 1H), 0.96-1.05 (m, 1H)

Table 11 contains representative compounds of the invention (the examples presented herein) and their mass observed and associated biological data, including BACE enzyme assay, BACE cell assay and Cathepsin D (Cat D) assay, inhibitory data expressed as μM IC₅₀'s. The assays procedures and data measurements are described hereinbelow.

TABLE 11

| Example No | Observed Mass | BACE1 Enzyme assay IC$_{50}$ (uM) | BACE cell assay IC$_{50}$ (uM) | CatD IC$_{50}$ (μM) |
|---|---|---|---|---|
| 2b-rac | 372 | 0.6045 | 0.109 | 81.3 |
| 2b-A | 372 | 0.2526 | 0.059 | >400.0 |
| 2b-B | 372 | 41.247 | >10.0 | 42.8 |
| 28 | 441.1 | 0.1175 | 0.0765 | 907.85 |
| 29 | 467.1 | 0.2065 | 0.656 | 462.46 |
| 30 | 424.9 | 0.0432 | 0.0285 | 469.07 |
| 31 | 422.9 | 0.306 | 0.0282 | 339.22 |
| 32 | 410.8 | 1.22 | 0.232 | 1021.9 |
| 33 | 432.1 | 0.0054 | 0.0014 | 116 |
| 34 | 432.1 | 6.215 | 1.75 | 622.6 |
| 35 | 446.1 | 0.0016 | 0.0006 | 255.77 |
| 36 | 446.1 | 0.2955 | 0.176 | 526.5 |
| 37 | 402.2 | 0.0698 | 0.0164 | 364.12 |
| 38 | 402 | 16.5 | 3.15 | 2618.4 |
| 39 | 457 | 0.0469 | 0.0179 | 109.25 |
| 40 | 457 | 6.495 | 1.91 | 516.14 |
| 41 | 407.2 | 0.1345 | 0.0284 | 238.44 |
| 42 | 455.1 | 0.0277 | 0.0444 | 735.56 |
| 43 | 425.2 | 0.0225 | 0.0314 | 595.96 |
| 44 | 416.1 | 0.0142 | 0.017 | 376.16 |
| 45 | 432.2 | 0.0555 | 0.0372 | 3449.4 |
| 46 | 450.1 | 0.018 | 0.0046 | 173.5 |
| 47 | 450.1 | 21.15 | 1.76 | 967.7 |
| 48 | 410.8 | 0.0439 | 0.0141 | 154 |
| 49 | 415.8 | 0.0308 | 0.0082 | 202 |
| 50 | 415.8 | 26.621 | >15.6 | 1746.2 |
| 51 | 458.9 | 0.0627 | 0.0143 | 113 |
| 52 | 458.9 | >40.0 | >15.6 | 1630.1 |
| 53 | 425.9 | 0.0616 | 2.38 | 577.31 |
| 54 | 425.9 | 2.51 | 2.24 | 459.52 |
| 55 | 411 | 0.0362 | 0.0431 | 859.98 |
| 56 | 422.9 | 0.0129 | 0.003 | 302.76 |
| 57 | 422.9 | 2.25 | 0.455 | 332.73 |
| 58 | 422 | 0.158 | 0.179 | 821.91 |
| 59 | 401.9 | 0.0345 | 0.0242 | 899.1 |
| 60 | 410.9 | >40.0 | >15.6 | >400.0 |
| 61 | 463.9 | 0.1668 | 0.0701 | 1780.3 |
| 62 | 435.8 | 0.0266 | 0.0397 | 1099.3 |
| 63 | 422.1 | 0.0637 | 0.0584 | 99.75 |
| 64 | 422.1 | 6.185 | >15.6 | 191 |
| 65 | 402 | 21.15 | >15.6 | >400.0 |
| 66 | 436 | 0.0153 | 0.0274 | 825.02 |

TABLE 11-continued

| Example No | Observed Mass | BACE1 Enzyme assay IC$_{50}$ (uM) | BACE cell assay IC$_{50}$ (uM) | CatD IC$_{50}$ (μM) |
|---|---|---|---|---|
| 67 | 436 | 26.45 | >15.6 | 1285.9 |
| 68 | 375 | 0.065 | 0.0063 | 476.18 |
| 69 | 463.9 | 0.126 | 0.0372 | 439.58 |
| 70 | 440.8 | 0.0568 | 0.0386 | 378.87 |
| 71 | 444.8 | 0.0276 | 0.0273 | 477.76 |
| 72 | 407.9 | 0.0763 | 0.0604 | 1112.3 |
| 73 | 411.8 | 0.1145 | 0.331 | 274.5 |
| 74 | 454.7 | 0.0247 | 0.0181 | 282.5 |
| 75 | 402.9 | 0.165 | 0.284 | 347.61 |
| 76 | 410.9 | 0.0266 | 0.0302 | 684.31 |
| 77 | 402 | 0.0268 | 0.0226 | 697.75 |
| 78 | 406.9 | >40.0 | >15.6 | >400.0 |
| 79 | 406.9 | 3.0389 | 0.1195 | 941.65 |
| 80 | 401.9 | 7.95 | 0.183 | >400.0 |
| 81 | 401.9 | >40 | >15.6 | >400 |
| 82 | 404.9 | 2.74 | 0.157 | >400.0 |
| 83 | 404.9 | >40.0 | >15.6 | >400.0 |
| 84 | 437.9 | 0.4945 | 0.361 | >400.0 |
| 85 | 423.9 | 0.034 | 0.0067 | 373.1 |
| 86 | 447.8 | 0.0759 | 0.0094 | 891.6 |
| 87 | 472.8 | 0.0323 | 0.0135 | 164.5 |
| 88 | 417.9 | 0.0294 | 0.0098 | 301.5 |
| 89 | 437.9 | 0.0731 | 0.0245 | 574.2 |
| 90 | 491.9 | 0.0136 | 0.0213 | 913 |
| 91 | 431.9 | 0.0506 | 0.0073 | 260 |
| 92 | 427 | 17.05 | >15.6 | 769.5 |
| 93 | 418 | 0.0191 | 0.0131 | 1301.3 |
| 94 | 418 | 31.911 | >15.6 | 1922 |
| 95 | 431.9 | 0.0035 | 0.008 | 143 |
| 96 | 446 | 0.001 | 0.0033 | 467.37 |
| 97 | 427 | 0.0371 | 0.0505 | 1281.2 |
| 98 | 418 | 0.0443 | 0.033 | 1160.8 |
| 99 | 426.8 | 0.0227 | 0.0195 | 1053 |
| 100 | 422.9 | 0.0611 | 0.0209 | 190.5 |
| 101 | 437 | 0.0971 | 0.0598 | 258.46 |
| 102 | 490.9 | 0.0356 | 0.013 | 591.85 |
| 103 | 407.9 | 0.1215 | 0.0574 | 762.63 |
| 104 | 424 | 0.0873 | 0.0339 | 374.14 |
| 105 | 394 | 39.34 | 2.105 | 1616 |
| 106 | 394 | 0.252 | 0.0456 | 216 |
| 107 | 428.9 | 0.0196 | 0.0578 | 213 |
| 108 | 428.9 | 10.365 | >15.6 | 471.87 |
| 109 | 419.9 | 12.05 | >15.6 | >400.0 |
| 110 | 467.9 | 26.194 | >17.4 | 1482.5 |
| 111 | 449.9 | 6.505 | 3.79 | 1001 |
| 112 | 425.9 | >40.5 | >15.8 | 4184 |
| 113 | 419.9 | 0.0275 | 0.0392 | >618.0 |
| 114 | 467.8 | 0.0098 | 0.0198 | 158.5 |
| 115 | 449.9 | 0.0021 | 0.0059 | 42.45 |
| 116 | 472.9 | 0.0185 | 0.0411 | 81.884 |
| 117 | 393 | 0.0211 | 0.0053 | 471.71 |
| 118 | 393 | 1.56 | 0.2207 | 1279.1 |
| 119 | 412 | 0.0559 | 0.0524 | 2992.6 |
| 120 | 490.1 | 0.05 | 0.247 | 351.42 |
| 121 | 424.9 | 0.0833 | 0.0616 | 206 |
| 122 | 439 | 0.099 | 0.0148 | 1074.1 |
| 123 | 424.9 | 0.0305 | 0.0122 | 257.25 |
| 124 | 424.9 | 3.53 | 1.21 | 1232.4 |
| 125 | 457 | 0.0806 | 0.0086 | >400.0 |
| 126 | 454.9 | 0.0835 | 0.0146 | 1203.8 |
| 127 | 433.8 | 0.0395 | 0.0078 | 996.82 |
| 128 | 452.9 | 0.0508 | 0.0161 | 1001.6 |
| 129 | 428.9 | 0.0389 | 0.0403 | 1275.4 |
| 130 | 407 | 0.0845 | 0.0586 | 987.71 |
| 131 | 421 | 0.185 | 0.0809 | 342.49 |
| 132 | 430 | 0.0214 | 0.0153 | 725.41 |
| 133 | 449.9 | 0.023 | 0.0158 | 558.46 |
| 134 | 454.9 | 0.1305 | 0.0604 | 1109.4 |
| 135 | 458.9 | 0.0256 | 0.0199 | 493.69 |
| 136 | 418 | 0.1195 | 0.0214 | 490.74 |
| 137 | 431.9 | 0.0448 | 0.0162 | 539.09 |
| 138 | 432 | 0.0362 | 0.0151 | 662.08 |
| 139 | 431.9 | 14.25 | 2.24 | 645.65 |
| 140 | 448 | 0.006 | 0.0059 | 86.9 |
| 141 | 439 | >40.0 | >15.6 | 654.54 |
| 142 | 410 | 0.0971 | 0.0263 | 229.08 |
| 143 | 408 | 0.125 | 0.0221 | 529.16 |
| 144 | 407.9 | >40.0 | 4.62 | 1336.8 |
| 145 | 422.9 | 0.153 | 0.0197 | 220 |
| 146 | 422.9 | >40.0 | >15.6 | 768.31 |
| 147 | 436 | 0.7315 | 1 | 706.05 |
| 148 | 446 | 0.195 | 0.448 | 848.58 |
| 149 | 433 | 0.1945 | 0.152 | 1703.3 |
| 150 | 416.9 | 0.0322 | 0.0182 | 238.37 |
| 151 | 431 | 24.805 | 1.07 | 302.5 |
| 152 | 424.9 | 0.1275 | 0.0476 | 403.83 |
| 153 | 473, 475 | 0.143 | 0.0762 | 555.42 |
| 154 | 430 | 0.24 | 0.109 | 514.64 |
| 155 | 424.1, 426 | >40.0 | >15.6 | 646.57 |
| 156 | 424.1, 426 | 0.055 | 0.0199 | 896.76 |
| 157 | 473.1, 475.1 | 28.314 | >15.6 | 395.99 |
| 158 | 473.1, 475.1 | 0.0403 | 0.0383 | 230.5 |
| 159 | 505.9, 508 | 0.2255 | 0.466 | 1047.2 |
| 160 | 476 | 0.0291 | 0.0808 | 2001.4 |
| 161 | 442 | >40.0 | >15.6 | 294.98 |
| 162 | 446 | 0.0085 | 0.0175 | 1063.5 |
| 163 | 449.9 | 0.0137 | 0.0179 | 464.44 |
| 164 | 431.9 | 0.0232 | 0.0109 | 949.93 |
| 165 | 491 | 0.0192 | 0.0606 | 383.22 |
| 166 | 380.9 | 0.0613 | 0.103 | 372.96 |
| 167 | 475 | 0.0124 | 0.0103 | 767.26 |
| 168 | 398.9 | 0.0116 | 0.0101 | 56.75 |
| 169 | 490.9 | 0.0366 | 0.0418 | 581.85 |
| 170 | 490.9 | 0.0867 | 0.56 | 444.85 |
| 171 | 475 | 0.0811 | 0.323 | 845.84 |
| 172 | 490 | 0.0824 | 0.446 | 360.35 |
| 173 | 474 | 0.0366 | 0.0789 | 1011.5 |
| 174 | 475 | 0.0233 | 0.0186 | 925.02 |
| 175 | 413 | 2.88 | 2.48 | 1344.4 |
| 176 | 395.9 | 0.1905 | 0.156 | 834.71 |
| 177 | 415.9 | 0.185 | 0.373 | 762.01 |
| 178 | 406.9 | 1.075 | 1.56 | 534.11 |
| 179 | 415.9 | 0.8705 | 0.661 | 474.39 |
| 180 | 425 | 0.0918 | 0.0449 | >1.65 |
| 181 | 416 | 1.4 | 1.14 | 580.11 |
| 182 | 455.1 | 13.1 | 3.36 | 565.49 |
| 183 | 422.9 | 0.0998 | 0.0218 | 882.02 |
| 184 | 446 | 0.3575 | 0.62 | 1087.4 |
| 185 | 405 | 0.1066 | 0.148 | 752.56 |
| 186 | 440.9 | 0.061 | 0.0345 | 767.7 |
| 187 | 408 | 3.44 | 1.41 | 667.11 |
| 188 | 459 | 0.04 | 0.0279 | 159 |
| 189 | 489 | 0.1195 | 0.386 | 770 |
| 190 | 391 | 0.151 | 0.0735 | 1465.3 |
| 191 | 457 | 0.4145 | 0.5355 | 1073.1 |
| 192 | 384 | 0.0256 | 0.0079 | 590.78 |
| 193 | 427.1 | 0.0449 | 0.0108 | 875.42 |
| 194 | 390.2 | 0.1425 | 0.027 | 1225.6 |
| 195 | 389.2 | 0.1241 | 0.0156 | 759.19 |
| 196 | 397.9 | 0.0324 | 0.009 | 703.01 |
| 197 | 414.1 | 0.0066 | 0.0023 | 260.5 |
| 198 | 407.1 | 0.0338 | 0.0152 | 348.84 |
| 199 | 428.1 | 0.0022 | 0.0005 | 958.61 |
| 200 | 446.1 | 0.189 | 0.025 | 464.93 |
| 201 | 423 | 0.0638 | 0.0179 | 515.09 |
| 202 | 409.1 | 0.4995 | 0.159 | 430.21 |
| 203 | 427.1 | 0.0089 | 0.0039 | 303.02 |
| 204 | 385 | 0.1455 | 0.0335 | 293.5 |
| 205 | 413 | 0.0274 | 0.0089 | 820.68 |
| 206 | 415.1 | 0.0094 | 0.0064 | 310.79 |
| 207 | 433 | 0.0578 | 0.0176 | 370.2 |
| 208 | 410.9 | 0.15 | 3.64 | 489.48 |
| 209 | 472.9 | 0.0908 | 0.0765 | 958.31 |
| 210 | 461.8 | 0.0039 | 0.0096 | 569.43 |
| 211 | 460.8 | 0.0126 | 0.0147 | >400.0 |
| 212 | 472.9 | 0.0469 | 0.0385 | 928.32 |
| 213 | 472.9 | 2.415 | 1.31 | 1128 |
| 214 | 470.7 | 0.0093 | 0.0132 | 459.3 |
| 215 | 461.9 | 0.0017 | 0.0043 | 1932.3 |
| 216 | 461.8 | 0.8375 | 1.28 | 500.14 |
| 217 | 474.9 | 0.0151 | 0.0116 | 206.03 |
| 218 | 428.9 | 0.861 | >15.6 | >400.0 |

TABLE 11-continued

| Example No | Observed Mass | BACE1 Enzyme assay IC$_{50}$ (uM) | BACE cell assay IC$_{50}$ (uM) | CatD IC$_{50}$ (μM) |
|---|---|---|---|---|
| 219 | 447.9 | 0.0063 | 0.0068 | 65.8 |
| 220 | 465.8 | 0.0188 | 0.0169 | 690.71 |
| 221 | 447.9 | 0.0027 | 0.0033 | 51.05 |
| 222 | 447.8 | 0.701 | 0.885 | 493.18 |
| 223 | 431.9 | 0.0184 | 0.0314 | 541.28 |
| 224 | 465.8 | 0.0105 | 0.0252 | 509.92 |
| 225 | 465.8 | 8.27 | 3.82 | 1340.3 |
| 226 | 423.8 | 0.0895 | 0.0394 | 363 |
| 227 | 417.8, 419.8 | 0.0469 | 0.0105 | 2256.3 |
| 228 | 417.8, 419.9 | 0.0419 | 0.0059 | 1013.9 |
| 229 | 422.9, 424.9 | 0.0341 | 0.0064 | 956.16 |
| 230 | 394.1, 396 | 11.95 | 2.23 | >400.0 |
| 231 | 394.1, 396 | 0.165 | 0.0277 | 389.59 |
| 232 | 431 | 0.0164 | 0.0418 | 587.65 |
| 233 | 445.1 | 0.0057 | 0.024 | 243.5 |
| 234 | 424 | 0.283 | 0.0596 | >14.8 |
| 235 | 437.9, 440.9 | 0.1255 | 0.0188 | 1806.9 |
| 236 | 475 | 0.104 | 0.296 | 4249.4 |
| 237 | 457.1 | 0.0377 | 0.0323 | 326.91 |
| 238 | 444 | 0.0214 | 0.0178 | 5917.5 |
| 239 | 382.1 | >40.0 | >15.6 | >400.0 |
| 240 | 344.1 | 0.821 | 0.712 | 48.15 |
| 241 | 396.1 | >40.0 | >15.6 | >400.0 |
| 242 | 384.1 | >40.0 | >15.6 | 1909.5 |
| 243 | 380.1 | 24.421 | 4.07 | 1026.3 |
| 244 | 370.1 | 5.37 | 1.98 | 318.54 |
| 245 | 450 | >40.0 | >15.6 | 447.24 |
| 246 | 464.1 | >40.0 | >15.6 | 323.7 |
| 247 | 358.1 | 25.543 | 4.34 | 486.4 |
| 248 | 407 | 40.486 | >15.6 | 1229.8 |
| 249 | 407 | >40.0 | >15.6 | 1586.3 |
| 250 | 471.1 | 0.0218 | 0.603 | 77.5 |
| 251 | 382 | 4.7 | 2 | 190 |
| 252 | 438 | >40.0 [2] | >15.6 | 270.5 |
| 253 | 370.1 | 34.304 | >15.6 | 188 |
| 254 | 386.1 | >40.0 [2] | >15.6 | 2563.5 |
| 255 | 388.1 | >40.0 [2] | >15.6 | 666.15 |
| 256 | 406.1 | 6.66 | 2.18 | 331 |
| 257 | 358 | 1.84 | 2.54 | 376.54 |
| 258 | 368 | 20.054 | 2.6 | 117 |
| 259 | 446.1 | 0.6595 | 0.473 | 668.25 |
| 260 | 340.1 | 5.17 | 3.19 | 103.95 |
| 261 | 412 | 0.037 | 1.59 | 444 |
| 262 | 400.1 | 0.2455 | 0.144 | 203.5 |
| 263 | 392.9 | 0.525 | 0.289 | 1060.3 |
| 264 | 392.9 | 35.904 | >15.6 | >400.0 [2] |
| 265 | 392.9 | 0.265 | 0.0279 | 397 |
| 266 | 391 | 0.817 | 0.776 | 1164.7 |
| 267 | 456.9 | 0.0415 | 0.015 | 1015.2 |
| 268 | 446 | | | |
| 269 | 398 | 0.0936 | 0.0533 | 715.76 |
| 270 | 409.1 | 0.0669 | 0.0122 | 646.37 |
| 271 | 409.1 | 24.087 | 2.33 | >400.0 |
| 272 | 406.1 | 0.1425 | 0.0274 | 1733.6 |
| 273 | 406.1 | 36.33 | 2.66 | 1973 |
| 274 | 452.9 | 0.0322 | 0.012 | 537.75 |
| 275 | 452.9 | 3.605 | 0.906 | 1129.8 |
| 276 | 409.1 | 0.1375 | 0.0242 | 918.19 |
| 277 | 400.1 | 0.0568 | 0.0192 | 1561.6 |
| 278 | 400.1 | 9.51 | 2.64 | 904.39 |
| 279 | 430.1 | 0.0056 | 0.0086 | 123.5 |
| 280 | 430.1 | 4.78 | 2.89 | 1473.8 |
| 281 | 443 | 0.0441 | 0.006 | 2867 |
| 282 | 405 | 0.1955 | 0.0243 | 649.74 |
| 283 | 414.1 | 0.031 | 0.0075 | 1579.9 |
| 284 | 439.1 | 0.1225 | 0.0149 | 752.05 |
| 285 | 444 | 0.0022 | 0.0006 | 1834.7 |
| 286 | 411.1 | 1.57 | 1.12 | 724.59 |
| 287 | 411.1 | 1.93 | 2.11 | 1625.7 |
| 288 | 419.1 | 3.345 | 2.22 | 1255.7 |
| 289 | 453.2 | 0.305 | 0.116 | 699.95 |
| 290 | 505 | 0.0141 | 0.0222 | 251.5 |
| 291 | 453.2 | 1.145 | 1.87 | 148 |
| 292 | 377.1 | 0.3005 | 0.279 | 689.7 |
| 293 | 391.1 | 0.271 | 0.601 | 1661.3 |
| 294 | 404 | 0.3135 | 0.0612 | 684.34 |
| 295 | 407 | 0.0903 | 0.0129 | 464.36 |
| 296 | 455 | 4.185 | 3.51 | 1859.4 |
| 297 | 439 | 0.1835 | 0.0074 | 834.64 |
| 298 | 416.9 | 0.099 | 0.0332 | >400.0 |
| 299 | 422.1 | 0.0305 | 0.014 | 465.44 |
| 300 | 436.1 | 0.1415 | 0.0405 | 447.11 |
| 301 | 420 | 0.3525 | 0.031 | 714.94 |
| 302 | 443 | 0.0315 | 0.0141 | 810.69 |
| 303 | 439.1 | 0.03 | 0.0283 | 334.88 |
| 304 | 421.1 | 0.0522 | 0.0359 | 354.98 |
| 305 | 435 | 0.1175 | 0.0696 | 287.99 |
| 306 | 425.1 | 0.0419 | 0.0256 | 1036.8 |
| 307 | 425.1 | 0.413 | 0.139 | >400.0 |
| 308 | 442.9 | 0.0177 | 0.0321 | 186 |
| 309 | 430 | 0.0743 | 0.0387 | 421.05 |
| 310 | 430 | >40.0 | >15.6 | 1771.5 |
| 311 | 430 | 0.0466 | 0.0174 | 293.79 |
| 312 | 442.9 | 0.0377 | 0.0179 | 441.81 |
| 313 | 401 | 0.0248 | 0.0176 | 466.88 |
| 314 | 415 | 0.0467 | 0.0891 | 420.55 |
| 315 | 505.9 | 0.0936 | 0.0927 | 556.39 |
| 316 | 505.9 | >40.0 | >15.6 | 1076.7 |
| 317 | 448 | 0.0028 | 0.0014 | 41 |
| 318 | 448 | 4.07 | 1.49 | 370.02 |
| 319 | 372 | 10.75 | | >400.0 |
| 320 | 372 | 0.0565 | 0.0213 | >400.0 |
| 321 | 412 | 0.339 | 0.295 | 212.5 |
| 322 | 373 | 1.99 | 0.1845 | 521.42 |
| 323 | 373 | >40.0 | >15.6 | >400.0 |
| 324 | 367 | 0.1495 | 0.0283 | 182 |
| 325 | 367 | >40.0 | Undefined | 1294.4 |
| 326 | 375.9 | 0.2425 | 0.0323 | 279 |
| 327 | 375.9 | 2.135 | 0.703 | 1316.3 |
| 328 | 409.9 | 0.1034 | 0.0116 | 511.67 |
| 329 | 409.9 | >40.0 | 9.6 | 1611 |
| 330 | 403 | 0.1005 | 0.0326 | 139 |
| 331 | 403 | 26.7 | >15.6 | 1511.9 |
| 332 | 438.8 | >40.0 | >15.6 | 163 |
| 333 | 376, 377.9 | 0.1297 | 0.0132 | 815.58 |
| 334 | 376, 377.9 | 0.0944 | 0.0089 | 401.92 |
| 335 | 376, 377.9 | 14.05 | 1.42 | >400.0 |
| 336 | 373 | 0.4355 | 0.0416 | >400.0 |
| 337 | 394.1 | 3.345 | | >400.0 |
| 338 | 394.1 | >40.0 | | 56.55 |
| 339 | 394 | 8.11 | | >400.0 |
| 340 | 394 | 0.5065 | 0.0796 | >400.0 |
| 341 | 434.2 | 3.41 | 3.41 | 2885.6 |
| 342 | 434.2 | 0.0598 | 0.12 | 50.55 |
| 343 | 425.2 | 0.0949 | 0.0546 | >44.4 |
| 344 | 430 | 430 | 0.0982 | 596.19 |
| 345 | 416.1 | 0.0713 | 0.0543 | 282 |
| 346 | 407.2 | 0.0539 | 0.0176 | 204.89 |
| 347 | 417 | 0.1325 | 0.0624 | 105.75 |
| 348 | 430.1 | 0.456 | 0.106 | 738.32 |
| 349 | 458.9 | 0.0829 | 0.222 | 88.357 |
| 350 | 458.9 | 0.0319 | 0.0628 | >14.8 |
| 351 | 458.9 | 2.815 | 2.52 | >14.8 |
| 352 | 442.9 | 0.0391 | 0.0593 | 192.21 |
| 353 | 434.9 | 0.0639 | 0.0503 | 141.05 |
| 354 | 430.9 | 12.65 | 1.46 | 292 |
| 355 | 430.9 | >40.0 | >15.6 | 2745.5 |
| 356 | 446.9 | 0.0659 | 0.0494 | 725.38 |
| 357 | 474.9 | 0.375 | 0.918 | 322.62 |
| 358 | 403.1 | 2.09 | 0.134 | >400.0 |
| 359 | 431.9 | 0.0291 | 0.0656 | 251.18 |
| 360 | 428 | 1.26 | 0.139 | 843.04 |
| 361 | 452 | 0.0278 | 0.207 | >400.0 |
| 362 | 434 | 0.0335 | 0.254 | 399.58 |
| 363 | 441 | 0.0682 | 0.13 | >44.4 |
| 364 | 431.1 | 0.224 | 0.122 | 596.24 |
| 365 | 469.1 | 0.2045 | 0.254 | >44.4 |
| 366 | 461 | >13.7 | >16.0 | 127.61 |
| 367 | 461 | 0.0515 | 0.524 | 102.63 |
| 368 | 340.1 | 2.74 | 1.33 | 121 |
| 369 | 386.1 | 6.635 | 3.02 | 19.2 |
| 370 | 436.1, 438.1 | 13.65 | 8.85 | 63.6 |

TABLE 11-continued

| Example No | Observed Mass | BACE1 Enzyme assay IC$_{50}$ (uM) | BACE cell assay IC$_{50}$ (uM) | CatD IC$_{50}$ (μM) |
|---|---|---|---|---|
| 371 | 402 | 11.16 | 2.67 | 102.35 |
| 372 | 402 | 9.415 | 4.94 | 85.45 |
| 373 | 418 | 0.159 | 0.0318 | 234 |
| 374 | 435.8 | 0.0954 | 0.0779 | 115.5 |
| 375 | 352.1 | 5.995 | 2.53 | 78.85 |
| 376 | 394.1 | 2.1 | 1.15 | 52.9 |
| 377 | 397.1 | 2.845 | 1.11 | 177 |
| 378 | 411 | 13.85 | 2.13 | 77.4 |
| 379 | 326.1 | 1.41 | 0.564 | 188.5 |
| 380 | 467 | 0.143 | 0.145 | 336.16 |
| 381 | 467 | 3.445 | 1.67 | 83.3 |
| 382 | 483 | 3.07 | 0.993 | 263 |
| 383 | 429 | 0.968 | 0.352 | 206 |
| 384 | 467 | 0.315 | 1.37 | 82.55 |
| 385 | 423 | 0.253 | 1.74 | 153 |
| 386 | 443.9 | 0.0251 | 0.0085 | 1815.7 |
| 387 | 430 | 0.0391 | 0.0145 | 352.1 |
| 388 | 419.9 | 0.0352 | 0.0069 | 1272.6 |
| 389 | 445 | 0.0915 | 0.0747 | 732.46 |
| 390 | 416 | 0.025 | 0.0205 | 441.28 |
| 391 | 446 | 0.0116 | 0.0175 | 1353.2 |
| 392 | 407.2 | | | |
| 393 | 408 | 0.1975 | 0.0243 | 147 |
| 394 | 444 | 0.134 | 0.289 | 1066.6 |
| 395 | 452.1 | 0.0144 | 0.0737 | 476.95 |
| 396 | 432 | 0.017 | 0.151 | 197.5 |
| 397 | 430.1 | 0.081 | 0.009 | >400 |
| 398 | 434 | 0.0335 | 0.0123 | 690.32 |
| 399 | 446.1 | 0.0706 | 0.0208 | 1090 |
| 400 | 425.9 | | | |
| 401 | 414 | 0.1081 | 0.0575 | 555.02 |
| 402 | 414 | 0.976 | 0.318 | 205.5 |
| 403 | 428.1 | 2.855 | 0.677 | 468.84 |
| 404 | 413.1 | 0.291 | 0.252 | 131.5 |
| 405 | 441 | 0.0237 | 0.215 | 398.53 |
| 406 | 464.1 | 0.0759 | 0.861 | 8908.4 |
| 407 | 442.1 | 0.0296 | 0.301 | 169.85 |
| 408 | 482.1 | 0.0463 | 1.58 | 346.95 |
| 409 | 471 | 0.327 | 0.514 | 748.15 |
| 410 | 458.9 | | | |
| 411 | 472 | 0.0076 | 0.112 | 359.77 |
| 412 | 492.1 | 0.1285 | 0.984 | 640.34 |
| 413 | 478.1 | 0.145 | 0.865 | >400.0 |
| 414 | 434.1 | 0.048 | 0.146 | 924.06 |
| 415 | 448.1 | 0.043 | 0.0551 | 747.3 |
| 416 | 490.1 | 0.0121 | 2.5 | 228.15 |
| 417 | 422.1 | 0.1154 | 0.0876 | 1465.1 |
| 418 | 476.1 | 0.0261 | 0.916 | 890.72 |
| 419 | 441 | 0.0332 | 0.0293 | 275.5 |
| 420 | 439 | 0.0515 | 0.0187 | 532.83 |
| 421 | 446.9 | 14.15 | >15.6 | 223.5 |
| 422 | 465 | 5.245 | 4.06 | 68.2 |
| 423 | 374.9 | 0.3965 | 0.0441 | 591.98 |
| 424 | 471 | 1.035 | 0.254 | 831.86 |
| 425 | 408 | 0.6133 | 0.5905 | 240.27 |
| 426 | 408 | 1.2365 | 3.1 | 195.65 |
| 427 | 372 | >40.0 | >15.6 | >400.0 |
| 428 | 372 | >40.0 | >15.6 | 1522.3 |
| 429 | 372 | 1.0475 | 3.36 | 72.85 |
| 430 | 372 | >40.0 | >15.6 | 1016.5 |
| 431 | 354.2 | 4.685 | 1.59 | 91.6 |
| 432 | 384 | 33.135 | 3.68 | 177.69 |
| 433 | 364.1 | 23.099 | 4.41 | 612.81 |
| 434 | 361.1 | 1.21 | 0.561 | 385.6 |
| 435 | 387 | 8.625 | 4.79 | 315.5 |
| 436 | 452.9 | >36.0 | >14.1 | 343.18 |
| 437 | 423 | 2.185 | 0.384 | 659.31 |
| 438 | 390 | 0.5 | 0.126 | 792.77 |
| 439 | 407 | 0.473 | 0.32 | 489.92 |
| 440 | 418.1 | >40.0 | >15.6 | 249.59 |
| 441 | 441 | 0.0252 | 0.01585 | 444.19 |
| 442 | 442 | 0.0544 | 0.0134 | 1137.4 |
| 443 | 423 | 0.0373 | 0.01365 | 517.38 |
| 444 | 457 | 0.0105 | 0.0313 | 171 |
| 445 | 393 | 0.2905 | 0.031 | 1270.5 |
| 446 | 425.1 | 0.05585 | 0.107 | 657.71 |
| 447 | 431.1 | 0.139 | 0.167 | 500.52 |
| 448 | 448.1 | 0.11735 | 0.0863 | 169 |
| 449 | 469.1 | 0.1245 | 0.268 | 79.35 |
| 450 | 418.1 | 0.05025 | 0.00817 | >400 |
| 451 | 430.1 | 5.385 | 6.28 | 959.56 |

The present invention also provides methods for making compounds of Formulas I-III, and sub-formulas therein. For example, the compounds of the present invention and additional examples may be made by the following methods, as similarly described in the literature references mentioned below.

In one embodiment of the invention, there is provided a method of making a compound of Formula I-A having a general structure of

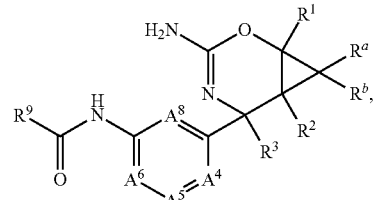

the method comprising the step of reacting a compound 20

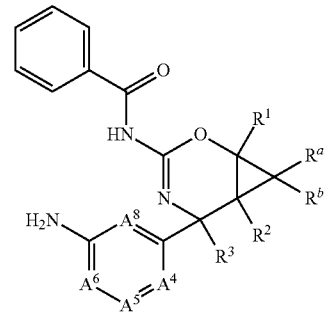

wherein $A^4$, $A^5$, $A^6$, $A^8$, each $R^1$, each $R^2$ and $R^3$ of Formula I-A are as defined herein, with a compound having the structure $R^9$—COOH, wherein $R^9$ is as defined herein, to make a compound of Formula I-A.

In one embodiment of the invention, there is provided a method of making a compound of Formula I-B having a general structure of

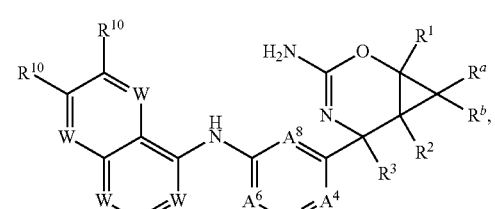

the method comprising the step of reacting a compound 20

20

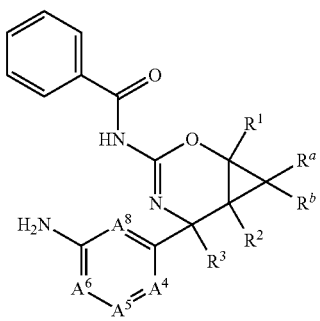

wherein $A^4$, $A^5$, $A^6$, $A^8$, each $R^1$, each $R^2$ and $R^3$ of Formula I-B are as defined herein, with a compound having the structure

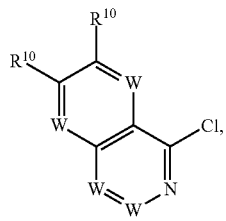

wherein each W and each $R^{10}$ are, independently, as defined herein, in the presence of acid to make a compound of Formula I-B.

In one embodiment of the invention, there is provided a method of making a compound of Formula I-C

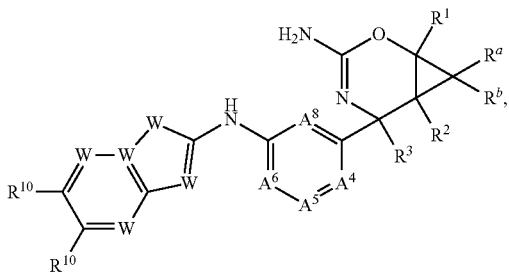

the method comprising the step of reacting a compound 20

20

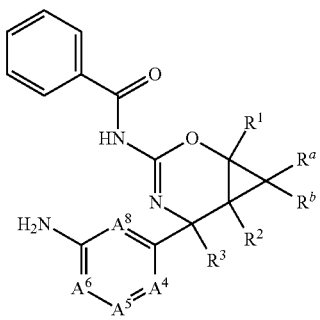

wherein $A^4$, $A^5$, $A^6$, $A^8$, each $R^1$, each $R^2$ and $R^3$ of Formula I-C are as defined herein, with a compound having the structure

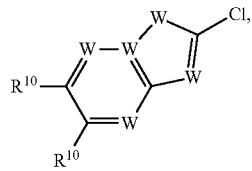

wherein each W and each $R^{10}$ are, independently, as defined herein, to make a compound of Formula I-C.

In another embodiment of the invention, there is provided a method of making a compound of Formula II having a general formula of

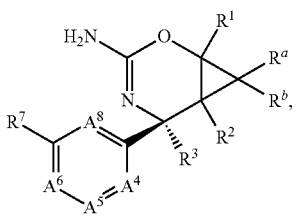

the method comprising the step of reacting a compound 30

30

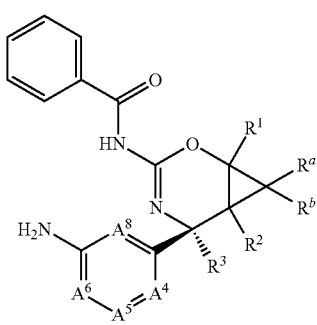

wherein $A^4$, $A^5$, $A^6$, $A^8$, each $R^2$, $R^3$ and $R^7$ of Formula II are as defined herein, with a compound having either structure of $R^9$—COOH in the presence of a base or $R^9$—Cl in the presence of an acid, wherein $R^9$ is as defined herein, to make a compound of Formula II.

As can be appreciated by the skilled artisan, the above synthetic schemes and representative examples are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

For example, in these procedures, the steps may be preceded, or followed, by additional protection/deprotection steps as necessary. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. For example, protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, 3$^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, 2$^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, 2$^{nd}$ edition, Wiley-VCH, (1997); and L. Paquette, editor, Encyclopedia of Reagents for Organic Synthesis, John Wiley and Sons (1995).

Salts, including pharmaceutically acceptable salts, of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary and suitable salts, and their preparation, are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the H$^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., EtOAc; ethers including aliphatic ethers, e.g., Et$_2$O and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including CH$_3$CN; halogenated hydrocarbons, including CH$_2$Cl$_2$, CHCl$_3$ and CCl$_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, H$_2$SO$_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction.

The invention further encompasses "intermediate" compounds, including structures produced from the synthetic procedures described, whether isolated or generated in-situ and not isolated, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

The invention also provides new starting materials and/or intermediates, as well as processes for the preparation thereof. In select embodiments, such starting materials are used and reaction conditions so selected as to obtain the desired compound(s). Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

Compounds of the present invention can possess, in general, one or more asymmetric carbon atoms and are thus capable of existing in the form of optical isomers as well as in the form of racemic or non-racemic mixtures thereof. While shown without respect to stereochemistry in Formulas I-III, the present invention includes such optical isomers and diastereomers, as well as the racemic and resolved, enantiomerically pure R and S stereoisomers, as well as other mixtures of R and S stereoisomers and pharmaceutically acceptable salts thereof.

The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt. All such isomeric forms of such compounds are expressly included in the present invention.

The compounds of the invention may also be represented in multiple tautomeric forms. Tautomers often exist in equilibrium with each other, and interconvert under environmental and physiological conditions. The compounds of the invention may also occur in cis- or trans- or E- or Z-double bond isomeric forms. The invention expressly includes all tautomeric forms of the compounds described herein.

All crystal forms of the compounds described herein are expressly included in the present invention.

The present invention also includes isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$ (deuterium), $^{3}H$ (tritium), $^{13}C$, $^{14}C$, $^{15}N$, $^{16}O$, $^{17}O$, $^{31}P$, $^{32}P$, $^{35}S$, $^{18}F$, and $^{36}Cl$.

Compounds of the present invention that contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Deuterated ($^{2}H$), Tritiated ($^{3}H$) and carbon-14, i.e., $^{14}C$, isotopes are particularly preferred for their ease of preparation and detection. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of this invention can generally be prepared by substituting a readily available isotopically labeled reagent for a non-isotopically labeled reagent.

Biological Evaluation

The compounds of the invention may be modified by appending appropriate functionalities to enhance selective biological properties. The pharmacokinetic and pharmacodynamic properties of a compound relate, directly and indirectly, to the ability of the compound to be effective for its intended use.

Although the pharmacological properties of the compounds of the invention (Formulas I-III) vary with structural change, in general, activity possessed by compounds of Formulas I-III may be demonstrated both in vitro as well as in vivo. The following exemplified pharmacological assays have been carried out with the compounds according to the invention, to assess and characterize the compound's ability to modulate BACE activity and to regulate the cleavage of amyloid beta precursor protein, thereby reducing or inhibiting the production of amyloid beta.

In Vitro Enzymatic BACE FRET (Fluorescence Resonance Energy Transfer) Assay (Enzyme Assay Data in the Example Table I)

The assay buffer used in this screen is 0.05 M acetate, pH 4.2, 10% DMSO final, 100 uM genapol (which is a nonionic detergent, below its Critical Micelle Concentration). The Beta Secretase enzyme (0.2 nM) is pre-incubated for one hour with inhibitors, typically in about 1 uL of DMSO according to a serial dilution, are added thereto. This assay is effectively started by the addition of FRET substrate (50 nM) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. Proteolytic cleavage of the FRET substrate releases quenching of fluorescence (excitation 488 nm and emission 425 nm).

Where available, the in-vitro BACE FRET enzyme data for each of the Examples is provided in Table 1.

In Vitro BACE Cell-Based Assay

The cell-based assay measures inhibition or reduction of Aβ40 in conditioned medium of test compound treated cells expressing amyloid precursor protein.

Cells stably expressing Amyloid Precursor Protein (APP) were plated at a density of 40K cells/well in 96 well plates (Costar). The cells were cultivated for 24 hours at 37° C. and 5% $CO_2$ in DMEM supplemented with 10% FBS. The test compounds were then added to cells in 10-point dose response concentrations with the starting concentration being either 100 µM or 10 µM. The compounds were diluted from stock solutions in DMSO and the final DMSO concentration of the test compounds on cells was 0.1%. After 24 h of incubation with the test compounds the supernatant conditioned media was collected and the Aβ40 levels were determined using a sandwich ELISA. The $IC_{50}$ of the compound was calculated from the percent of control or percent inhibition of Aβ40 as a function of the concentration of the test compound.

The sandwich ELISA to detect Aβ40 was performed in 96 well microtiter plates, which were pre-treated with goat anti-rabbit IgG (Pierce). The capture and detecting antibody pair that were used to detect Aβ40 from cell supernatants were affinity purified pAb40 (Biosource) and biotinylated 6E10 (Signet Labs Inc.), respectively. The optimal concentration for the pAb40 antibody was 3 µg/ml in Superblock/TBS (Pierce) that was supplemented with 0.05% Tween 20 (Sigma). Optimal concentration for the detection antibody 6E10-biotinylated was 0.5 µg/ml in Superblock/TBS (Pierce) that had been supplemented with 2% normal goat serum and 2% normal mouse serum.

Cellular supernatants were incubated with the capture antibody for 3 h at 4° C., followed by 3 wash steps in TBS-tween (0.05%). The detecting antibody incubation was for 2 h at 4° C., again followed by the wash steps as described previously. The final readout of the ELISA is Time-Resolved Fluorescence (counts per minute) using Delfia reagents Streptavidin-Europium and Enhancement solutions (Perkin Elmer) and the Victor 2 multilabel counter (Perkin Elmer).

Where available, the in-vitro BACE cell based data for each of the Examples is provided in Table 1.

In Vitro Enzymatic Cathepsin D (Cat D) FRET (Fluorescence Resonance Energy Transfer) Assay Recombinant Cat D was expressed in CHO cells. The assay buffer for CathepsinD is 0.05 M citrate pH 3.5, 10% DMSO final, 5 mM CHAPS. The Cat D enzyme (9 nM) is pre-incubated for one hour with inhibitors, typically in about 1 uL of DMSO according to a serial dilution, is added thereto. The assays are effectively started by the addition of different FRET substrates (20 nM for Cat D) and the combination is incubated for one hour. The FRET assay is terminated with by addition of Tris buffer, which raises the pH to neutrality, and the fluorescence is determined. The FRET substrate is a peptide with commercially available fluorophore and quencher, on opposite sides of the BACE cleavage site. The Cat D substrate peptide sequence is based on sequence #1 of Table 1 from Gulnik et al. FEBS Letters v413 p379-384 1997. Proteolytic cleavage of the FRET substrate releases quenching of fluorescence (Cat D excitation 500 nm and emission 580 nm).

Alternatively, a Cat D assay may also be run according to the procedure described in the article, Characterization of new fluorgenic substrates for the rapid and sensitive assay of cathepsin E and cathepsin D, *J. Biochem.*, 125:1137, 1999. In addition, the cathepsin D and cathepsin E assays are described in PCT publication WO2011069934. This WIPO publication describes BACE inhibitor compounds having an amide linker connecting two aromatic groups with extremely poor cathepsin D and/or cathepsin E inhibitory activity (see Table 2 (?)).

Where available, the in-vitro Cat D FRET assay data for each of the Examples, conducted by the first procedure, is provided. For example, the compound of example 43 has a Cat D IC$_{50}$ value of >400 uM. As shown by the high micromolar Cat D data (very poorly active or inactive against cat D), the compounds of the present invention possess the unexpected property of little to no ability to inhibit the activity of Cat D. It was surprisingly found that incorporation of an amino- or amido-linker between the core of the compounds and the R$^7$ and R$^9$ groups, respectively, has conferred a significantly reduced, poor or no potency on the protein Cat D. Thus, with this surprising selectivity profile, the compounds of the present invention are believed to minimize, reduce or completely eliminate any risk of retinal atrophy and abnormal development of the eye and of the retinal pigmented epithelium as it relates to the normal function and activity of Cat D.

In Vivo Inhibition of Beta-Secretase

Several animal models, including mouse, rat, dog, and monkey, may be used to screen for inhibition of beta-secretase activity in vivo following administration of a test compound sample. Animals used in this invention can be wild type, transgenic, or gene knockout animals. For example, the Tg2576 mouse model, prepared and conducted as described in Hsiao et al., 1996, *Science* 274, 99-102, and other non-transgenic or gene knockout animals are useful to analyze in vivo inhibition of Amyloid beta peptide (Abeta) production in the presence of inhibitory test compounds. Generally, 2 to 18 month old Tg2576 mice, gene knockout mice or non-transgenic animals are administered test compounds formulated in vehicles, such as cyclodextran, phosphate buffers, hydroxypropyl methylcellulose or other suitable vehicles. One to twenty-four hours following the administration of compound, animals are sacrificed, and brains as well as cerebrospinal fluid (CSF) and plasma are removed for analysis of A-beta levels and drug or test compound concentrations (Dovey et al., 2001, *Journal of Neurochemistry*, 76,173-181) Beginning at time 0, animals are administered by oral gavage, or other means of delivery such as intravenous injection, an inhibitory test compound of up to 100 mg/kg in a standard, conventional formulation, such as 2% hydroxypropyl methylcellulose, 1% Tween80. A separate group of animals receive 2% hydroxypropyl methylcellulose, 1% Tween80 alone, containing no test compound, and serve as a vehicle-control group. At the end of the test period, animals are sacrificed and brain tissues, plasma or cerebrospinal fluid are collected. Brains are either homogenized in 10 volumes (w/v) of 0.2% diethylamine (DEA) in 50 mM NaCl (Best et al., 2005, *Journal of Pharmacology and Experimental Therapeutics*, 313, 902-908), or in 10 volumes of 0.5% TritonX-100 in Tris-buffered saline (pH at about 7.6). Homogenates are centrifuged at 355,000 g, 4° C. for 30 minutes. CSF or brain supernatants are then analyzed for the presence of A-beta peptide by specific sandwich ELISA assays based on ECL (Electrochemiluminescence) technology. For example, rat Abeta40 is measured using biotinylated-4G8 (Signet) as a capture antibody and Fab40 (an in-house antibody specific to the C-terminal of Abeta40) as a detection antibody. For example, 4 hours after administration of 30 mg/kg oral dose of the test compound in 2% hydroxypropyl methylcellulose, 1% Tween80 (pH2.2) to 200 g male Sprague Dawley rats, amyloid beta peptide levels are measured for reduction by X % and Y % in cerebrospinal fluid and brain, respectively, when compared to the levels measured in the vehicle-treated or control mice.

Actual vehicles used: Oral: 2% HPMC, 1% Tween80, pH 2.2

IV: 5% EtOH, 45% Propylene glycol in 5% Dextrose

The compounds of the invention may be shown to reduce the formation and/or deposition of amyloid beta peptide in the cerebrospinal fluid (CSF) as well as in the brain of a mouse or rat at either 3 mpk, 10 mpk or 30 mpk (mpk=mg compound per kg weight of the animal) dosing concentrations after 4 hrs. The following examples exhibited the following percent Abeta 40 reductions at 10 mpk (unless otherwise noted) in the CSF and brain of the rat, respectively.

| Ex. No. | % reduction of rat CSF levels at 10 pmk | % reduction of rat brain levels at 10 mpk |
| --- | --- | --- |
| 127 | 67 | 50 |
| 320 | 82 (at 30 mpk) | 62 (at 30 mpk) |
| 320 | 66 | 46 |
| 117 | 78 | 71 |
| 228 | 54 | 33 |
| 76 | 64 | 60 |
| 229 | 41 | 8 |
| 77 | 78 | 71 |
| 192 | 81 | 71 |
| 71 | 80 | 73 |
| 193 | 75 | 67 |
| 96 | 24 | 1 |
| 95 | 82 | 77 |
| 199 | 62 | 42 |
| 163 | 33 | 14 |
| 74 | 56 | 46 |
| 113 | 65 | 58 |
| 70 | 65 | 51 |
| 237 | 72 | 67 |
| 174 | 46 | 26 |
| 44 | 80 | 73 |
| 45 | 31 | 6 |
| 283 | 75 | 69 |
| 238 | 8 | 16 |
| 281 | 70 | 72 |
| 93 | 76 | 83 |
| 99 | 63 | 58 |
| 43 | 70 | 59 |
| 283 | 61 (3 mpk) | 44 (3 mpk) |
| 162 | 11 | −7 |
| 77 | 66 (3 mpk) | 46 (3 mpk) |
| 44 | 69 (3 mpk) | 52 (3 mpk) |
| 281 | 55 (3 mpk) | 34 (3 mpk) |

-continued

| Ex. No. | % reduction of rat CSF levels at 10 pmk | % reduction of rat brain levels at 10 mpk |
|---|---|---|
| 66 | 59 | 42 |
| 167 | 60 | 41 |
| 306 | 13 | −1 |
| 391 | 54 | 24 |
| 388 | 21 | 4 |
| 130 | 49 | 23 |
| 312 | 30 | −1 |
| 267 | −1 | 11 |
| 302 | 37 | 9 |
| 303 | 57 | 50 |
| 304 | 41 | 20 |
| 419 | 57 | 42 |
| 90 | 48 | 31 |
| 415 | 27 | 14 |
| 390 | 71 | 54 |
| 299 | 74 | 62 |

INDICATIONS

According to the amyloid cascade hypothesis, cerebral deposition of amyloid-beta peptide (Aβ) is critical for Alzheimer's disease (AD) pathogenesis. Aβ generation is initiated when β-secretase (BACE1) cleaves the amyloid precursor protein. De Meyer et al re-affirm the believed role which the accumulation of beta-amyloid protein (A-beta) in cerebral spinal fluid (CSF) in a subject plays in the progression of symptoms, initially revealed as mild cognitive impairment, which ultimately leads to AD. Arch Neurol. 67(8):949-956, 2010. Amyloid-b (Ab) peptides generated from amyloid precursor protein (APP) by proteolytic cleavage, such as by aspartyl protease enzymes including beta-secreatase (BACE) and gamma-secretase, likely play a causal role in AD pathogenesis (Tanzi and Bertram, Cell, (120): 545-555, 2005; Walsh and Selkoe, Neuron, (44): 181-193, 2004). Although the precise mechanisms of Ab toxicity are unclear, oligomeric forms of Ab may contribute to cognitive decline by altering synaptic structure and function (Palop and Mucke, Nat. Neuroscience, (13): 812-818, 2010; Selkoe, Behavioral Brain Res., (192): 106-113, 2008; Shankar et al., Nat. Medicine (14): 837-842, 2008). Transgenic mouse models that overexpress mutant APP and produce high levels of Ab show amyloid plaque deposition, synaptic deficits, learning and memory impairments, and other behavioral abnormalities (Games et al., Nature, (373): 523-527, 1995; tz et al., Molecular Psychiatry (9): 664-683, 2004; Hsia et al., Proc. Natl. Academy of Science USA (96): 3228-3233, 1999; Hsiao et al., Science (274): 99-102, 1996, citing Harris et al, Neuron (68): 428-441, 2010).

For more than a decade, BACE1 has been a prime target for designing drugs to prevent or treat AD. However, development of such agents has turned out to be extremely challenging, with major hurdles in cell penetration, oral bioavailability/metabolic clearance, and brain access.

MK-8931, a small molecule inhibitor of BACE (structure unknown) was tested in a two-part randomised, double-blind, placebo-controlled phase 1 clinical trial in 88 healthy individuals (18-45 years old). MK-8931 seemed to be generally well tolerated (66 patients), and no serious adverse events were reported. A major goal of the trial was to determine whether MK-8931 was able to enter the brain and block β secretase. To monitor this, biomarkers of BACE1 activity in the CSF were measured, including Aβ40 and Aβ42, as was soluble peptide APP (sAPPβ), a direct product of BACE1 cleavage of APP. MK-8931 significantly reduced CSF Aβ concentrations in a sustained and dose-dependent manner. At 36 h post-dose, a single dose of 100 mg reduced CSF Aβ40 concentrations by 75% and a single dose of 550 mg by 92%. Similar reductions of CSF concentrations of Aβ42 and sAPPβ, the BACE1-cleaved ectodomain of APP, were also observed. Vassar & Yan, Lancet Neurology, 13:319-329 (2014). Currently, MK-8931 is enrolling mild-to-moderate Alzheimer's Disease patients in a Ph III trial; and enrolling participants with prodomal Alzheimer's disease in a Ph III safety and efficacy trial. (US clinical trials; Merck Newsroom, 2014).

Bapineuzamab, a monoclonal amino-terminus specific anti-amyloid antibody is presently in Phase III clinical trials for the treatment of AD. Alzheimer's Research & Therapy, 1:2, 2009. Each of the known genetic causes of AD is linked to A-beta. Dementia, Down's Syndrome to APP over-production, are all believed to be linked to the deposition of A-beta on the brain. With methods for identifying brain amyloid deposition, positron emission scanning (PET) and CSF measurements of Ab42, identification of AD suffering individuals needing treatment is becoming easier amd more common. It is firmly believed that by reducing the formation of A-beta, one can begin to pre-treat AD. Vassar et al, Journal of Neuroscience, 29 (41):12787-12794, 2009. One published pathway for treatment of AD is inhibition of beta-secretase. Tirrell, Bloomberg News, The Boston Globe, Jan. 7, 2010.

The US biotech company CoMentis is developing an orally bioavailable small molecule CTS-21166, a highly potent, highly selective and efficacious brain-penetrating beta-secretase inhibitor. CoMentis successfully completed a Phase I study of CTS-21166 in healthy volunteers in 2008. Results indicated that CTS-21166 was safe, well-tolerated and pharmacodynamically active at all dose levels. All clinical subjects administered CTS-21166 showed area-under-curve (AUC) reduction in plasma A-Beta40 reductions ranging from 40-75%. Because of the urgent need for AD treatment, Phase II studies for CTS-2166 are planned, or ongoing, for AD patients. In preclinical studies, CTS-21166 exhibits excellent efficacy, selectivity, brain penetration and pharmacologic activity.

Using a fragment-based chemistry strategy, Eli Lilly and company generated LY2811376 [(S)-4-(2,4-difluoro-5-pyrimidin-5-yl-phenyl)-4-methyl-5,6-dihydro-4H-[1,3]thiazin-2-ylamine], an orally available non-peptidic BACE1 inhibitor that produces profound Aβ-lowering effects in animals. The biomarker changes obtained in preclinical animal models translate into man at doses of LY2811376 that were safe and well tolerated in healthy volunteers (US Ph I Clinical trial—www.clinicaltrials.gov). Prominent and long-lasting Aβ reductions in lumbar CSF were measured after oral dosing of 30 or 90 mg of LY2811376. This represents the first translation of BACE1-driven biomarker changes in CNS from preclinical animal models to man. Because of toxicology findings identified in longer-term preclinical studies, this compound is no longer progressing in clinical development. However, BACE1 remains a viable target because the adverse effects reported here were recapitulated in LY2811376-treated BACE1 KO mice and thus are unrelated to BACE1 inhibition. The magnitude and duration of central Aβ reduction obtainable with BACE1 inhibition positions this protease as a tractable small-molecule target through which to test the amyloid hypothesis in man. Neuroscience, 31(46):16507-16515, 2011

The compounds of the invention have been shown to modulate, and specifically inhibit the activity of the beta-secretase enzyme, thereby reducing the A-beta peptide fragments. Accordingly, compounds of the invention are useful for, but not limited to, the prevention or treatment of beta-secretase related diseases, including Alzheimer's disease. The compounds of the invention have the ability to modulate the activity of beta secretase enzyme, thereby regulating the production of amyloid beta (Abeta peptide) and reducing the formation and deposition of Abeta peptide in both the cerebral spinal fluid as well as in the brain, resulting in a decrease of amyloid plaque on the brain. In one embodiment of the invention, there is provided a method of treating a disorder related to a beta-secretase enzyme in a subject, the method comprising administering to the subject an effective dosage amount of a compound of Formulas I, II, III, and sub-formulae thereof. In another embodiment, there is provided a method of reducing production of amyloid beta, and of reducing plaque formation on the brain. In another embodiment, there is provided a method for the treatment, prevention or amelioration of a disease or disorder characterized by the elevated beta-amyloid deposits or beta-amyloid levels in a subject, the method comprising administering to the subject a therapeutically effective amount of a compound according to any of Formulas I-III. In yet another embodiment, the invention provides a method of treating Alzheimer's disease, cognitive impairment including mild, moderate and/or severe, Down's Syndrome, cognitive decline, senile dementia, cerebral amyloid angiopathy or a neurodegenerative disorder.

Accordingly, the compounds of the invention would be useful in therapy as CNS agents in treating neurological disorders and related conditions in subjects.

In one embodiment, the compounds of the invention are provided for the manufacture of a medicament, or a pharmaceutical composition, for the therapeutic and/or prophylactic treatment of diseases and disorders characterized by elevated levels of β-amyloid and/or β-amyloid oligomers and/or b-amyloid plaques and further deposits, including Alzheimer's Disease. In another embodiment, the invention provides compounds, in effective dosage amounts, for the therapeutic and/or prophylactic treatment of AD. Thus, the compounds of the invention may be used to treat prodromol patients, i.e., subjects exhibiting the biomarkers and/or hallmarks of developing AD.

Besides being useful for human treatment, the compounds of the invention may be useful for veterinary treatment of companion animals, exotic animals and farm animals, including mammals, rodents, and the like. For example, animals including horses, dogs, and cats may be treated with compounds provided herein.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating neurological disorders and beta-secretase mediated diseases with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, and even more advantageously between about 0.1 and about 10 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable excipient, which includes diluents, carriers, adjuvants and the like (collectively referred to herein as "excipient" materials) as described herein, and, if desired, other active ingredients. A pharmaceutical composition of the invention may comprise an "effective amount" of a compound of the invention or an "effective dosage amount" of a compound of the invention. An "effective dosage amount" of a compound of the invention includes an amount less than, equal to or greater than an effective amount of the compound. For example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or other "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hardshell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, and preferably from about 0.1 to about 10 mg/kg.

For pulmonary administration, the pharmaceutical composition may be administered in the form of an aerosol or with an inhaler including dry powder aerosol.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Accordingly, in yet another embodiment of the present invention, there is provided a method of manufacturing a medicament, the method comprising combining an amount of a compound according to Formulas I-III with a pharmaceutically acceptable carrier to manufacture the medicament.

In yet another embodiment, the invention provides a method of manufacturing a medicament for the treatment of Alzheimer's disease, the method comprising combining an amount of a compound according to Formulas I-III with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of beta-secretase, gamma-secretase and/or other reagents known in influence the formation and/or deposition of amyloid beta, otherwise responsible for the formation of plaque on the brain.

If formulated as a fixed dose, such combination products employ the compounds of this invention within the accepted dosage ranges. Compounds of Formulas I, II and III may also be administered sequentially with other known medicinal agents. The invention is not limited in the sequence of administration; compounds of the invention may be administered either prior to, simultaneously with or after administration of the known anti-inflammatory agent.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:

1. A compound of Formula I

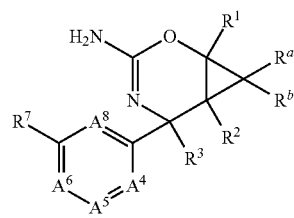

or a stereoisomer, tautomer, hydrate, solvate or pharmaceutically acceptable salt thereof, wherein
$A^4$ is $CR^4$ or N;
$A^5$ is $CR^5$ or N;
$A^6$ is $CR^6$ or N;

$A^8$ is $CR^8$ or N, provided that no more than two of $A^4$, $A^5$, $A^6$ and $A^8$ is N;

each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)C_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$, —O—$R^9$ or —S—$R^9$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —C(O)NHCH$_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl, provided the compound is not N-(3-((1R,5R,6R)-3-amino-5-methyl-2-oxa-4-azabicyclo[4.1.0]hept-3-en-5-yl)-4-fluorophenyl)-3-methoxy-1,7-naphthyridin-8-amine; or N-(3-((1R,5R,6R)-3-amino-5-methyl-2-oxa-4-azabicyclo[4.1.0]hept-3-en-5-yl)-4-fluorophenyl)-5-methoxy-2-pyrazinecarboxamide.

2. The compound according to claim 1, or a stereoisomer or pharmaceutically acceptable salt thereof, wherein each of $R^1$ and $R^2$, independently, is H, F, $CH_3$, $CH_2F$, $CHF_2$ or $CF_3$.

3. The compound according to claim 1, or a stereoisomer or pharmaceutically acceptable salt thereof, wherein each of $R^a$ and $R^b$, independently, is H, F, $CH_3$, $CH_2F$, $CHF_2$ or $CF_3$.

4. The compound according to claim 1, or a stereoisomer or pharmaceutically acceptable salt thereof, wherein each of $R^1$ and $R^2$, independently, is H, F or $CF_3$.

5. The compound according to claim 1, or a stereoisomer or pharmaceutically acceptable salt thereof, wherein each of $R^a$ and $R^b$, independently, is H or F.

6. The compound according to claim 1, or a stereoisomer or pharmaceutically acceptable salt thereof, wherein each of $R^1$ and $R^2$, independently, is H, F or $CF_3$; and each of $R^a$ and $R^b$, independently, is H or F.

7. The compound according to claim 1, or a stereoisomer or pharmaceutically acceptable salt thereof, wherein each of $R^1$, $R^2$, $R^a$ and $R^b$, independently, is H.

8. The compound according to claim 6, or a stereoisomer or pharmaceutically acceptable salt thereof, wherein $R^3$ is $CH_3$, $CF_3$, $CH_2F$ or $CHF_2$.

9. The compound according to claim 1, or a stereoisomer or pharmaceutically acceptable salt thereof, wherein $R^7$ is —NH—$CH_2$—$R^9$ or —NH—C(=O)—$R^9$;

or $R^7$ is

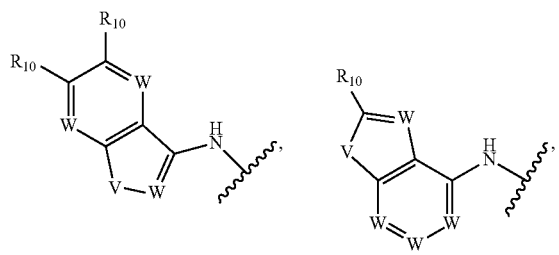

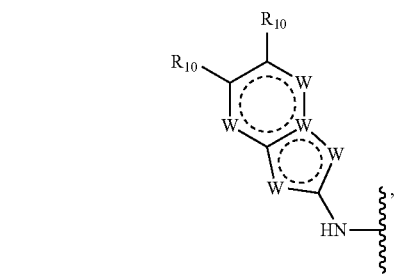

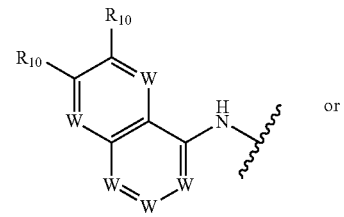 or

-continued

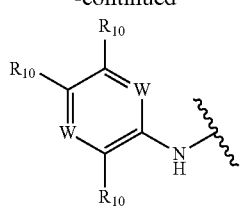

wherein V is NR$^{10}$, O or S; and each W, independently, is CH, CF, CCl, CCH$_3$ or N.

10. The compound according to according to claim 1, or a stereoisomer or pharmaceutically acceptable salt thereof, wherein A$^4$ is CR$^4$ or N;

A$^5$ is CR$^5$ or N;

A$^6$ is CR$^6$ or N;

A$^8$ is CR$^8$ or N, provided that no more than one of A$^4$, A$^5$, A$^6$ and A$^8$ is N;

each of R$^a$ and R$^b$, independently, is H, F, Cl, CF$_3$, OCF$_3$, methyl, ethyl, CN, OH, OCH$_3$, SCH$_3$, NHCH$_3$, C(O)CH$_3$ or CH$_2$OCHF$_2$;

each of R$^1$ and R$^2$, independently, is H, F, Cl, CF$_3$, OCF$_3$, methyl, ethyl, CN, OH, OCH$_3$, SCH$_3$, NHCH$_3$, C(O)CH$_3$ or CH$_2$OCHF$_2$;

R$^3$ is C$_{1-4}$alkyl, C$_{1-4}$haloalkyl, CH$_2$OH, CH$_2$OCHF$_2$ or cyclopropyl; and each of R$^4$, R$^5$, R$^6$ and R$^8$, independently, is H, F, Cl, CF$_2$H, CH$_2$F, CF$_3$, OCF$_3$, methyl, ethyl, CN, OH, OCH$_3$, SCH$_3$, NHCH$_3$ or C(O)CH$_3$.

11. The compound according to claim 6, or a stereoisomer or pharmaceutically acceptable salt thereof, wherein each of R$^1$ and R$^2$, independently, is H, F or CF$_3$;

each of R$^a$ and R$^b$, independently, is H or F;

R$^3$ is CH$_3$, CF$_3$, CH$_2$F or CHF$_2$; and

R$^7$ is —NH—R$^9$, —NH—C(=O)—R$^9$ or

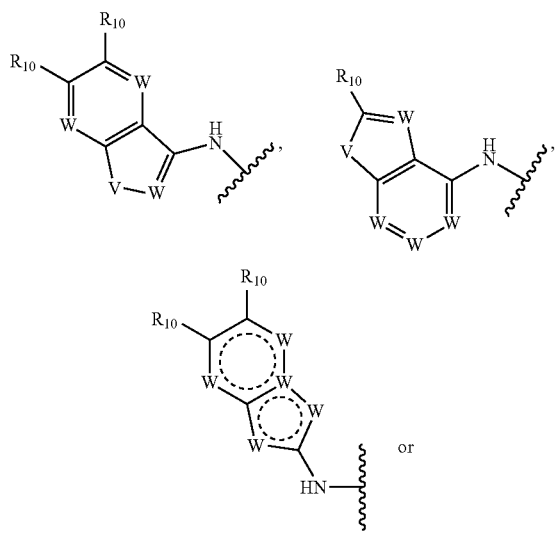

-continued

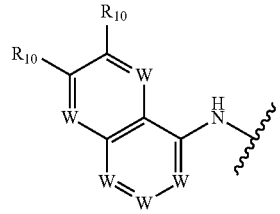

wherein V is NR$^{10}$, O or S; and each W, independently, is CH, CF, CCl, CCH$_3$ or N.

12. The compound according to claim 1, or a stereoisomer or pharmaceutically acceptable salt thereof, wherein R$^7$ is —NH—C(=O)—R$^9$.

13. The compound according to claim 1, or a stereoisomer or pharmaceutically acceptable salt thereof, wherein R$^7$ is

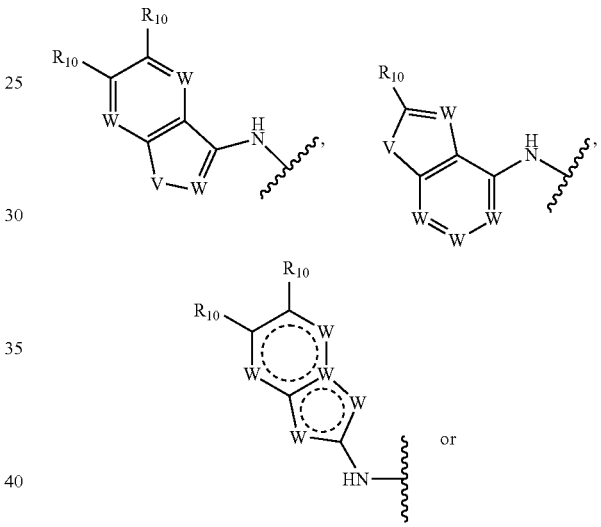

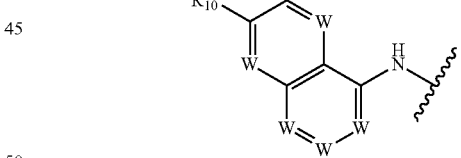

wherein V is NR$^{10}$, O or S; and each W, independently, is CH, CF, CCl, CCH$_3$ or N.

14. The compound according to claim 1, or a stereoisomer or pharmaceutically acceptable salt thereof, wherein A$^4$ is CR$^4$;

A$^5$ is CR$^5$ or N;

A$^6$ is CR$^6$; and

A$^8$ is CR$^8$ or N, provided only one of A$^5$ and A$^8$ is N, and wherein each of R$^4$, R$^5$, R$^6$ and R$^8$, independently, is H, F, Cl, CF$_3$, CF$_2$H, CH$_2$F or CH$_3$.

15. A compound according to claim 1, or a stereoisomer, tautomer, hydrate, solvate or pharmaceutically acceptable salt thereof, having a Formula II:

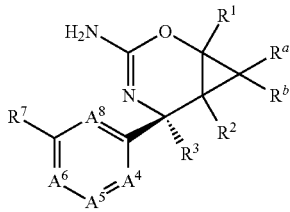

II wherein $A^4$ is $CR^4$ or N;

$A^5$ is $CR^5$ or N;

$A^6$ is $CR^6$ or N;

$A^8$ is $CR^8$ or N, provided that no more than two of $A^4$, $A^5$, $A^6$ and $A^8$ is N;

each of $R^a$ and $R^b$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

each of $R^1$ and $R^2$, independently, is H, F, Cl, $C_{1-6}$-alkyl, $C_{2-4}$alkenyl, $C_{2-4}$alkynyl, CN, —$CH_2OC_{1-6}$-alkyl, —$OC_{1-6}$-alkyl, —$S(O)C_{1-6}$-alkyl, —$NHC_{1-6}$-alkyl or —$C(O)C_{1-6}$-alkyl, wherein each of the $C_{1-6}$-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, halo, haloalkyl, haloalkoxyl, $C_{1-4}$-alkyl, CN, OH, $OC_{1-4}$-alkyl, $S(O)C_{1-4}$-alkyl, $NHC_{1-4}$-alkyl or $C(O)C_{1-4}$-alkyl;

$R^7$ is —NH—$R^9$, —NH—C(=O)—$R^9$, —C(=O)NH—$R^9$;

or $R^7$ is

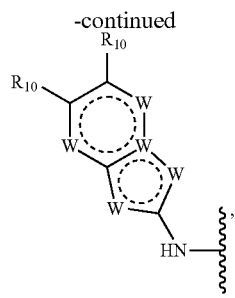

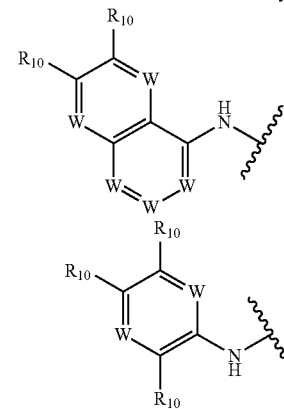

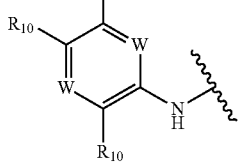

wherein V is $NR^{10}$, O or S; and each W, independently, is CH, CF, CCl, $CCH_3$ or N;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

16. The compound according to claim 15, or a stereoisomer, tautomer or pharmaceutically acceptable salt thereof, wherein $A^4$ is $CR^4$ or N;

$A^5$ is $CR^5$ or N;

$A^6$ is $CR^6$ or N;

A⁸ is CR⁸ or N, provided no more than one of A⁴, A⁵, A⁶ and A⁸ is N;

each of Rᵃ and Rᵇ, independently, is H, F, CH₃, CH₂F, CHF₂ or CF₃;

each of R¹ and R², independently, is H, F, CH₃, CH₂F, CHF₂ or CF₃;

R³ is C₁₋₄alkyl, C₁₋₄haloalkyl, CH₂OH, CH₂OCHF₂ or cyclopropyl; and each of R⁴, R⁵, R⁶ and R⁸, independently, is H, F, Cl, CF₂H, CH₂F, CF₃, OCF₃, methyl, ethyl, CN, OH, OCH₃, SCH₃, NHCH₃ or C(O)CH₃.

17. The compound according to claim 15, or a stereoisomer or pharmaceutically acceptable salt thereof, wherein A⁴ is CR⁴;

A⁵ is CR⁵;

A⁶ is CR⁶; and

A⁸ is CR⁸; wherein each of R⁴, R⁵, R⁶ and R⁸, independently, is H, F, CF₃, CF₂H, CH₂F or CH₃;

R³ is CH₃, CF₃, CH₂F or CHF₂; and

R⁷ is —NH—C(=O)—R⁹ or

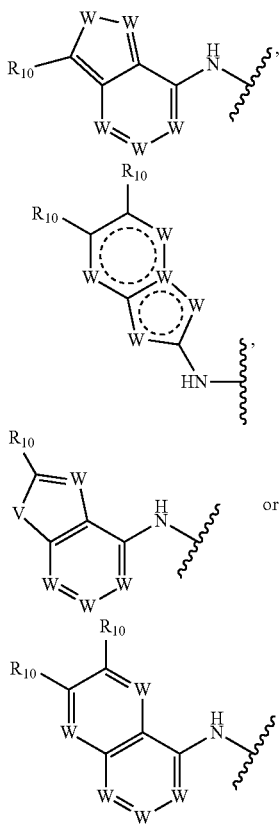

wherein V is NR¹⁰, O or S; and
each W, independently, is CH, CF, CCl or N.

18. The compound according to claim 15, or a stereoisomer or pharmaceutically acceptable salt thereof, wherein R⁷ is —NH—C(=O)—R⁹.

19. The compound according to claim 15, or a stereoisomer or pharmaceutically acceptable salt thereof, wherein R⁷ is

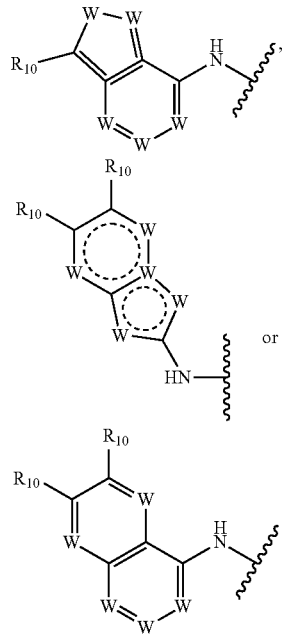

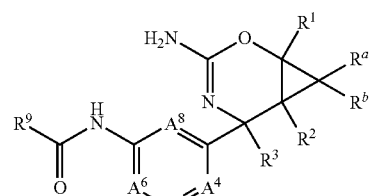

wherein V is NR¹⁰, O or S; and
each W, independently, is CH, CF, CCl, CCH₃ or N.

20. The compound according to claim 15, or a stereoisomer or pharmaceutically acceptable salt thereof, wherein each of R¹ and R², independently, is H, F or CF₃; and each of Rᵃ and Rᵇ, independently, is H or F.

21. The compound according to claim 1, or a stereoisomer or pharmaceutically acceptable salt thereof, having a Formula II-A

I-A wherein
A⁴ is CR⁴ or N;
A⁵ is CR⁵ or N;
A⁶ is CR⁶ or N;
A⁸ is CR⁸ or N, provided that no more than one of A⁴, A⁵, A⁶ and A⁸ is N;
each of Rᵃ and Rᵇ, independently, is H, F, Cl, C₁₋₆-alkyl, C₂₋₄alkenyl, C₂₋₄alkynyl, CN, —CH₂OC₁₋₆-alkyl, —OC₁₋₆-alkyl, —S(O)C₁₋₆-alkyl, —NHC₁₋₆-alkyl or —C(O)C₁₋₆-alkyl, wherein each of the C₁₋₆-alkyl, C₂₋₄alkenyl, C₂₋₄alkynyl, and C₁₋₆-alkyl portion of —CH₂OC₁₋₆-alkyl, —OC₁₋₆-alkyl, —S(O)C₁₋₆-alkyl, —NHC₁₋₆-alkyl and —C(O)C₁₋₆-alkyl are optionally substituted with 1-4 substituents of F, oxo or OH;
each of R¹ and R², independently, is H, F, Cl, C₁₋₆-alkyl, C₂₋₄alkenyl, C₂₋₄alkynyl, CN, —CH₂OC₁₋₆-alkyl, —OC₁₋₆-alkyl, —S(O)C₁₋₆-alkyl, —NHC₁₋₆-alkyl or —C(O)C₁₋₆-alkyl, wherein each of the C₁₋₆-alkyl, $C_{2-4}$alkenyl, $C_{2-4}$alkynyl, and $C_{1-6}$-alkyl portion of —$CH_2OC_{1-6}$-alkyl, —$OC_{1-6}$-alkyl, —$S(O)C_{1-6}$-alkyl, —$NHC_{1-6}$-alkyl and —$C(O)C_{1-6}$-alkyl are optionally substituted with 1-4 substituents of F, oxo or OH;

$R^3$ is $C_{1-4}$alkyl, $CH_2OC_{1-4}$alkyl, $CH_2OH$, $C_{1-4}$haloalkyl or cyclopropyl, wherein each of the $C_{1-4}$alkyl, $CH_2OC_{1-4}$alkyl, $C_{1-4}$haloalkyl and cyclopropyl is optionally substituted with 1-4 F atoms;

each of $R^4$, $R^5$, $R^6$ and $R^8$, independently, is H, F, Cl or $CH_3$;

$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

22. The compound according to claim 21, or a stereoisomer, tautomer or pharmaceutically acceptable salt thereof, wherein $A^4$ is $CR^4$;
$A^5$ is $CR^5$;
$A^6$ is $CR^6$;
$A^8$ is $CR^8$; wherein each of $R^4$, $R^5$, $R^6$ and $R^8$, independently, is H, F, Cl, $CF_2H$, $CH_2F$, $CF_3$, $OCF_3$, methyl, ethyl, CN, OH, $OCH_3$, $SCH_3$, $NHCH_3$ or $C(O)CH_3$;
each of $R^a$ and $R^b$, independently, is H, F, $CH_3$, $CH_2F$, $CHF_2$ or $CF_3$;
each of $R^1$ and $R^2$, independently, is H, F, $CH_3$, $CH_2F$, $CHF_2$ or $CF_3$;
$R^3$ is $CH_3$, $C_2H_5$, $CF_2H$ or $CH_2F$;
$R^9$ is acetyl, $C_{1-6}$-alkyl, $C_{2-4}$alkenyl, $C_{2-4}$alkynyl or a fully or partially unsaturated 3-, 4-, 5-, 6- or 7-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the $C_{1-6}$-alkyl, $C_{2-4}$alkenyl, $C_{2-4}$alkynyl and ring are optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

23. The compound according to claim 21, or a stereoisomer or pharmaceutically acceptable salt thereof, wherein
$A^4$ is $CR^4$ or N;
$A^5$ is $CR^5$ or N;
$A^6$ is $CR^6$ or N;
$A^8$ is $CR^8$ or N, wherein each of $R^4$, $R^5$, $R^6$ and $R^8$, independently, is H, F, Cl or $CH_3$, provided no more than one of $A^4$, $A^5$, $A^6$ and $A^8$ is N;
each of $R^1$, $R^2$, $R^a$ and $R^b$, independently, is H; and
$R^3$ is $CF_3$, $CH_3$, $CF_2H$ or $CH_2F$.

24. The compound according to claim 1, or a pharmaceutically acceptable salt thereof, having a Formula II-A

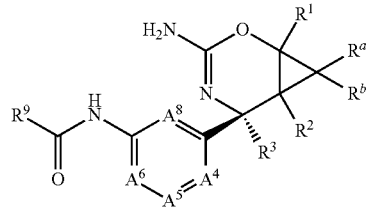

II-A wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F,
provided that no more than one of $A^5$ and $A^8$ is N;
each of $R^a$ and $R^b$, independently, is H or F;
each of $R^1$ and $R^2$, independently, is H or F;
$R^3$ is $CH_3$, $CF_3$, $CH_2F$ or $CHF_2$;
$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S, wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —$C(O)NHCH_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

25. The compound according to claim 24, or a pharmaceutically acceptable salt thereof, wherein each of $R^a$, $R^b$, $R^1$ and $R^2$, independently, is H.

26. The compound according to claim 24, or a pharmaceutically acceptable salt thereof, wherein $R^3$ is $CH_3$, $CH_2F$ or $CHF_2$.

27. The compound according to claim 24, or a pharmaceutically acceptable salt thereof, wherein $R^3$ is $CH_2F$ or $CHF_2$.

28. The compound according to claim 24, or a pharmaceutically acceptable salt thereof, wherein $R^3$ is $CH_2F$.

29. The compound according to claim 24, or a pharmaceutically acceptable salt thereof, wherein $R^3$ is $CHF_2$.

30. The compound according to claim 24, or a pharmaceutically acceptable salt thereof, wherein $A^4$ is CF or CCl;
    $A^5$ is CH, CF, $CH_3$ or N; and
    $A^8$ is CH.

31. The compound according to claim 24, or a pharmaceutically acceptable salt thereof, wherein $A^4$ is CF;
    $A^5$ is CH, CF or N; and
    $A^8$ is CH.

32. The compound according to claim 24, or a pharmaceutically acceptable salt thereof, wherein $A^4$ is CCl;
    $A^5$ is CH or CF; and
    $A^8$ is CH.

33. The compound according to claim 24, or a pharmaceutically acceptable salt thereof, wherein
    $R^9$ is a ring selected from phenyl, pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$; and
    each $R^{10}$, independently, is halo, haloalkyl, CN, OH, $NO_2$, $NH_2$, $SF_5$, acetyl, —C(O)$NHCH_3$, oxo, cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$ alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl.

34. The compound according to claim 24, or a pharmaceutically acceptable salt thereof, wherein $R^9$ is a ring selected from pyridyl, pyrimidyl, pyrazinyl, pyridazinyl, pyrazolyl, pyrazolo[3,4-c]pyridinyl, oxazolyl, isoxazolyl, thiazolyl, isothiazolyl or thienyl, wherein the ring is optionally substituted with 1-5 substituents of $R^{10}$.

35. The compound according to claim 24, or a pharmaceutically acceptable salt thereof, wherein $R^9$ is

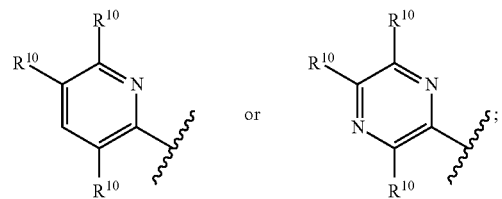

and
    each $R^{10}$, independently, is H, F, Cl, Br, $CF_3$, $CHF_2$, $CH_2F$, CN, OH, —C(O)$NHCH_3$, cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl or $C_{1-6}$thioalkoxyl, wherein each of the cyclopropylmethoxy, 2-propynyloxy, 2-butynyloxy, $C_{1-6}$alkyl, $C_{2-6}$alkenyl, $C_{2-6}$alkynyl, $C_{3-6}$cycloalkyl, $C_{1-6}$alkoxyl and $C_{1-6}$thioalkoxyl is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, $C_{1-3}$alkylamino-, $C_{1-3}$dialkylamino, $C_{1-3}$thioalkoxyl, oxazolyl or thiazolyl.

36. The compound according to claim 24, or a pharmaceutically acceptable salt thereof, wherein $R^3$ is $CHF_2$; and $R^9$ is

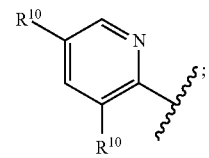

and
    each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

37. The compound according to claim 24, or a pharmaceutically acceptable salt thereof, wherein $R^3$ is $CH_2F$; and $R^9$ is

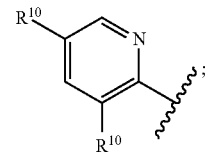

and
    each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

38. The compound according to claim 24, or a pharmaceutically acceptable salt thereof, wherein $R^3$ is $CHF_2$; and $R^9$ is

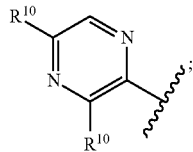

and
each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

39. The compound according to claim 24, or a pharmaceutically acceptable salt thereof, wherein $R^3$ is $CH_2F$; and $R^9$ is

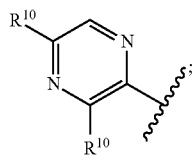

and
each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.

40. The compound according to claim 1, or a stereoisomer, tautomer, hydrate, solvate or pharmaceutically acceptable salt thereof, having a Formula II-B:

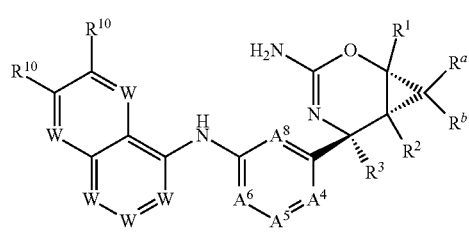

wherein
$A^4$ is $CR^4$, wherein $R^4$ is H, F or Cl;
$A^5$ is $CR^5$ or N, wherein $R^5$ is H, F, Cl or $CH_3$;
$A^6$ is CH;
$A^8$ is $CR^8$ or N, wherein $R^8$ is H or F,
provided that no more than one of $A^5$ and $A^8$ is N;
each of $R^a$ and $R^b$, independently, is H or F;
each of $R^1$ and $R^2$, independently, is H or F;
$R^3$ is $CH_3$, $CF_3$, $CH_2F$ or $CHF_2$;
$R^9$ is a fully unsaturated 5- or 6-membered monocyclic or 8-, 9- or 10-membered bicyclic ring formed of carbon atoms, said ring optionally including 1-4 heteroatoms if monocyclic or 1-5 heteroatoms if bicyclic, said heteroatoms selected from O, N or S,
wherein the ring is optionally substituted, independently, with 1-5 substituents of $R^{10}$; and
each $R^{10}$, independently, is H, halo, haloalkyl, CN, OH, $NO_2$, $NH_2$, $SF_5$, acetyl, —C(O)$NHCH_3$, oxo, cyclopropylmethoxy, 2-butynyloxy, $C_{1-6}$alkyl, $C_{2-6}$alkenyl, $C_{2-6}$ alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolyl, pyrrolidinyl, tetrahydropyrrolyl, piperazinyl, oxetan-3-yl, imidazo-pyridinyl or dioxolyl, wherein each of the cyclopropylmethoxy, 2-butynyloxy, $C_{1-6}$alkyl, $C_{2-6}$alkenyl, $C_{2-6}$alkynyl, $C_{3-6}$cycloalkyl, $C_{1-6}$alkylamino-, $C_{1-6}$dialkylamino-, $C_{1-6}$alkoxyl, $C_{1-6}$thioalkoxyl, morpholinyl, pyrazolyl, isoxazolyl, dihydropyranyl, pyrrolidinyl, oxetan-3-yl or dioxolyl, is optionally substituted independently with 1-5 substituents of F, Cl, CN, $NO_2$, $NH_2$, OH, oxo, $CF_3$, $CHF_2$, $CH_2F$, methyl, methoxy, ethyl, ethoxy, $CH_2CF_3$, $CH_2CHF_2$, propyl, propoxy, isopropyl, isopropoxy, cyclopropyl, butyl, butoxyl, cyclobutyl, isobutoxy, tert-butoxy, isobutyl, sec-butyl, tert-butyl, cyclopentyl, cyclohexyl, $C_{1-3}$alkylamino-, $C_{1-3}$dialkylamino, $C_{1-3}$thioalkoxyl tetrahydropyranyl, tetrahydropyrrolyl or oxetan-3yl; and
each W, independently, is CH, CF, CCl, $CCH_3$ or N.

41. The compound according claim 40, or a pharmaceutically acceptable salt thereof, wherein each of $R^a$, $R^b$, $R^1$ and $R^2$, independently, is H.

42. The compound according to claim 40, or a pharmaceutically acceptable salt thereof, wherein $R^3$ is $CH_3$, $CH_2F$ or $CHF_2$.

43. The compound according to claim 40, or a pharmaceutically acceptable salt thereof, wherein $R^3$ is $CH_2F$ or $CHF_2$.

44. The compound according to claim 40, or a pharmaceutically acceptable salt thereof, wherein $R^3$ is $CH_2F$.

45. The compound according to claim 40, or a pharmaceutically acceptable salt thereof, wherein $R^3$ is $CHF_2$.

46. The compound according to claim 40, or a pharmaceutically acceptable salt thereof, wherein $A^4$ is CF or CCl;
$A^5$ is CH, CF, $CH_3$ or N; and
$A^8$ is CH.

47. The compound according to claim 40, or a pharmaceutically acceptable salt thereof, wherein $A^4$ is CF;
$A^5$ is CH, CF or N; and
$A^8$ is CH.

48. The compound according to claim 40, or a pharmaceutically acceptable salt thereof, wherein $A^4$ is CCl;
$A^5$ is CH or CF; and
$A^8$ is CH.

49. The compound according to claim 40, or a pharmaceutically acceptable salt thereof, wherein

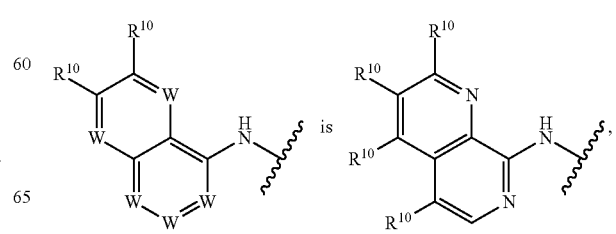

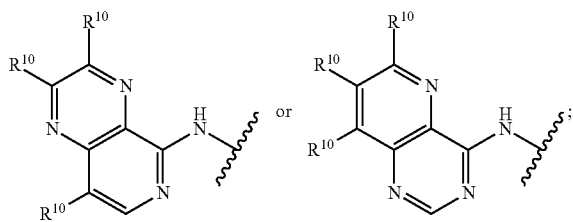
and
each $R^{10}$, independently, is H, F, Cl, Br, $CH_3$, $CHF_2$, $CH_2F$, CN, 2-propynyloxy, 2-butynyloxy or $C_{1-2}$alkoxyl, wherein the $C_{1-2}$alkoxyl is optionally substituted independently with 1-5 substituents of F, Cl, methyl, methoxy, ethyl, ethoxy, oxazolyl or thiazolyl.
50. The compound of claim 1, or a stereoisomer or pharmaceutically acceptable salt thereof, selected from
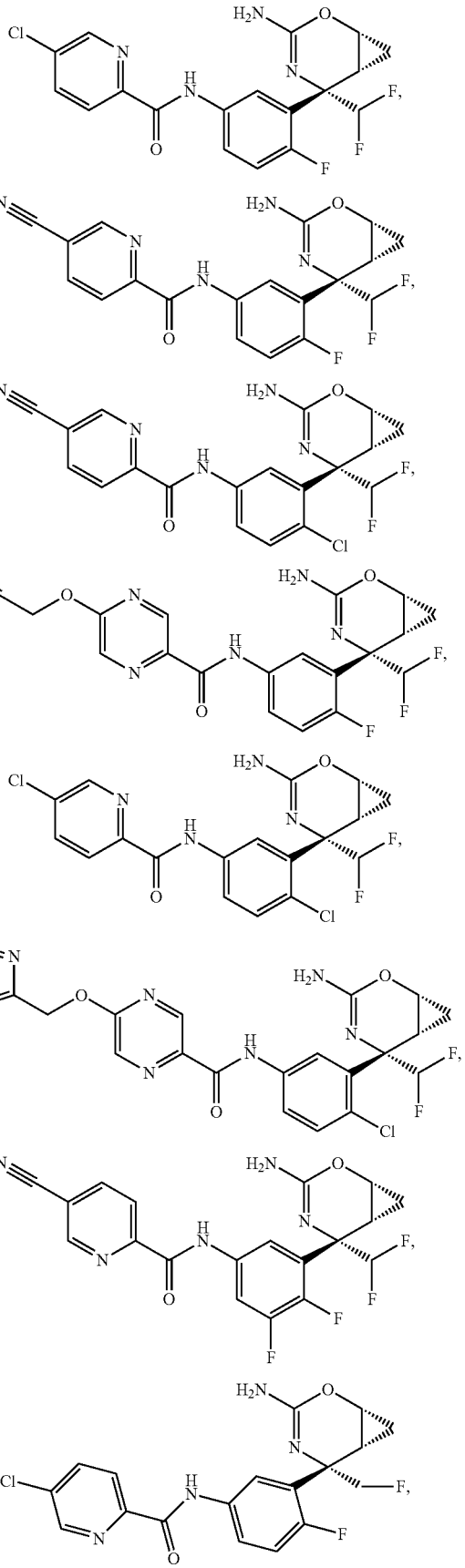

-continued

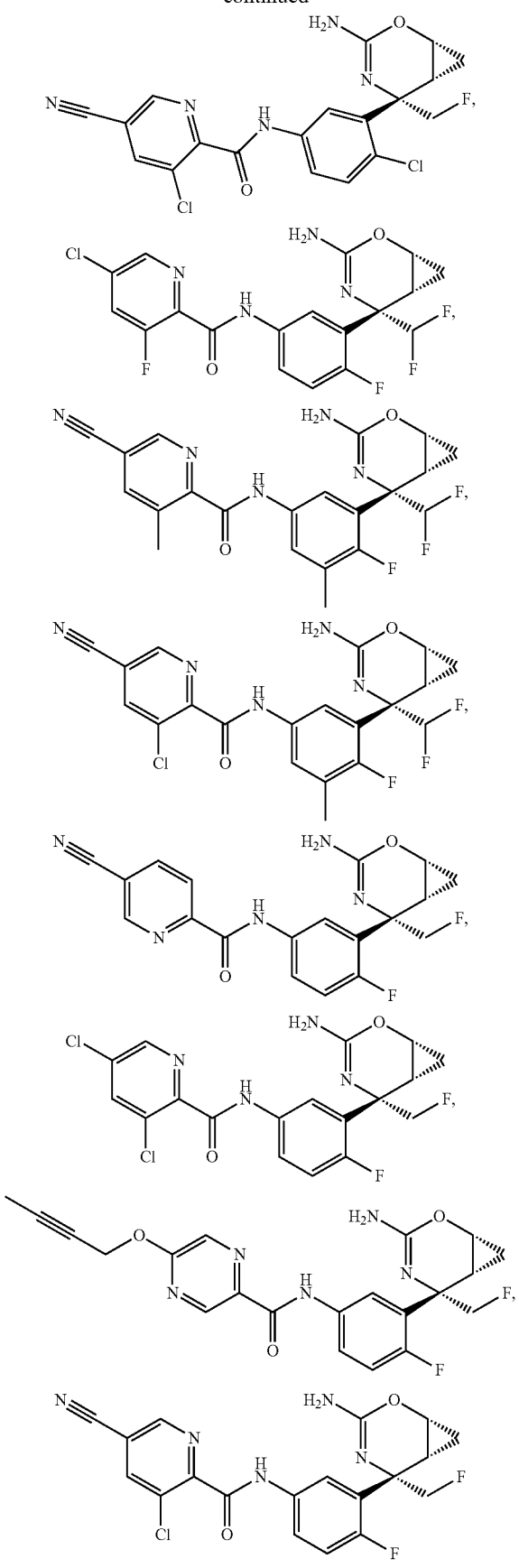

-continued

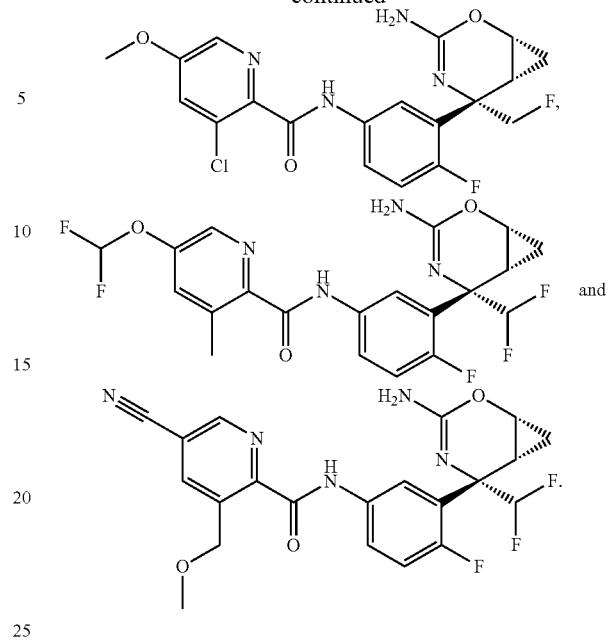

51. The compound of claim 1, or a tautomer or pharmaceutically acceptable salt thereof, selected from N-(3-((1R,5S,6R)-3-amino-5-(difluoromethyl)-2-oxa-4-azabicyclo[4.1.0]hept-3-en-5-yl)-4-fluorophenyl)-5-chloro-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-5-cyano-3-methylpicolinamide;

N-(3-((1R,5S,6R)-3-amino-5-(difluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-3-chloro-5-methoxypicolinamide;

N-(3-((1R,5S,6R)-3-amino-5-(difluoromethyl)-2-oxa-4-azabicyclo[4.1.0]hept-3-en-5-yl)-4-fluorophenyl)-3,5-dichloropicolinamide;

N-(3-((1R,5S,6R)-3-amino-5-(difluoromethyl)-2-oxa-4-azabicyclo[4.1.0]hept-3-en-5-yl)-4-fluorophenyl)-5-bromopicolinamide;

N-(3-((1R,5S,6R)-3-amino-5-(difluoromethyl)-2-oxa-4-azabicyclo[4.1.0]hept-3-en-5-yl)-4-fluorophenyl)-5-chloropicolinamide;

N-(3-((1R,5S,6R)-3-amino-5-(difluoromethyl)-2-oxa-4-azabicyclo[4.1.0]hept-3-en-5-yl)-4-fluorophenyl)-5-cyanopicolinamide;

N-(3-((1S,5R,6S)-3-amino-5-(fluoromethyl)-2-oxa-4-azabicyclo[4.1.0]hept-3-en-5-yl)-2,4-difluorophenyl)-5-methoxypicolinamide;

N-(3-((1R,5S,6R)-3-amino-5-(difluoromethyl)-2-oxa-4-azabicyclo[4.1.0]hept-3-en-5-yl)-4-chlorophenyl)-5-cyanopicolinamide;

N-(3-((1R,5S,6R)-3-amino-5-(difluoromethyl)-2-oxa-4-azabicyclo[4.1.0]hept-3-en-5-yl)-4-fluorophenyl)-5-(prop-2-yn-1-yloxy)pyrazine-2-carboxamide trifluoroacetate;

N-(3-((1R,5S,6R)-3-amino-5-(difluoromethyl)-2-oxa-4-azabicyclo[4.1.0]hept-3-en-5-yl)-4-chlorophenyl)-5-chloropicolinamide;

N-(3-((1R,5S,6R)-3-amino-5-(difluoromethyl)-2-oxa-4-azabicyclo[4.1.0]hept-3-en-5-yl)-4-chlorophenyl)-5-(oxazol-4-ylmethoxy)pyrazine-2-carboxamide;

N-(3-((1R,5S,6R)-3-amino-5-(fluoromethyl)-2-oxa-4-azabicyclo[4.1.0]hept-3-en-5-yl)-4-fluorophenyl)-5-chloropicolinamide;

N-(3-((1R,5S,6R)-3-amino-5-(difluoromethyl)-2-oxa-4-azabicyclo[4.1.0]hept-3-en-5-yl)-4-fluoro-5-methylphenyl)-5-cyano-3-methylpicolinamide;

N-(3-((1R,5S,6R)-3-amino-5-(difluoromethyl)-2-oxa-4-azabicyclo[4.1.0]hept-3-en-5-yl)-4-fluoro-5-methylphenyl)-3-chloro-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-3,5-dichloropicolinamide;

N-(3-((1R,5S,6R)-3-amino-5-(fluoromethyl)-2-oxa-4-azabicyclo[4.1.0]hept-3-en-5-yl)-4-fluorophenyl)-5-(but-2-yn-1-yloxy)pyrazine-2-carboxamide;

N-(3-((1R,5S,6R)-3-amino-5-(fluoromethyl)-2-oxa-4-azabicyclo[4.1.0]hept-3-en-5-yl)-4-fluorophenyl)-3-chloro-5-cyanopicolinamide;

N-(3-((1R,5S,6R)-3-amino-5-(fluoromethyl)-2-oxa-4-azabicyclo[4.1.0]hept-3-en-5-yl)-4-fluorophenyl)-3-chloro-5-methoxypicolinamide;

N-(3-((1R,5S,6R)-3-amino-5-(difluoromethyl)-2-oxa-4-azabicyclo[4.1.0]hept-3-en-5-yl)-4-fluorophenyl)-5-(difluoromethoxy)-3-methylpicolinamide;

N-(3-((1R,5S,6R)-3-amino-5-(fluoromethyl)-2-oxa-4-azabicyclo[4.1.0]hept-3-en-5-yl)-4-chlorophenyl)-5-cyano-3-methylpicolinamide;

N-(3-((1R,5S,6R)-3-benzamido-5-methyl-2-oxa-4-azabicyclo[4.1.0]hept-3-en-5-yl)-4-fluorophenyl)-5-methoxypyrazine-2-carboxamide; or N-(3-((1R,5S,6R)-3-amino-5-(fluoromethyl)-2-oxa-4-azabicyclo[4.1.0]hept-3-en-5-yl)-4-chlorophenyl)-5-cyano-3-(methoxymethyl)picolinamide.

52. A pharmaceutical composition comprising a compound according to claim 1 and a pharmaceutically acceptable excipient.

53. A pharmaceutical composition comprising a compound according to claim 50 and a pharmaceutically acceptable excipient.

54. A pharmaceutical composition comprising a compound according to claim 51 and a pharmaceutically acceptable excipient.

55. A method of reducing beta amyloid peptide levels in the cerebral spinal fluid of a subject, the method comprising administering to the subject an effective dosage amount of a compound according to claim 1.

56. A method of treating Alzheimer's disease, cognitive impairment or a combination thereof in a subject, the method comprising administering to the subject an effective dosage amount of a compound according to claim 1.

57. A method of treating a neurological disorder selected from mild cognitive impairment, Down's syndrome, Hereditary cerebral hemorrhage with dutch-type amyloidosis, cerebral amyloid angiopathy, degenerative dementia, dementia associated with Parkinson's disease, dementia associated with supranuclear palsy, dementia associated with cortical basal degeneration, diffuse lewy body type of Alzheimer's disease or a combination thereof in a subject, the method comprising administering to the subject an effective dosage amount of a compound according to claim 1.

58. A method of reducing the formation of plaque on the brain of a subject, the method comprising administering to the subject an effective dosage amount of a compound according to claim 1.

59. A process for preparing a compound of Formula I according to claim 1, the process comprising the step of reacting a protected compound 20

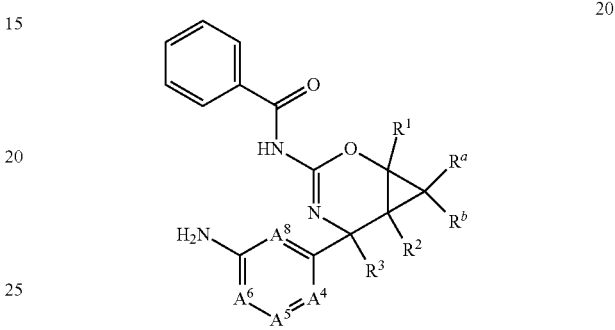

wherein each $R^1$ and each $R^2$, $R^3$, $A^4$, $A^5$, $A^6$ and $A^8$ of compound 20 are as defined in claim 1, with a compound having the structure or $R^9$—C(=O)OH in the presence of an acid activating agent or $R^9$—Cl in the presence of a base, wherein $R^9$ is as defined in claim 1 to prepare the compound according to claim 1.

60. A process for preparing a compound of Formula I-A according to claim 1, the process comprising the step of reacting a compound 20

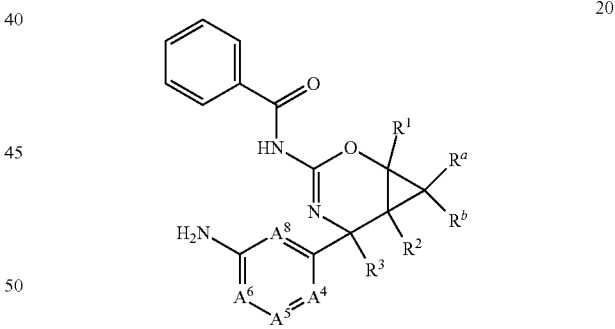

wherein each $R^1$ and each $R^2$, $R^3$, $A^4$, $A^5$, $A^6$ and $A^8$ of compound 20 are as defined in claim 1, with a compound having the structure $R^9$—COOH, wherein $R^9$ is as defined in claim 1 to prepare the compound according to claim 1.

* * * * *